US012265040B2

(12) United States Patent
Ichihara et al.

(10) Patent No.: US 12,265,040 B2
(45) Date of Patent: Apr. 1, 2025

(54) SENSOR DEVICE

(71) Applicants: SONY GROUP CORPORATION, Tokyo (JP); SONY SEMICONDUCTOR SOLUTIONS CORPORATION, Kanagawa (JP)

(72) Inventors: Takuya Ichihara, Tokyo (JP); Norihito Mihota, Saitama (JP); Atsushi Yamada, Kanagawa (JP); Sachio Iida, Chiba (JP); Takahiro Oishi, Kangawa (JP); Minoru Ishida, Tokyo (JP)

(73) Assignees: Sony Group Corporation, Tokyo (JP); Sony Semiconductor Solutions Corporation, Kanagawa (JP)

( * ) Notice: Subject to any disclaimer, the term of this patent is extended or adjusted under 35 U.S.C. 154(b) by 21 days.

(21) Appl. No.: 18/251,895

(22) PCT Filed: Nov. 8, 2021

(86) PCT No.: PCT/JP2021/040925
§ 371 (c)(1),
(2) Date: May 5, 2023

(87) PCT Pub. No.: WO2022/102555
PCT Pub. Date: May 19, 2022

(65) Prior Publication Data
US 2024/0011924 A1    Jan. 11, 2024

(30) Foreign Application Priority Data

Nov. 12, 2020 (JP) .................................. 2020-188862
Nov. 1, 2021 (JP) .................................. 2021-178680

(51) Int. Cl.
*G01N 22/04* (2006.01)
(52) U.S. Cl.
CPC .................................... *G01N 22/04* (2013.01)

(58) Field of Classification Search
CPC ...... G01N 22/04; G01N 33/245; G01N 33/246
See application file for complete search history.

(56) References Cited

U.S. PATENT DOCUMENTS

| 6,147,503 A | 11/2000 | Nelson et al. |
| 2004/0083833 A1* | 5/2004 | Hitt ...................... A01G 25/167 73/866.5 |

(Continued)

FOREIGN PATENT DOCUMENTS

| EP | 3605152 | 2/2020 |
| JP | H01-285843 | 11/1989 |

(Continued)

OTHER PUBLICATIONS

International Search Report and Written Opinion prepared by the Japan Patent Office on Dec. 15, 2021, for International Application No. PCT/JP2021/040925, 2 pgs.

*Primary Examiner* — Neel D Shah
*Assistant Examiner* — Adam S Clarke
(74) *Attorney, Agent, or Firm* — SHERIDAN ROSS P.C.

(57) ABSTRACT

A device for measuring the amount of moisture in a medium that includes a transmission antenna that sends a signal as an electromagnetic wave, a reception antenna that receives the electromagnetic wave sent from the transmission antenna and transmitted through a medium, a measurement section that measures the electromagnetic wave propagated to the reception antenna, and a sensor casing. The sensor device further includes a transmission substrate that includes a plurality of wiring layers and a reception substrate that includes a plurality of wiring layers, or a first covering layer that partially covers an outer periphery of the transmission substrate and a second covering layer that partially covers an outer periphery of the reception substrate The coverings are formed of an electromagnetic wave absorption material. The sensor casing includes a transmission probe casing that (Continued)

accommodates the transmission substrate and a reception probe casing that accommodates the reception substrate.

16 Claims, 368 Drawing Sheets

(56) References Cited

U.S. PATENT DOCUMENTS

| | | |
|---|---|---|
| 2018/0224382 A1 | 8/2018 | Golombek et al. |
| 2020/0182906 A1 | 6/2020 | Yamada et al. |

FOREIGN PATENT DOCUMENTS

| | | |
|---|---|---|
| JP | H02-045740 | 2/1990 |
| WO | WO 2018/221051 | 12/2018 |

\* cited by examiner

Fig. 5
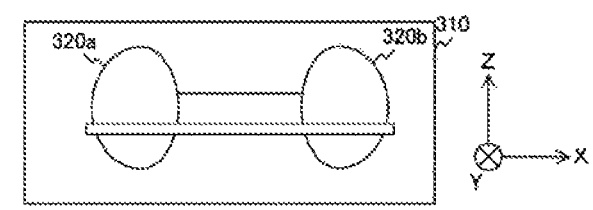
a
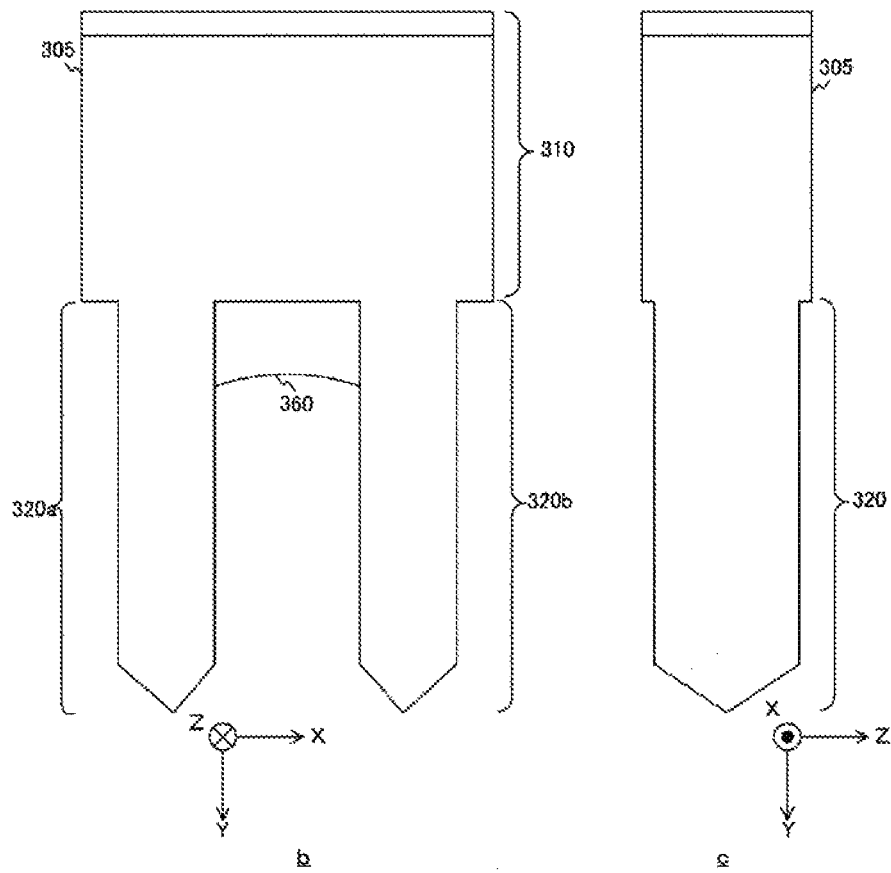
b                c

Fig. 14
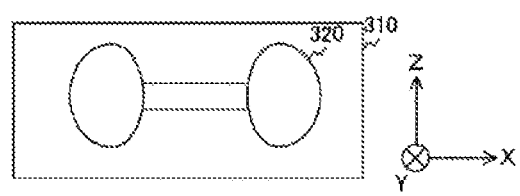
a
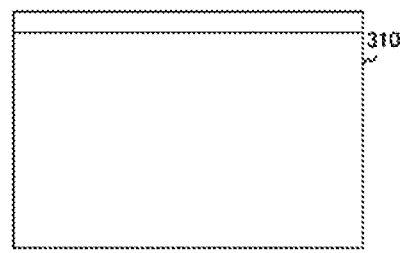 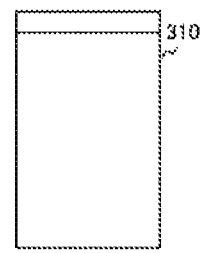
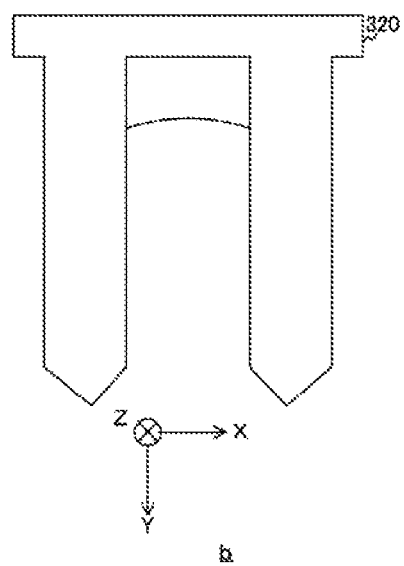 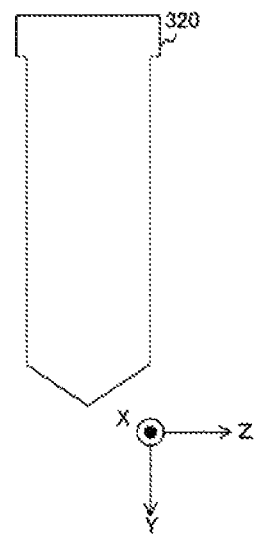
b c

Fig. 25
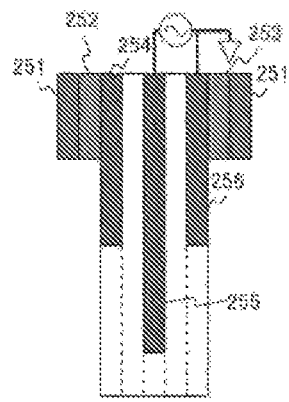
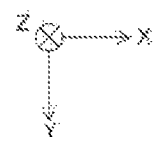

Fig. 31
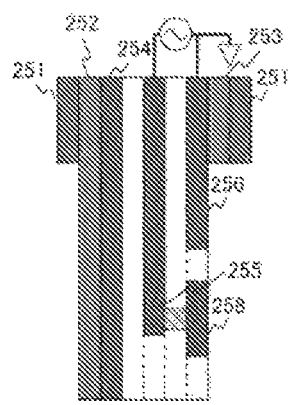

Fig. 37
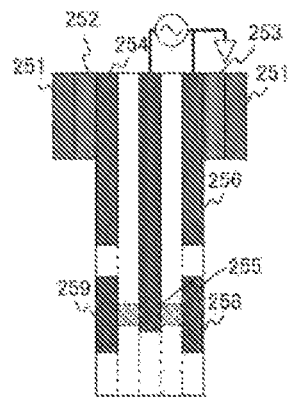
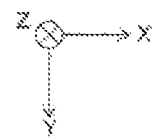

Fig. 44
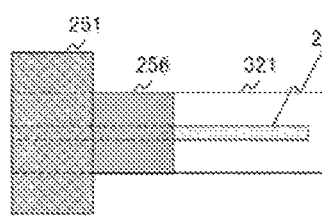
a
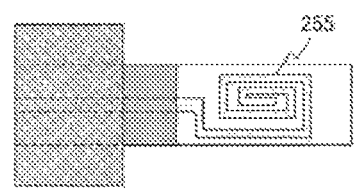
d
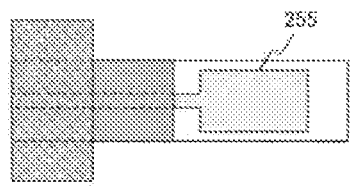
b
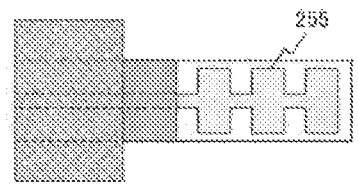
e
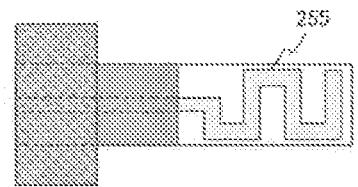
c
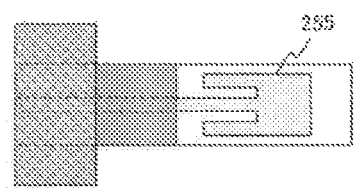
f Fig. 74
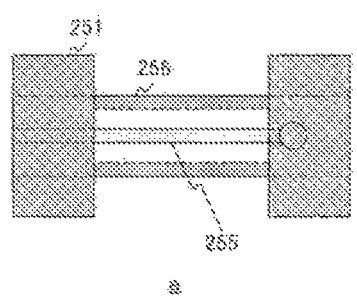
a
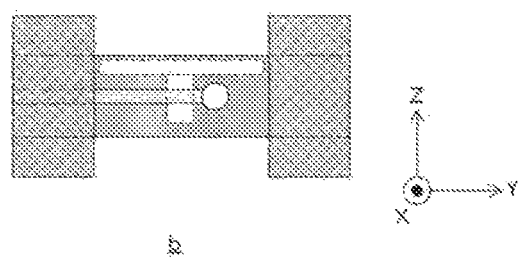
b Fig. 97
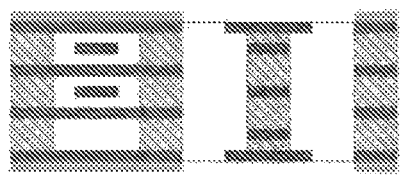

Fig. 120
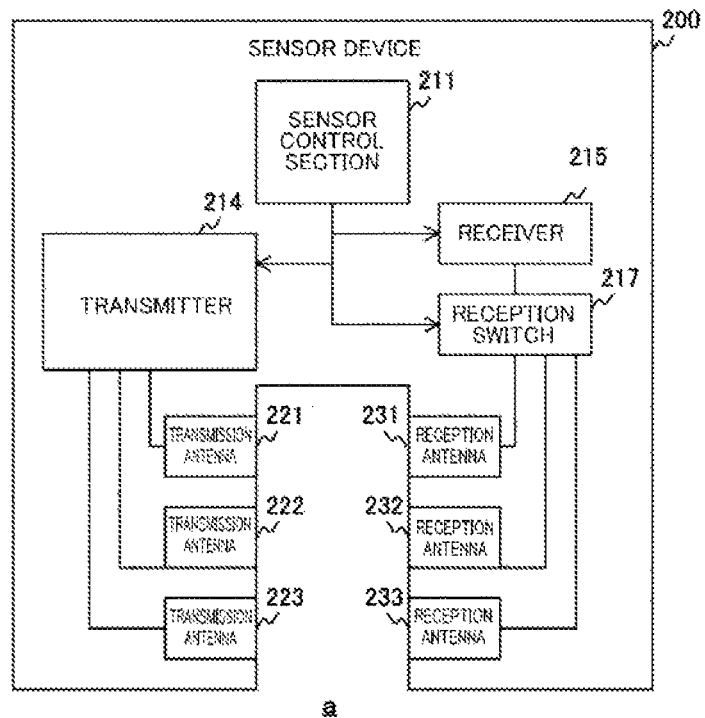
a
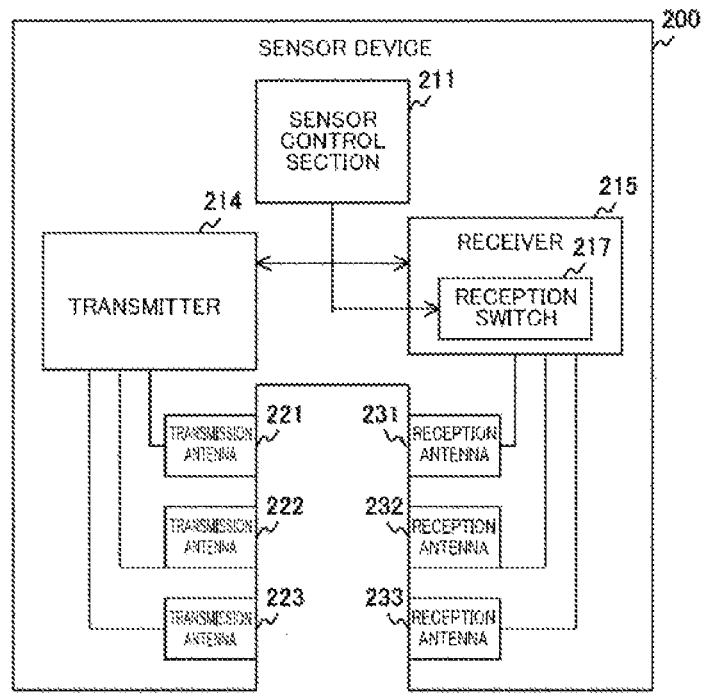
b

Fig. 156
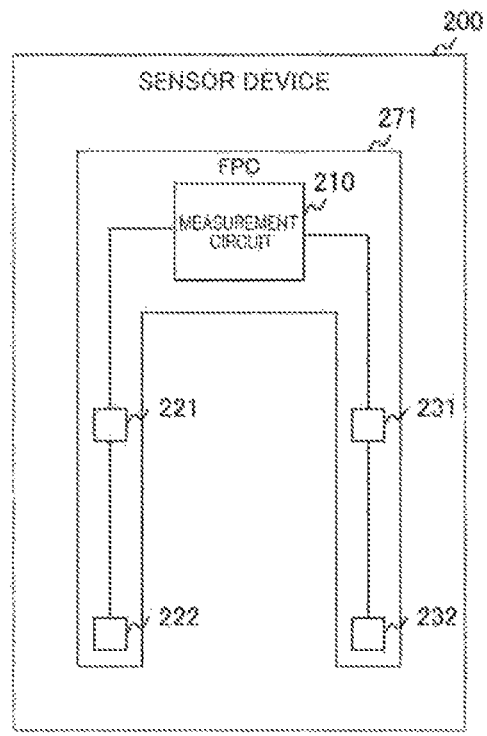
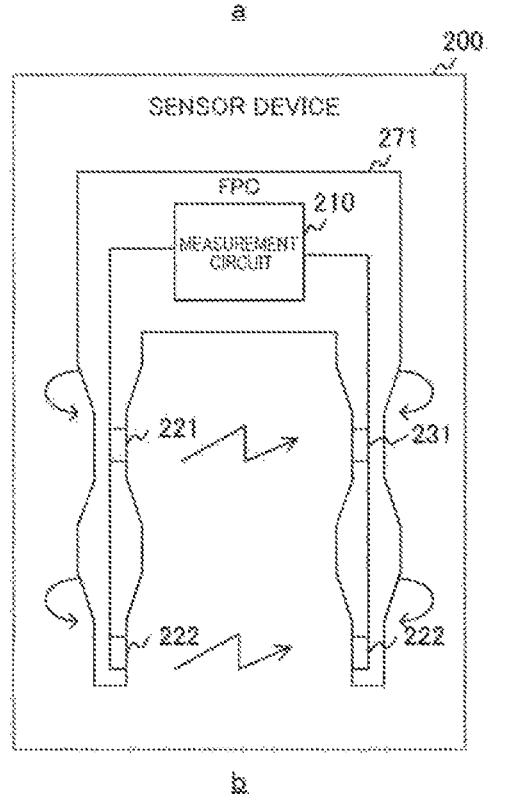

Fig. 157
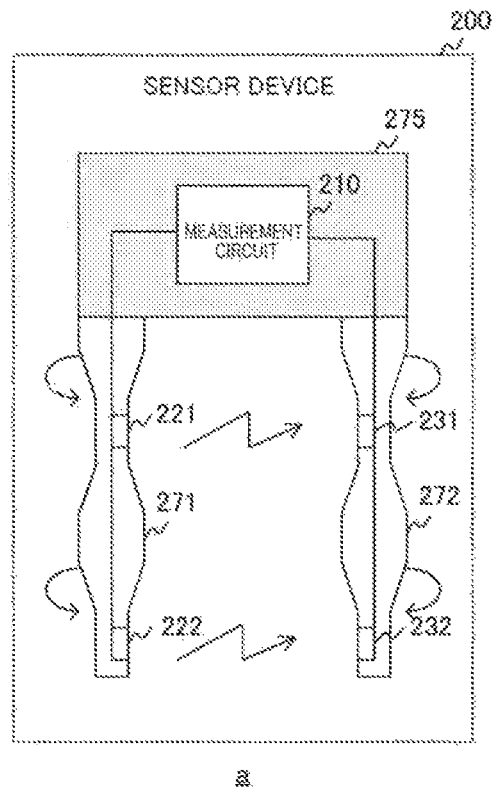
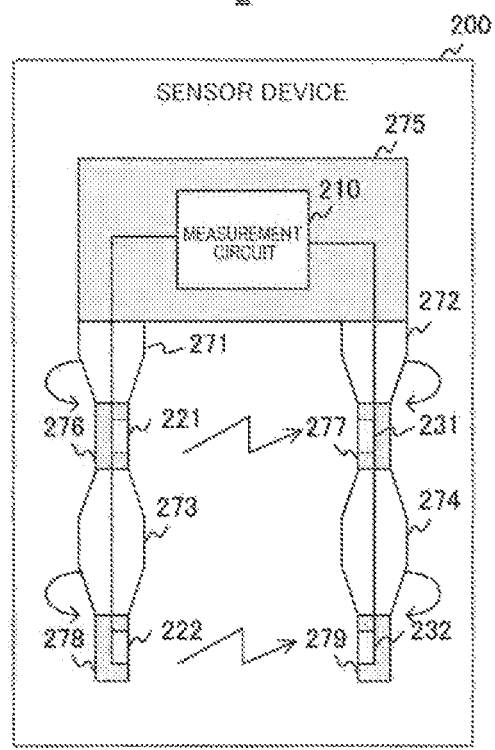
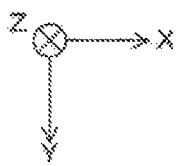

Fig. 159
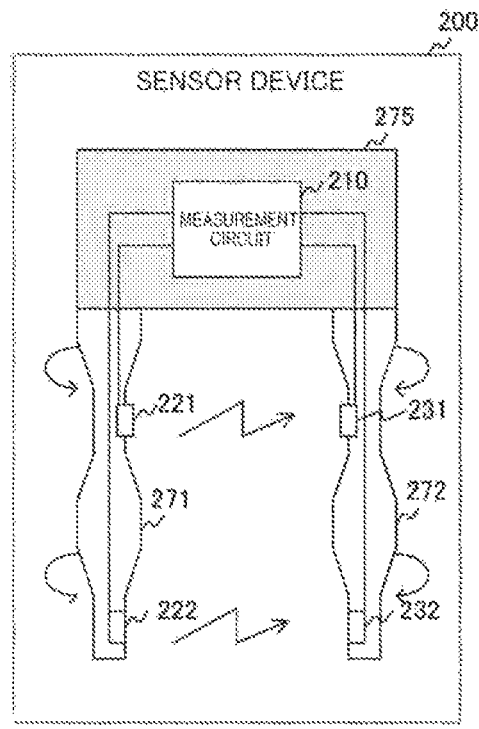
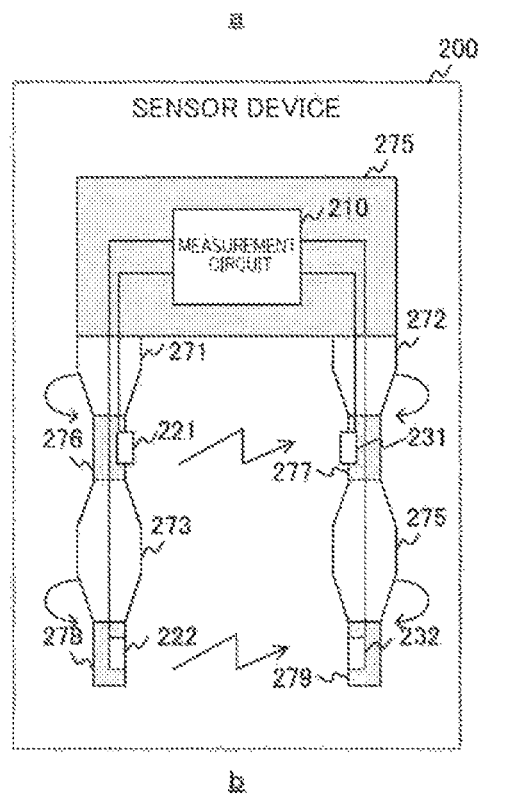

Fig. 160
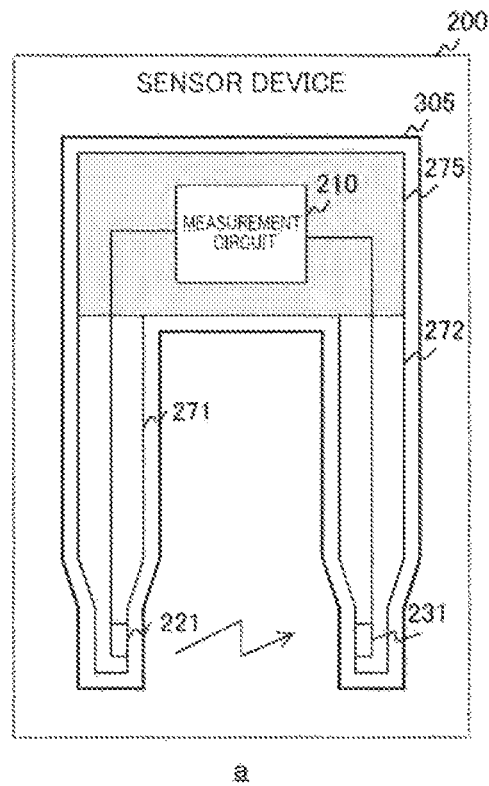
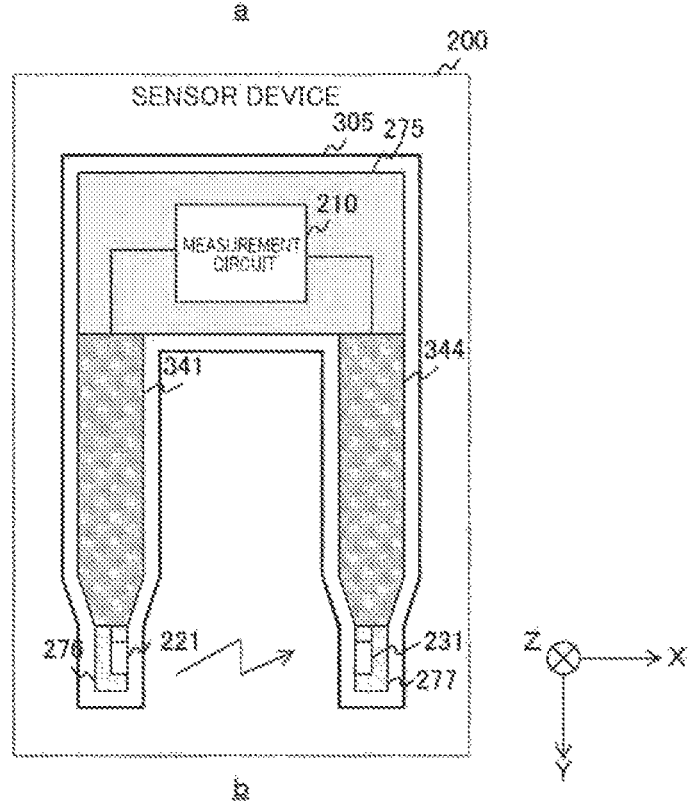

Fig. 161
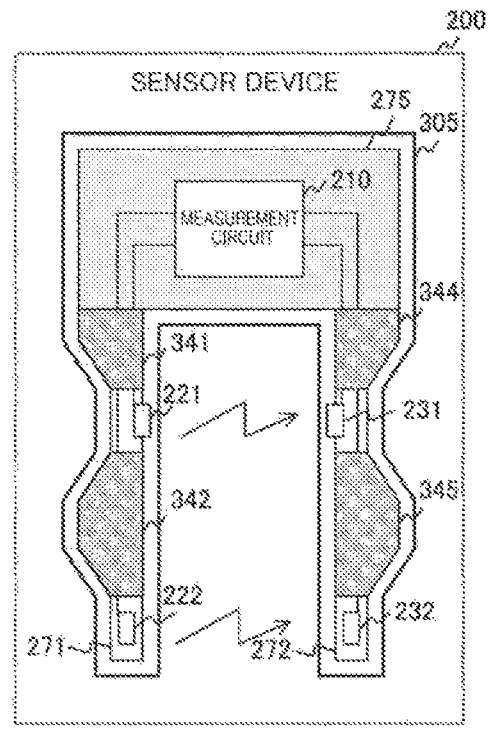
a
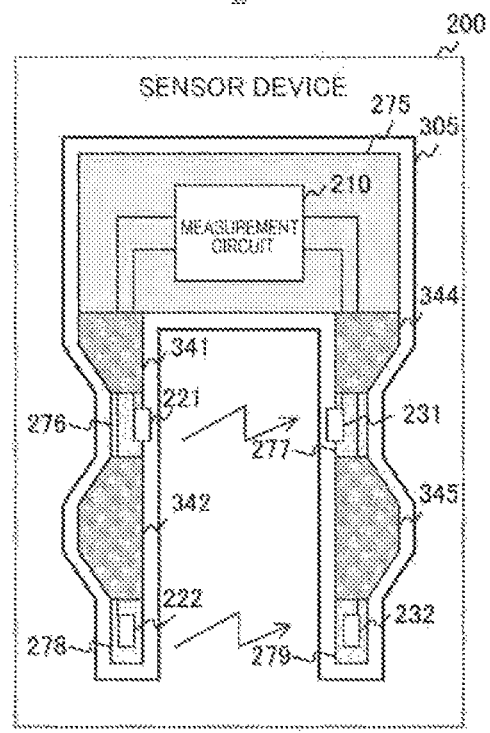
b

Fig. 162
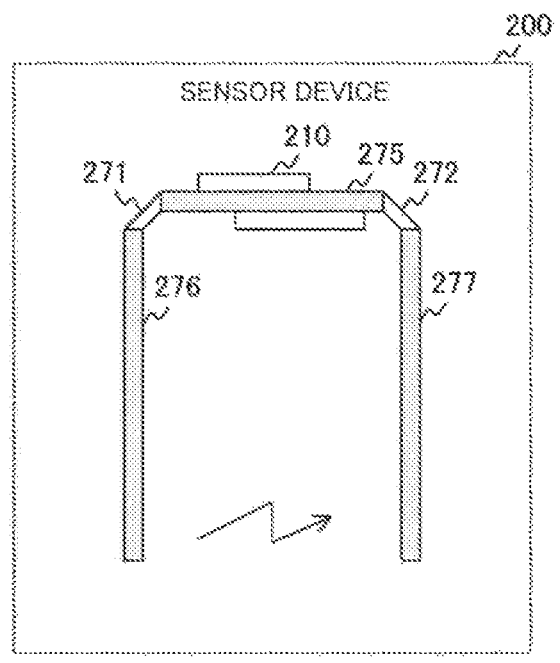
a
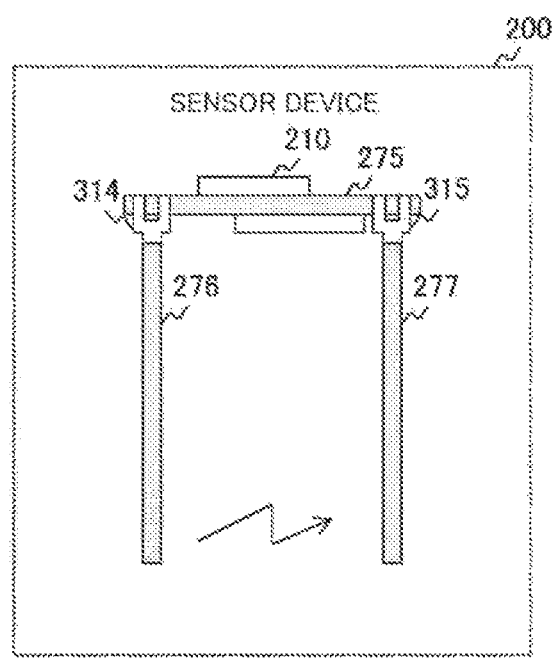
b
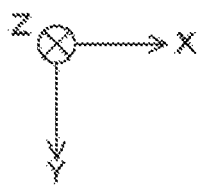

Fig. 164
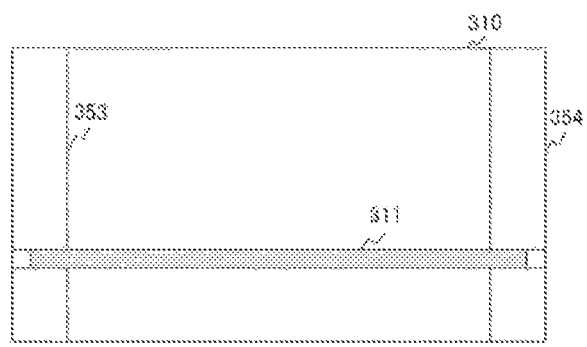
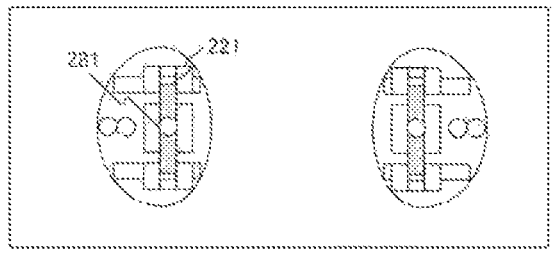

Fig. 175
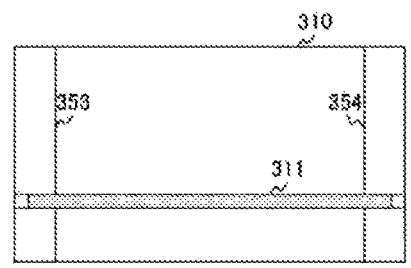
a
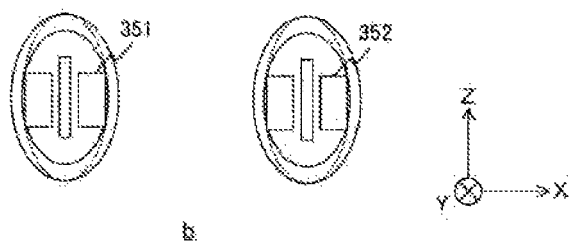
b

Fig. 180
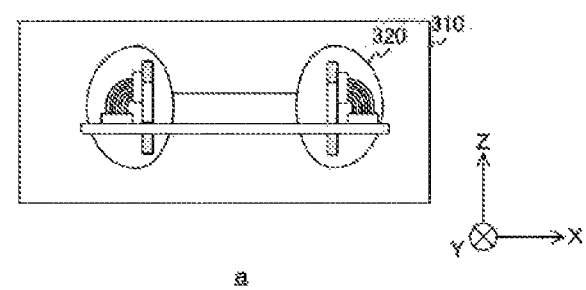
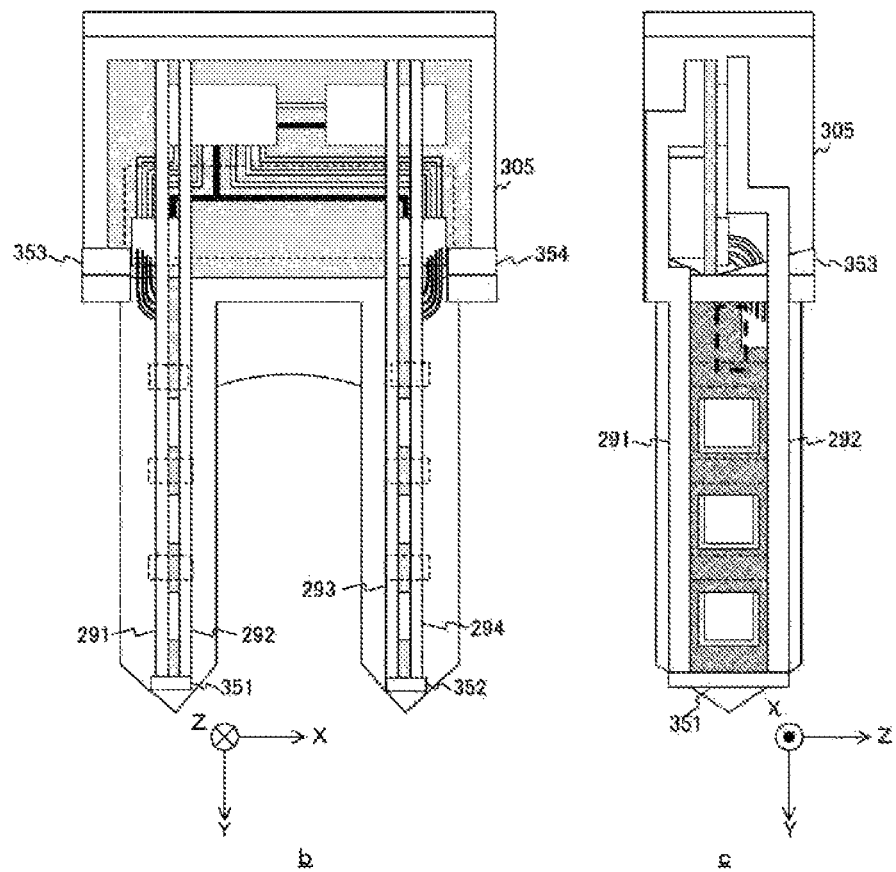

Fig. 184
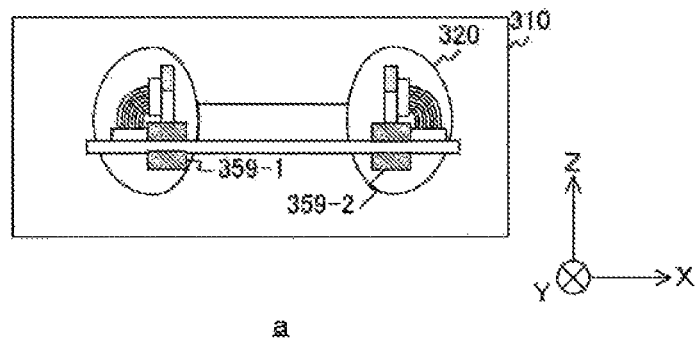
a
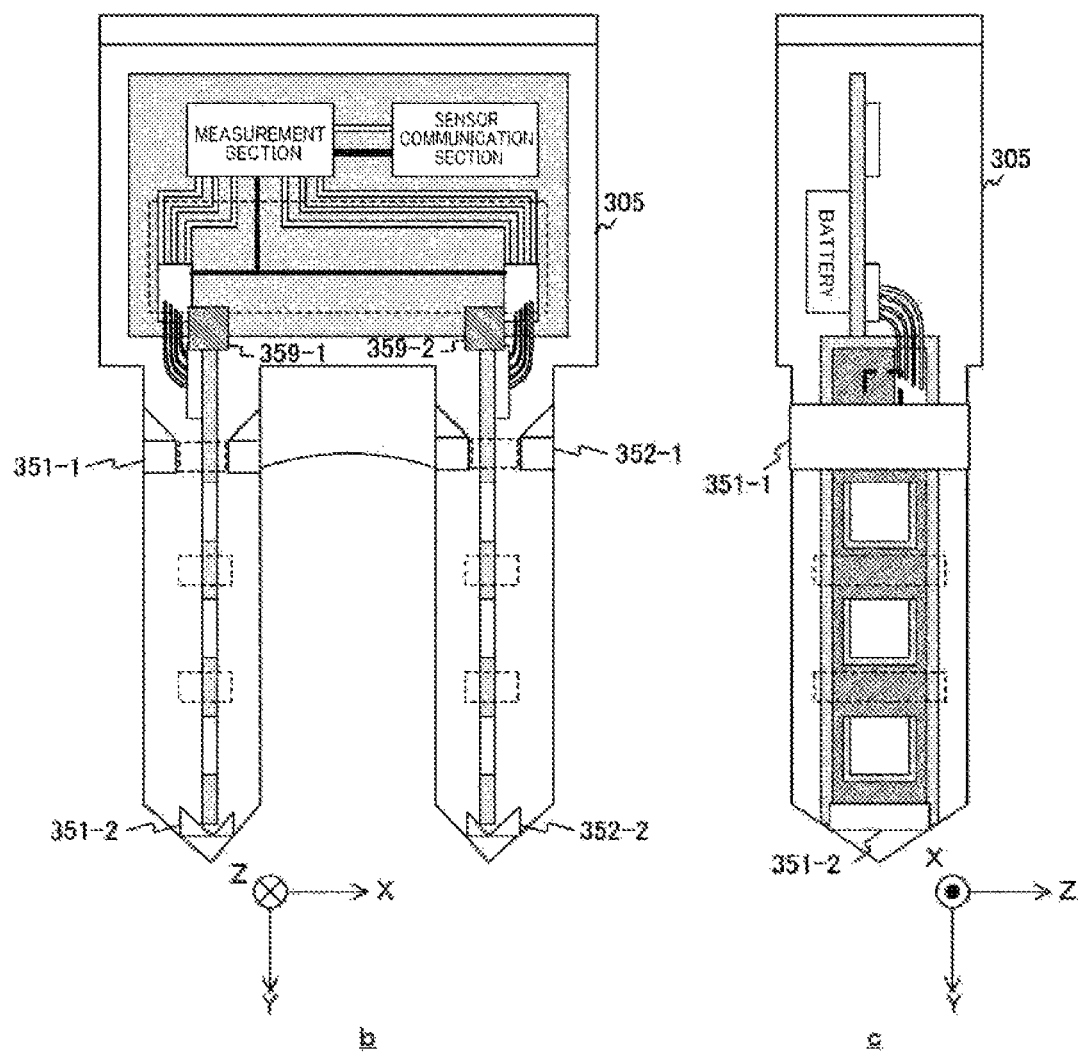
b            c

Fig. 185
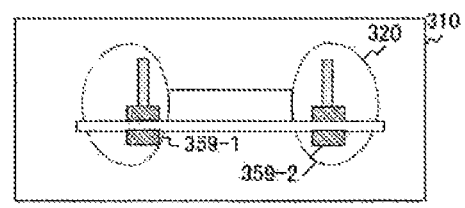
a
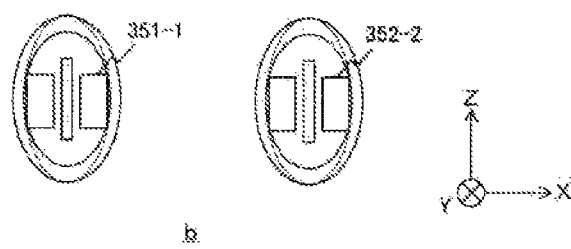
b

Fig. 189
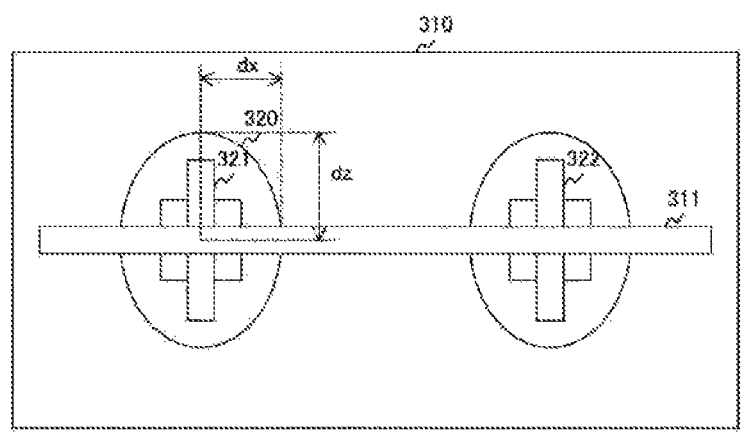
a
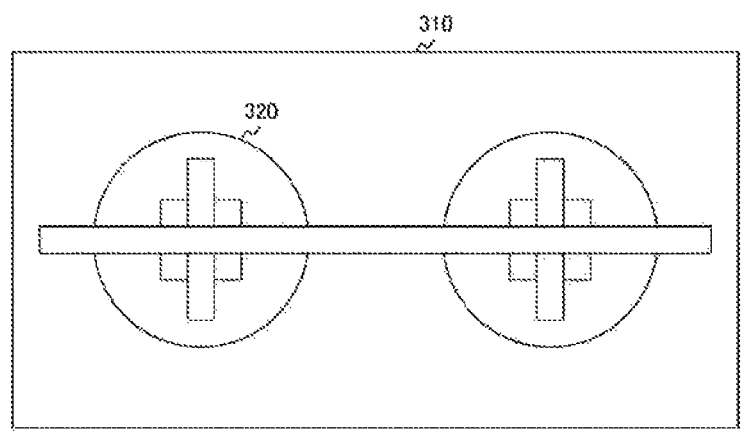
b

Fig. 207
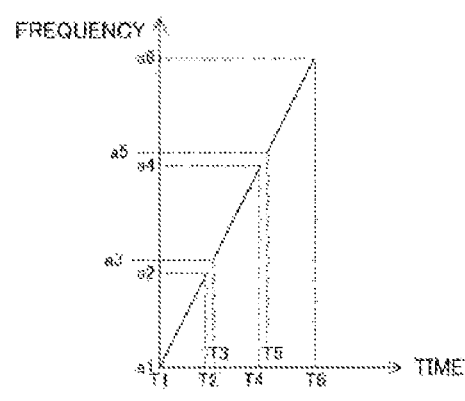
a
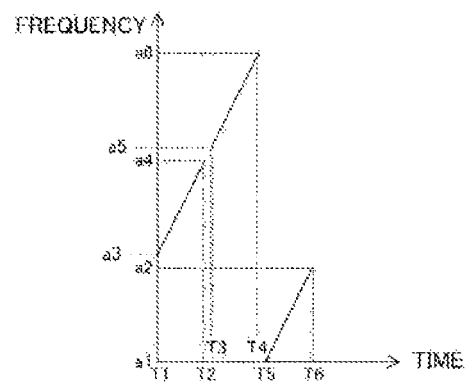
b
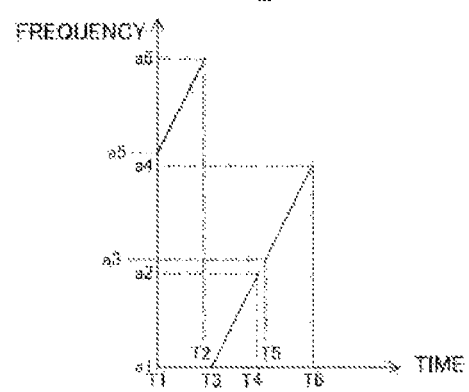
c

Fig. 209
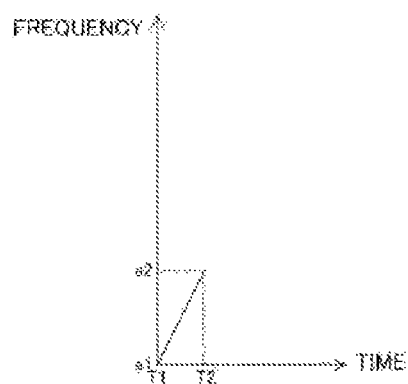
a
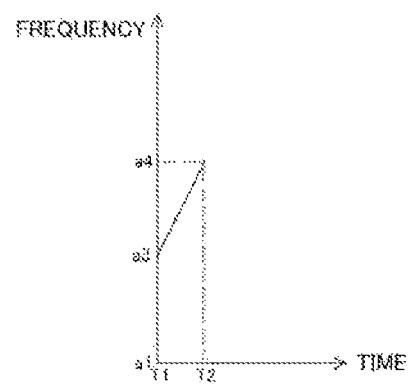
b
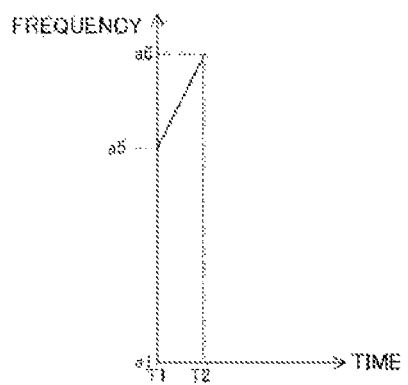
c

Fig 211
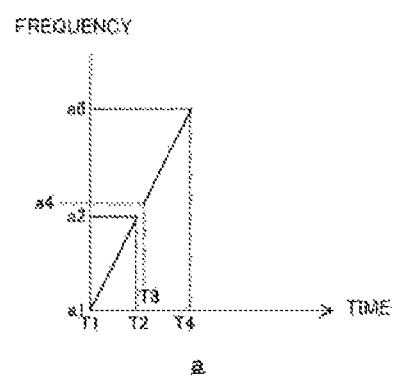
a
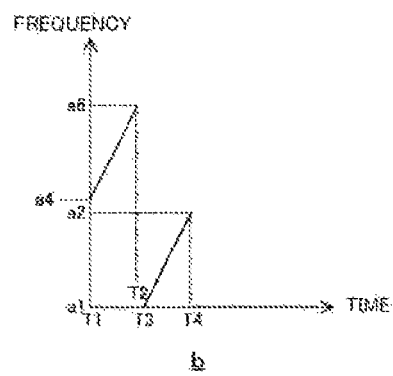
b

Fig. 233
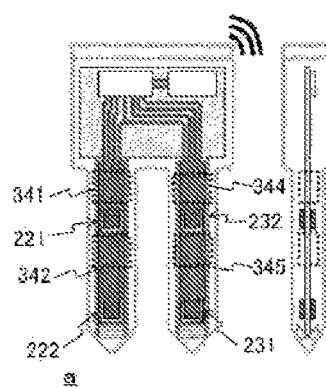
a
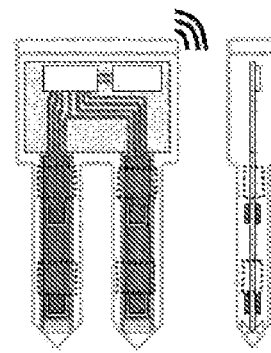
b

Fig. 255
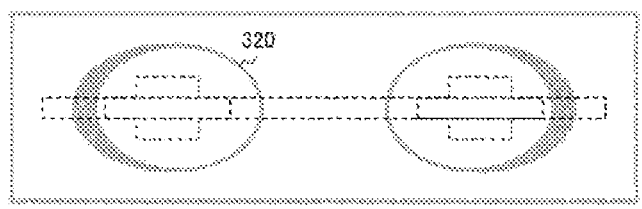
a
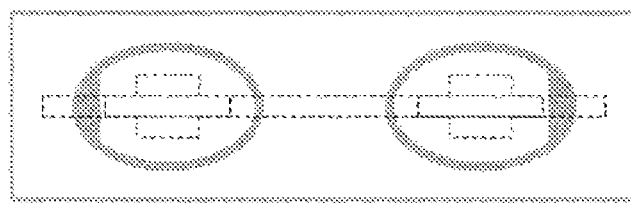
b
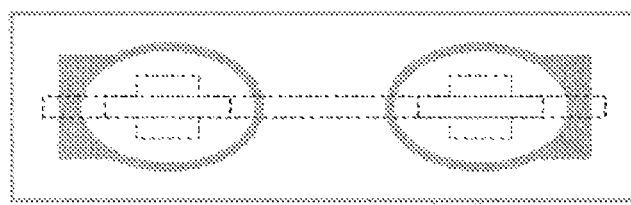
c
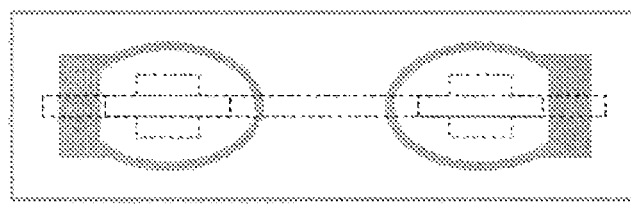
d

Fig. 256
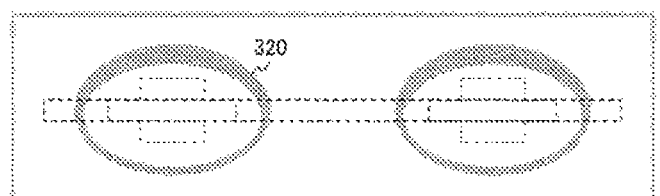
a
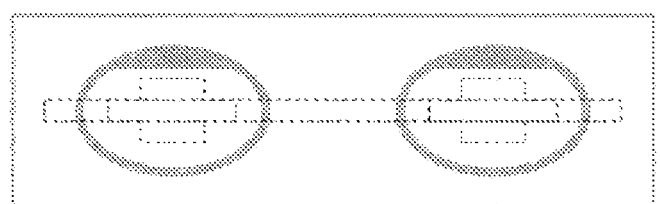
b
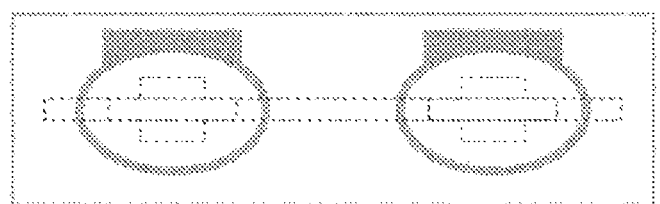
c
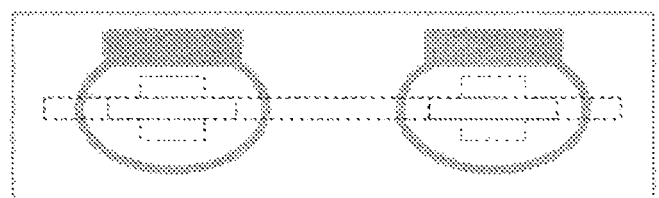
d

Fig. 259
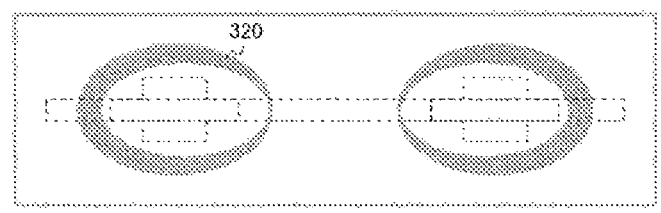
a
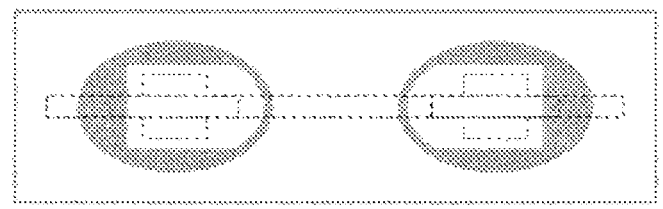
b
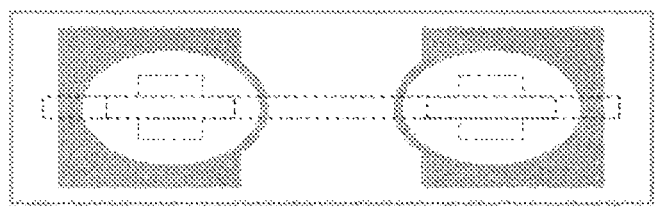
c
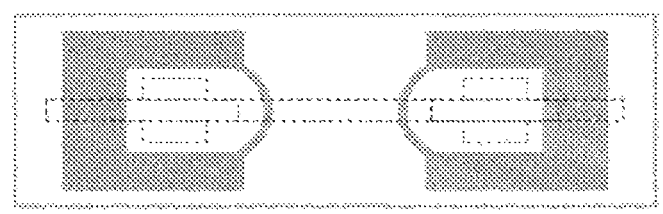
d

Fig. 260
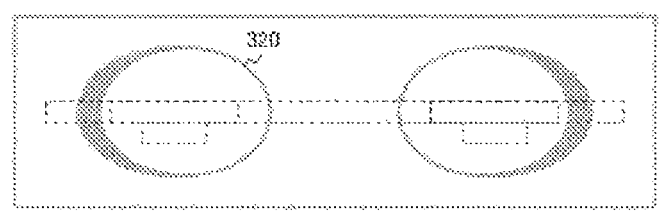
a
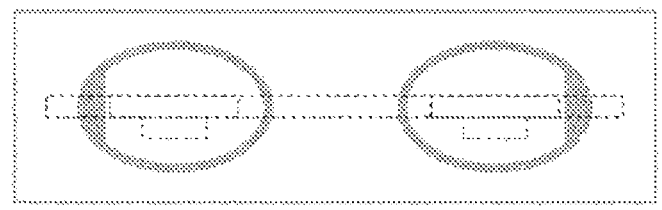
b
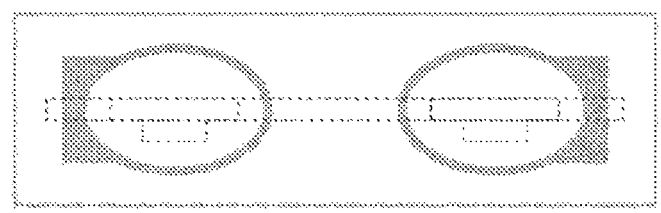
c
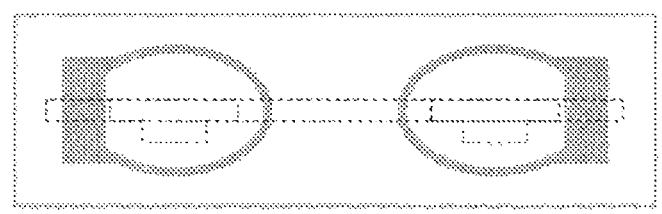
d

Fig. 261
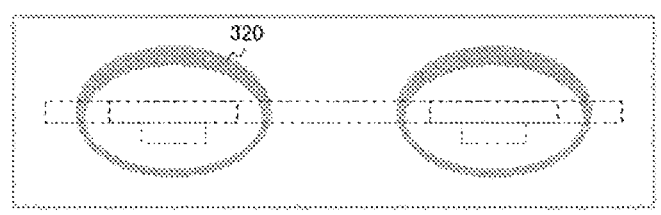
a
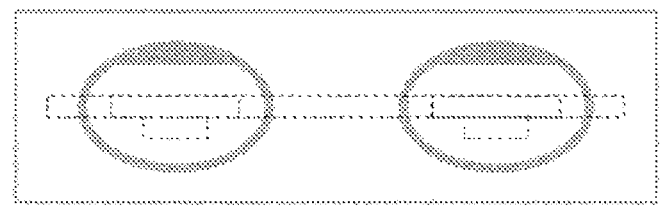
b
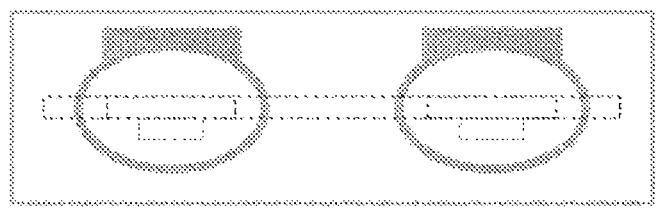
c
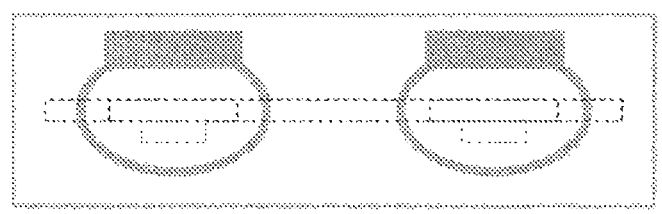
d

Fig. 262
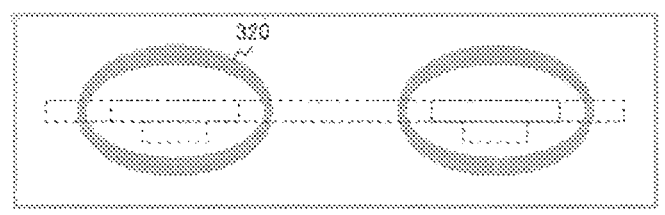
a
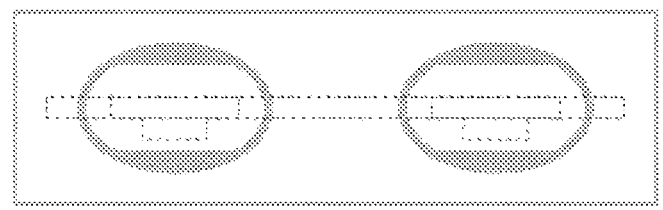
b
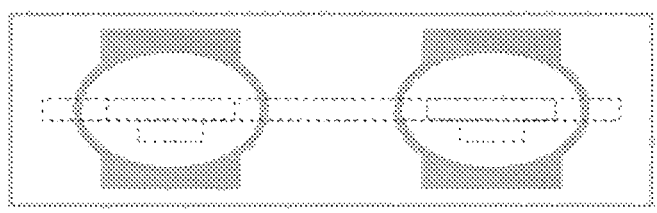
c
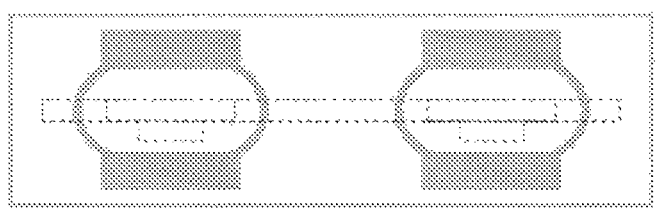
d

Fig. 263
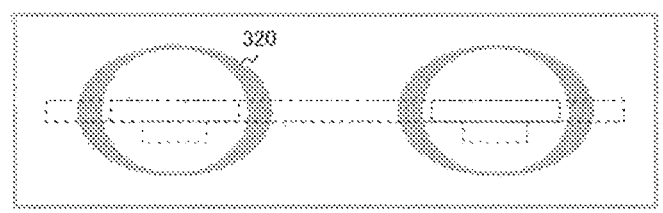
a
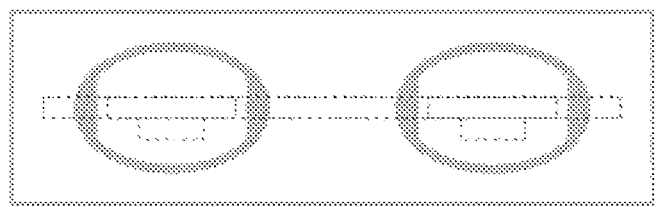
b
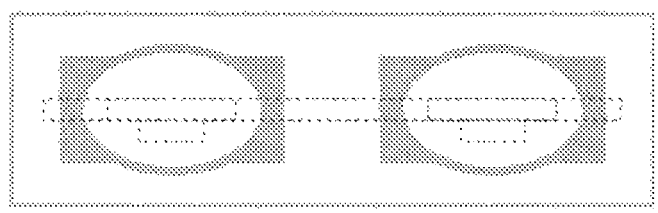
c
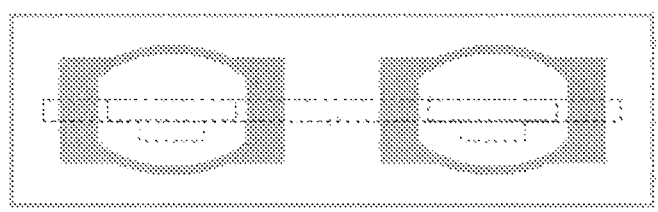
d

Fig. 264
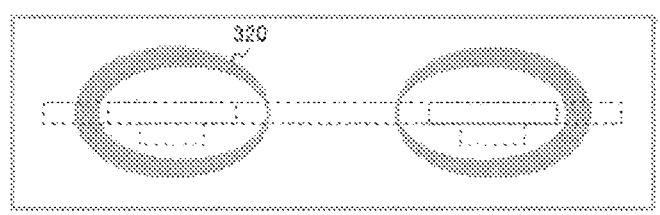
a
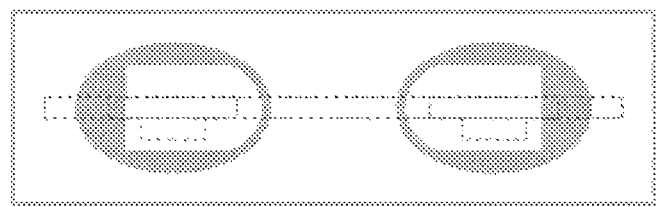
b
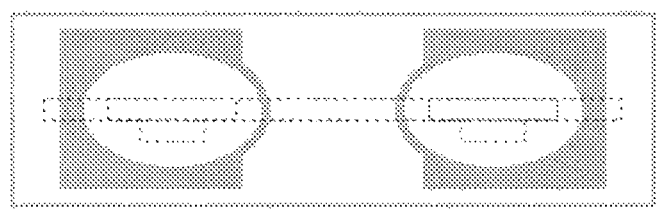
c
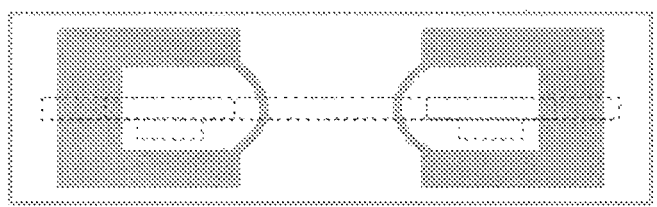
d

Fig. 268
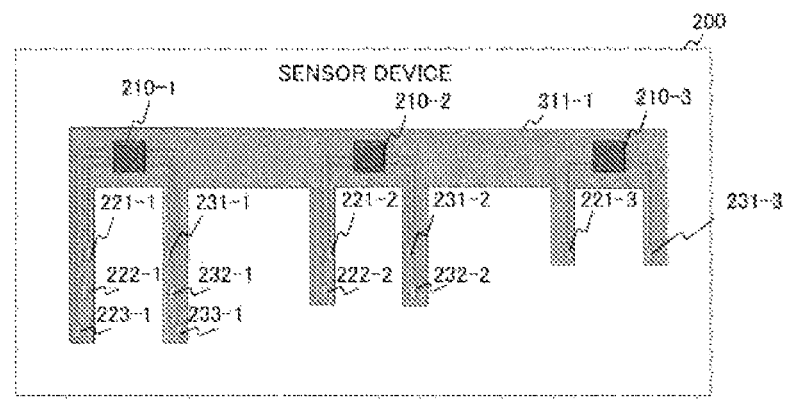
a
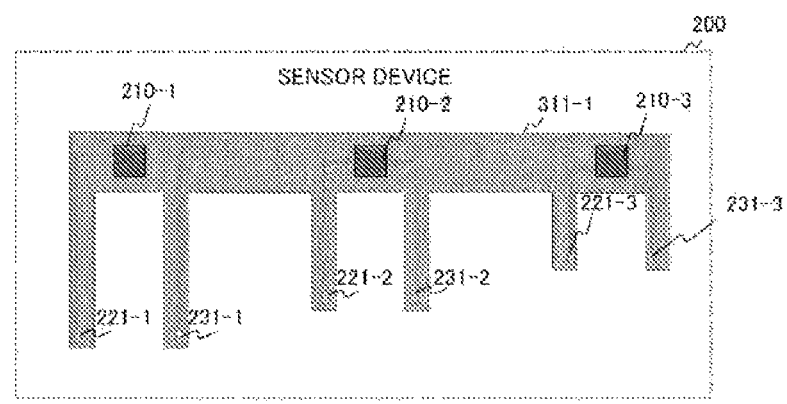
b

Fig. 277
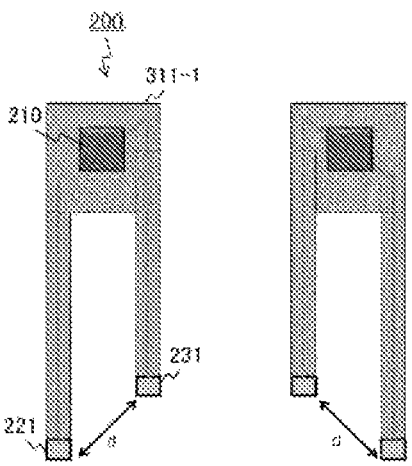
a     b
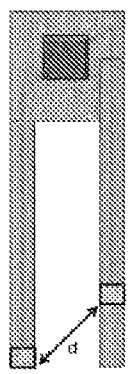
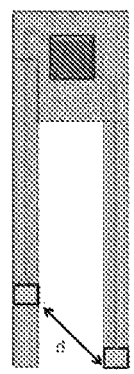
c     d
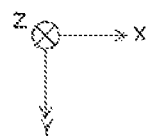

Fig. 286
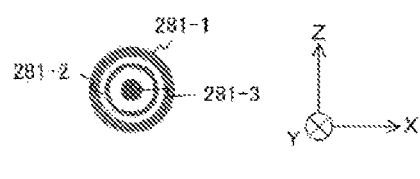
a
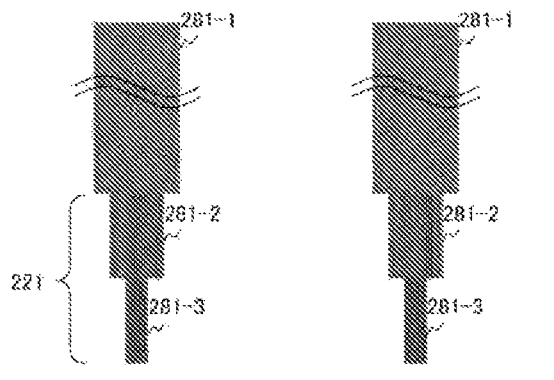
b          c

Fig. 294
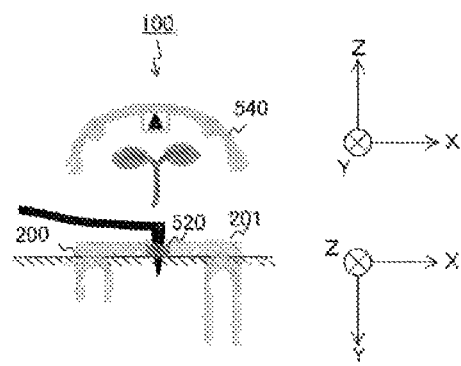
a
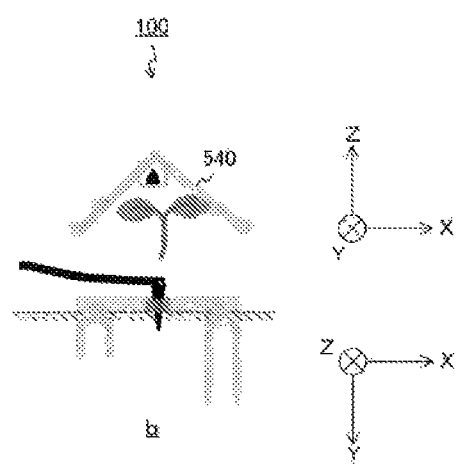
b

Fig. 298
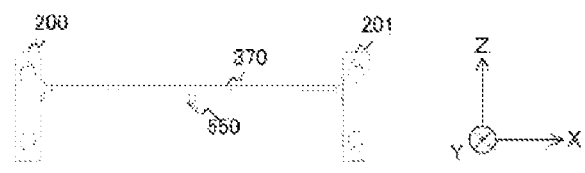
a
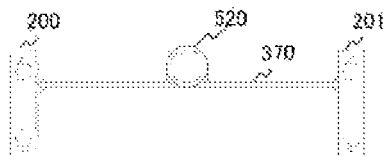
b

Fig. 325
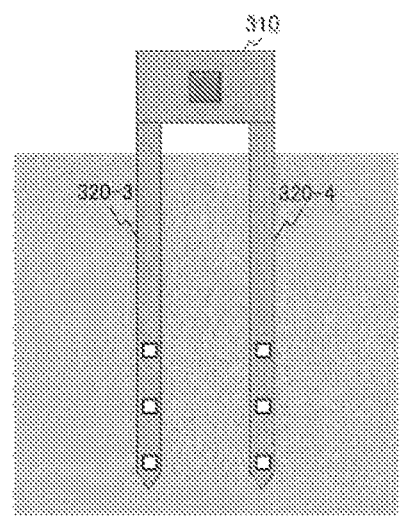
a
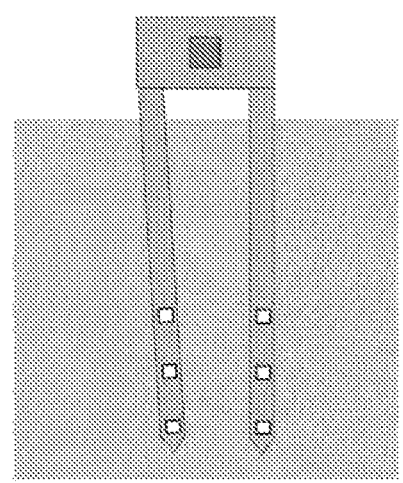
b

Fig. 326
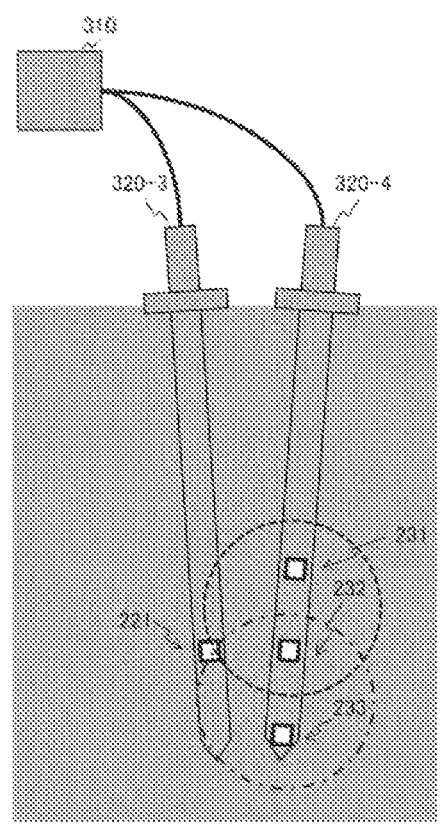
a
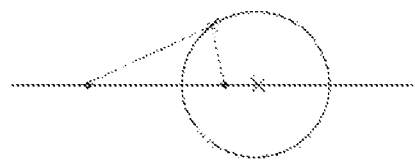
b

Fig. 341
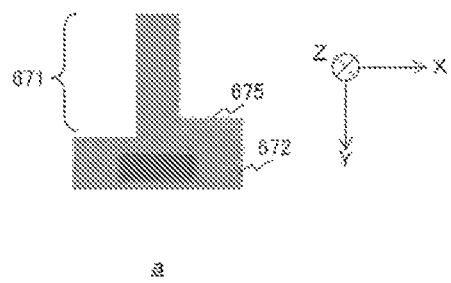
a
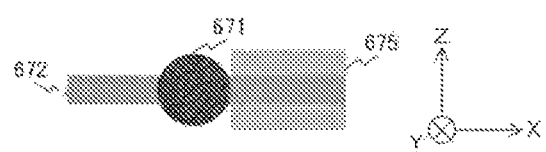
b

Fig. 342
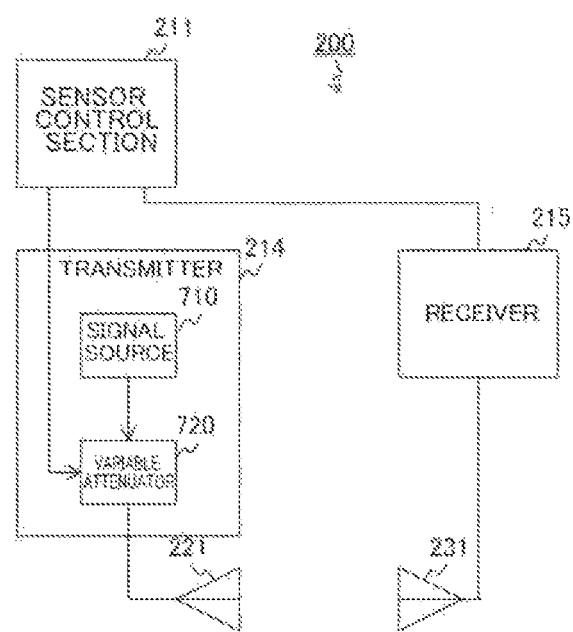
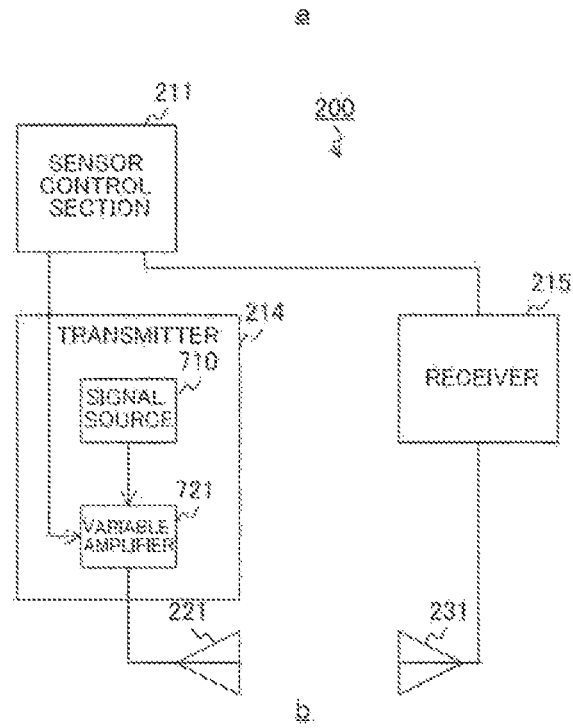

Fig. 347
a
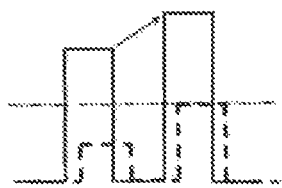
b a  b  c  d

SENSOR DEVICE

CROSS REFERENCE TO RELATED APPLICATIONS

This application is a national stage application under 35 U.S.C. 371 and claims the benefit of PCT Application No. PCT/JP2021/040925, having an international filing date of 8 Nov. 2021, which designated the United States, which PCT application claimed the benefit of Japanese Patent Application Nos. 2020-188862, filed 12 Nov. 2020, and 2021-178680, filed 1 Nov. 2021, the entire disclosures of each of which are incorporated herein by reference.

TECHNICAL FIELD

The present technology relates to a sensor device. Specifically, the present technology relates to a sensor device provided with a pair of probes.

BACKGROUND ART

In the related art, devices and equipment for measuring amounts of moisture in media such as soil have widely been used in the fields of agriculture, environmental research, and the like. For example, a sensor device for measuring the amount of moisture in a medium on the basis of results of transmitting and receiving electromagnetic waves propagating through the medium between a pair of probes has been proposed (see PTL 1, for example). Such a scheme using electromagnetic waves for measuring moisture is called a microwave scheme. On the other hand, a scheme of replacing electrical resistance or electrical capacitance values with amounts of moisture are called an electrical resistance scheme and an electrical capacitance scheme.

CITATION LIST

Patent Literature

[PTL 1]
Specification of US 2018/0224382 A1

SUMMARY

Technical Problem

For the aforementioned sensor device, the microwave scheme is used to increase the measurement speed as compared with the electrical resistance scheme and the electrical capacitance scheme. However, there is a concern that the performance of the device such as the accuracy of measuring the amounts of moisture may be degraded due to the influence of noise and the like occurring in the electromagnetic waves.

The present technology was made in view of such circumstances, and an object thereof is to improve performance of a device for measuring amounts of moisture in media.

Solution to Problem

The present technology was made in order to solve the aforementioned problem, and a first aspect thereof is a sensor device including: a transmission antenna that sends a signal as an electromagnetic wave; a reception antenna that receives the electromagnetic wave sent from the transmission antenna and transmitted through a medium; a measurement section that measures the electromagnetic wave propagated to the reception antenna; and a sensor casing, the sensor device further including a transmission substrate that is an electronic substrate including a plurality of wiring layers and a reception substrate that is an electronic substrate including a plurality of wiring layers, or a first covering layer that partially covers an outer periphery of the transmission substrate and is formed of an electromagnetic wave absorption material and a second covering layer that partially covers an outer periphery of the reception substrate and is formed of an electromagnetic wave absorption material, in which the sensor casing includes a transmission probe casing that is a part of the sensor casing and accommodates the transmission substrate and a reception probe casing that is another part of the sensor casing and accommodates the reception substrate, the transmission substrate includes a transmission path for transmission and a transmission exposure section that configures a part of the transmission antenna, the transmission path for transmission is formed using the wiring layers included in the transmission substrate, includes a first shield layer and a first signal line in a superimposed manner, and is electrically connected to the measurement section, the transmission exposure section is a conductor that is formed using the wiring layers included in the transmission substrate, is electrically connected to the first signal line, and is exposed from the first shield layer or the first covering layer, the reception substrate includes a transmission path for reception and a reception exposure section that configures a part of the reception antenna, the transmission path for reception is formed using the wiring layers included in the reception substrate, includes a second shield layer and a second signal line in a superimposed manner, and is electrically connected to the measurement section, the reception exposure section is a conductor that is formed using the wiring layers included in the reception substrate, is electrically connected to the second signal line, and is exposed from the second shield layer or the second covering layer, each of the transmission exposure section and the reception exposure section has a larger size both in a second direction and in a third direction than in a first direction and extends parallel with a plane defined by the second direction and the third direction, the first direction being a direction of the superimposition, the second direction being a direction that is orthogonal to the first direction and is parallel with an extending direction of the transmission path, the third direction orthogonal to the first and second directions, and the transmission path for transmission and the transmission exposure section formed using the wiring layers included in the transmission substrate and the transmission path for reception and the reception exposure section formed using the wiring layers included in the reception substrate are disposed to face each other such that an extending direction of the plane of the transmission exposure section and an extending direction of the plane of the reception exposure section are parallel with each other, and are disposed at positions separated from each other by a predetermined distance, with the extending directions and the positions fixed in the sensor casing. This provides an effect that accuracy of measuring the amount of moisture is improved.

Also, in the first aspect, the transmission exposure section may be a transmission element included in the transmission antenna, and the reception exposure section may be a reception element included in the reception antenna. This provides an effect that signals are transmitted and received between the antennas.

Also, in the first aspect, in the transmission probe casing, a distance from a center of the transmission substrate to a casing end of the transmission probe casing in a direction vertical to the plane of the transmission substrate may be shorter than a distance from the center of the transmission substrate to a casing end of the transmission probe casing in a direction parallel to the plane of the transmission substrate, and in the reception probe casing, a distance from a center of the reception substrate to a casing end of the reception probe casing in a direction vertical to the plane of the reception substrate may be shorter than a distance from the center of the reception substrate to a casing end of the reception probe casing in a direction parallel to the plane of the reception substrate. This provides an effect that accuracy of measuring the amount of moisture is further improved.

Also, in the first aspect, the sensor device may further include: a positioning section that fixes the extending directions and the positions of the transmission substrate and the reception substrate. This provides an effect that the positions of the electronic substrates can be fixed.

Also, in the first aspect, the positioning section may be fixed to the sensor casing and may be integrated with the sensor casing. This provides an effect that the positions of the electronic substrates can be fixed.

Also, in the first aspect, the sensor casing itself may have a structure including the positioning section. This provides an effect that the positions of the electronic substrates can be fixed.

Also, in the first aspect, the extending directions and the positions of the transmission substrate and the reception substrate may be fixed by each of the transmission substrate and the reception substrate being caused to abut the casing at least at two or more points. This provides an effect that the positions of the electronic substrates can be fixed.

Also, in the first aspect, the sensor device may include a structure obtained by curing a resin in the surroundings of each of the transmission substrate and the reception substrate, the strength of the structure obtained by curing the resin in the surroundings of the transmission substrate may be equal to or greater than double the strength of the transmission substrate, and the strength of the structure obtained by curing the resin in the surroundings of the reception substrate may be equal to or greater than double the strength of the reception substrate. This provides an effect that the positions of the electronic substrates can be fixed.

Also, in the first aspect, the transmission probe casing may be formed using an electromagnetic wave transmissive material such that the strength of the casing is higher than the strength of the transmission base plate, and the reception probe casing may be formed using an electromagnetic wave transmissive material such that the strength of the casing is higher than the strength of the reception substrate. This provides an effect that deformation of the substrates is prevented.

Also, in the first aspect, the component thickness of a part of the transmission probe casing may be thicker than the component thickness of the other parts in a section that is orthogonal to the extending direction of the casing, and the component thickness of a part of the reception probe casing may be thicker than the component thickness of the other parts in a section that is orthogonal to the extending direction of the casing. This provides an effect that the component thickness is set to an appropriate value.

Also, in the first aspect, the component thickness of the transmission probe casing end portion located in a direction parallel to the transmission substrate from the center of the substrate may be thicker than the component thickness of the transmission probe casing located in a direction orthogonal to the transmission substrate from the center of the substrate in a section that is orthogonal to the extending direction of the transmission probe casing, and the component thickness of the reception probe casing end portion located in a direction parallel to the reception substrate from the center of the substrate may be thicker than the component thickness of the reception probe casing located in a direction orthogonal to the reception substrate from the center of the substrate in a section that is orthogonal to the extending direction of the reception probe casing. This provides an effect that the component thickness is set to an appropriate value.

Also, in the first aspect, in regard to the component thicknesses at end portions of the transmission probe casing located in a direction orthogonal to the transmission substrate from the center of the substrate, the component thickness at the end portion located on a side further from the reception substrate may be thicker than the component thickness at the end portion located on a side closer to the reception substrate in a section that is orthogonal to the extending direction of the transmission probe casing, and in regard to the component thicknesses at end portions of the reception probe casing located in a direction orthogonal to the reception substrate from the center of the substrate, the component thickness at the end portion located on a side further from the transmission substrate may be thicker than the component thickness at the end portion located on a side closer to the transmission substrate in a section that is orthogonal to the extending direction of the reception probe casing. This provides an effect that the component thickness is set to an appropriate value.

Also, in the first aspect, the transmission substrate may include a plurality of vias that are connected to the first shield layer and a shield structure that is configured of an array of the plurality of vias on a side of the first signal line, and the reception substrate may include a plurality of vias that are connected to the second shield layer and a shield structure that is configured of an array of the plurality of vias on a side of the second signal line. This provides an effect that noise is reduced.

Also, in the first aspect, the transmission substrate may include a plurality of the transmission antennas, and the reception substrate may include a plurality of the reception antennas.

Also, in the first aspect, the transmission path for transmission connected to the plurality of transmission antennas may be provided independently for each of the plurality of antennas in the transmission substrate, and the transmission path for reception connected to the plurality of reception antennas may be provided independently for each of the plurality of antennas in the reception substrate. This provides an effect that noise is reduced.

Also, in the first aspect, the measurement circuit may perform control of selecting the transmission antennas one by one in accordance with a predefined order from among the plurality of transmission antennas and causing the selected transmission antenna to transmit the electromagnetic wave. This provides an effect that the amounts of moisture in a plurality of depths are measured in order.

BRIEF DESCRIPTION OF DRAWINGS

FIG. 5 is an example of an overall view of a sensor casing according to the first embodiment of the present technology.

FIG. 14 is an example of an overall view of the sensor casing with the casing separated therefrom according to the first embodiment of the present technology.

FIG. 25 is an example of a sectional view of a probe with a second structure when seen from the front according to the first embodiment of the present technology.

FIG. 31 is an example of a sectional view of a probe with a third structure when seen from the front according to the first embodiment of the present technology.

FIG. 37 is an example of a sectional view of a probe with a fourth structure when seen from the front according to the first embodiment of the present technology.

FIG. 44 is a diagram illustrating another example of the shape of the transmission antenna applied to the first structure according to the first embodiment of the present technology.

FIG. 73 is a diagram illustrating an example of the shape of a transmission antenna applied to the seventh structure including the slot formed therein according to the first embodiment of the present technology.

FIG. 74 is a diagram illustrating an example of the shape of a transmission antenna applied to the eighth structure including the slot formed therein according to the first embodiment of the present technology.

FIG. 97 is an example of a sectional view of the intra-probe substrate with the nine-layer structure according to the first embodiment of the present technology.

FIG. 120 is a block diagram illustrating a configuration example of a sensor device 2 provided with a switch only on a reception side according to the first embodiment of the present technology.

FIG. 121 is an example of a timing chart of the time-division driving according to the first embodiment of the present technology.

FIG. 122 is an example of a timing chart illustrating operations of each section in the sensor device according to the first embodiment of the present technology.

FIG. 123 is an example of a timing chart of the time-division driving when a signal processing timing is changed according to the first embodiment of the present technology.

FIG. 124 is an example of a timing chart illustrating operations of each section in the sensor device when a signal processing timing is changed according to the first embodiment of the present technology.

FIG. 125 is an example of a timing chart of the time-division driving when signal processing and data transmission timings are changed according to the first embodiment of the present technology.

FIG. 126 is an example of a timing chart illustrating operations of each section in the sensor device when signal processing and data transmission timings are changed according to the first embodiment of the present technology.

FIG. 127 is an example of a timing chart of the time-division driving when an order of transmission and reception wave detecting operations is changed according to the first embodiment of the present technology.

FIG. 128 is an example of a timing chart illustrating operations of each section in the sensor device when the order of the transmission and reception wave detecting operations is changed according to the first embodiment of the present technology.

FIG. 129 is a diagram illustrating an example of transmission signals of each antenna in control examples a, b, and c according to the first embodiment of the present technology.

FIG. 130 is a diagram illustrating an example of a transmission signal of each antenna in a control example d according to the first embodiment of the present technology.

FIG. 131 is a diagram illustrating an example of the sensor device including the measurement section casing with a reduced thickness according to the first embodiment of the present technology.

Figure 132:
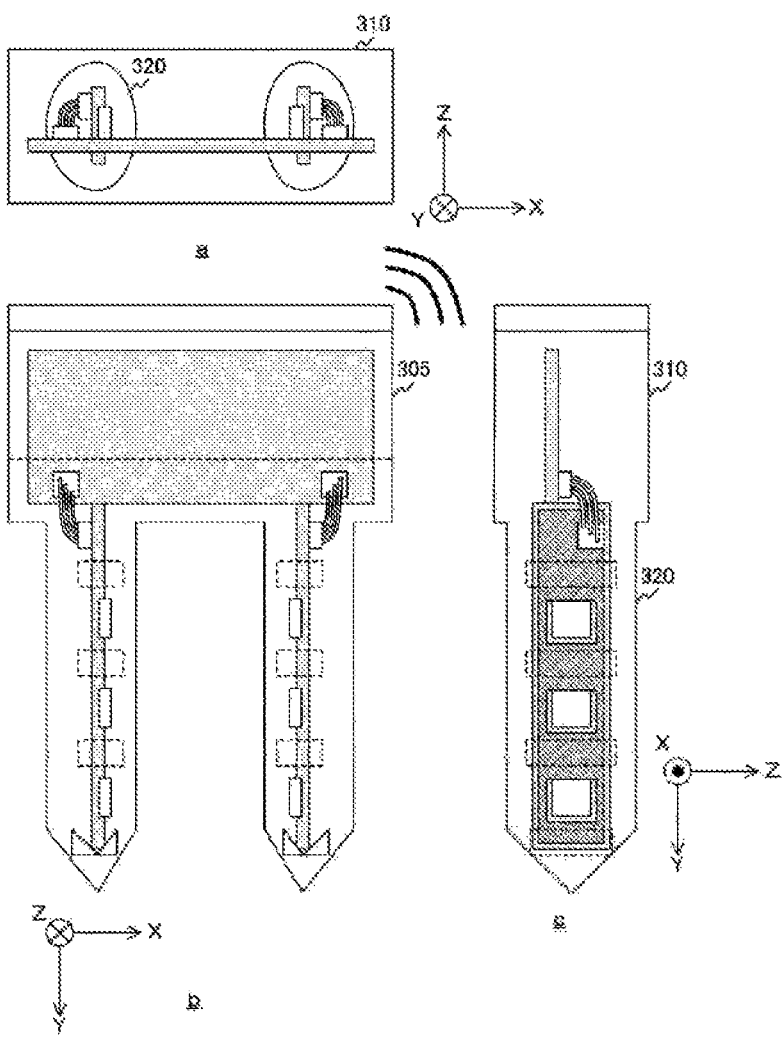

FIG. 132 is a diagram illustrating an example of the sensor device including the measurement section casing with an increased thickness according to the first embodiment of the present technology.

Figure 133:
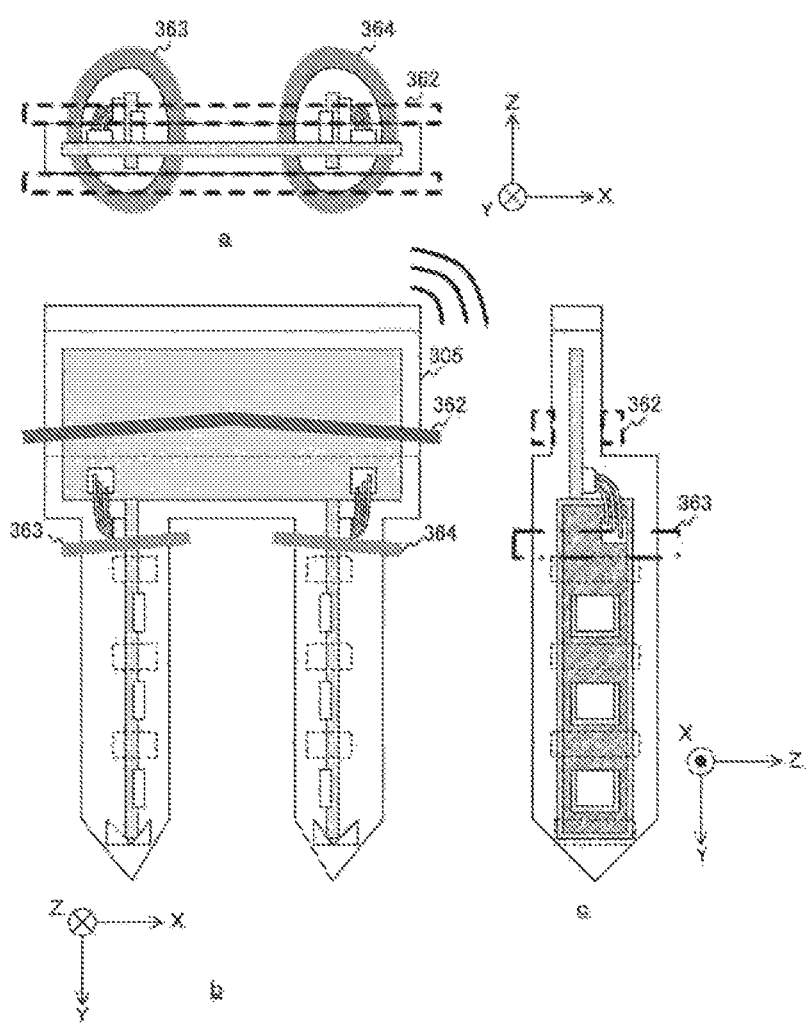

FIG. 133 is a diagram illustrating an example of the sensor device including the measurement section casing with a reduced thickness and including gutters added thereto according to the first embodiment of the present technology.

Figure 134:
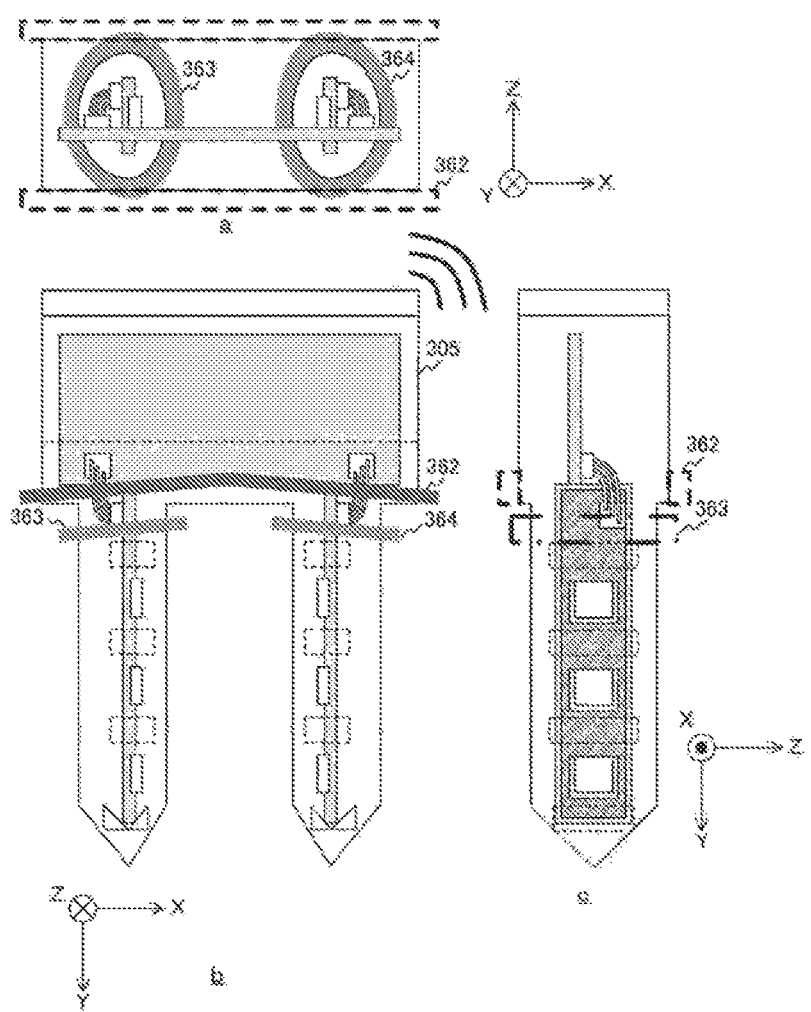

FIG. 134 is a diagram illustrating an example of the sensor device including the measurement section casing with an increased thickness and including gutters added thereto according to the first embodiment of the present technology.

Figure 135:
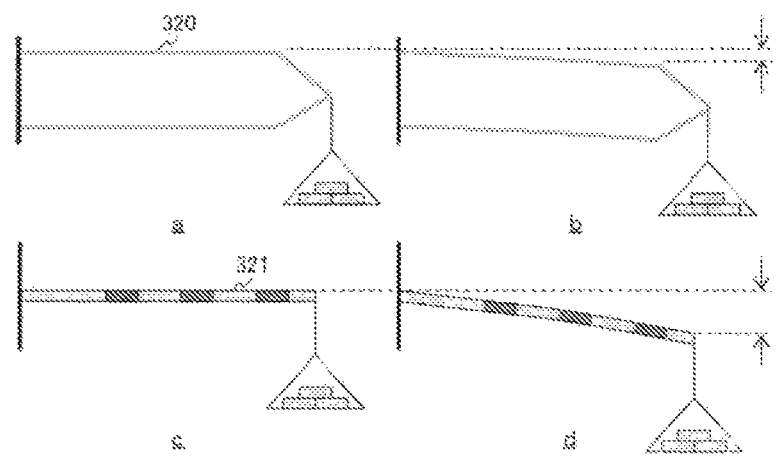

FIG. 135 is a diagram for explaining strength of the probe casing according to the first embodiment of the present technology.

Figure 136:
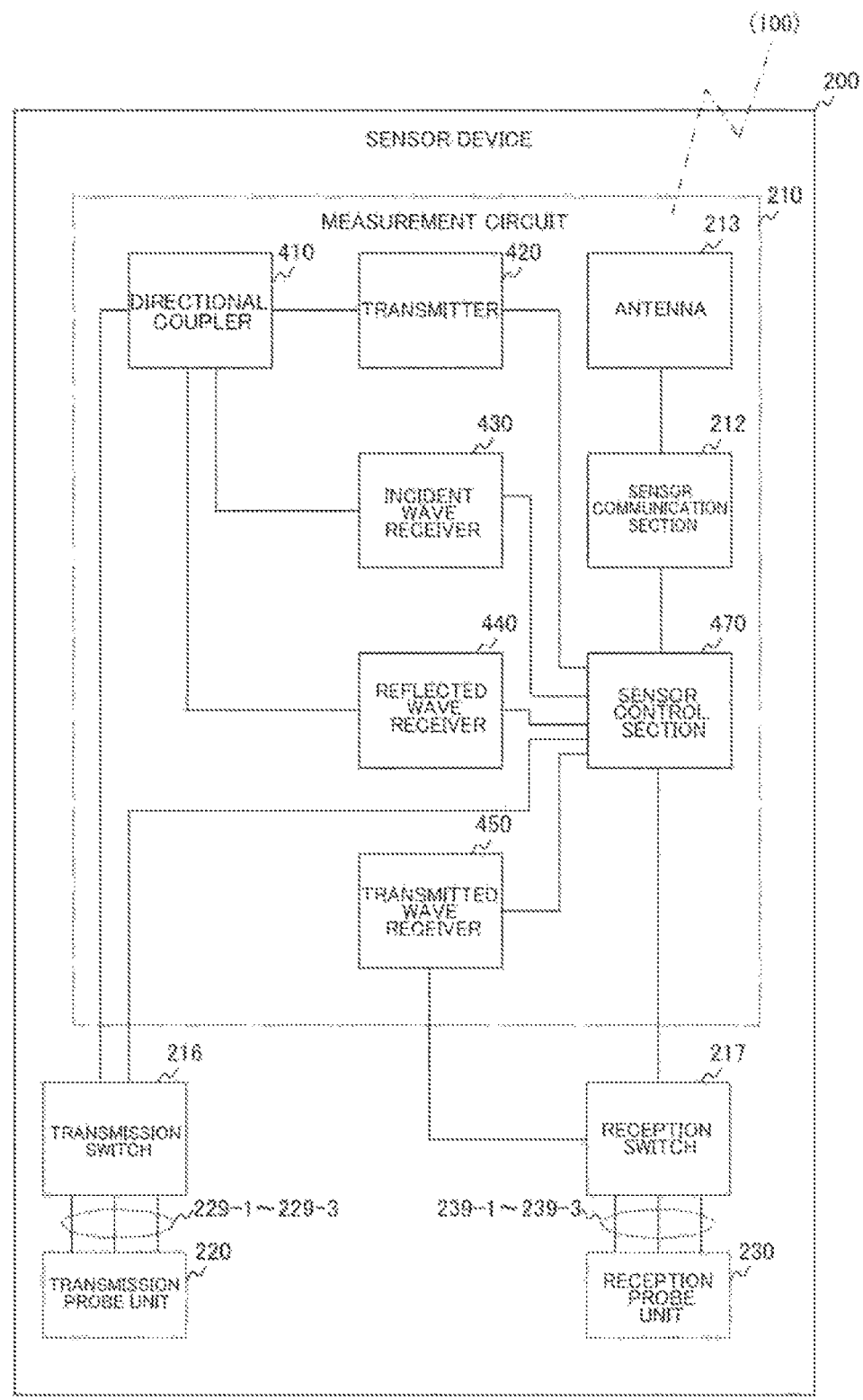

FIG. 136 is a block diagram illustrating a configuration example of a measurement circuit according to the first embodiment of the present technology.

Figure 137:
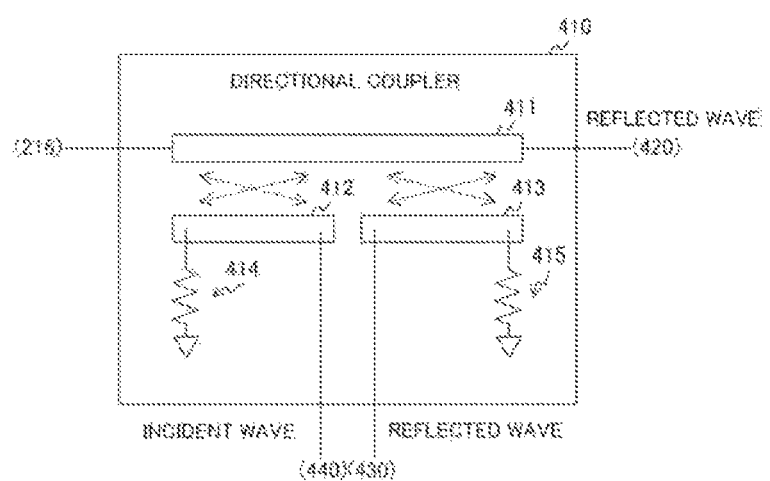

FIG. 137 is a diagram illustrating a configuration example of a directional coupler according to the first embodiment of the present technology.

Figure 138:
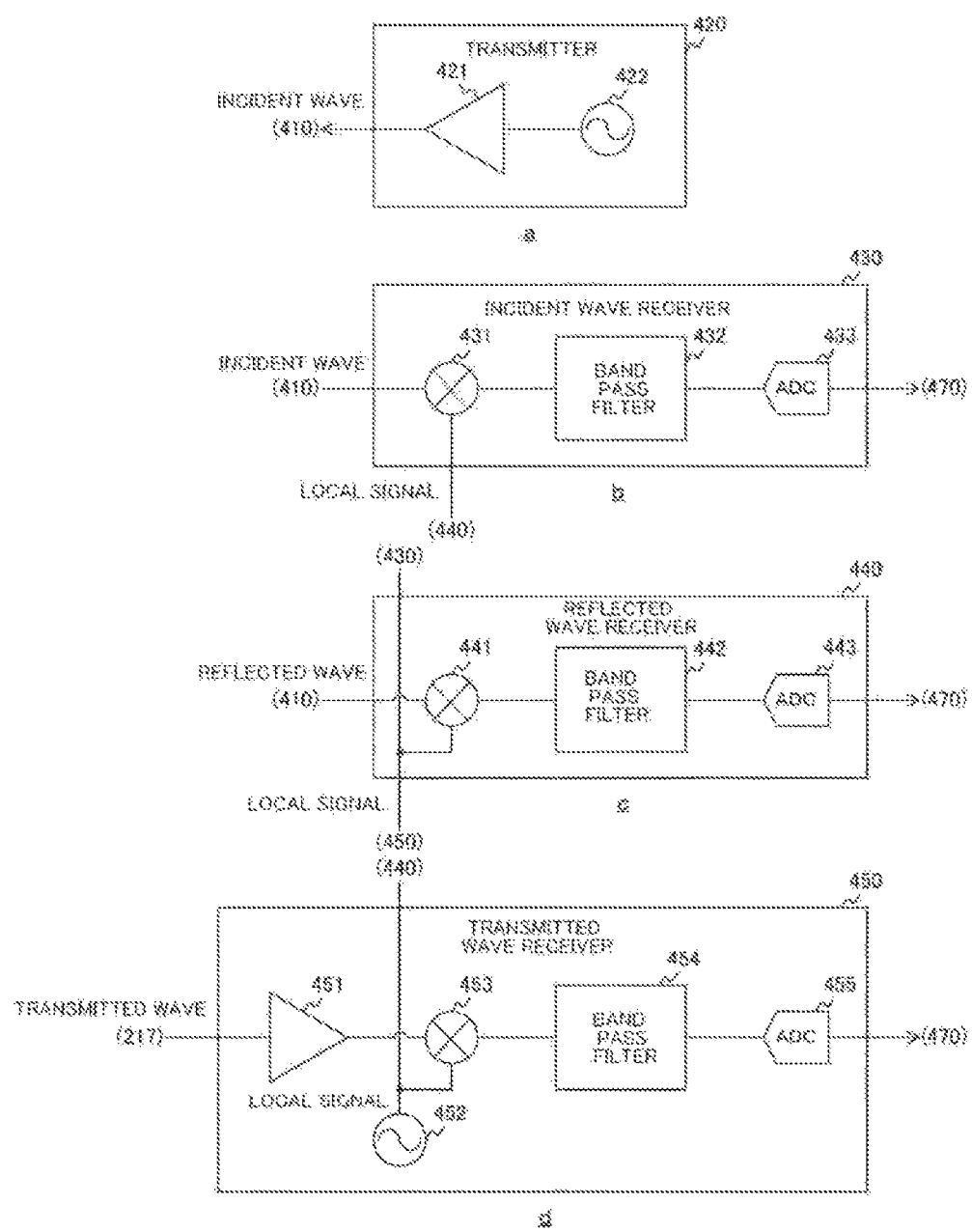

FIG. 138 is a circuit diagram illustrating a configuration example of a transmitter and a receiver according to the first embodiment of the present technology.

Figure 139:
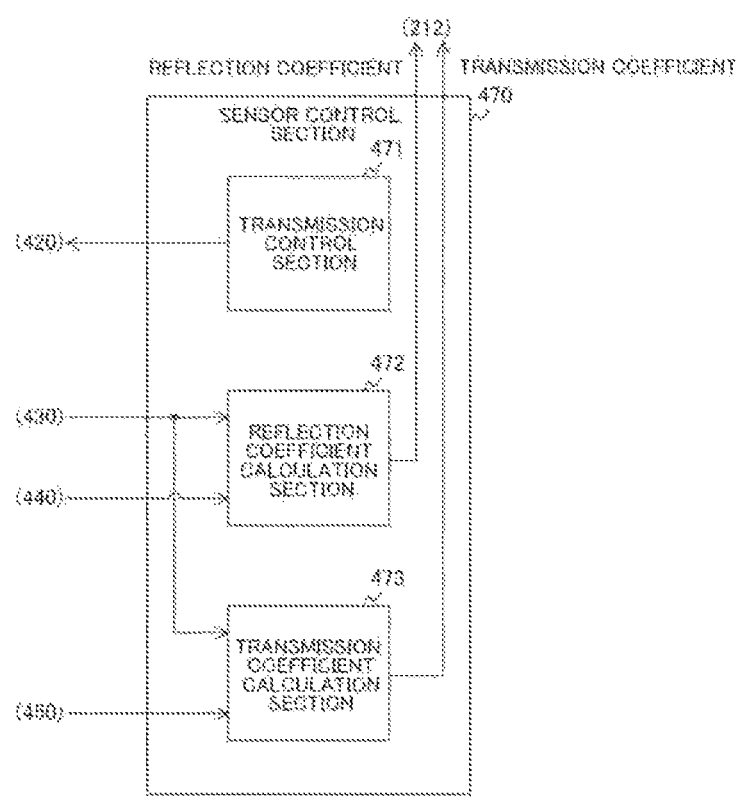

FIG. 139 is a block diagram illustrating a configuration example of a sensor control section according to the first embodiment of the present technology.

Figure 140:
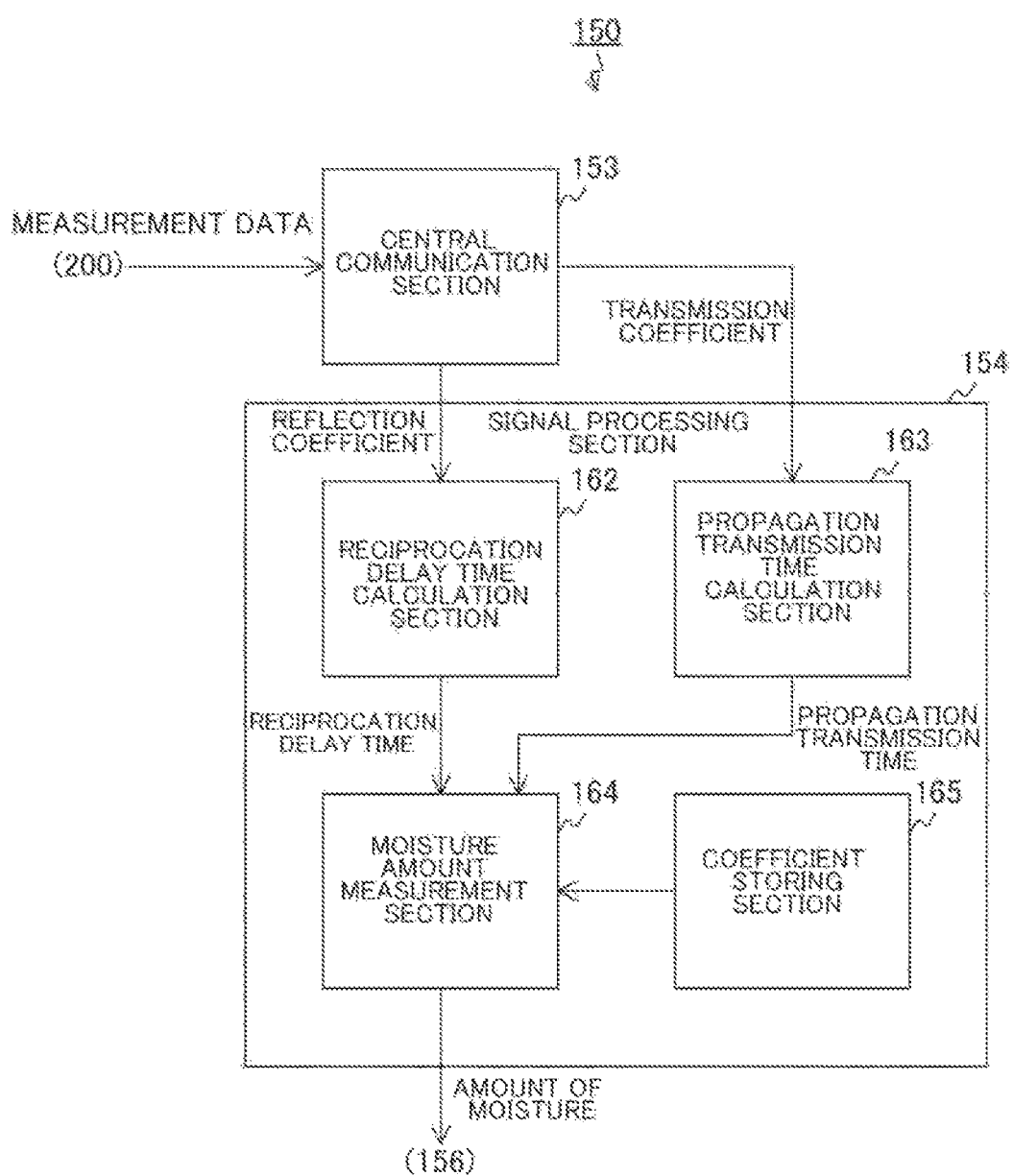

FIG. 140 is a block diagram illustrating a configuration example of a signal processing section in the central processing unit according to the first embodiment of the present technology.

Figure 141:
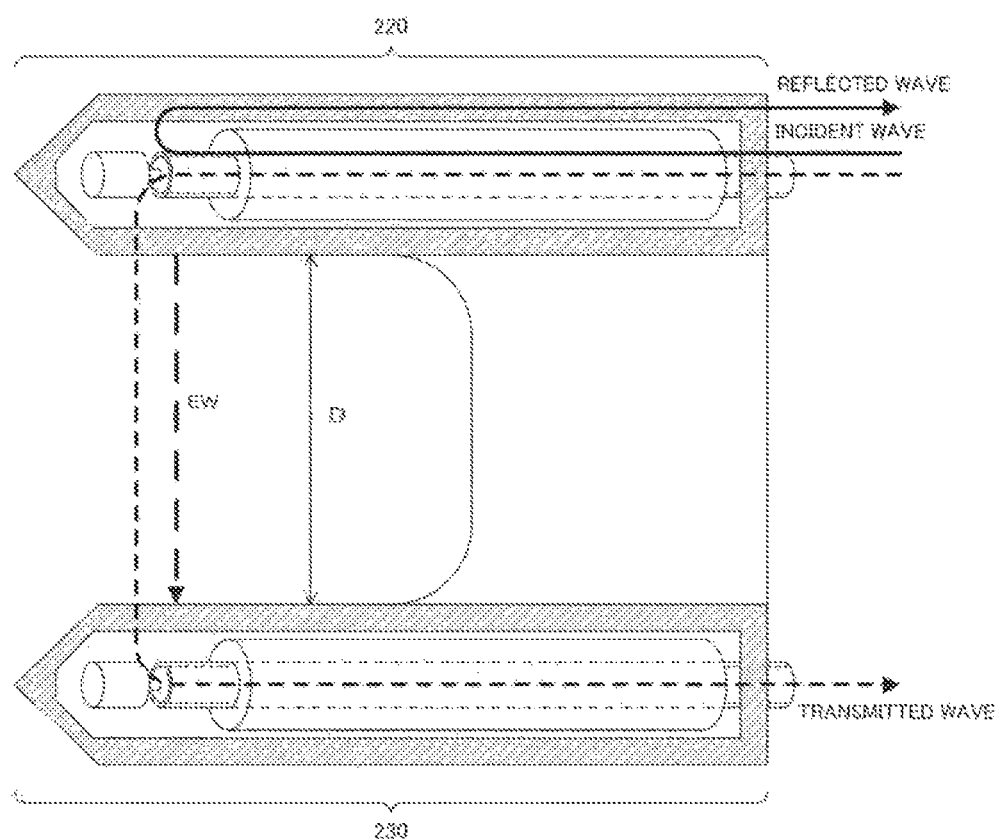

FIG. 141 is a diagram for explaining a propagation path and a transmission path of electromagnetic waves and an electrical signal according to the first embodiment of the present technology.

Figure 142:
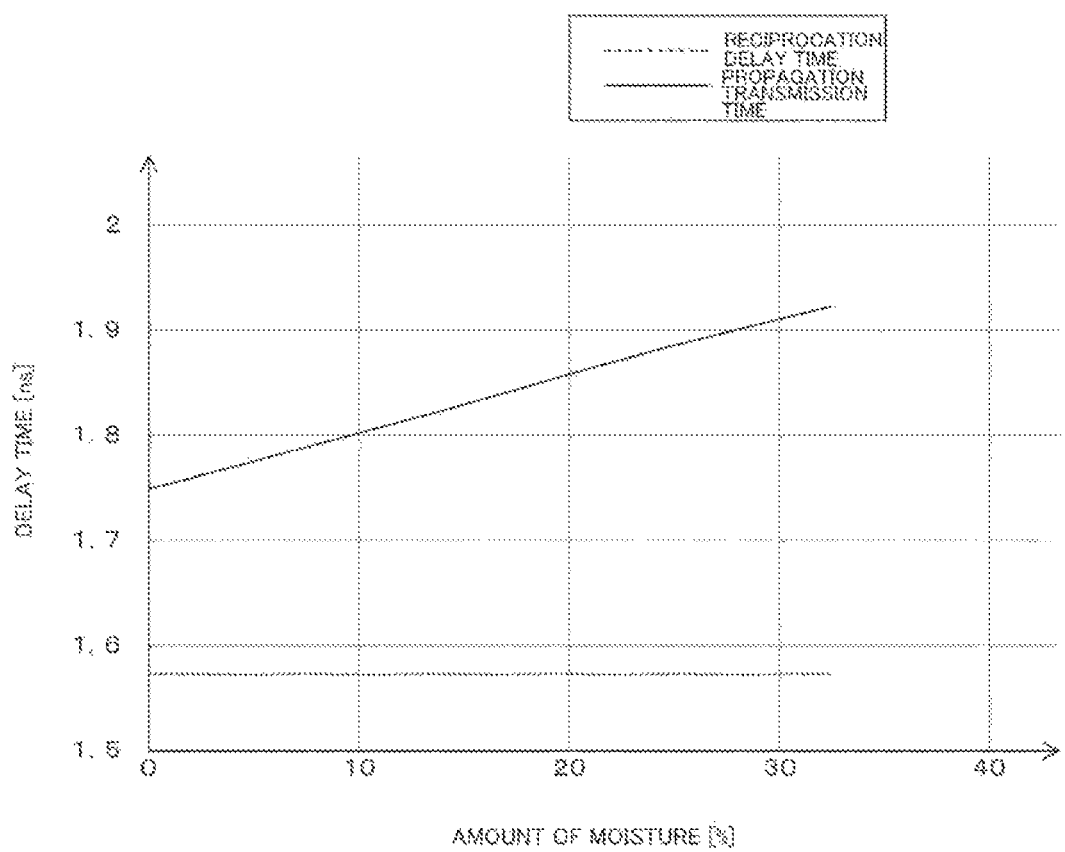

FIG. 142 is a graph illustrating an example of a relationship of a reciprocation delay time and a propagation transmission time with the amount of moisture according to the first embodiment of the present technology.

Figure 143:
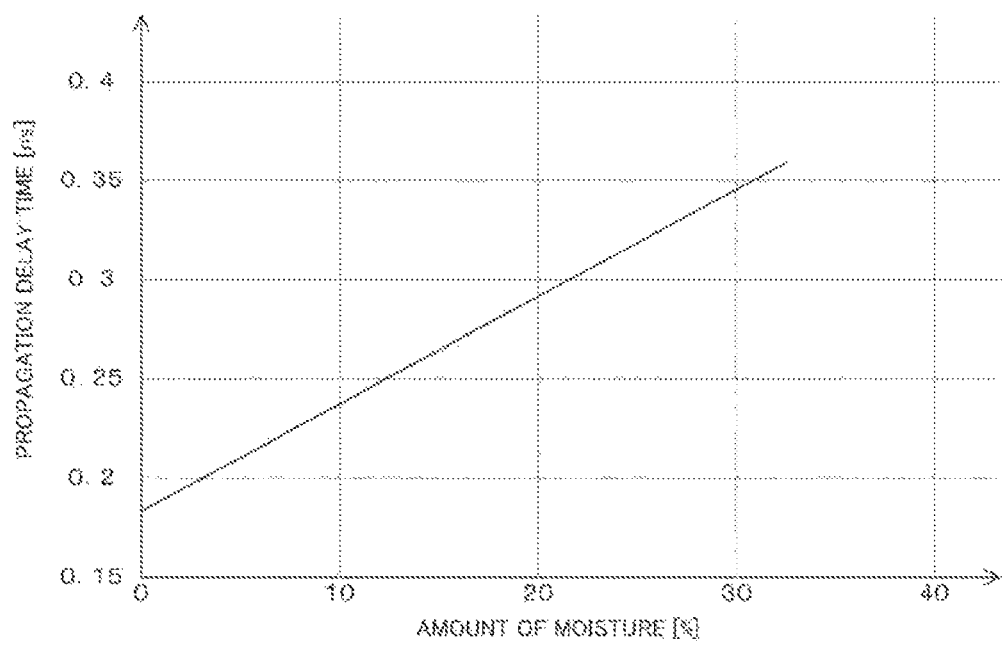

FIG. 143 is a graph illustrating an example of a relationship between a propagation delay time and the amount of moisture according to the first embodiment of the present technology.

Figure 144:
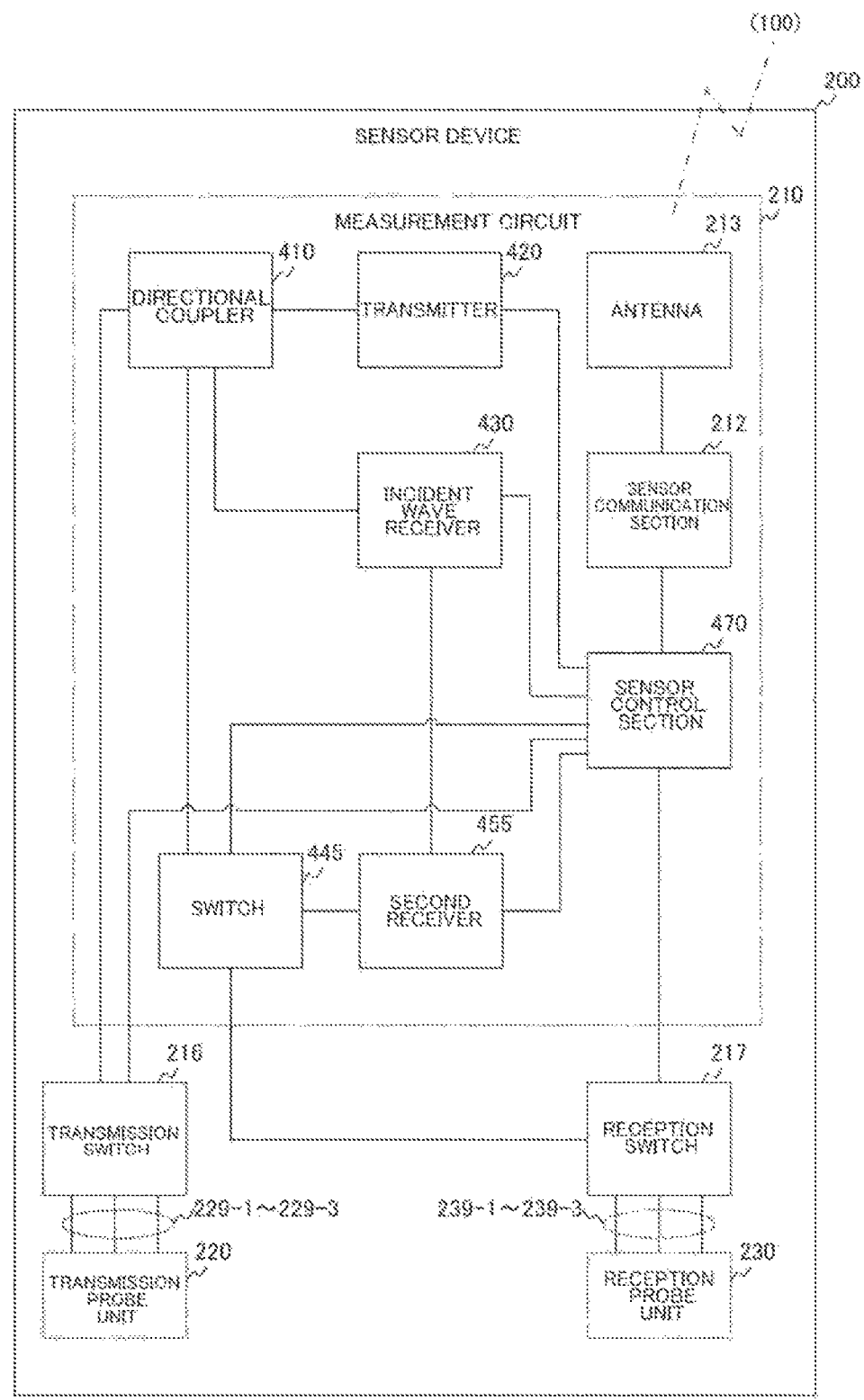

FIG. 144 is a block diagram illustrating another configuration example of the measurement circuit according to the first embodiment of the present technology.

Figure 145:
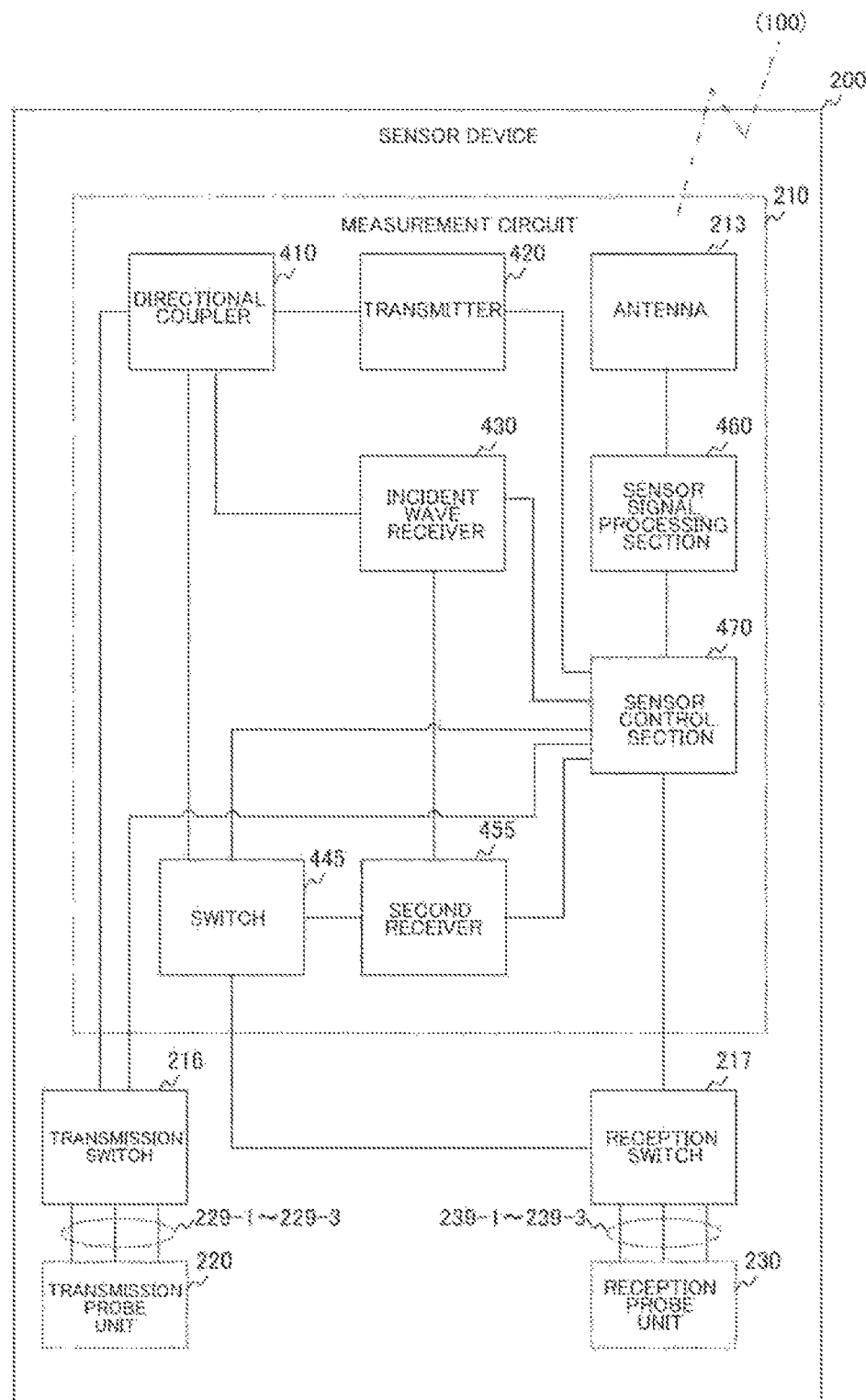

FIG. 145 is a block diagram illustrating another configuration example of the sensor device according to the first embodiment of the present technology.

Figure 146:
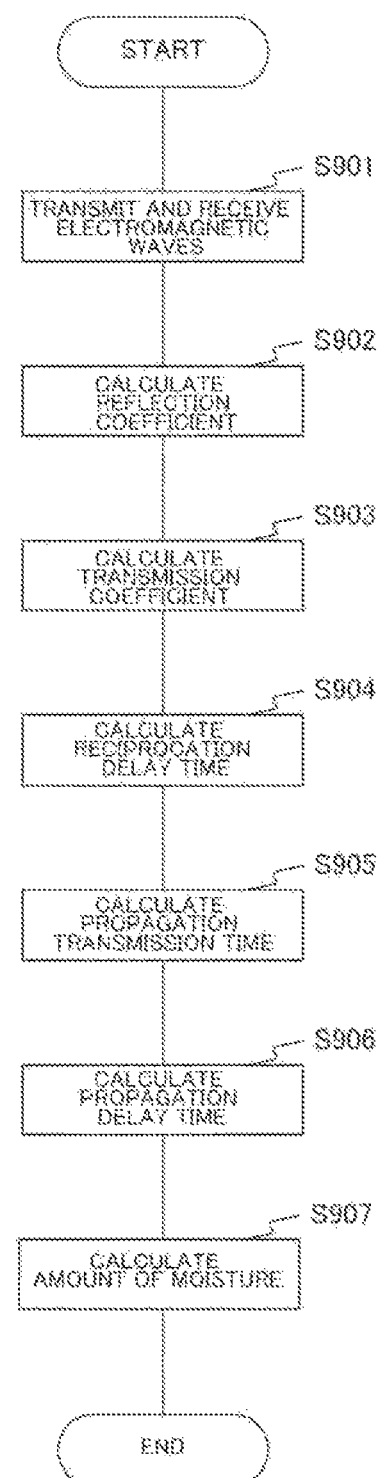

FIG. 146 is a flowchart illustrating an example of operations of a moisture measurement system according to the first embodiment of the present technology.

Figure 147:

FIG. 147 is a diagram illustrating an example of a covered part of a radio wave absorption section according to the first embodiment of the present technology.

Figure 148:
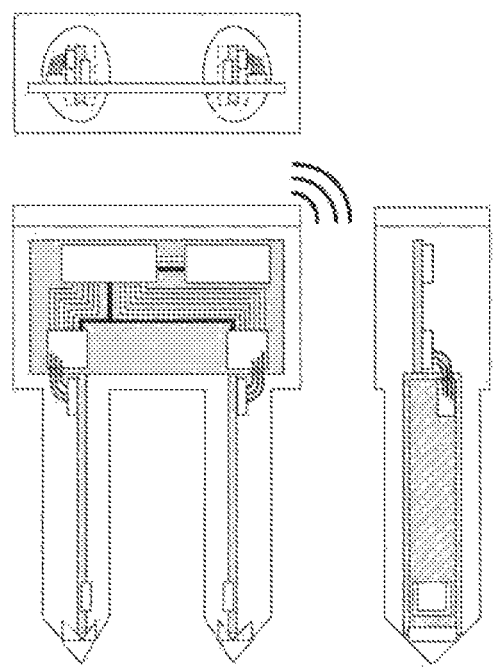

FIG. 148 is a diagram illustrating a comparative example in which there is no covering with the radio wave absorption section.

Figure 149:
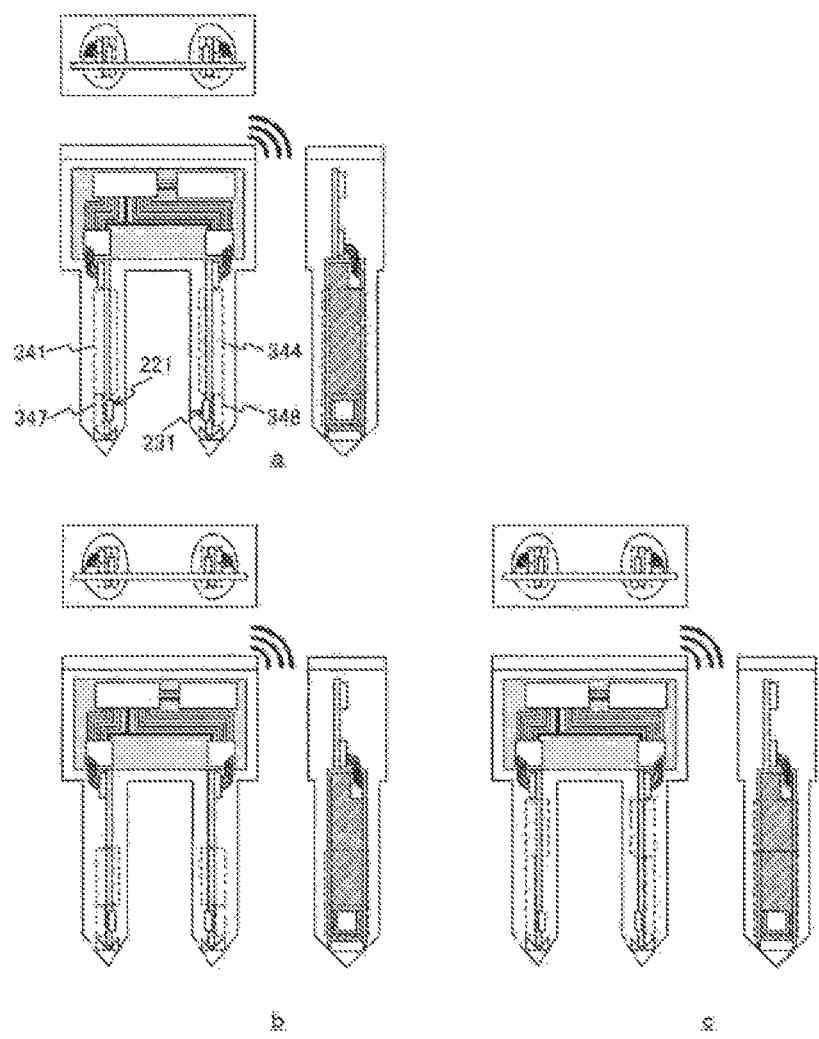

FIG. 149 is a diagram illustrating an example in which one surface of the intra-probe substrate is covered according to the first embodiment of the present technology.

Figure 150:
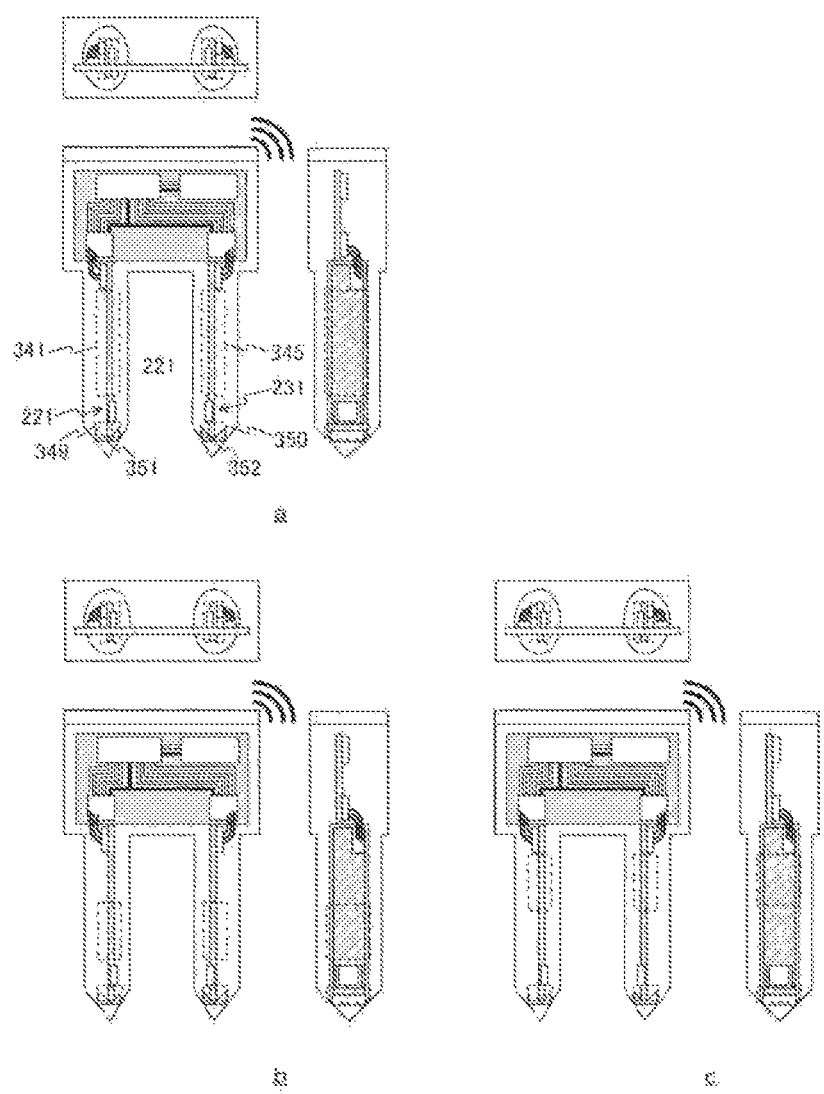

FIG. 150 is a diagram illustrating an example in which distal ends of the probes are further covered according to the first embodiment of the present technology.

Figure 151:
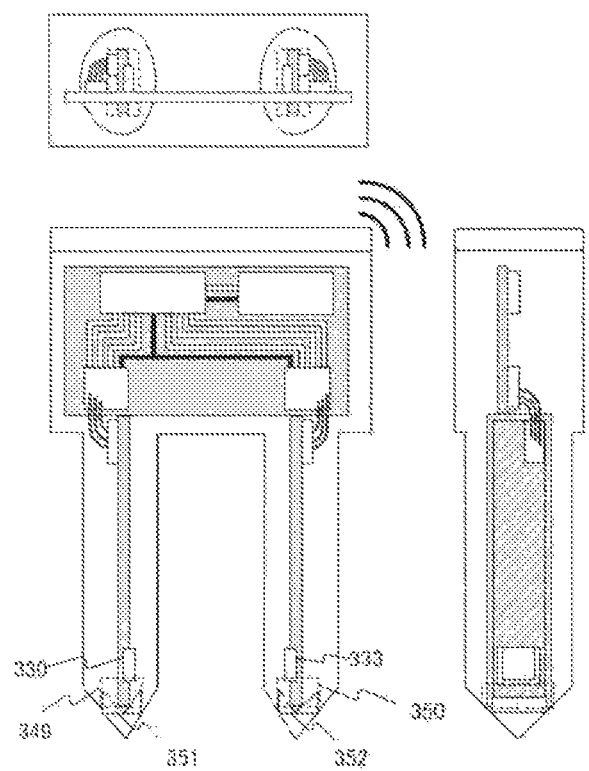

FIG. 151 is a diagram illustrating an example in which only the distal ends are covered according to the first embodiment of the present technology.

Figure 152:
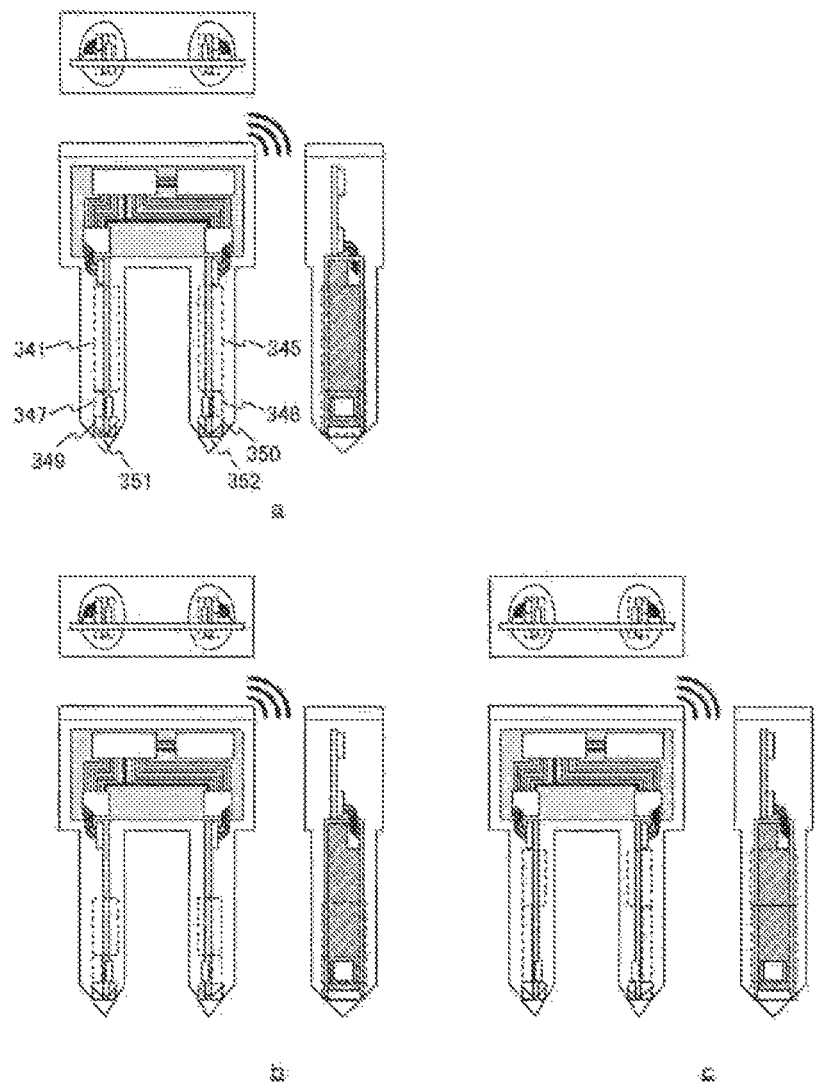

FIG. 152 is a diagram illustrating an example in which the one surface and the distal end of the intra-probe substrate are covered according to the first embodiment of the present technology.

Figure 153:
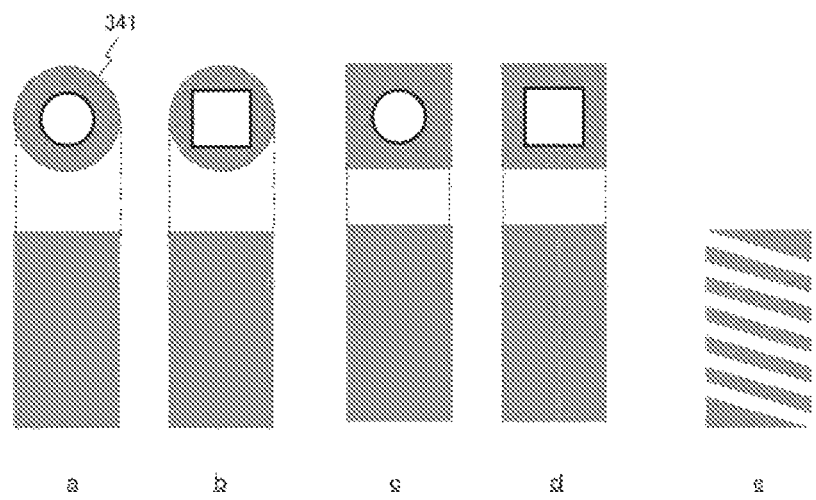

FIG. 153 is a diagram illustrating an example of the shape of the radio wave absorption section according to the first embodiment of the present technology.

Figure 154:
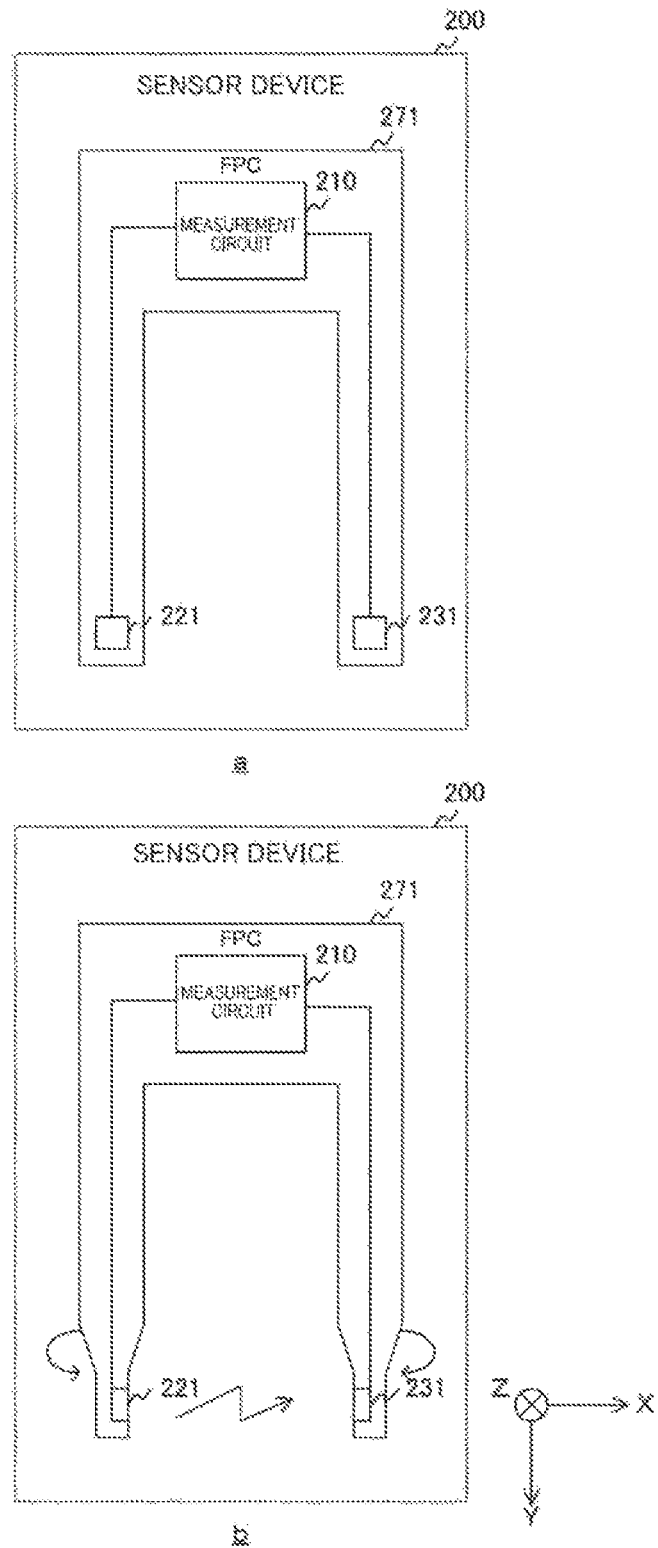

FIG. 154 is a diagram illustrating an example of a sensor device using a flexible substrate according to a first modification example of the first embodiment of the present technology.

Figure 155:
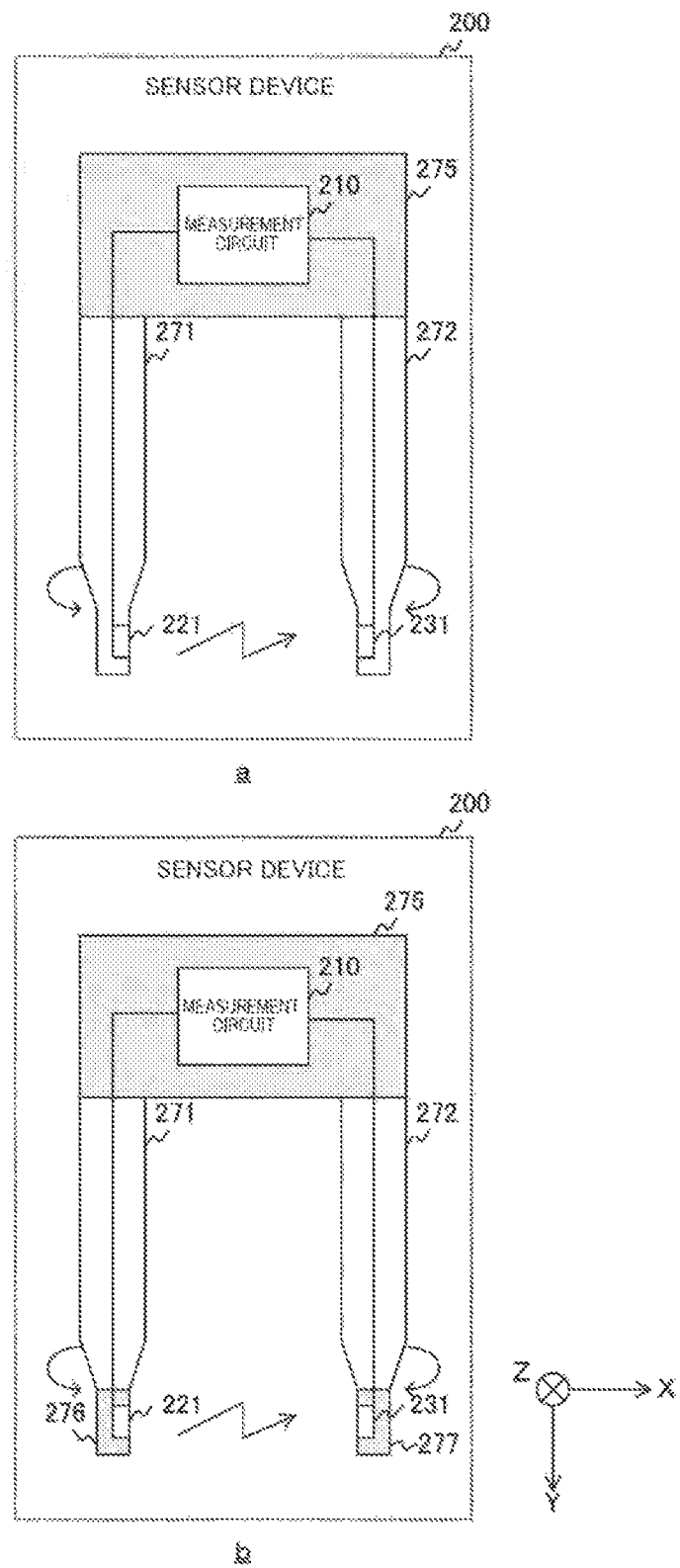

FIG. 155 is a diagram illustrating an example of the sensor device using the flexible substrates and rigid substrates according to the first modification example of the first embodiment of the present technology.

FIG. 156 is a diagram illustrating an example of the sensor device when the number of antennas is increased according to the first modification example of the first embodiment of the present technology.

FIG. 157 is a diagram illustrating an example of the sensor device using the flexible substrate and the rigid substrate when the number of antennas is increased according to the first modification example of the first embodiment of the present technology.

Figure 158:
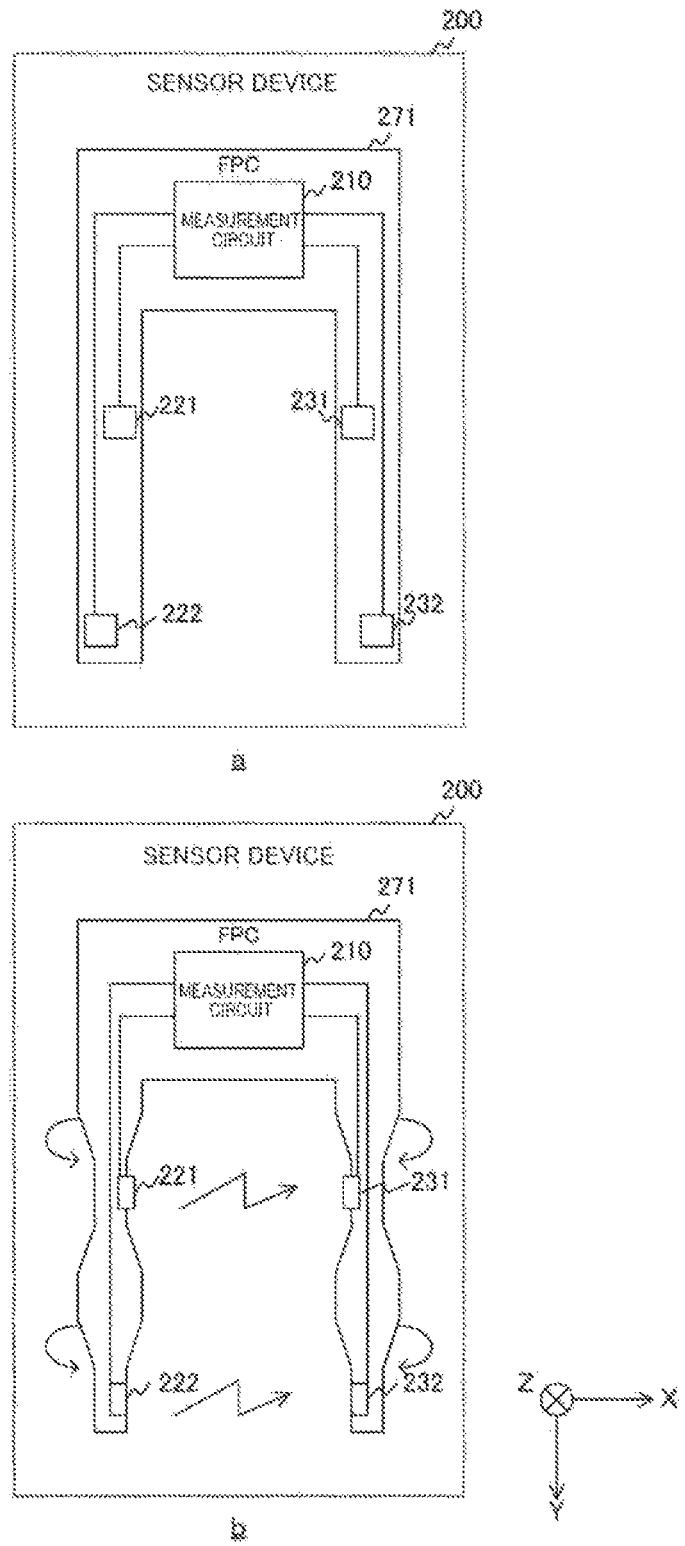

FIG. 158 is a diagram illustrating an example of the sensor device including a transmission path arranged for each antenna according to the first modification example of the first embodiment of the present technology.

FIG. 159 is a diagram illustrating an example of the sensor device including the transmission path arranged for each antenna and using the flexible substrate and the rigid substrate according to the first modification example of the first embodiment of the present technology.

FIG. 160 is a diagram illustrating an example of the sensor device in which the substrate is arranged in a hard shell sensor casing according to the first modification example of the first embodiment of the present technology.

FIG. 161 is a diagram illustrating an example of the sensor device in which the number of antennas is increased and the substrate is arranged in the hard shell sensor casing according to the first modification example of the first embodiment of the present technology.

FIG. 162 is a diagram illustrating an example of the sensor device according to the first modification example and that in a comparative example of the first embodiment of the present technology.

Figure 163:
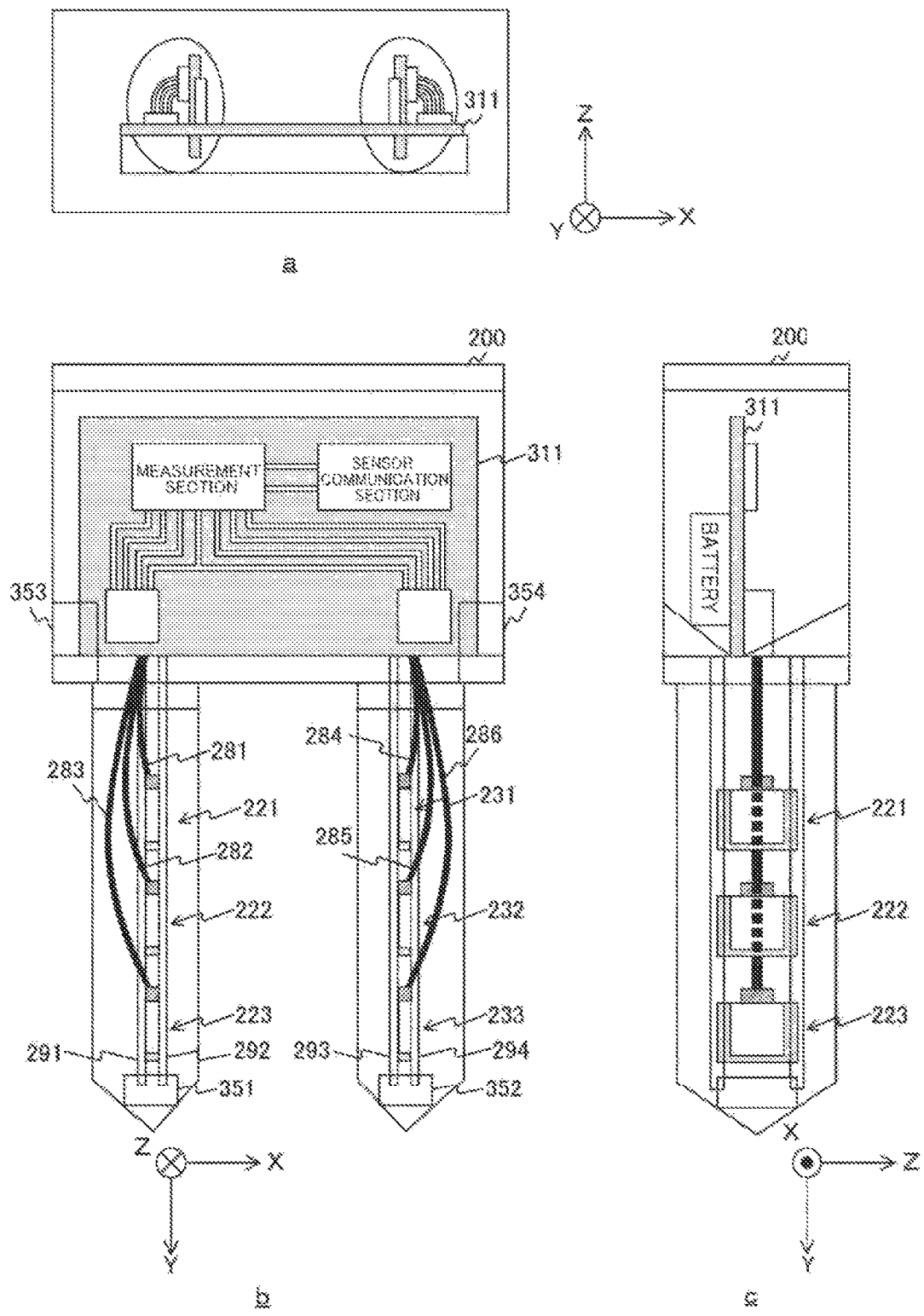

FIG. 163 is a diagram illustrating an example of a sensor device according to a third modification example of the first embodiment of the present technology.

FIG. 164 is a diagram illustrating an example of a top view and a sectional view of the sensor device according to the third modification example of the first embodiment of the present technology.

Figure 165:
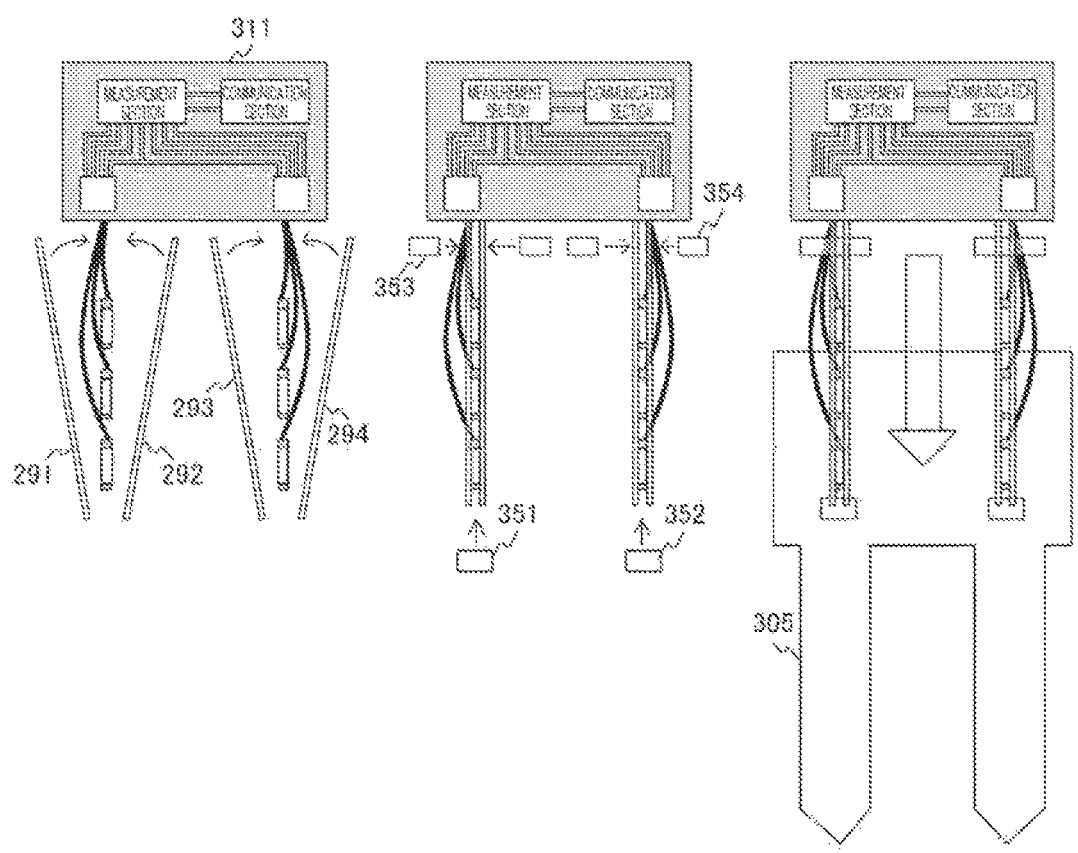

FIG. 165 is a diagram for explaining a method for accommodating substrates according to the third modification example of the first embodiment of the present technology.

Figure 166:
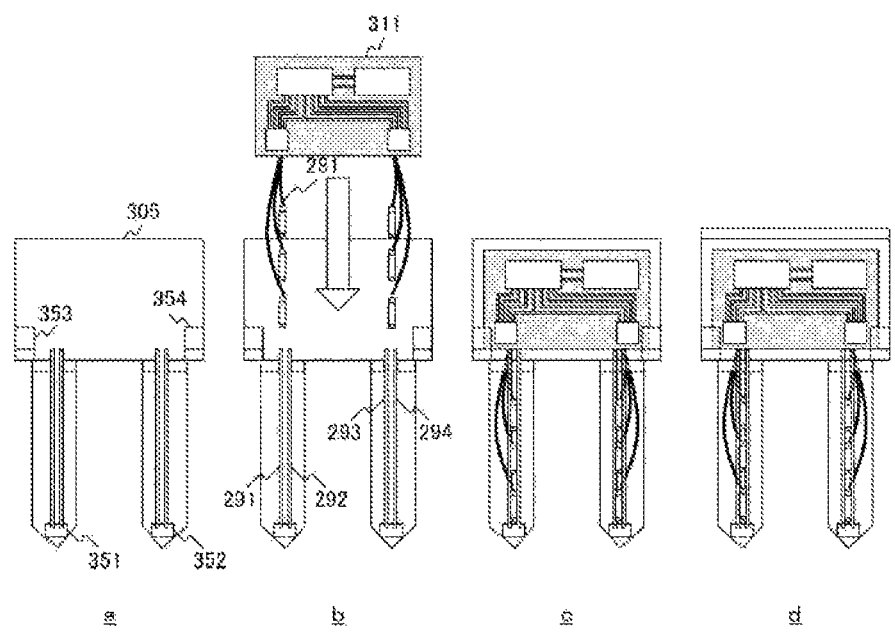

FIG. 166 is a diagram for explaining another example of the method for accommodating the substrates according to the third modification example of the first embodiment of the present technology.

Figure 167:
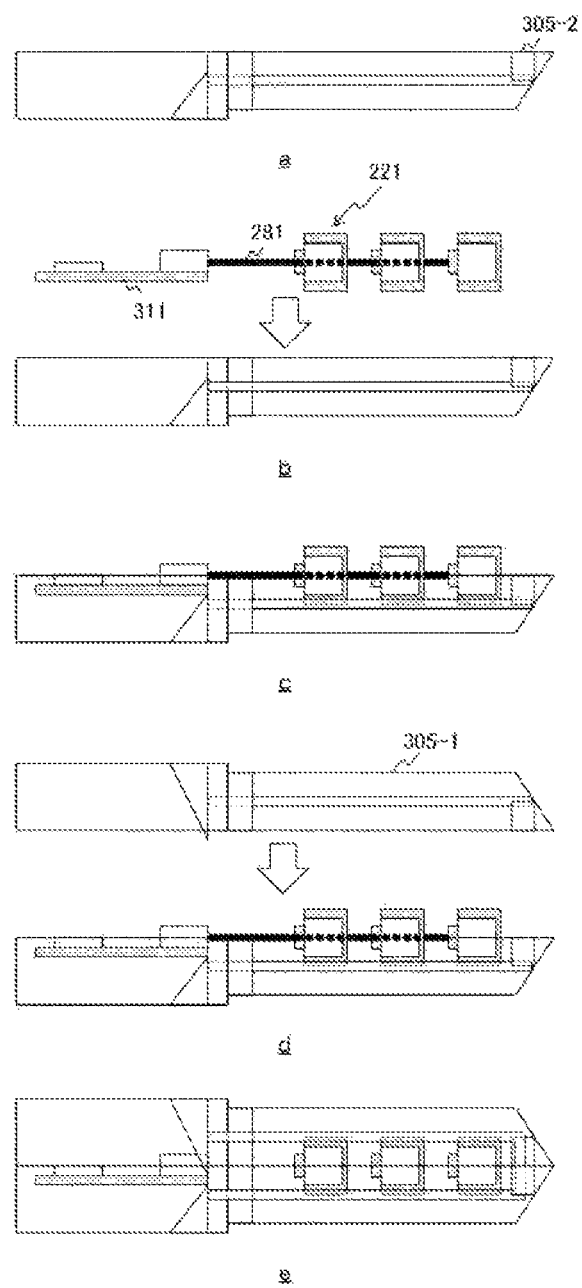

FIG. 167 is a diagram for explaining another example of the method for accommodating the substrates according to the third modification example of the first embodiment of the present technology.

Figure 168:
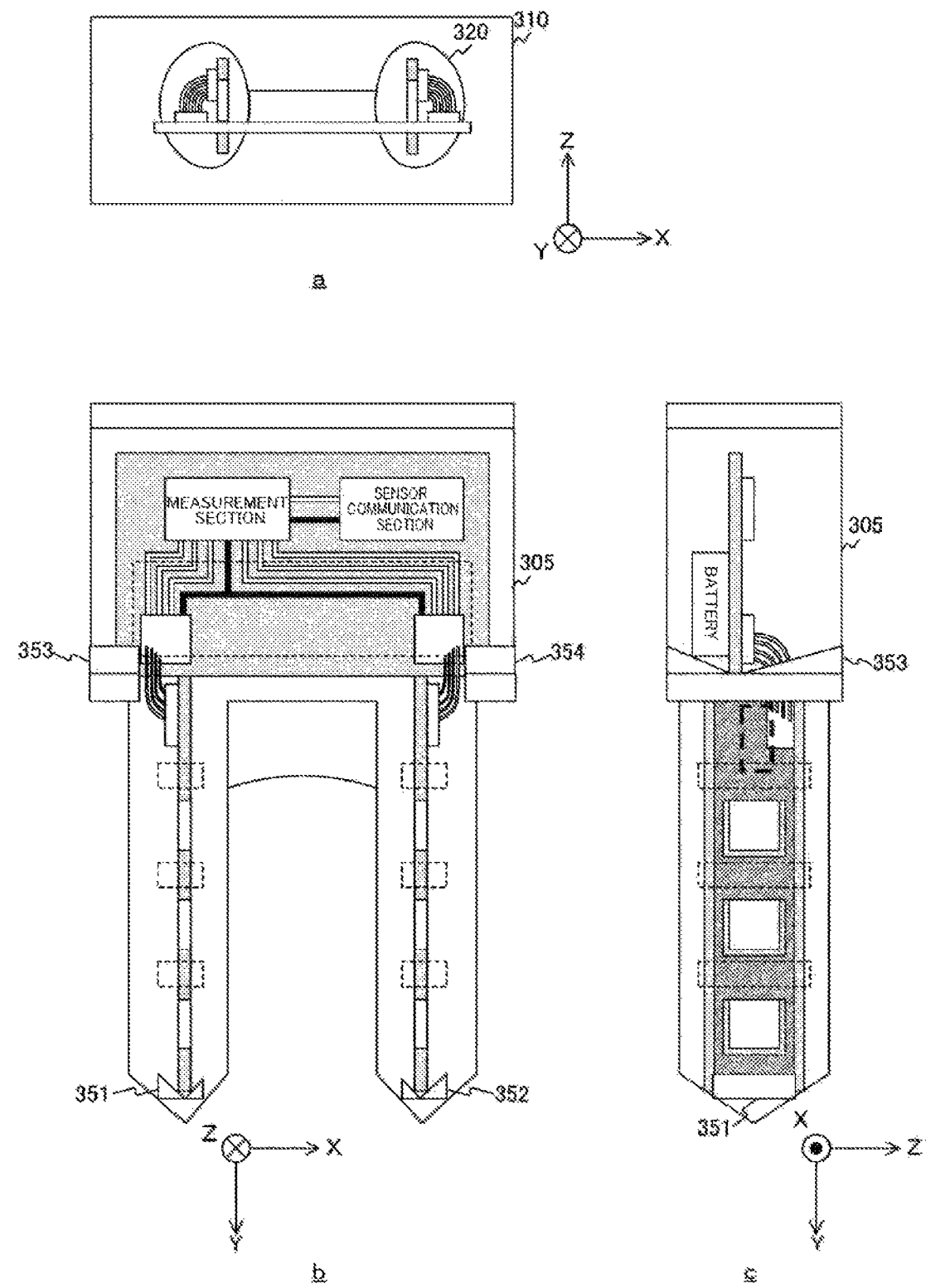

FIG. 168 is a diagram illustrating an example of a sensor device according to a fourth modification example of the first embodiment of the present technology.

Figure 169:
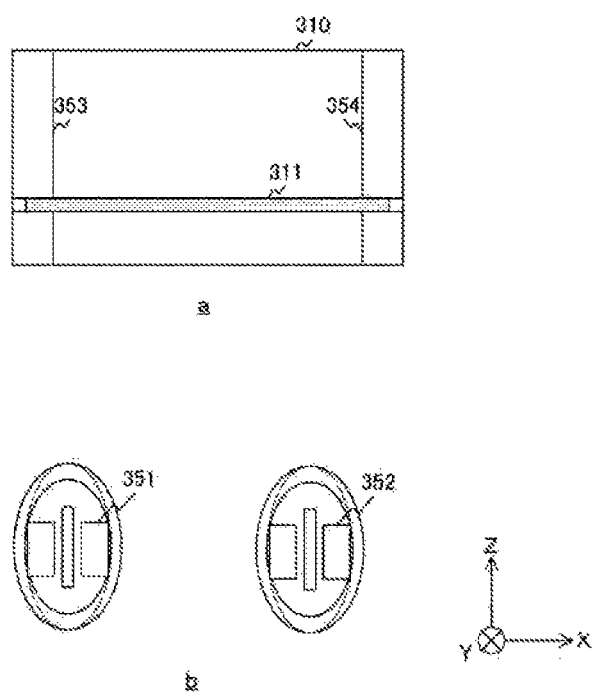

FIG. 169 is a diagram illustrating an example of a top view and a sectional view of the sensor device according to the fourth modification example of the first embodiment of the present technology.

Figure 170:
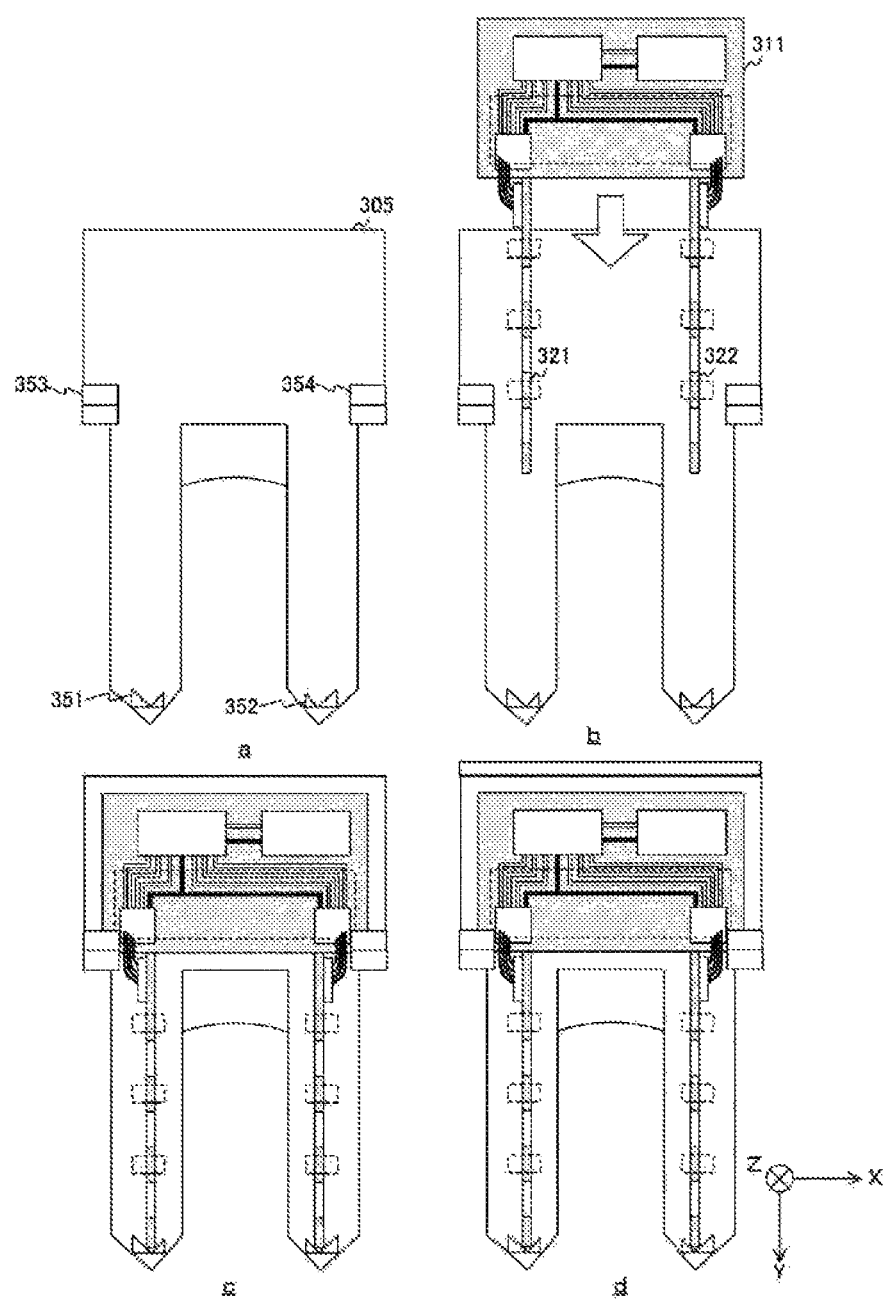

FIG. 170 is a diagram for explaining a method for accommodating substrates according to the fourth modification example of the first embodiment of the present technology.

Figure 171:
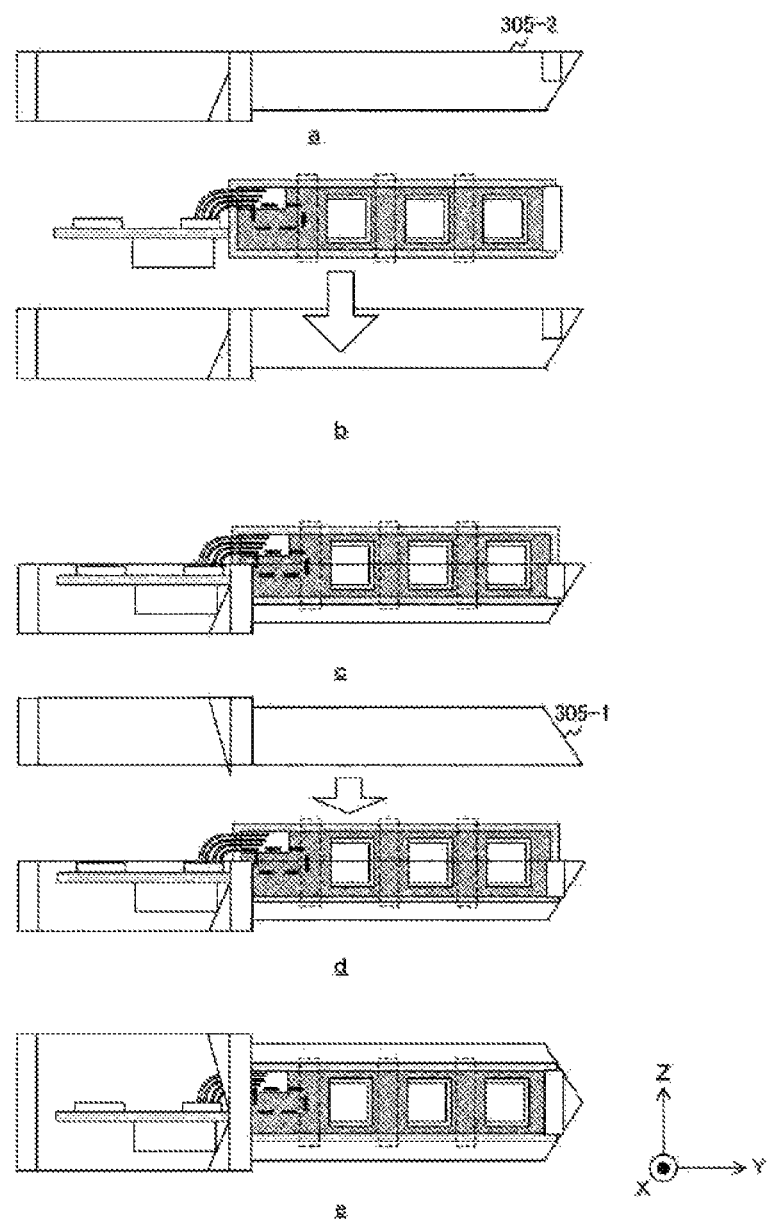

FIG. 171 is a diagram for explaining another example of the method for accommodating the substrates according to the fourth modification example of the first embodiment of the present technology.

Figure 172:
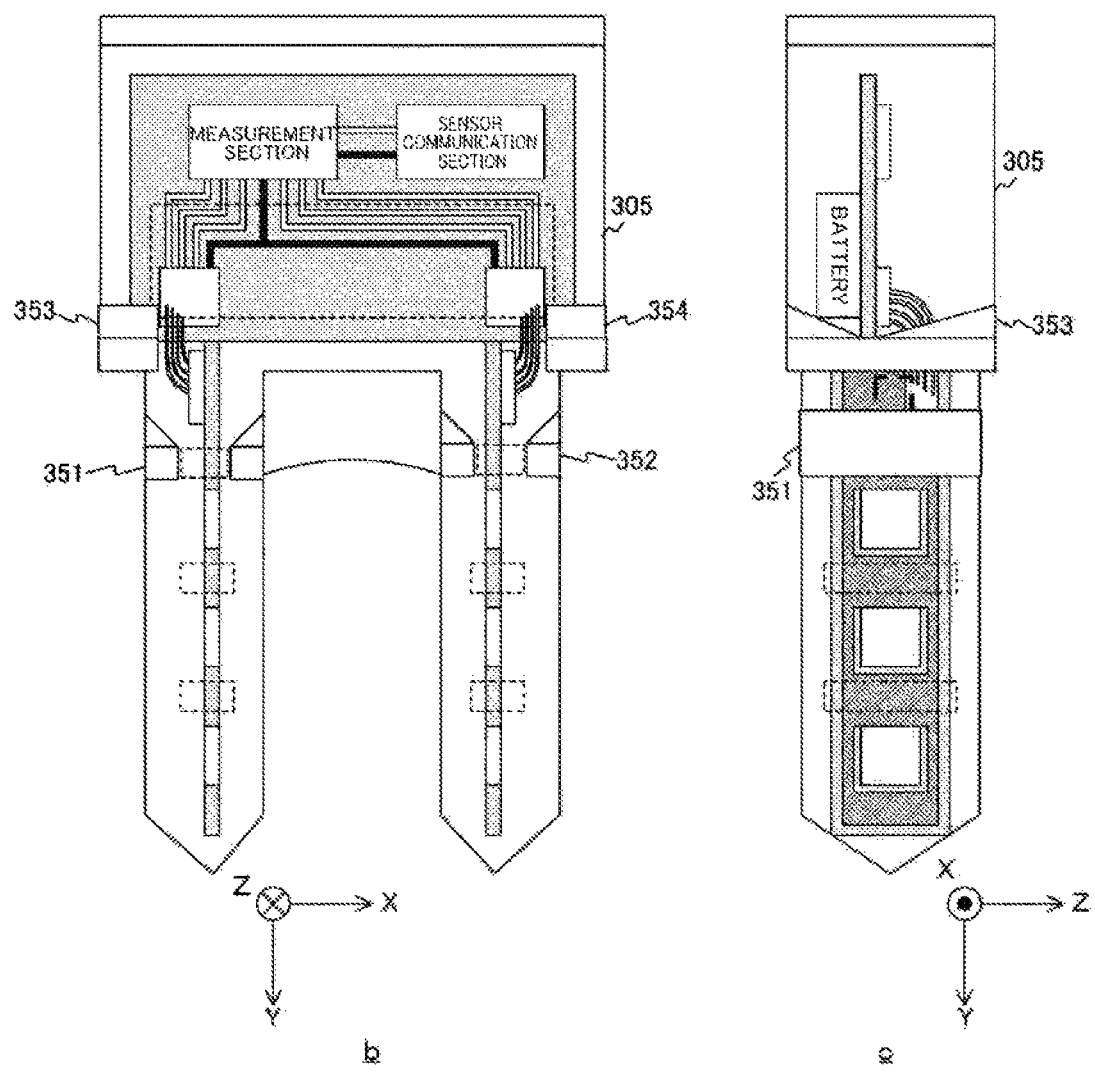

FIG. 172 is a diagram illustrating an example of the sensor device with the position of a positioning section changed according to the fourth modification example of the first embodiment of the present technology.

Figure 173:
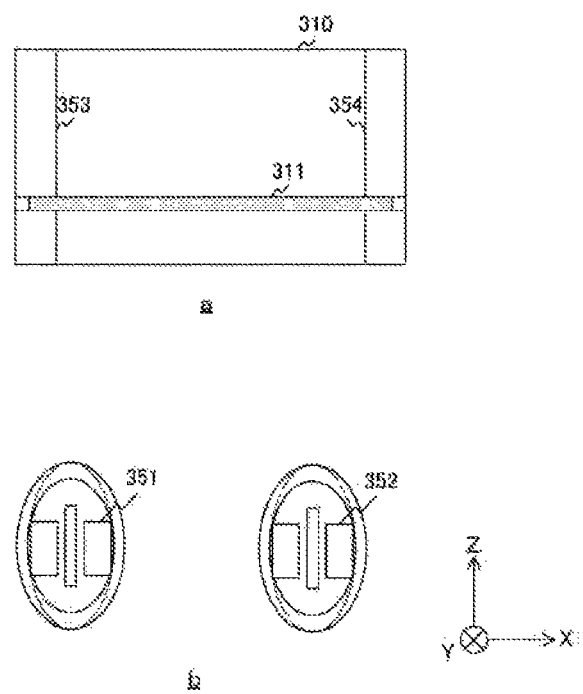

FIG. 173 is a diagram illustrating an example of a top view and a sectional view of the sensor device with the position of the positioning section changed according to the fourth modification example of the first embodiment of the present technology.

Figure 174:
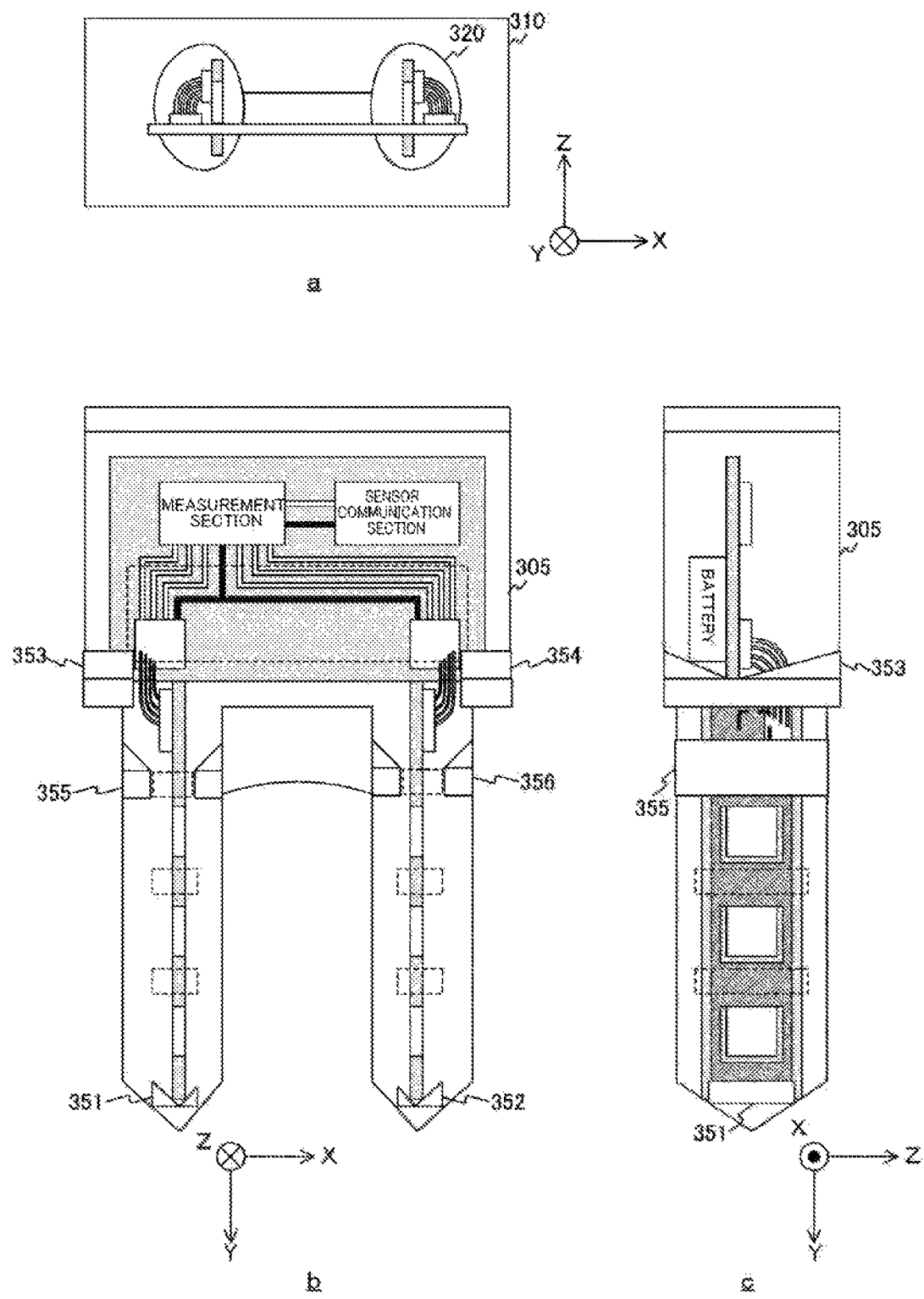

FIG. 174 is a diagram illustrating an example of the sensor device including the positioning section added thereto according to the fourth modification example of the first embodiment of the present technology.

FIG. 175 is a diagram illustrating an example of a top view and a sectional view of the sensor device including the positioning section added thereto according to the fourth modification example of the first embodiment of the present technology.

Figure 176:
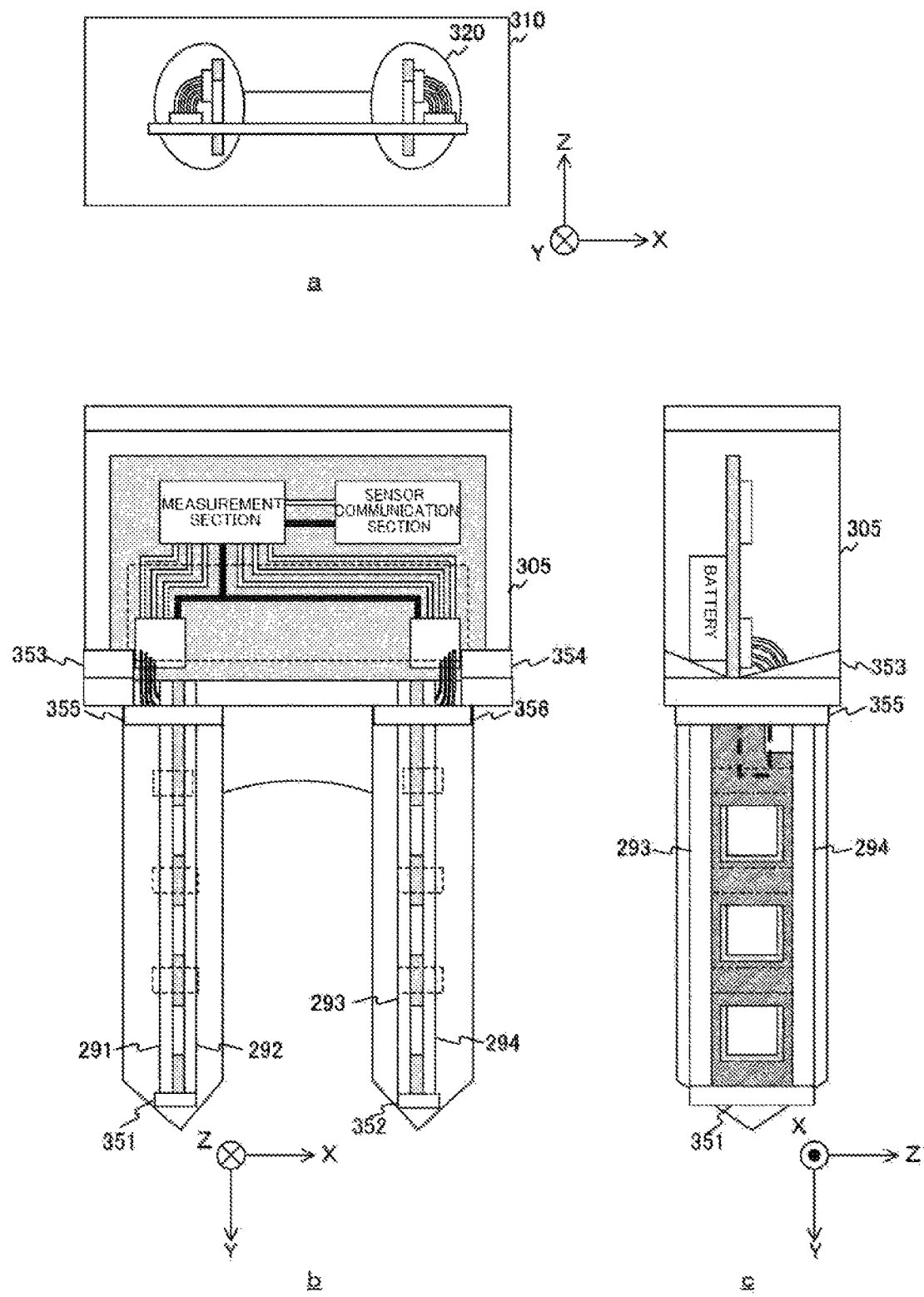

FIG. 176 is a diagram illustrating an example of the sensor device including the positioning section with a different shape according to the fourth modification example of the first embodiment of the present technology.

Figure 177:
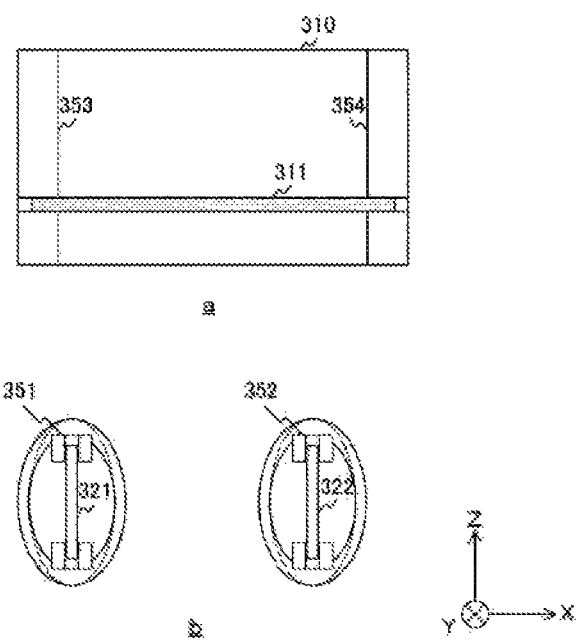

FIG. 177 is a diagram illustrating an example of a top view and a sectional view of the sensor device including the positioning section with a different shape according to the fourth modification example of the first embodiment of the present technology.

Figure 178:
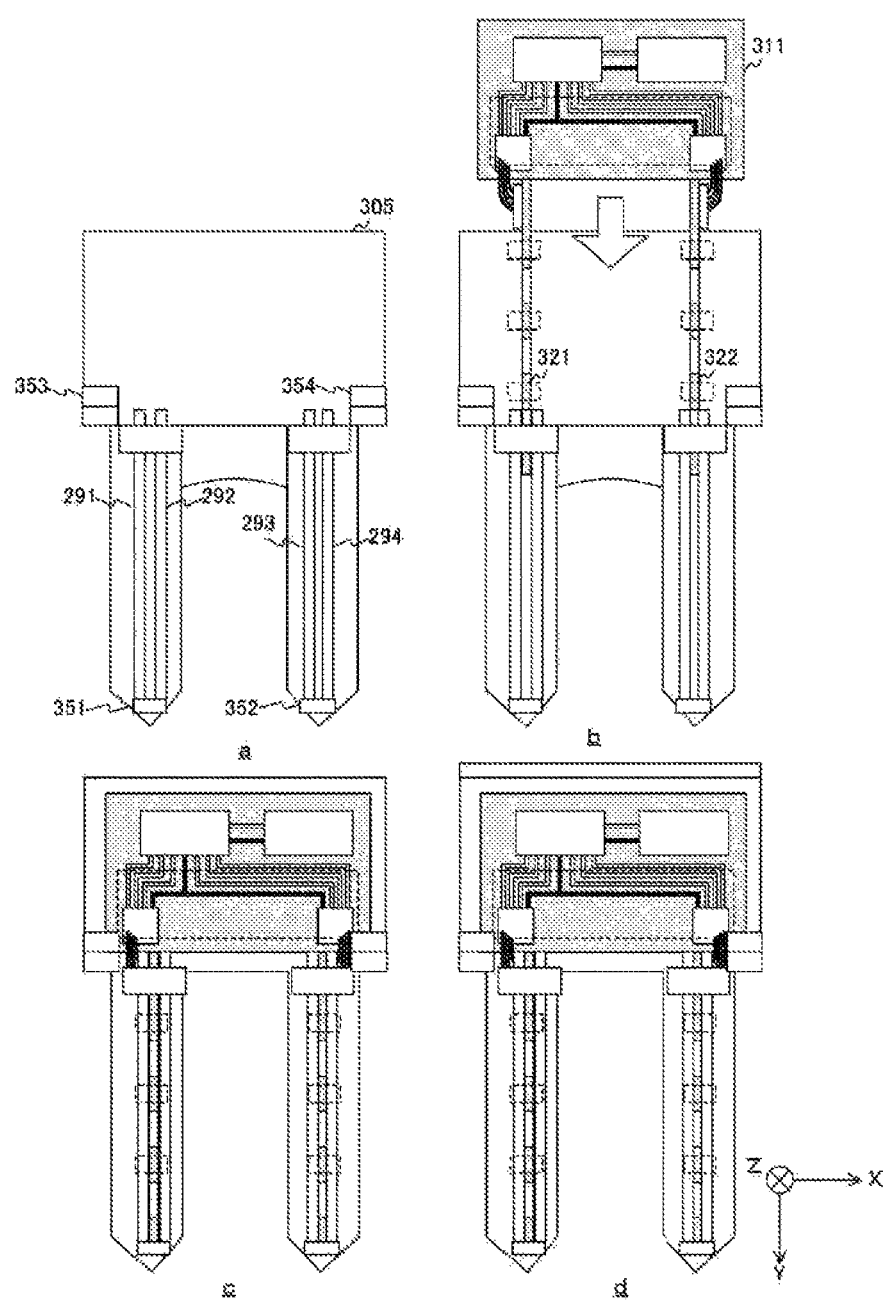

FIG. 178 is a diagram for explaining a method for accommodating the substrates in a case where the shape of the positioning section is different according to the fourth modification example of the first embodiment of the present technology.

Figure 179:
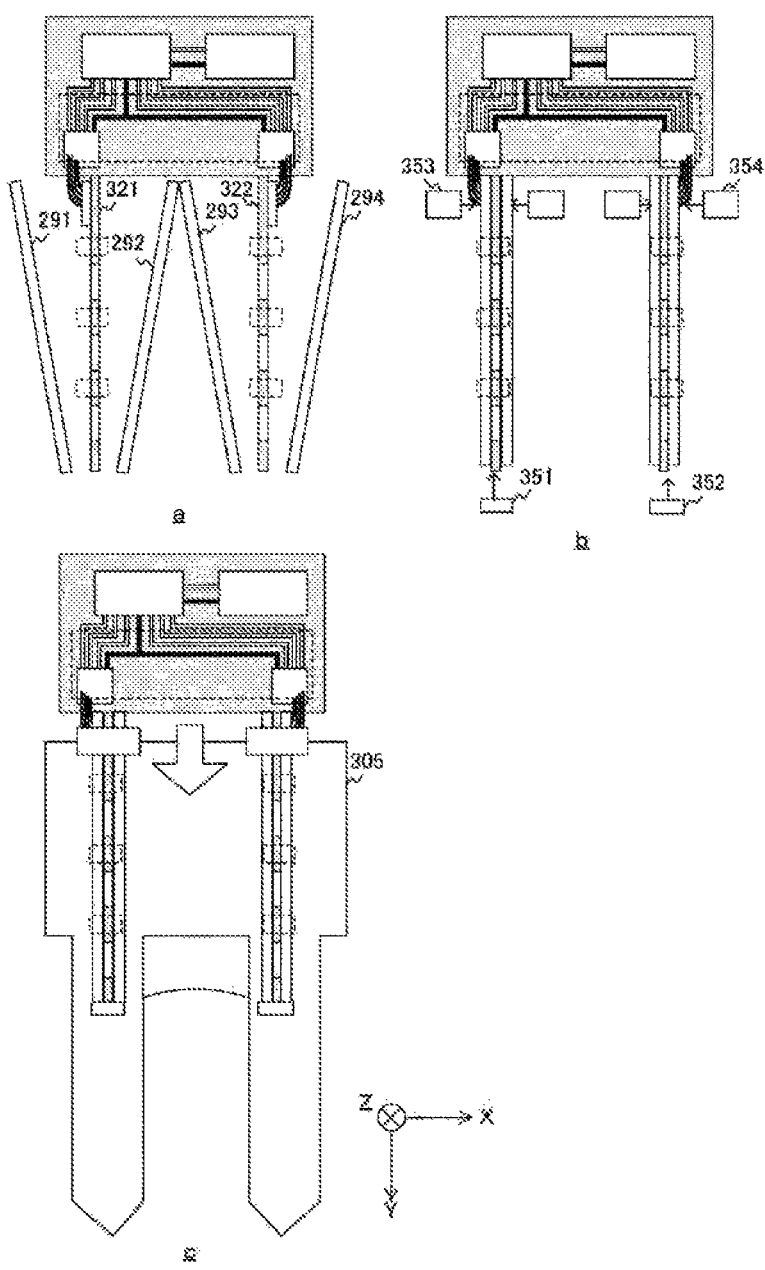

FIG. 179 is a diagram for explaining another example of the method for accommodating the substrates in a case where the shape of the positioning section is different according to the fourth modification example of the first embodiment of the present technology.

FIG. 180 is a diagram illustrating an example of the sensor device with frames extended according to the fourth modification example of the first embodiment of the present technology.

Figure 181:
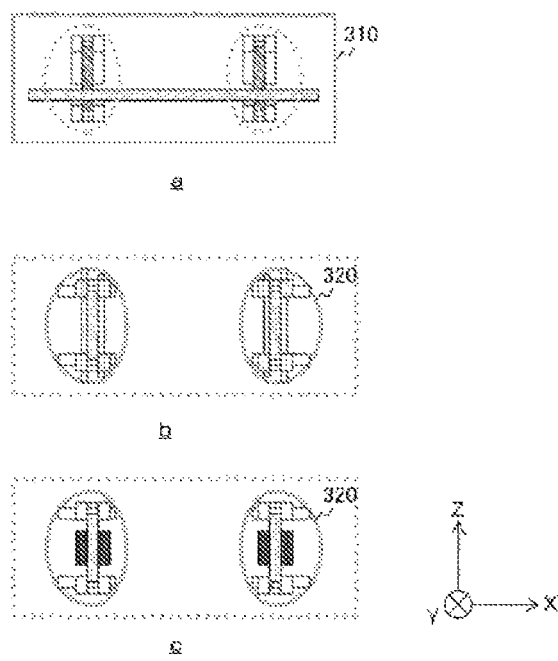

FIG. 181 is a diagram illustrating an example of a top view and a sectional view of the sensor device with the extended frames extended according to the fourth modification example of the first embodiment of the present technology.

Figure 182:
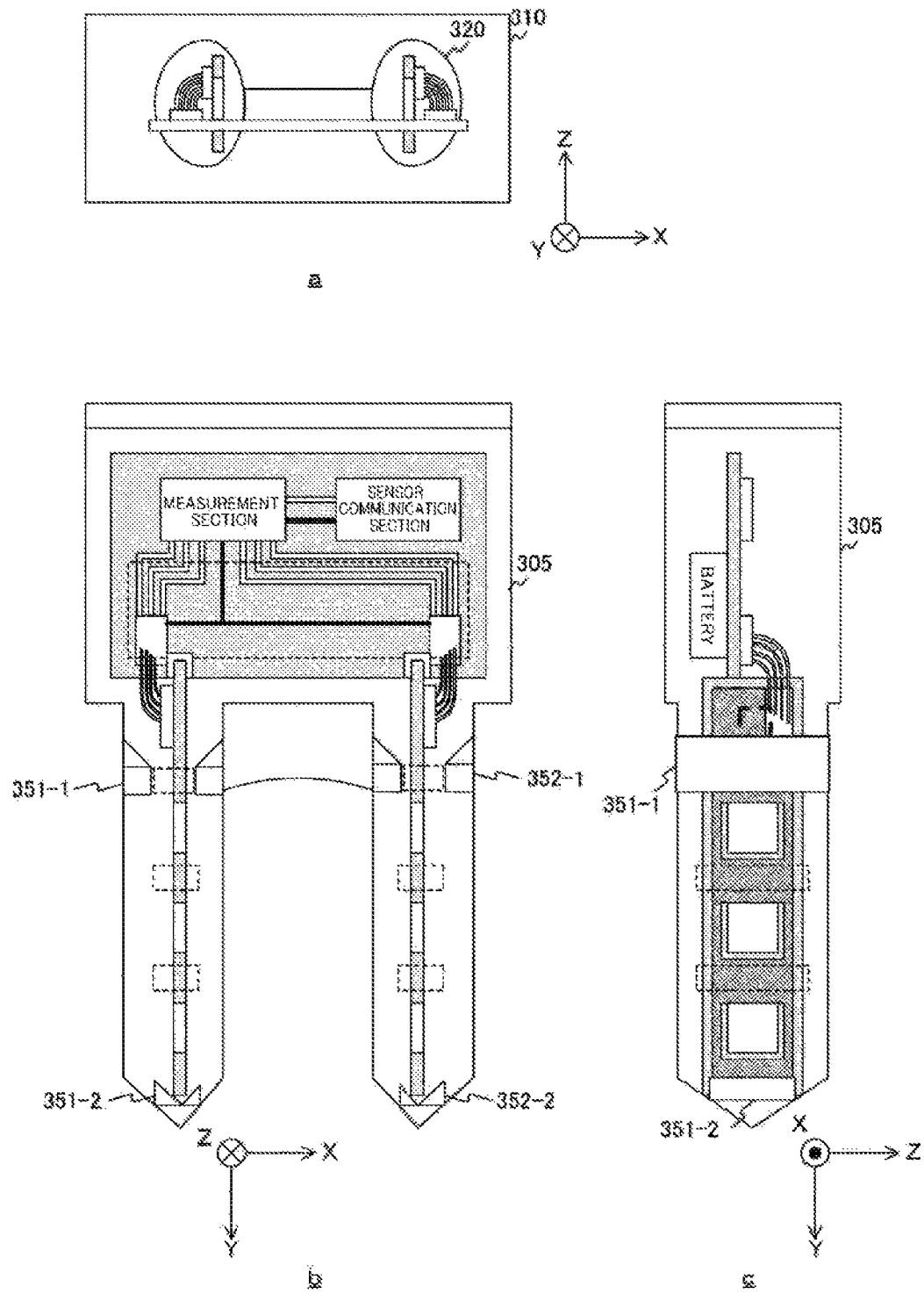

FIG. 182 is a diagram illustrating an example of the sensor device with the positioning section reduced from the inside of the measurement section casing according to the fourth modification example of the first embodiment of the present technology.

Figure 183:
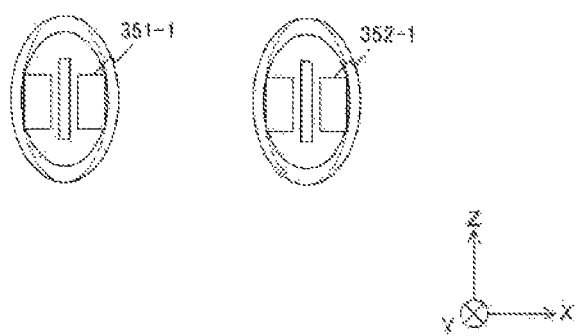

FIG. 183 is a diagram illustrating an example of a sectional view of the sensor device with the positioning section reduced from the inside of the measurement section casing according to the fourth modification example of the first embodiment of the present technology.

FIG. 184 is a diagram illustrating an example of the sensor device with jigs added thereto according to the fourth modification example of the first embodiment of the present technology.

FIG. 185 is a diagram illustrating an example of a top view and a sectional view of the sensor device with the jigs added thereto according to the fourth modification example of the first embodiment of the present technology.

Figure 186:
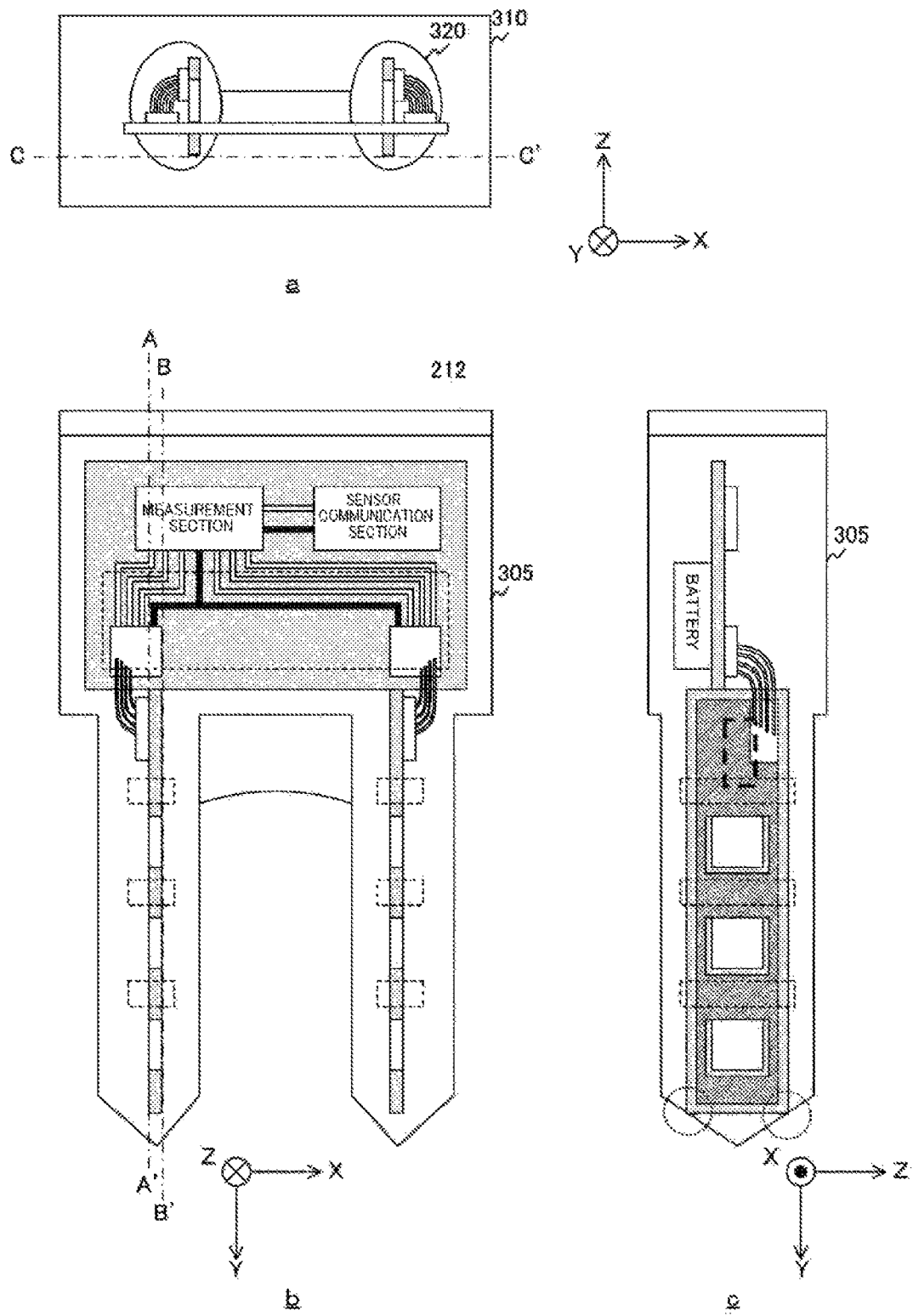

FIG. 186 is a diagram illustrating an example of the sensor device in which the intra-probe substrate is caused to abut the sensor casing according to the fourth modification example of the first embodiment of the present technology.

Figure 187:
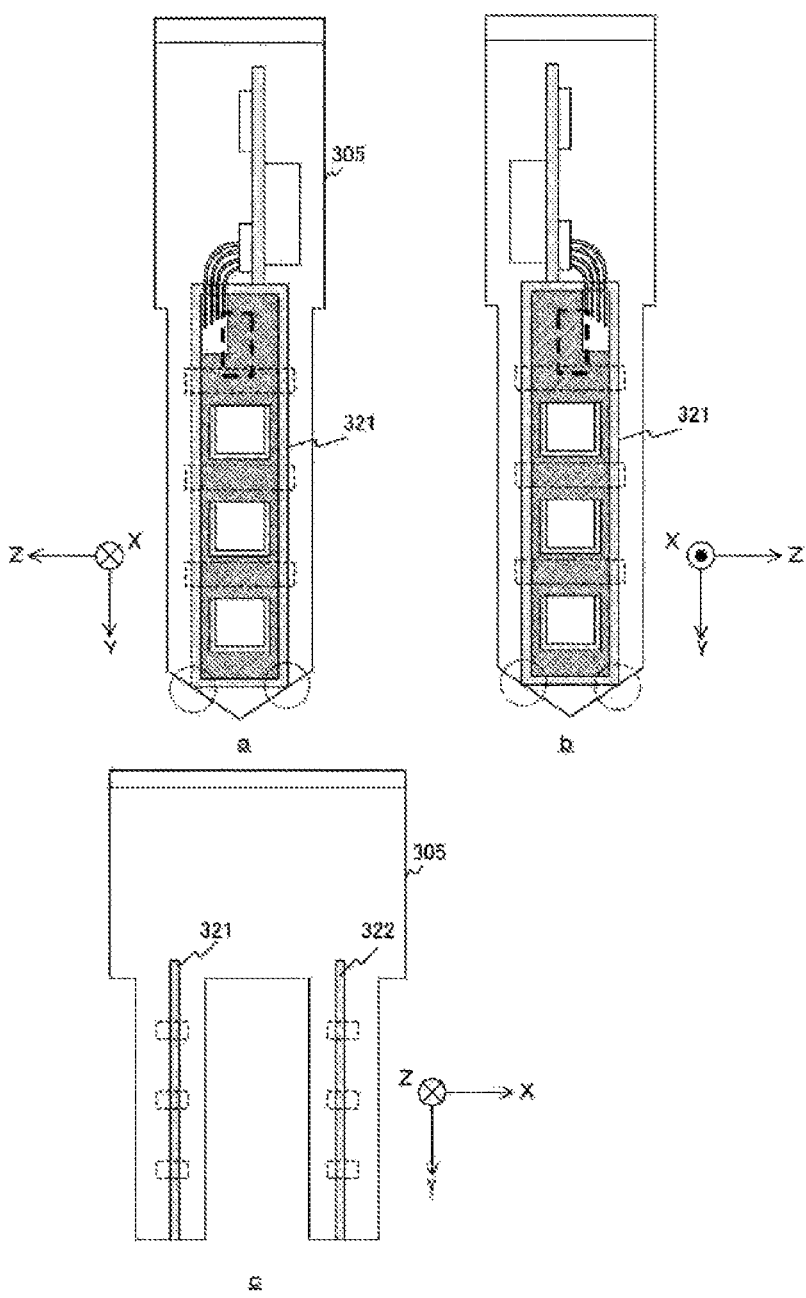

FIG. 187 is an example of a sectional view of the sensor casing according to the fourth modification example of the first embodiment of the present technology.

Figure 188:
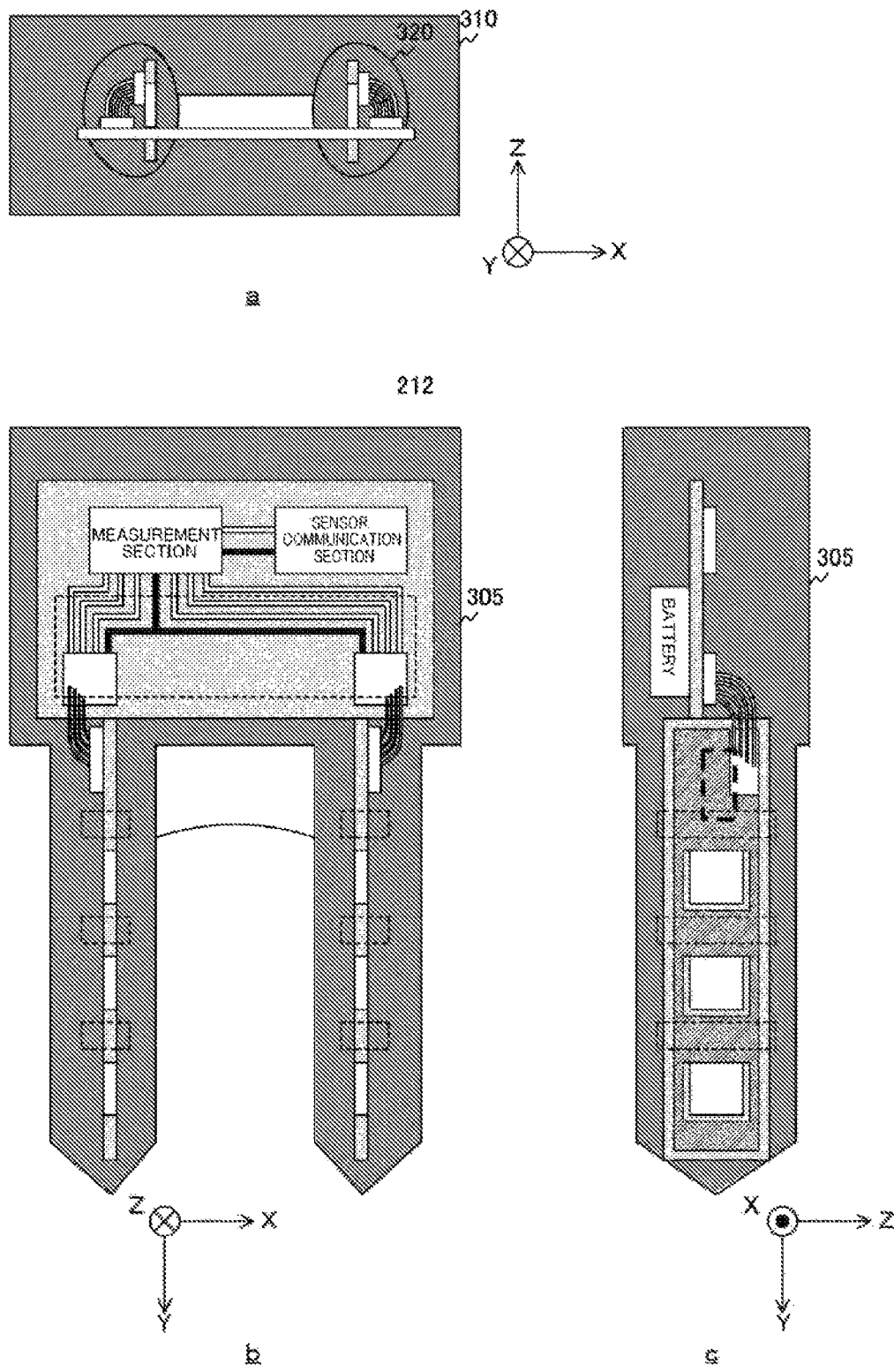

FIG. 188 is a diagram illustrating an example of the sensor device filled with a resin according to the fourth modification example of the first embodiment of the present technology.

FIG. 189 is an example of sectional views of a probe casing 320 when seen from the top in the fourth modification example of the first embodiment of the present technology and a comparative example.

Figure 190:
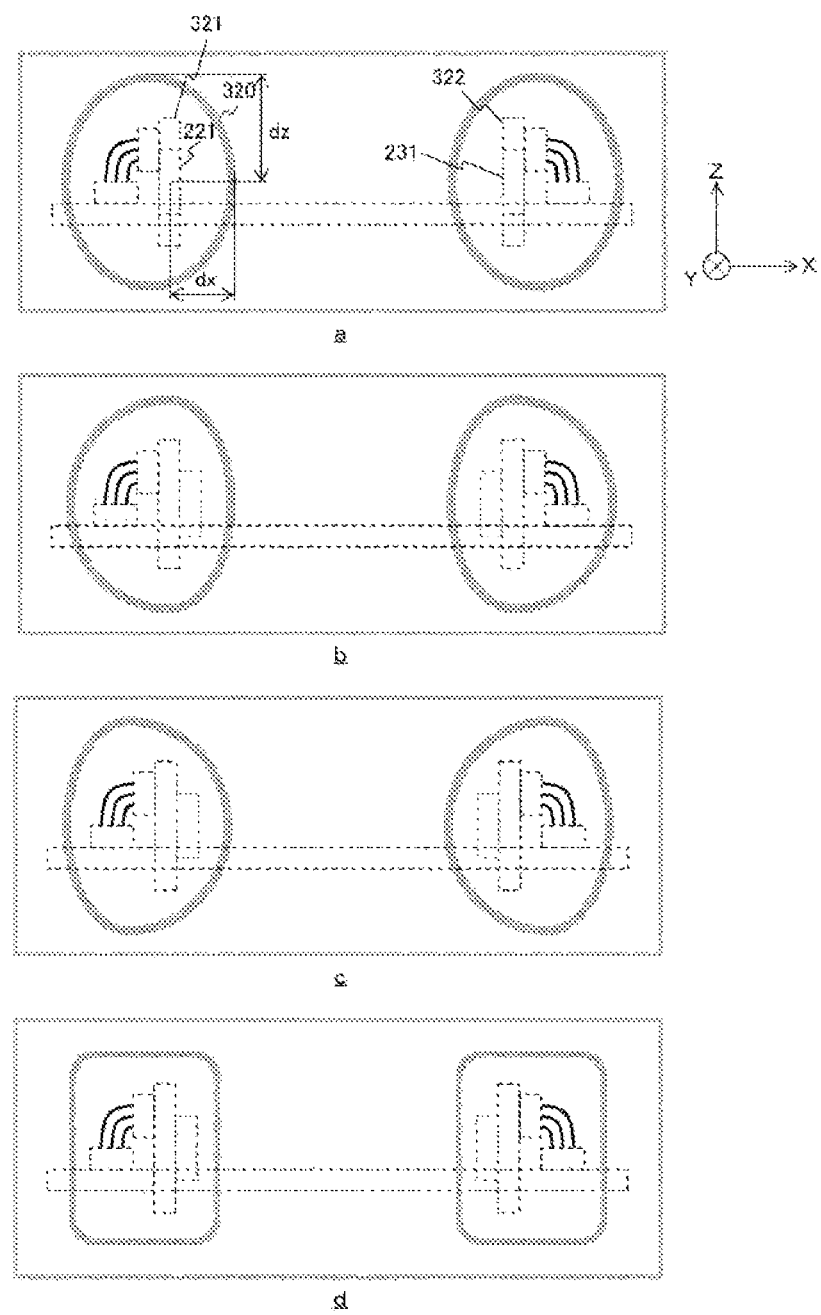

FIG. 190 is an example of a sectional view of a probe casing when seen from the top according to a fifth modification example of the first embodiment of the present technology.

Figure 191:
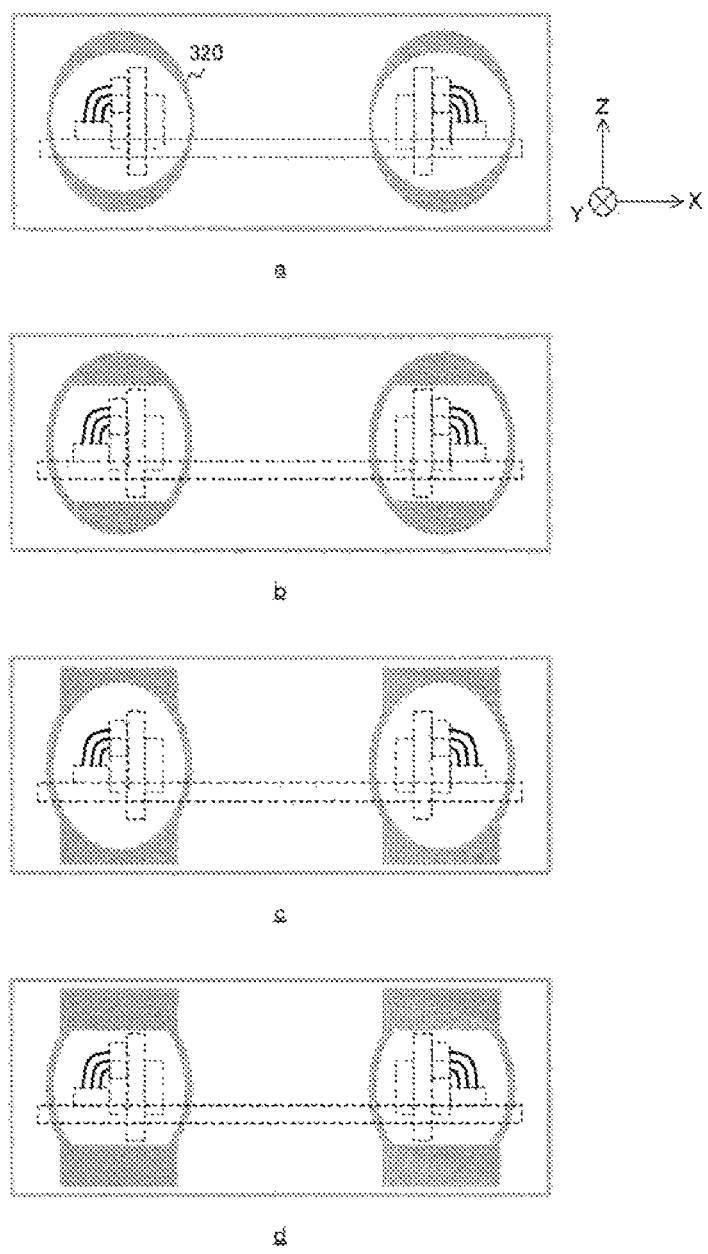

FIG. 191 is an example of a sectional view of the probe casing with a component thickness in a direction parallel with the intra-probe substrate increased by double-side radiation according to the fifth modification example of the first embodiment of the present technology.

Figure 192:
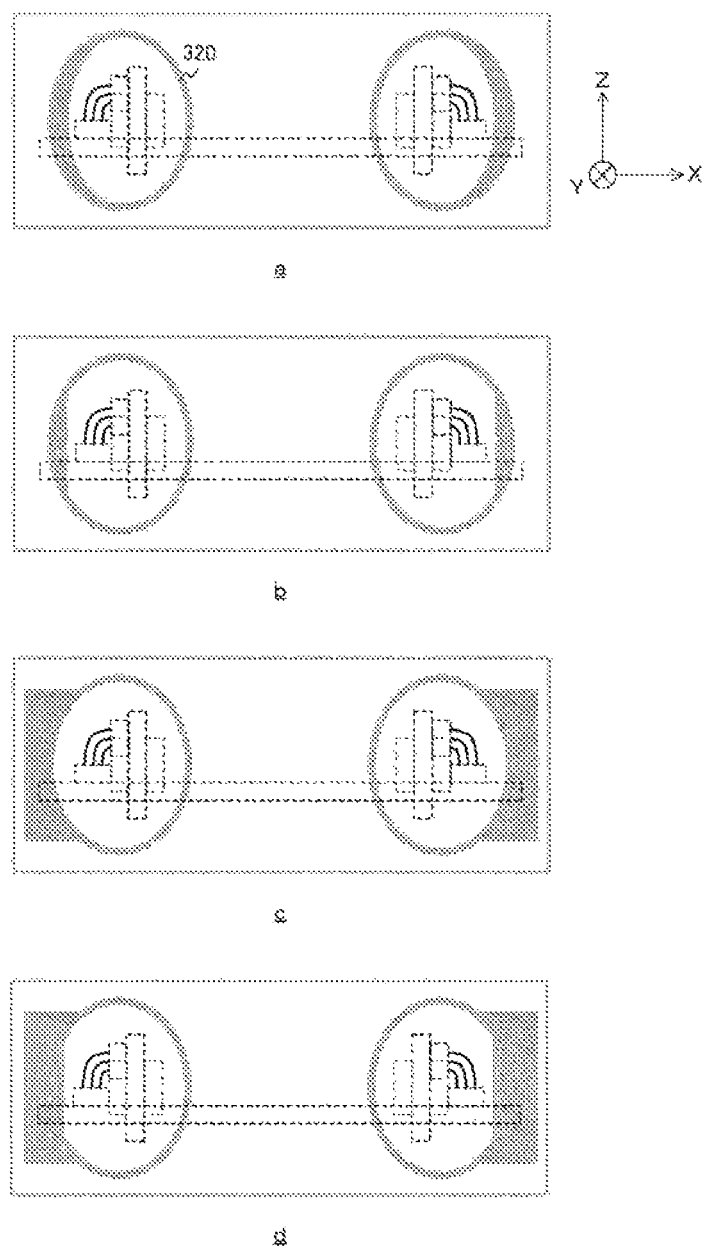

FIG. 192 is an example of a sectional view of the probe casing with a component thickness in a direction perpendicular to the intra-probe substrate increased by double-side radiation according to the fifth modification example of the first embodiment of the present technology.

Figure 193:
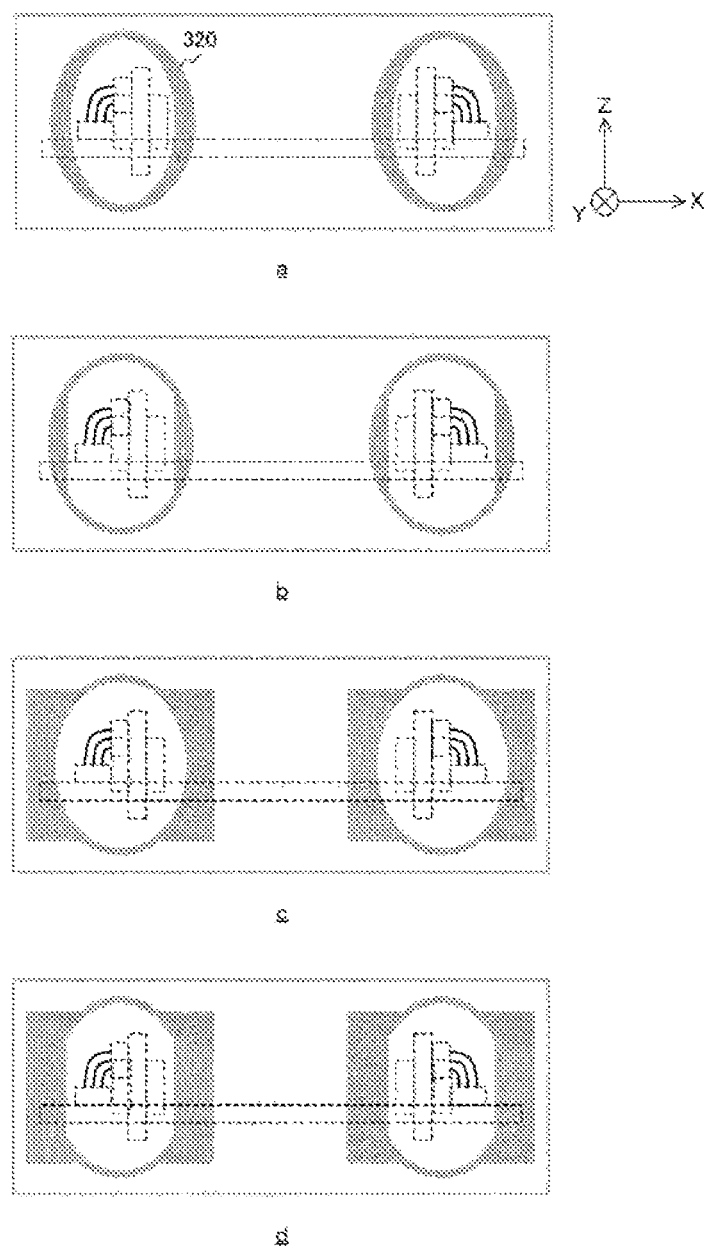

FIG. 193 is another example of a sectional view of the probe casing with the component thickness in the direction perpendicular to the intra-probe substrate increased by double-side radiation according to the fifth modification example of the first embodiment of the present technology.

Figure 194:
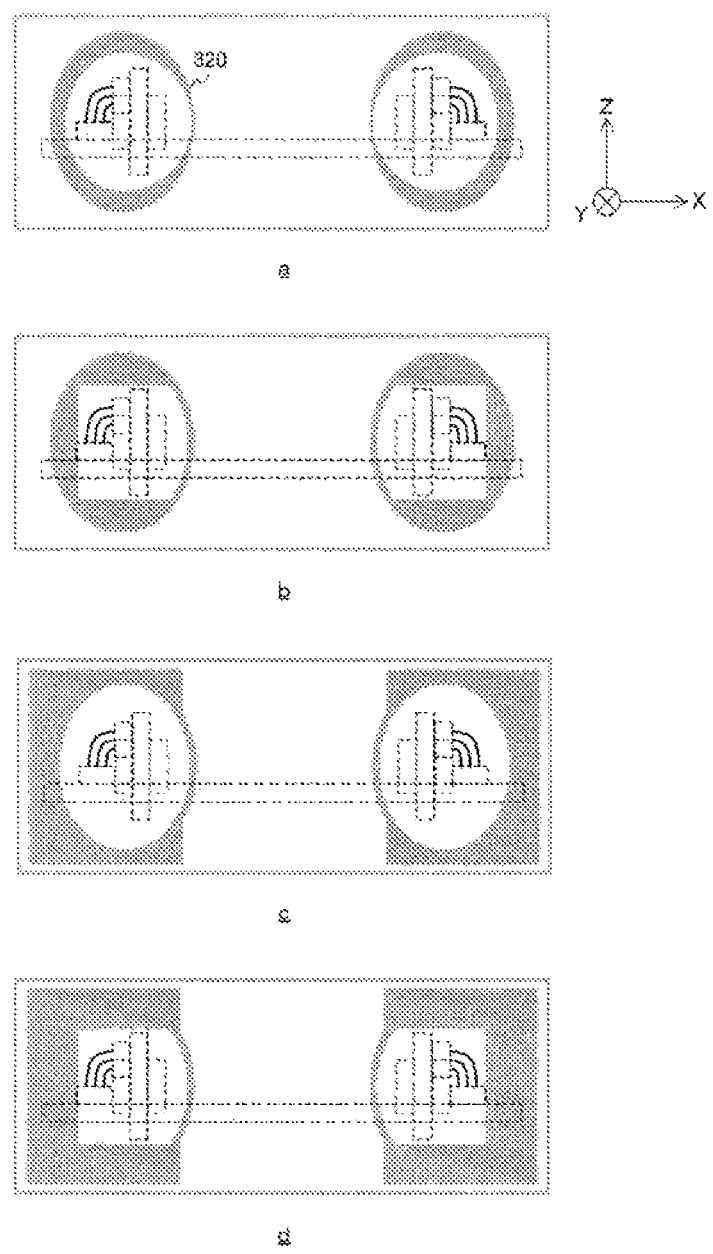

FIG. 194 is an example of a sectional view of the probe casing with the component thickness in the direction perpendicular to and outside the intra-probe substrate increased by double-side radiation according to the fifth modification example of the first embodiment of the present technology.

Figure 195:
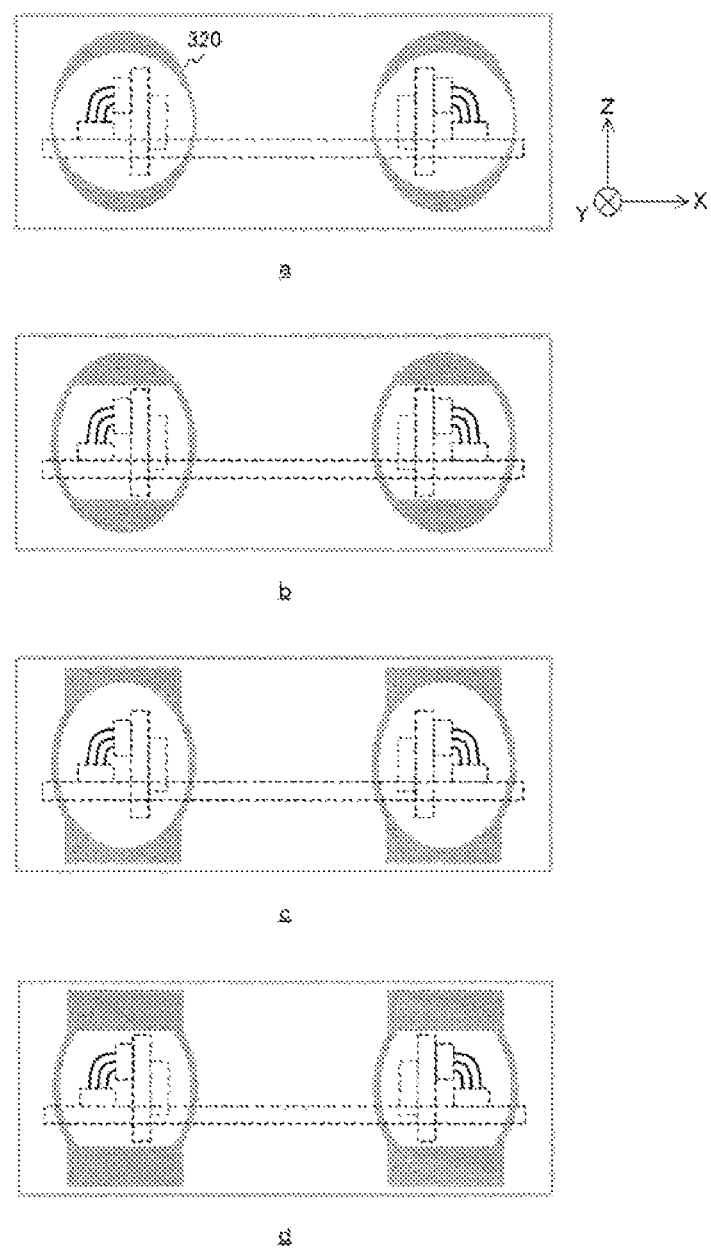

FIG. 195 is an example of a sectional view of the probe casing with the component thickness in the direction parallel to the intra-probe substrate increased by one-side radiation according to the fifth modification example of the first embodiment of the present technology.

Figure 196:
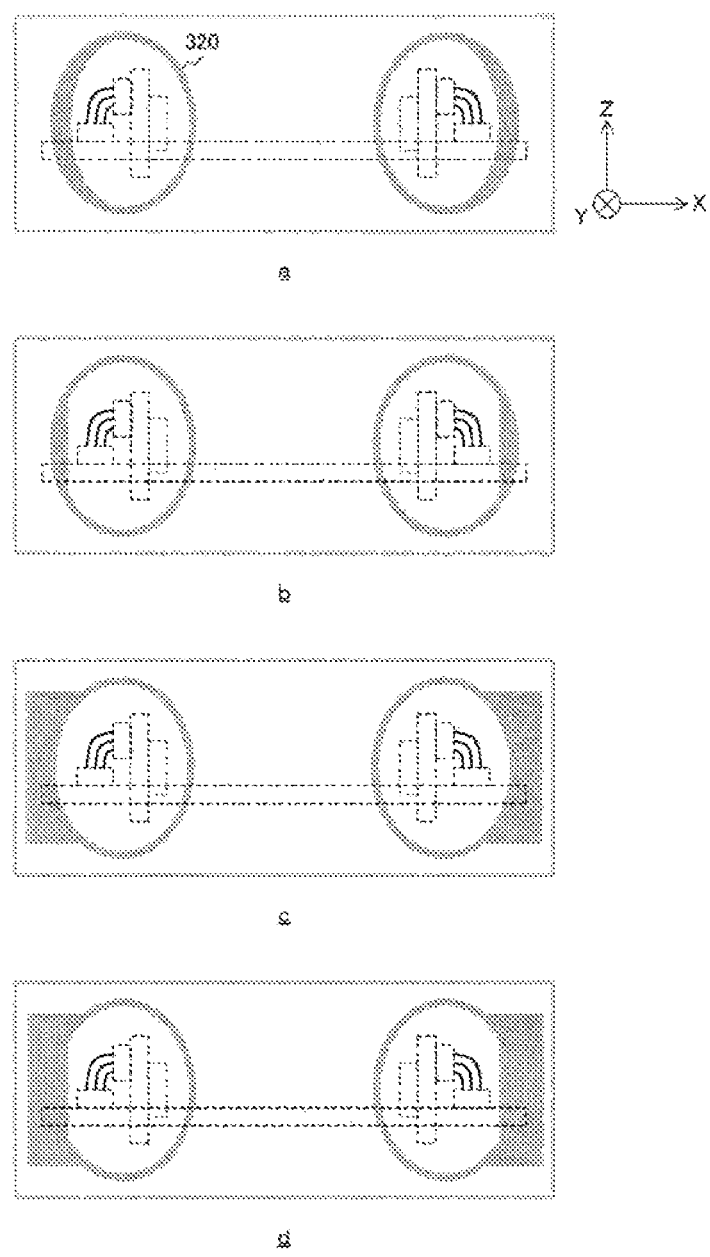

FIG. 196 is an example of a sectional view of the probe casing with the component thickness in the direction perpendicular to the intra-probe substrate increased by one-side radiation according to the fifth modification example of the first embodiment of the present technology.

Figure 197:
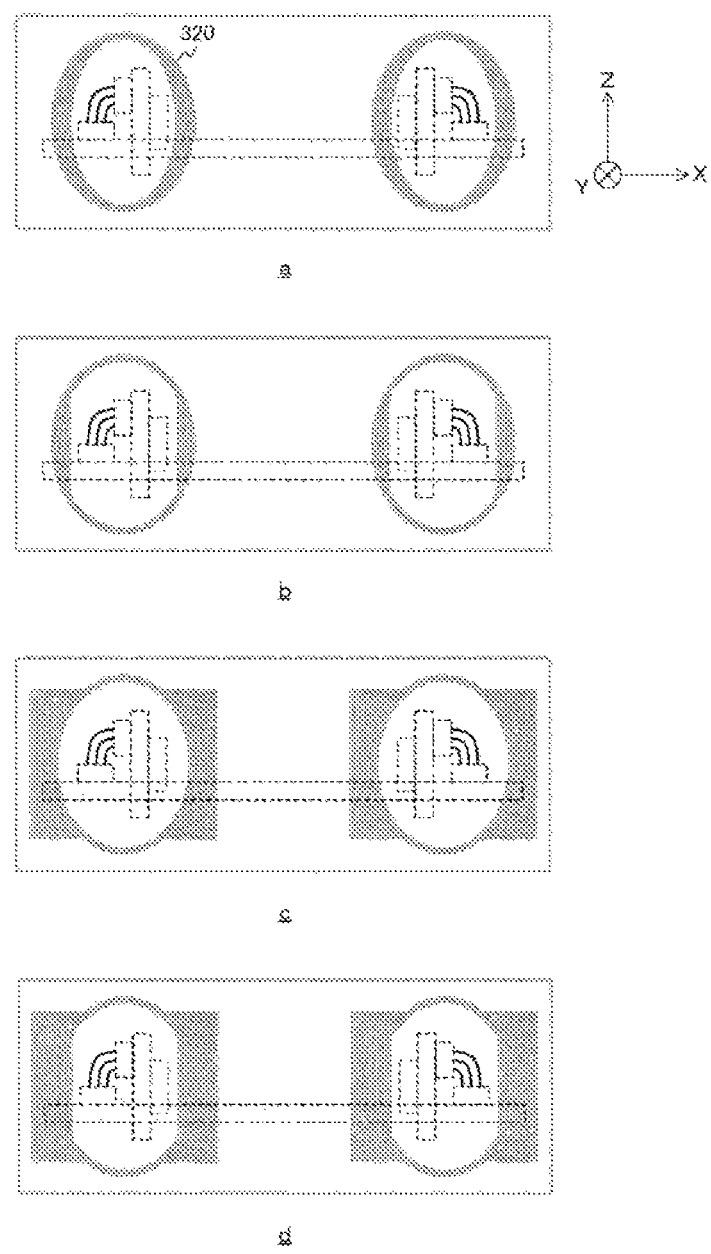

FIG. 197 is another example of a sectional view of the probe casing with the component thickness in the direction perpendicular to the intra-probe substrate increased by one-side radiation according to the fifth modification example of the first embodiment of the present technology.

Figure 198:
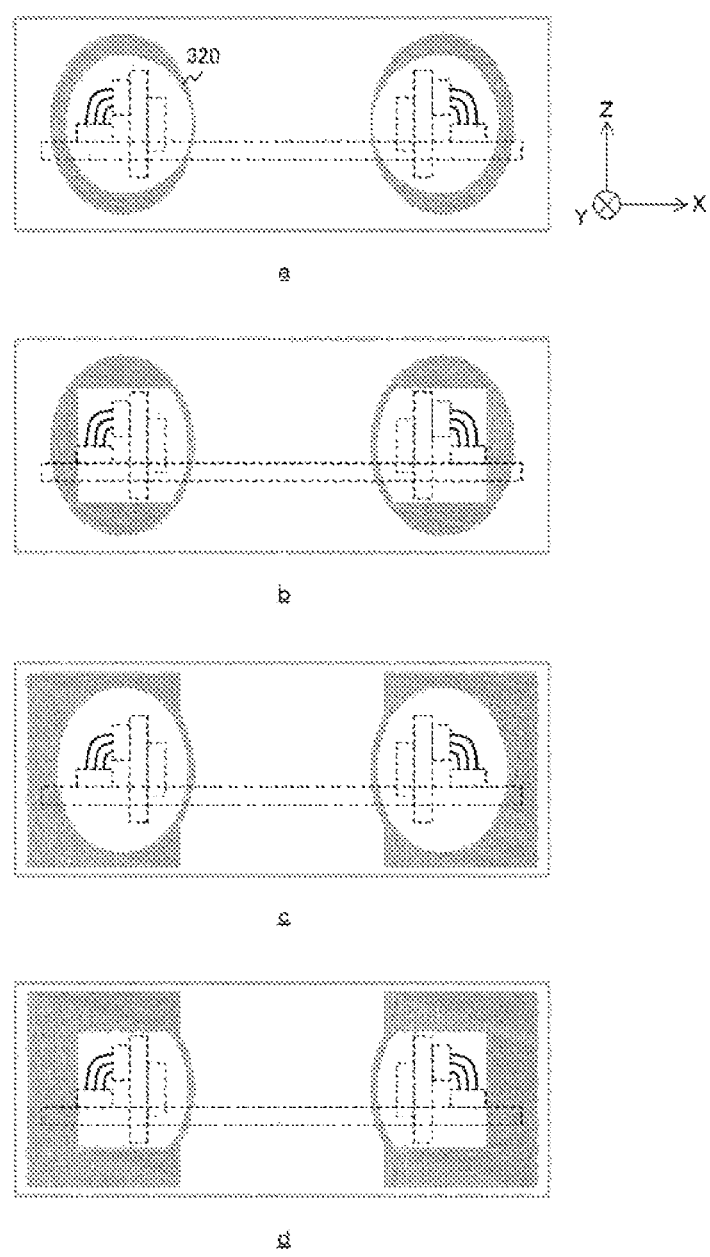

FIG. 198 is an example of a sectional view of the probe casing with the component thickness in the direction perpendicular to and outside the intra-probe substrate increased by one-side radiation according to the fifth modification example of the first embodiment of the present technology.

Figure 199:
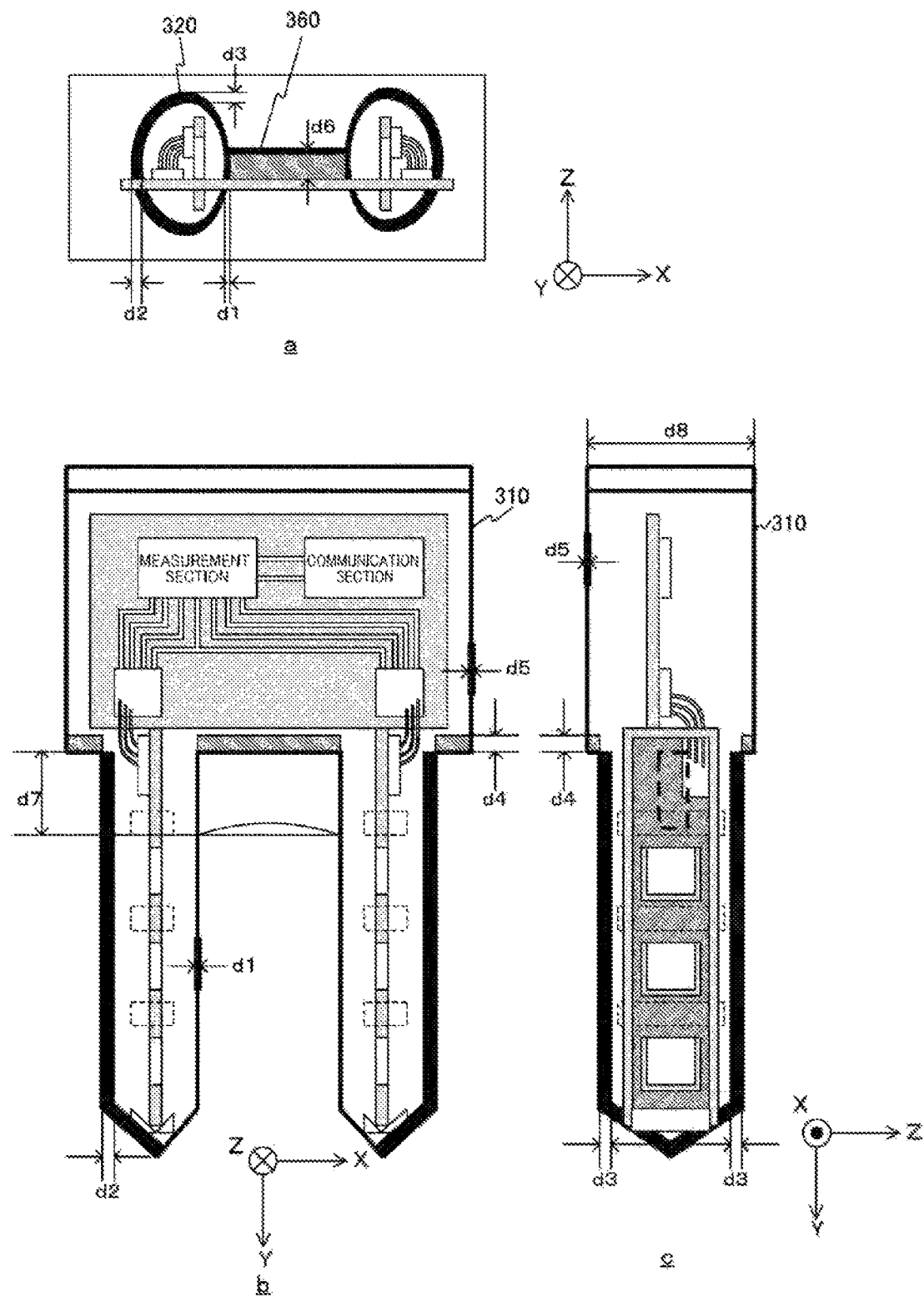

FIG. 199 is a diagram for explaining a setting example of the component thickness of the sensor casing according to the fifth modification example of the first embodiment of the present technology.

Figure 200:
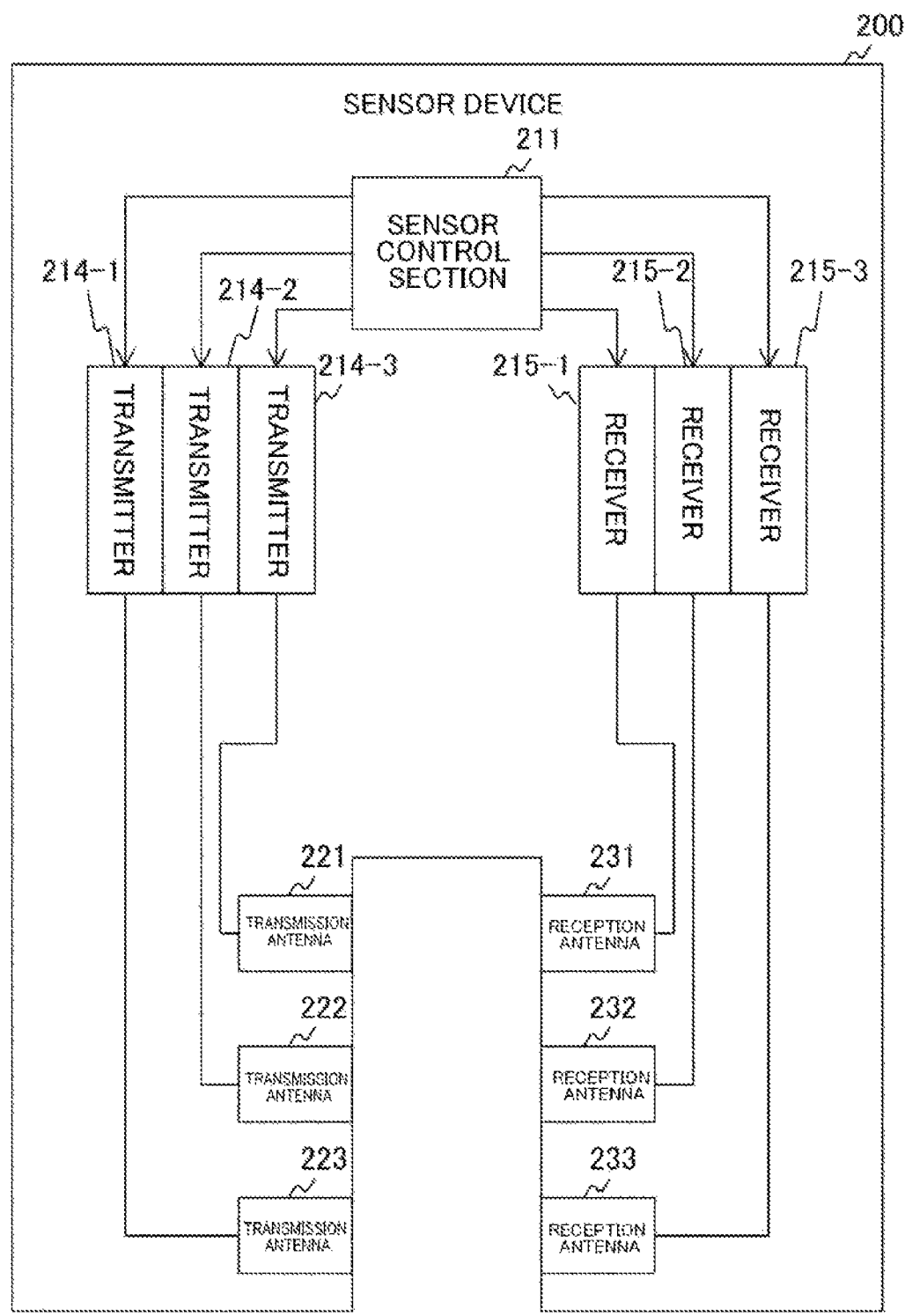

FIG. 200 is a diagram illustrating a configuration example of a sensor device including a transceiver provided for each antenna according to a sixth modification example of the first embodiment of the present technology.

Figure 201:
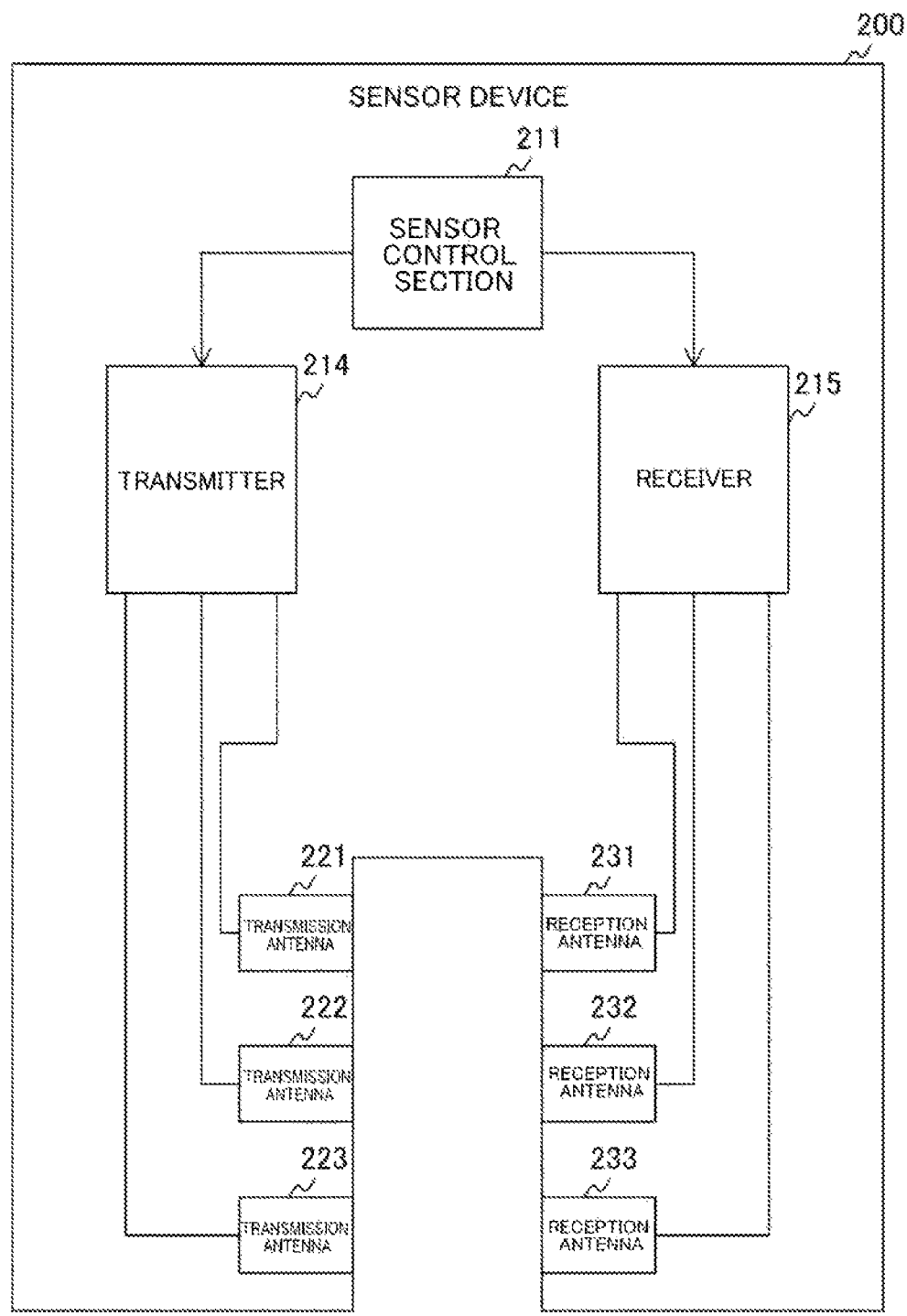

FIG. 201 is a diagram illustrating a configuration example of the sensor device including one transmitter and one receiver according to the sixth modification example of the first embodiment of the present technology.

Figure 202:
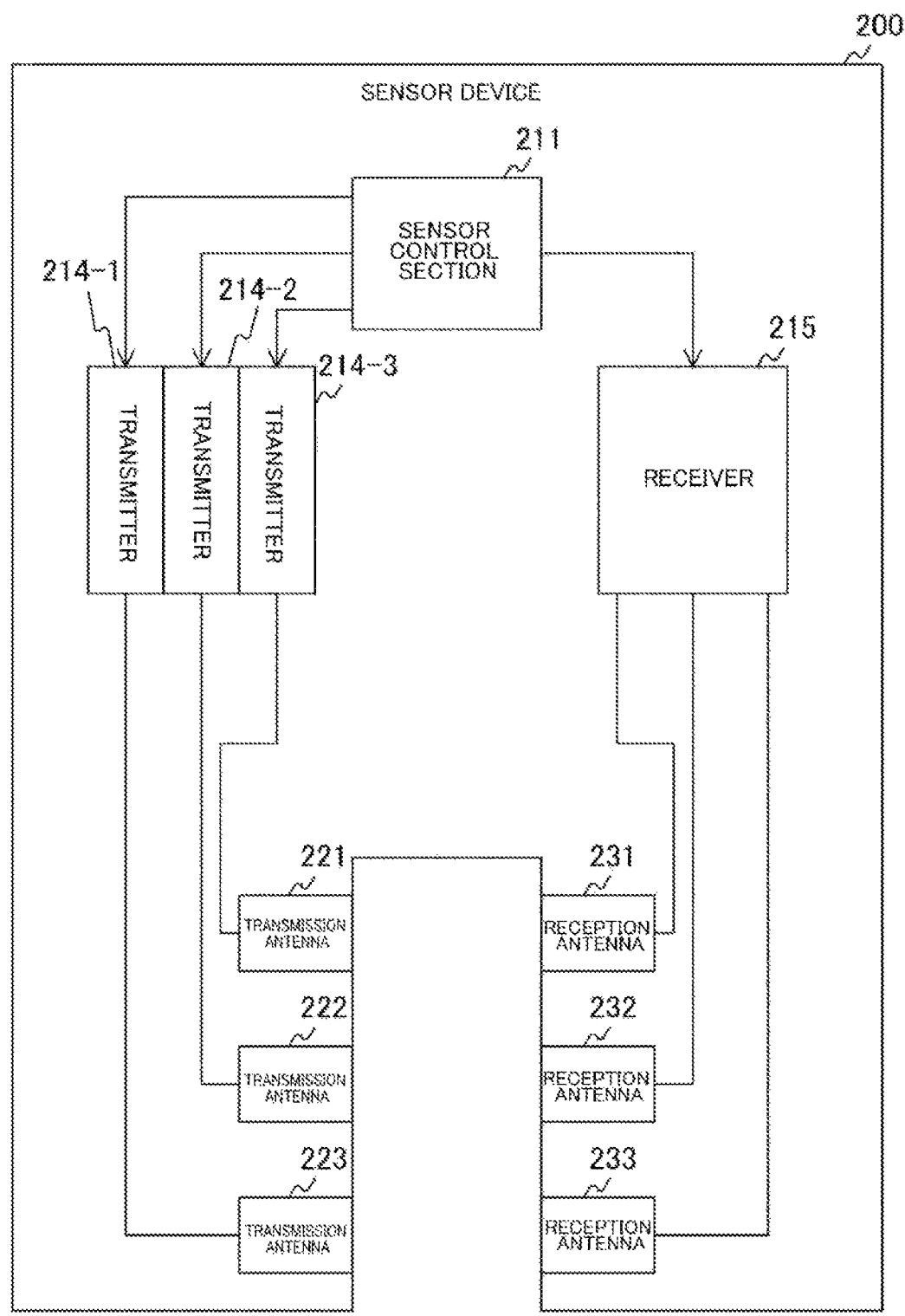

FIG. 202 is a diagram illustrating a configuration example of the sensor device including one receiver according to the sixth modification example of the first embodiment of the present technology.

Figure 203:
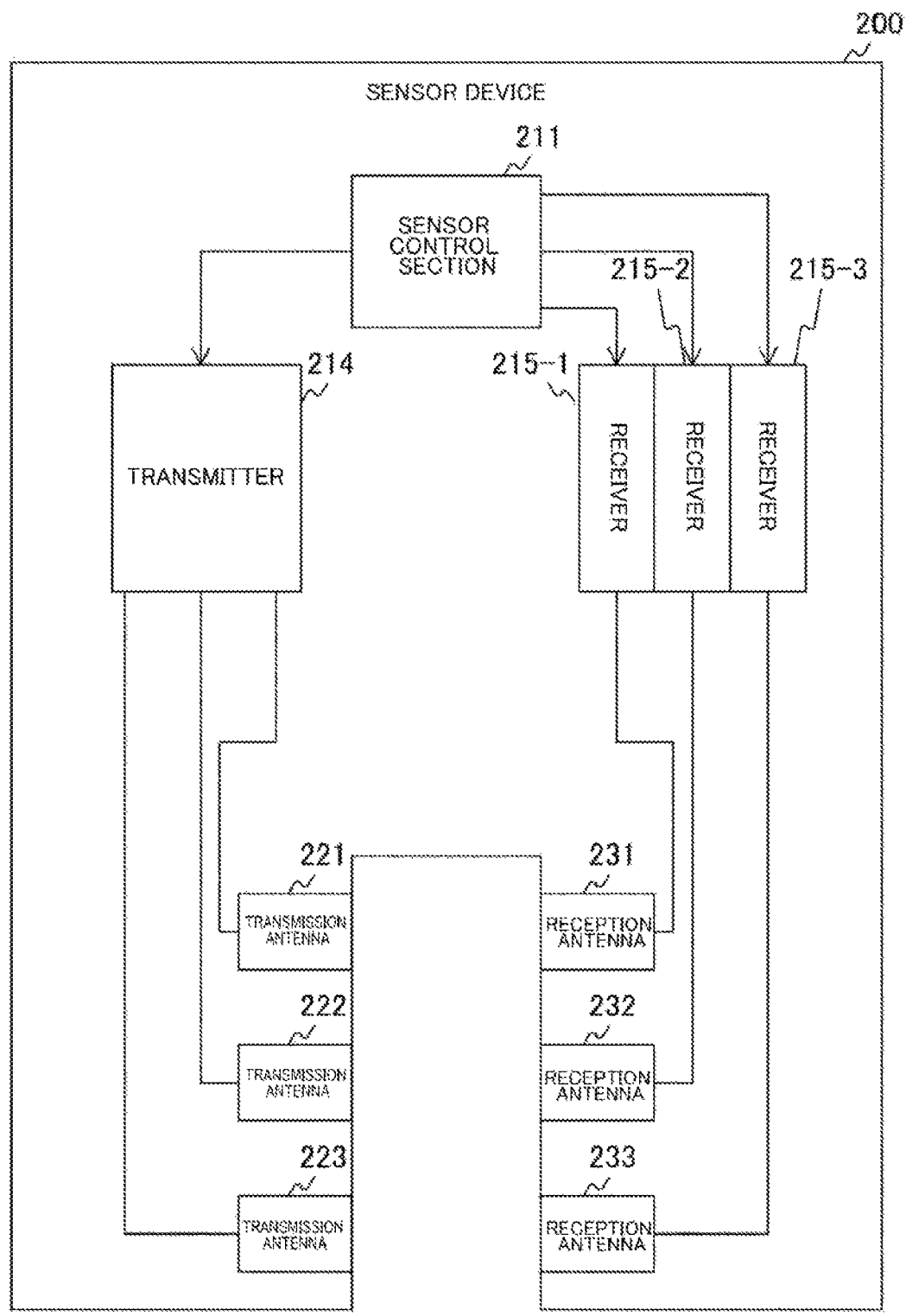

FIG. 203 is a diagram illustrating a configuration example of the sensor device including one transmitter according to the sixth modification example of the first embodiment of the present technology.

Figure 204:
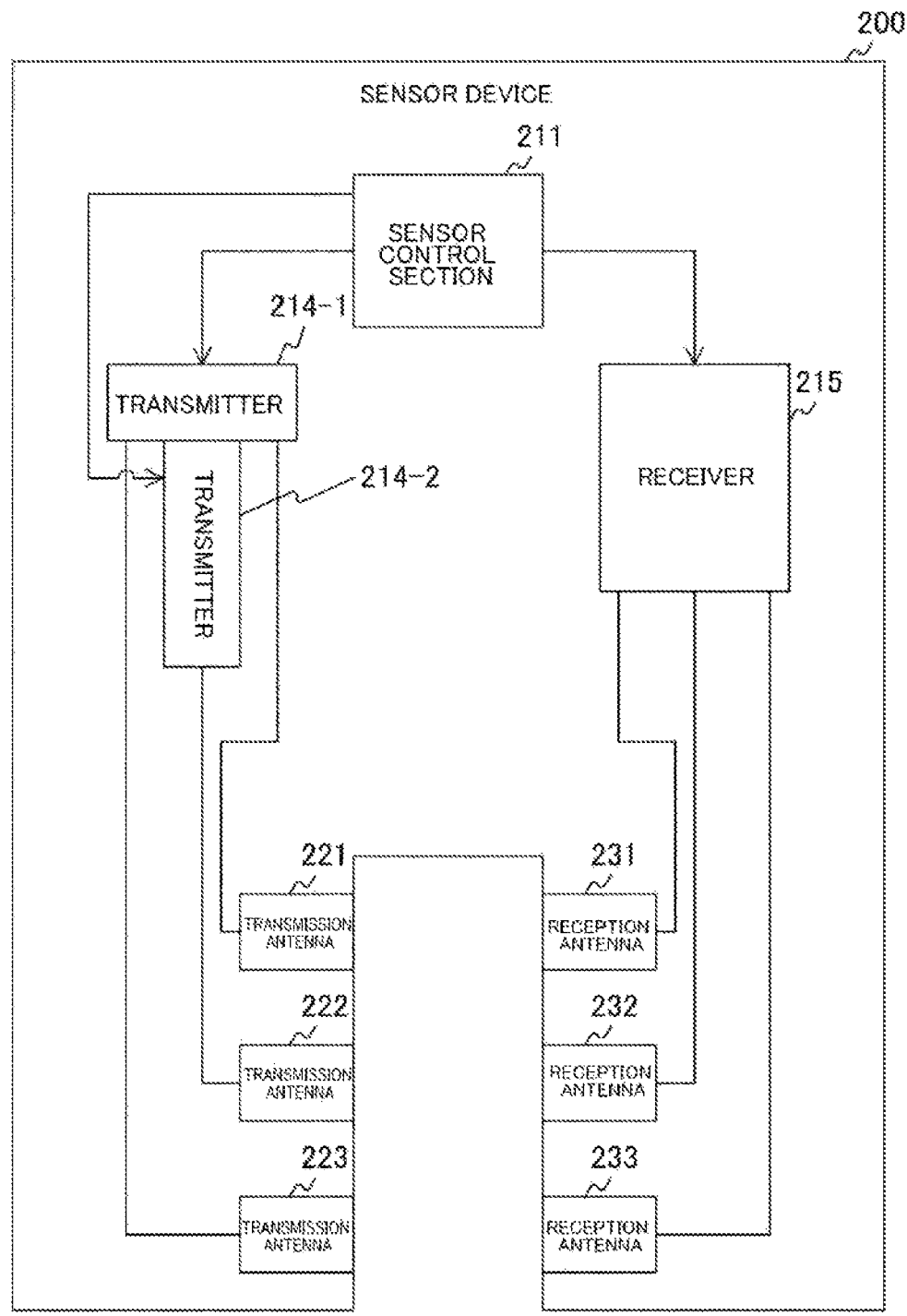

FIG. 204 is a diagram illustrating another example of the sensor device including a plurality of transmitters according to the sixth modification example of the first embodiment of the present technology.

Figure 205:
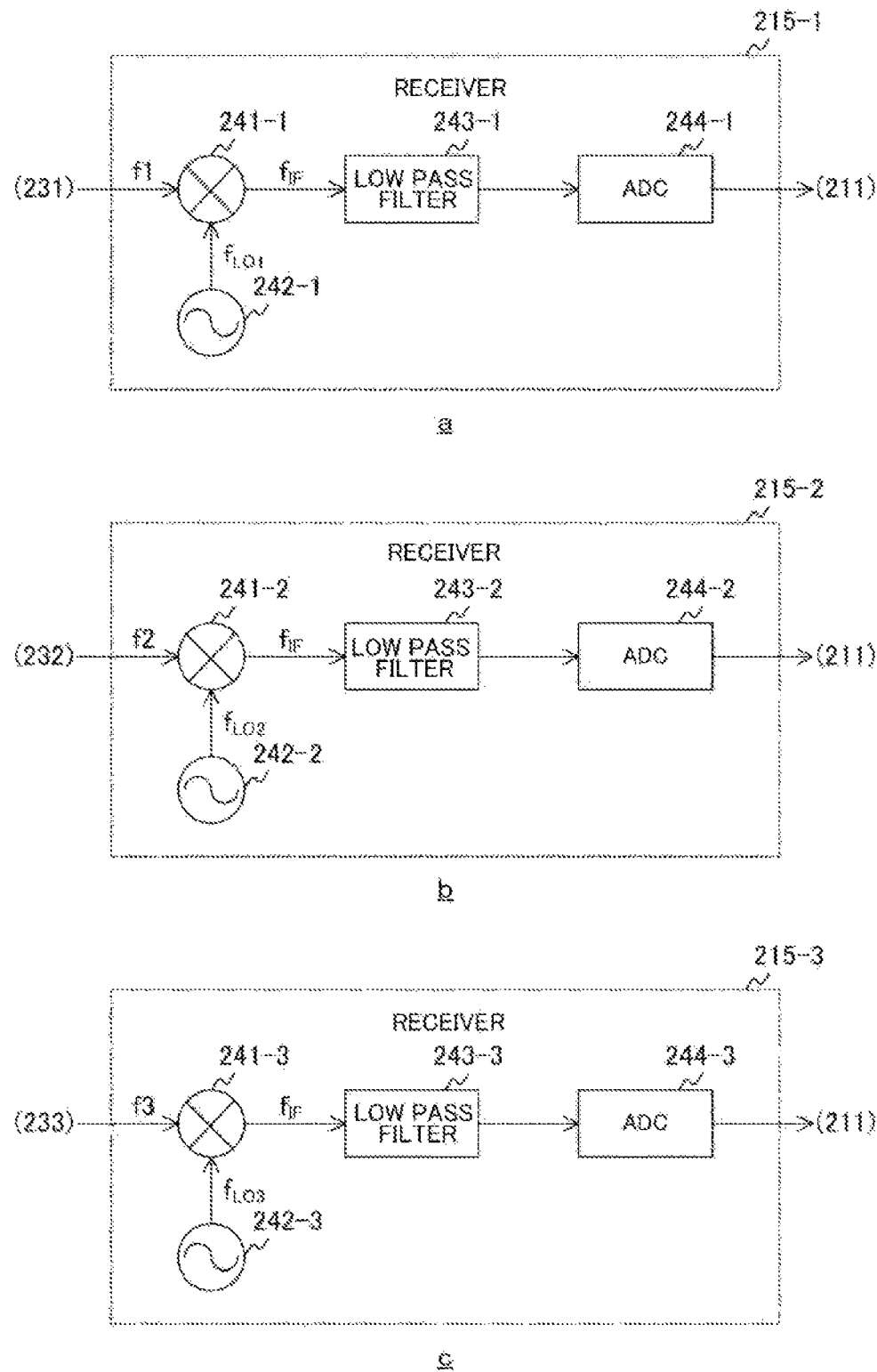

FIG. 205 is a block diagram illustrating a configuration example of the receiver according to the sixth modification example of the first embodiment of the present technology.

Figure 206:
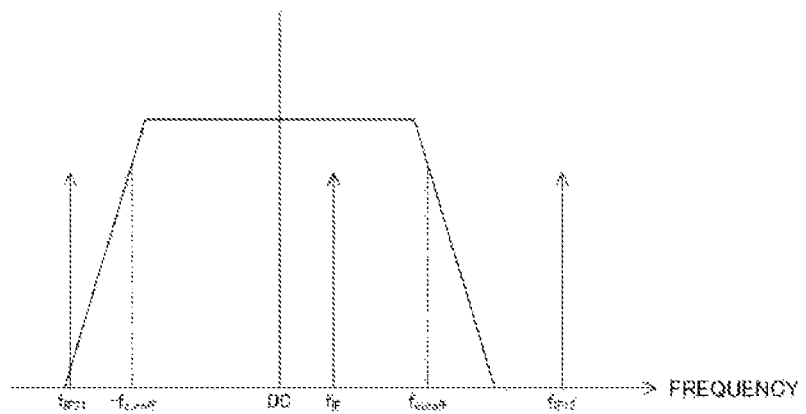

FIG. 206 is a diagram illustrating an example of a frequency property of a reception signal according to the sixth modification example of the first embodiment of the present technology.

FIG. 207 is an example of a timing chart for frequency-division driving according to the sixth modification example of the first embodiment of the present technology.

Figure 208:
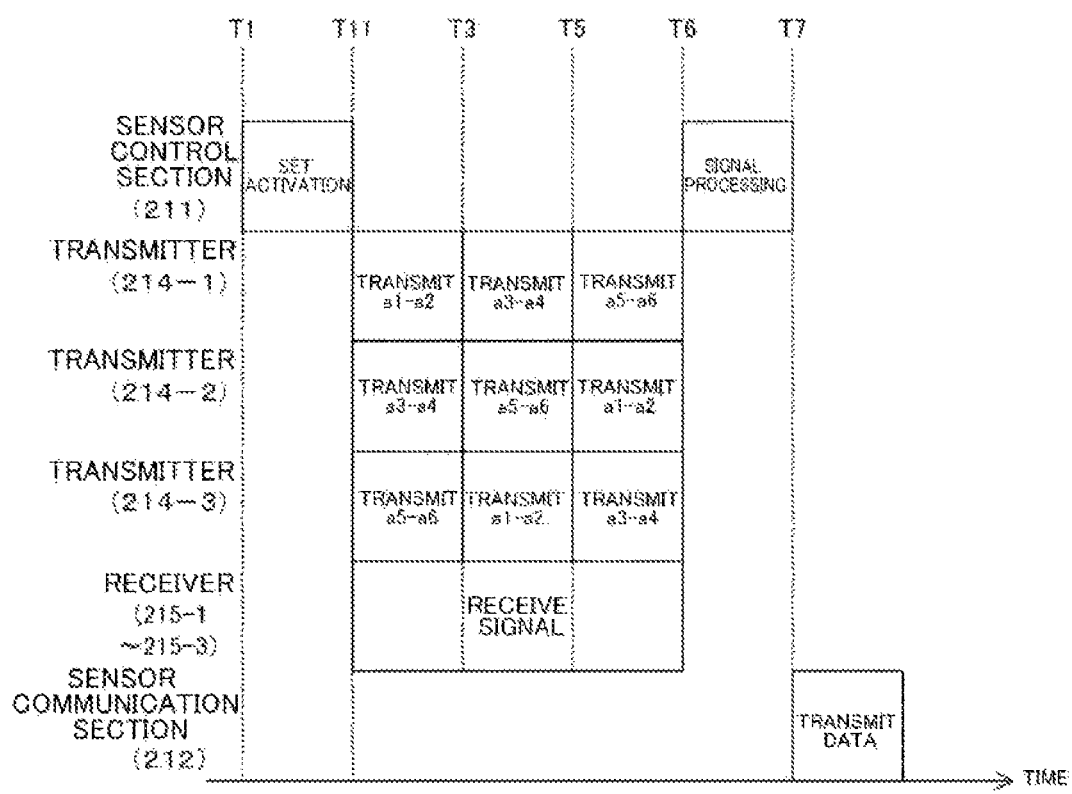

FIG. 208 is an example of a timing chart illustrating operations of each section in the sensor device according to the sixth modification example of the first embodiment of the present technology.

FIG. 209 is an example of a timing chart for frequency-division driving when a sweep period is shortened according to the sixth modification example of the first embodiment of the present technology.

Figure 210:
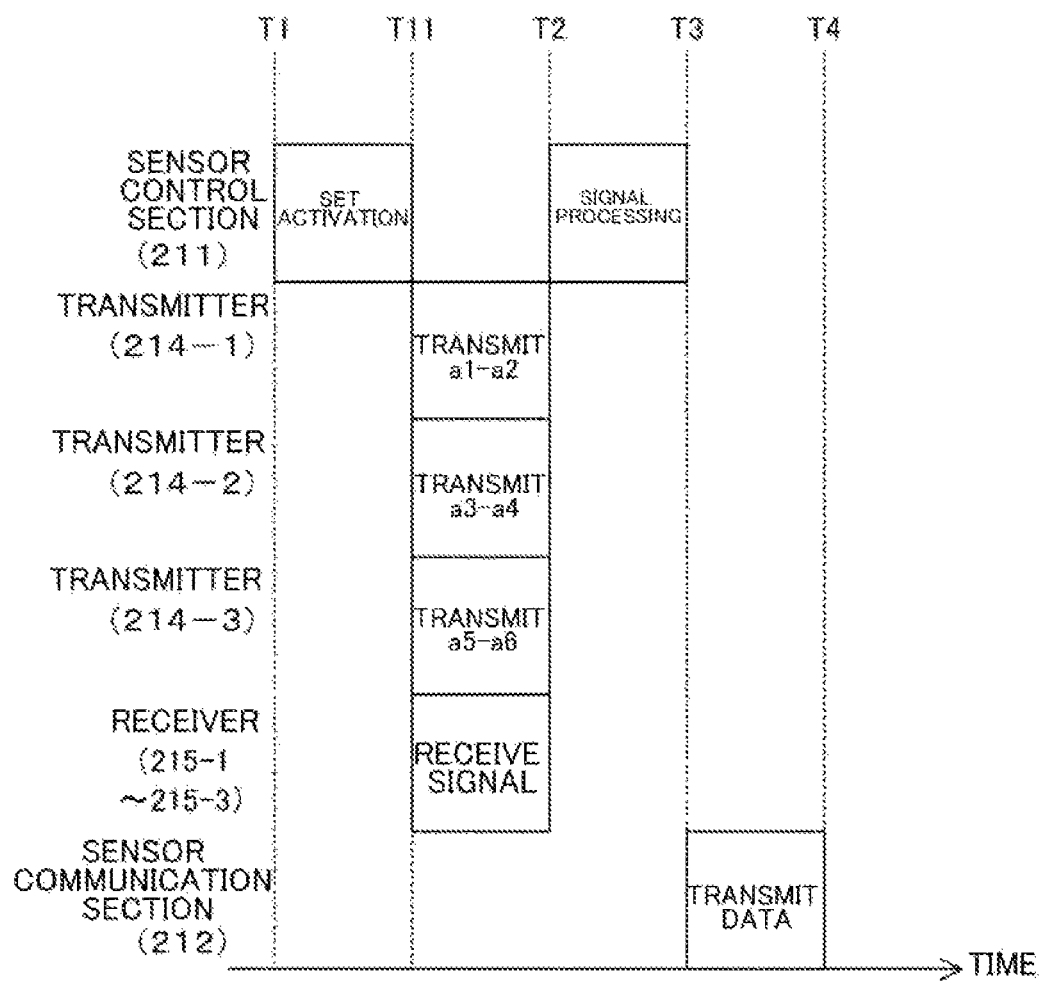

FIG. 210 is an example of a timing chart illustrating operations of each section in the sensor device when the sweep period is shortened according to the sixth modification example of the first embodiment of the present technology.

FIG. 211 is an example of a timing chart for frequency-division driving in which frequencies of two antennas are the same according to the sixth modification example of the first embodiment of the present technology.

Figure 212:
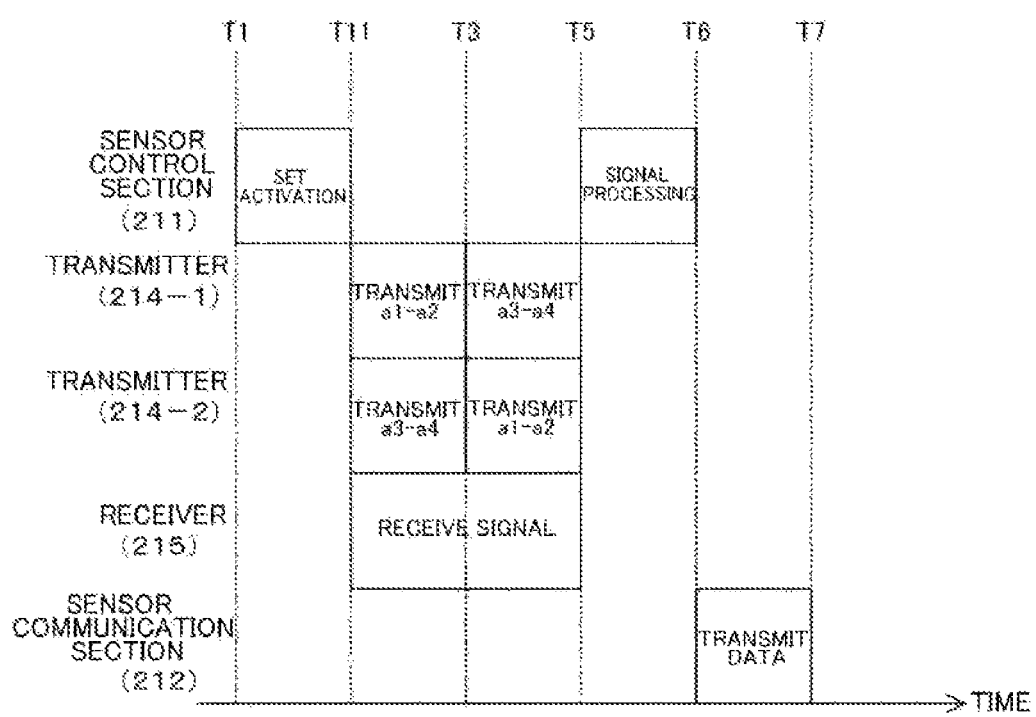

FIG. 212 is an example of a timing chart illustrating operations of each section in the sensor device in which the frequencies of the two antennas are the same according to the sixth modification example of the first embodiment of the present technology.

Figure 213:
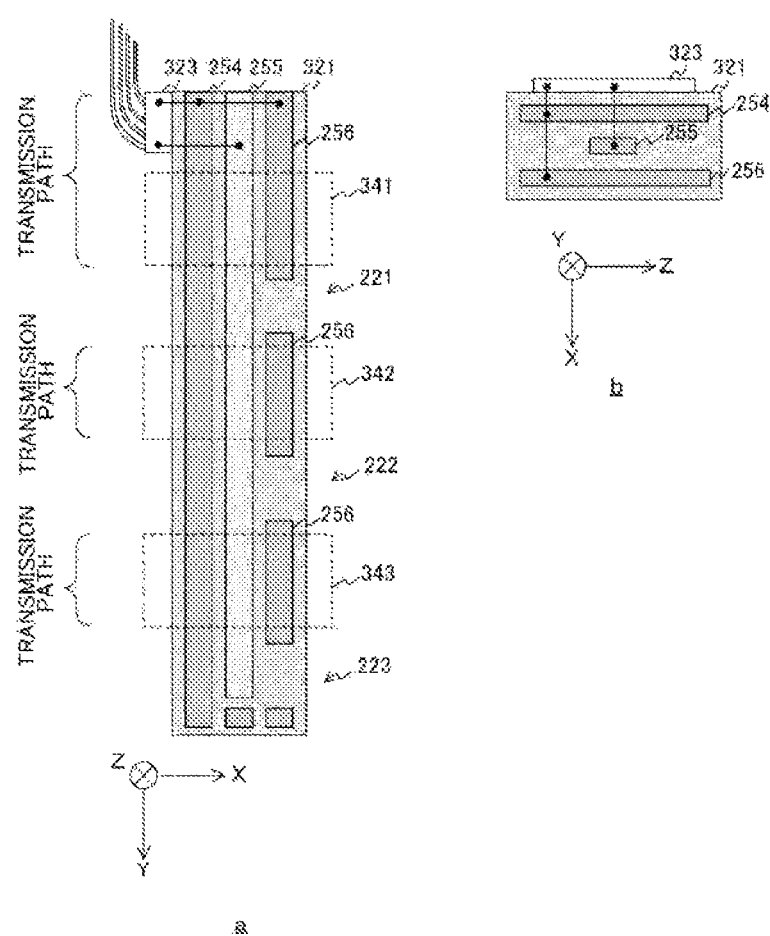

FIG. 213 is a diagram illustrating an example of a sectional view of an intra-probe substrate according to a seventh modification example of the first embodiment of the present technology.

Figure 214:
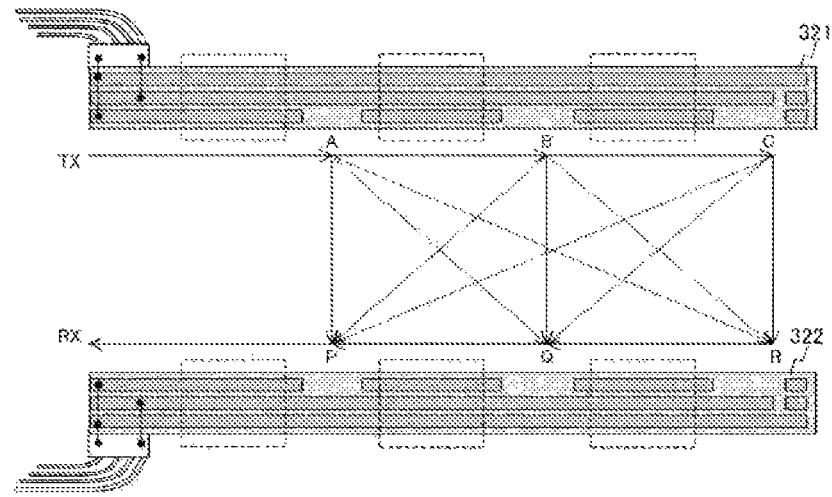

FIG. 214 is a diagram illustrating a signal transmission path for each antenna according to the seventh modification example of the first embodiment of the present technology.

Figure 215:
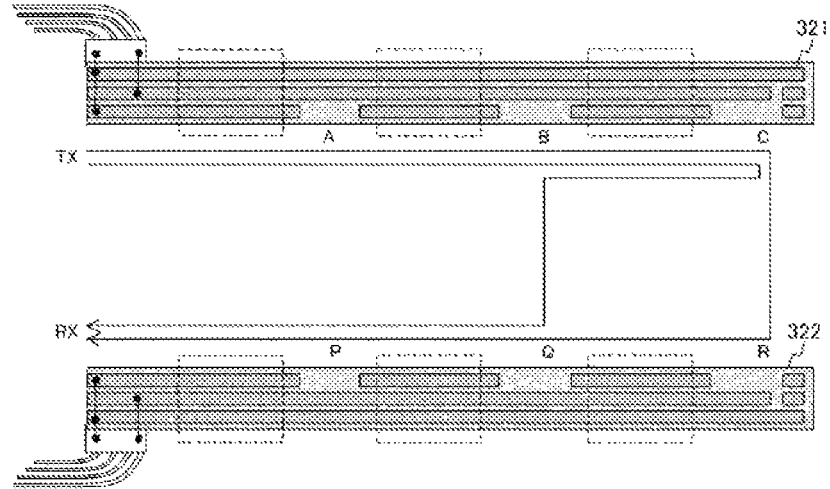

FIG. 215 is a diagram illustrating signal transmission paths of two systems according to the seventh modification example of the first embodiment of the present technology.

Figure 216:
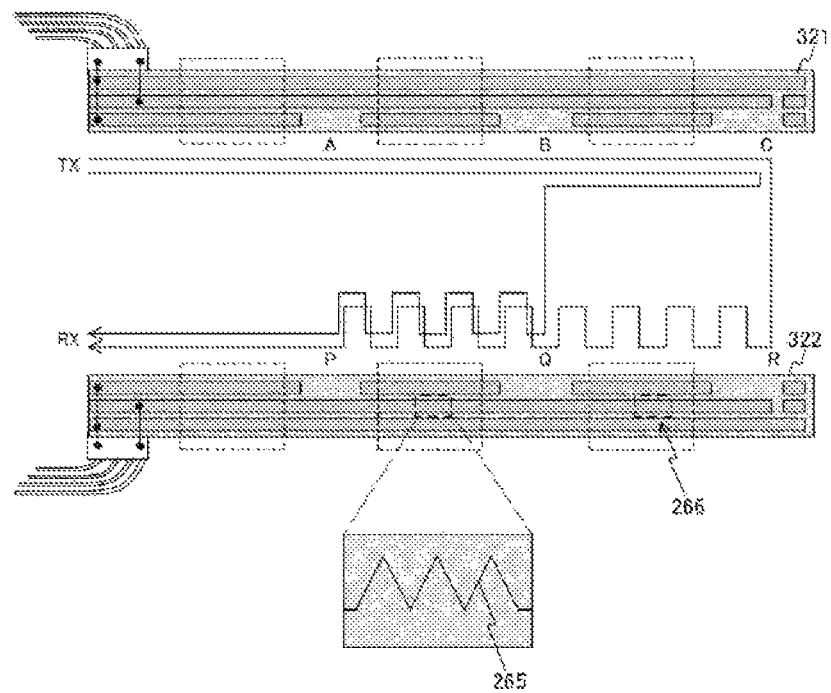

FIG. 216 is a diagram illustrating an example of the sensor device provided with a delay line according to the seventh modification example of the first embodiment of the present technology.

Figure 217:
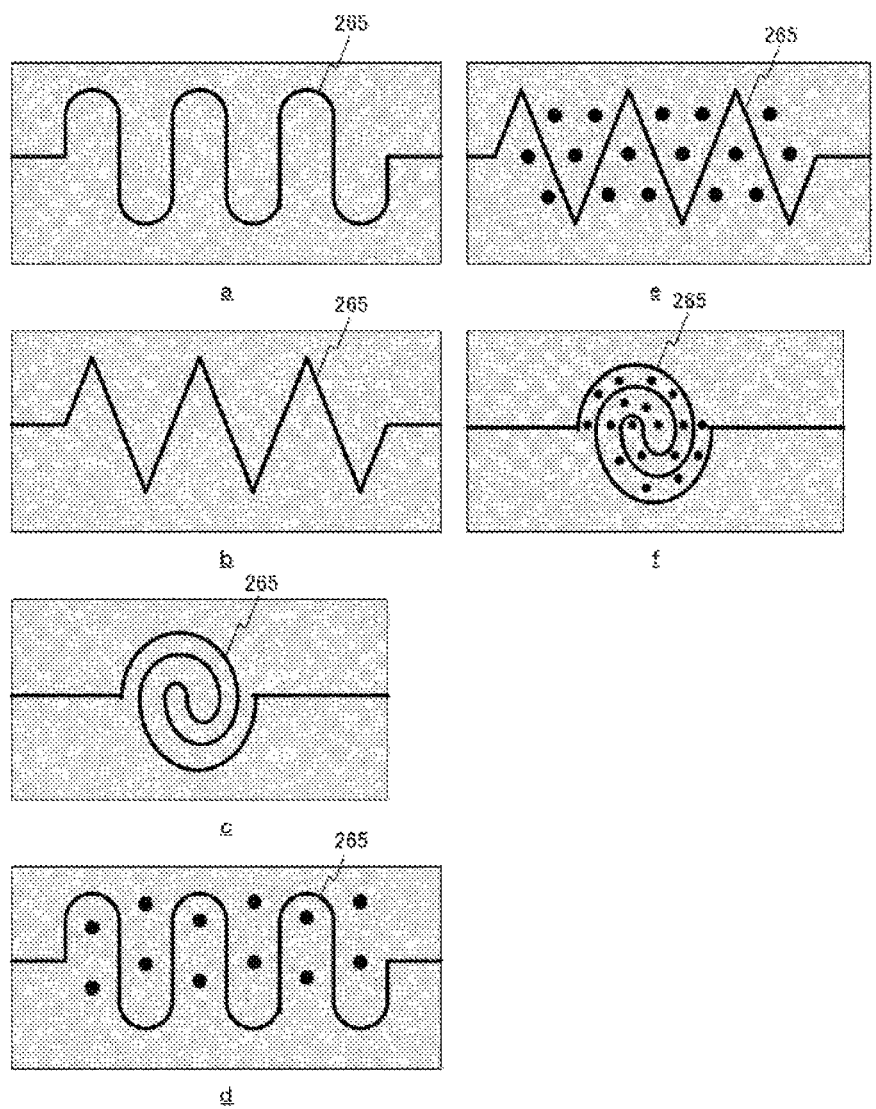

FIG. 217 is a diagram illustrating an example of the shape of the delay line according to the seventh modification example of the first embodiment of the present technology.

Figure 218:
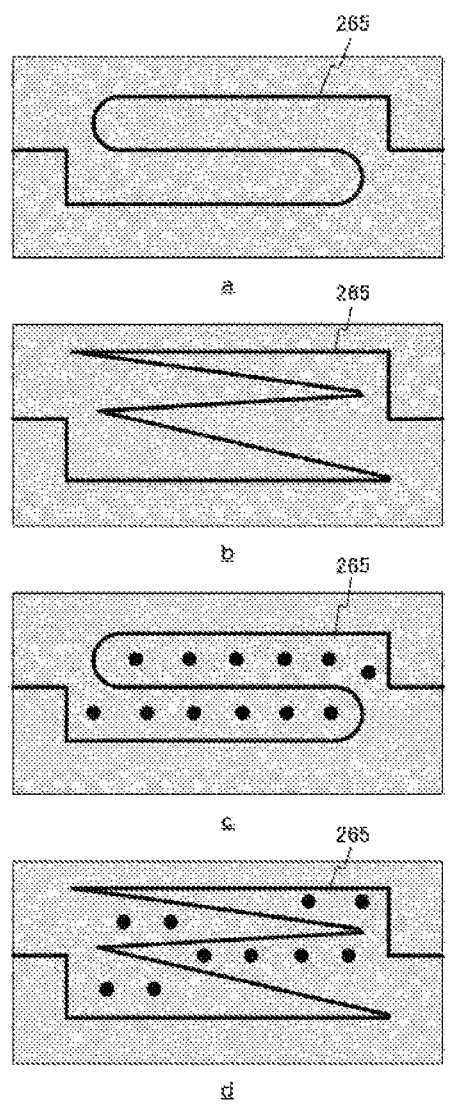

FIG. 218 is a diagram illustrating another example of the shape of the delay line according to the seventh modification example of the first embodiment of the present technology.

Figure 219:
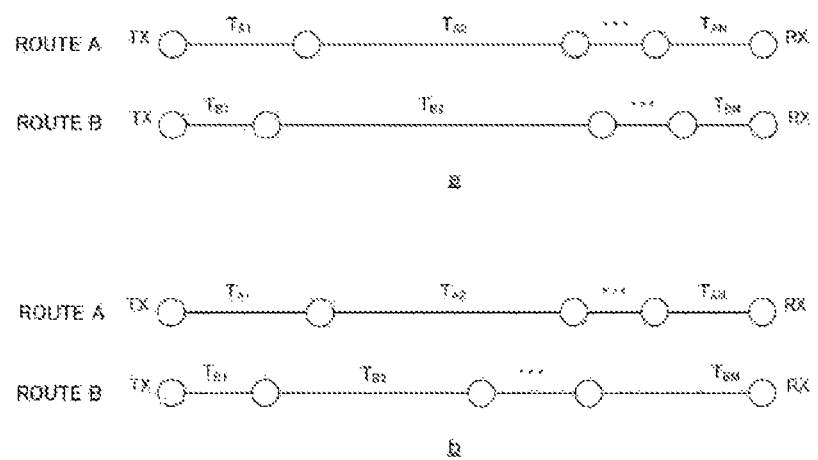

FIG. 219 is a diagram for explaining a method for setting the amount of delay of the delay line according to the seventh modification example of the first embodiment of the present technology.

Figure 220:
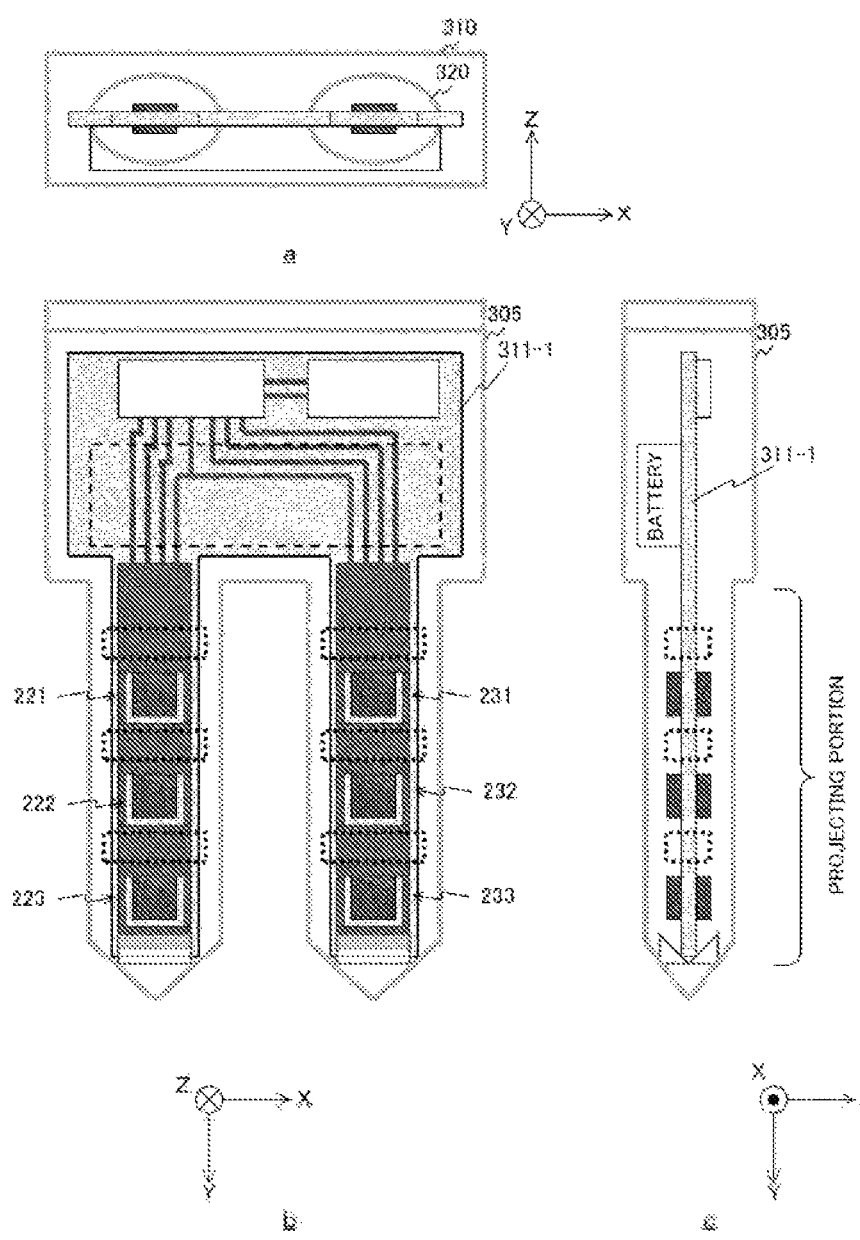

FIG. 220 is a diagram illustrating an example of a sensor device according to a second embodiment of the present technology.

Figure 221:
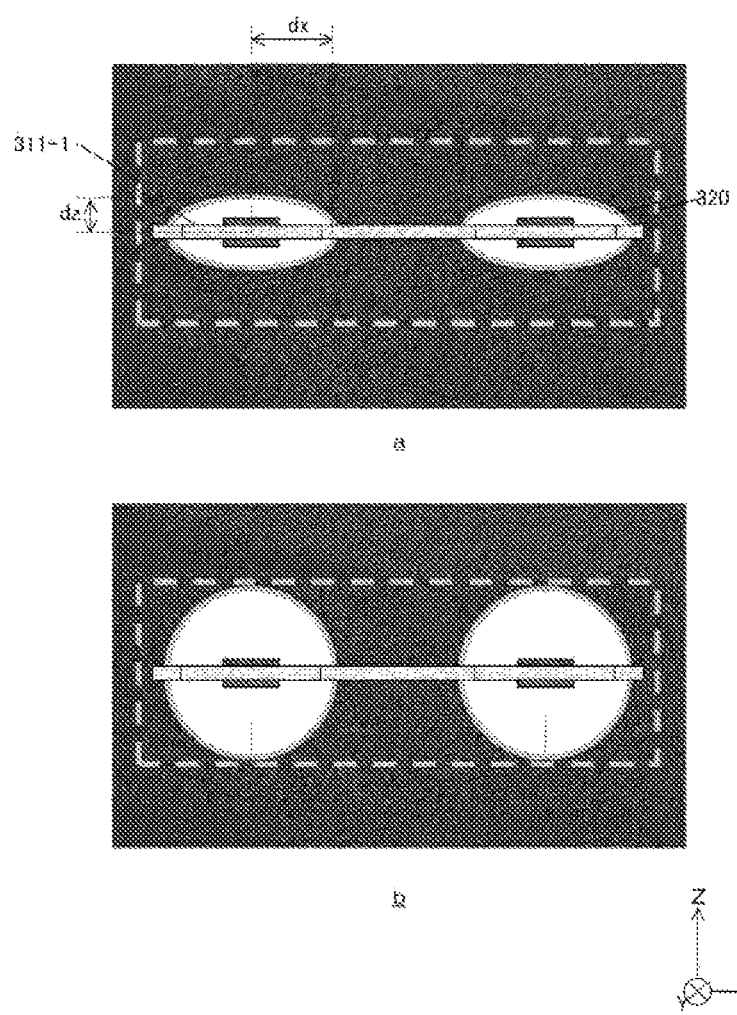

FIG. 221 is an example of sectional views of the sensor device when seen from the top in the second embodiment of the present technology and a comparative example.

Figure 222:
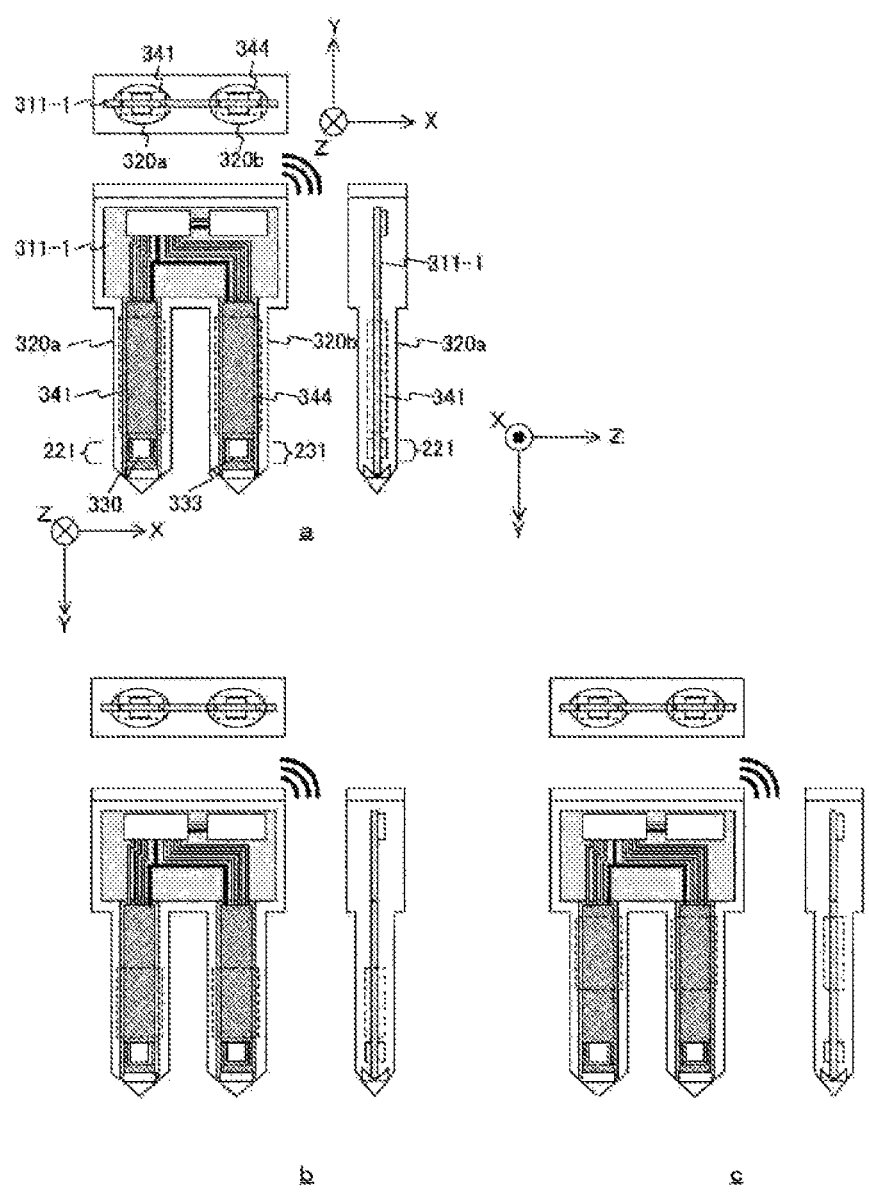

FIG. 222 is a diagram illustrating an example of covered parts of radio wave absorption sections at the time of double-side radiation according to the second embodiment of the present technology.

Figure 223:
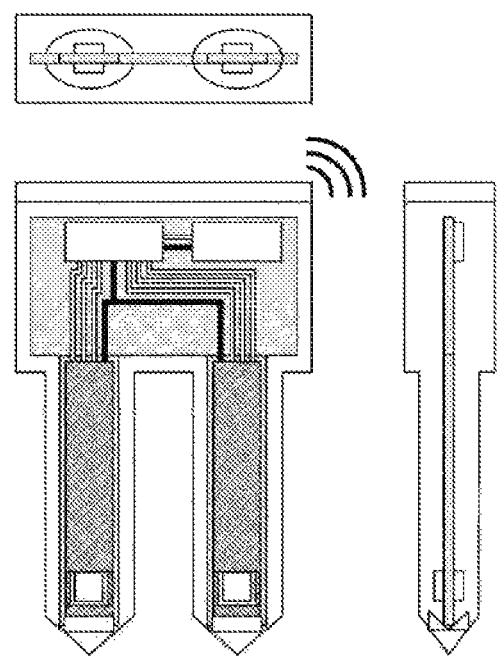

FIG. 223 is a diagram illustrating an example in which there is no covering with the radio wave absorption sections at the time of double-side radiation according to the second embodiment of the present technology.

Figure 224:
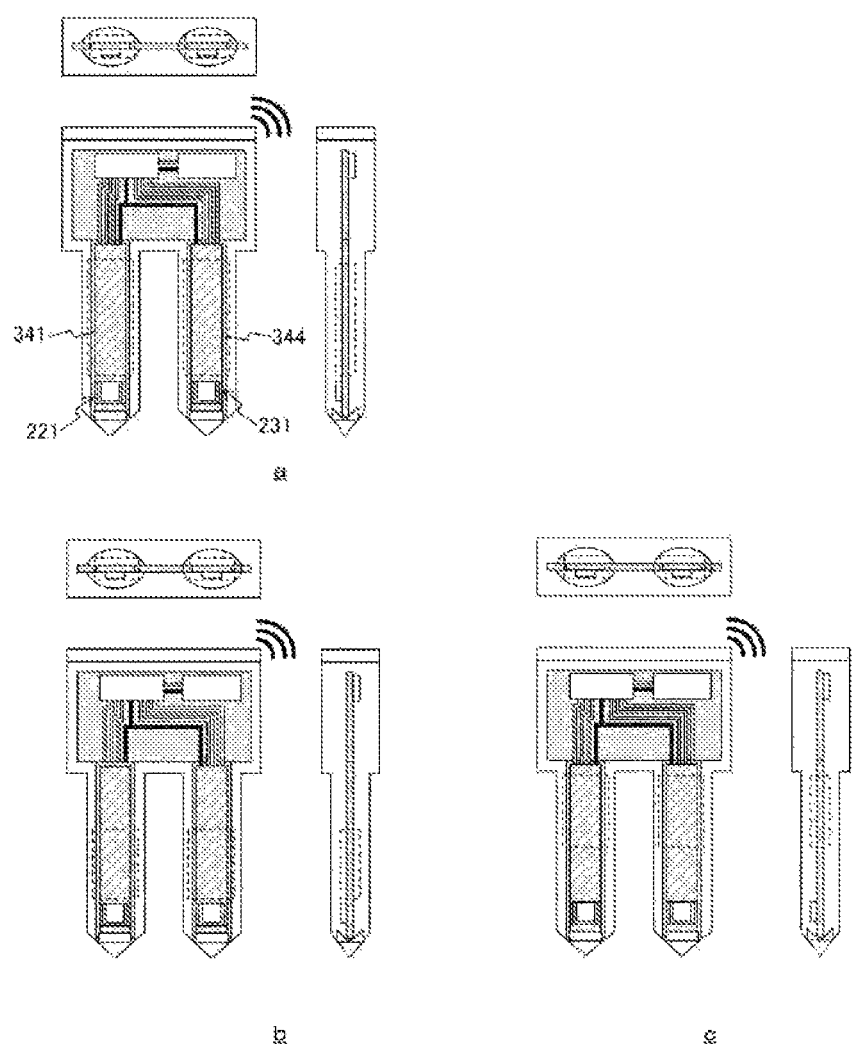

FIG. 224 is a diagram illustrating an example of covered parts of the radio wave absorption sections at the time of one-side radiation according to the second embodiment of the present technology.

Figure 225:
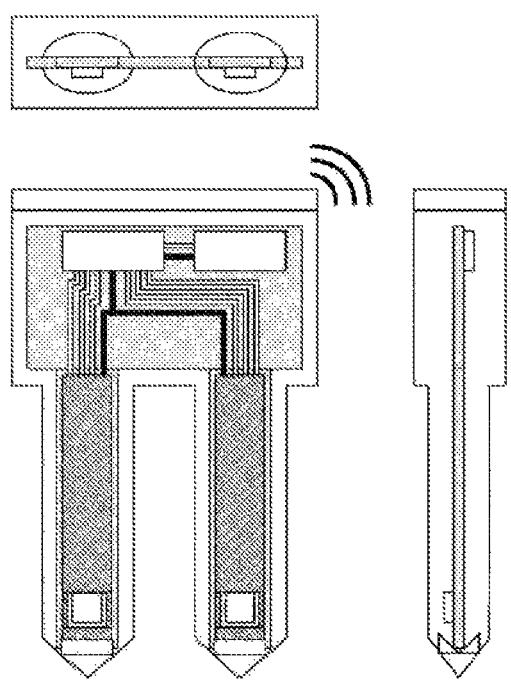

FIG. 225 is a diagram illustrating an example in which there is no covering with the radio wave absorption sections at the time of one-side radiation according to the second embodiment of the present technology.

Figure 226:
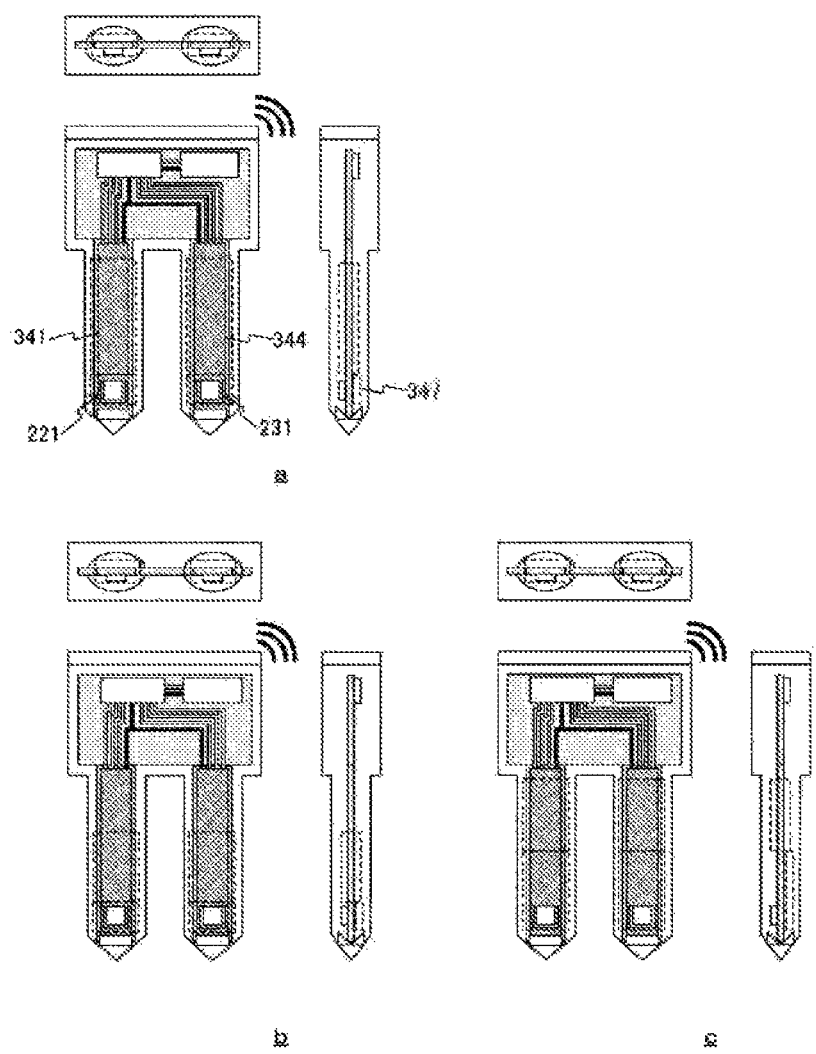

FIG. 226 is a diagram illustrating an example in which one surface is covered at the time of one-side radiation according to the second embodiment of the present technology.

Figure 227:
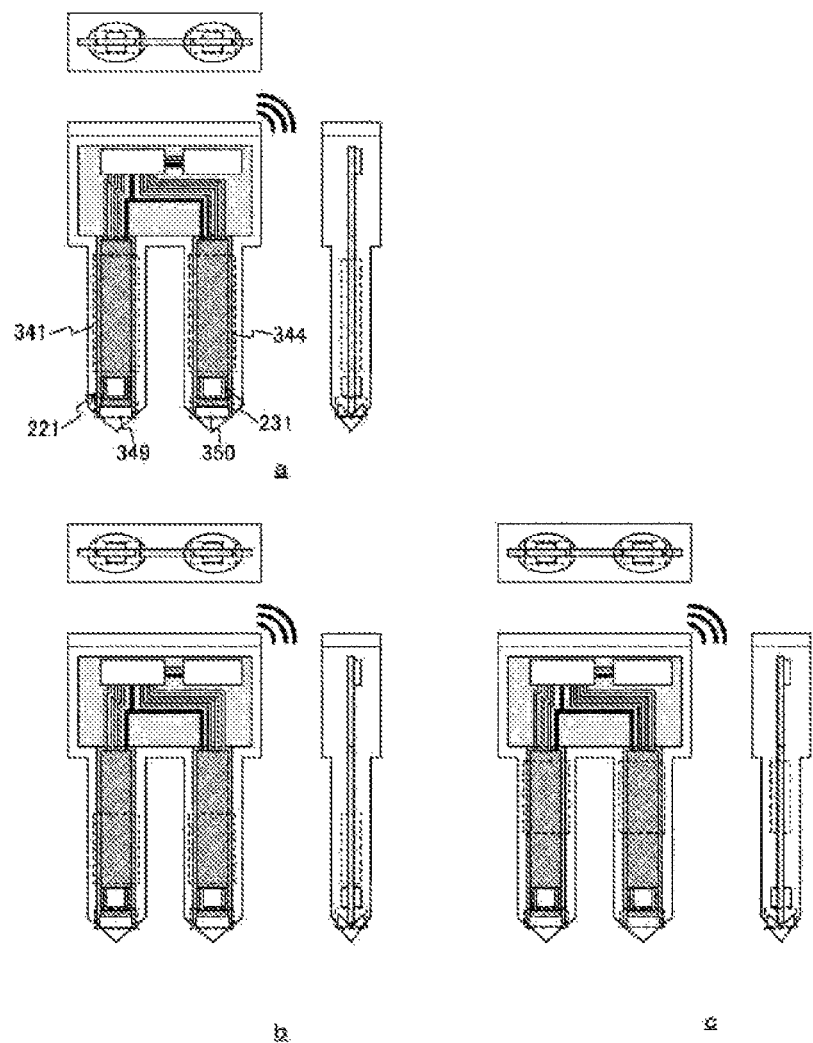

FIG. 227 is a diagram illustrating an example in which a transmission path and a distal end are covered at the time of double-side radiation according to the second embodiment of the present technology.

Figure 228:
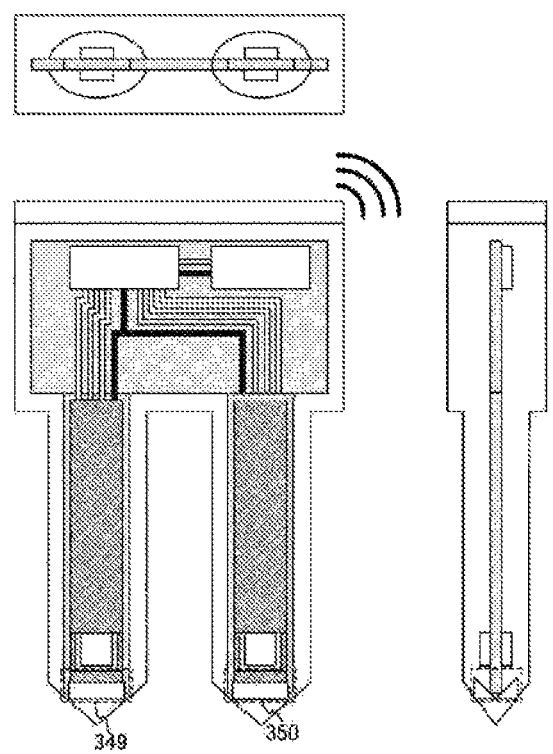

FIG. 228 is a diagram illustrating an example in which only the distal end is covered at the time of double-side radiation according to the second embodiment of the present technology.

Figure 229:
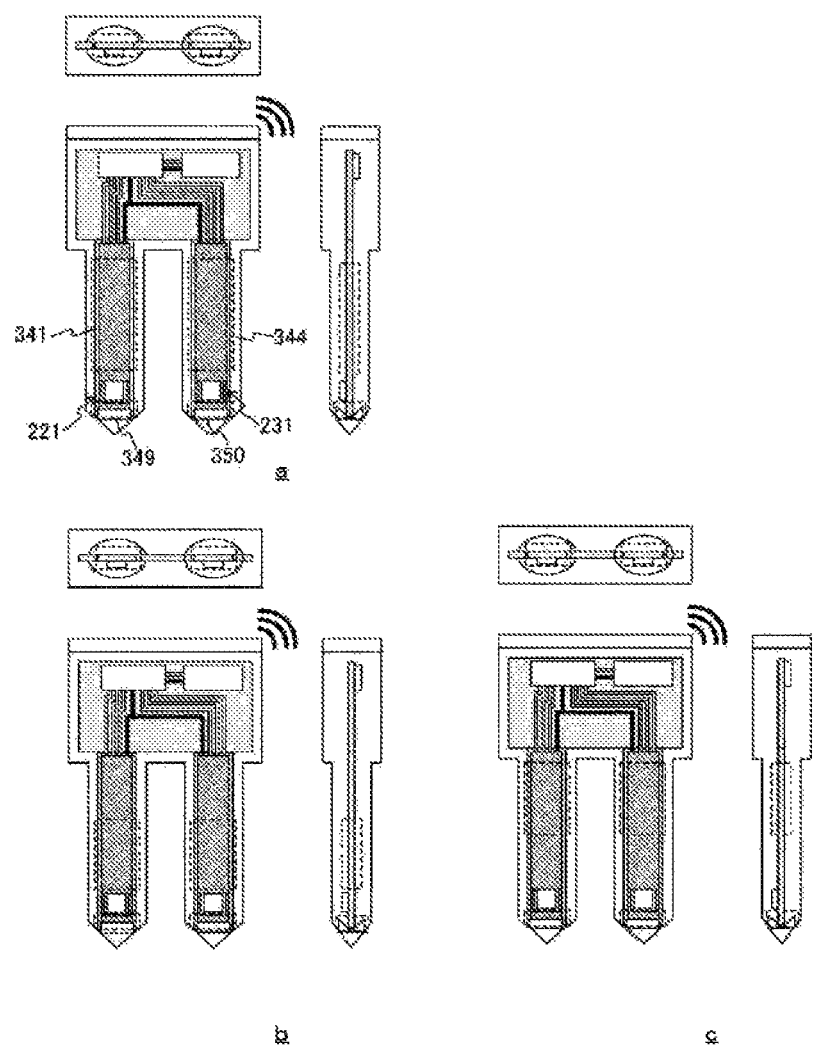

FIG. 229 is a diagram illustrating an example in which the transmission path and the distal end are covered at the time of one-side radiation according to the second embodiment of the present technology.

Figure 230:
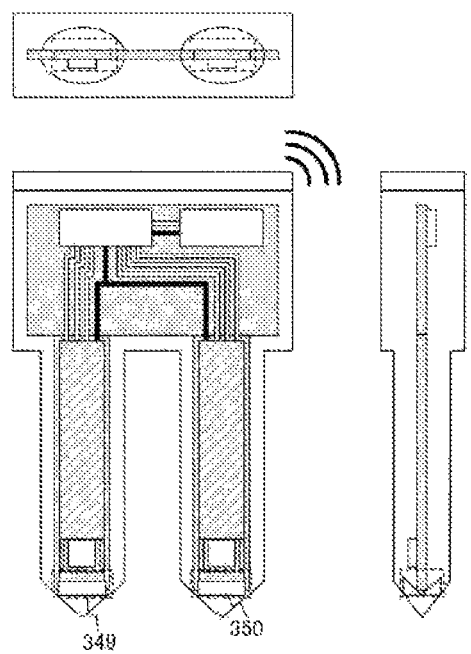

FIG. 230 is a diagram illustrating an example in which only the distal end is covered at the time of one-side radiation according to the second embodiment of the present technology.

Figure 231:
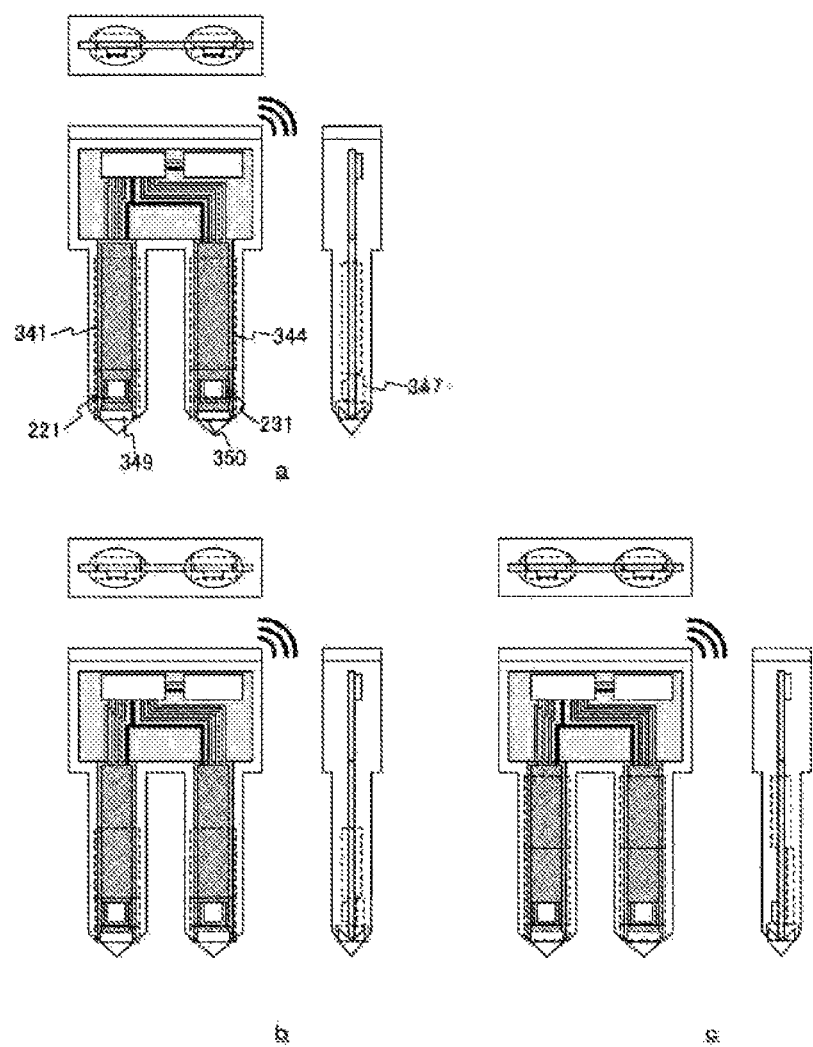

FIG. 231 is a diagram illustrating an example in which the transmission path, the one surface, and the distal end are covered at the time of one-side radiation according to the second embodiment of the present technology.

Figure 232:
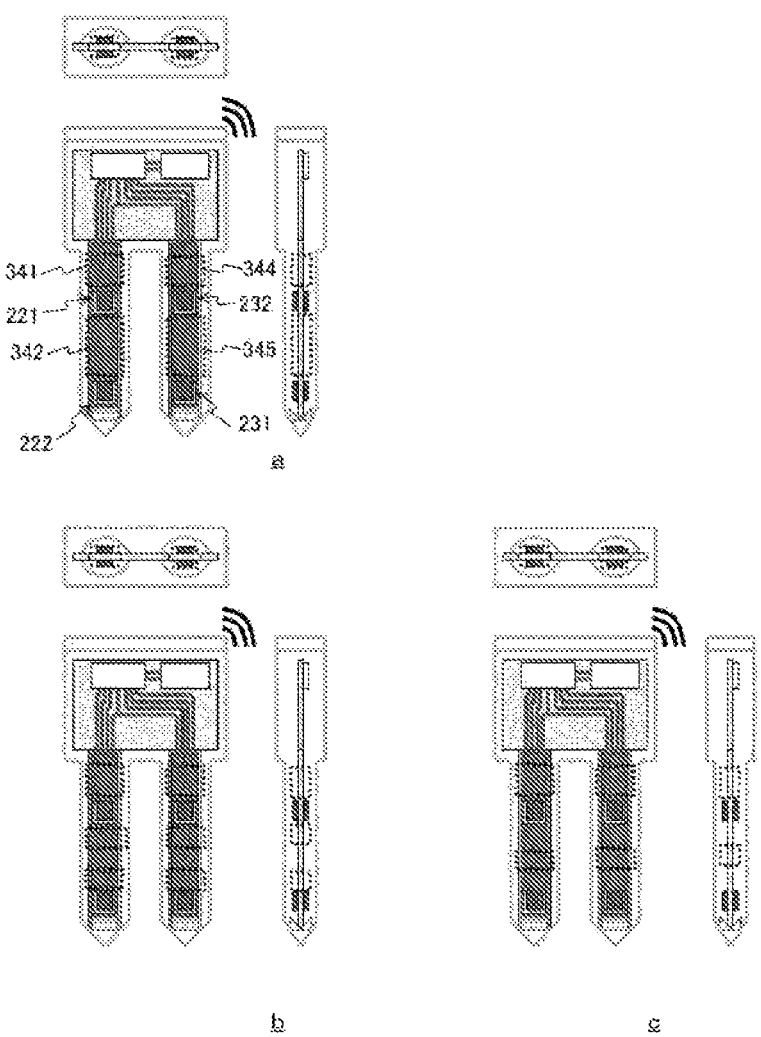

FIG. 232 is a diagram illustrating an example of the covered parts of the radio wave absorption sections when a plurality of antenna pairs for double-side radiation are provided according to the second embodiment of the present technology.

FIG. 233 is a diagram illustrating another example of the covered parts of the radio wave absorption sections when the plurality of antenna pairs for double-side radiation are provided according to the second embodiment of the present technology.

Figure 234:
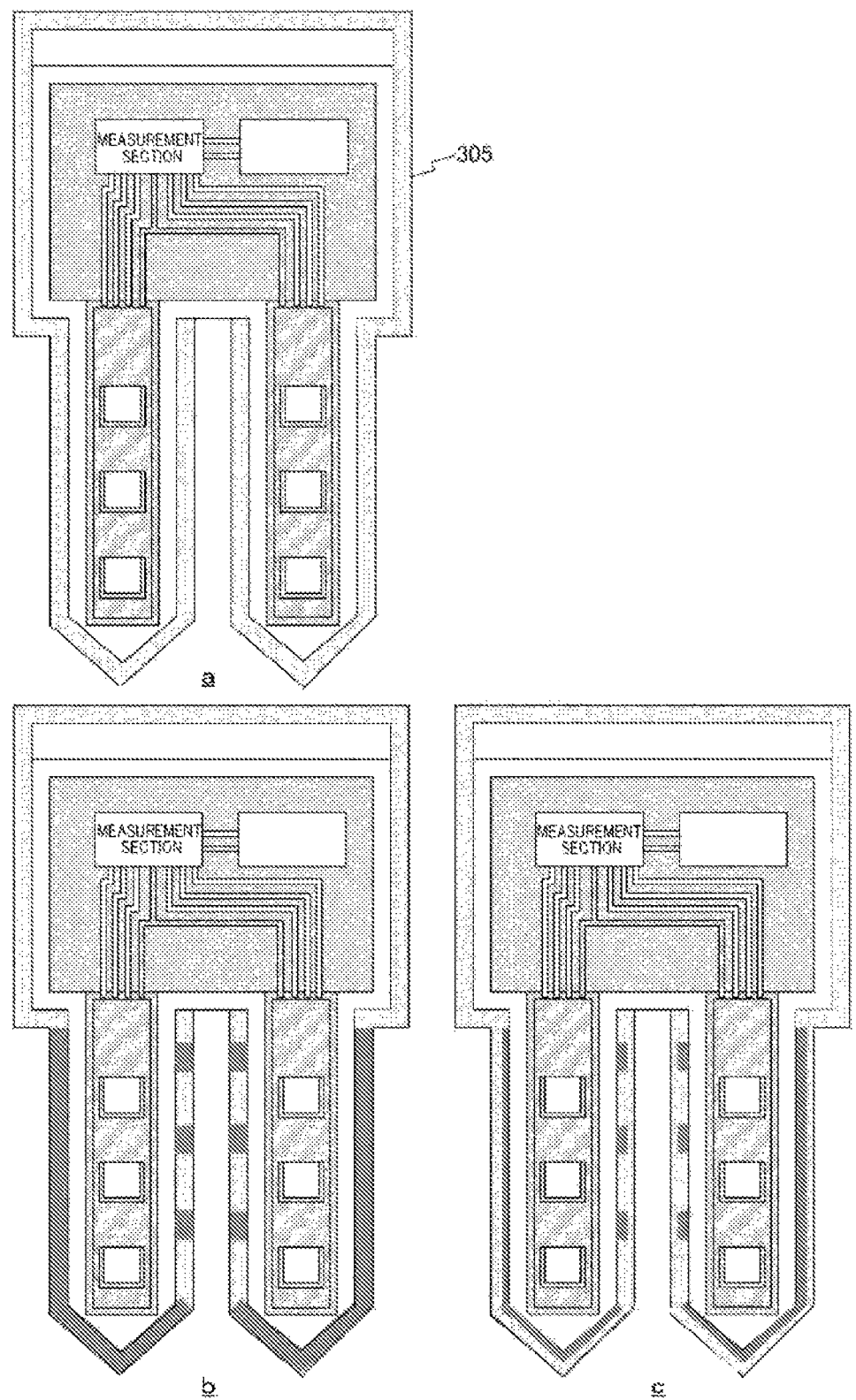

FIG. 234 is a diagram illustrating an example in which the radio wave absorption sections are formed in a sensor casing according to the second embodiment of the present technology.

Figure 235:
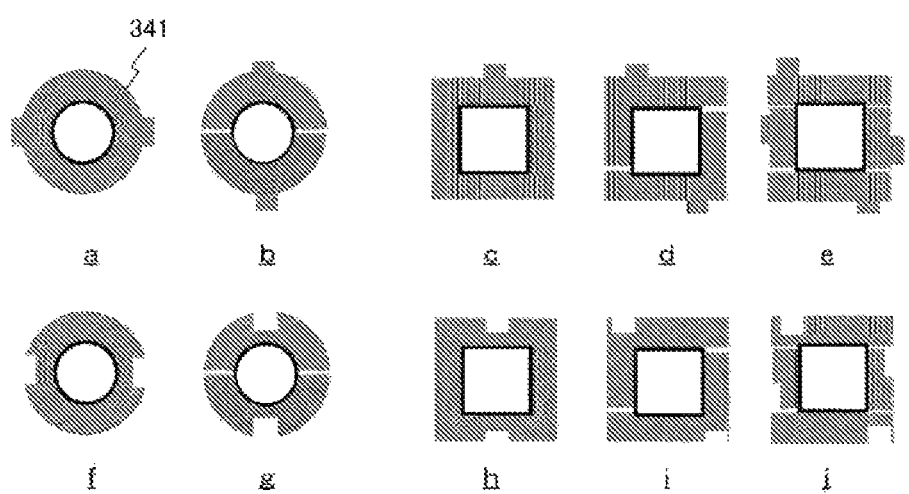

FIG. 235 is a diagram illustrating an example of the shape of the radio wave absorption sections according to the second embodiment of the present technology.

Figure 236:
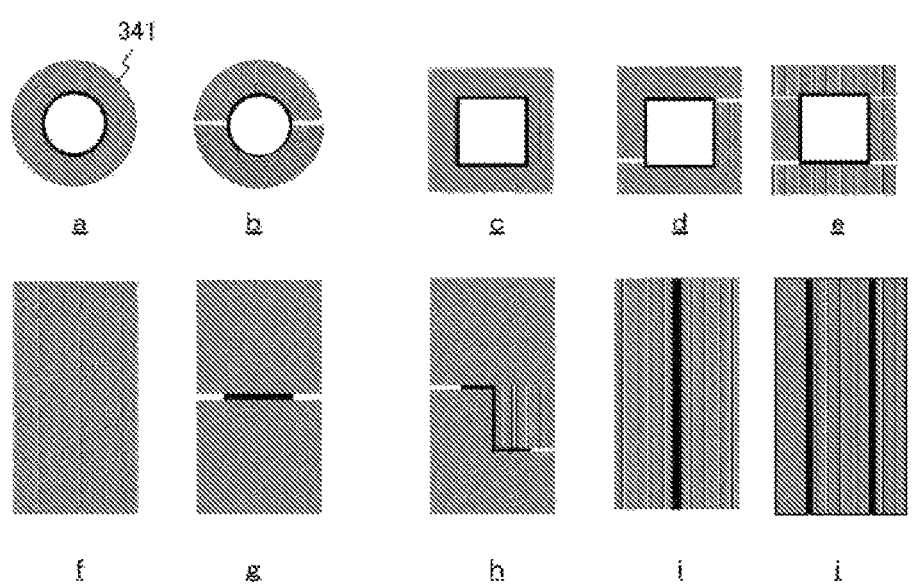

FIG. 236 is a diagram illustrating another example of the shape of the radio wave absorption sections according to the second embodiment of the present technology.

Figure 237:
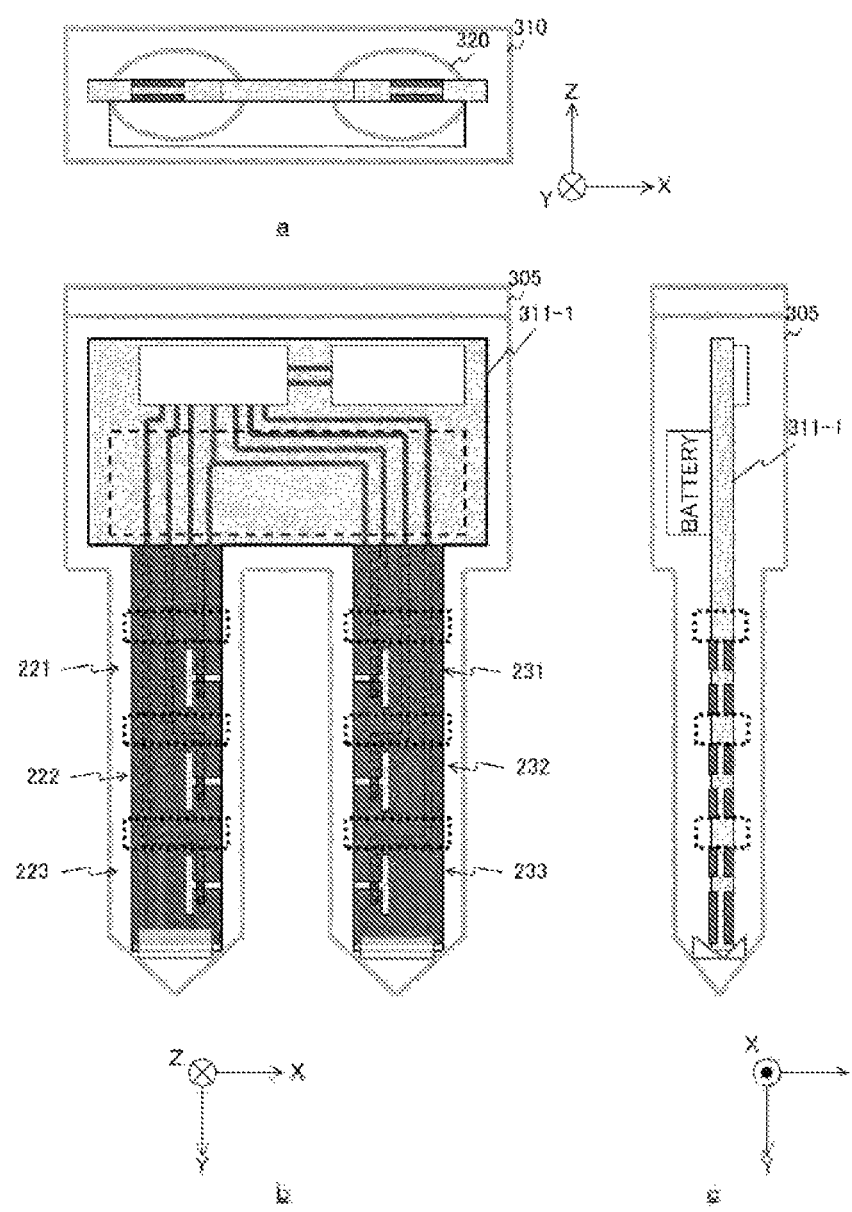

FIG. 237 is a diagram illustrating an example of a sensor device provided with a slot-shaped antenna according to a first modification example of the second embodiment of the present technology.

Figure 238:
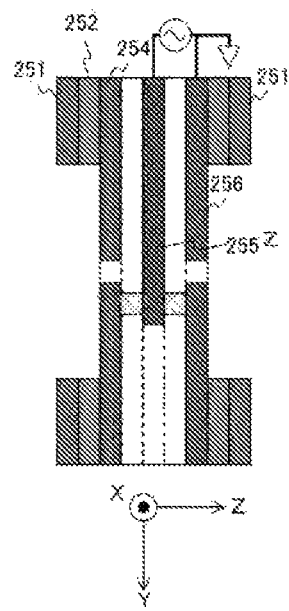

FIG. 238 is a diagram for explaining a structure of a plane-shaped and slot-shaped lateral radiation-type antenna according to the first modification example of the second embodiment of the present technology.

Figure 239:
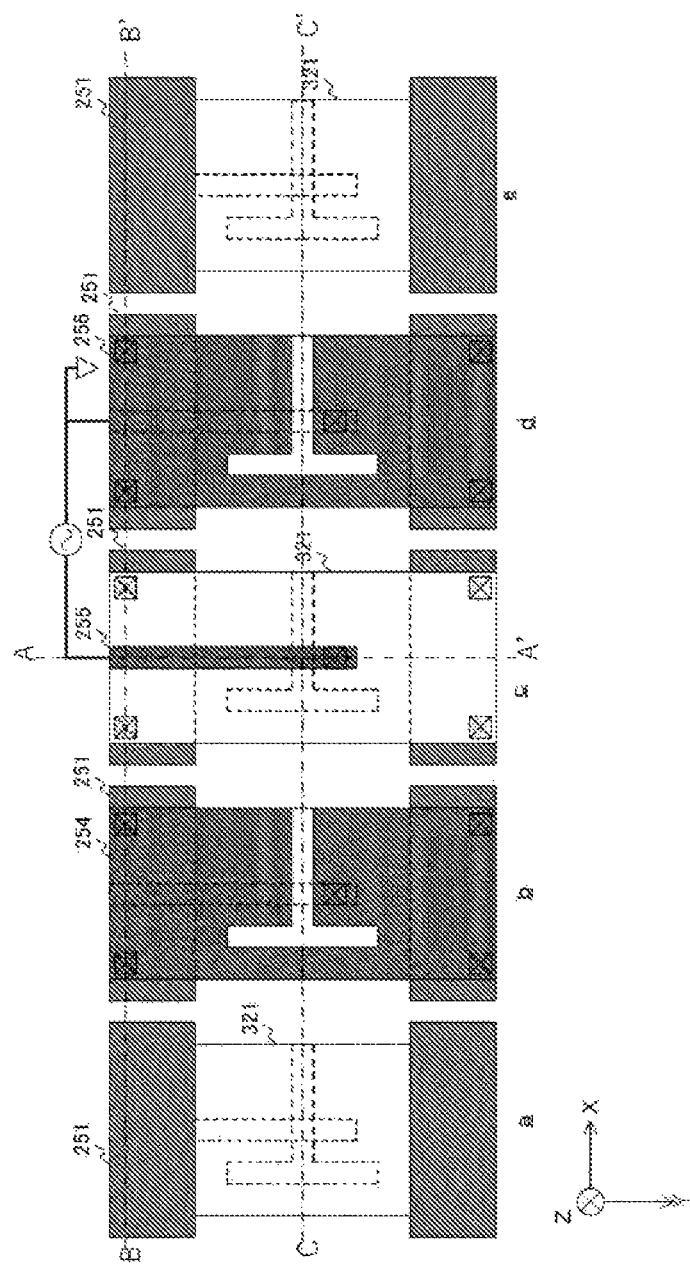

FIG. 239 is a diagram for explaining the structure of the plane-shaped and slot-shaped lateral radiation-type antenna according to the first modification example of the second embodiment of the present technology.

Figure 240:
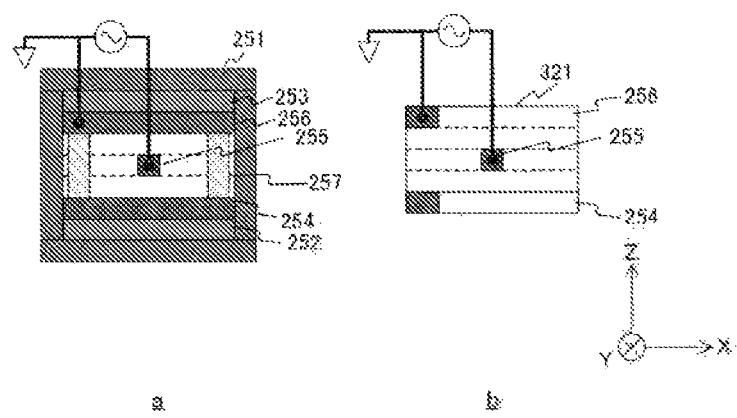

FIG. 240 is a diagram for explaining the structure of the plane-shaped and slot-shaped lateral radiation-type antenna according to the first modification example of the second embodiment of the present technology.

Figure 241:
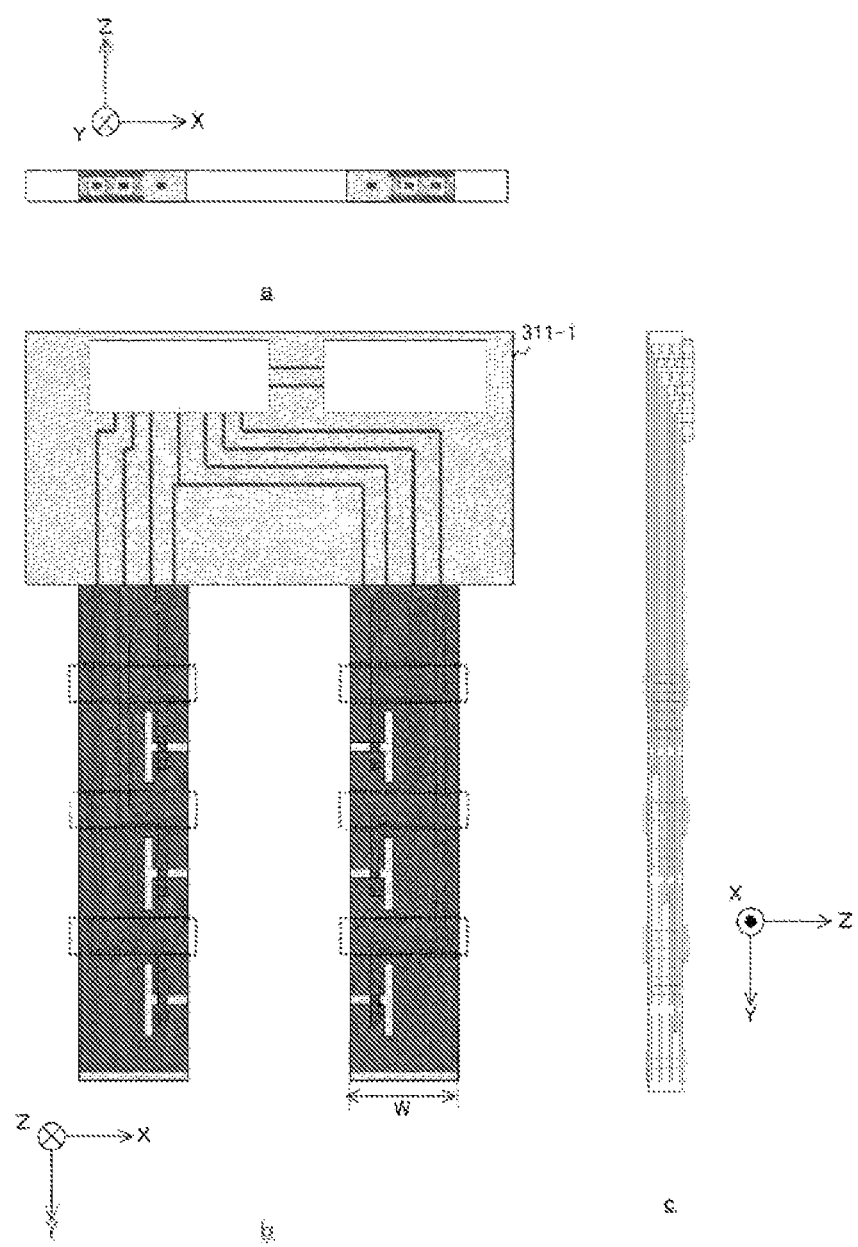

FIG. 241 is a diagram illustrating a configuration example of an electronic substrate according to a second modification example of the second embodiment of the present technology.

Figure 242:
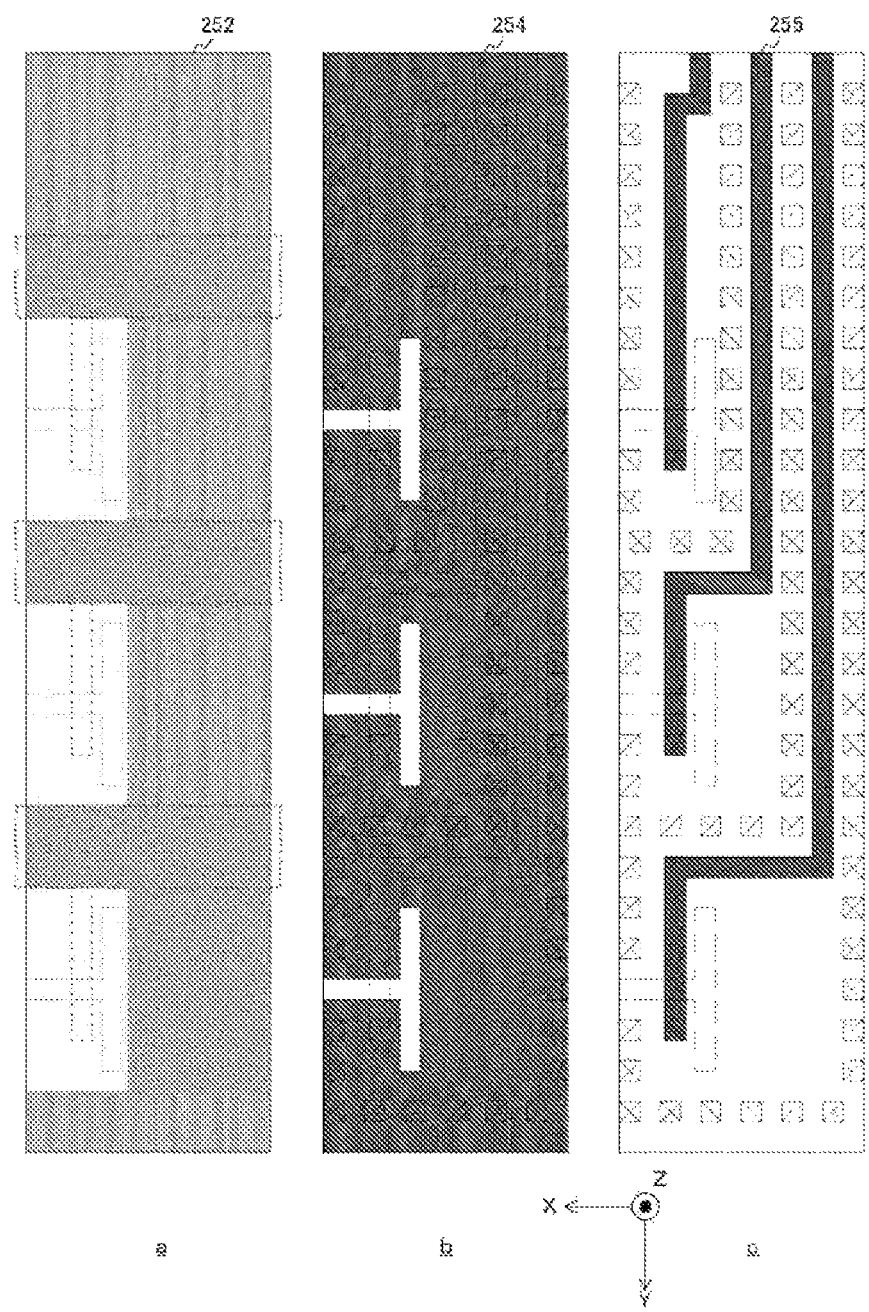

FIG. 242 is a diagram illustrating an example of a plan view of first to third layers from among five layers of the electronic substrate according to the first modification example of the second embodiment of the present technology.

Figure 243:
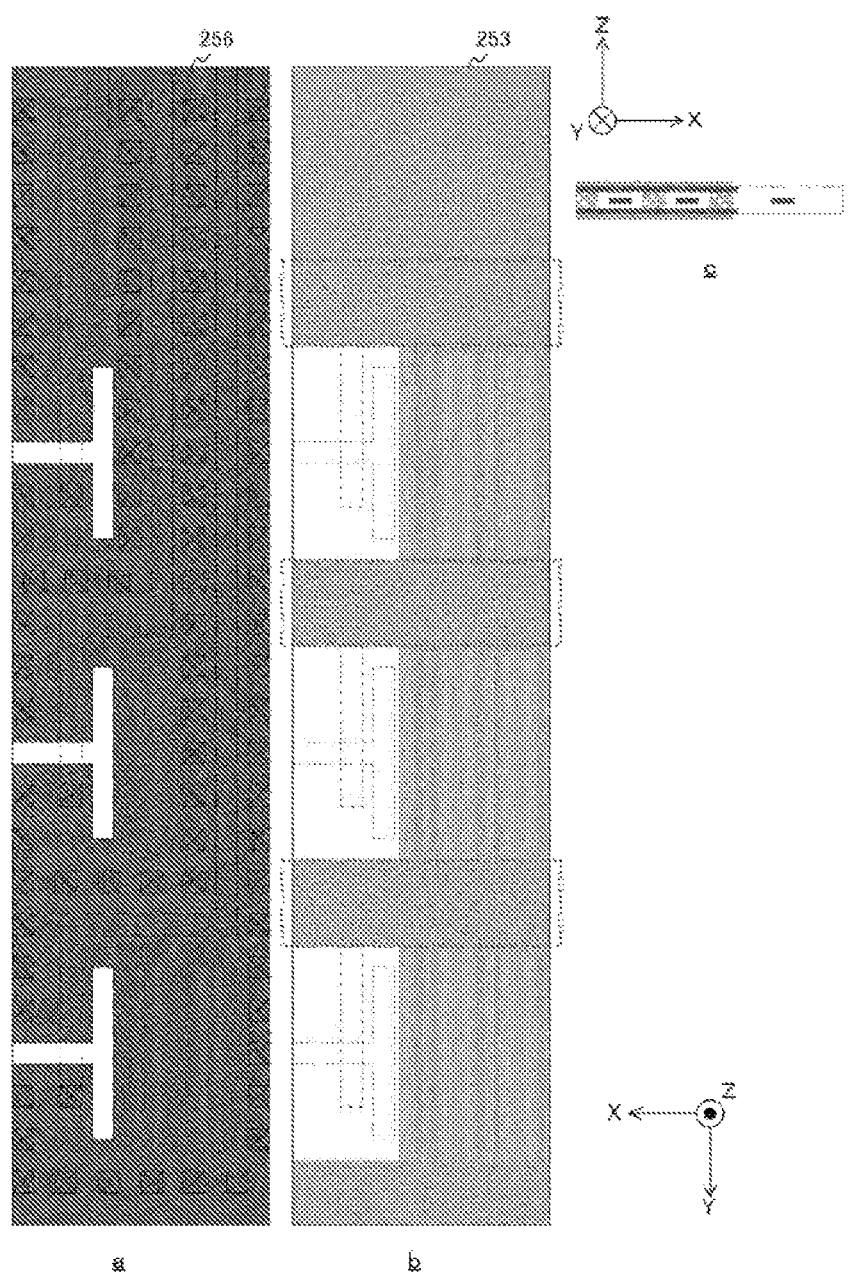

FIG. 243 is a diagram illustrating an example of a plan view and a top view of fourth and fifth layers from among the five layers of the electronic substrate according to the first modification example of the second embodiment of the present technology.

Figure 244:
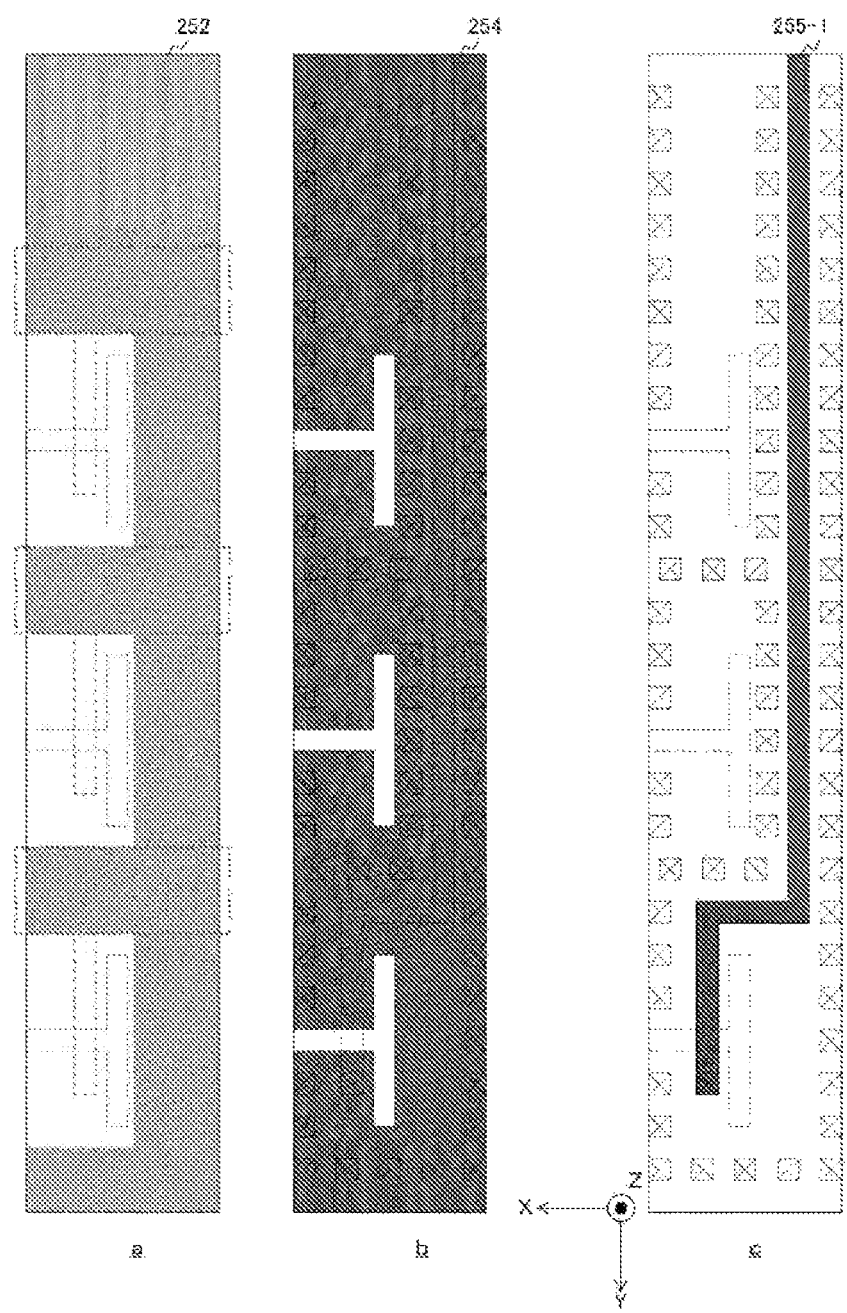

FIG. 244 is a diagram illustrating an example of a plan view of first to third layers from among seven layers of the electronic substrate according to the first modification example of the second embodiment of the present technology.

Figure 245:
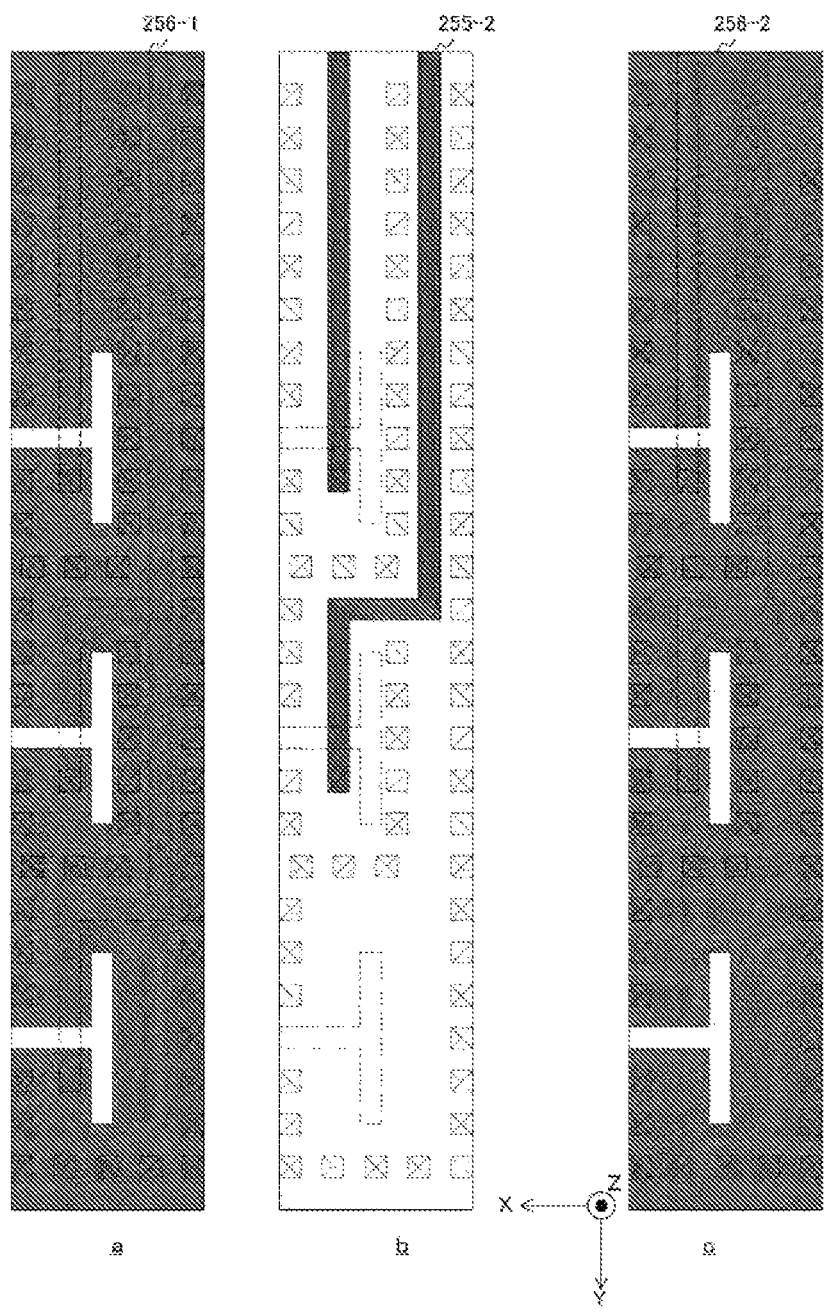

FIG. 245 is a diagram illustrating an example of a plan view of fourth to sixth layers from among the seven layers of the electronic substrate according to the first modification example of the second embodiment of the present technology.

Figure 246:
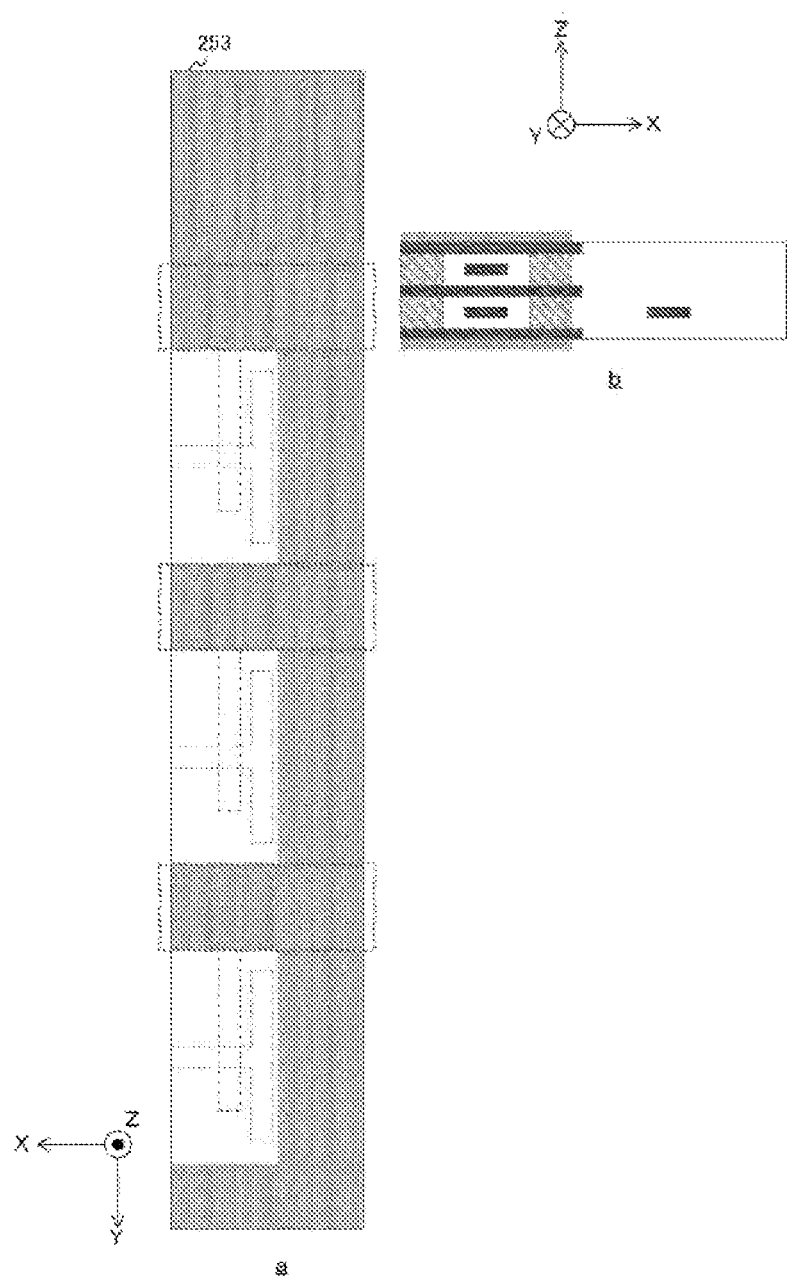

FIG. 246 is a diagram illustrating an example of a plan view and a top view of a seventh layer from among the seven layers of the electronic substrate according to the first modification example of the second embodiment of the present technology.

Figure 247:

FIG. 247 is a diagram illustrating an example of a plan view of first to third layers from among nine layers of the electronic substrate according to the first modification example of the second embodiment of the present technology.

Figure 248:
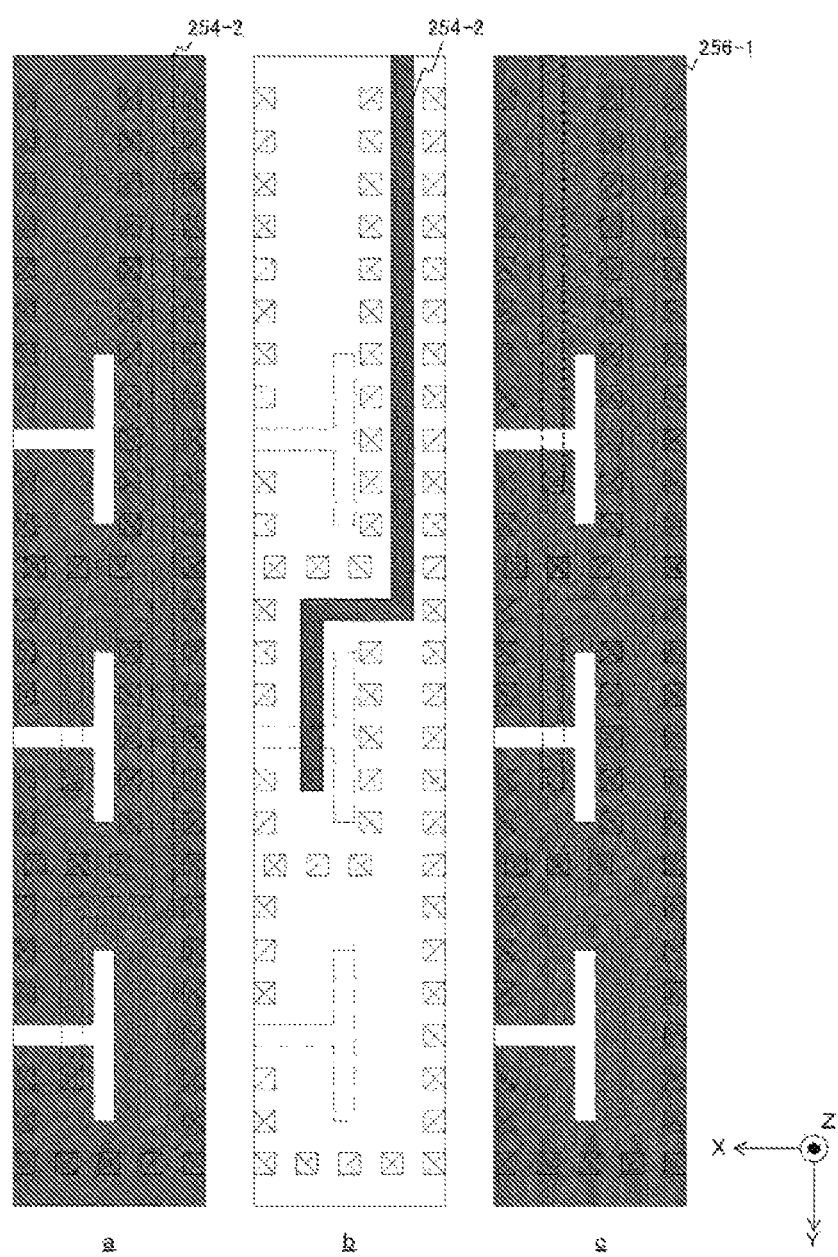

FIG. 248 is a diagram illustrating an example of a plan view of fourth to sixth layers from among the nine layers of the electronic substrate according to the first modification example of the second embodiment of the present technology.

Figure 249:
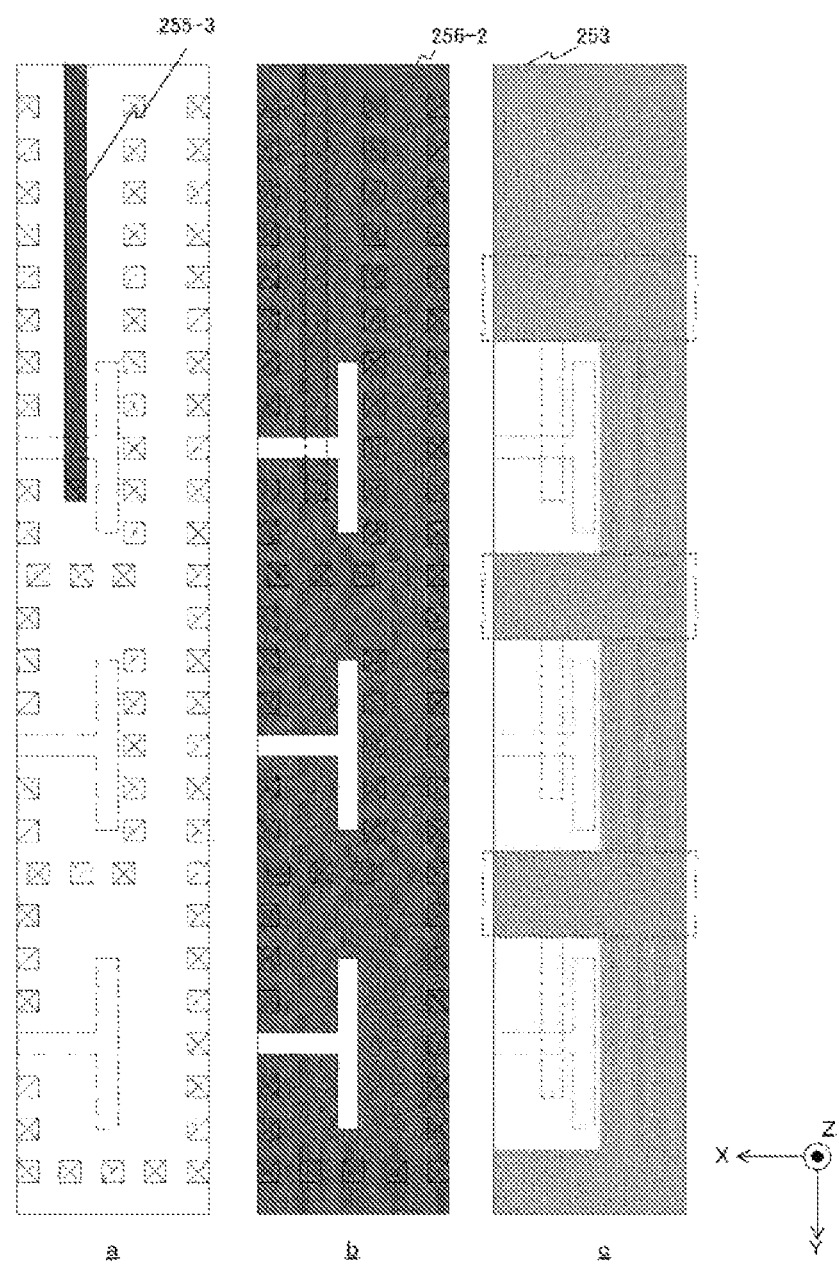

FIG. 249 is a diagram illustrating an example of a plan view of seventh to ninth layers from among the nine layers of the electronic substrate according to the first modification example of the second embodiment of the present technology.

Figure 250:
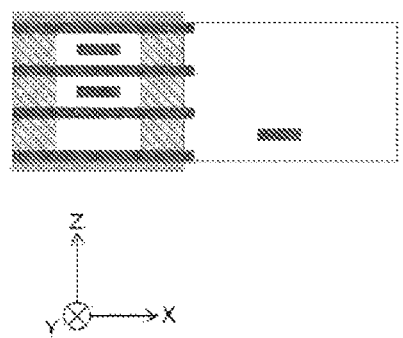

FIG. 250 is a diagram illustrating an example of a top view of the electronic substrate with a nine-layer structure according to the first modification example of the second embodiment of the present technology.

Figure 251:
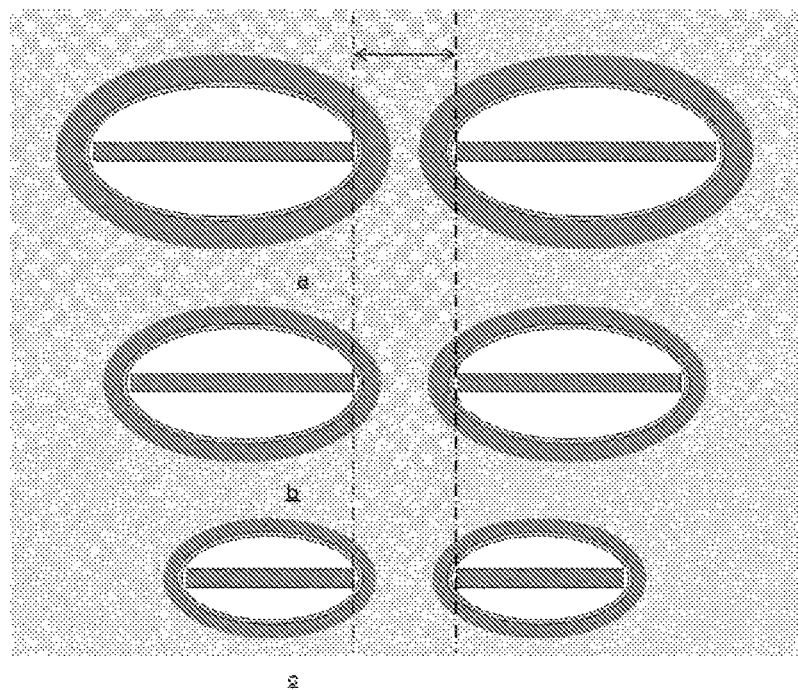

FIG. 251 is a diagram for explaining the width of the substrate according to the first modification example of the second embodiment of the present technology.

Figure 252:
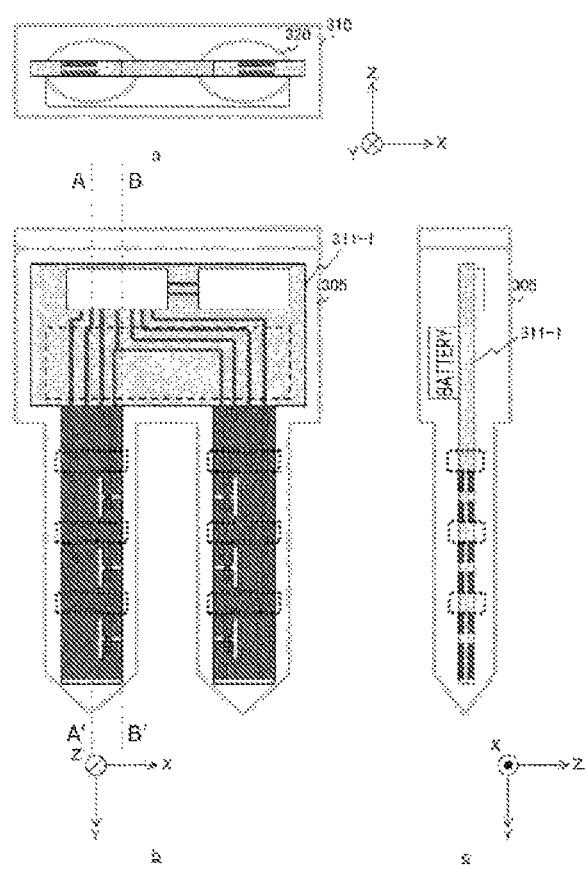

FIG. 252 is a diagram illustrating an example of the sensor device in which the intra-probe substrate is caused to abut the sensor casing according to the second modification example of the second embodiment of the present technology.

Figure 253:
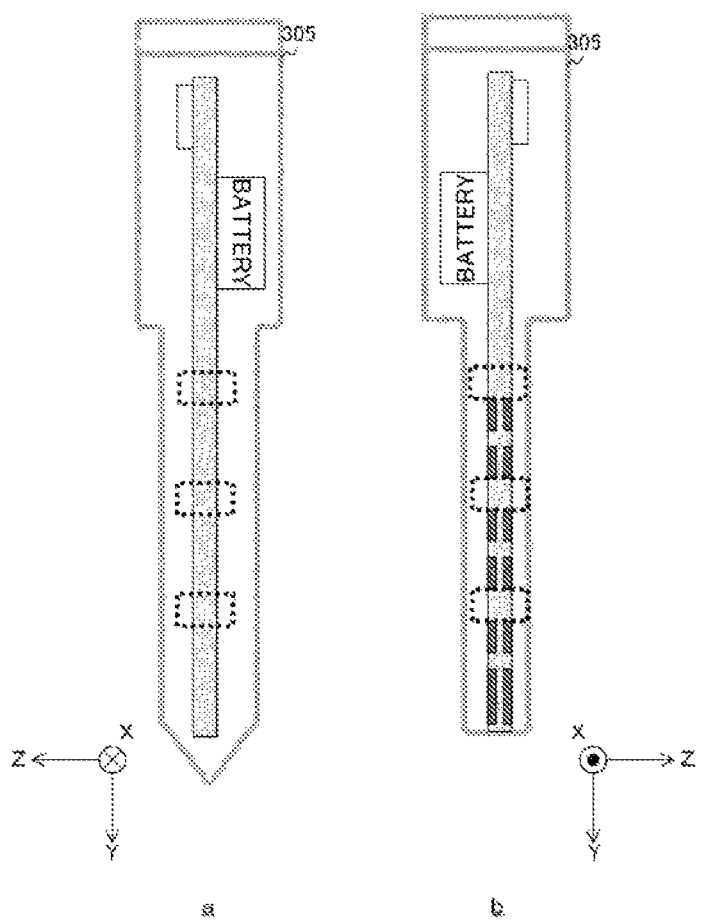

FIG. 253 is an example of a sectional view of the sensor casing according to the second modification example of the second embodiment of the present technology.

Figure 254:
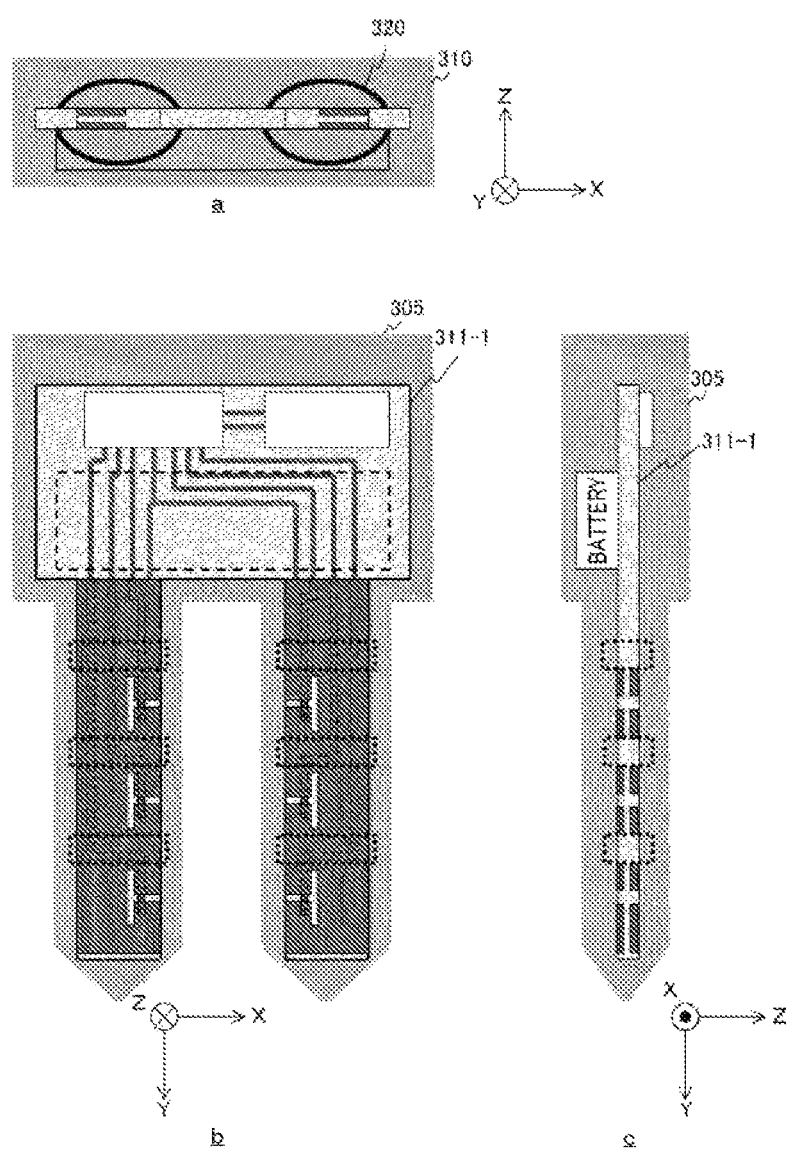

FIG. 254 is a diagram illustrating an example of a sensor device filled with a resin according to a third modification example of the second embodiment of the present technology.

FIG. 255 is an example of a sectional view of a probe casing with a component thickness in a direction parallel to an electronic substrate increased by double-side radiation according to a fourth modification example of the second embodiment of the present technology.

FIG. 256 is an example of a sectional view of the probe casing with a component thickness in a direction perpendicular to the electronic substrate increased by double-side radiation according to the fourth modification example of the second embodiment of the present technology.

Figure 257:
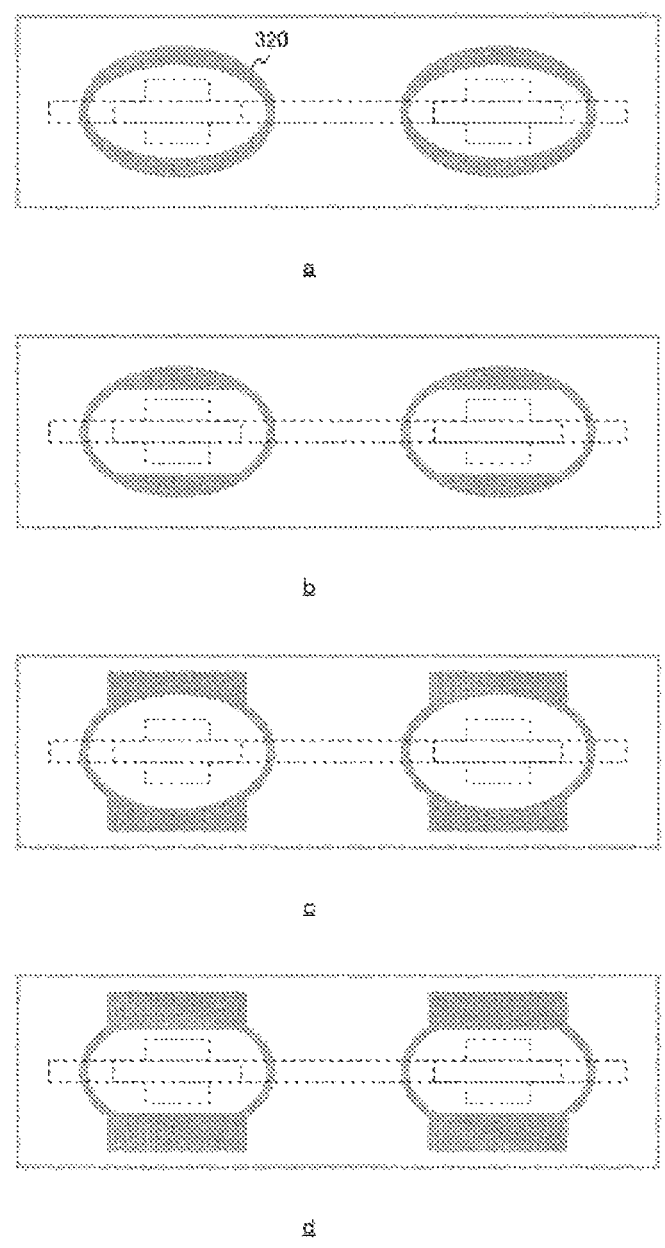

FIG. 257 is another example of a sectional view of the probe casing with a component thickness in the direction perpendicular to the electronic substrate increased by double-side radiation according to the fourth modification example of the second embodiment of the present technology.

Figure 258:
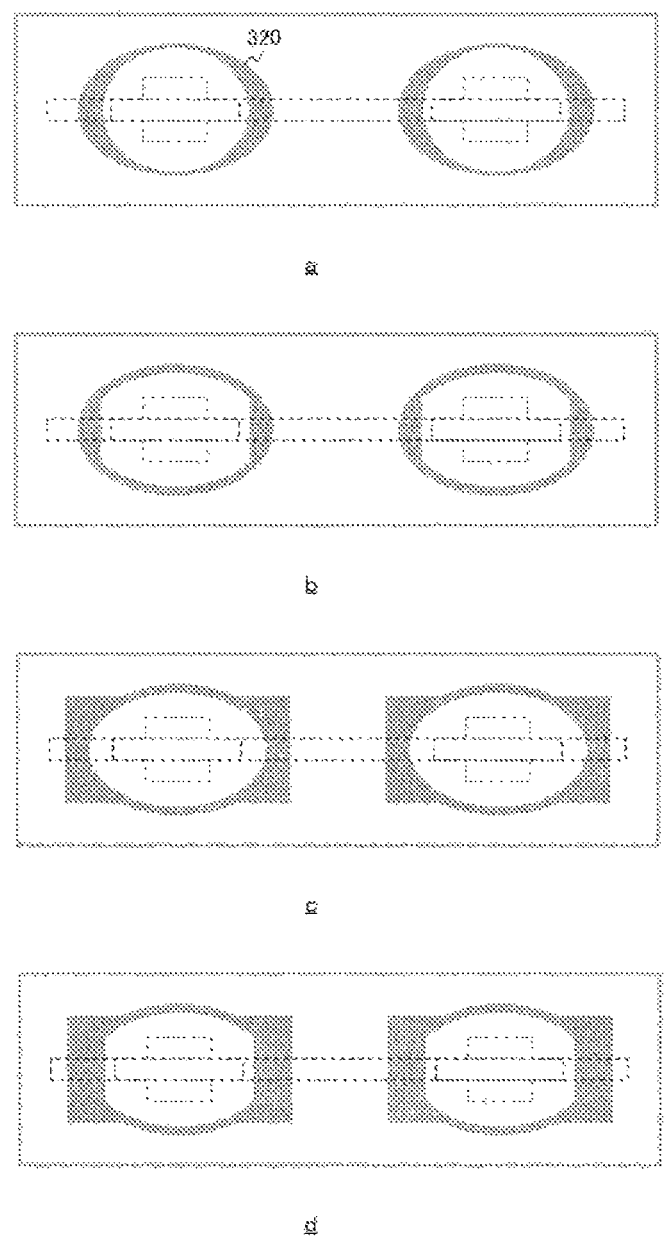

FIG. 258 is another example of a sectional view of the probe casing with a component thickness in the direction parallel to the electronic substrate increased by double-side radiation according to the fourth modification example of the second embodiment of the present technology.

FIG. 259 is an example of a sectional view of the probe casing with a component thickness in the direction perpendicular to and outside the electronic substrate increased by double-side radiation according to the fourth modification example of the second embodiment of the present technology.

FIG. 260 is an example of a sectional view of a probe casing with a component thickness in the direction parallel to the electronic substrate increased by double-side radiation according to the fourth modification example of the second embodiment of the present technology.

FIG. 261 is an example of a sectional view of the probe casing with a component thickness in the direction perpendicular to the electronic substrate increased by double-side radiation according to the fourth modification example of the second embodiment of the present technology.

FIG. 262 is another example of a sectional view of the probe casing with a component thickness in the direction perpendicular to the electronic substrate increased by double-side radiation according to the fourth modification example of the second embodiment of the present technology.

FIG. 263 is another example of a sectional view of the probe casing with a component thickness in the direction parallel to the electronic substrate increased by double-side radiation according to the fourth modification example of the second embodiment of the present technology.

FIG. 264 is an example of a sectional view of the probe casing with a component thickness in the direction perpendicular to and outside the intra-probe substrate increased by double-side radiation according to the fourth modification example of the second embodiment of the present technology.

Figure 265:
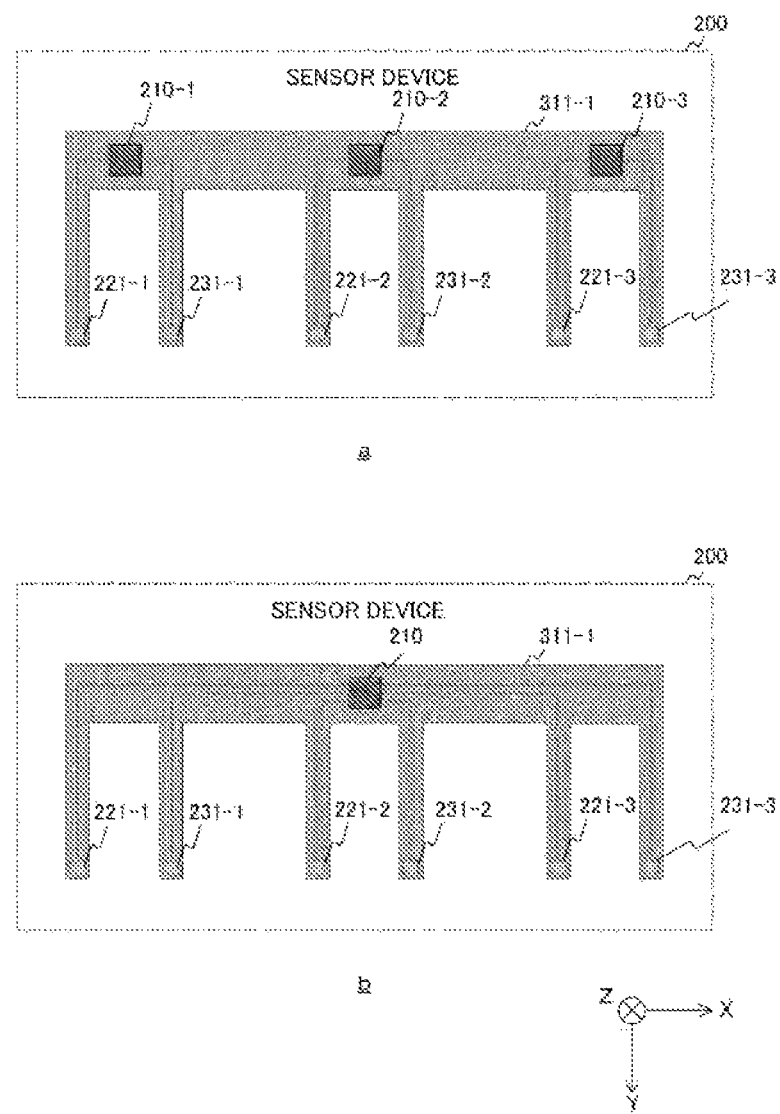

FIG. 265 is a diagram illustrating a configuration example of a sensor device according to a fifth modification example of the second embodiment of the present technology.

Figure 266:
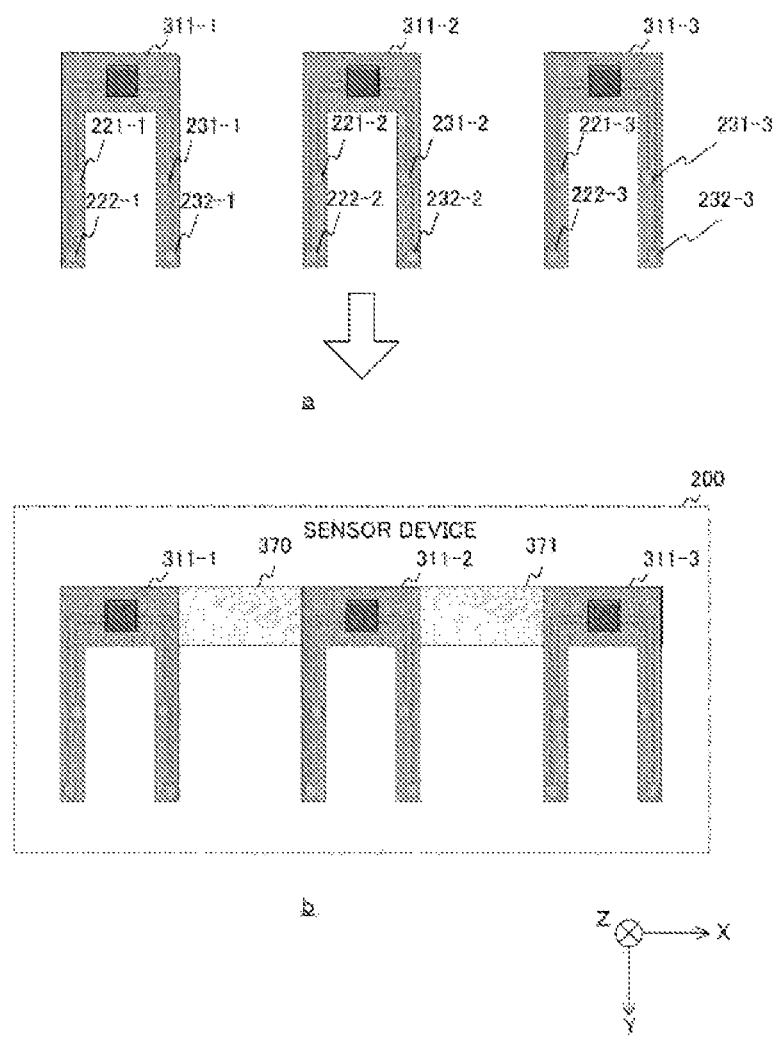

FIG. 266 is a diagram illustrating an example of the sensor device before and after connection of an electronic substrate according to the fifth modification example of the second embodiment of the present technology.

Figure 267:
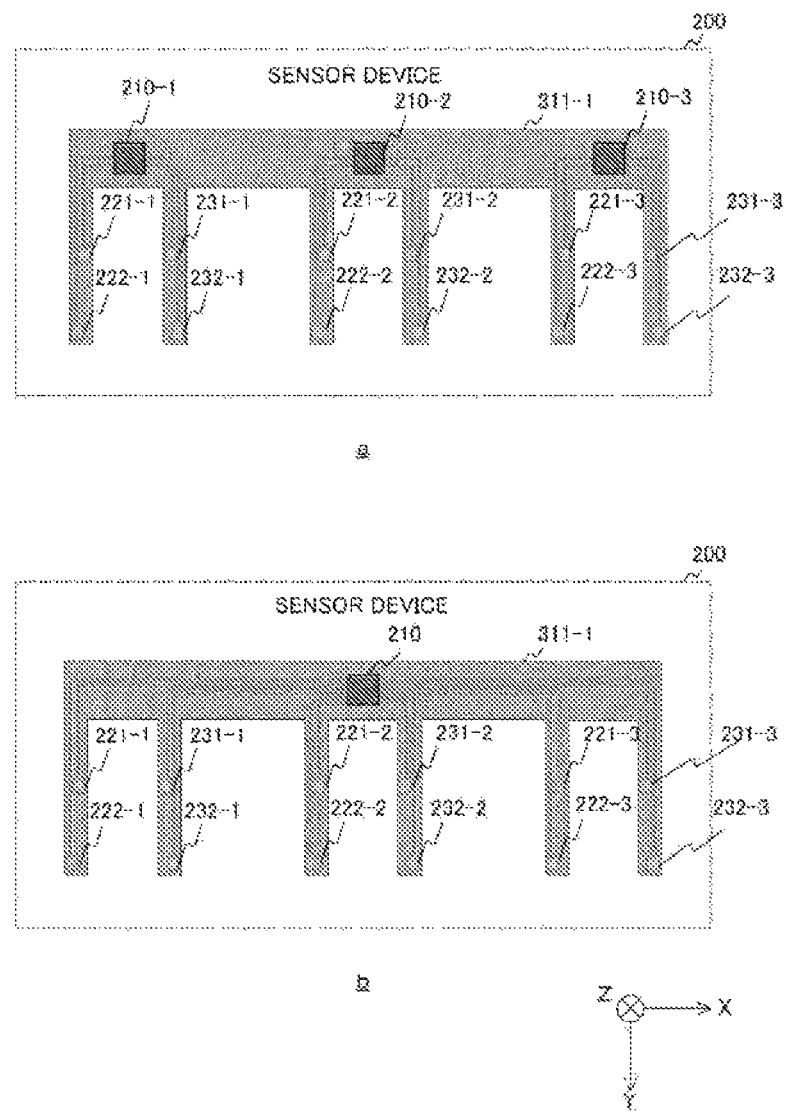

FIG. 267 is a diagram illustrating a configuration example of the sensor device including a plurality of pairs of antennas provided for each probe according to the fifth modification example of the second embodiment of the present technology.

FIG. 268 is a diagram illustrating a configuration example of the sensor device including probe pairs with different lengths according to the fifth modification example of the second embodiment of the present technology.

Figure 269:
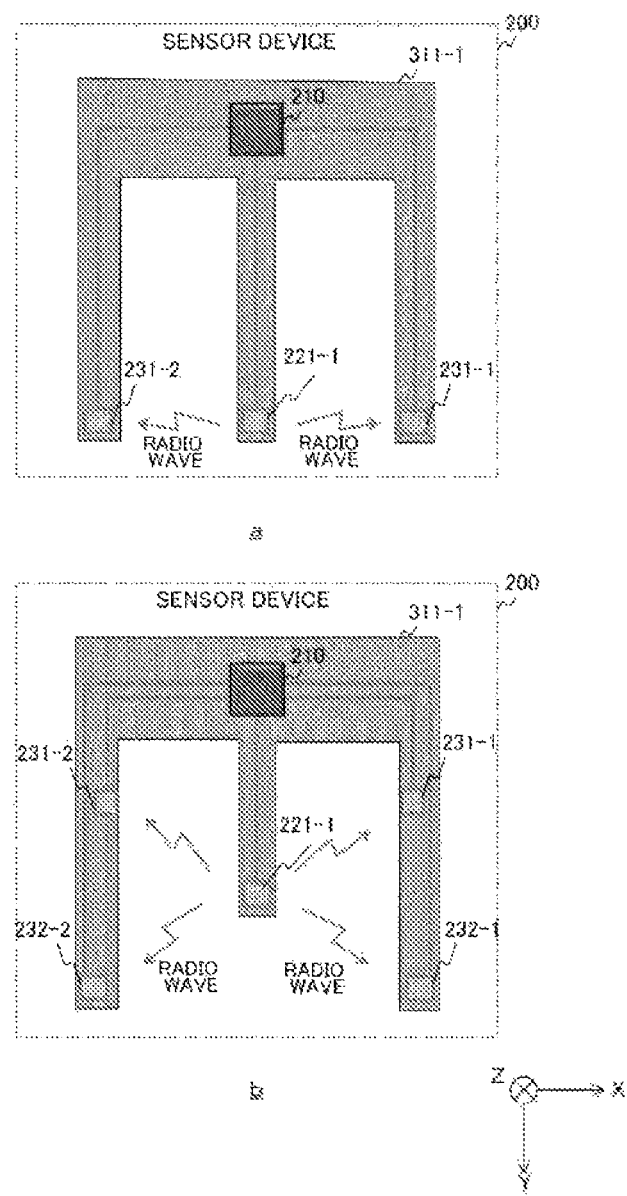

FIG. 269 is a diagram illustrating a configuration example of the sensor device in which a transmission antenna is shared by a plurality of reception antennas according to the fifth modification example of the second embodiment of the present technology.

Figure 270:
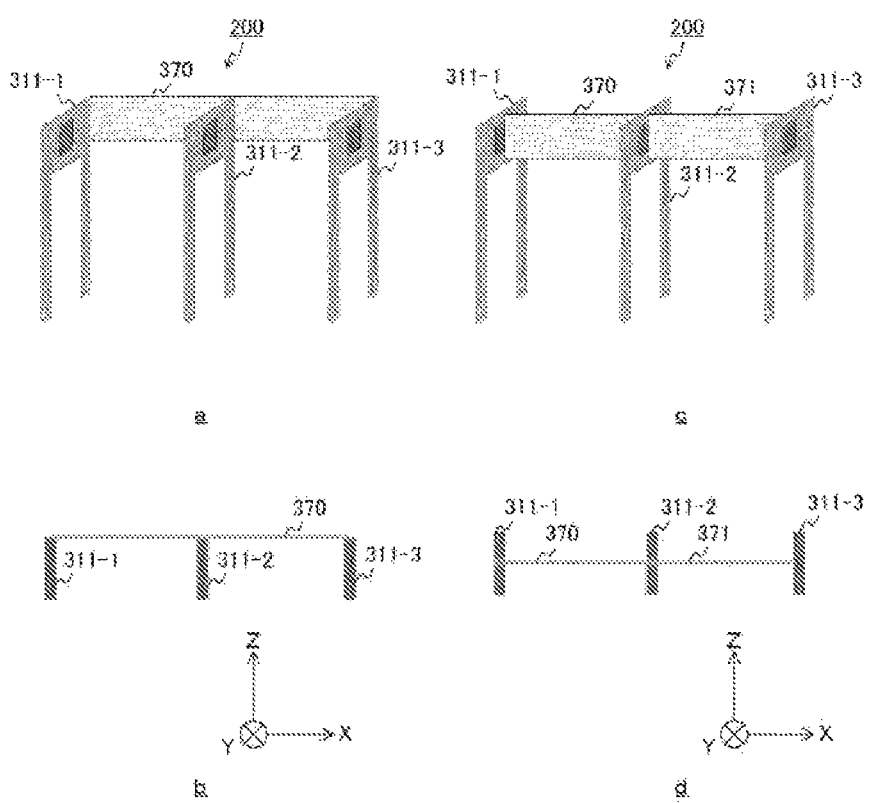

FIG. 270 is a diagram illustrating a configuration example of the sensor device in which substrate surfaces of electronic substrates face each other according to the fifth modification example of the second embodiment of the present technology.

Figure 271:
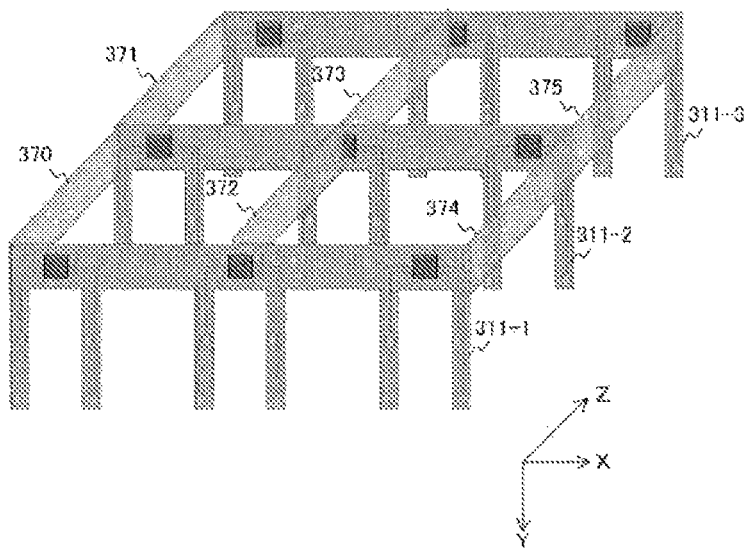

FIG. 271 is a diagram illustrating a configuration example of the sensor device that performs measurement at a plurality of points aligned in a two-dimensional lattice shape according to the fifth modification example of the second embodiment of the present technology.

Figure 272:
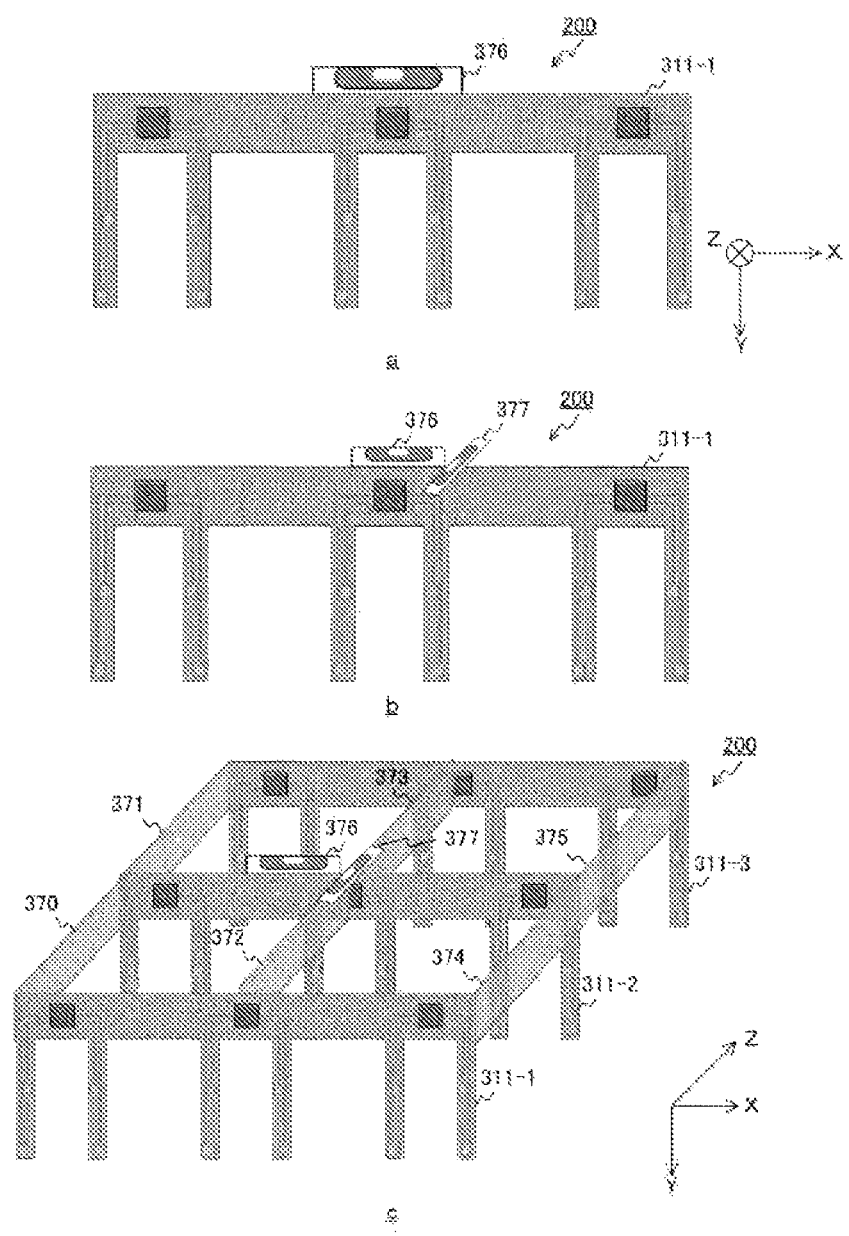

FIG. 272 is a diagram illustrating a configuration example of the sensor device including a level added thereto according to the fifth modification example of the second embodiment of the present technology.

Figure 273:
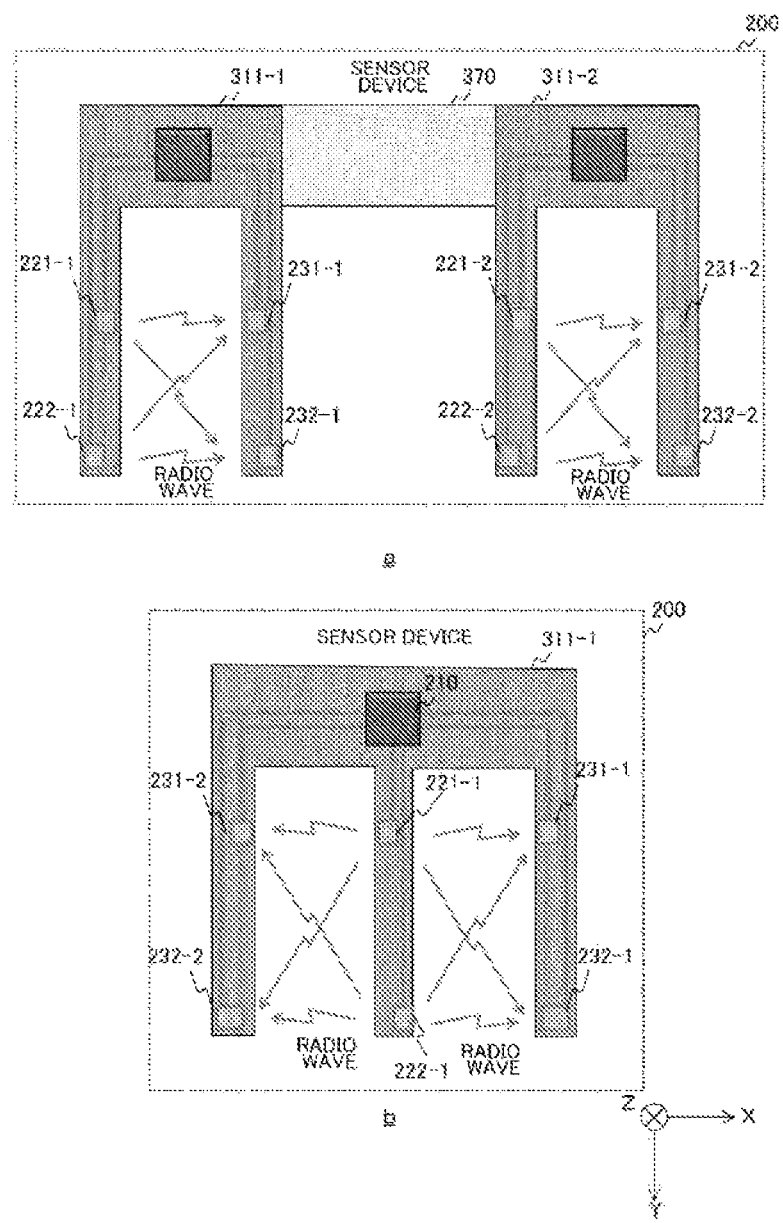

FIG. 273 is a diagram illustrating a configuration example of the sensor device in which transmission and reception directions of electromagnetic waves intersect each other according to the fifth modification example of the second embodiment of the present technology.

Figure 274:
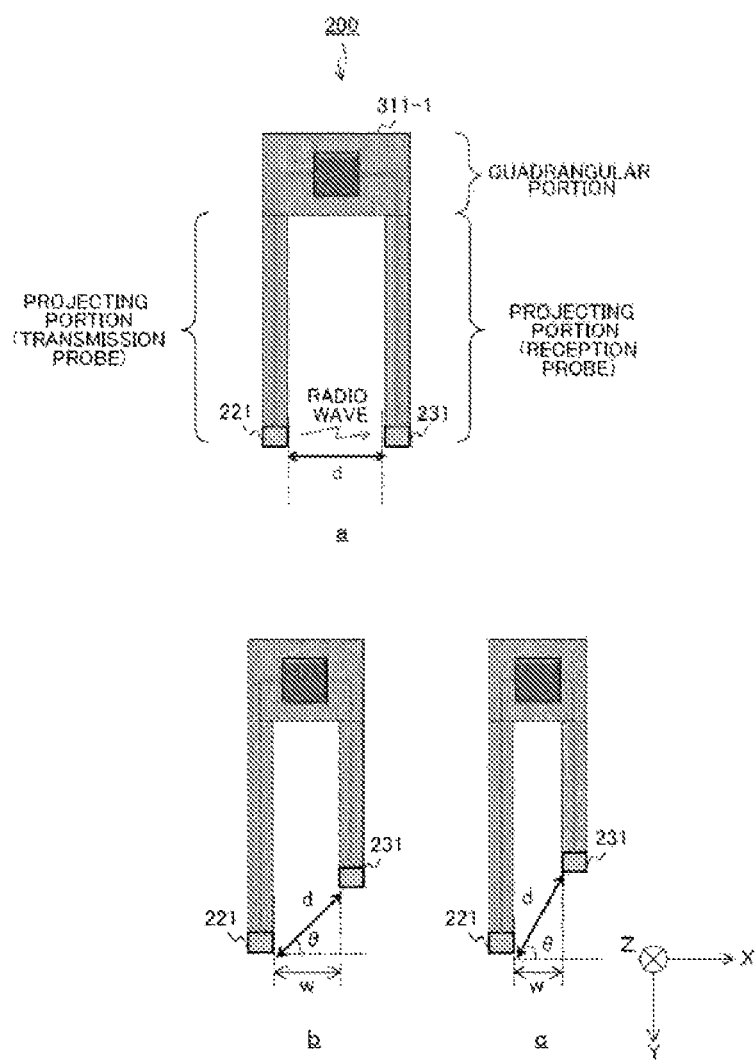

FIG. 274 is a diagram for explaining effects when the positions of antennas are asymmetric according to a sixth modification example of the second embodiment of the present technology.

Figure 275:
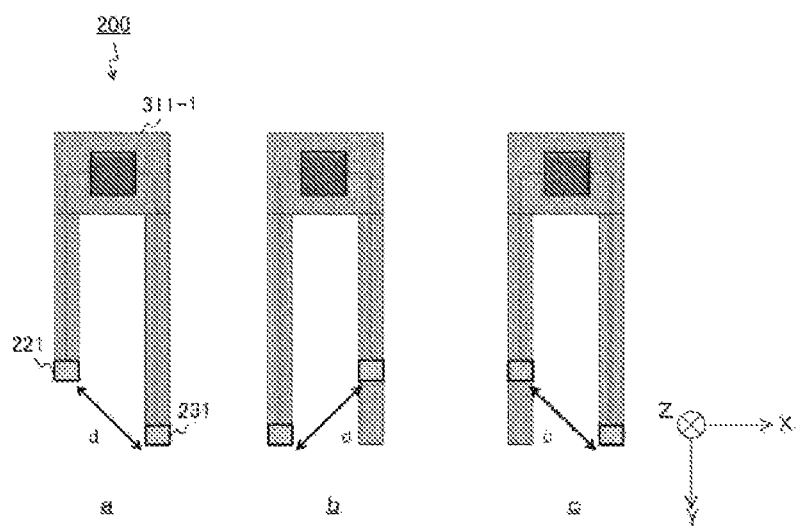

FIG. 275 is a diagram illustrating a configuration example of a sensor device according to the sixth modification example of the second embodiment of the present technology.

Figure 276:
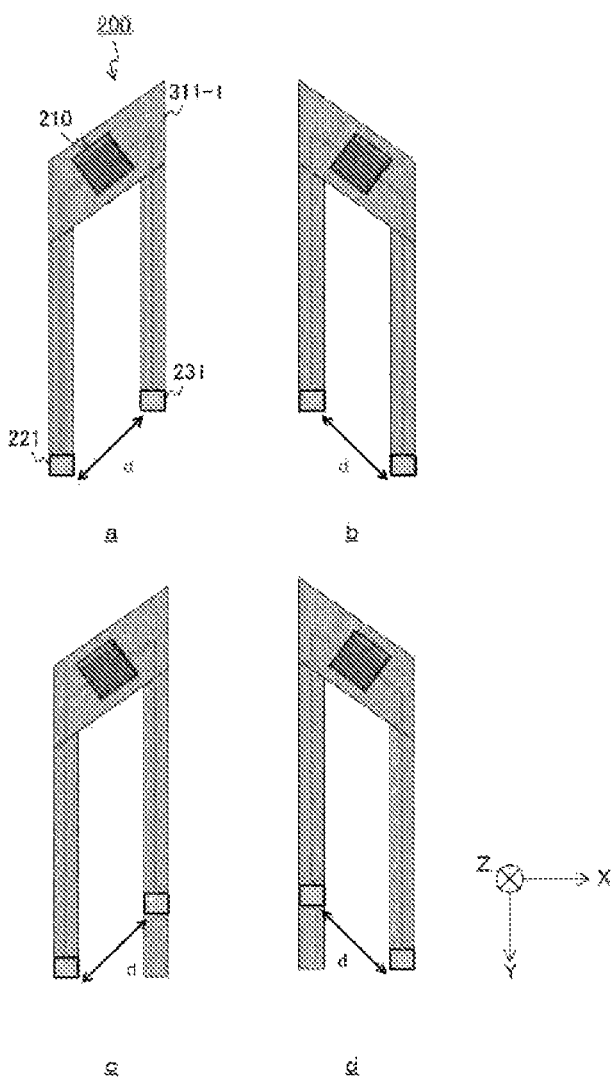

FIG. 276 is a diagram illustrating a configuration example of the sensor device in which a quadrangular portion has a parallelogram according to the sixth modification example of the second embodiment of the present technology.

FIG. 277 is a diagram illustrating a configuration example of the sensor device in which the quadrangular portion has a rectangular shape and the transmission path lengths are made to coincide with each other on the transmission side and the reception side according to the sixth modification example of the second embodiment of the present technology.

Figure 278:
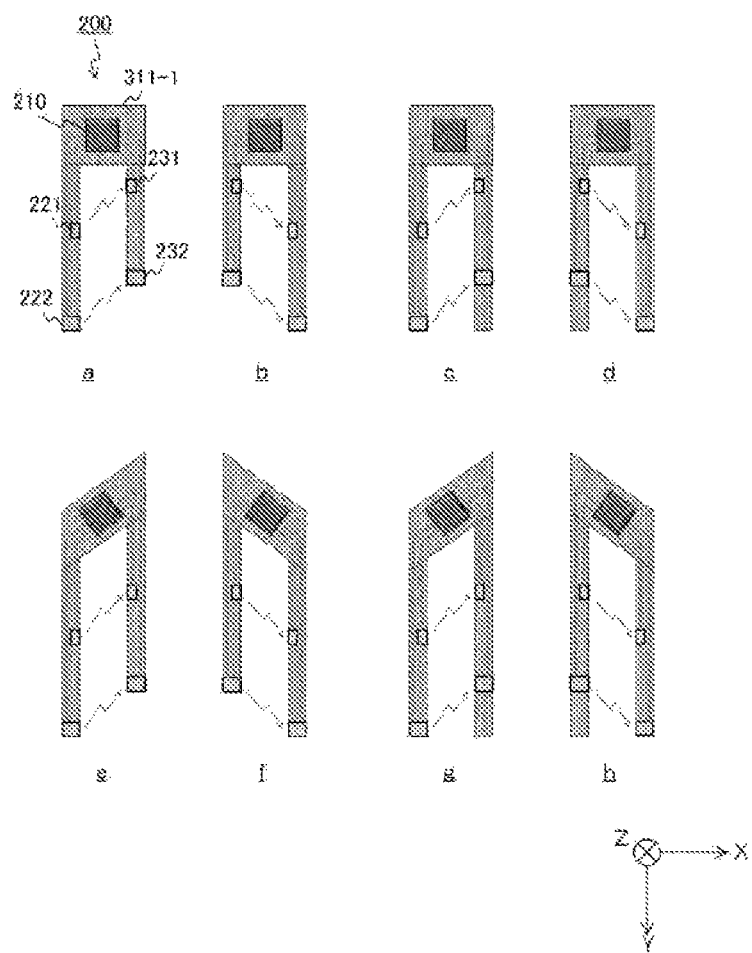

FIG. 278 is a diagram illustrating a configuration example of the sensor device that performs measurement at a plurality of points according to the sixth modification example of the second embodiment of the present technology.

Figure 279:
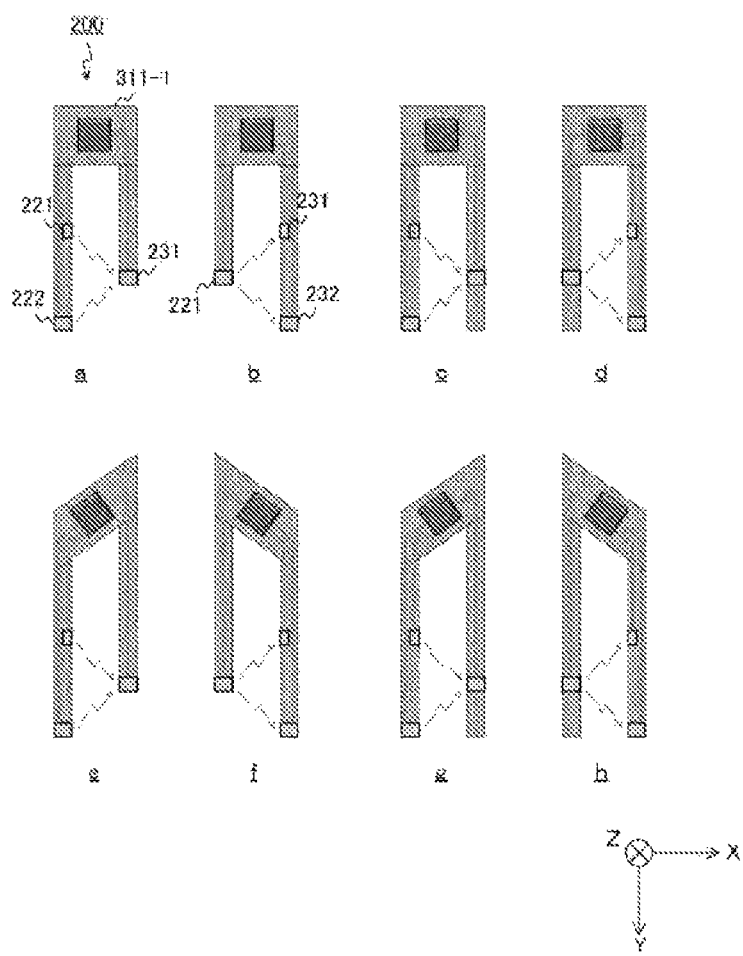

FIG. 279 is a diagram illustrating a configuration example of the sensor device that shares an antenna to perform measurement at two points according to the sixth modification example of the second embodiment of the present technology.

Figure 280:
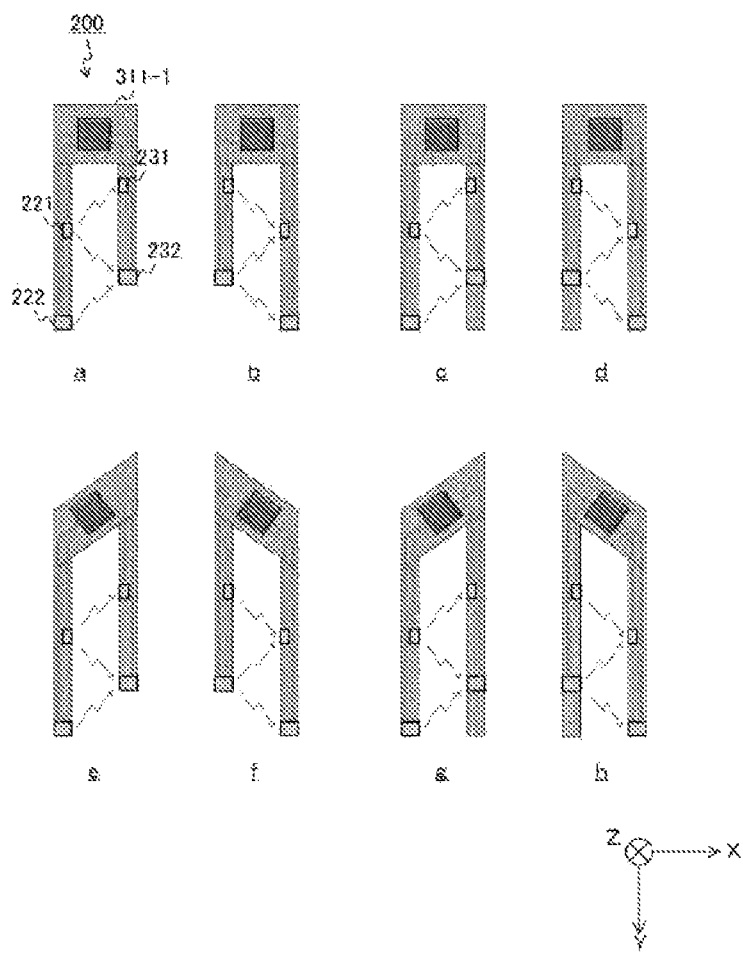

FIG. 280 is a diagram illustrating a configuration example of the sensor device that shares an antenna to perform measurement at three or more points according to the sixth modification example of the second embodiment of the present technology.

Figure 281:
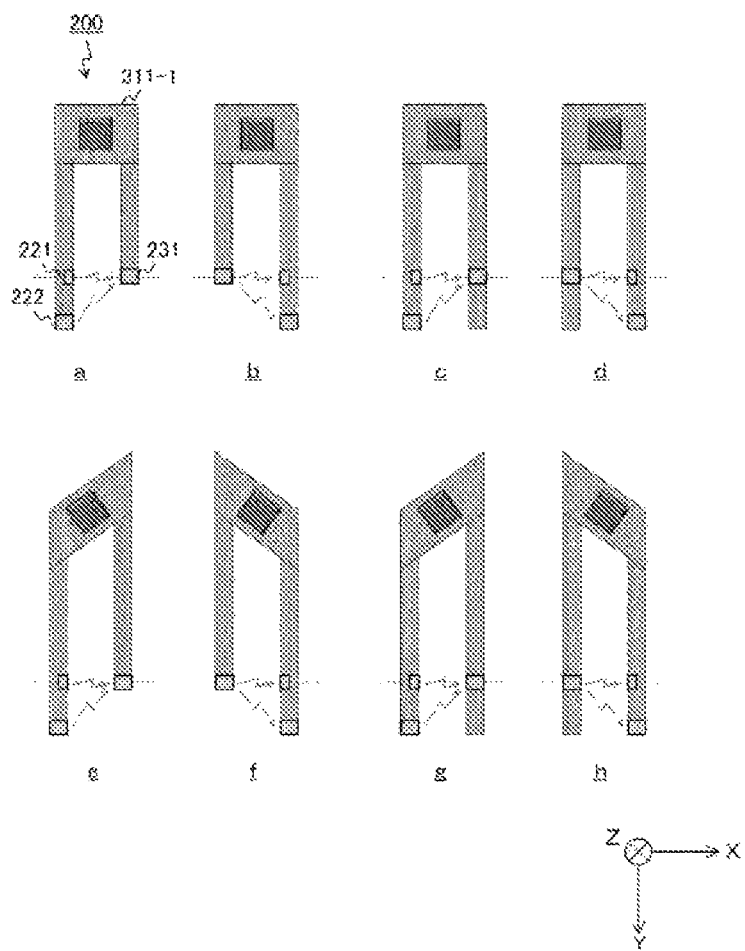

FIG. 281 is a diagram illustrating another example of the sensor device that shares an antenna to perform measurement at two points according to the sixth modification example of the second embodiment of the present technology.

Figure 282:
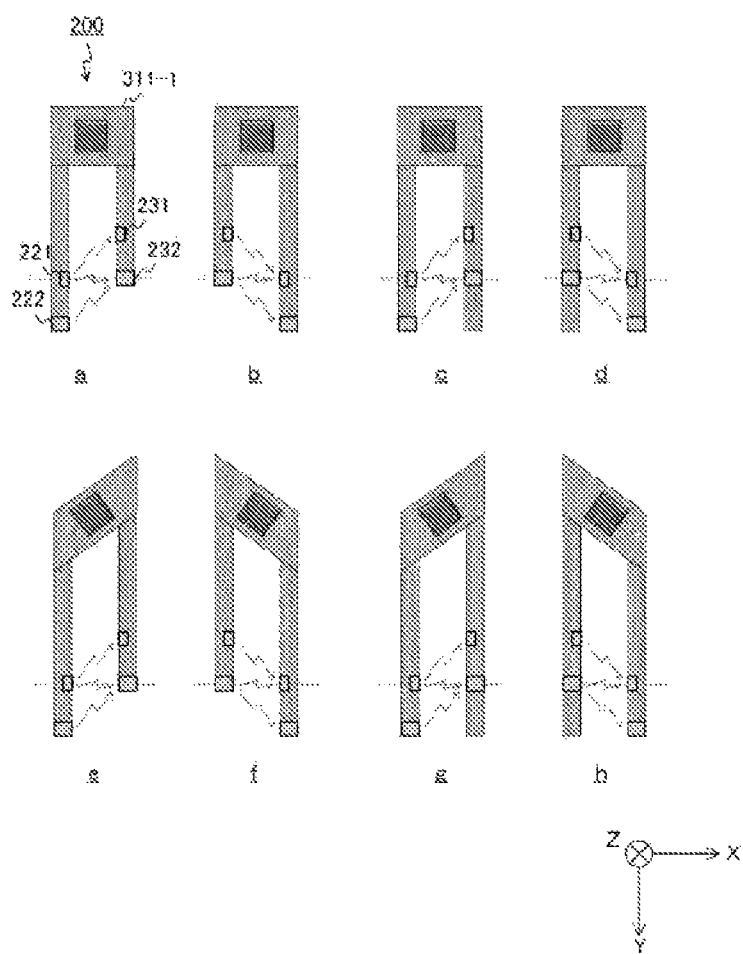

FIG. 282 is a diagram illustrating another example of the sensor device that shares an antenna to perform measurement at three or more points according to the sixth modification example of the second embodiment of the present technology.

Figure 283:
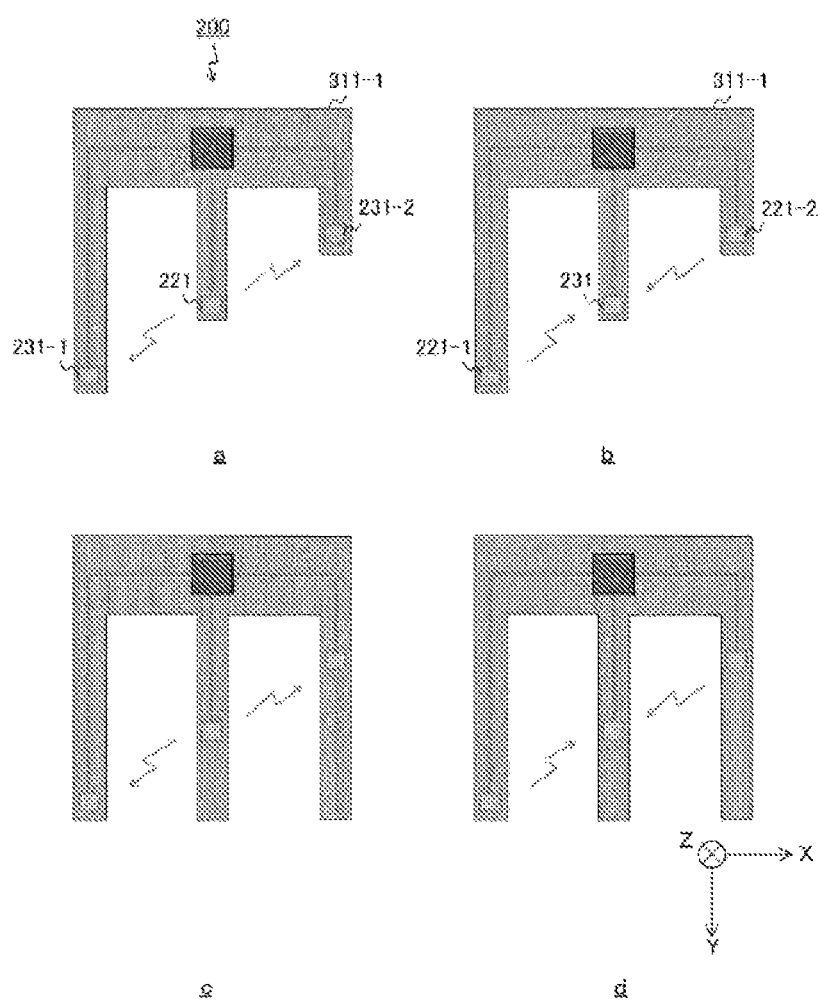

FIG. 283 is a diagram illustrating a configuration example of the sensor device in which the number of probes is increased according to the sixth modification example of the second embodiment of the present technology.

Figure 284:
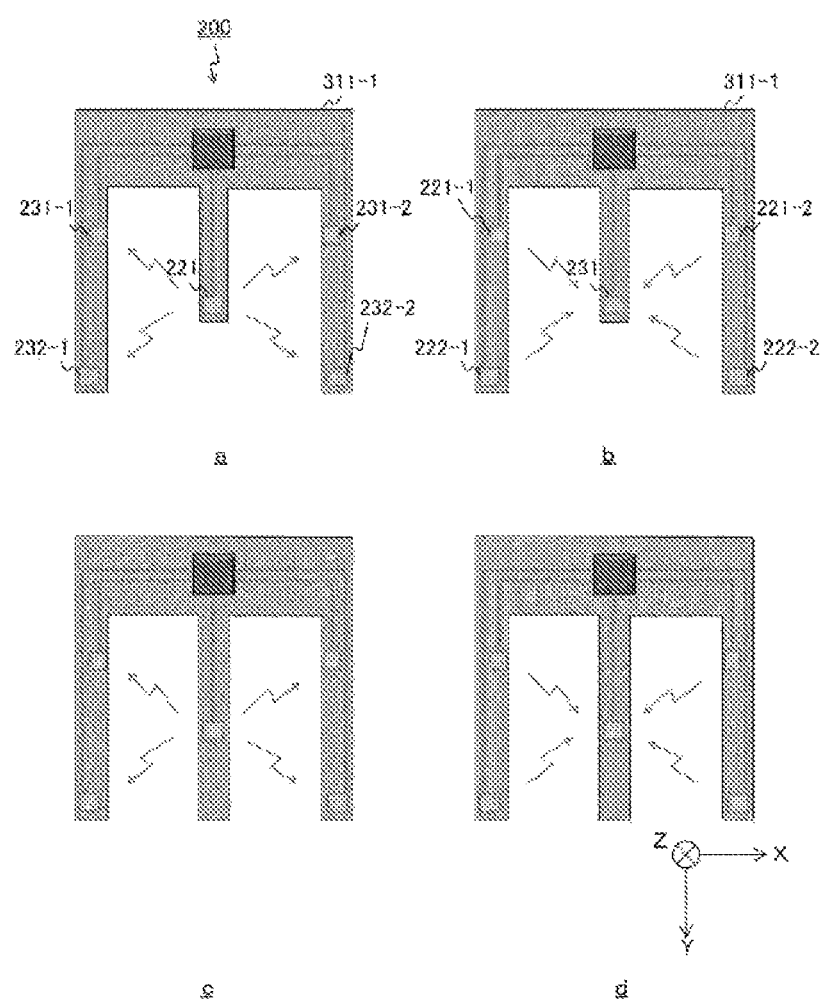

FIG. 284 is a diagram illustrating a configuration example of the sensor device in which the numbers of probes and antennas are increased according to the sixth modification example of the second embodiment of the present technology.

Figure 285:
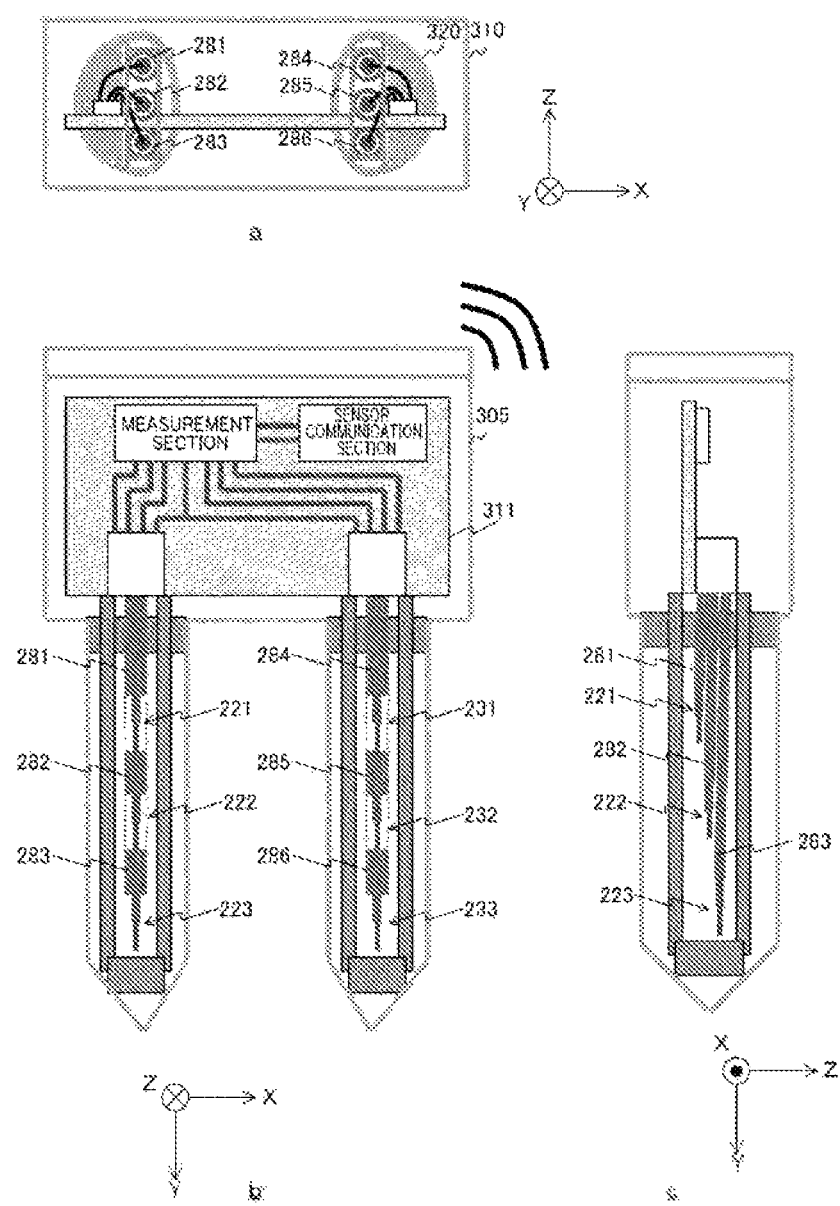

FIG. 285 is a diagram illustrating an example of a sensor device according to a third embodiment of the present technology.

FIG. 286 is an example of a sectional view and a side view of an antenna according to the third embodiment of the present technology.

Figure 287:
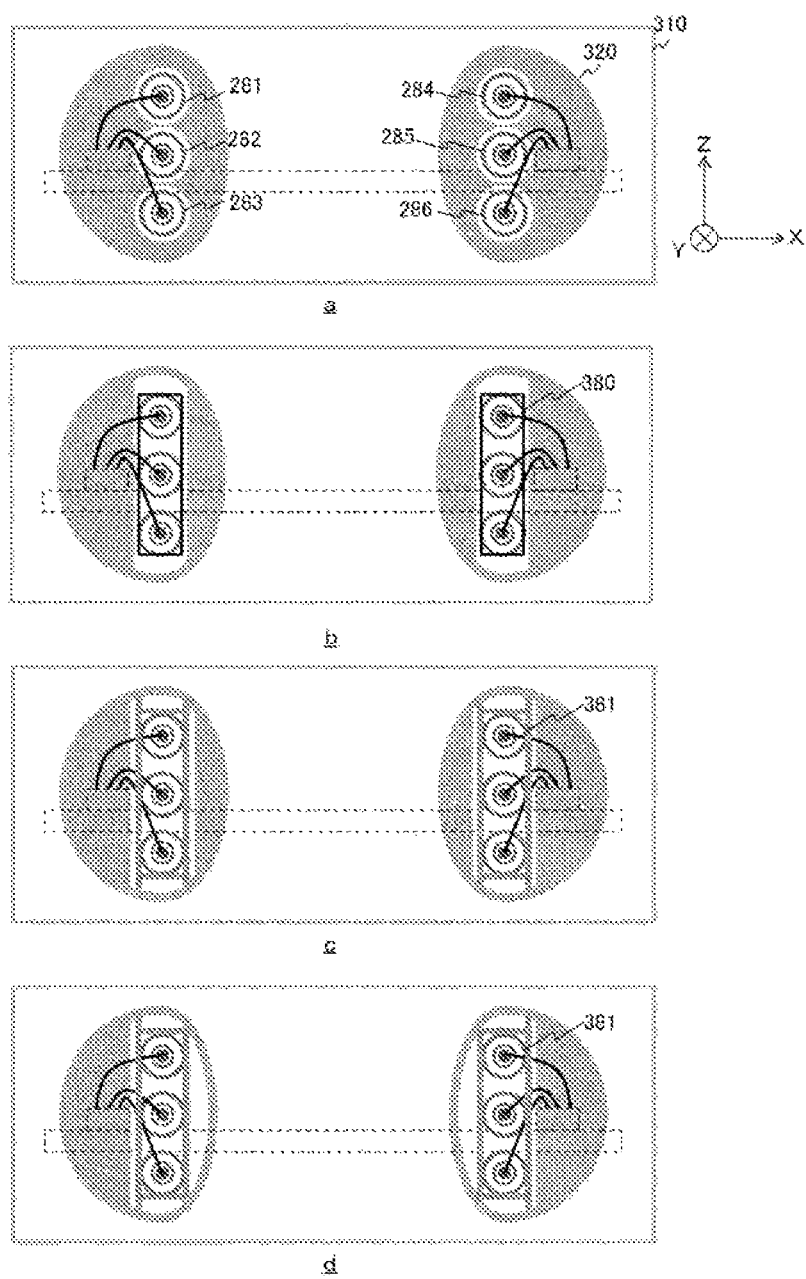

FIG. 287 is a diagram illustrating an example of a sectional view of a coaxial cable according to the third embodiment of the present technology.

Figure 288:
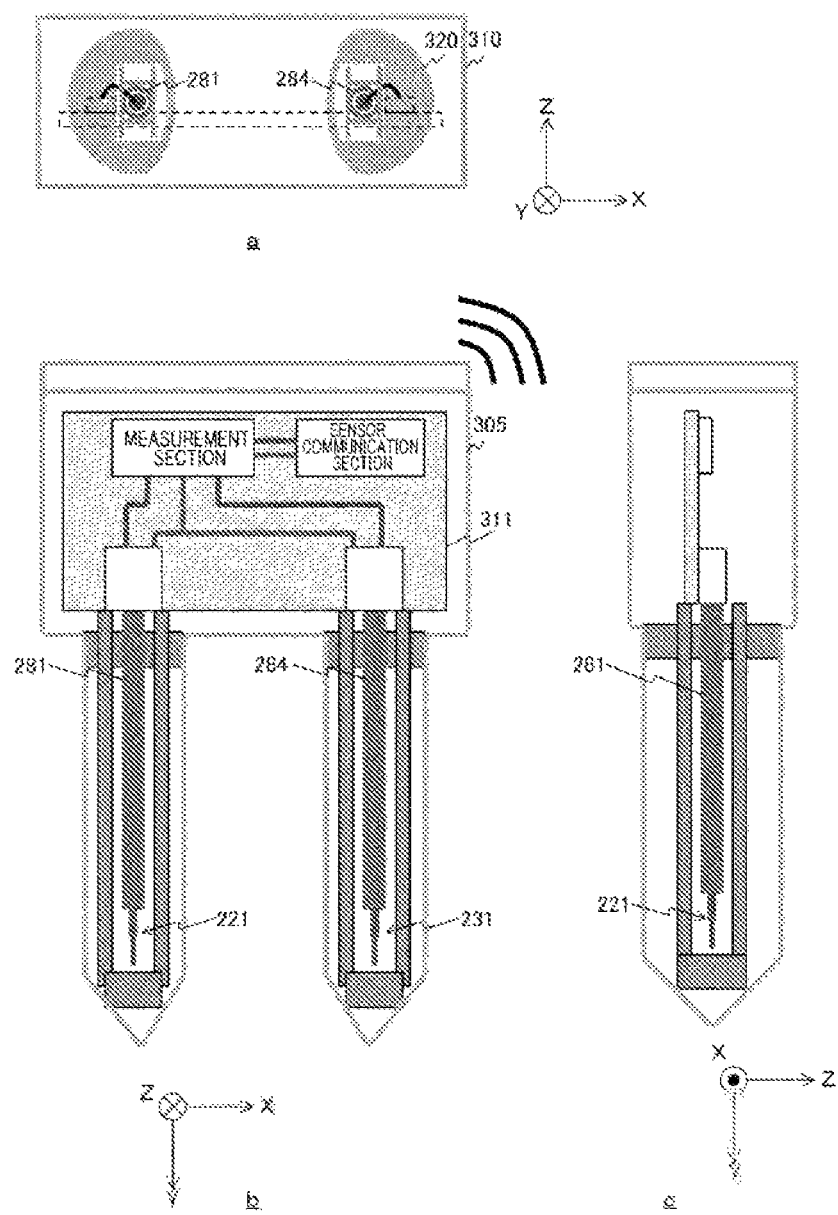

FIG. 288 is a diagram illustrating an example of the sensor device in which the number of antennas is reduced according to the third embodiment of the present technology.

Figure 289:
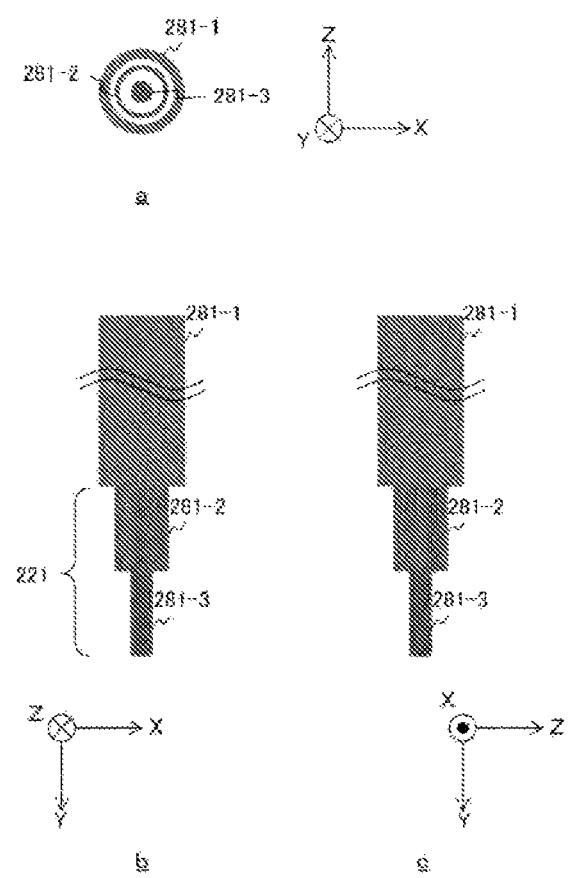

FIG. 289 is an example of a sectional view and a side view of the antenna when the number of antennas is reduced according to the third embodiment of the present technology.

Figure 290:
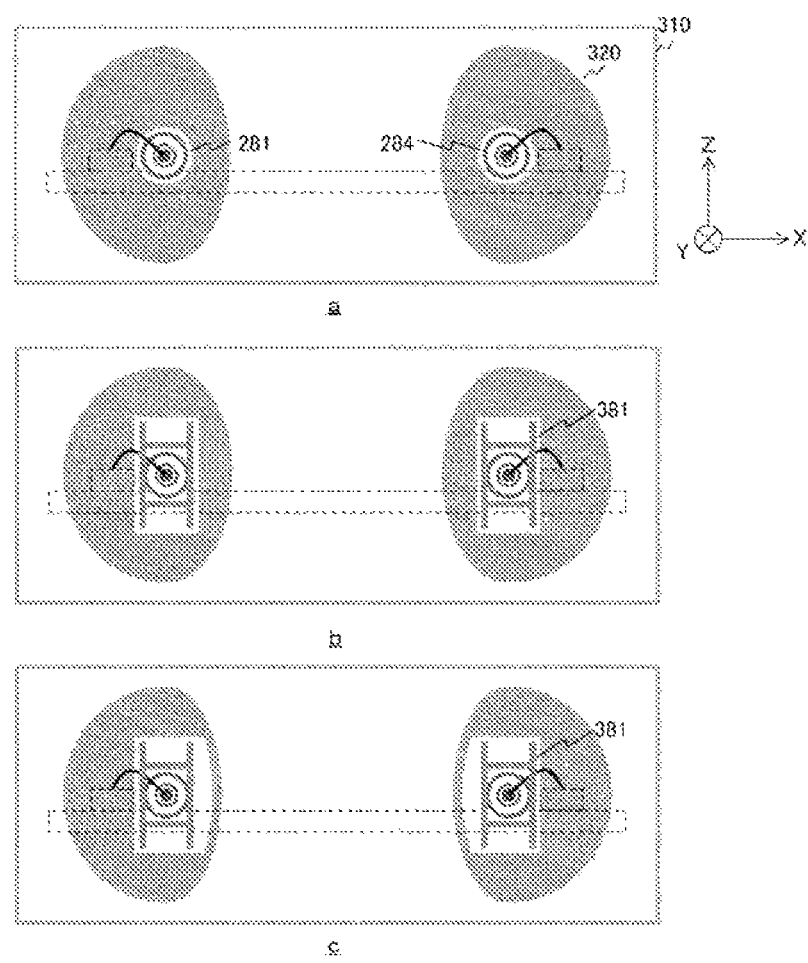

FIG. 290 is a diagram illustrating an example of a sectional view of the coaxial cable when the number of antennas is reduced according to the third embodiment of the present technology.

Figure 291:
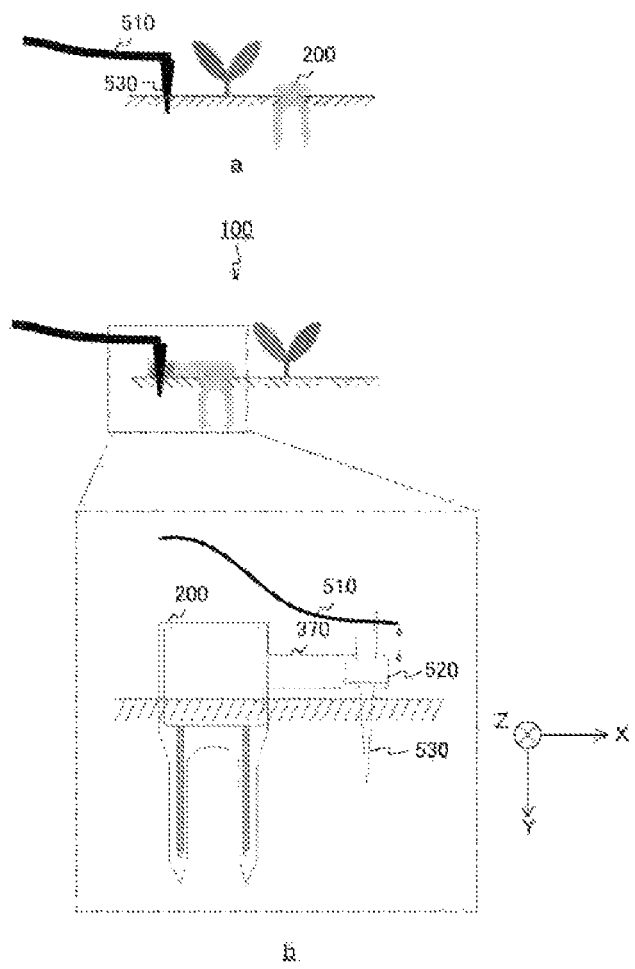

FIG. 291 is a diagram illustrating an example of moisture measurement systems according to a fourth embodiment and a comparative example of the present technology.

Figure 292:
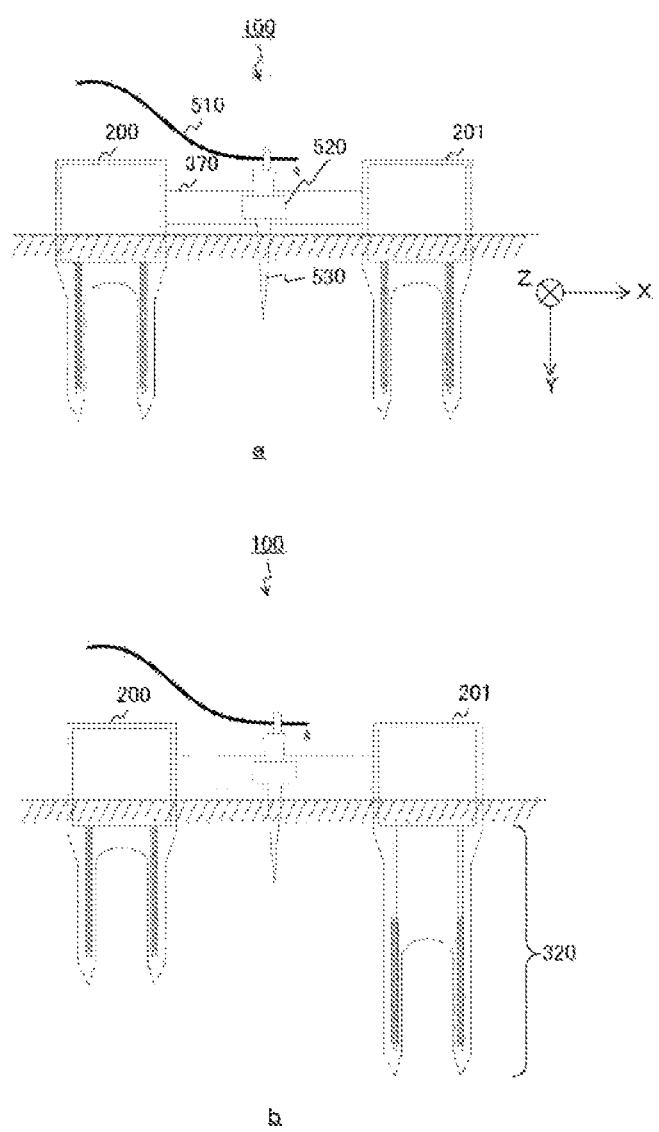

FIG. 292 is a diagram illustrating an example of the moisture measurement system in which a plurality of sensor devices are coupled according to the fourth embodiment of the present technology.

Figure 293:
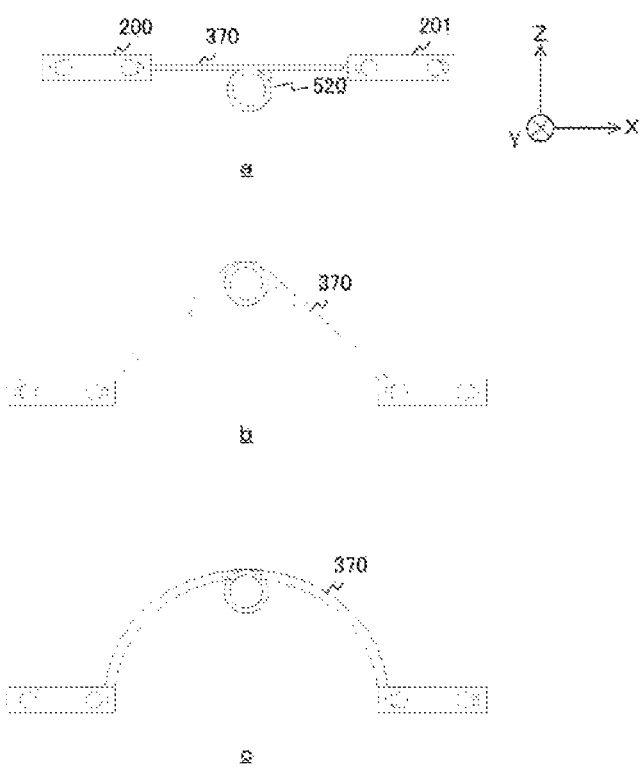

FIG. 293 is an example of a top view of the moisture measurement system in which the plurality of sensor devices are coupled according to the fourth embodiment of the present technology.

FIG. 294 is a diagram illustrating an example of the moisture measurement system provided with a support member according to the fourth embodiment of the present technology.

Figure 295:
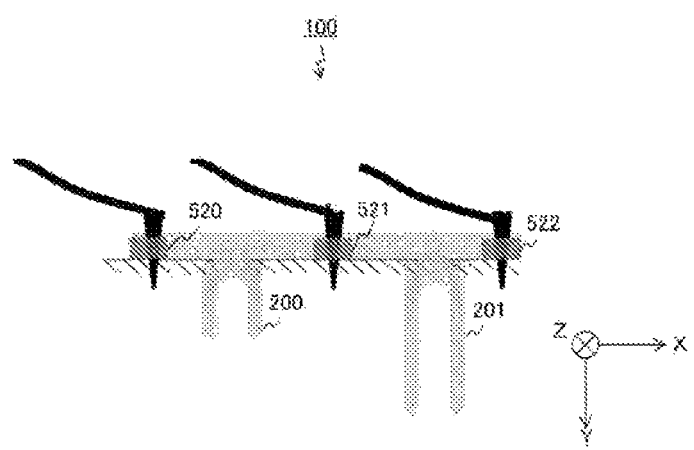

FIG. 295 is a diagram illustrating an example of the moisture measurement system in which the plurality of sensor devices and a plurality of watering nozzle holders are coupled according to the fourth embodiment of the present technology.

Figure 296:
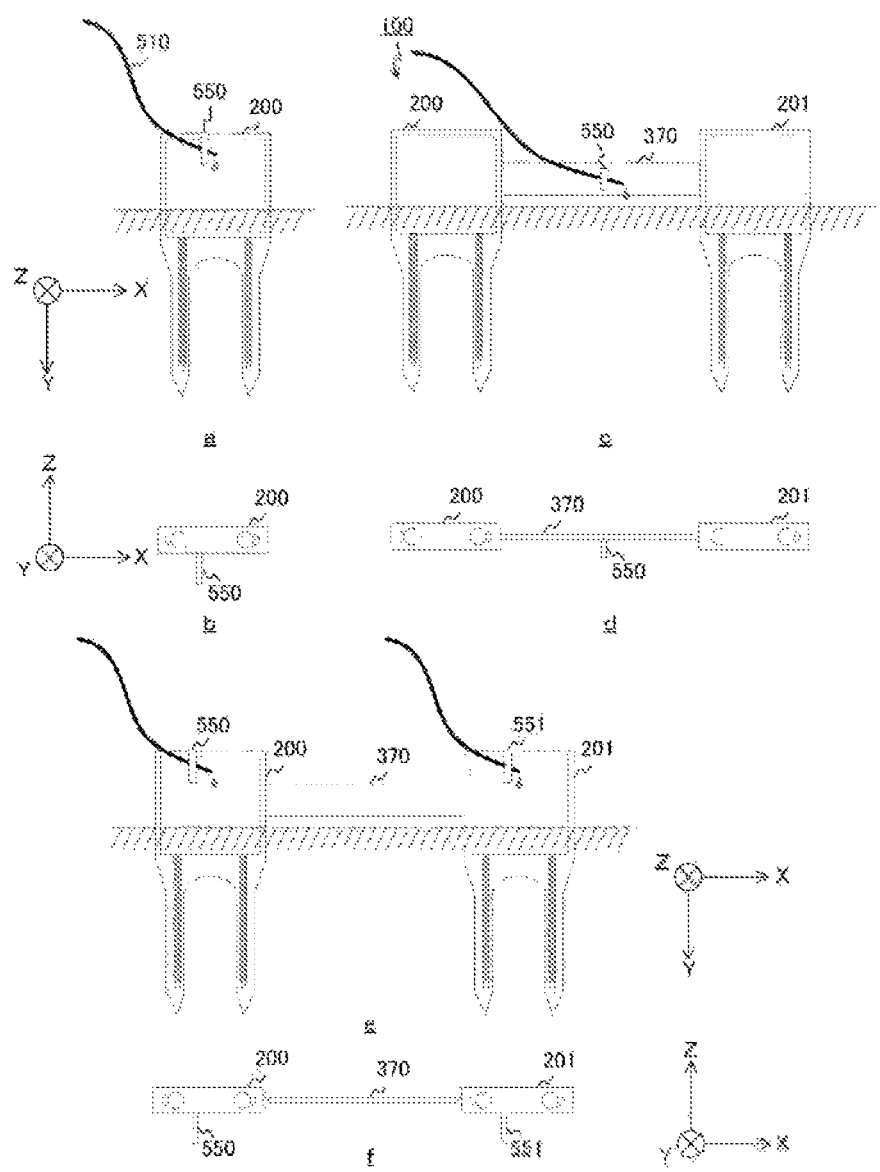

FIG. 296 is a diagram illustrating the moisture measurement system with a watering tube holder coupled thereto according to the fourth embodiment of the present technology.

Figure 297:
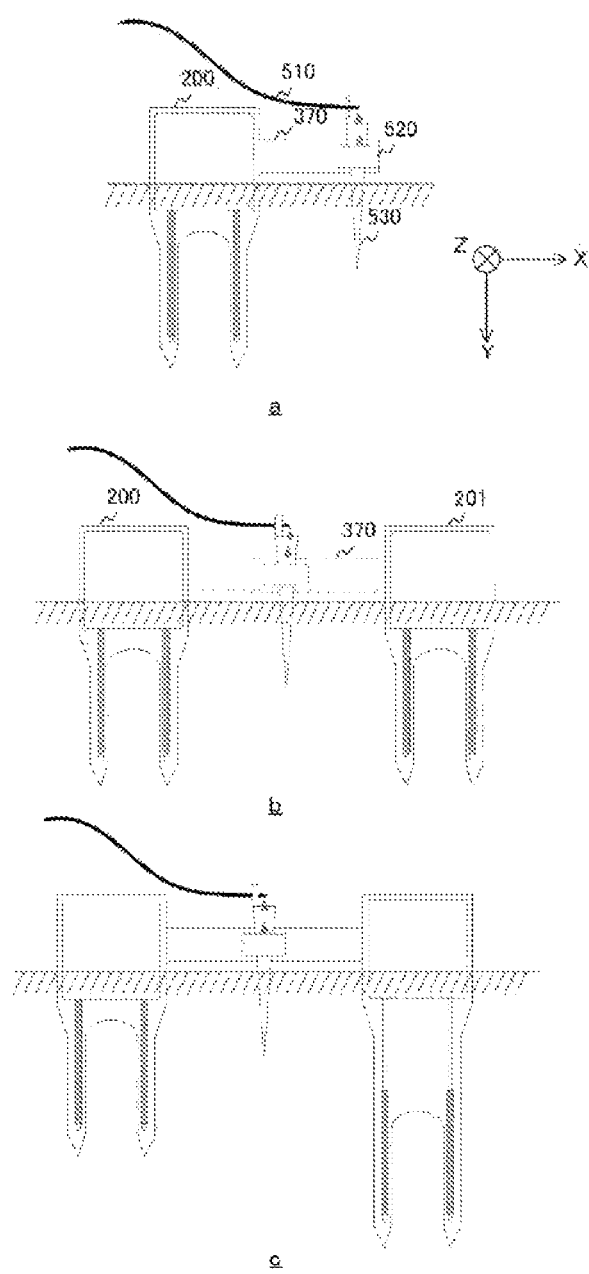

FIG. 297 is a diagram illustrating an example of the moisture measurement system that performs watering via a watering nozzle according to the fourth embodiment of the present technology.

FIG. 298 is a diagram illustrating an example of the moisture measurement system in which a probe alignment direction and a line segment that is parallel to a coupling portion are orthogonal to each other according to the fourth embodiment of the present technology.

Figure 299:
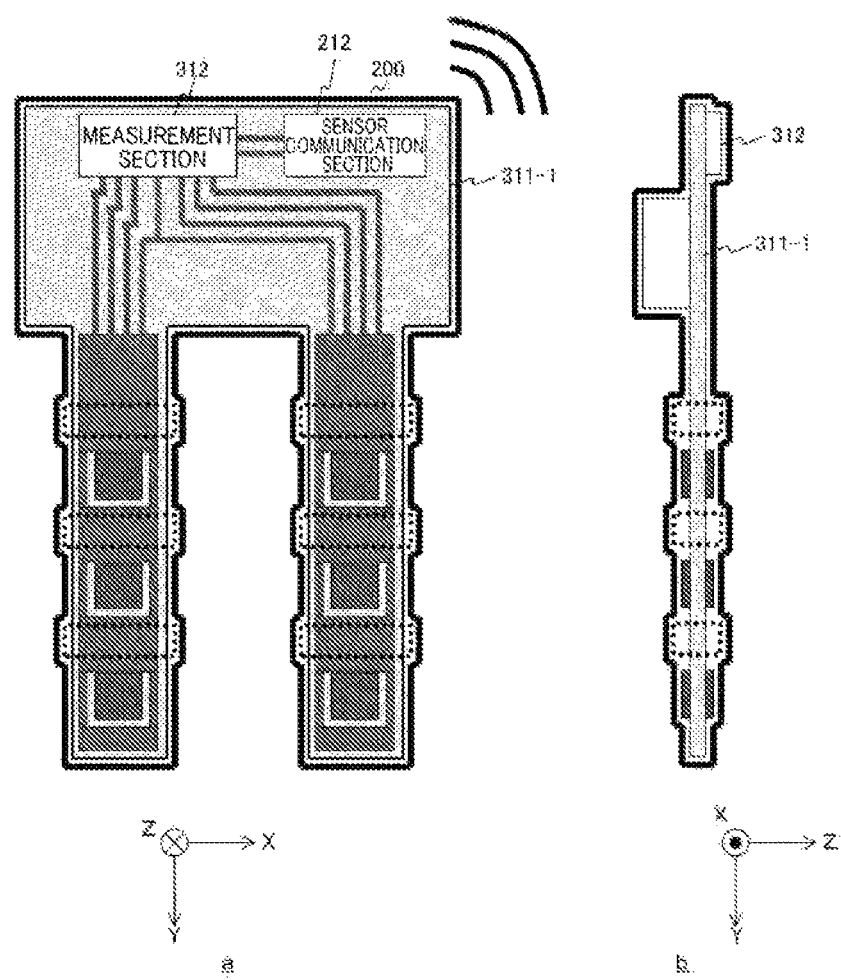

FIG. 299 is a diagram illustrating an example of a front view and a side view of a sensor device according to a fifth embodiment of the present technology.

Figure 300:
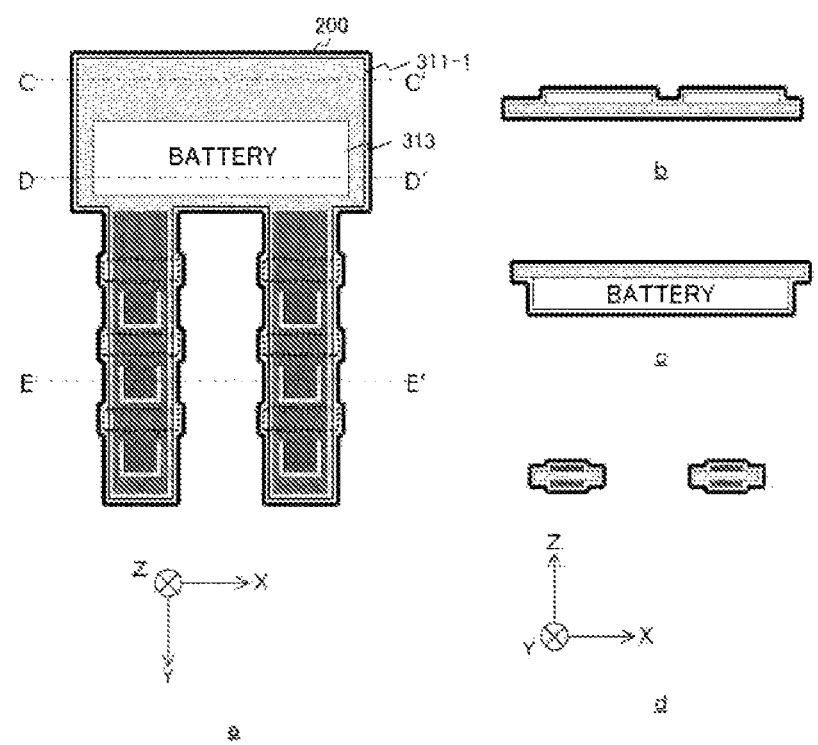

FIG. 300 is a diagram illustrating an example of a back view and a sectional view of the sensor device according to the fifth embodiment of the present technology.

Figure 301:
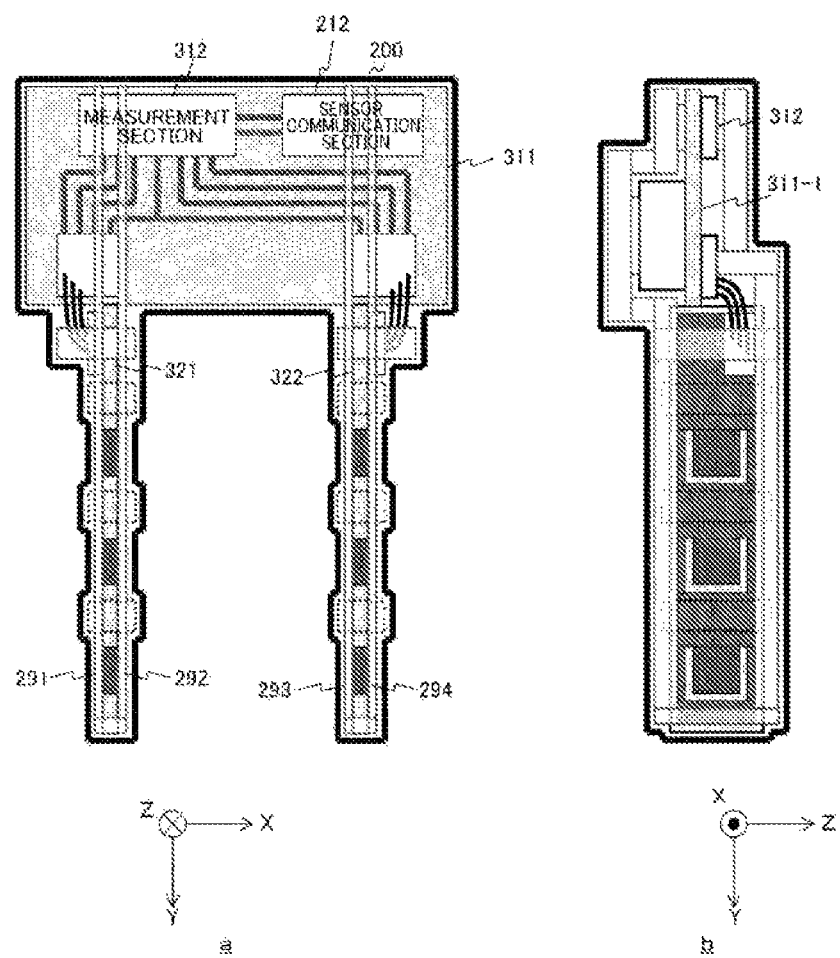

FIG. 301 is a diagram illustrating an example of a back view and a sectional view of the sensor device including substrates caused to be orthogonal to each other and including a frame according to the fifth embodiment of the present technology.

Figure 302:
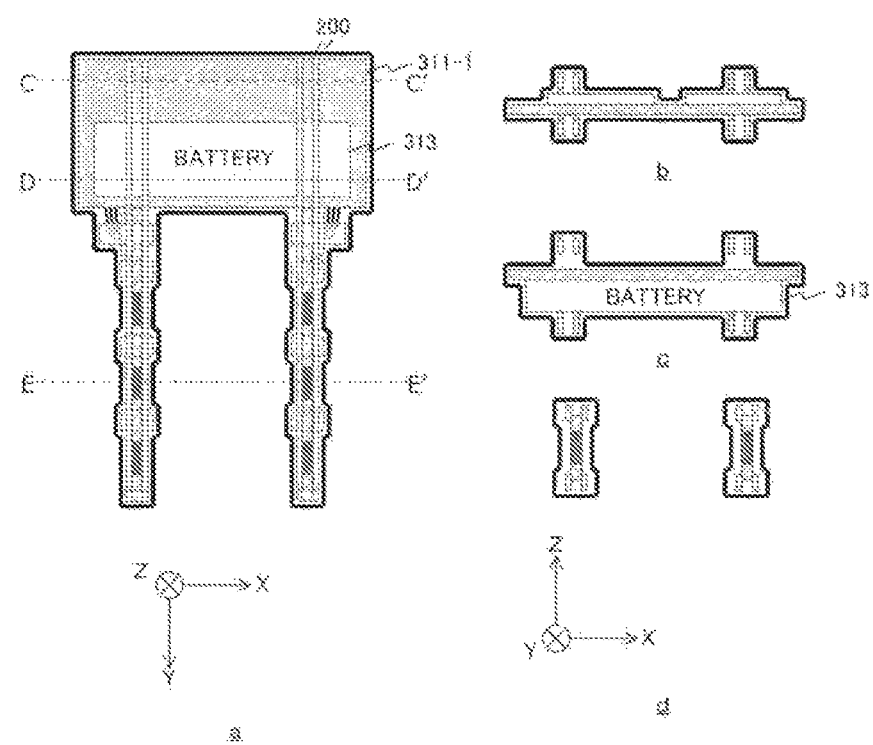

FIG. 302 is a diagram illustrating an example of a back view and a sectional view of the sensor device including substrates caused to be orthogonal to each other and including the frame according to the fifth embodiment of the present technology.

Figure 303:
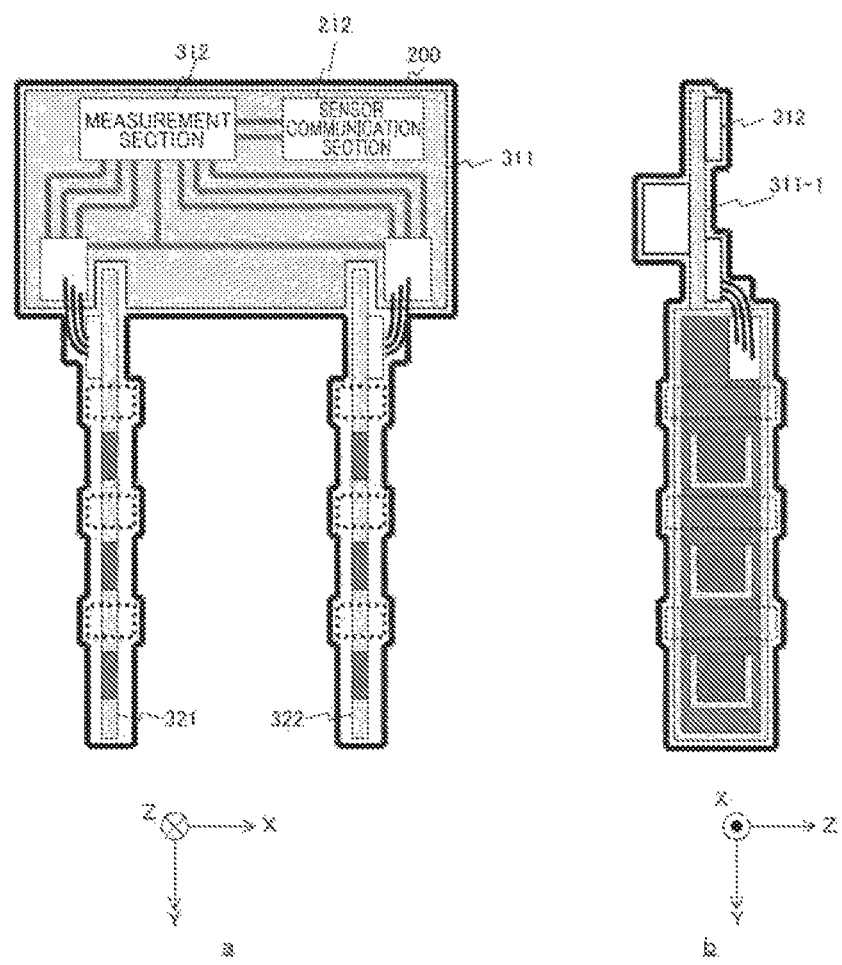

FIG. 303 is a diagram illustrating an example of a back view and a sectional view of the sensor device including the substrates caused to be orthogonal to each other according to the fifth embodiment of the present technology.

Figure 304:
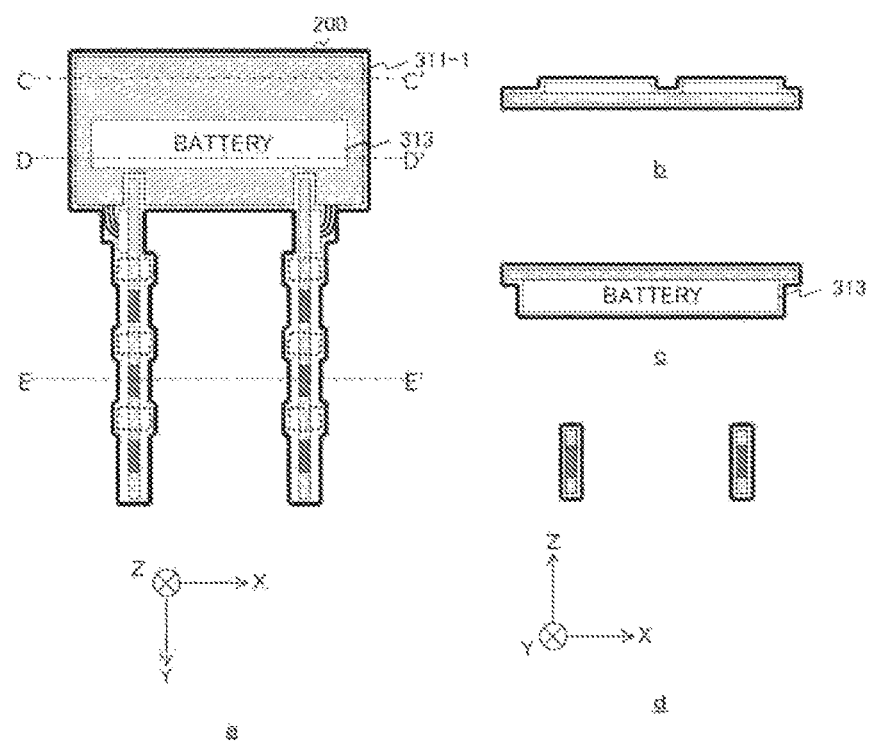

FIG. 304 is a diagram illustrating an example of a back view and a sectional view of the sensor device including the substrates caused to be orthogonal to each other according to the fifth embodiment of the present technology.

Figure 305:
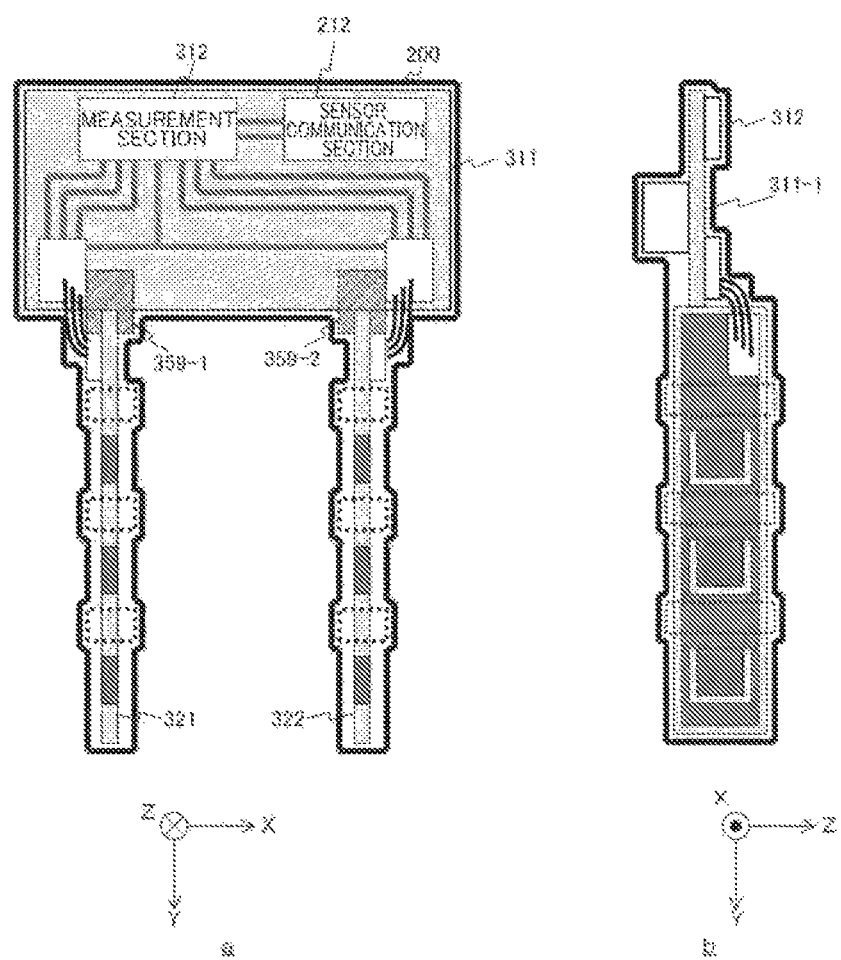

FIG. 305 is a diagram illustrating an example of a back view and a sectional view of the sensor device including the substrates caused to be orthogonal to each other and including a jig according to the fifth embodiment of the present technology.

Figure 306:
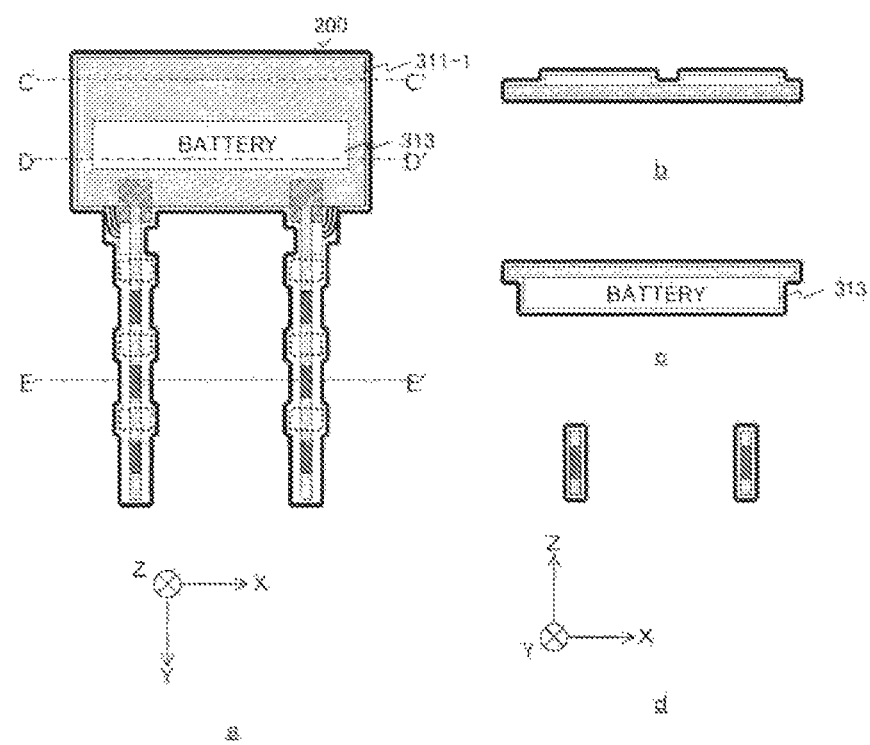

FIG. 306 is a diagram illustrating an example of a back view and a sectional view of the sensor device including the substrates caused to be orthogonal to each other and including the jig according to the fifth embodiment of the present technology.

Figure 307:
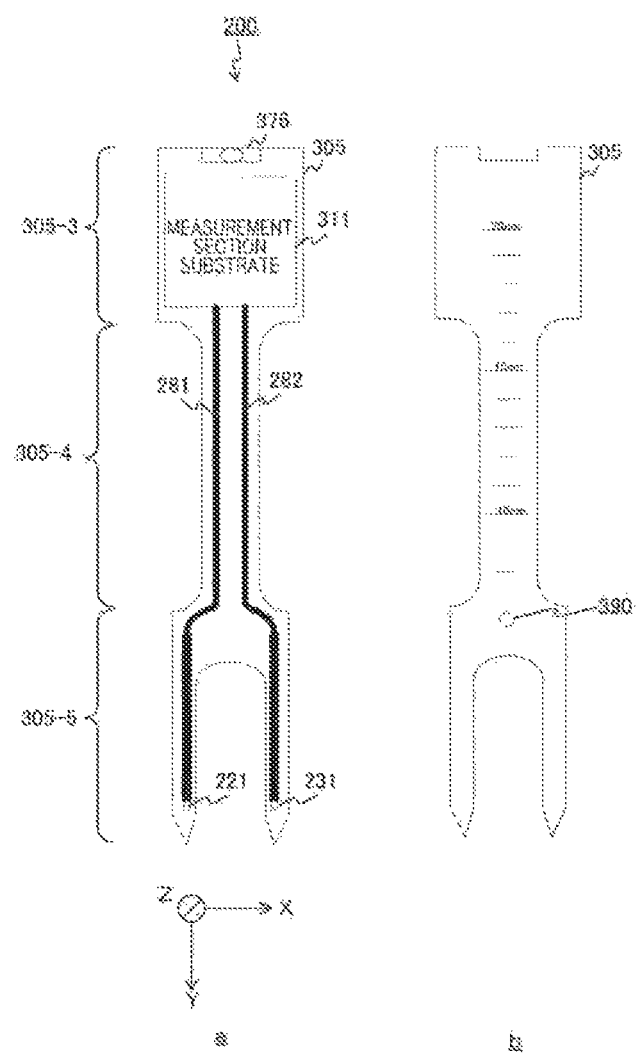

FIG. 307 is a diagram illustrating an example of a sensor device according to a sixth embodiment of the present technology.

Figure 308:
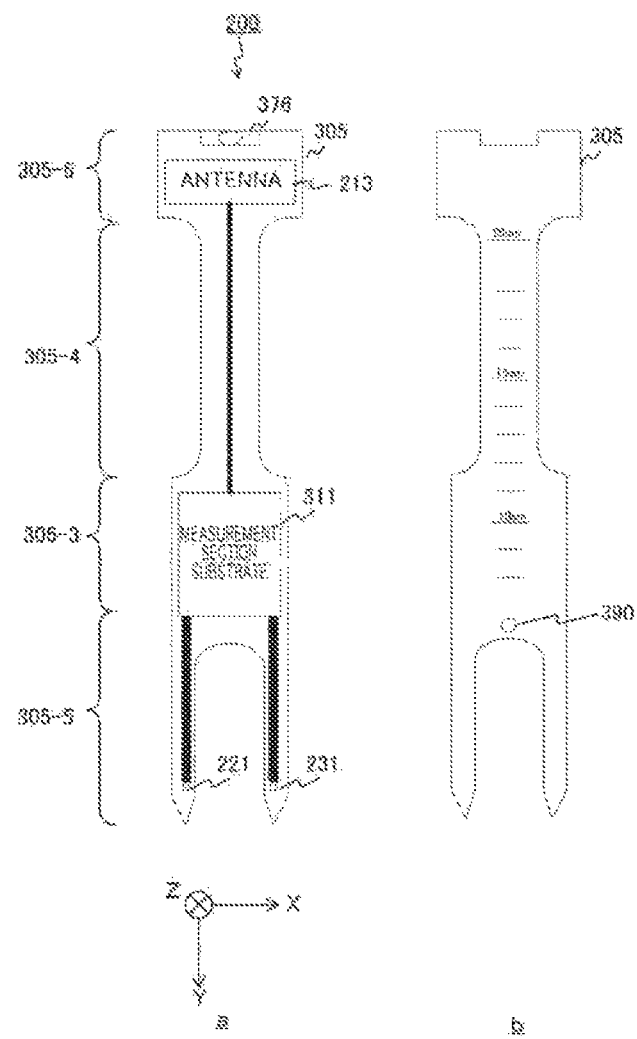

FIG. 308 is a diagram illustrating an example of the sensor device in which the position of a main body section has been changed according to the sixth embodiment of the present technology.

Figure 309:
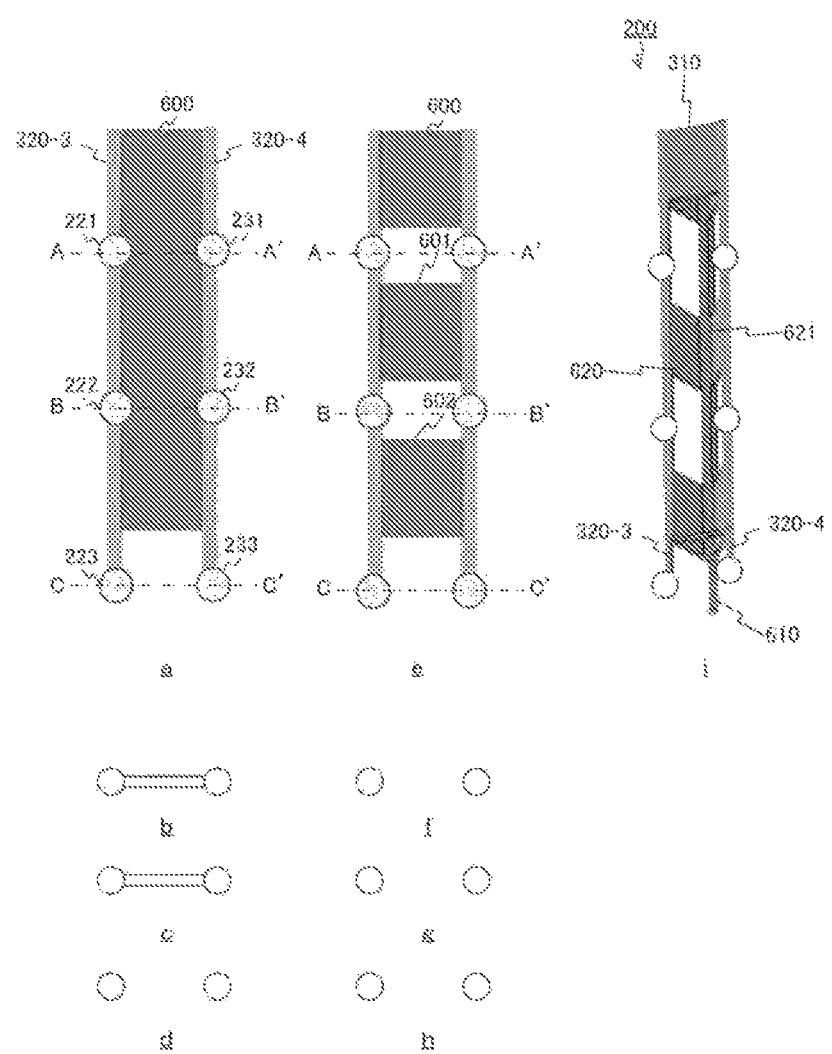

FIG. 309 is a diagram illustrating an example of sensor devices according to a seventh embodiment and comparative examples of the present technology.

Figure 310:
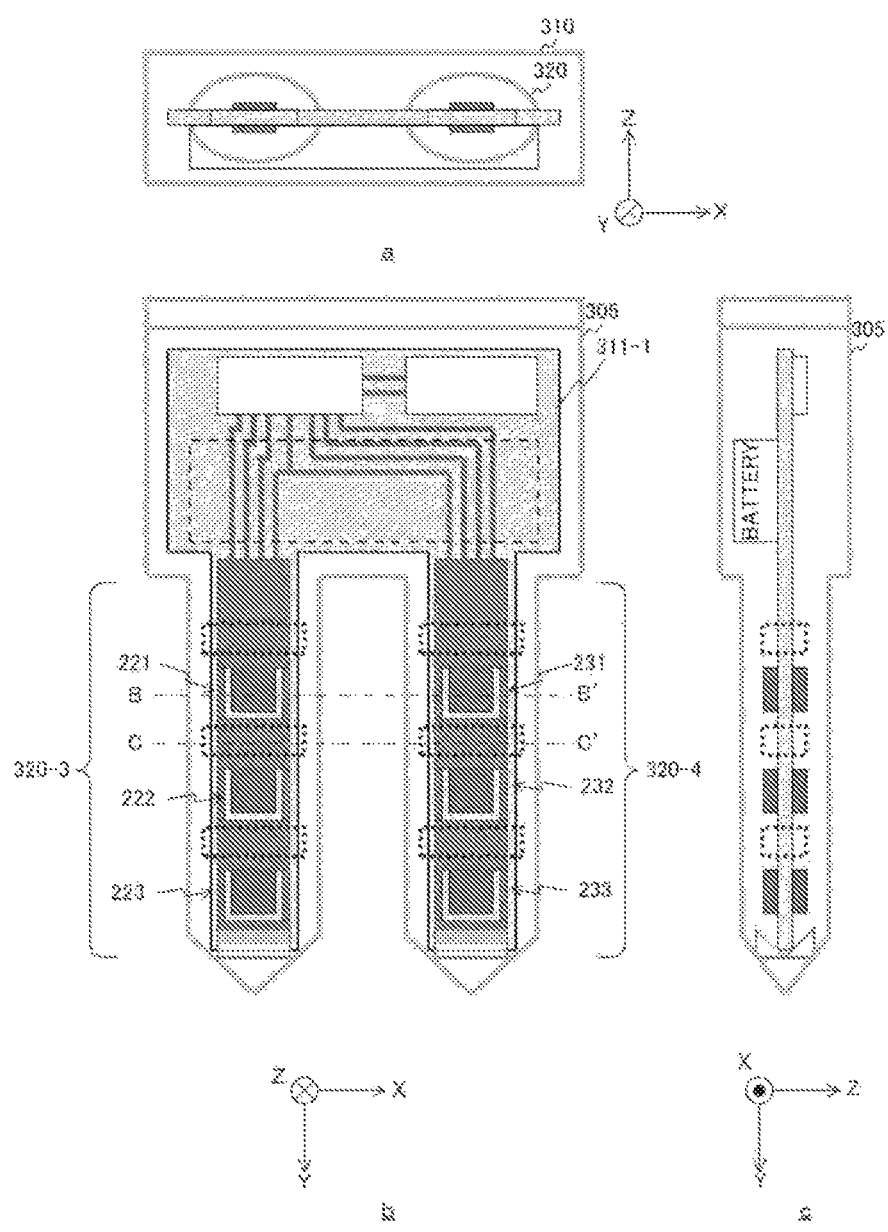

FIG. 310 is a diagram illustrating an example of a cut surface of the sensor device according to the seventh embodiment of the present technology.

Figure 311:
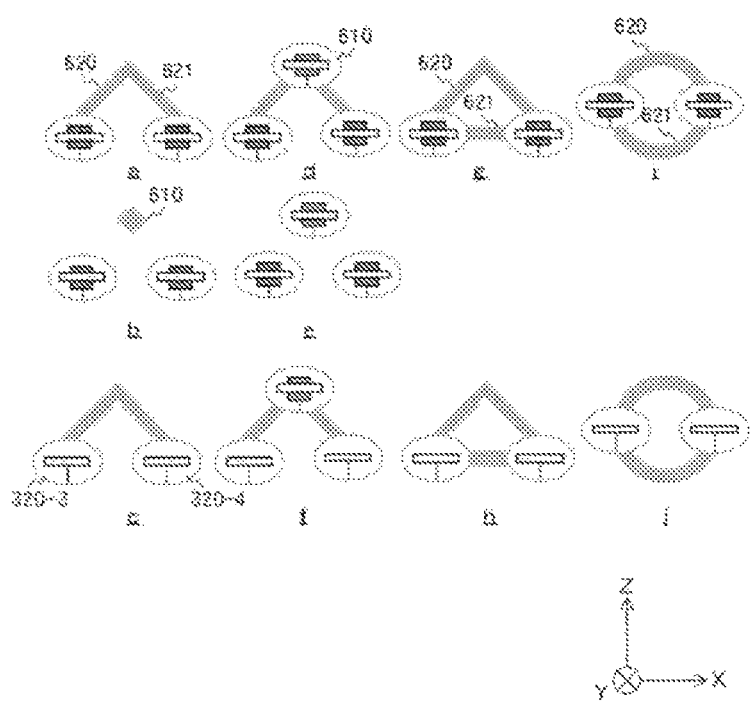

FIG. 311 is a diagram illustrating an example of a sectional view of the sensor device according to the seventh embodiment of the present technology.

Figure 312:
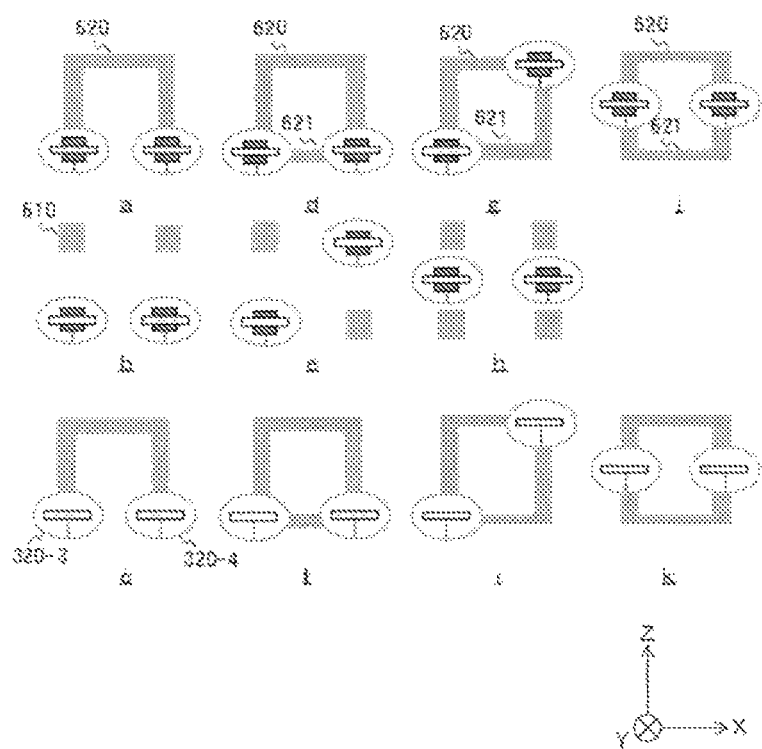

FIG. 312 is a diagram illustrating an example of a sectional view of a rectangle of the sensor device according to the seventh embodiment of the present technology.

Figure 313:
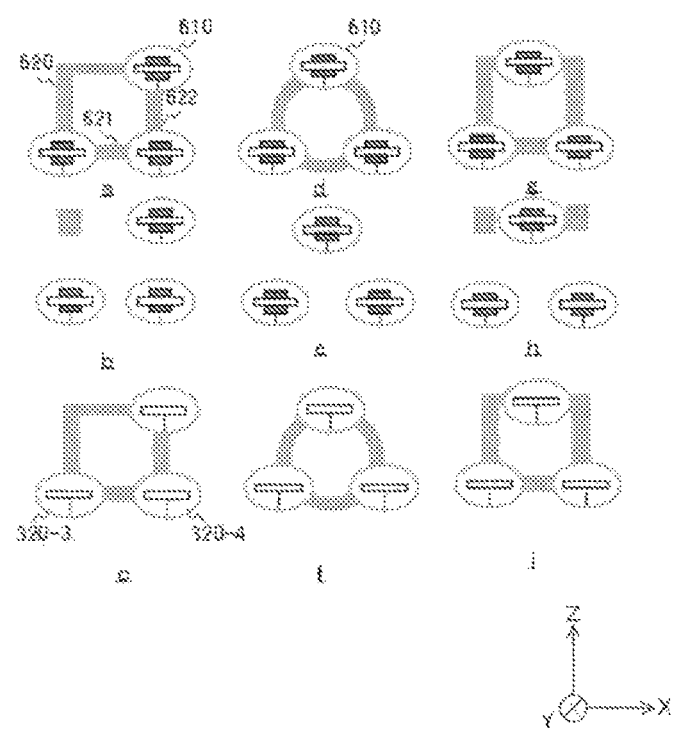

FIG. 313 is a diagram illustrating an example of a sectional view of the sensor device including three probes according to the seventh embodiment of the present technology.

Figure 314:
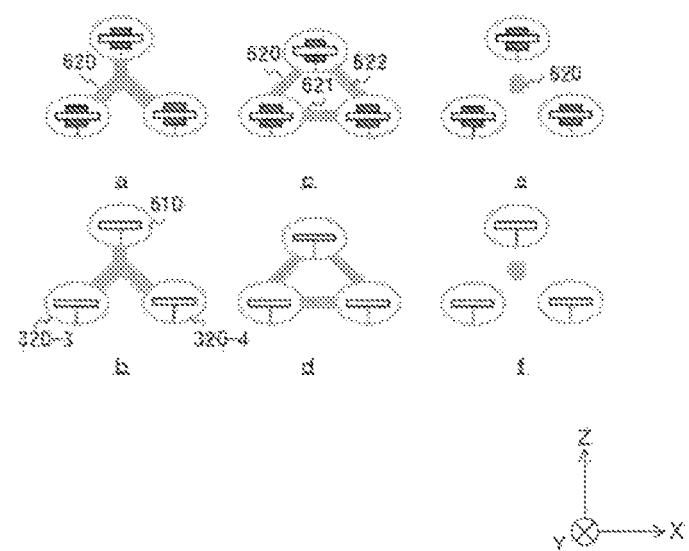

FIG. 314 is a diagram illustrating another example of a sectional view of the sensor device including the three probes according to the seventh embodiment of the present technology.

Figure 315:
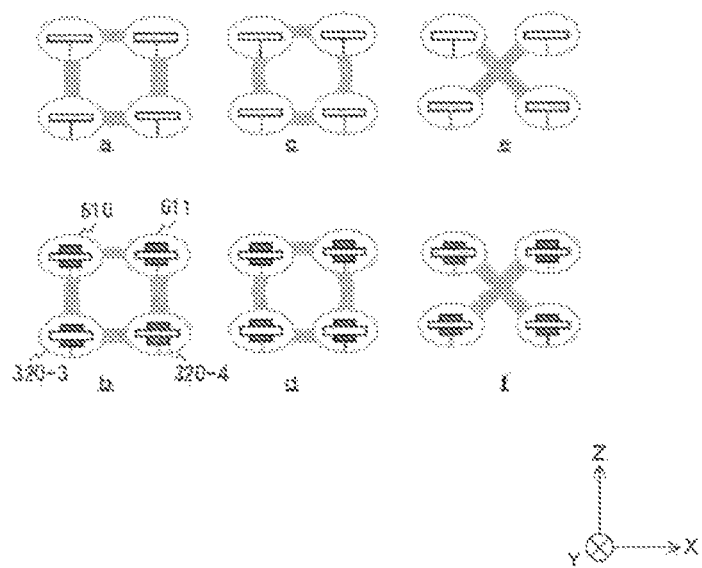

FIG. 315 is a diagram illustrating an example of a sectional view of the sensor device including four probes according to the seventh embodiment of the present technology.

Figure 316:
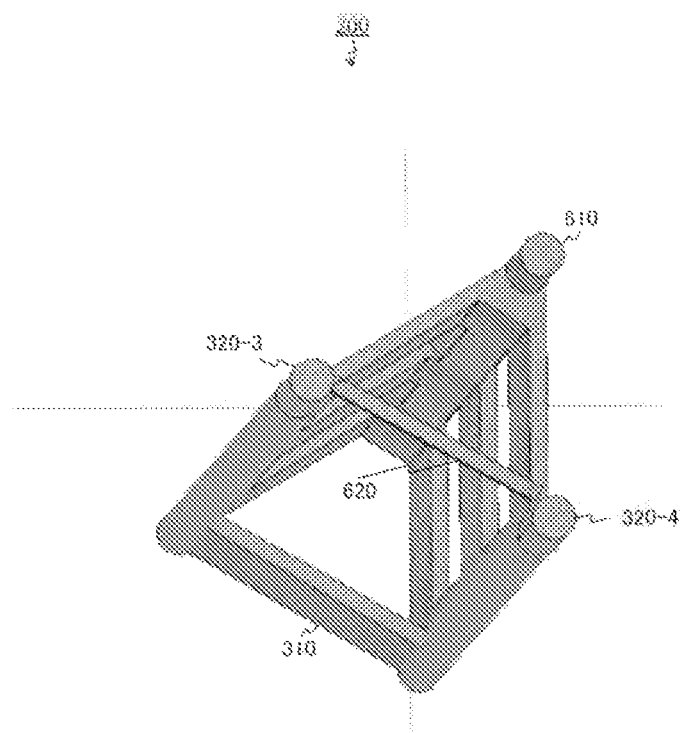

FIG. 316 is an example of a perspective view of the sensor device according to the seventh embodiment of the present technology.

Figure 317:
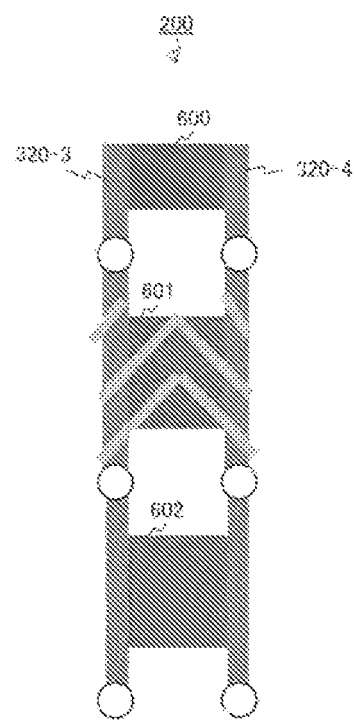

FIG. 317 is an example of a sensor device 200 including a groove provided in a spacer according to the seventh embodiment of the present technology.

Figure 318:
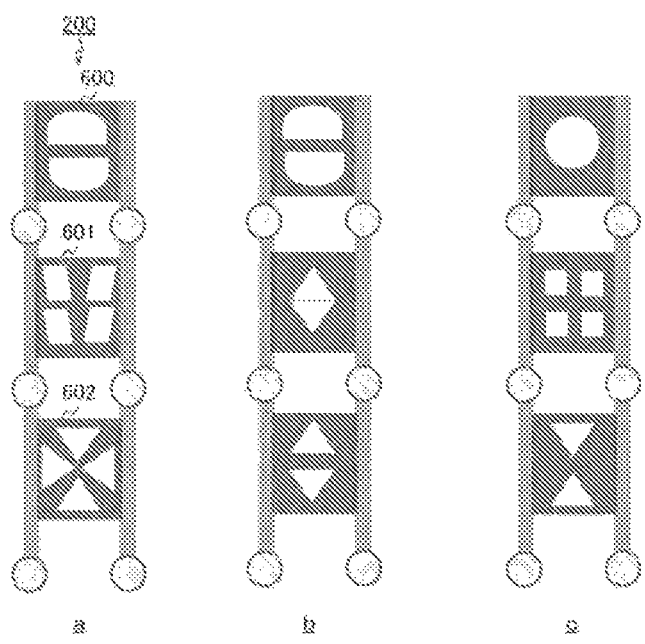

FIG. 318 is a diagram illustrating an example of the groove of the spacer according to the seventh embodiment of the present technology.

Figure 319:
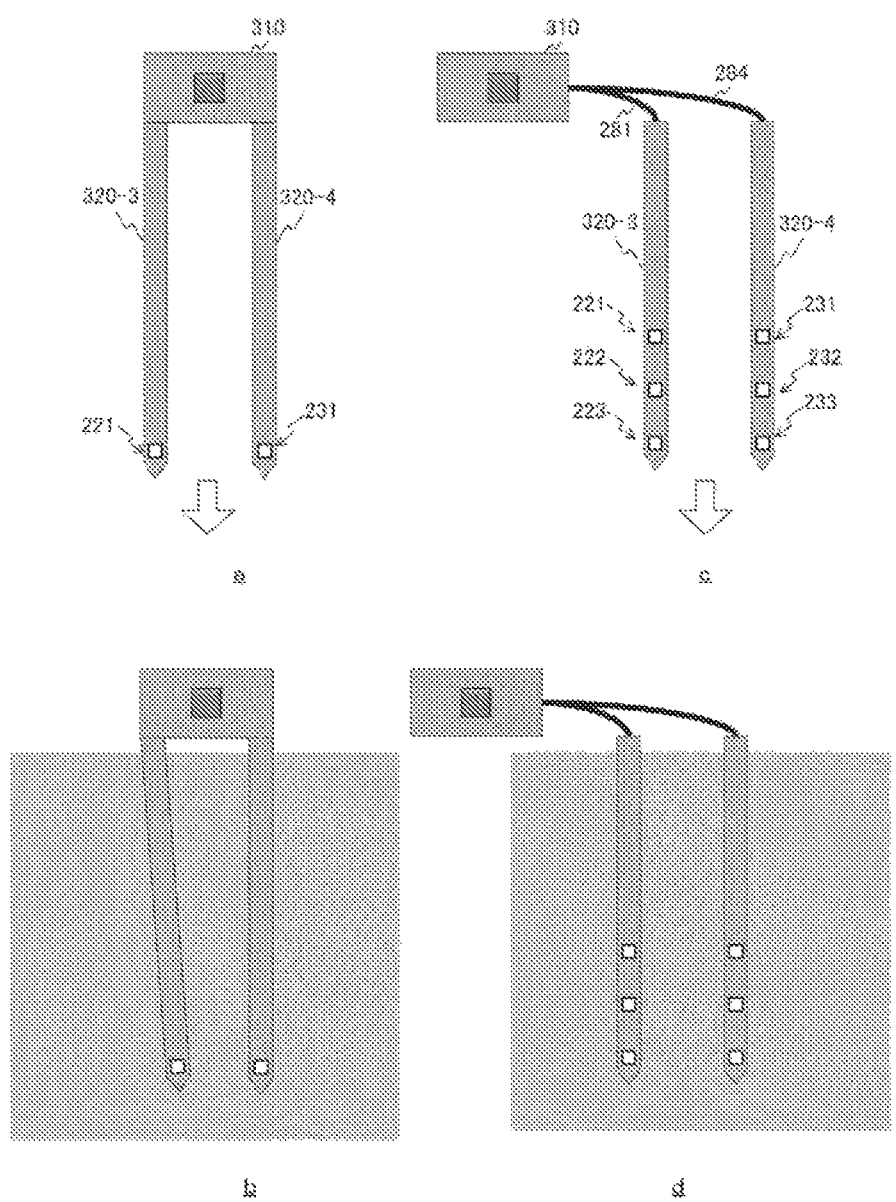

FIG. 319 is a diagram illustrating an example of sensor devices according to a comparative example and an eighth embodiment of the present technology.

Figure 320:
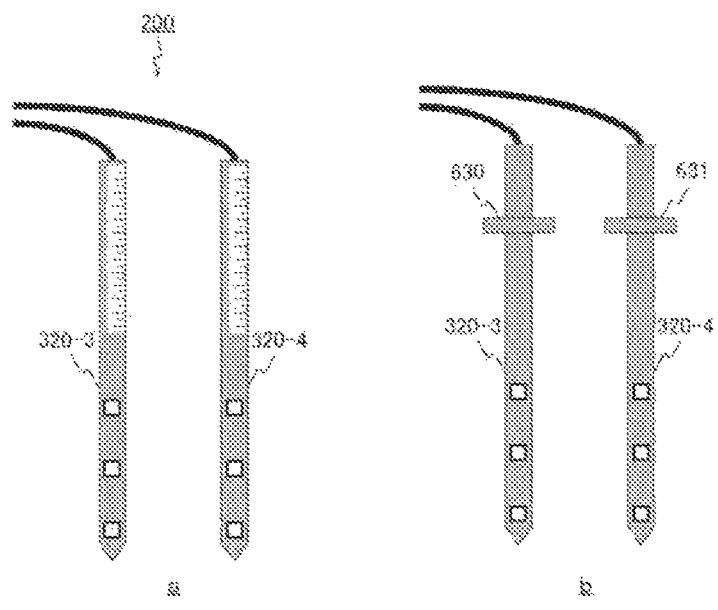

FIG. 320 is a diagram illustrating an example of the sensor device provided with scales and stoppers according to the eighth embodiment of the present technology.

Figure 321:
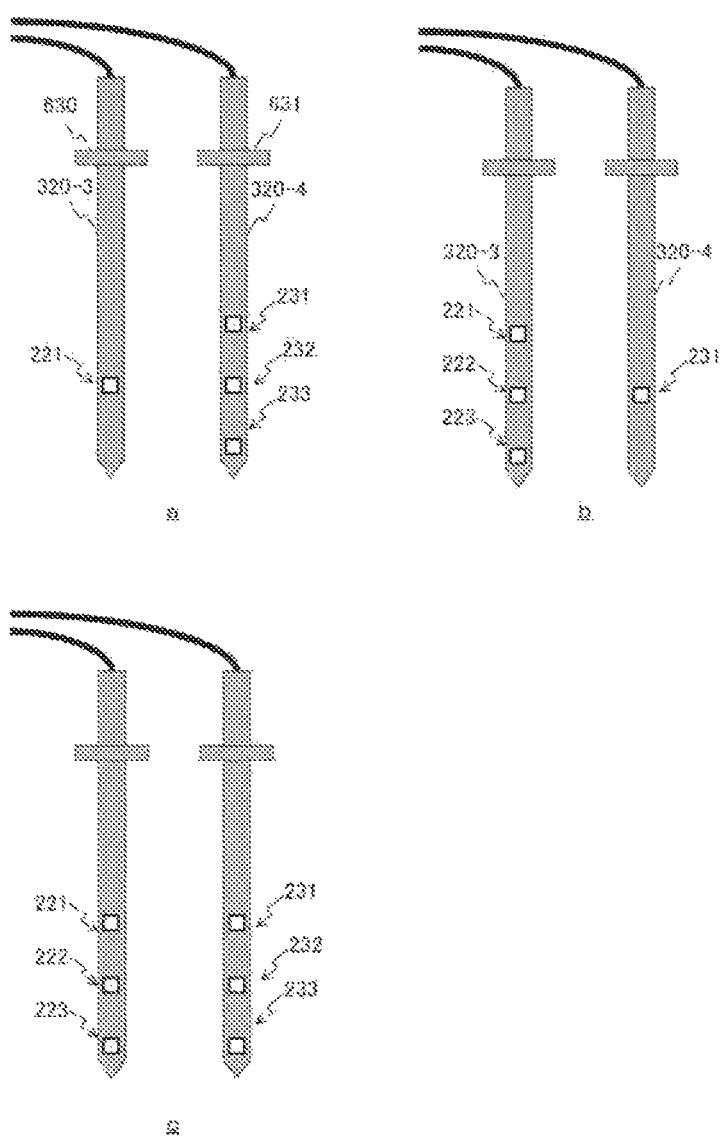

FIG. 321 is a diagram illustrating an example of the numbers of antennas on a transmission side and a reception side according to the eighth embodiment of the present technology.

Figure 322:
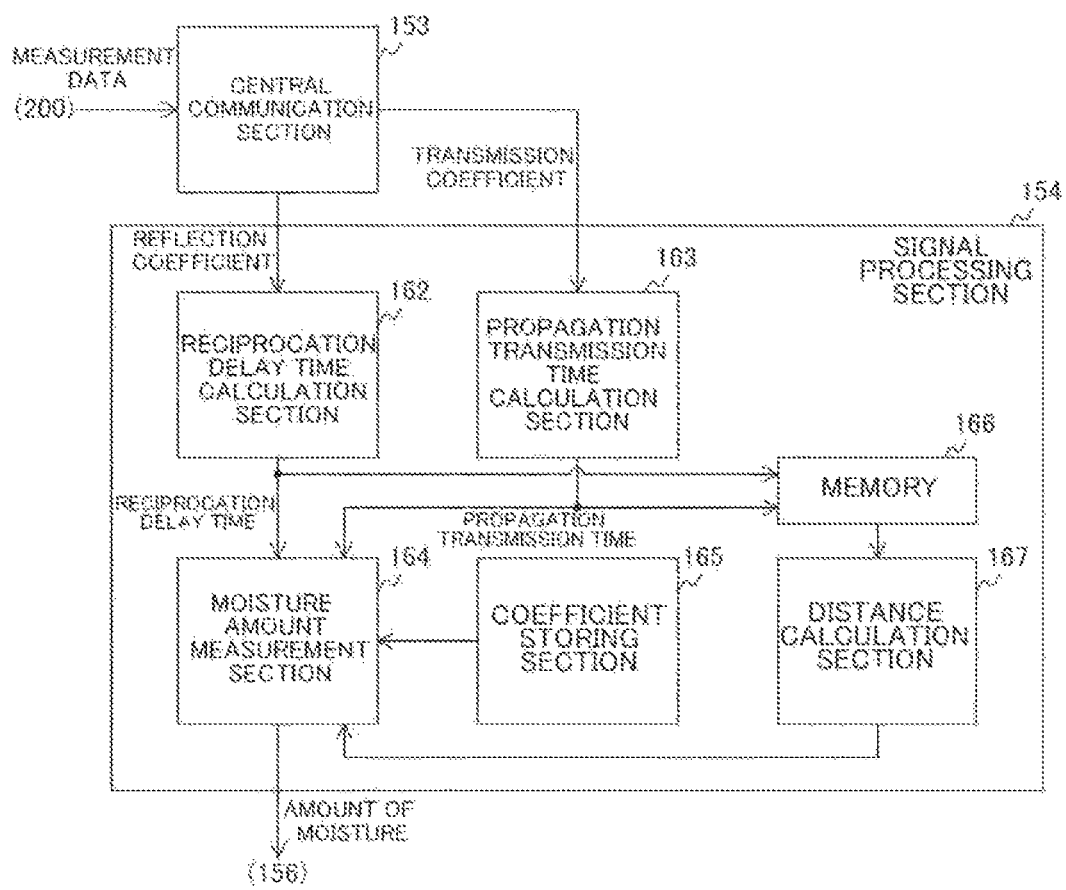

FIG. 322 is a block diagram illustrating a configuration example of a signal processing section in a central processing unit according to the eighth embodiment of the present technology.

Figure 323:
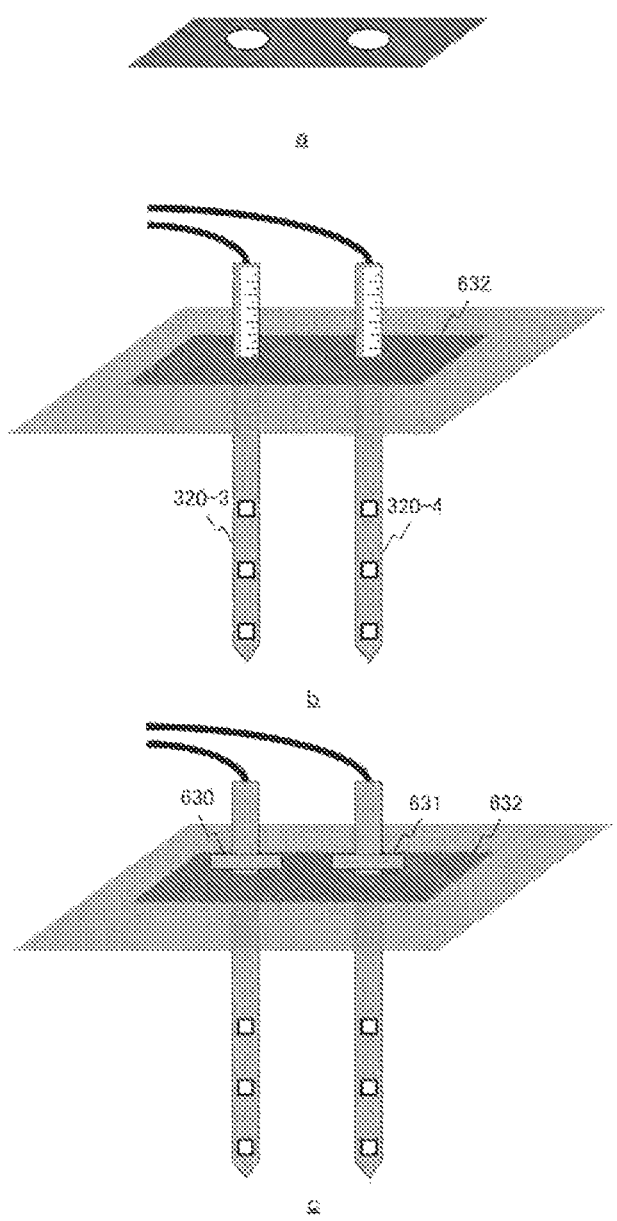

FIG. 323 is a diagram illustrating an example of the sensor device including a memory with a plate-shaped member attached thereto and including a stopper according to the eighth embodiment of the present technology.

Figure 324:
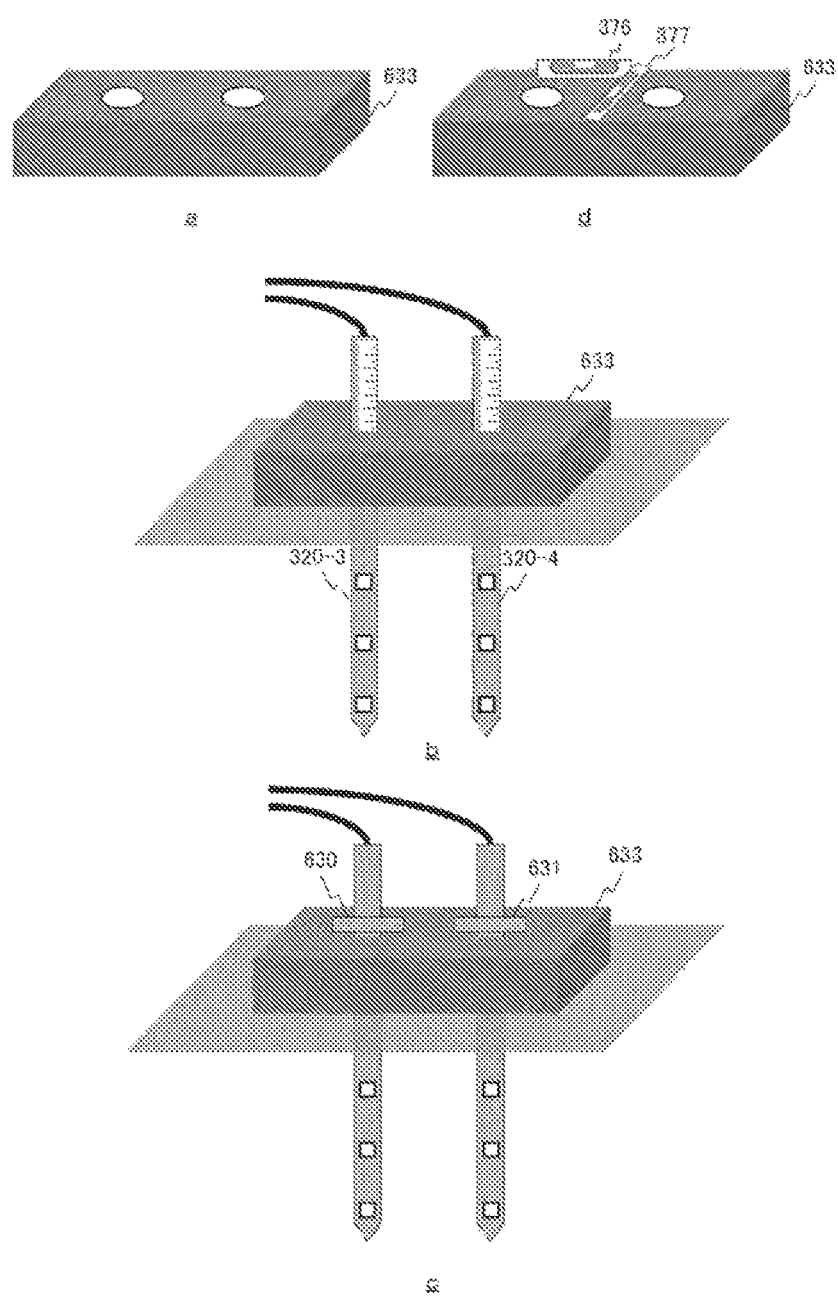

FIG. 324 is a diagram illustrating an example of the sensor device including a memory with a rectangular parallelepiped member attached thereto and including the stopper according to the eighth embodiment of the present technology.

FIG. 325 is a diagram illustrating an example of the sensor device from which a probe casing is not separated according to the eighth embodiment of the present technology.

FIG. 326 is a diagram for explaining a method for measuring the distance between antennas according to the eighth embodiment of the present technology.

Figure 327:
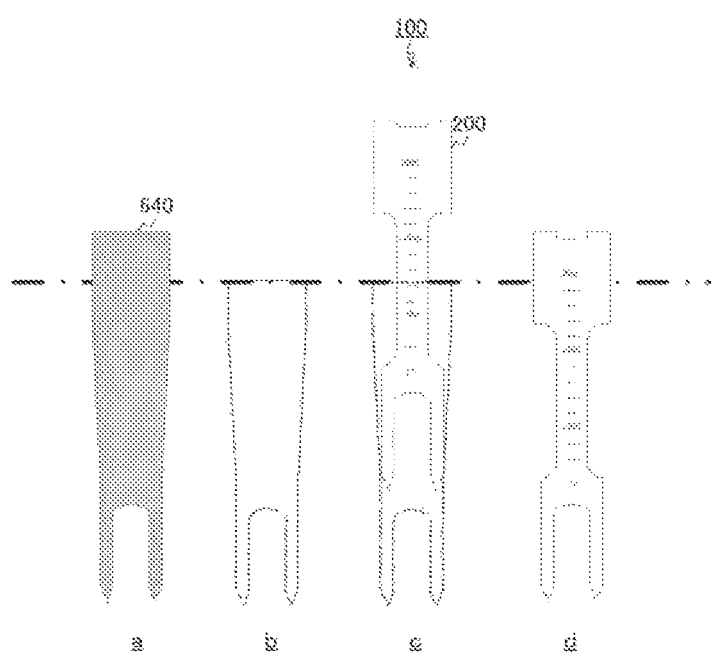

FIG. 327 is a diagram illustrating an example of a method for inserting a sensor device according to a ninth embodiment of the present technology.

Figure 328:
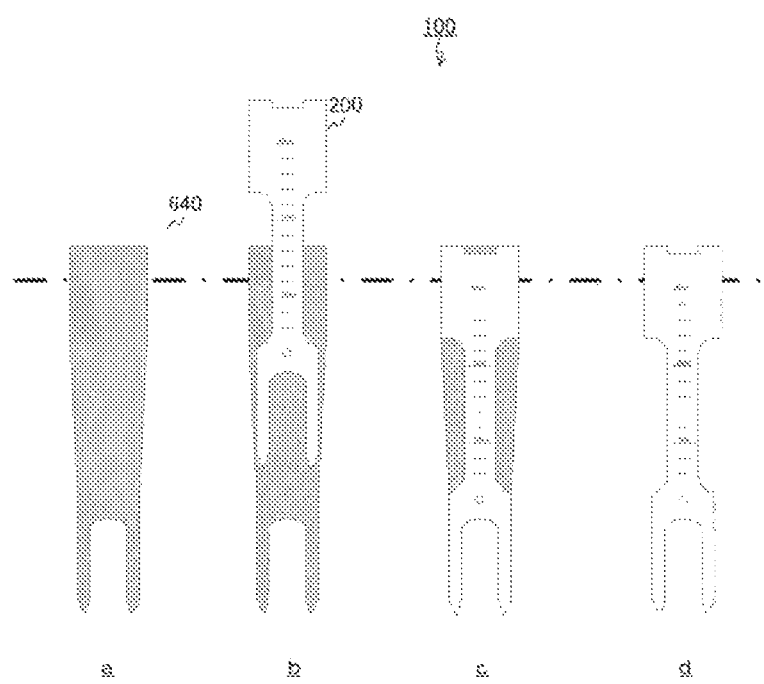

FIG. 328 is a diagram illustrating another example of the method for inserting the sensor device according to the ninth embodiment of the present technology.

Figure 329:
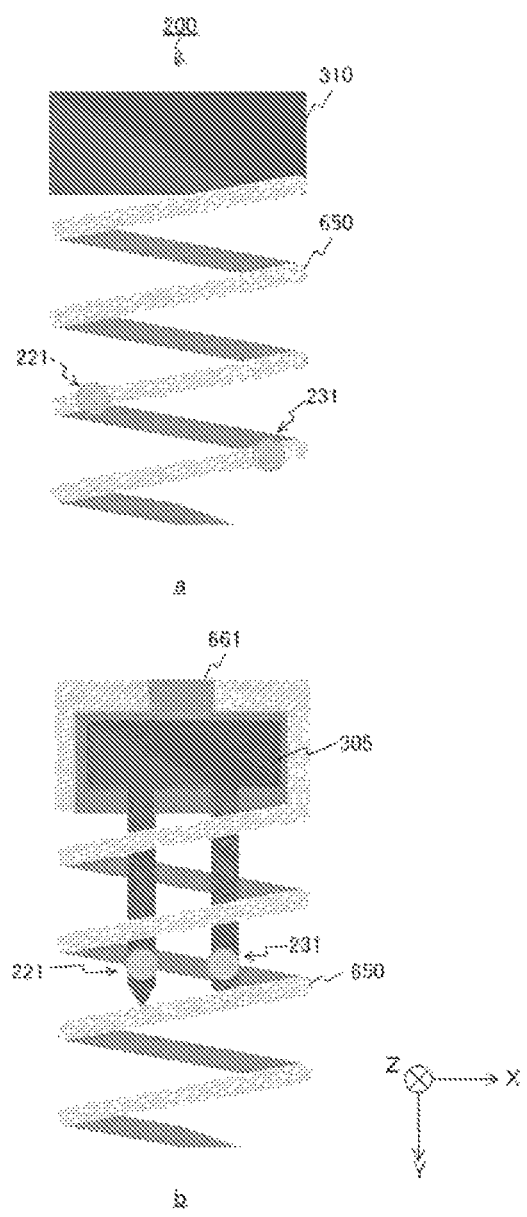

FIG. 329 is a diagram illustrating an example of a sensor device according to a tenth embodiment of the present technology.

Figure 330:
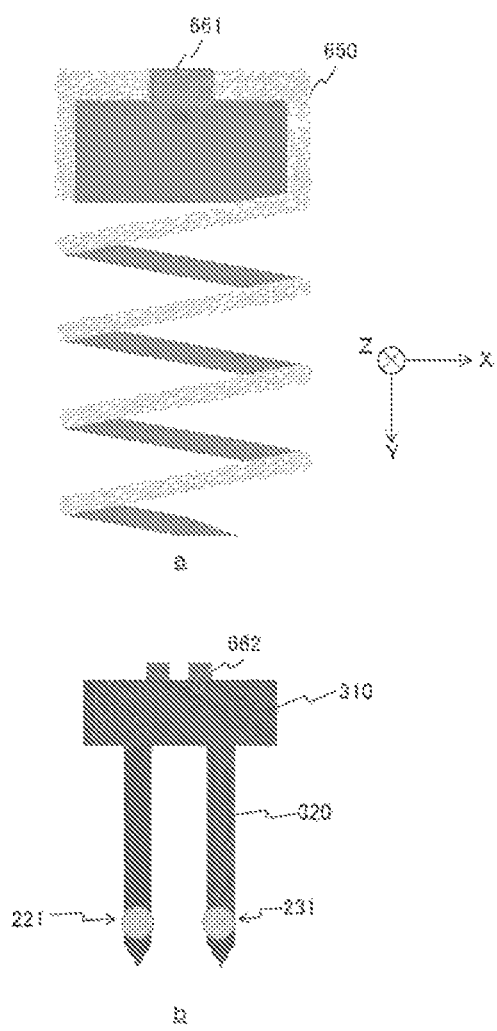

FIG. 330 is a diagram illustrating an example of a spiral-shaped member and a sensor casing according to the tenth embodiment of the present technology.

Figure 331:
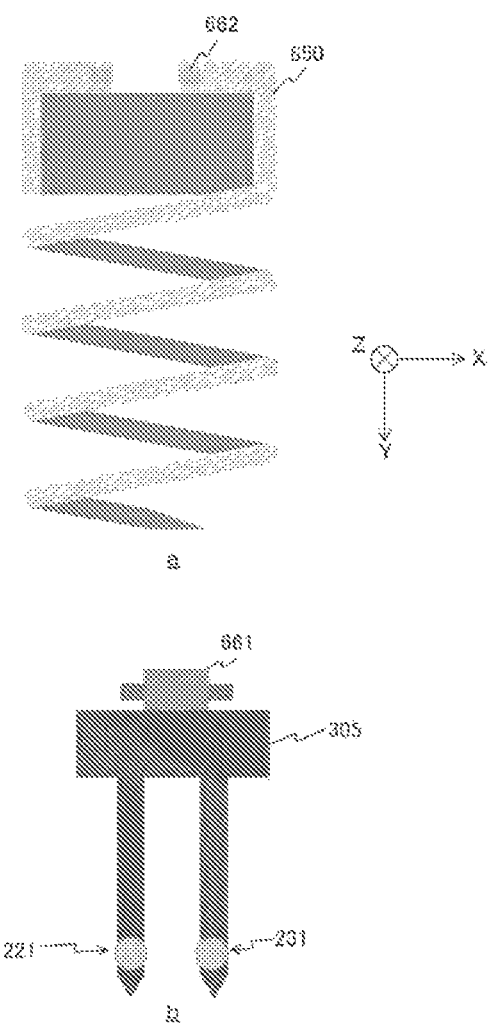

FIG. 331 is a diagram illustrating another example of the spiral-shaped member and the sensor casing according to the tenth embodiment of the present technology.

Figure 332:
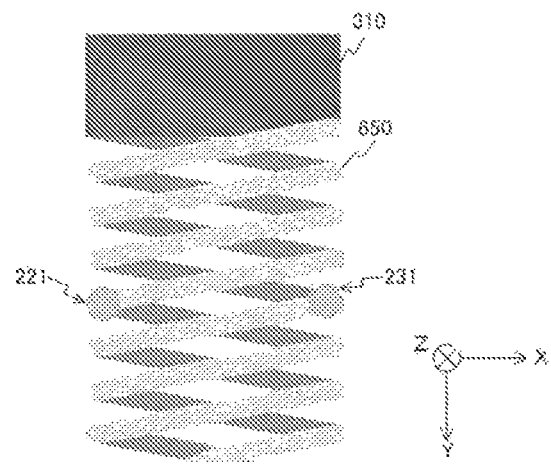

FIG. 332 is a diagram illustrating an example of the sensor device provided with a double-spiral probe according to the tenth embodiment of the present technology.

Figure 333:
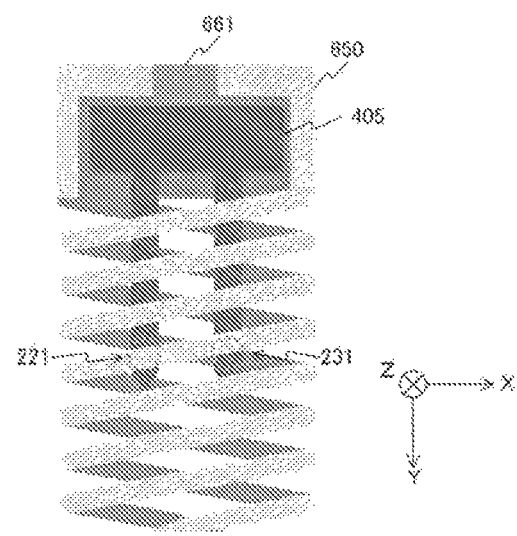

FIG. 333 is a diagram illustrating an example of the sensor device provided with a spiral-shaped member of double spirals according to the tenth embodiment of the present technology.

Figure 334:
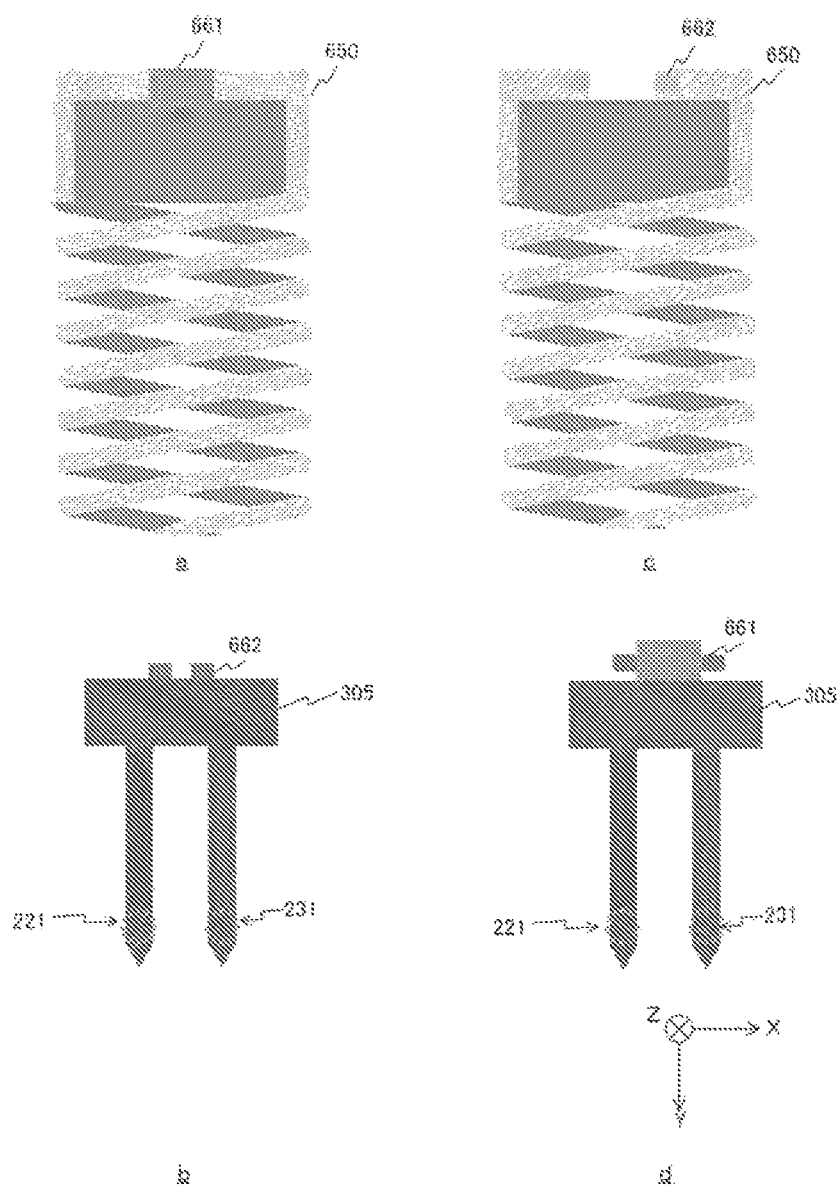

FIG. 334 is a diagram illustrating an example of the spiral-shaped member of double spirals and a sensor casing according to the tenth embodiment of the present technology.

Figure 335:
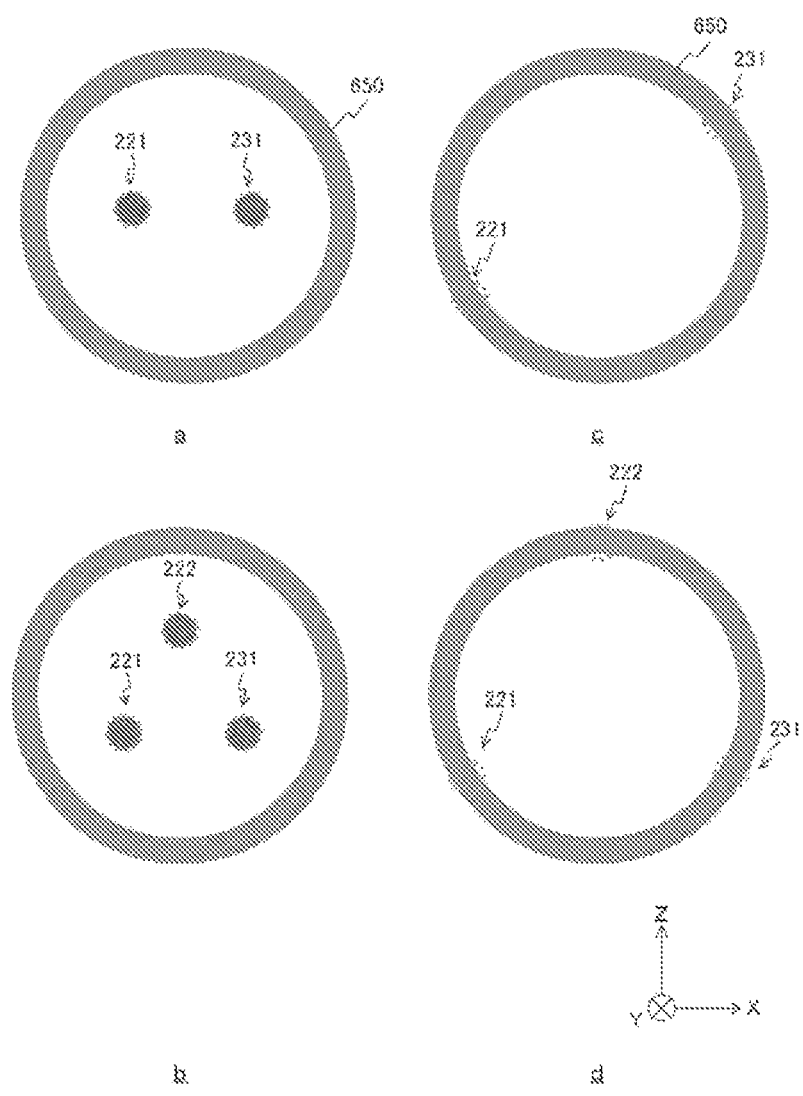

FIG. 335 is a diagram illustrating an example of a positional relationship between the spiral-shaped member and an antenna according to the tenth embodiment of the present technology.

Figure 336:
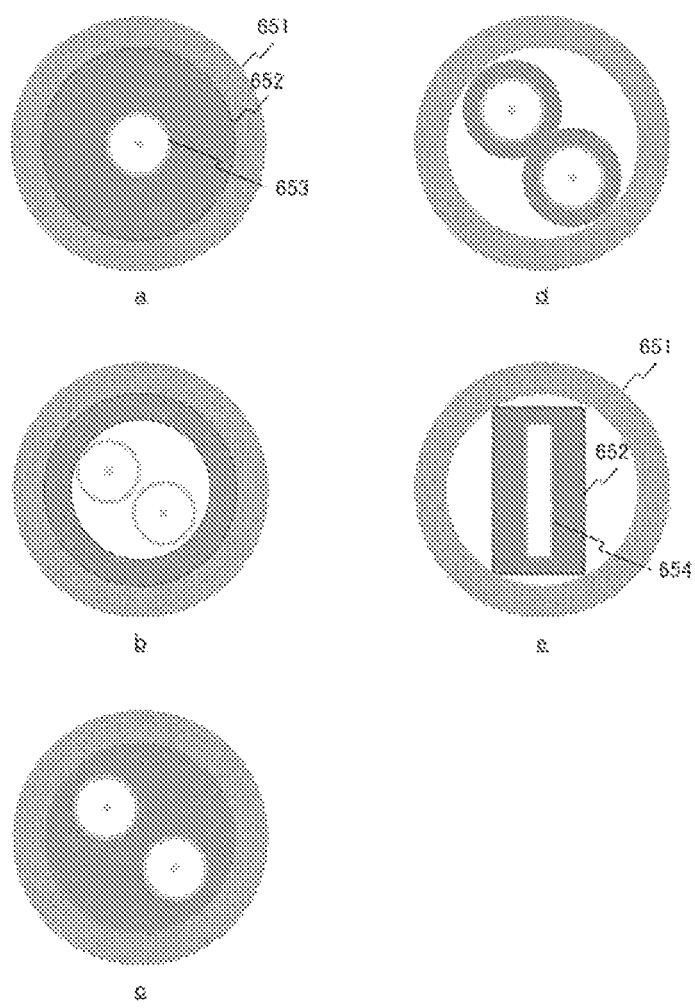

FIG. 336 is an example of a sectional view of the spiral-shaped member according to the tenth embodiment of the present technology.

Figure 337:
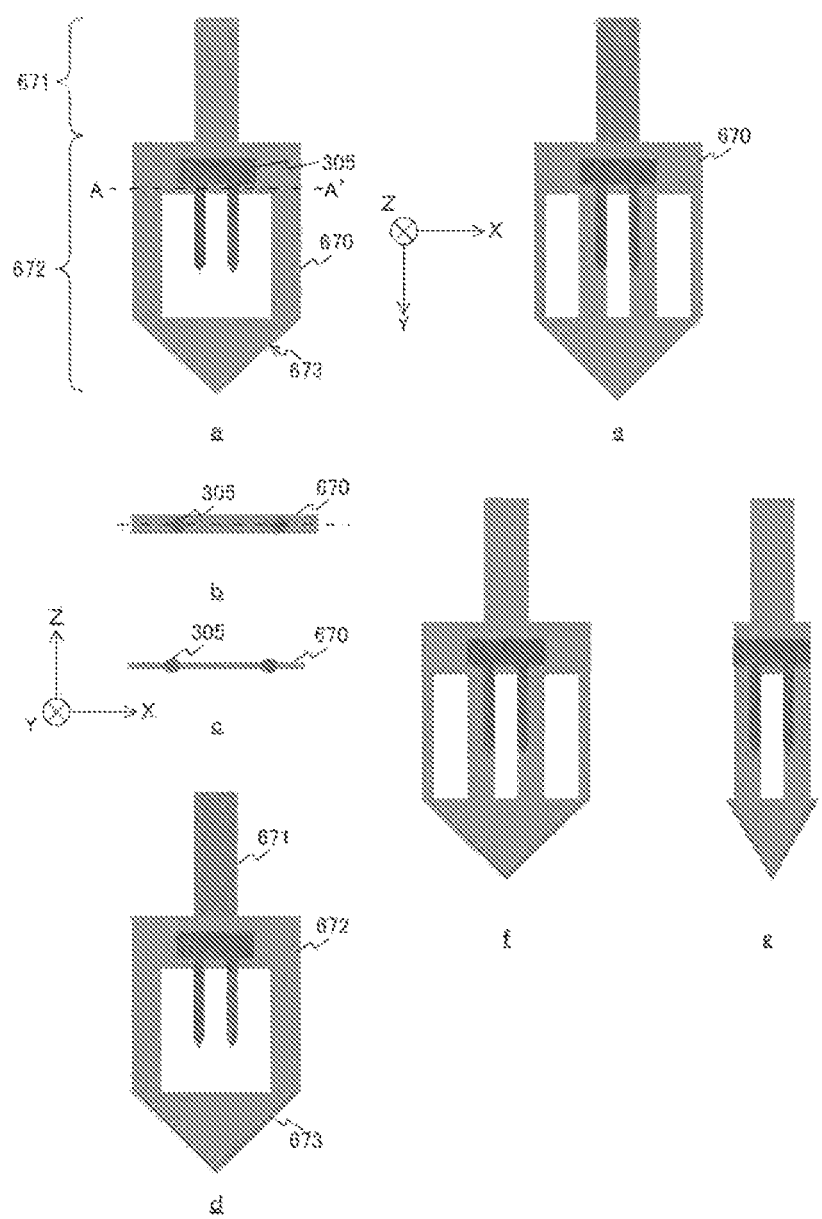

FIG. 337 is a diagram illustrating an example of the sensor device including a shovel-shaped casing according to the tenth embodiment of the present technology.

Figure 338:
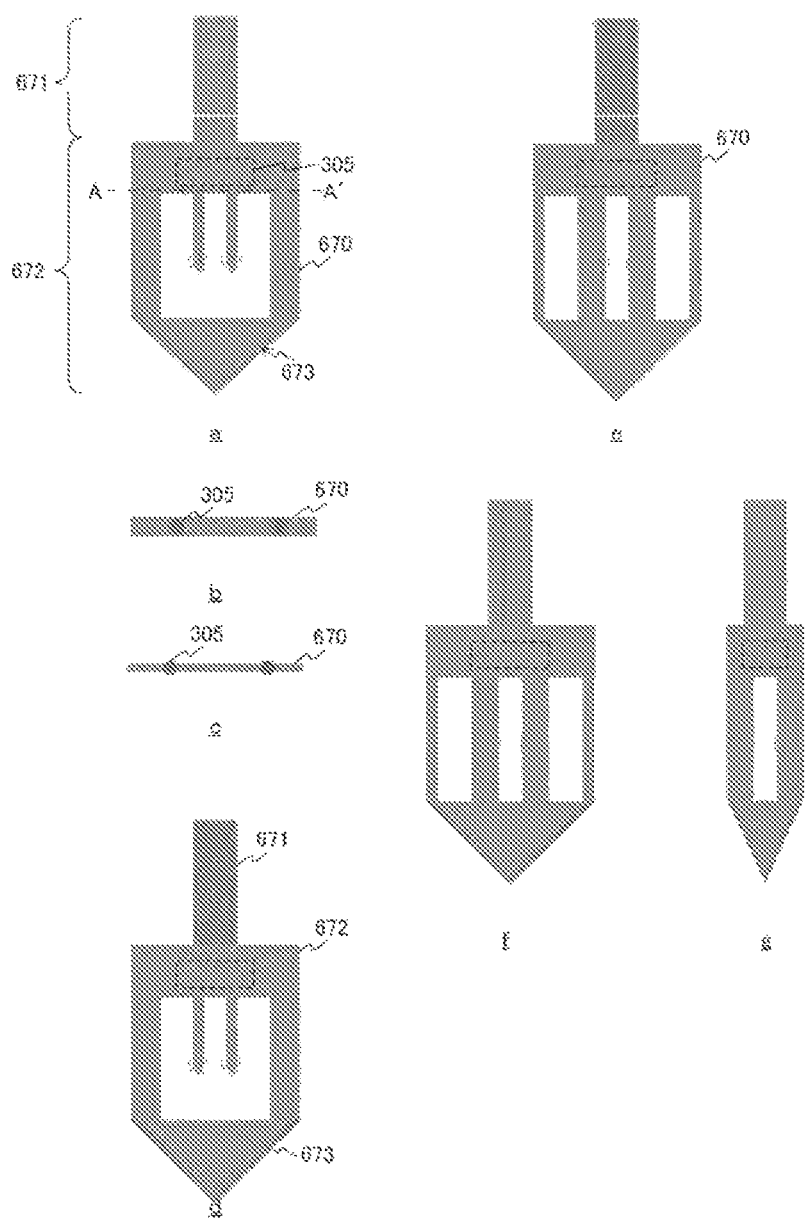

FIG. 338 is a diagram illustrating an example of the shovel-shaped casing according to the tenth embodiment of the present technology.

Figure 339:
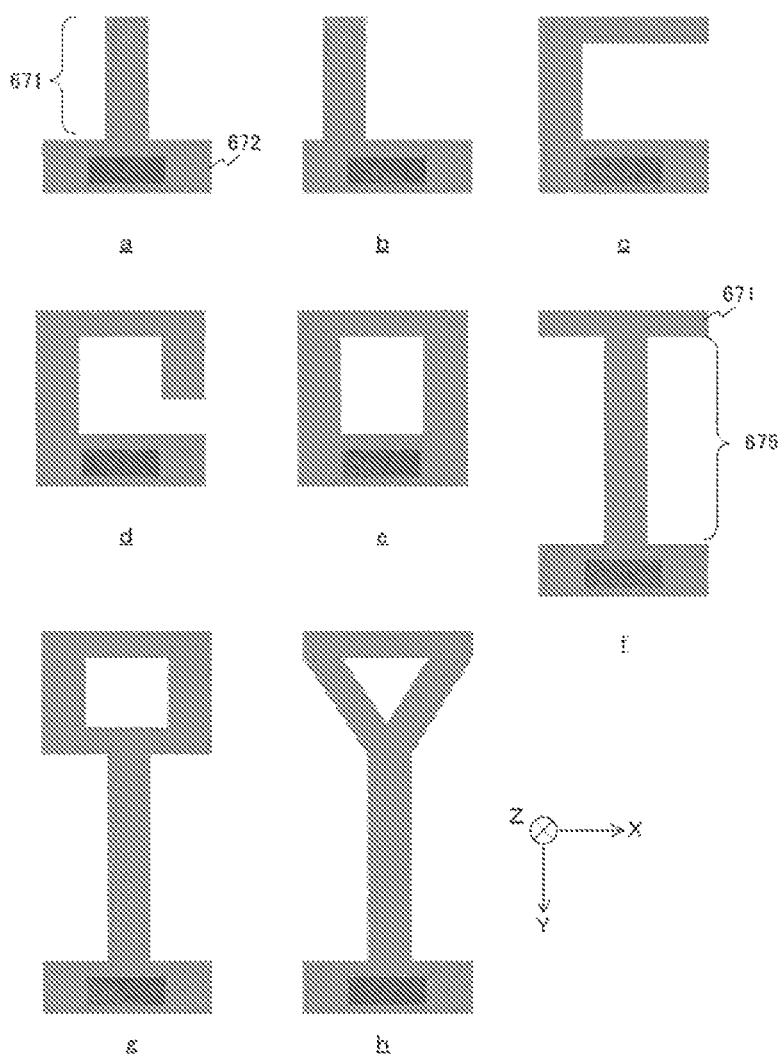

FIG. 339 is a diagram illustrating an example of the shape of a grip according to the tenth embodiment of the present technology.

Figure 340:
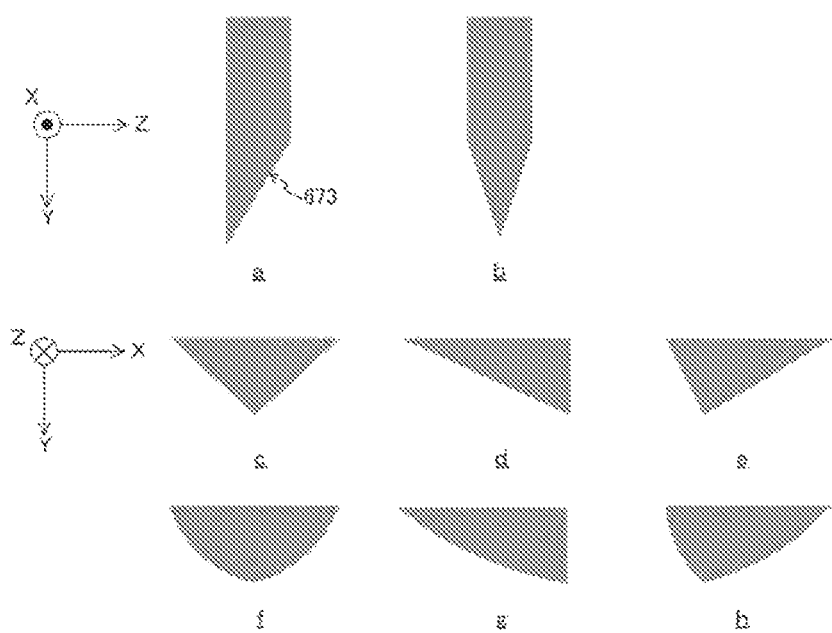

FIG. 340 is a diagram illustrating an example of the shape of a blade according to the tenth embodiment of the present technology.

FIG. 341 is a diagram illustrating an example of the sensor device with a scaffold member added thereto according to the tenth embodiment of the present technology.

FIG. 342 is a block diagram illustrating an example of a sensor device according to the eleventh embodiment of the present technology.

Figure 343:
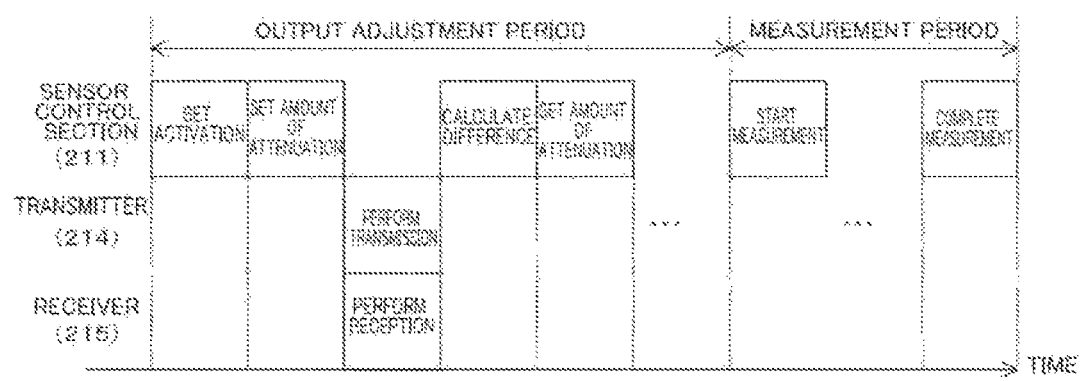

FIG. 343 is an example of a timing chart illustrating operations of each section in the sensor device according to the eleventh embodiment of the present technology.

Figure 344:
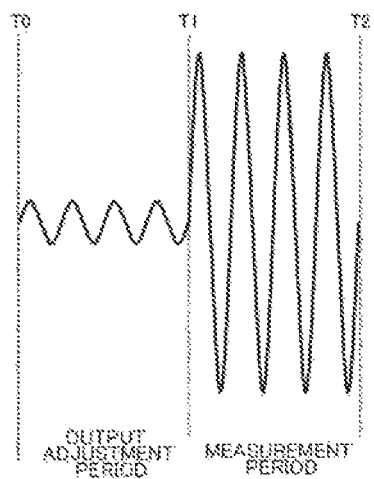

FIG. 344 is a diagram illustrating an example of a transmission waveform according to the eleventh embodiment of the present technology.

Figure 345:
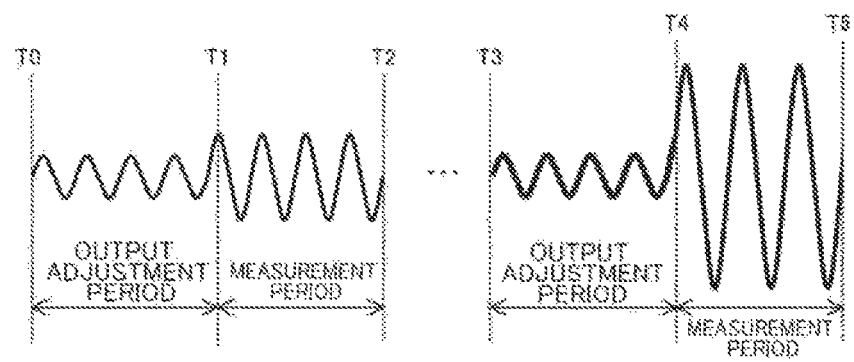

FIG. 345 is a diagram illustrating an example of a transmission waveform when transmission power is adjusted in accordance with the amount of moisture according to the eleventh embodiment of the present technology.

Figure 346:
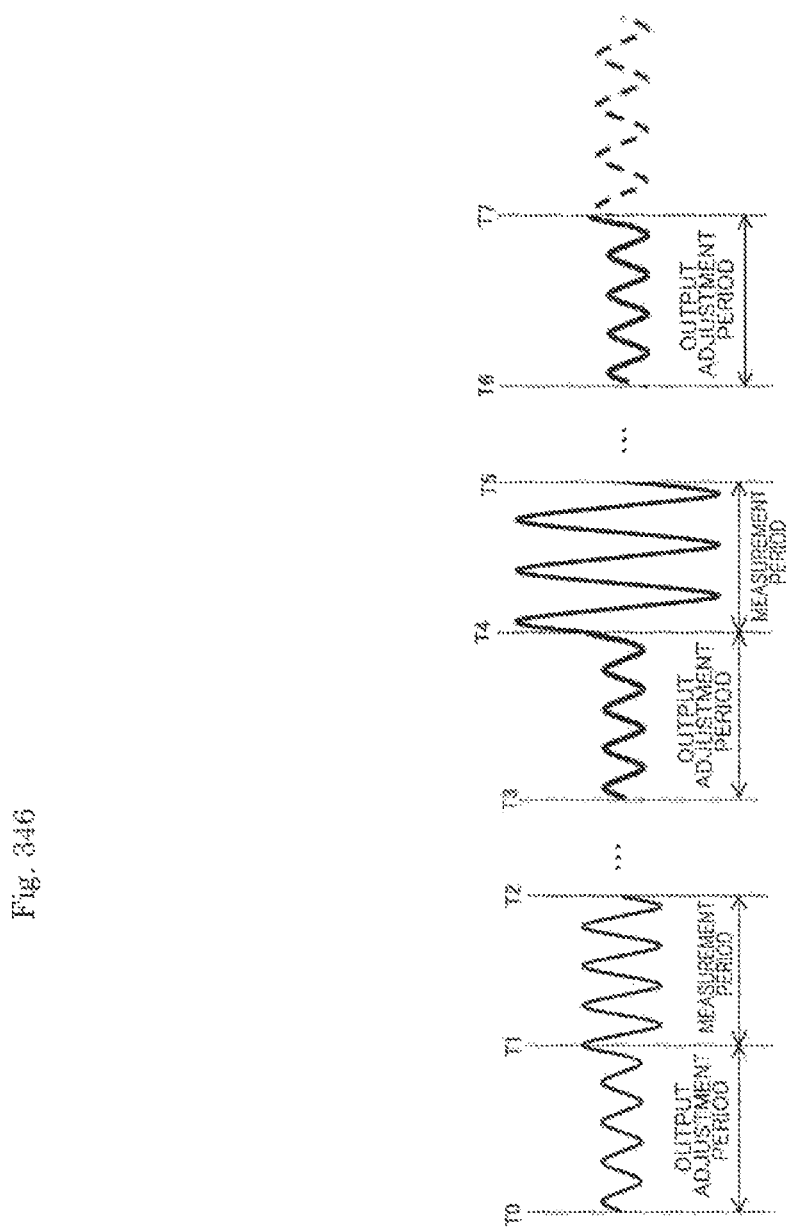

FIG. 346 is a diagram illustrating an example of a transmission waveform when transmission power is adjusted in accordance with the amount of moisture and an error is output as needed according to the eleventh embodiment of the present technology.

FIG. 347 is a diagram illustrating an example of waveforms of transmission and reception signals according to the eleventh embodiment of the present technology.

Figure 348:
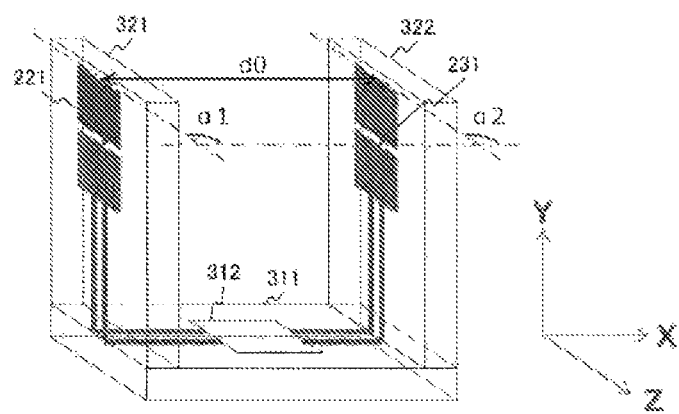

FIG. 348 is a diagram illustrating a configuration example of a sensor device according to a twelfth embodiment of the present technology.

Figure 349:
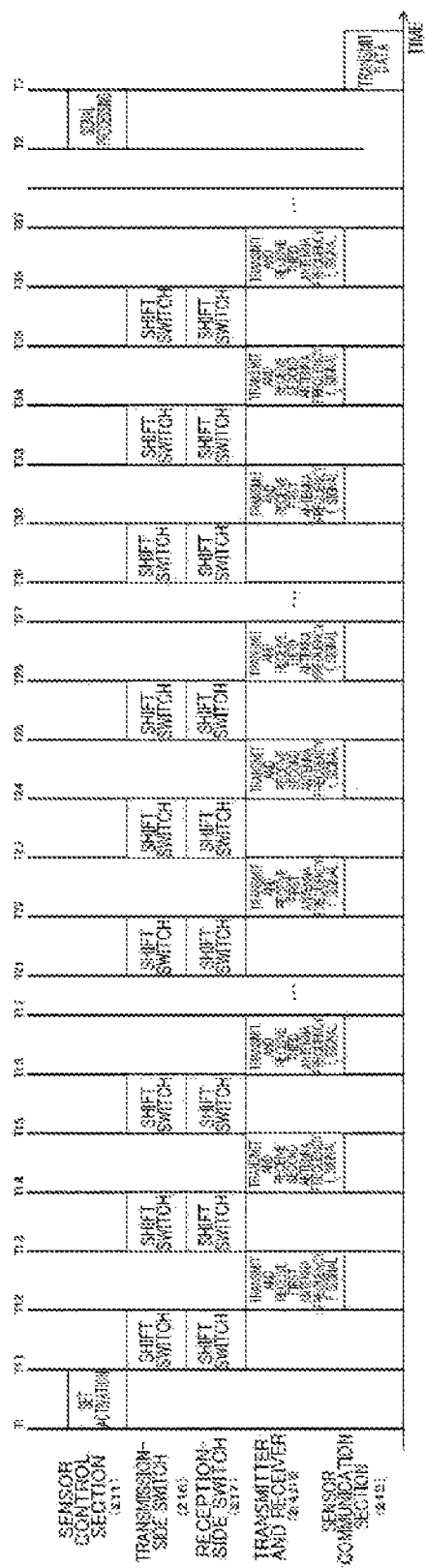

FIG. 349 is a timing chart illustrating operations of each section in the sensor device when an order of transmission and reception wave detecting operations is changed according to the first embodiment of the present technology.

Figure 350:
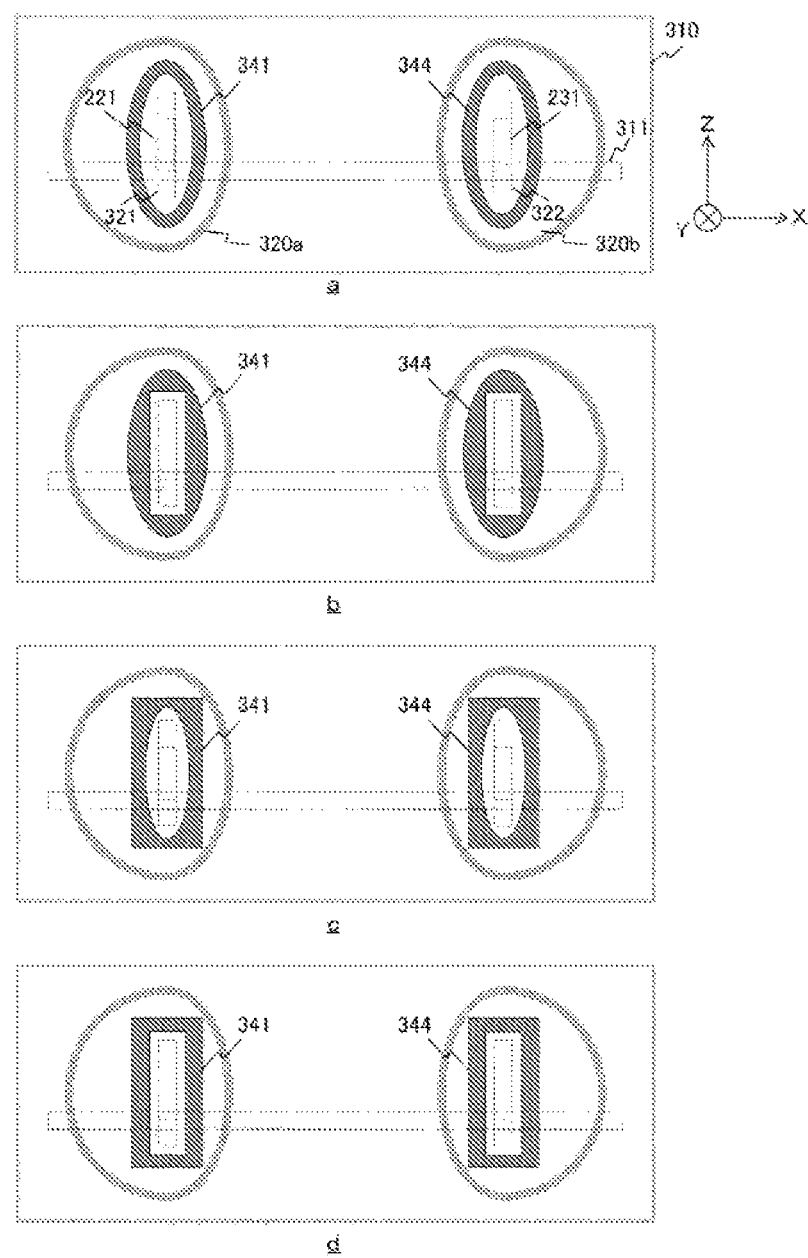

FIG. 350 is a top view of the sensor device 200 in a case where each of the radio wave absorption sections illustrated in FIGS. 153a to 153d is applied to the radio wave absorption section included in the sensor device illustrated in FIG. 147a as examples of applications to the sensor device.

Figure 351:
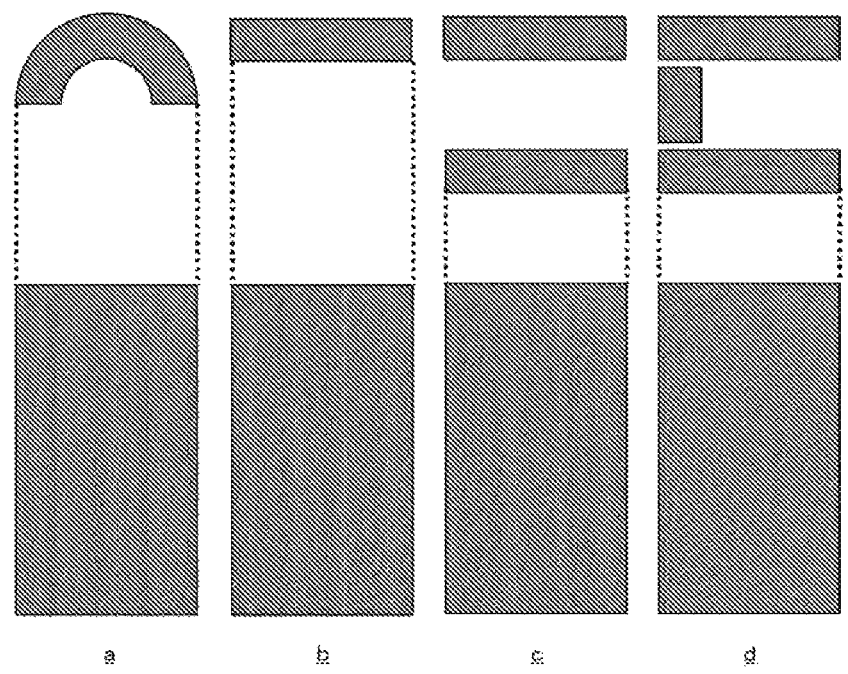

FIG. 351 is a diagram illustrating another example of the shape of the radio wave absorption section according to the first embodiment of the present technology.

Figure 352:
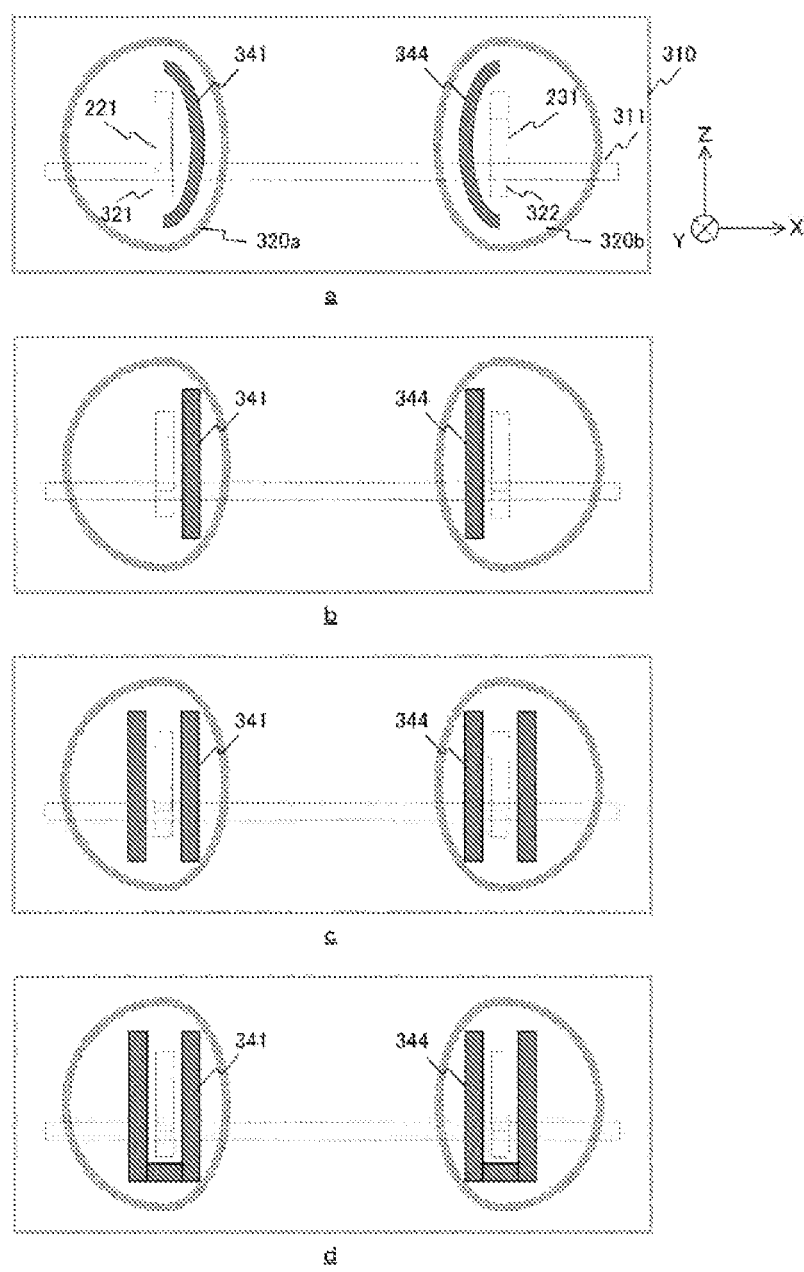

FIG. 352 is a diagram illustrating another example of the shape of the radio wave absorption section according to the first embodiment of the present technology.

Figure 353:
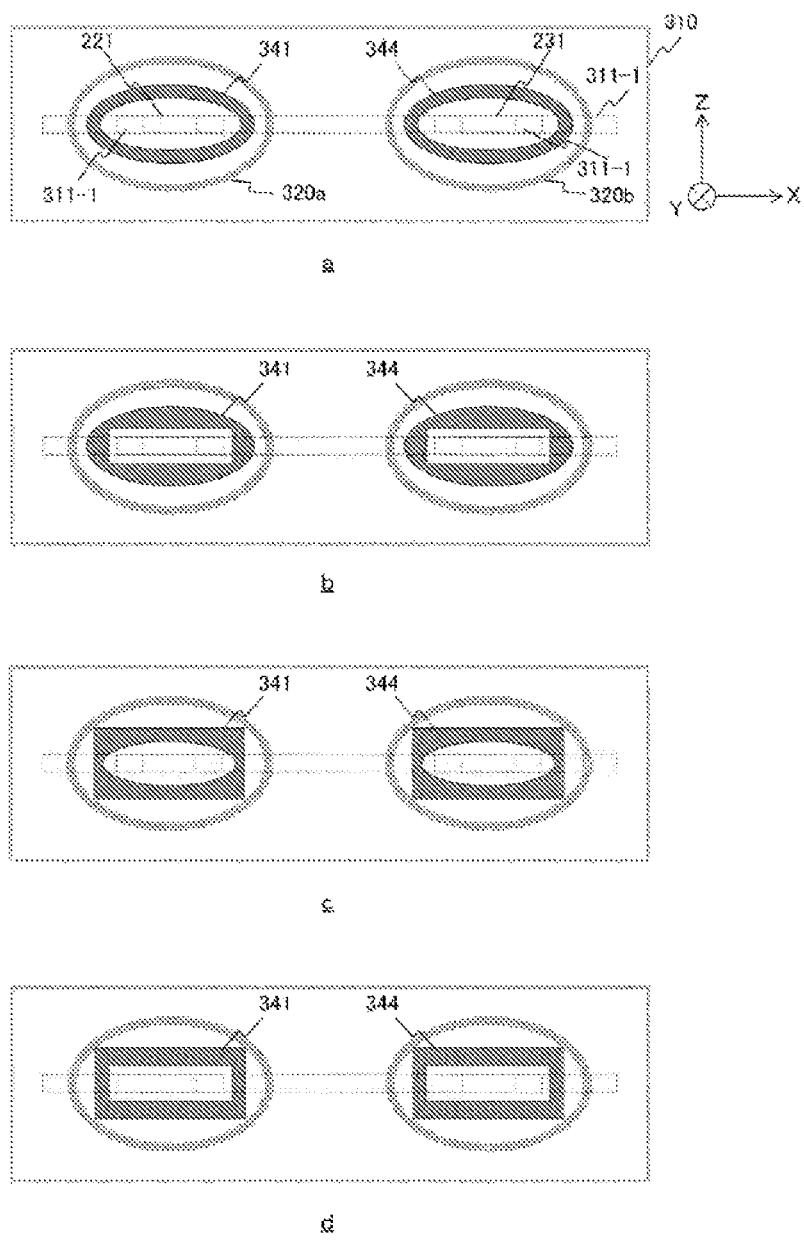

FIG. 353 is a top view (transparent view) of the sensor device in a case where each of the radio wave absorption sections illustrated in FIGS. 153a to 153d is applied to the radio wave absorption section included in the sensor device illustrated in FIG. 222a as examples of applications to the sensor device.

Figure 354:
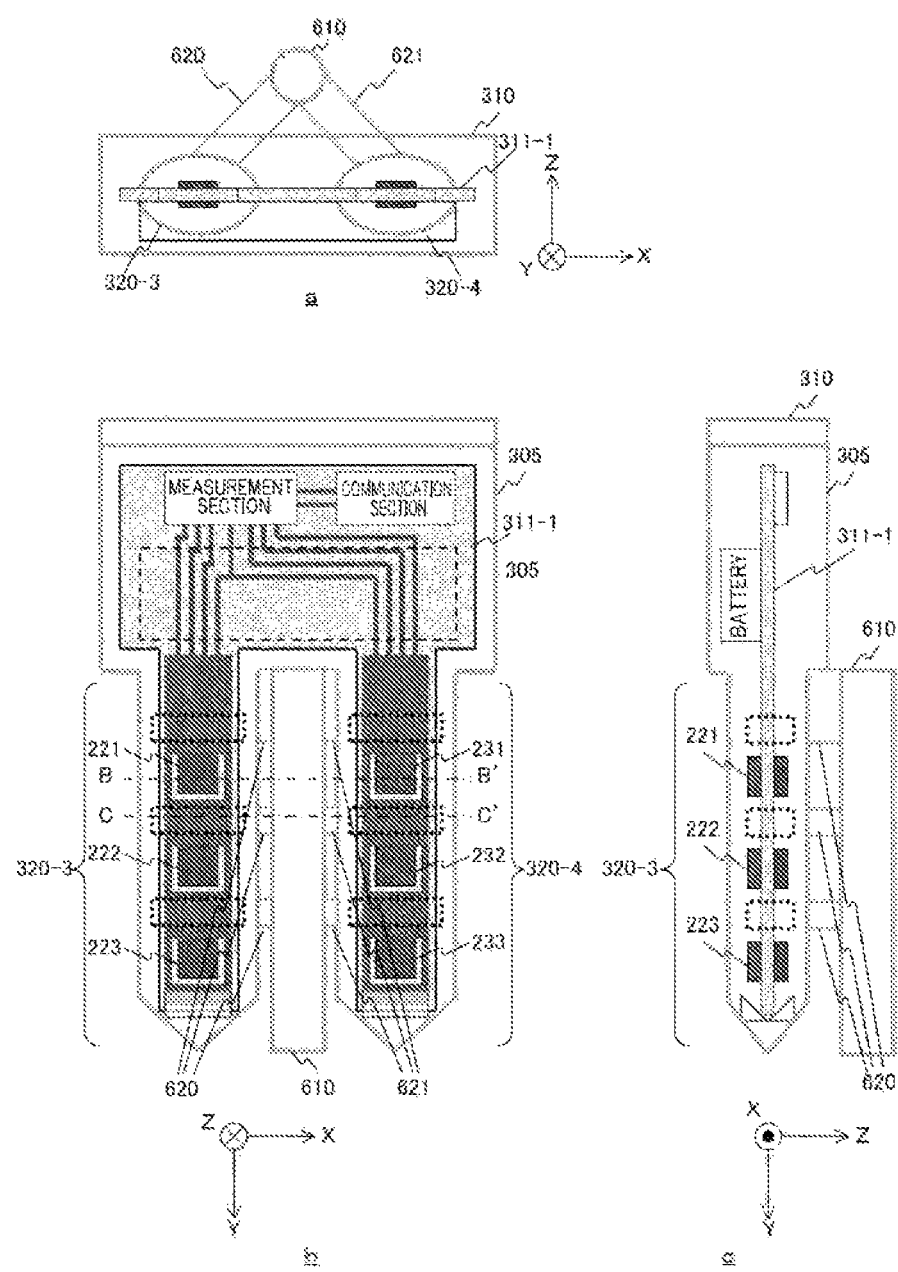

FIG. 354 is a diagram illustrating an example of a cut surface of the sensor device according to the seventh embodiment of the present technology.

Figure 355:
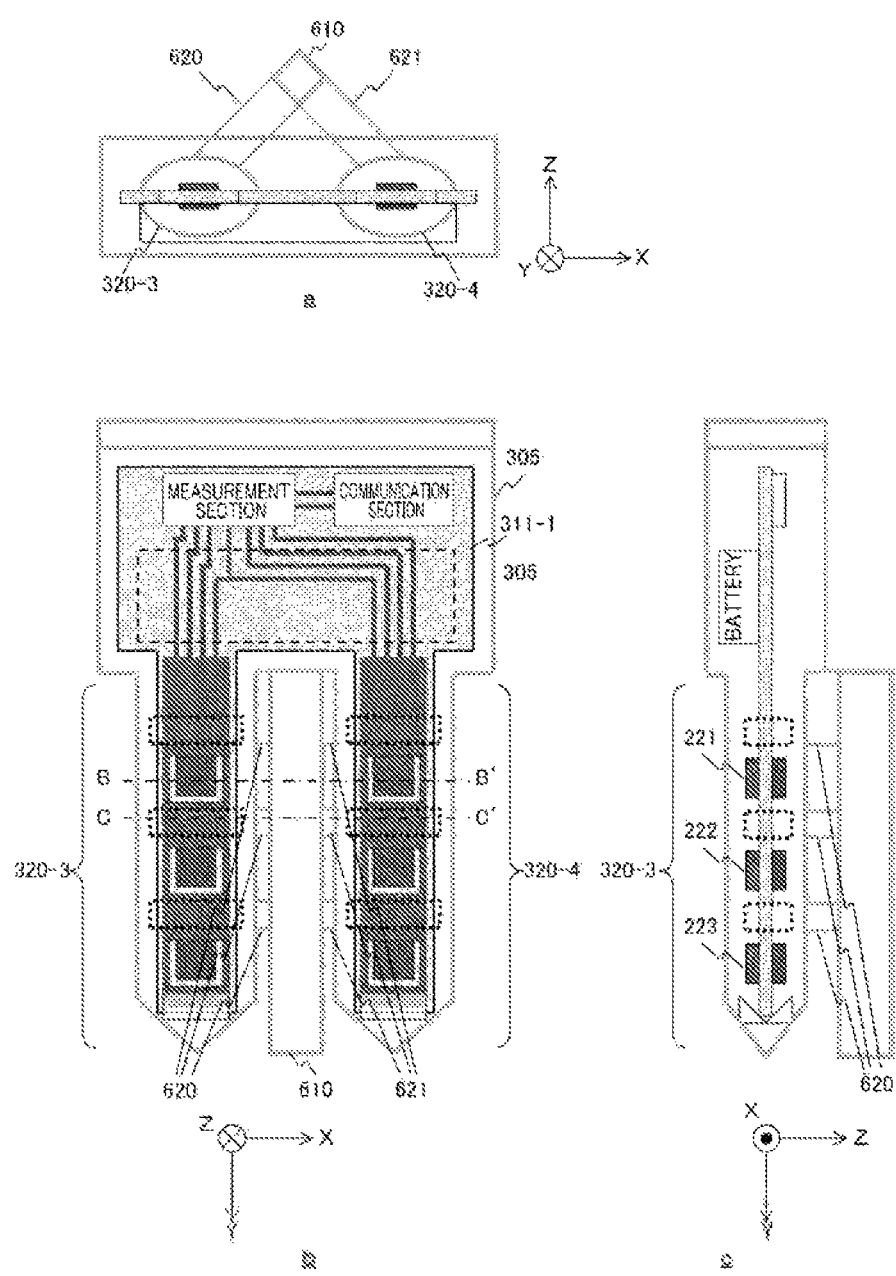

FIG. 355 is a diagram illustrating an example of a cut surface of the sensor device according to the seventh embodiment of the present technology.

Figure 356:
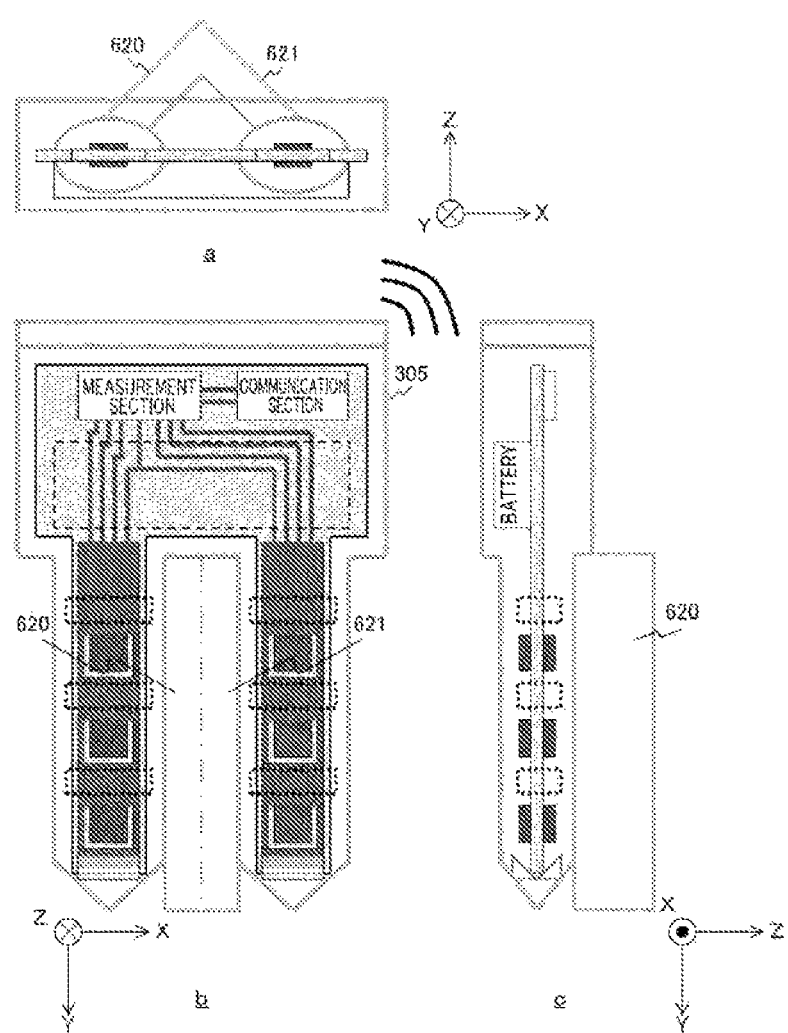

FIG. 356 is a diagram illustrating a structure of a sensor device in a case of a combination of FIGS. 311a and 311c.

Figure 357:
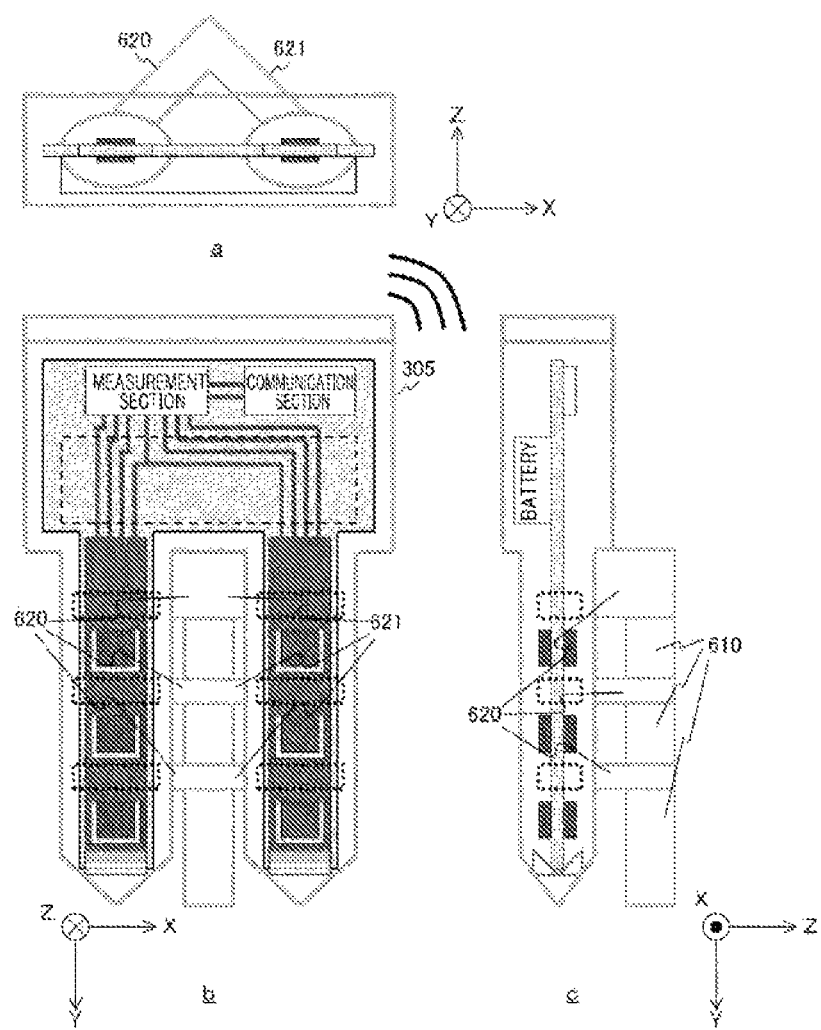

FIG. 357 is a diagram illustrating a structure of a sensor device in a case of a combination of FIGS. 311b and 311c.

Figure 358:
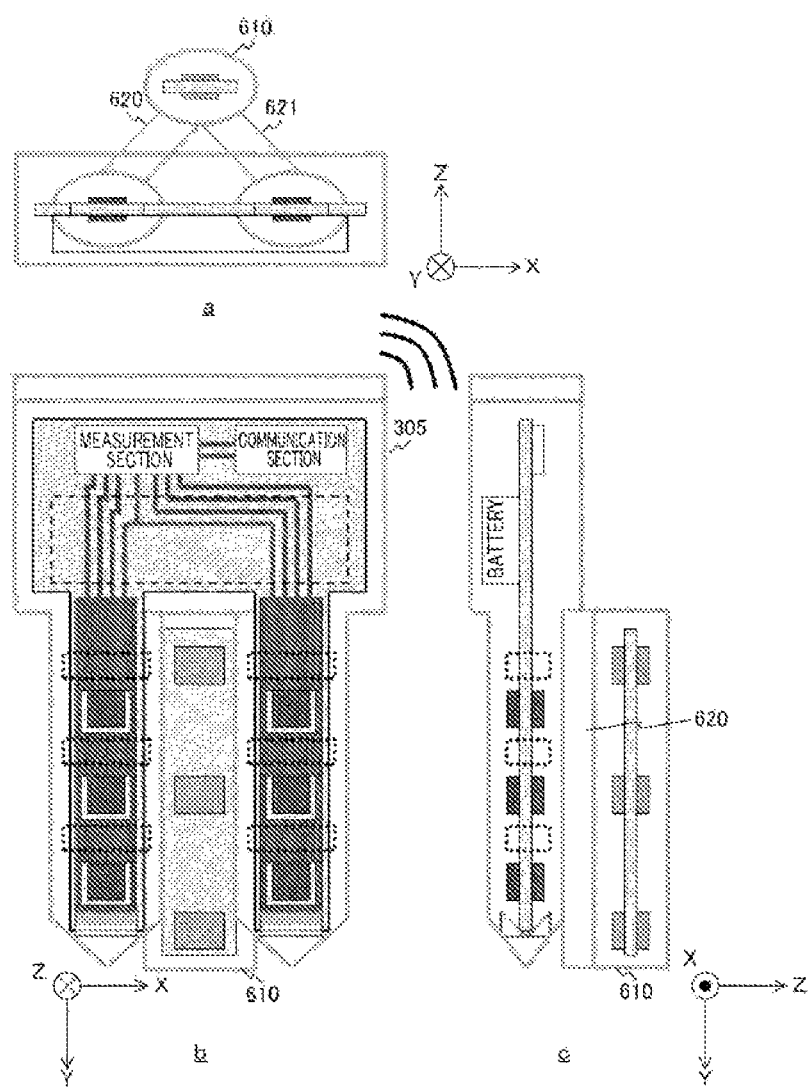

FIG. 358 is a diagram illustrating a structure of a sensor device in a case of a combination of FIGS. 311d and 311f.

Figure 359:
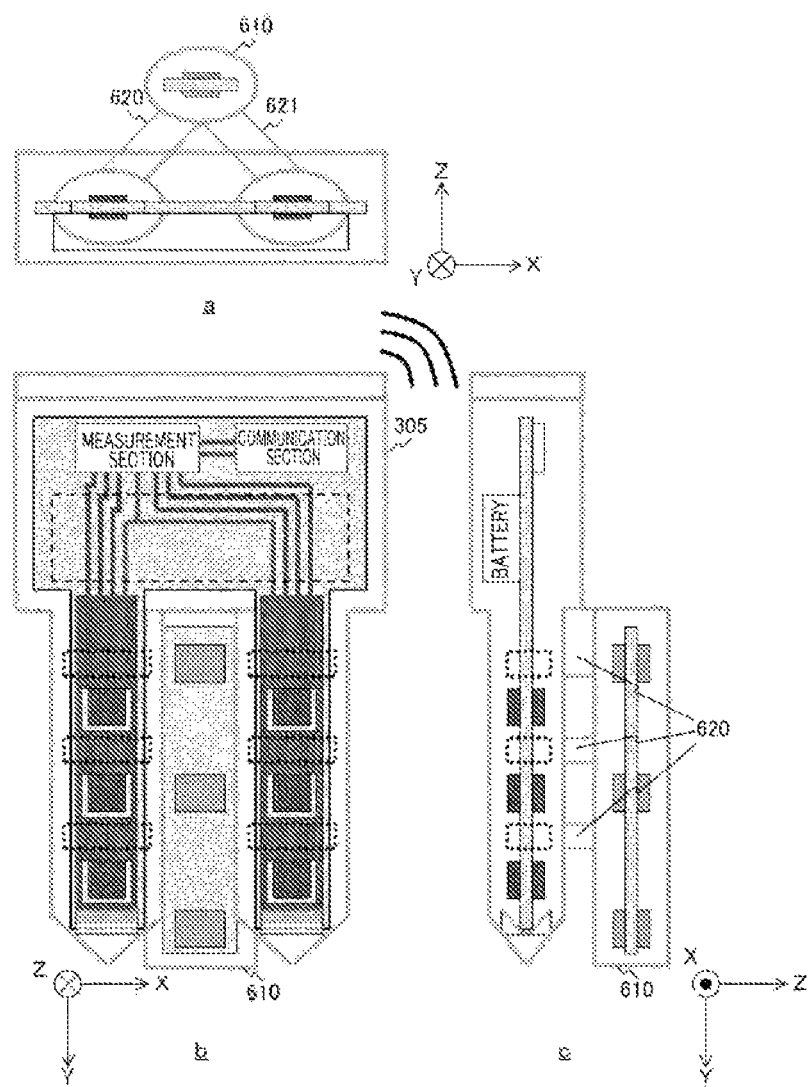

FIG. 359 is a diagram illustrating a structure of a sensor device in a case of a combination of FIGS. 311e and 311f.

Figure 360:
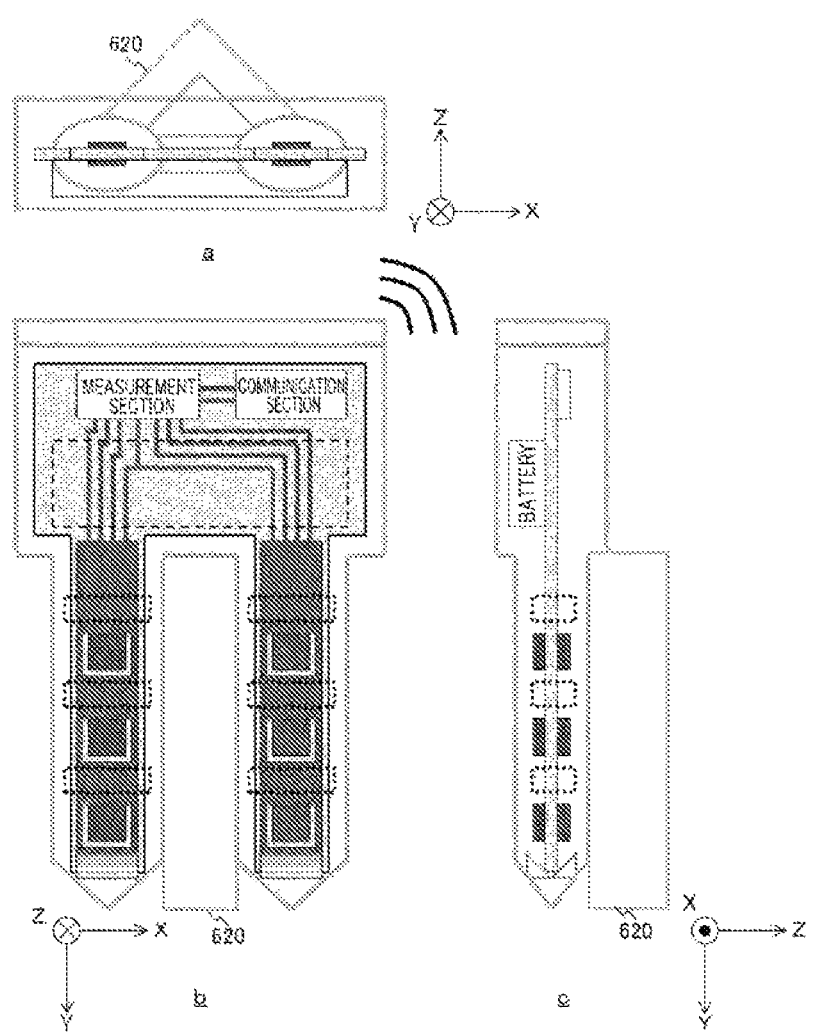

FIG. 360 is a diagram illustrating a structure of a sensor device in a case of a combination of FIGS. 311g and 311h.

Figure 361:
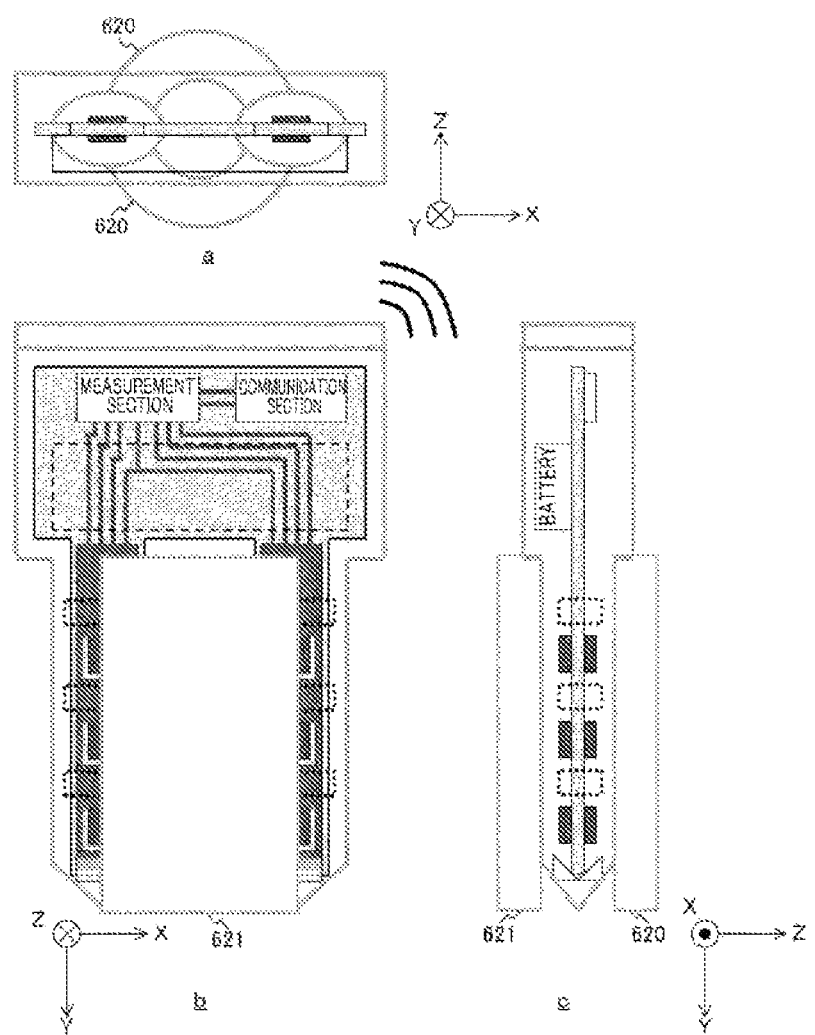

FIG. 361 is a diagram illustrating a structure of a sensor device in a case of a combination of FIGS. 311i and 311j.

Figure 362:
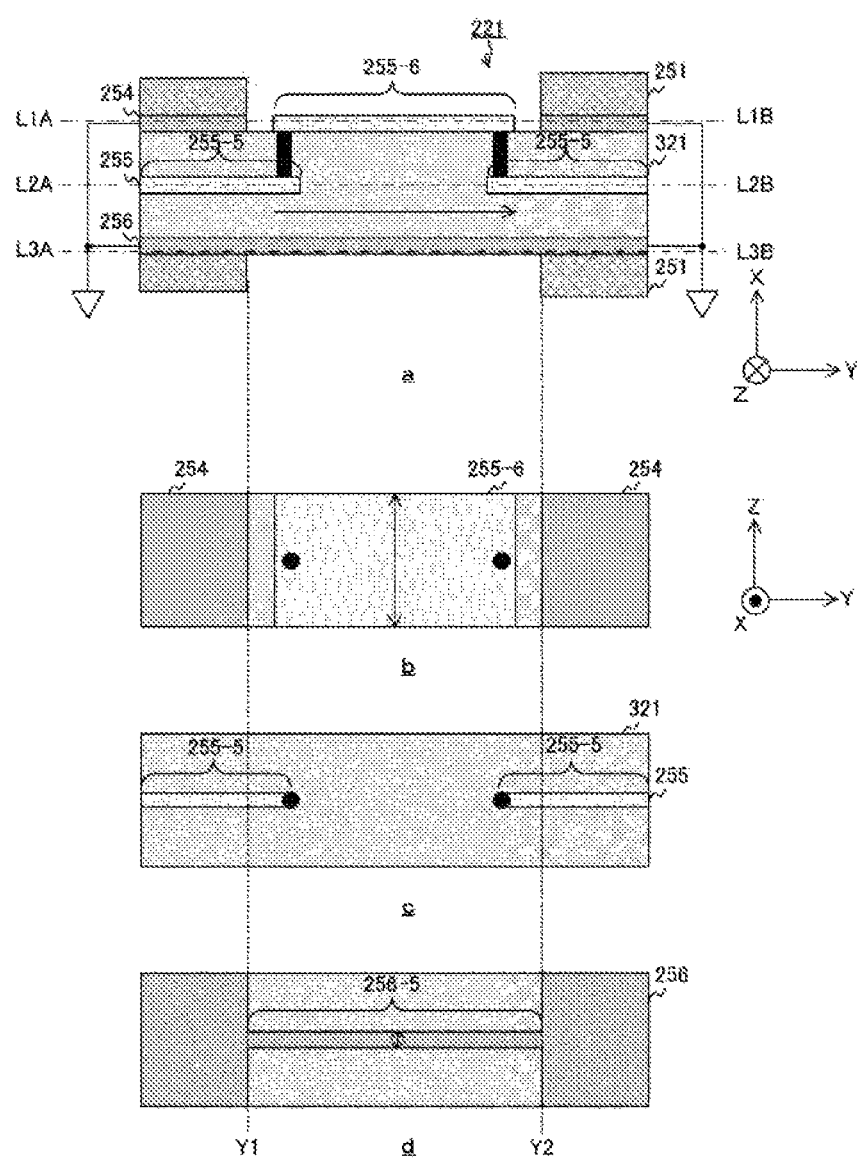

FIG. 362 is an example of a sectional view and a plan view illustrating a configuration example of a transmission antenna according to a thirteenth embodiment of the present technology.

Figure 363:
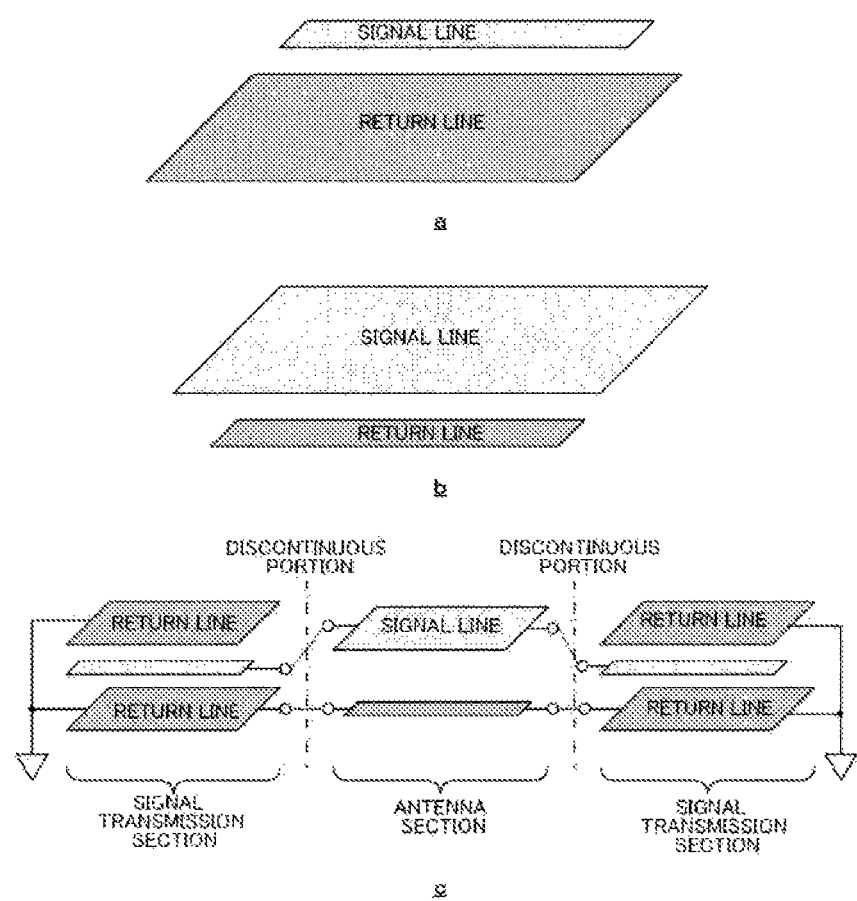

FIG. 363 is a diagram for explaining a principle of the transmission antenna according to the thirteenth embodiment of the present technology.

Figure 364:
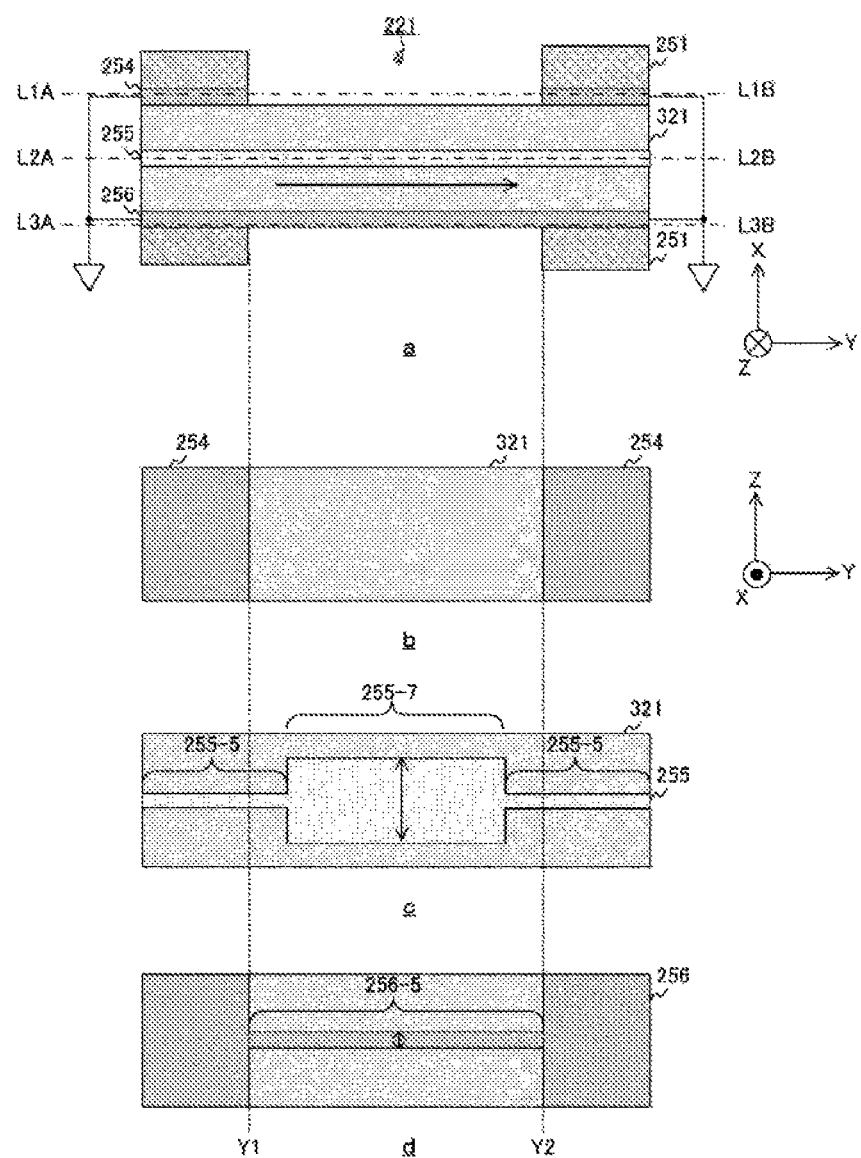

FIG. 364 is an example of a sectional view and a plan view illustrating a configuration example of a transmission antenna of another type according to the thirteenth embodiment of the present technology.

Figure 365:
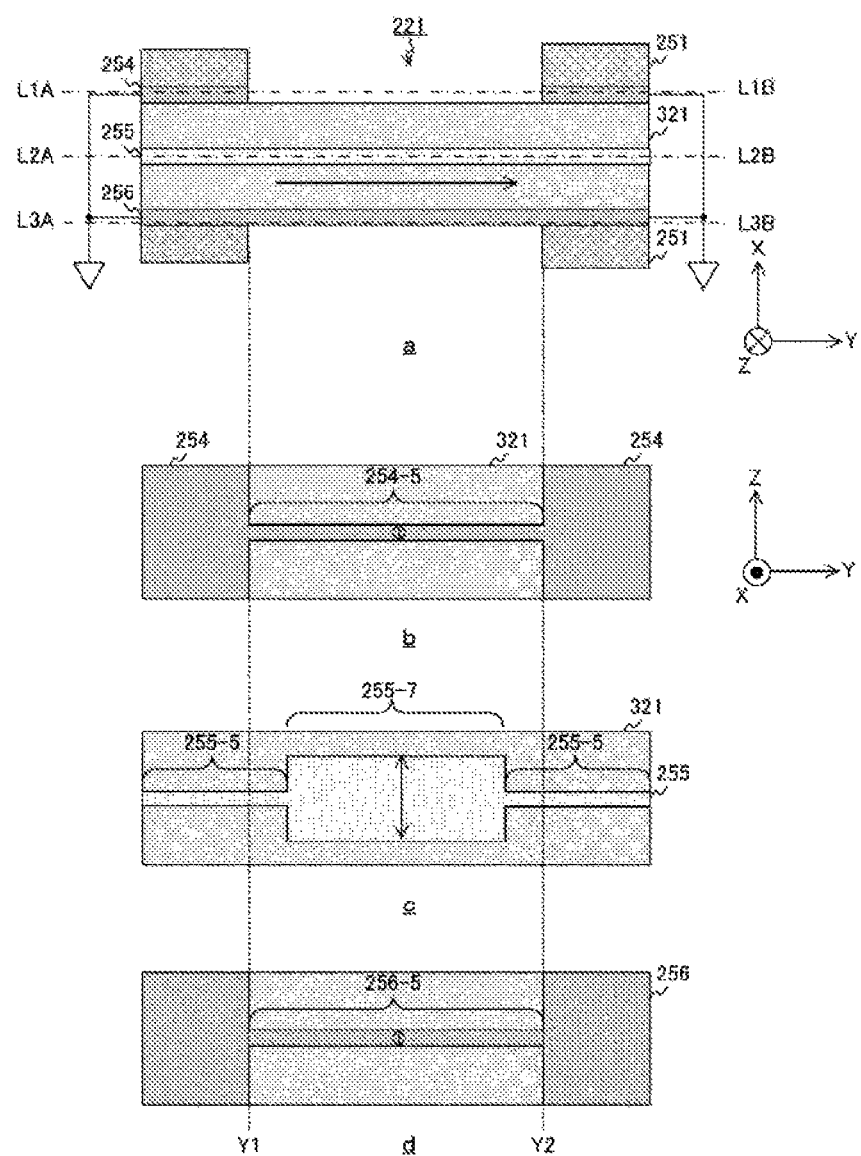

FIG. 365 is an example of a sectional view and a plan view illustrating a configuration example of a transmission antenna of another type according to the thirteenth embodiment of the present technology.

Figure 366:
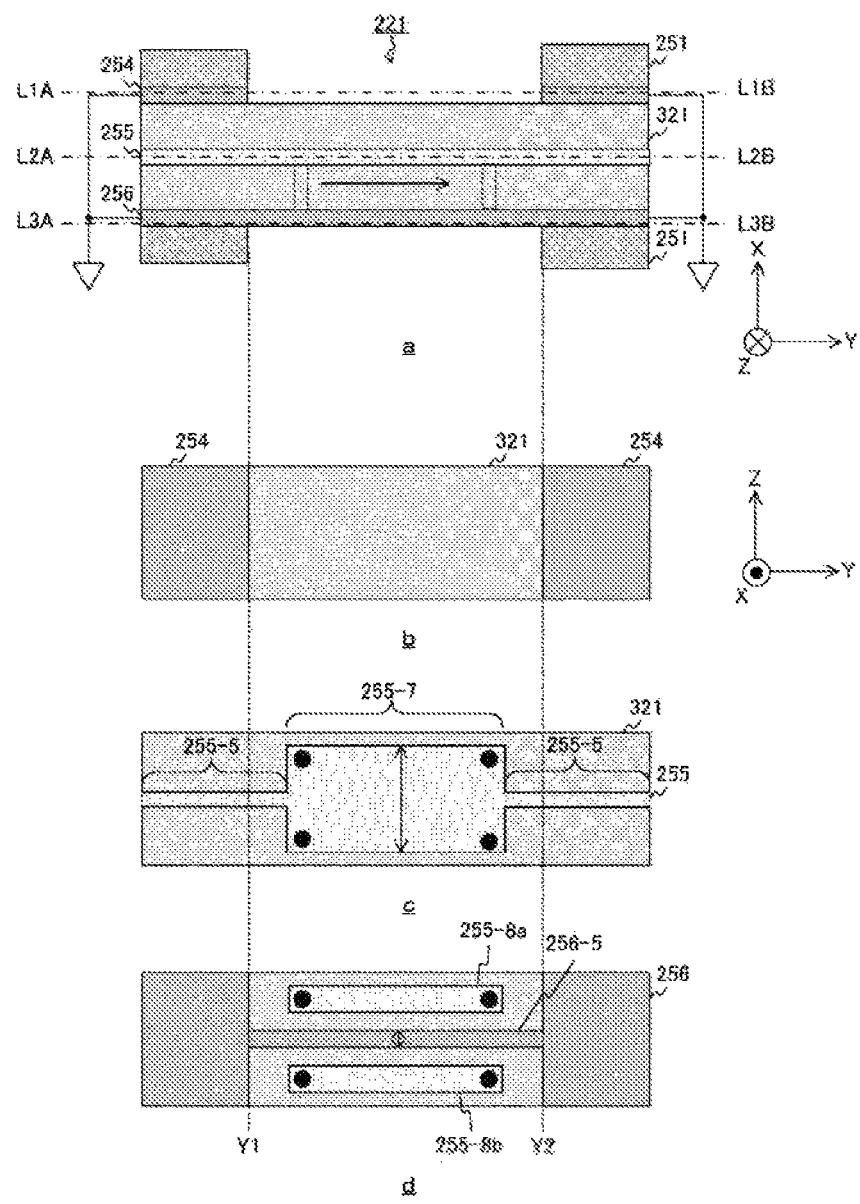

FIG. 366 is an example of a sectional view and a plan view illustrating a configuration example of a transmission antenna of another type according to the thirteenth embodiment of the present technology.

Figure 367:
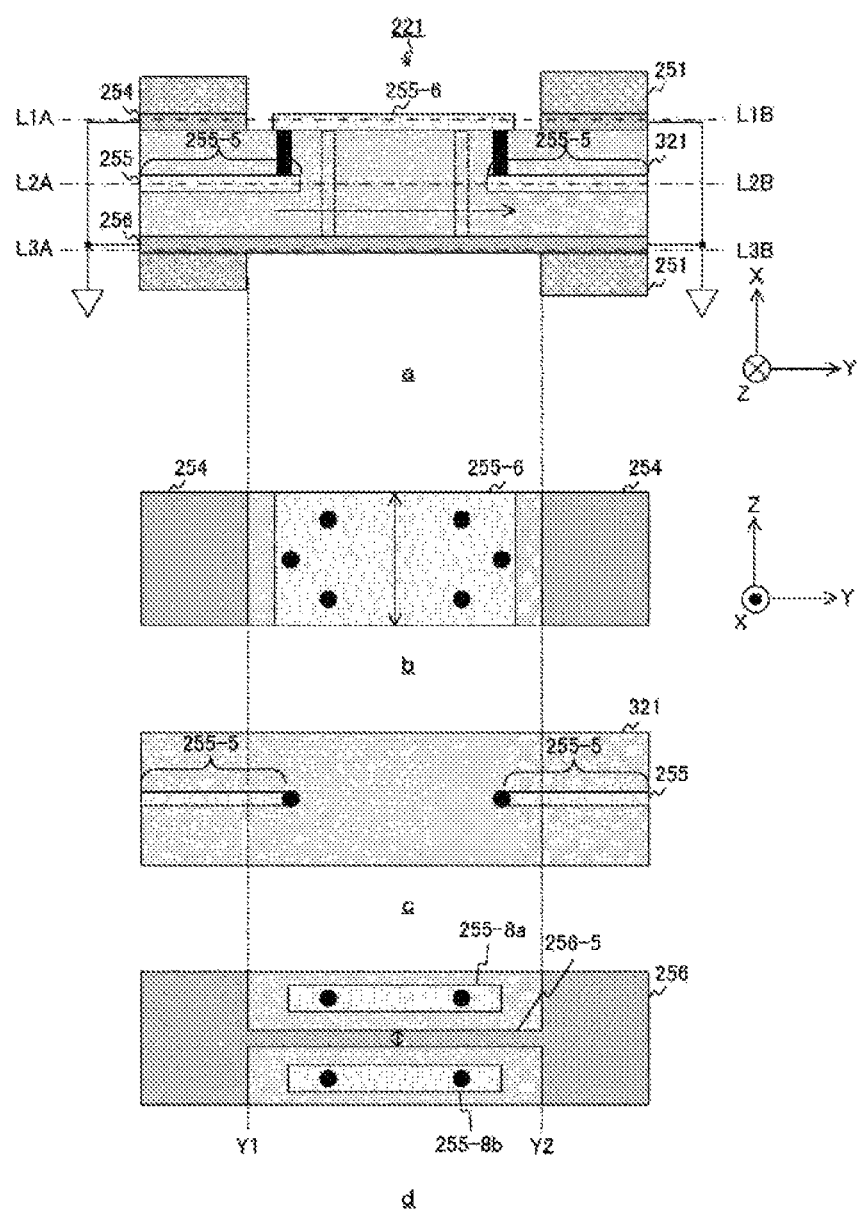

FIG. 367 is an example of a sectional view and a plan view illustrating a configuration example of a transmission antenna of another type according to the thirteenth embodiment of the present technology.

Figure 368:
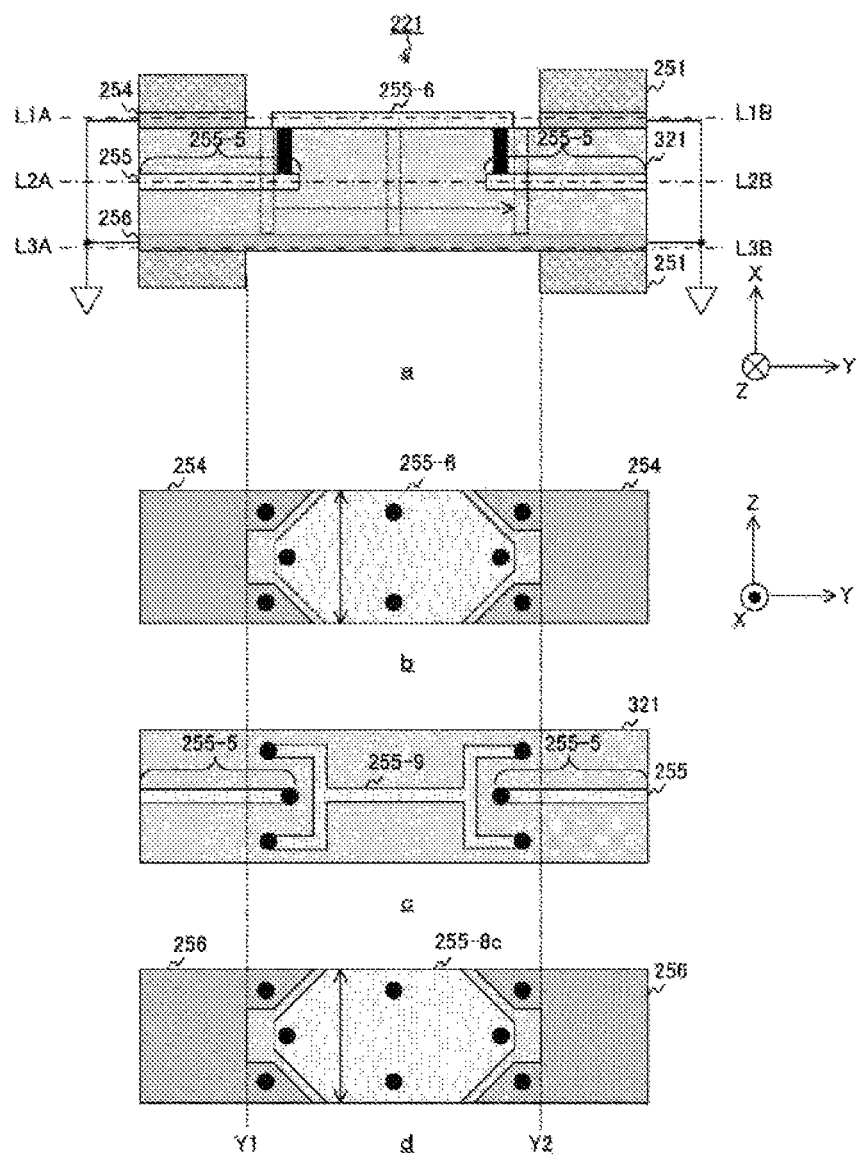

FIG. 368 is an example of a sectional view and a plan view illustrating a configuration example of a transmission antenna of another type according to the thirteenth embodiment of the present technology.

DESCRIPTION OF EMBODIMENTS

Modes for carrying out the present technology (hereinafter, referred to as "embodiments") will be described below. The description will be given in the following order.
1. First embodiment (example in which measurement section substrate and intra-probe substrate are connected in orthogonal to manner)
2. Second embodiment (example in which antenna is formed in one electronic substrate)
3. Third embodiment (example including columnar antenna)
4. Fourth embodiment (example in which watering nozzle is fixed at appropriate position)
5. Fifth embodiment (example in which no sensor casing is included)
6. Sixth embodiment (example in which stem is connected to probe)
7. Seventh embodiment (example in which pillar and reinforcing section are added)
8. Eighth embodiment (example in which pair of probe casings are separated)
9. Ninth embodiment (example in which guide is inserted before insertion of sensor device)
10. Tenth embodiment (example in which spiral-shaped member and shovel-shaped casing are included)
11. Eleventh embodiment (example in which transmission power is adjusted)
12. Twelfth embodiment (example in which measurement section substrate is disposed at position where probe extending direction and substrate plane are vertical to each other)
13. Thirteenth embodiment (example in which part of signal line in split line is increased in thickness)

1. First Embodiment

Configuration Example of Moisture Measurement System

Figure 1:
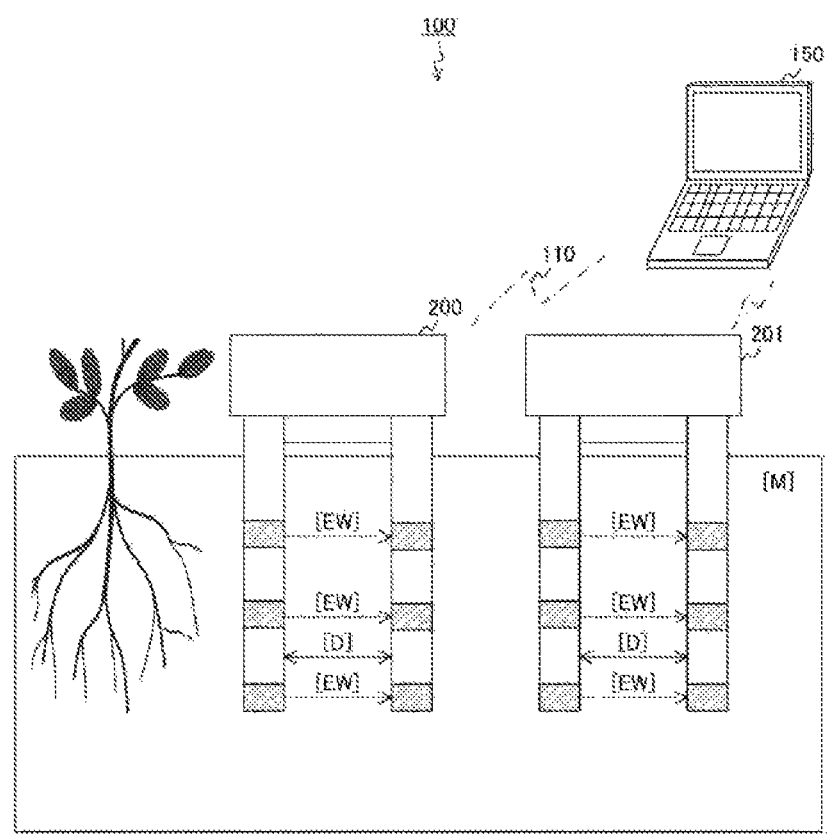
FIG. 1 is an example of an overall view of a moisture measurement system according to a first embodiment of the present technology.

FIG. 1 is an example of an overall view of a moisture measurement system 100 according to the first embodiment of the present technology. The moisture measurement system 100 is adapted to measure the amount of moisture contained in a medium M and includes a central processing unit 150 and at least one sensor device such as sensor devices 200 and 201. As the medium M, soil for growing crops are conceivable, for example.

The sensor device 200 is adapted to acquire data necessary to measure the amount of moisture as measurement data. Content of the measurement data will be described later. The sensor device 200 transmits the measurement data to the central processing unit 150 via a communication path 110 (such as a wireless communication path). A configuration of the sensor device 201 is similar to that of the sensor device 200. The central processing unit 150 is adapted to measure the amount of moisture using the measurement data. Note that the communication path 110 may be a wired communication path.

Note that it is also possible to provide a plurality of central processing units 150 in the moisture measurement system 100.

A user uses the sensor device 200 or 201 by applying a load thereto from above to insert it into the soil. The sensor device 200 or the like is used with at least an antenna part (an antenna 213 in FIG. 3, which will be described later) in the sensor device 200 or the like exposed upward from the soil surface such that communication with the central processing unit 150 can be established. The gray parts in the drawing illustrate antennas (transmission antennas 221 to 223 and reception antennas 231 to 233 in FIG. 3, which will be described later). Note that the above antenna part (the above antenna 213) may be used in a manner of being buried in the soil as long as it is possible to establish communication with the central processing unit 150 at the depth.

Each of the sensor devices 200 and 201 includes a pair of probes. The length of the probes is 5 centimeters (cm) to 200 centimeters (cm). The probes are provided with one to forty antennas, which will be described later. It is thus possible to measure moisture at a plurality of depths within the soil depth range of 5 centimeters (cm) to 200 centimeters (cm).

Configuration Example of Central Processing Unit

Figure 2:
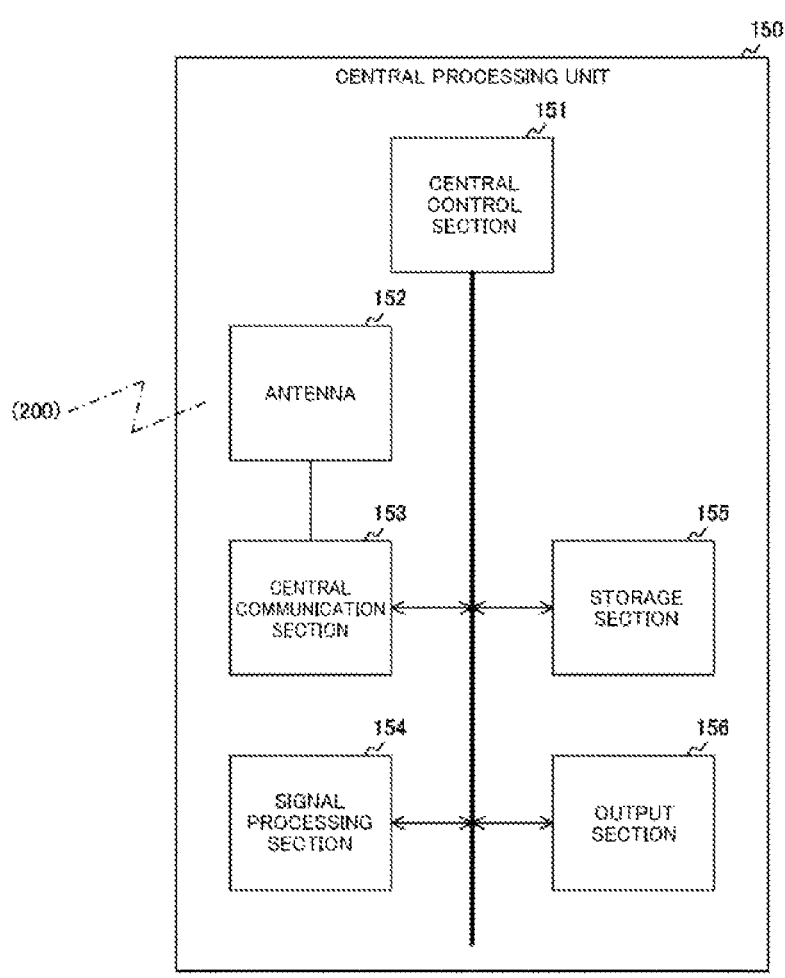
FIG. 2 is a block diagram illustrating a configuration example of a central processing unit according to the first embodiment of the present technology.

FIG. 2 is a block diagram illustrating a configuration example of the central processing unit 150 according to the first embodiment of the present technology. The central processing unit 150 includes a central control section 151, an antenna 152, a central communication section 153, a signal processing section 154, a storage section 155, and an output section 156.

The central control section 151 is adapted to control the entire central processing unit 150. The central communication section 153 is adapted to transmit information (for example, an instruction regarding measurement) to the sensor device 200 or 201 via the antenna 152 and receive measurement data from the sensor device 200 or 201.

The signal processing section 154 is adapted to obtain the amount of moisture on the basis of the measurement data. The storage section 155 is adapted to store a result of measuring the amount of moisture and the like. The output section 156 is adapted to output the result of measuring the amount of moisture to a display device (not illustrated) and the like.

Configuration Example of Sensor Device

Figure 3:
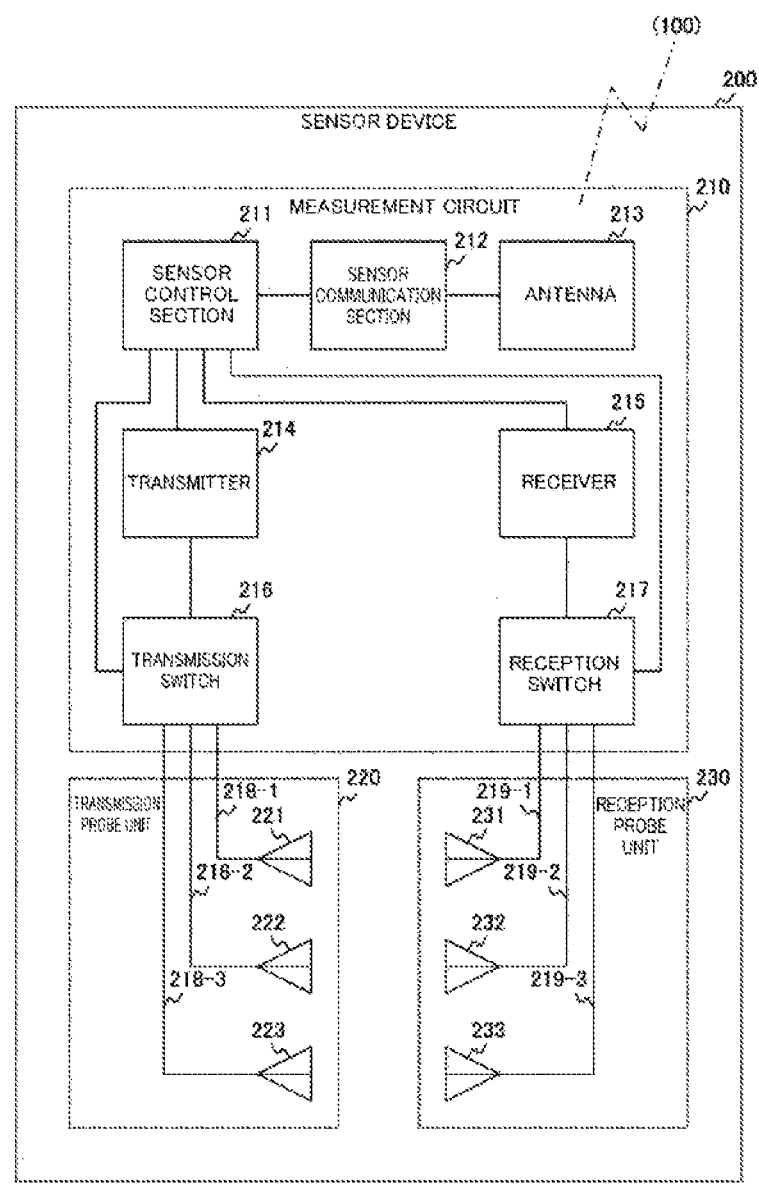
FIG. 3 is a block diagram illustrating a configuration example of a sensor device according to the first embodiment of the present technology.

FIG. 3 is a block diagram illustrating a configuration example of the sensor device 200 according to the first embodiment of the present technology. The sensor device 200 includes a measurement circuit 210, a transmission probe unit 220, and a reception probe unit 230. In the measurement circuit 210, a sensor control section 211, a sensor communication section 212, an antenna 213, a transmitter 214, a receiver 215, a transmission switch 216, and a reception switch 217 are disposed.

A predetermined number of transmission antennas such as transmission antennas 221 to 223 are provided in the transmission probe unit 220. A predetermined number of reception antennas such as reception antennas 231 to 233 are provided in the reception probe unit 230.

The sensor control section 211 is adapted to control each circuit in the measurement circuit 210. The transmission switch 216 is adapted to select any one of the transmission antennas 221 to 223 and connect the selected one to the transmitter 214 in accordance with control of the sensor control section 211. The reception switch 217 is adapted to select any one of the reception antennas 231 to 233 and connect the selected one to the receiver 215 in accordance with control of the sensor control section 211. The transmission antennas 221 to 223 are connected to the transmission switch 216 via transmission paths 218-1 to 218-3. Also, the reception antennas 231 to 233 are connected to the reception switch 217 via the transmission paths 219-1 to 219-3.

The transmitter 214 is adapted to transmit an electrical signal at a predetermined frequency as a transmission signal via a selected transmission antenna. As an incident wave in the transmission signal, a continuous wave (CW), for example, is used. The transmitter 214 switches the frequency in order at a step of 50 megahertz (MHz) in a frequency band of 1 gigahertz (GHz) to 9 gigahertz (GHz), for example, and transmits the transmission signal.

The receiver 215 is adapted to receive a transmitted wave via a selected reception antenna. Here, the transmitted wave is obtained by the reception antenna converting an electromagnetic wave transmitted through the medium between the probes into an electrical signal.

The sensor communication section 212 is adapted to receive information (an instruction regarding measurement) sent from the central processing unit 150 and transmit data indicating a reception result of the receiver 215 as measurement data to the central processing unit 150 via the antenna 213.

Note that the configuration of the sensor device 201 is similar to that of the sensor device 200.

Figure 4:
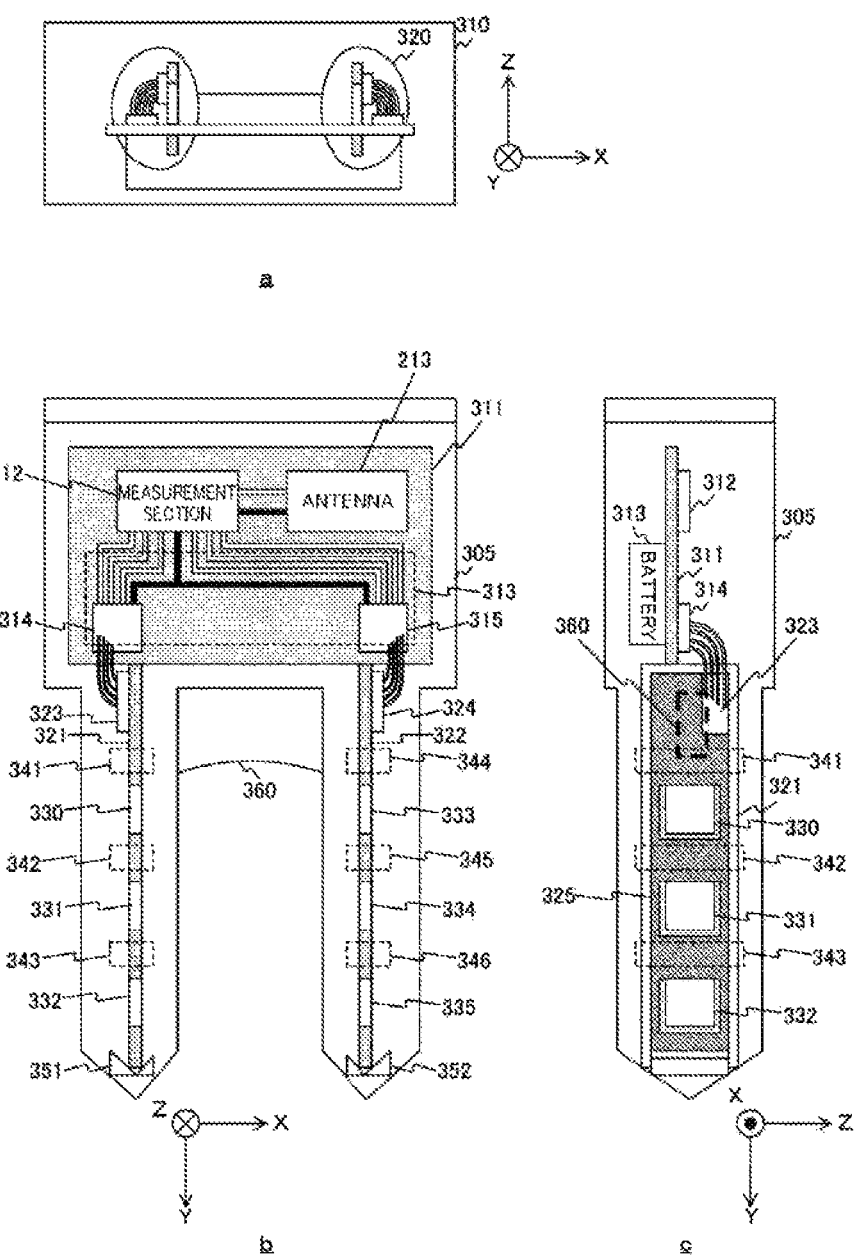
FIG. 4 is an example of an overall view of the sensor device according to the first embodiment of the present technology.

FIG. 4 is an example of an overall view of the sensor device 200 according to the first embodiment of the present technology. In the drawing, a is a transparent view seen from above the sensor device 200 on the assumption that the soil insertion side is a lower side (in other words, a diagram in which features of each section of the sensor device 200 seen from above are illustrated in an overlapping manner). In the drawing, b is a front view of the sensor device 200. In the drawing, c is a transparent view of the sensor device 200 seen from a side (in other words, a diagram in which features of each section of the sensor device 200 are seen from the side are illustrated in an overlapping manner). Note that three-view drawings below in the specification will be transparent views (diagrams illustrating features of each section in an overlapping manner) similarly to FIG. 4 unless particularly indicated otherwise.

The sensor device 200 includes a sensor casing 305 with a pair of projecting portions provided at a lower portion thereof. FIG. 5 is an example of an overall view of the sensor casing 305 as will be described later. The part of the sensor casing 305 where the pair of projecting portions are provided will be referred to as a probe casing 320 for convenience, and the other part will be referred to as a measurement section casing 310 for convenience. Also, a casing accommodating the transmission probe unit 220 will be referred to as a probe casing 320a, and a casing accommodating the reception probe unit 230 will be referred to as a probe casing 320b. Furthermore, a combination of the transmission probe unit 220 and the probe casing 320a accommodating it will be referred to as a transmission probe, and a combination of the reception probe unit 230 and the probe casing 320*b* accommodating it will be referred to as a reception probe.

A measurement section substrate 311 is disposed in the measurement section casing 310. The measurement section substrate 311 is an electronic substrate (a wiring substrate in another way of referring to it) including a plurality of laminated wiring layers. The measurement circuit 210 is formed in the measurement section substrate 311. Here, a measurement section 312 in FIG. 4 represents the measurement circuit 210 in FIG. 3. In FIG. 3, the antenna 213 is included in the measurement circuit 210. On the other hand, the antenna 213 is disposed outside the measurement circuit 210 in FIG. 4, and this represents a modification example of the measurement circuit 210 illustrated in FIG. 3. In FIG. 4, a mode in which the antenna 213 is included in the measurement circuit 210 may also be adopted. A battery 313, a connector 314, and a connector 315 are further connected to the measurement substrate 311. Note that the measurement section 312 in FIG. 4 may be configured of one semiconductor device or may be configured using a plurality of semiconductor devices. The measurement section 312, the connector 314, and the connector 315 are connected by a strip line including signal lines and shield layers. In the drawing, the three white thick lines illustrate the signal lines, and the black thick lines illustrate the shield layers, for convenience. Although the strip line shielding parts between signal lines is formed by disposing shield wirings between the signal lines and disposing shield layers above and below the signal lines in a direction orthogonal to the substrate plane in practice, FIG. 4 provides simplified indication.

Also, intra-probe substrates 321 and 322, radio wave absorption sections 341 to 346, and positioning sections 351 and 352 are disposed in the probe casing 320.

The intra-probe substrate 321 is an electronic substrate (a wiring substrate in another way of referring to it) including a plurality of laminated wiring layers. A connector 323, radiation elements 330 to 332, a shield layer 325, and a plurality of signal lines (not illustrated) are formed in the intra-probe substrate 321. Note that, a plurality of shield layers are formed in the intra-probe substrate 321. A part including the radiation element 330 and a part of the shield layer 325 exposed from the radio wave absorption section 341 or the like functions as one transmission antenna 221. The same applies to the radiation elements 331 and 332, and these function as transmission antennas 222 and 223, respectively. In the drawing, three transmission antennas are aligned. The connector 323 is connected to the radiation elements 330 to 332 included in the transmission antennas 221 to 223 by the transmission paths 218-1 to 218-3 that are independent for each transmission antenna. These transmission paths are formed by the strip lines in which each of the plurality of signal lines is shielded by shield layers, shield wirings, or shield vias formed in the intra-probe substrate 321 both in the substrate parallel direction (the left and right sides of the signal line) and in the substrate vertical direction (the sides above and below the signal line). On the other hand, the measurement section 312 and the connector 314 are connected by transmission paths that are independent for each of the transmission antennas in the measurement section substrate 311 as well, and these transmission paths are formed by the strip line using the signal lines and the shield layers included in the measurement section substrate 311. In this manner, the measurement section 312 and all the transmission antennas (the transmission antennas 221 to 223 in the examples in FIGS. 3 and 4) included in the sensor device 200 are connected via transmission paths (the strip lines, in particular) that are independent for each of the transmission antennas.

The intra-probe substrate 322 is also an electronic substrate (a wiring substrate in another way of referring to it) including a plurality of laminated wiring layers. A connector 324, elements (reception elements) 333 to 335, a shield layer 326, and a plurality of signal lines (not illustrated) are formed in the intra-probe substrate 322. Note that a plurality of shield layers are also formed in the intra-probe substrate 322. A part including the element (reception element) 333 and a part of the shield layer 326 exposed from the radio wave absorption section 344 and the like functions as one reception antenna 231. The same applies to the radiation elements 334 and 335, and these function as reception antennas 232 and 233, respectively. In the drawing, three reception antennas are aligned. The connector 324 is connected to the elements (reception elements) 333 to 335 included in the reception antennas 231 to 233 by the transmission paths 219-1 to 219-3 that are independent for each of the reception antennas. These transmission paths are formed by strip lines in which each of the plurality of signal lines is shielded by the shield layers, the shield wirings, or shield vias formed in the intra-probe substrate 322 both in the substrate parallel direction (the left and right sides of the signal lines) and in the substrate vertical direction (the sides above and below the signal lines). On the other hand, the measurement section 312 and the connector 315 are connected by the transmission paths that are independent for each of the reception antennas in the measurement section substrate 311 as well, and these transmission paths are formed by the strip lines using the signal lines and the shield layers included in the measurement section substrate 311. In this manner, the measurement section 312 and all the reception antennas (the reception antennas 231 to 233 in the examples of FIGS. 3 and 4) included in the sensor device 200 are connected by the transmission paths (the strip lines, in particular) that are independent for each of the transmission antennas.

The part including the probe casing 320*a* and the intra-probe substrate 321 in FIG. 4 corresponds to the transmission probe unit 220 in FIG. 3. The part including the probe casing 320*b* and the intra-probe substrate 322 in FIG. 4 is provided with a reinforcing section 360 between these probe units corresponding to the reception probe unit 230 in FIG. 3.

Hereinafter, an axis that is parallel with the direction in which the sensor device 200 is inserted into the soil will be defined as a Y axis. The probe casings 320*a* and 320*b* extend in the Y-axis direction. The intra-probe substrates 321 and 322 also extend in the Y axis direction. An axis that is parallel with the direction orthogonal to the Y axis in a first plane including the center line of the intra-probe substrate 321 in the Y-axis direction and the center line of the intra-probe substrate 322 in the Y-axis direction will be defined as an X axis. In the sensor device 200 illustrated in FIG. 4, the measurement section substrate 311 extends in a second plane including a line that is parallel with the X-axis direction and a line that is parallel with the Y-axis direction. An axis that is vertical to the X axis and the Y axis will be defined as a Z axis. The above first and second planes are planes that are orthogonal to the Z axis.

As described above, the sensor device 200 is a device for measuring the amount of moisture in a medium on the basis of characteristics of electromagnetic waves propagated through a medium between the transmission and reception antennas.

Also, the shape of each of the transmission antennas and the reception antennas is a planar shape, and these are formed in electronic substrates such as the intra-probe substrates 321 and 322. Hereinafter, the configuration will be referred to as a "component (1)". This enables higher working precision and attachment precision of the antennas and thus more accurate moisture measurement as compared with the mode in which the antennas are formed as separate components and are then assembled with the electronic substrates (intra-probe substrates 321 and 322). Also, it is possible to form the electronic substrates and the antennas in compact sizes and to realize a small casing section. As a result, generation of unnecessary space in the casing is reduced, and this also enables accurate moisture measurement. This effect will be described later in detail.

Also, the transmission antennas and the reception antennas are disposed to face each other in a fixed manner in the sensor casing 305 such that the distance between the antennas is a predetermined distance. The configuration in which the two antennas are caused to face each other and are disposed in a fixed manner at a predetermined distance will be referred to as a "component (2)" below. It is thus possible to improve gains of the antennas, to enhance sensitivity, and to enable accurate moisture measurement as compared with the mode in which the plane-shaped antennas are not caused to face each other or the mode in which the two antennas are not disposed in a fixed manner at a predetermined distance.

The transmission paths 218-1 to 218-3 connecting the measurement section 312 included in the measurement section substrate 311 to the transmission antennas 221 to 223 and the transmission paths 219-1 to 219-3 connecting the measurement section 312 and the reception antennas 231 to 233 are formed using electronic substrates (the measurement section substrate 311 and the intra-probe substrates 321 and 322). The configuration will be referred to as a "component (3)" below. In this manner, it is possible to reduce expansion and contraction of the transmission paths and to enable accurate moisture measurement as compared with the mode in which the transmission paths are formed by coaxial cables.

Also, the sensor device 200 includes the measurement section substrate 311 and the intra-probe substrates 321 and 322 as electronic substrates, and the measurement section substrate 311 is disposed to be orthogonal to the intra-probe substrates 321 and 322. More specifically, (1) the measurement section substrate 311 is disposed to be parallel with the above first plane, (2) the intra-probe substrates 321 and 322 are disposed to face each other and are disposed to be orthogonal to the above first plane, and (3) as a result, the measurement section substrate 311 is disposed to be orthogonal to the intra-probe substrates 321 and 322. The configuration will be referred to as a "component (4)" below.

Also, the sensor casing 305 includes the probe casings 320a and 320b, the transmission antennas are disposed at a plurality of locations in the direction in which the probe casing 320a extends, and the reception antennas are also disposed at a plurality of locations in the direction in which the probe casing 320b extends. The configuration will be referred to as a "component (5)" below.

Also, the transmission paths include a plurality of transmission paths that individually connect the measurement section 312 included in the measurement section substrate 311 and each of all the transmission antennas included in the sensor device 200 and a plurality of transmission paths that individually connect the measurement section 312 included in the measurement section substrate 311 and each of all the reception antennas included in the sensor device 200. The measurement section 312 included in the measurement section substrate 311 drives the plurality of transmission antennas and the plurality of reception antennas in a time division manner. The configuration will be referred to as a "component (6)" below.

Also, the transmission paths between the two substrates disposed to be orthogonal to each other (that is, between the measurement section substrate 311 and the intra-probe substrate 321 and between the measurement section substrate 311 and the intra-probe substrate 322) are connected via a transmission line that includes a plurality of shielded signal lines and has a higher flexibility than that of the measurement section substrates 311 and 312. The configuration will be referred to as a "component (7)" below. It is thus possible to dispose the plurality of plane-shaped transmission antennas and the plurality of plane-shaped reception antennas to face each other. As a result, it is possible to accurately measure moisture over the entire soil located between the plurality of transmission and reception antennas using the transmission and reception antennas with high gains.

Also, the probe casings 320a and 320b are formed of an electromagnetic wave transmissive material, and the strength of the probe casings 320a and 320b is higher than the strength of the electronic substrate stored therein. The configuration will be referred to as a "component (8)" below.

Also, the transmission antennas are formed in the intra-probe substrate 321, and the reception antennas are formed in the intra-probe substrate 322. In the sections of the probe casing 320a and the intra-probe substrate 321 in a direction orthogonal to the extending directions (Y-axis direction) of the probe casing 320a and the intra-probe substrate 321, (1) the distance from the center of the intra-probe substrate 321 to a casing end of the probe casing 320a in the direction vertical to the intra-probe substrate 321 is shorter than (2) the distance from the center of the intra-probe substrate 321 to a casing end of the probe casing 320a in the direction that is parallel with the intra-probe substrate 321. Similarly, in the sections of the probe casing 320b and the intra-probe substrate 322 in a direction orthogonal to the extending direction (Y-axis direction) of the probe casing 320b and the intra-probe substrate 322, (1) the distance from the center of the intra-probe substrate 322 to a casing end of the probe casing 320b in the direction vertical to the intra-probe substrate 322 is shorter than (2) the distance from the center of the intra-probe substrate 322 to a casing end of the probe casing 320b in the direction that is parallel with the intra-probe substrate 322. The configuration will be referred to as a "component (9)" below. The sensor device 200 illustrated in the drawing includes a transmission path covering section for transmission that is formed using a material that absorbs electromagnetic waves and at least partially covers "the transmission path for transmission connecting the transmission elements (transmission antennas) and the measurement section" and a transmission path covering section for reception that is formed using a material that absorbs electromagnetic waves and at least partially covers "the transmission path for reception connecting the reception elements (reception antennas) and the measurement section".

The transmission probe unit includes the above transmission path covering section for transmission, and the reception probe unit also includes the above transmission path covering section for reception.

Additionally, the sensor casing 305 includes the measurement section casing 310 and the probe casing 320. The part of the probe casing 320 accommodating the transmission antennas is the transmission probe casing 320a, and the part thereof accommodating the reception antennas is the reception probe casing 320*b*. The transmission probe casing 320*a* and the reception probe casing 320*b* are fixed to and integrated with the measurement section casing 310 in this mode. Note that it is also possible to adopt a state in which these are separated as will be described later.

Here, a mode of the sensor casing 305 in which a plurality of split components of the sensor casing 305 are formed in advance and these components are fixed to and integrated with each other may also be adopted. Also, a mode of the sensor casing 305 in which the transmission probe casing, the reception probe casing, and the measurement section casing 310 are formed as an integrated element at the time of forming these components may also be adopted.

Although the sensor casing 305 includes the reinforcing section 360 to enhance strength of the casing, it is also possible to adopt a configuration in which no reinforcing section 360 is provided.

The reinforcing section 360 has a structure in which it is connected to at least two of the transmission probe casing 320*a*, the reception probe casing 320*b*, and the measurement section casing 310. A structure in which it is connected to these three components may also be adopted.

Also, the entire sensor casing 305 may be formed using a material that transmits electromagnetic waves. Alternatively, at least parts that are the closest to the transmission elements (transmission antennas) and the reception elements (reception antennas) may be formed using a material that transmits electromagnetic waves, and at least a part of the other parts may be formed using a material that is different from the above material.

FIG. 5 is an example of an overall view of the sensor casing 305 according to the first embodiment of the present technology. In the drawing, a is a transparent view of the sensor casing 305 seen from the above. In the drawing, b is a front view of the sensor casing 305. In the drawing, c is a sectional view of the sensor casing 305. In the sensor casing 305, the casing accommodating the transmission probe unit 220 will be referred to as a probe casing 320*a*, the casing accommodating the reception probe unit 230 will be referred to as a probe casing 320*b*, and a reinforcing structure disposed between the probe casings 320*a* and 320*b* to enhance the strength of the probe casings 320*a* and 320*b* will be referred to as a reinforcing section 360. Not only the antenna parts from and to which the electromagnetic waves are transmitted and received but also at least the part corresponding to the casing accommodating the transmission antennas and the transmission path for transmission and the part corresponding to the casing accommodating the reception antennas and the transmission path for reception are entirely formed of an electromagnetic wave transmissive material.

The measurement section casing 310 accommodating the measurement section substrate is in a state where it is disposed to stand relative to the soil (in other words, a state where the measurement section casing 310 is disposed to extend in the above first plane direction) when it is inserted into the soil. More specifically, the thickness (the size in the Z-axis direction) of the measurement section casing 310 is thinner than both the width (the size in the X-axis direction) and the height (the size in the Y-axis direction) of the measurement section casing 310.

The sensor casing 305 including the reinforcing section 360 is formed by an electromagnetic wave transmissive material. Examples of the electromagnetic wave transmissive material include inorganic materials such as polymer materials, glass, and polytetrafluoroethylene (PTEF). As the polymer materials, polycarbonate (PC), polyethersulfone (PES), polyetheretherketone (PEEK), polystyrene sulfonic acid (PSS), and the like are used. As other polymer materials, polymethylmethacrylate (PMMA), polyethylene terephthalate (PET), and the like are also used.

Figure 6:
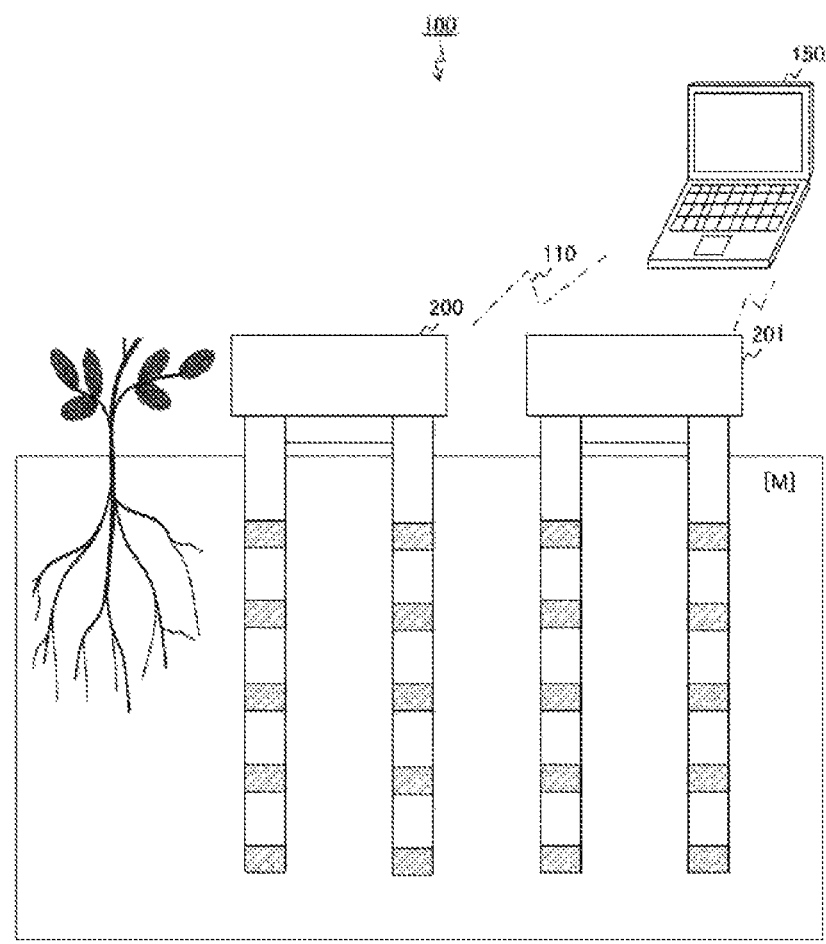
FIG. 6 is an example of an overall view of the moisture measurement system with antennas increased in number according to the first embodiment of the present technology.

FIG. 6 is another example of the first embodiment of the present technology, which is an example of an overall view of the moisture measurement system 100 in which the lengths of the transmission probe and the reception probe included in the sensor devices 200 and 201 are extended and the number of antennas disposed in the transmission probe and the reception probe is increased as compared with the moisture measurement system 100 illustrated in FIG. 1. The moisture measurement system 100 illustrated in FIG. 6 can more accurately measure moisture in the soil in a wider region (particularly, in a soil deep portion) of the soil than that of the moisture measurement system 100 illustrated in FIG. 1 by extending the lengths of the transmission probe and the reception probe, increasing the number of antennas to be disposed in the transmission probe and the reception probe, and further adding a reinforcing section 361 to enhance the strength of the transmission probe and the reception probe as will be described later with reference to FIGS. 7 and 8.

Figure 7:
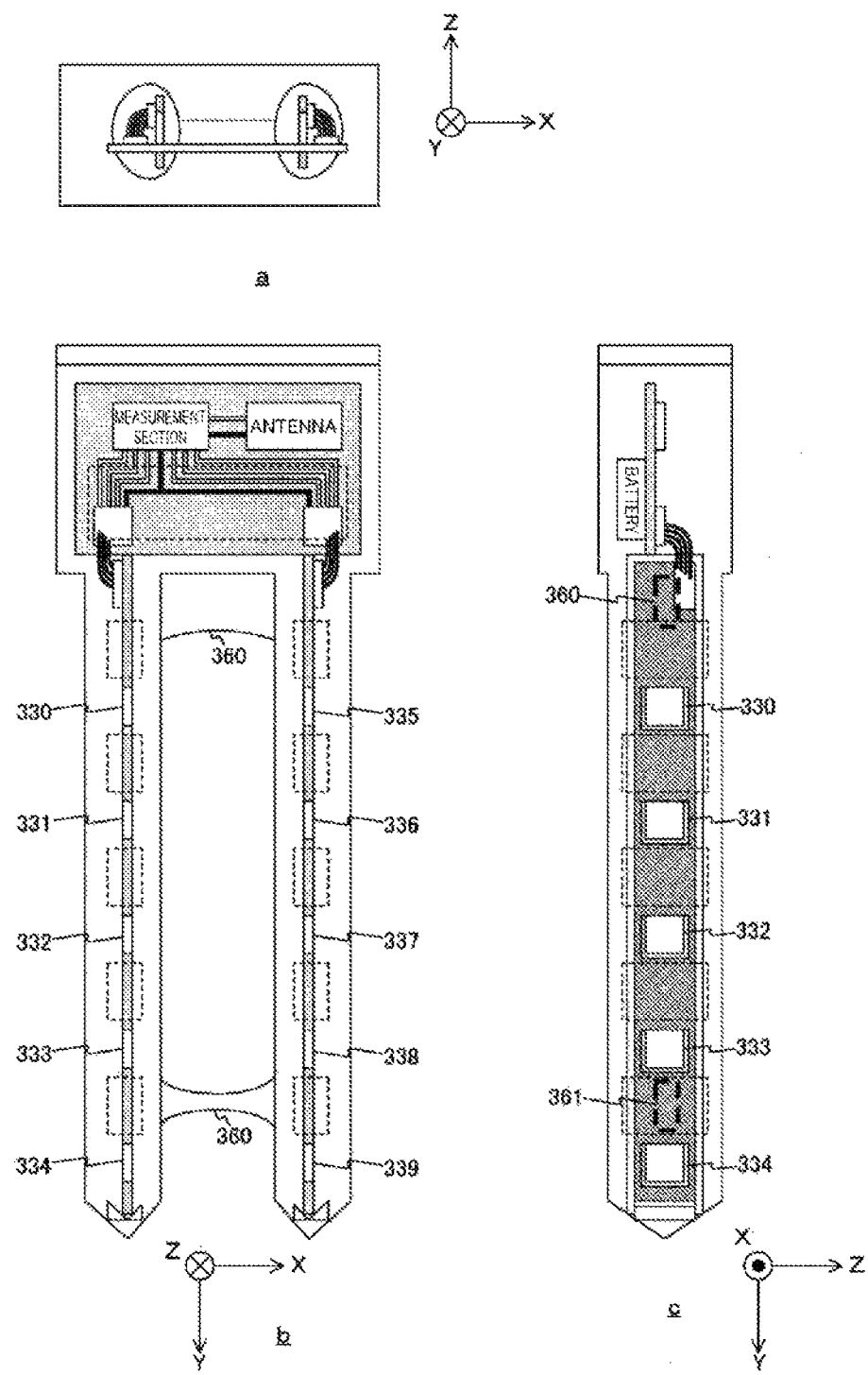
FIG. 7 is an example of an overall view of the sensor device with antennas increased in number according to the first embodiment of the present technology.

FIG. 7 is an example of an overall view of the sensor device 200 included in the moisture measurement system 100 illustrated in FIG. 6. The sensor device 200 illustrated in FIG. 7 has a structure in which the lengths of the transmission probe and the reception probe are extended, the number of antennas disposed in the transmission probe and the reception probe is increased, and the reinforcing section 361 to enhance the strength of the transmission probe and the reception probe is added as compared with the sensor device 200 illustrated in FIG. 4. In the example illustrated in FIG. 7, elements 330 to 339 are provided, and five transmission antennas and five reception antennas are formed. Note that the elements 330 to 334 denote radiation elements and 335 to 339 denote reception elements only in FIG. 7.

Figure 8:
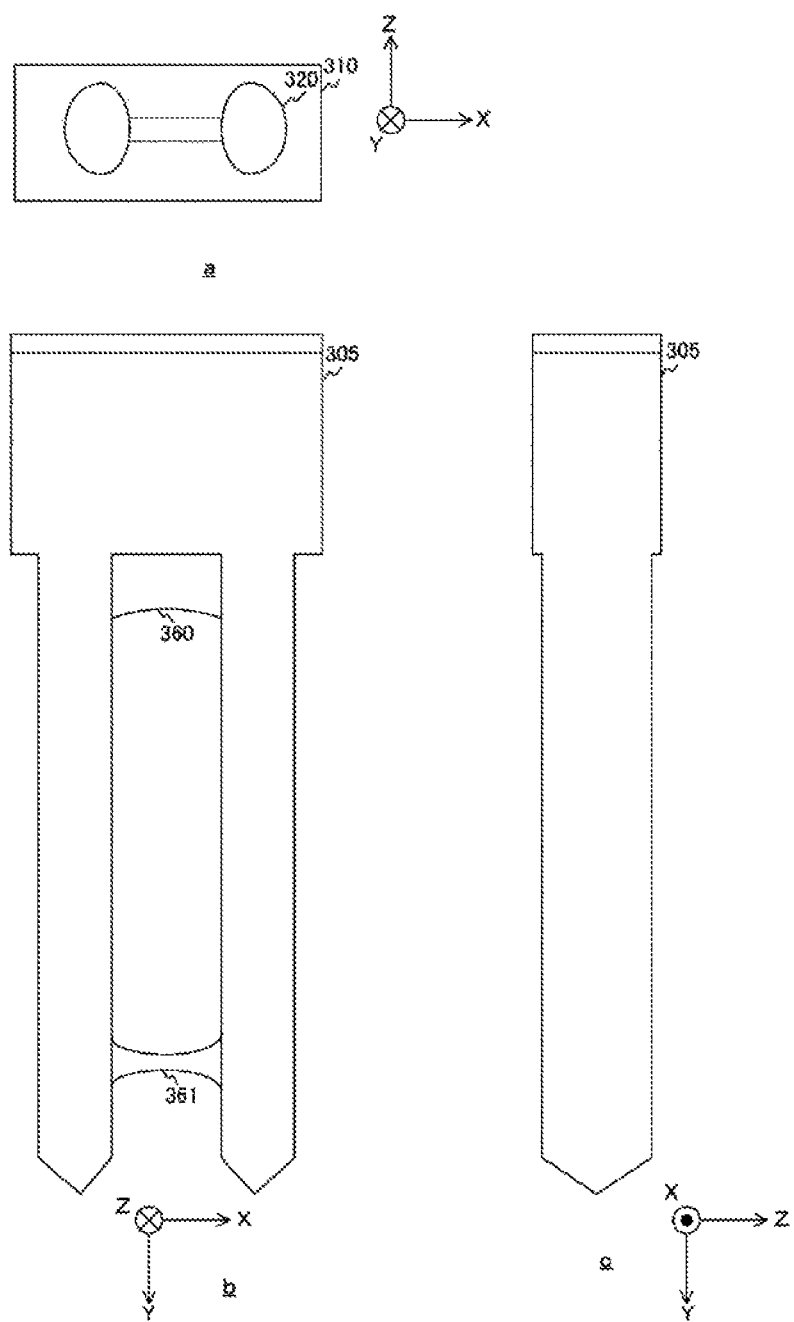
FIG. 8 is an example of an overall view of the sensor casing with antennas increased in number according to the first embodiment of the present technology.

FIG. 8 is an example of an overall view of the sensor casing 305 included in the sensor device 200 illustrated in FIG. 7. In order to enhance strength of the casing, the reinforcing section 361 is added to the lower portion of the probe casing 320.

In a case where the length of the probe casing 320 is long and the soil is hard, the probe casing 320 may be deformed and the distance between the transmission antennas and the reception antennas changes to a size that is different from the designed distance when a stress is applied to the sensor device 200 to insert it into the soil. The addition of the reinforcing section 361 reduces the likelihood of the deformation. Also, in a case where the soil is hard, breakage may occur between the measurement section casing 310 and the probe casing 320 when a stress is applied to the sensor device 200 to insert it into the soil. The addition of the reinforcing section 361 reduces the likelihood of the breakage.

Figure 9:
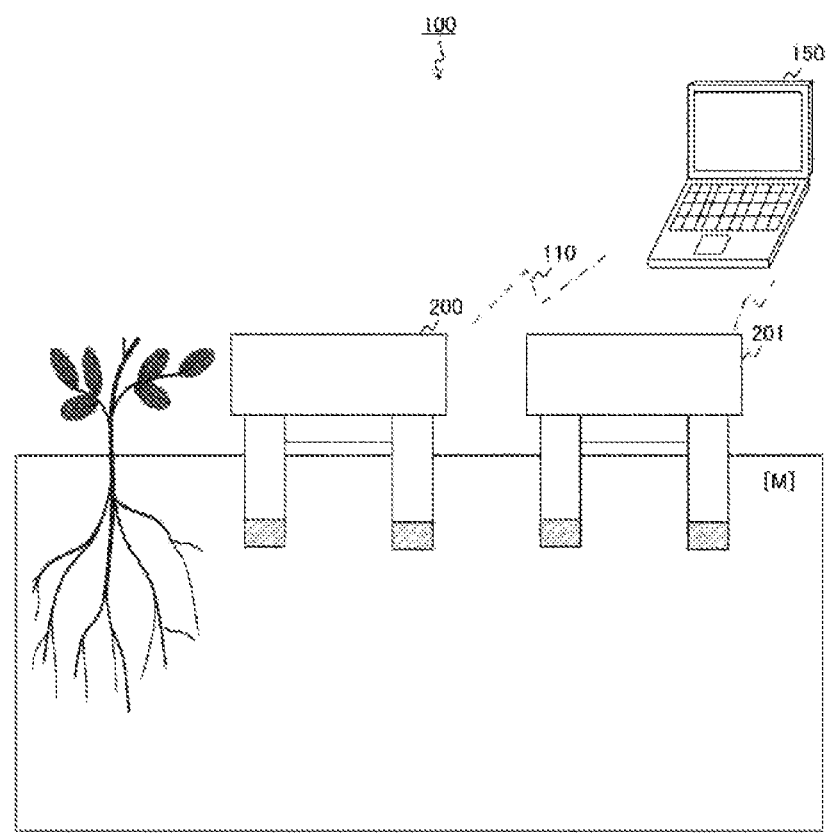
FIG. 9 is an example of an overall view of the moisture measurement system with antennas decreased in number according to the first embodiment of the present technology.

FIG. 9 is yet another example of the first embodiment of the present technology, which is an example of an overall view of the moisture measurement system 100 in which the number of antennas is reduced as compared with the moisture measurement system 100 illustrated in FIG. 1. As illustrated as an example in the drawing, it is also possible to provide one antenna on each of the transmission side and the reception side by reducing the number of antennas in the sensor device 200 or the like. It is also possible to measure the amount of moisture in the soil with simpler components (a configuration with a smaller number of components) by reducing the number of antennas. Additionally, it is also not necessary to provide means for driving a plurality of antennas. In this case, the components (5) and (6) are not needed. In a case where one transmission antenna and one reception antenna are provided, the connection of the transmission paths between the two substrates disposed to be orthogonal to each other (that is, between the measurement section substrate 311 and the intra-probe substrate 321 and between the measurement section substrate 311 and the intra-probe substrate 322) can also be formed using connectors made of metal, such as SMA connectors, for example In this case, the component (7) is also not needed.

Figure 10:
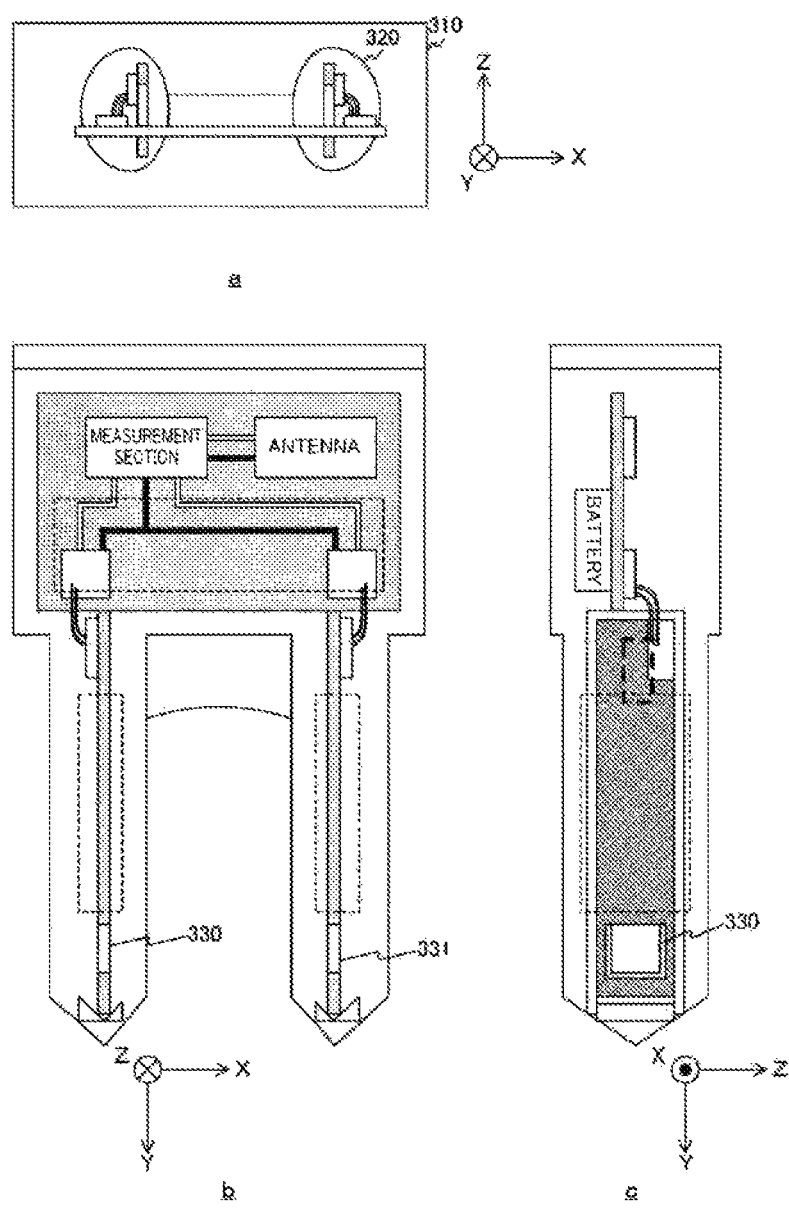
FIG. 10 is an example of an overall view of the sensor device with antennas decreased in number according to the first embodiment of the present technology.

FIG. 10 is an example of an overall view of the sensor device 200 included in the moisture measurement system 100 illustrated in FIG. 9.

Figure 11:
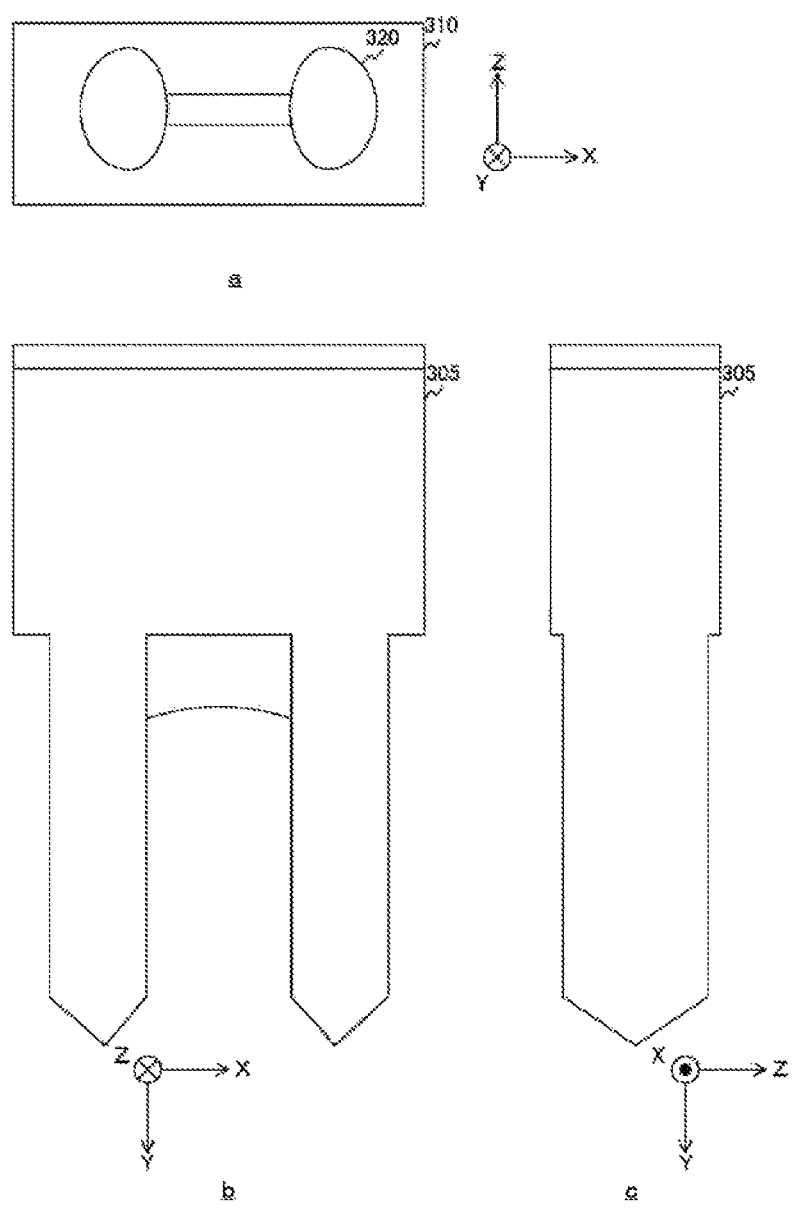
FIG. 11 is an example of an overall view of the sensor casing with antennas decreased in number according to the first embodiment of the present technology.

FIG. 11 is an example of an overall view of the sensor casing 305 included in the sensor device 200 illustrated in FIG. 10.

Figure 12:
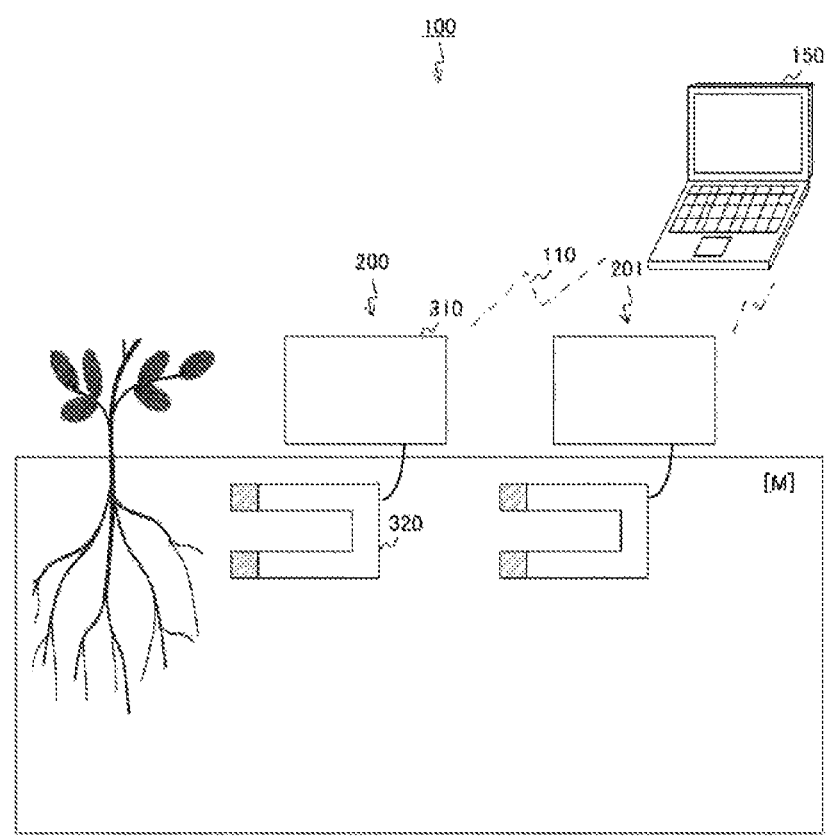
FIG. 12 is an example of an overall view of the moisture measurement system with the casing separated therefrom according to the first embodiment of the present technology.

FIG. 12 is yet another example of the first embodiment of the present technology, which is an example of an overall view of the moisture measurement system 100 in which each of casings included in the sensor devices 200 and 201 is split into two pieces. As illustrated as an example in the drawing, it is also possible to separate the measurement section casing 310 from the probe casing 320. The connection between the transmission paths formed in the measurement section substrate 311 and the transmission paths formed in the intra-probe substrates 321 and 322 is established by cables (for example, coaxial cables). The number of antennas in the probe casing 320 is one on each of the transmission side and the reception side. In this case, the components (5) to (7) are not needed. Also, if the measurement section casing 310 and the probe casing 320 are disposed at separated positions, and the direction in which the measurement section casing 310 is disposed relative to the soil surface does not affect rain falling and water sprinkling to the soil between the probe casings 320a and 320b as targets of measurement of moisture in the soil, the component (4) is also not needed.

Figure 13:
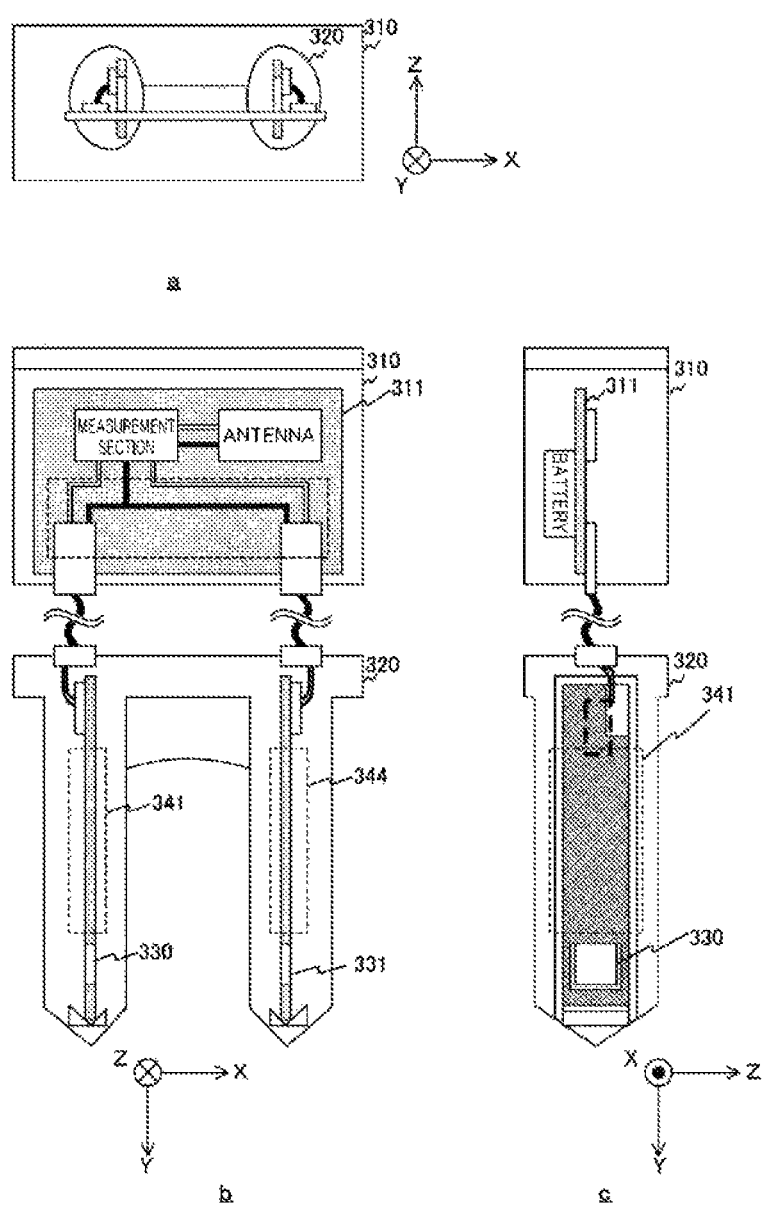
FIG. 13 is an example of an overall view of the sensor device with the casing separated therefrom according to the first embodiment of the present technology.

FIG. 13 is an example of an overall view of the sensor device 200 included in the moisture measurement system 100 illustrated in FIG. 12. In the case of the drawing, the number of antennas is one on each of the transmission side and the reception side. The measurement section casing 310 accommodating the measurement section substrate 311 forms one independent casing. Also, the probe casing 320a accommodating the intra-probe substrate where the transmission antenna 330 is formed and the probe casing 320b accommodating the intra-probe substrate 322 where the reception antenna 331 is formed are connected to form one independent probe casing 320. The probe casing 320 further includes the reinforcing section 360.

FIG. 14 is an example of an overall view of the sensor casing 305 included in the sensor device 200 illustrated in FIG. 13.

Figure 15:
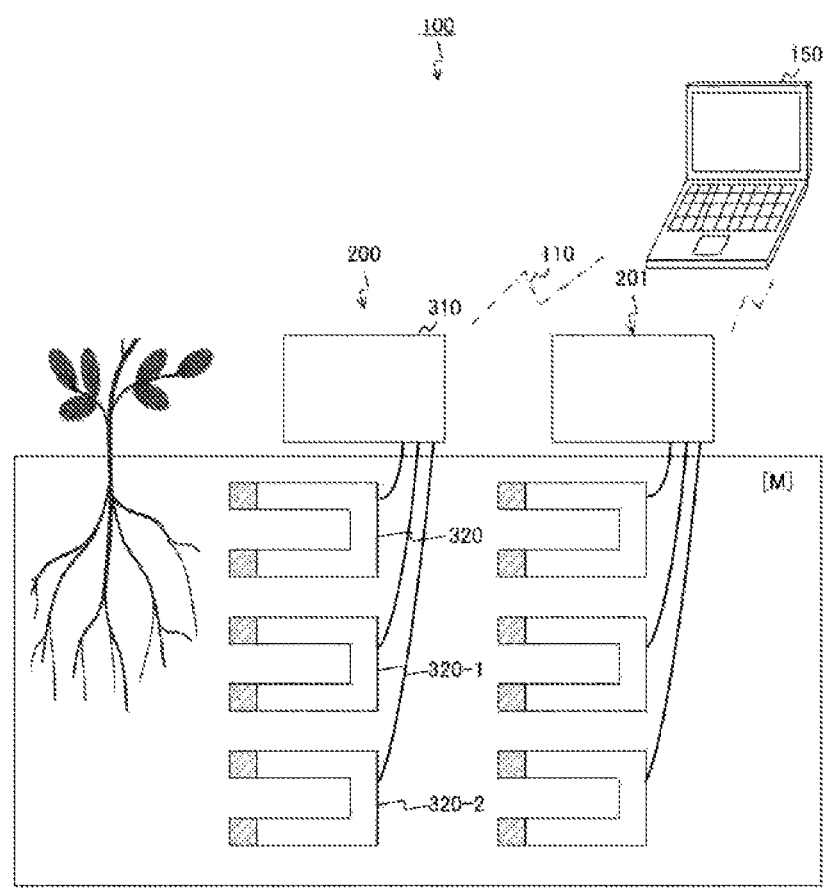
FIG. 15 is an example of an overall view of the moisture measurement system with the casing separated therefrom, in which a plurality of probe casings are provided for each sensor device, according to the first embodiment of the present technology.

FIG. 15 is yet another example of the first embodiment of the present technology, which is an example of an overall view of the moisture measurement system 100 in which the casings included in the sensor devices 200 and 201 are separated and a plurality of probe casings are provided for each sensor device. As illustrated as an example in the drawing, each of the sensor devices 200 and 201 includes a plurality of transmission antennas and reception antennas. In addition, a probe casing is provided for each pair of one transmission antenna and one reception antenna in each of the sensor devices 200 and 201. As illustrated as an example in the drawing, a configuration in which the measurement section casing 310 and a plurality of probe casings such as probe casings 320, 320-1, and 320-2 are provided for each sensor device 200 is adopted. The number of antennas in each probe casing is one on each of the transmission side and the reception side. In this case, the components (4) and (7) are not needed.

Figure 16:
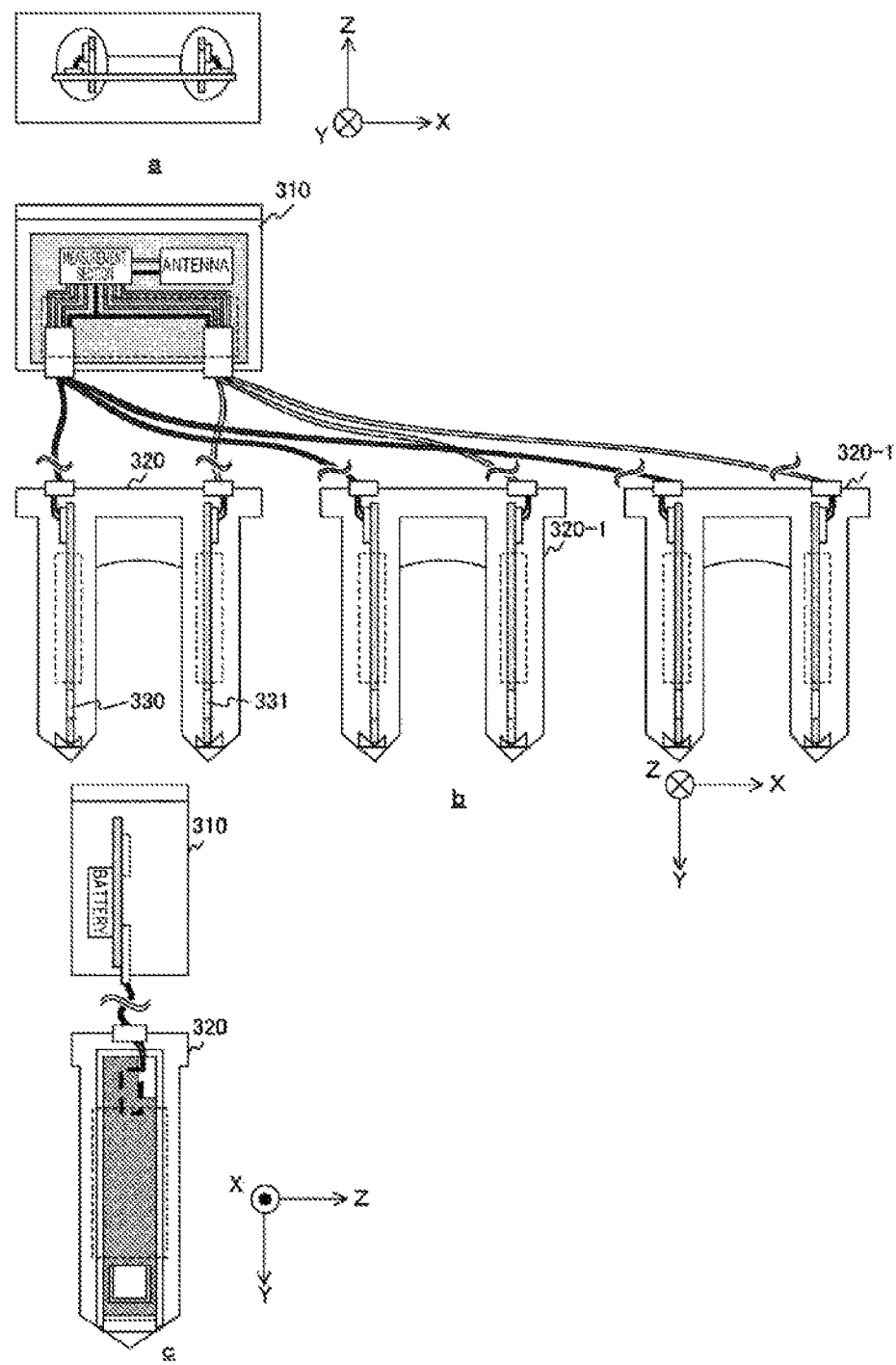
FIG. 16 is an example of an overall view of the sensor device with the casing separated therefrom, in which a plurality of probe casings are provided, according to the first embodiment of the present technology.

FIG. 16 is an example of an overall view of the sensor device 200 included in the moisture measurement system 100 illustrated in FIG. 15. In the case of the drawing, the number of antennas is one on each of the transmission side and the reception side.

Figure 17:
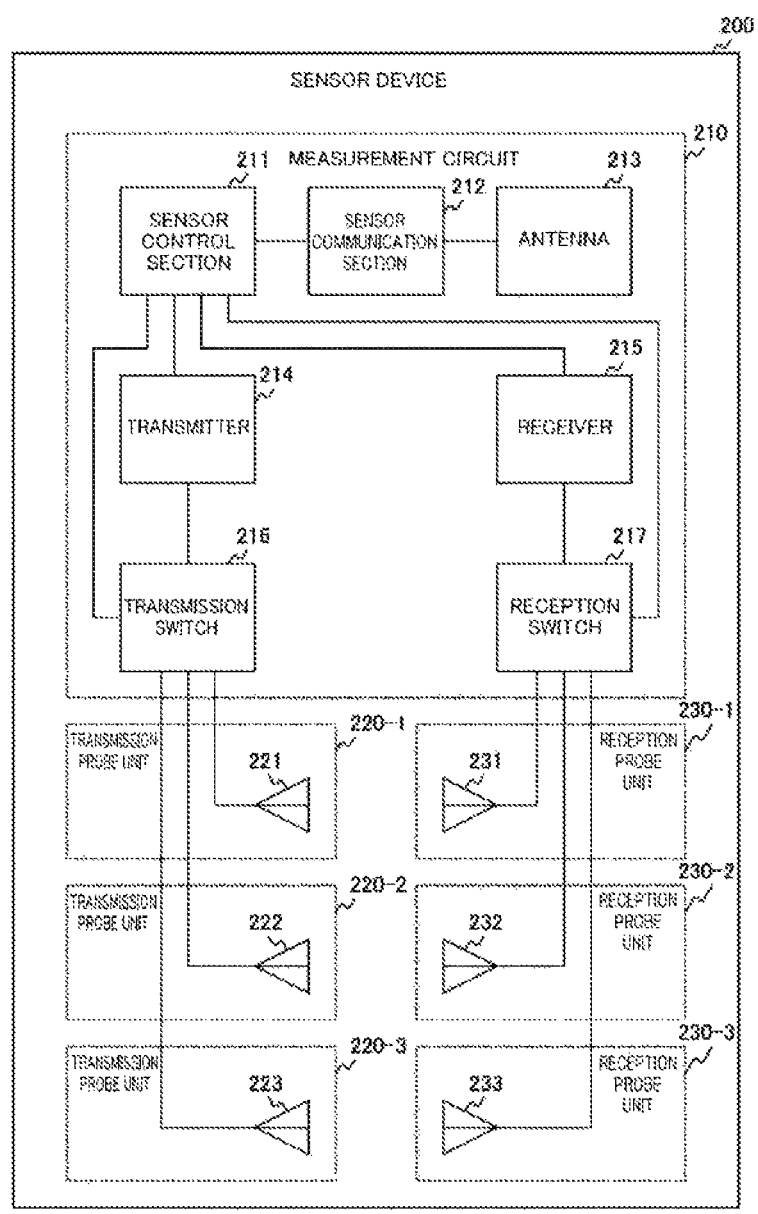
FIG. 17 is a block diagram illustrating a configuration example of the sensor device in FIG. 15 according to the first embodiment of the present technology.

FIG. 17 is a block diagram illustrating a configuration example of the sensor device 200 in FIG. 15. As illustrated as an example in the drawing, the transmission probe units 220-1 to 220-3 and the reception probe units 230-1 to 230-3 are disposed in the three separated probe casings. One antenna is disposed for each of the three pairs of units. For example, the transmission antennas 221 to 223 are disposed in the transmission probe units 220-1 to 220-3, and the reception antennas 231 to 233 are disposed in the reception probe units 230-1 to 230-3. These antennas are connected to the measurement circuit 210 via the mutually independent transmission paths.

Figure 18:
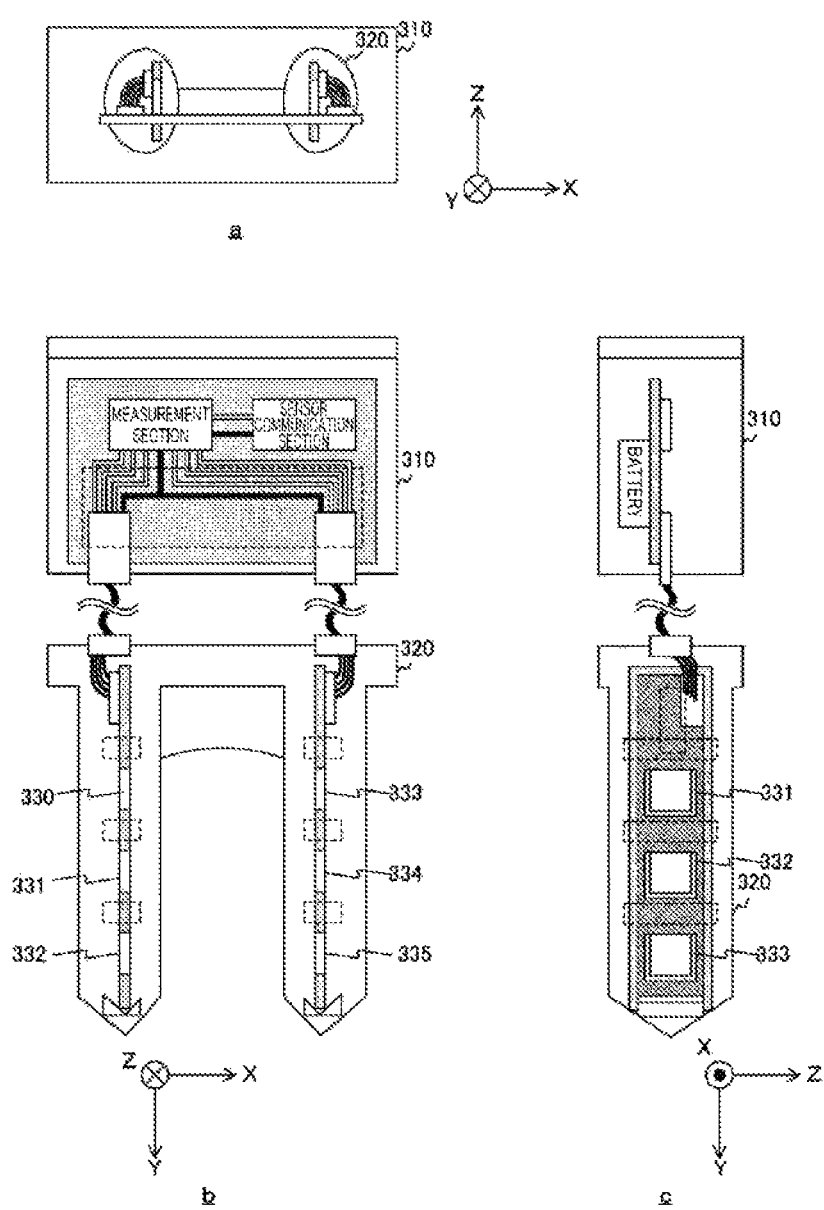
FIG. 18 is another example of an overall view of the sensor device with the casing separated therefrom according to the first embodiment of the present technology.

FIG. 18 is yet another example of the first embodiment of the present technology, which is another example of an overall view of the sensor device 200 in which a plurality of transmission antennas 330 to 332 and a plurality of reception antennas (333 to 335) are included and the probe casing 320 accommodating these and the measurement section casing 310 accommodating the measurement section substrate 311 are separated from each other. In a case where the measurement section casing 310 and the probe casing 320 are separated from each other, it is also possible to set the number of antennas to three on each of the transmission side and the reception side. In this case, the components (4) and (7) are not needed.

Configuration Example of Antenna

Figure 19:
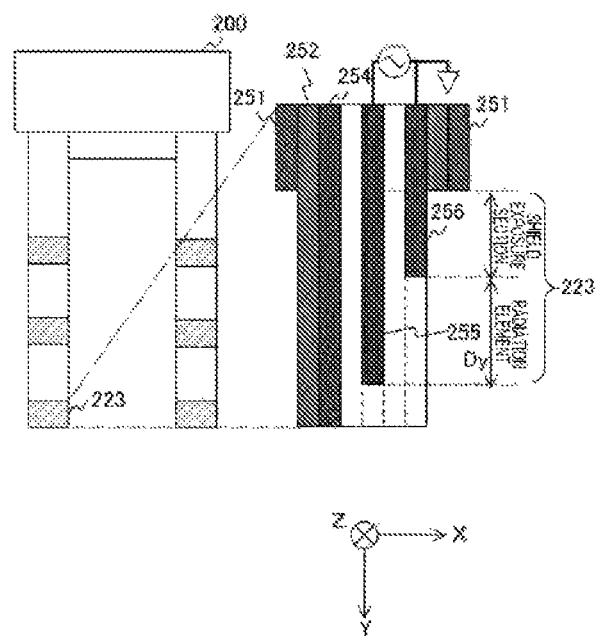
FIG. 19 is an example of a sectional view of a probe with a first structure when seen from the front according to the first embodiment of the present technology.

FIG. 19 is an example of a front view (the left drawing in FIG. 19) of the sensor device 200 and a sectional view (the right drawing in FIG. 19) of the transmission antenna 223 included in the intra-probe substrate 321 and the vicinity thereof when the sensor device 200 is seen from the front according to the first embodiment of the present technology. The drawing is an example of a sectional view of the transmission antenna 223 and the vicinity thereof when seen from the Z-axis direction. The part corresponding to each layer illustrated with a color in the right drawing in FIG. 19 illustrates a radio wave absorption material 251, a typical solder resist 252, a conductor shield layer 254, a conductor signal line 255, a conductor shield layer 256, a solder resist 253, a radio wave absorption material 251 in this order from the left side. The layer with no color applied thereto between the shield layer 254 and the signal line 255 and the layer with no color applied thereto between the shield layer 254 and the signal line 255 illustrate insulators. Note that the solder resists and the insulators transmit electromagnetic waves. Typically, the number of layers in the electronic substrate (wiring substrate) is called by the number of conductor layers included in the substrate. Therefore, the substrate in the right drawing in FIG. 19 is called a three-layer substrate. However, the radio wave absorption material 251, the shield layer 254, the signal line 255, the shield layer 256, and the radio wave absorption material 251 may be referred to as a first layer, a second layer, a third layer, a fourth layer, and a fifth layer, respectively, for convenience by focusing on transmission and shield of the electromagnetic waves and absorption of the electromagnetic waves in the specification.

The sectional views of the transmission antennas 221 and 222 are similar to that of the transmission antenna 223. If it is assumed that the direction from the transmission side to the reception side in the X-axis direction is defined as a right direction, the sectional views of the reception antennas 231 to 233 are horizontally symmetrical with the transmission antenna 223.

Figure 20:
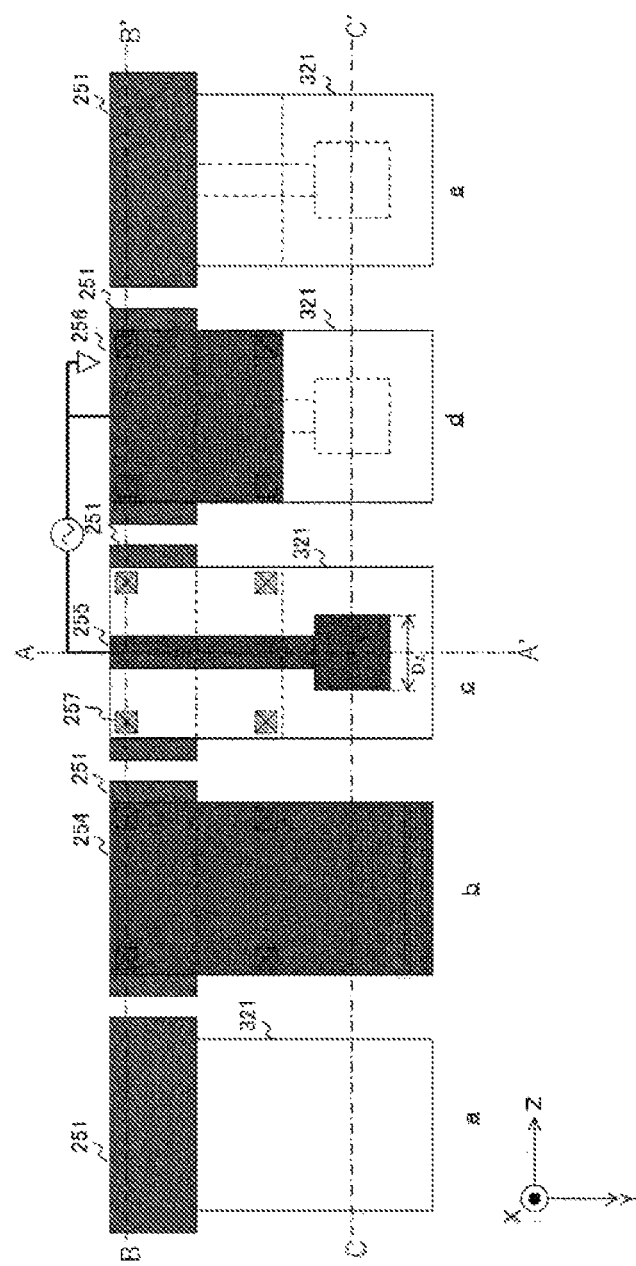
FIG. 20 is an example of a plan view of each layer in a probe casing with the first structure according to the first embodiment of the present technology.

FIG. 20 is an example of a plan view of each layer in the transmission antenna 223 and the vicinity thereof, the section of which is illustrated in the right diagram in FIG. 19. The drawing illustrates a plan view of each layer when the transmission antenna 223 and the vicinity thereof illustrated in the right diagram in FIG. 19 are seen from the X-axis direction of the sensor device 200. In the drawing, a is a plan view of the first layer: radio wave absorption material 251 in the right diagram in FIG. 18. In the drawing, b is a plan view of the second layer: shield layer 254. In the drawing, c is a plan view of the third layer: signal line 255. In the drawing, d is a plan view of the fourth layer: shield layer 256. In the drawing, e is a plan view of the fifth layer: radio wave absorption material 251. Also, the sectional view cut along the line A-A' corresponds to the sectional view in FIG. 18.

The second layer illustrated in FIG. 20b is a first wiring layer in which the shield layer 254 is arranged. The third layer illustrated in FIG. 20c is a second wiring layer in which a linear signal line 255 is arranged. The fourth layer illustrated in FIG. 20d is a third wiring layer in which the shield layer 256 is arranged. The width of the signal line 255 in the Z-axis direction is defined as Dz. The signs connecting squares and diagonals thereof with line segments illustrated in FIGS. 20b, 20c, and 20d represent vias (the reference sign 257 in FIG. 21a) connecting the shield layer 254 illustrated in FIG. 20b and the shield layer 256 illustrated in FIG. 20d. In FIGS. 20b and 20d, the signs represent the position of the via 257 connecting the shield layer 254 and the shield layer 256. In FIG. 20c, the sign represents a state where the via 257 passes through a side of the signal line 255. The shield layer 254 and the shield layer 256 have the same potential due to the via 257. The dotted line on the side closer to "A" illustrated in FIG. 20c out of the two dotted lines illustrated in FIG. 20c projects the outer line of the radio wave absorption material 251 illustrated in FIG. 20e to FIG. 20c for convenience. The dotted line on the side closer to "A'" in FIG. 20c projects the outer line of the shield layer 256 illustrated in FIG. 20d to FIG. 20c for convenience. The dotted lines illustrated in FIGS. 20d and 20e project the outer line of the signal line 255 illustrated in FIG. 20c to FIGS. 20d and 20e for convenience.

Figure 21:
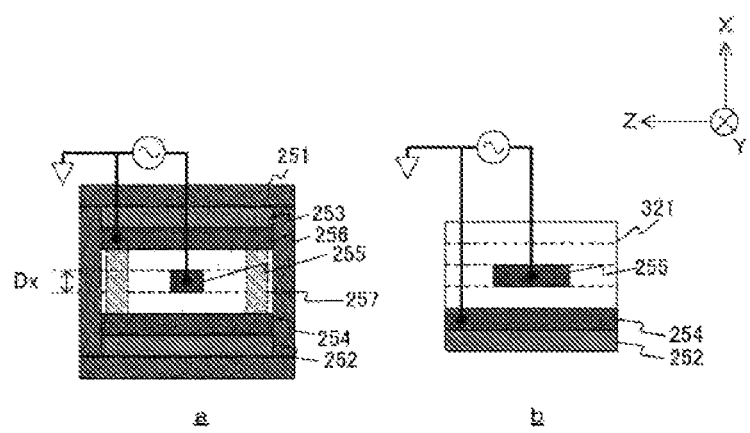
FIG. 21 is an example of a sectional view of the probe with the first structure when seen from the top according to the first embodiment of the present technology.

FIG. 21 is an example of a sectional view of the transmission antenna 223 and the vicinity thereof, the sectional views of which are illustrated in the right drawing in FIG. 19, when seen from the above. In FIG. 21, a is a sectional view cut along the line B-B' in FIG. 20. In FIG. 21, b is a sectional view cut along the line C-C' in FIG. 20.

The sectional view of the reception probe is similar to that of the transmission probe. The transmission probe is covered with a radio wave absorption material 251. The radio wave absorption section 341 and the like are formed by the radio wave absorption material 251.

Also, the solder resists 252 and 253 are formed between both surfaces of the intra-probe substrate 321 and the radio wave absorption material 251. The wiring layer in which the shield layer 254 is arranged, the wiring layer in which the signal line 255 is arranged, and the wiring layer in which the shield layer 256 is arranged are formed in the intra-probe substrate 321. The signal line 255 functions as a radiation element in the transmission antenna as will be described later. The thickness of the wiring layer in which the signal line 255 serving as a radiation element is arranged is defined as Dx. A ground potential is supplied to the shield layers 254 and 256, and the signal line 255 transmits and emits an AC signal (transmission signal) which is a transmission wave transmitted from the transmission antenna. Hereinafter, the signal line 255 that transmits and emits the transmission wave (transmission signal) may be referred to as a signal line layer. Also, a part of the signal line 255 related to radiation of the transmission wave, in particular, may be referred to as a radiation element. If this is applied to the reception antenna, the signal line 255 that receives and transmits a reception wave (reception signal) may be referred to as a signal line or a signal line layer, and the part of the conductor 255 regarding reception of the electromagnetic wave (the reception wave or the reception signal) received by the reception antenna may be referred to as a reception element.

As illustrated in FIGS. 19 to 21, the shield layer 254 and the shield layer 256 are disposed with insulators interposed between themselves on both the rear surface side (the side on which the shield layer 254 is disposed) and the front surface side (the side on which the shield layer 256 is disposed) of the electronic substrate (intra-probe substrate) where the signal line layer (signal line 255) is disposed, with respect to the signal line layers. With this structure, a transmission path (strip line) obtained by shielding both the rear surface side and the front surface side of the signal line layer with the shield layers 254 and 256 is formed. The transmission path (transmission path for transmission) is arranged independently for each antenna from all the transmission antennas included in the intra-probe substrate to the connector 323 in the intra-probe substrate 321. A similar transmission path (transmission path for reception) is arranged independently for each antenna from all the reception antennas included in the intra-probe substrate to the connector 324 in the intra-probe substrate 322.

The first layer: rear surface-side radio wave absorption material 251, the second layer: shield layer 254, the third layer: signal line layer (signal line 255), the fourth layer: shield layer 256, and the fifth layer: front surface-side radio wave absorption material 251 that are related to transmission and radiation (or reception) and shielding of the electromagnetic waves and absorption of the electromagnetic waves will be further described with reference to FIGS. 19 to 21. Note that the direction approaching the transmission source of transmission waves (a transmitter included in the measurement section) will be referred to as a transmission source direction while the direction away from the transmission source will be referred to as a distal end direction or simply tip direction in FIGS. 19 and 20 for convenience. In regard to the reception antenna, the direction approaching a reception destination (a receiver included in the measurement section) of a signal (reception waves) received by the reception antenna will be referred to as a reception destination direction, and the direction away from the reception destination will be referred to as a distal end direction or simply a tip direction for convenience. As illustrated as an example in the right diagram in FIG. 19 and FIG. 20, a part of the shield layer 254 is exposed from the rear surface-side electromagnetic wave absorption material 251 at a tip further from the distal end of the rear surface-side electromagnetic wave absorption material 251 on the rear surface side of the intra-probe substrate. In other words, a part of the shield layer 254 is exposed to a space (note that in the specification, a state where a member that shields or absorbs electromagnetic waves is not disposed outside a certain conductor may be referred to as "the conductor being exposed to a space" for convenience). Also, a part of the shield layer 256 is exposed from the front surface-side electromagnetic wave absorption material 251 at a tip further from the distal end of the front surface-side electromagnetic wave absorption material 251 on the front surface side of the intra-probe substrate. In other words, a part of the shield layer 256 is exposed to a space. Also, a part of the signal line layer (signal line 255) is exposed from the shield layer 256 at a tip further from the distal end of the shield layer 256. In other words, a part of the signal line layer is exposed to the space. The part of the signal line layer exposed from the shield layer 256 (the part exposed to the space) functions as a radiation element that transmits a transmission wave (in regard to the reception antenna, a part of the signal line layer exposed from the shield layer 256 (the part exposed to the space) functions as a reception element that receives electromagnetic waves (the transmission wave propagated from the transmission antenna through the medium, in other words, the reception wave)). In regard to the transmission antenna 223, the radiation element 332 corresponds thereto (in regard to the reception antenna 233, the reception element 335 corresponds thereto). The transmission wave is most significantly emitted in the direction vertical to the surface in which the radiation element extends, which is a surface on the side exposed from the shield layer. The direction in which the transmission wave is most significantly emitted will be referred to as a "main radiation direction" or simply "a direction in which the electromagnetic waves are emitted". Also, a part of the shield layer which is a part exposed from the electromagnetic wave absorption body 251 (in other words, exposed to the space) and disposed to be closer to the electromagnetic wave radiation direction than the radiation element will be referred to as a "shield exposure section" or simply a "shield section". The shield exposure section and the radiation element function as the transmission antenna 223. Here, the length of the radiation element in the Y-axis direction is defined as Dy. The part disposed in a region at the length that is equal to or less than the length Dy of the radiation element in the transmission source direction (the negative direction of the Y axis in FIGS. 19 and 20) from the line end of the shield exposure section, in particular, in the shield exposure section exposed to the space particularly effectively functions as a part of the transmission antenna 223. Thus, in the specification, a part including (1) the radiation element (the signal line layer exposed from the shield layer and exposed to the space) and (2) the structure disposed in the region at the length that is equal to or less than the length of the radiation element in the transmission source direction (the negative direction of the Y axis in FIGS. 19 and 20) from the distal end of the shield exposure section in the shield exposure section exposed from the electromagnetic wave absorption material and exposed to the space may be referred to as a "transmission antenna" for convenience. The same applies to the reception antenna. In the specification, a part including (1) the reception element (the signal line layer exposed from the shield layer and exposed to the space) and (2) the structure disposed in the region at the length that is equal to or less than the length of the reception element in the reception destination direction (the negative direction of the Y axis in FIGS. 18 and 19) from the distal end of the shield exposure section in the shield exposure section exposed from the electromagnetic wave absorption material and exposed to the space may be referred to as a "reception antenna".

As illustrated as an example in FIGS. 19 to 21, the plane-shaped transmission antenna 223 includes the shield section and the radiation element. The transmission antenna 223 is formed using an electronic substrate (such as the intra-probe substrate 321) including a plurality of wiring layers. The radiation element has a larger size Dz in a second direction (the width direction of the electronic substrate, the Z-axis direction in the drawing) that is orthogonal to a first direction than the size Dx of the size (the thickness direction of the electronic substrate, the X-axis direction in the drawing) in the first direction. Also, the size Dy in a third direction (the length direction in which the electronic substrate extends, the Y-axis direction in the drawing) that is orthogonal to both the first direction and the second direction is larger than Dx. In the specification, in a case where both Dz and Dy are larger than Dx in regard to the radiation element included in the transmission antenna, the transmission antenna is defined as a "plane-shaped antenna" and a "pane-shaped transmission antenna". Also, a part of the radiation element, which is a part extending in the plane defined by the second direction and the third direction, is defined as a "plane of the radiation element". Note that in regard to the transmission antenna, Dy may be preferably larger than both Dx and Dz. The same applies to the reception antenna. The structure of the reception antenna will be described with reference to FIGS. 19 to 21. In the reception element included in the reception antenna, the size Dz in the second direction (the width direction of the electronic substrate, the Z-axis direction in the drawing) that is orthogonal to the first direction is larger than the size Dx in the first direction (the thickness direction of the electronic substrate, the X-axis direction in the drawing). Also, the size Dy in the third direction (the length direction in which the electronic substrate extends, the Y-axis direction in the drawing) that is orthogonal to both the first direction and the second direction than Dx. In the specification, in a case where both Dz and Dy are larger than Dx in regard to the reception element included in the reception antenna, the reception antenna is defined as a "plane-shaped antenna" and a "plane-shaped reception antenna". Also, a part of the reception element, which is a part extending in a plane defined by the second direction and the third direction is defined as "a plane of the reception element". Note that in regard to the reception antenna, Dy may be preferably larger than both Dx and Dz.

As illustrated in FIGS. 20 and 21, the periphery (the periphery of the section that is orthogonal to the extending direction of the transmission path) of the transmission path including the signal line 255 to which a signal is given and the shield layer 256 to which the ground potential is given is covered with, surrounded, or wrapped by the radio wave absorption material 251. The radio wave absorption material 251 extends in the extending direction (Y-axis direction) of the transmission path, and the antennas (the transmission antenna and the reception antenna) are connected to the tip of the outer edge of the transmission path covered with the radio wave absorption material 251.

As illustrated in FIG. 19, the antenna is formed in the electronic substrate (such as the intra-probe substrate 321) including at least three laminated wiring layers (the first, the second, and the third wiring layers in order from the rear surface side to the front surface side). The antenna includes the signal line 255 to which a signal is given and shield layers 254 and 256 to which a ground potential is given. The signal line 255 in the antenna to which a signal is given is formed in the second wiring layer. The shield layer 254 is formed in the first wiring layer, and the shield layer 256 is formed in the third wiring layer.

As illustrated in FIG. 20, if the shape of the signal line 255 formed in the second wiring layer is projected to the third wiring layer, at least a part of the projection of the conductor 255 extends to a region where the shield layer 256 is not disposed. If the shape of the signal line 255 is projected to the first wiring layer, the shield layer 254 of the first wiring layer is disposed at the position where the projection of the signal line 255 is disposed.

With such a shape, electromagnetic waves are emitted in the front surface direction (the paper surface right direction, the positive direction of the X-axis) from the plane-shaped transmission antenna 223 according to the transmission antenna 223 illustrated in FIG. 19. In this manner, the antenna from which the electromagnetic waves are emitted from one side of the plane of the plane-shaped radiation element will be referred to as an "antenna of one-side reception", and this will be referred to as a "first structure" of the antenna in the specification. In the case of the reception antenna, the antenna which receives the electromagnetic waves from one side of the plane of the plane-shaped reception element will be referred to as an "antenna of one-side reception", and such a reception antenna corresponds to the first structure.

Figure 22:
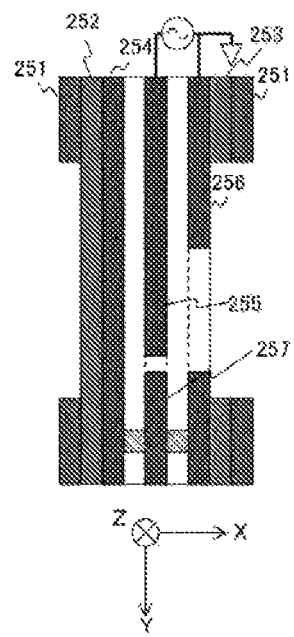
FIG. 22 is another example of a sectional view of the probe with the first structure when seen from the front according to the first embodiment of the present technology.

FIG. 22 is a sectional view representing another example of the first structure when the sensor device 200 is seen from the front similarly to FIG. 4b according to the first embodiment of the present technology. The drawing is an example of a sectional view of the transmission antenna 223 and the vicinity thereof when seen from the Z-axis direction.

Figure 23:
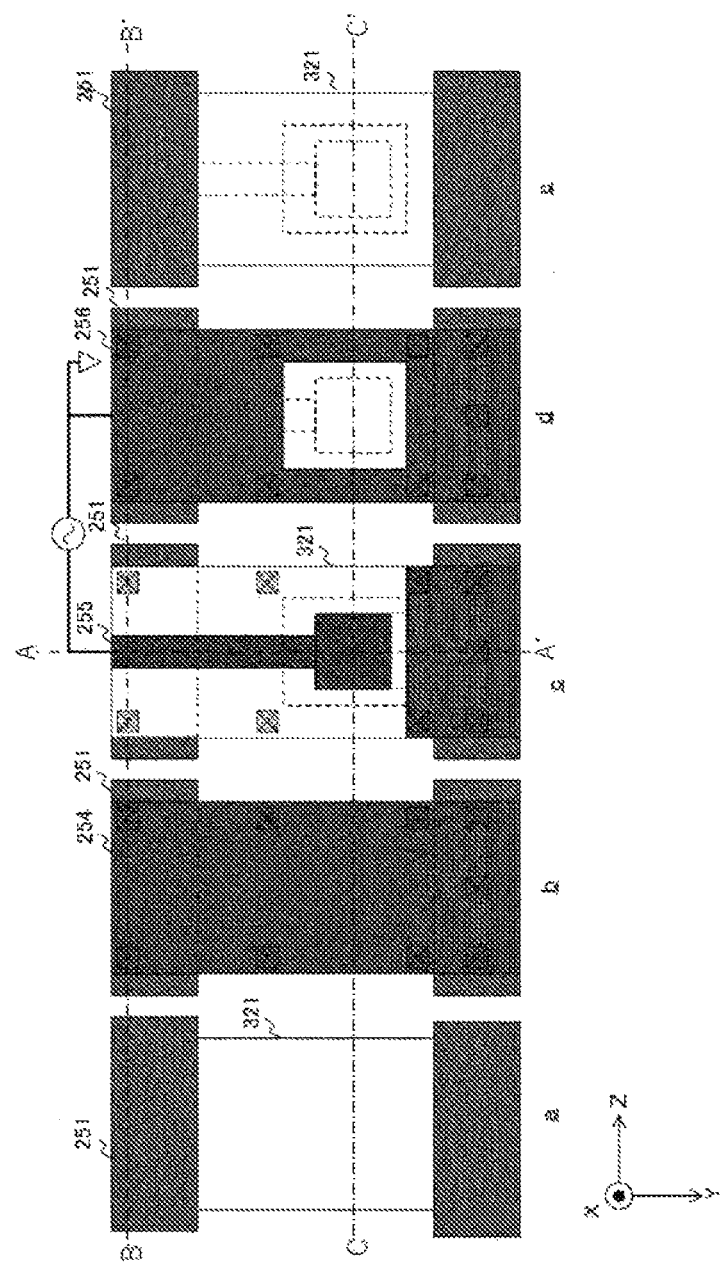
FIG. 23 is another example of a plan view of each layer in the probe casing with the first structure according to the first embodiment of the present technology.

FIG. 23 is a plan view of each layer according to another example of the first structure, the section of which is illustrated in FIG. 22.

Figure 24:
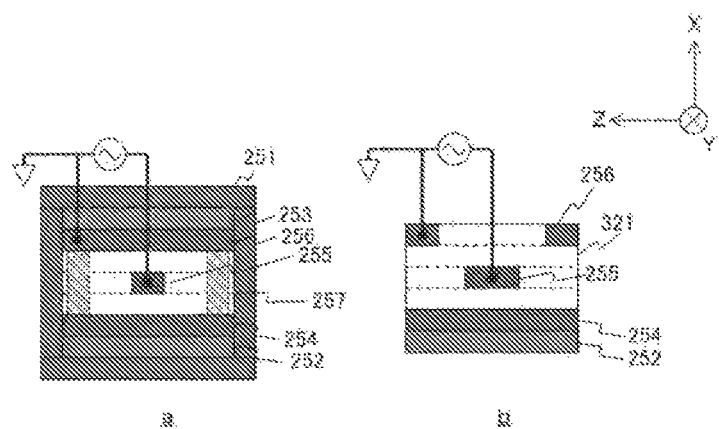
FIG. 24 is another example of a sectional view of the probe with the first structure when seen from the top according to the first embodiment of the present technology.

FIG. 24 is a sectional view of another example of the first structure, the section of which is illustrated in FIG. 22, when seen from the above.

In another example of the first structure illustrated as an example in FIGS. 22 to 24, the point that (1) the first wiring layer (shield layer 254) to which the ground potential is given extends on the further side than the radiation element (signal line 255) is the same as that in the first structure, while the points that (2) a part of the second wiring layer that is different from the radiation element and the signal line is used to form the conductor 257, to which the ground potential is given, in the region on the further side than the radiation element and (3) the third wiring layer (shield layer 256) passes through a side of projection of the radiation element to the third wiring layer and extends on the further side than the radiation element while avoiding the projection (the dotted line in FIG. 23d) to avoid superimposition on the radiation element are different from those in the first structure. The shape leads to an effect that it is possible to easily arrange the shield layer 256, at least to which the ground potential is given, in a case where the transmission antenna that is different from the transmission antenna 223 illustrated in FIGS. 22 to 24 is disposed at the tip of the transmission antenna 223. The same applies to the reception antenna. The points that (1) the first wiring layer (shield layer 254) to which the ground potential is given extends on the further side than the reception element (signal line 255) is the same as that in the first structure, while the points that (2) a part of the second wiring layer that is different from the reception element and the signal line is used to form the conductor 257 to which the ground potential is given in the region on the further side than the reception element and (3) the third wiring layer (shield layer 256) passes through a side of projection of the reception element to the third wiring layer (the dotted line in FIG. 23d) and extend on the further side than the reception element while avoiding the projection are different from those in the first structure. The shape leads to an effect that it is possible to easily arrange the shield layer 256, at least to which the ground potential is given, in a case where the reception antenna that is different from the reception antenna 233 illustrated in FIGS. 22 to 24 is disposed at the tip of the reception antenna 233.

FIG. 25 is an example of a sectional view of the second structure regarding the transmission antenna 223 included in the intra-probe substrate 321 and the vicinity thereof when the sensor device 200 is seen from the front similarly to FIG. 4b according to the first embodiment of the present technology.

FIG. 24 is an example of a plan view of each layer of the second structure, the section of which is illustrated in FIG. 25.

Figure 27:
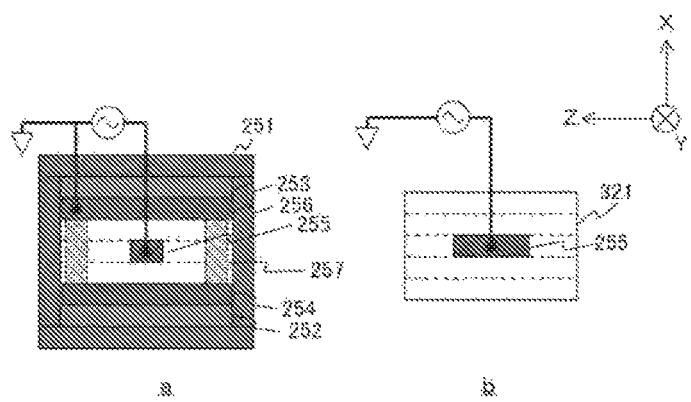
FIG. 27 is an example of a sectional view of the probe with the second structure when seen from the top according to the first embodiment of the present technology.

FIG. 27 is an example of a sectional view of the second structure, the section of which is illustrated in FIG. 25, when seen from the above.

Figure 26:
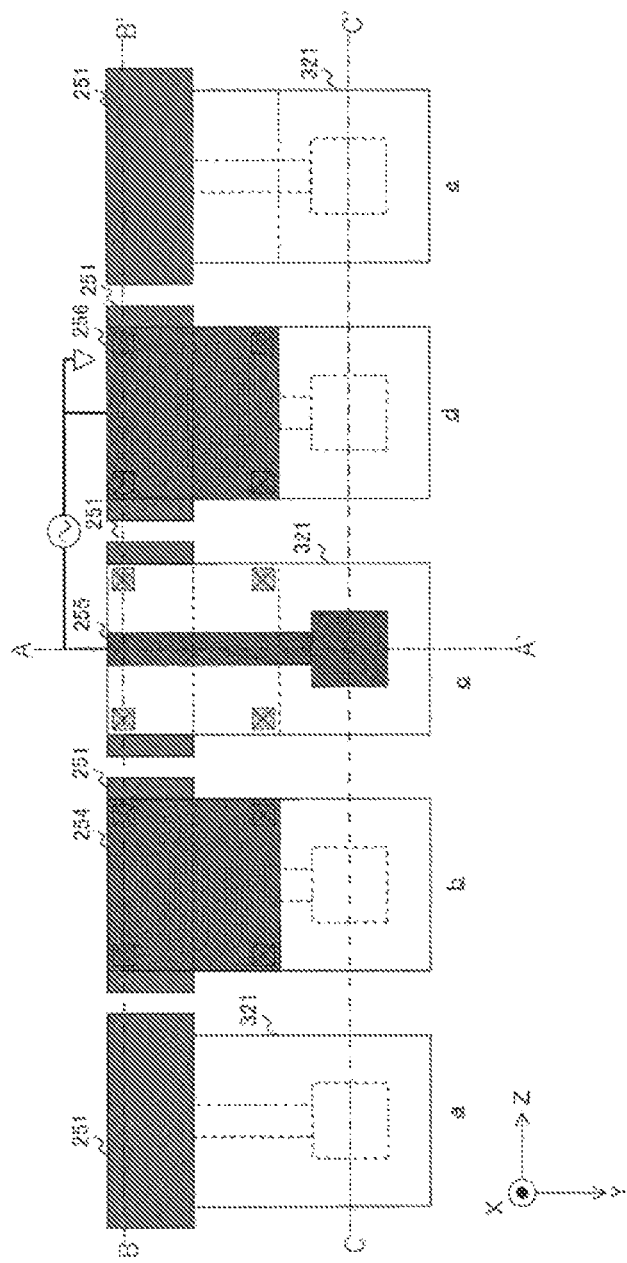
FIG. 26 is an example of a plan view of each layer in a probe casing with the second structure according to the first embodiment of the present technology.

As illustrated in FIGS. 25 and 26, if the shape of the signal line 255, which is formed in the second wiring layer, to which a signal is given, is projected to the first wiring layer disposed on the rear surface side (the paper surface left direction, the negative direction of the X axis) in the second structure, at least a part of the projection of the signal line 255 extends to a region where the conductor 254 is not disposed similarly to the third wiring layer disposed on the front surface side (the paper surface right direction, the positive direction of the X axis). With the shape, the transmission antenna 223 illustrated in FIG. 25 emits electromagnetic waves both in the front surface direction (the paper surface right direction, the positive direction of the X axis) and in the rear surface direction (the paper surface left direction, the negative direction of the X axis) from the plane-shaped transmission antenna 223. The antenna adapted such that the electromagnetic waves are emitted from both sides of the plane of the plane-shaped radiation element in this manner will be referred to as "double-side radiation antenna", and this will be defined as a "second structure" of the antenna in the specification. The transmission antenna with this structure leads to an effect that it is possible to more efficiently emit electromagnetic waves (transmission waves) as compared with the transmission antenna with the first structure. In the case of the reception antenna, the antenna adapted such that electromagnetic waves are received from both sides of the plane of the plane-shaped reception element will be referred to as a "double-side reception antenna", and such a reception antenna corresponds to the second structure. The reception antenna with this configuration leads to an effect that it is possible to more efficiently receive the electromagnetic waves (the transmission waves propagated and coming from the transmission antenna through the medium, in other words, the reception waves) as compared with the reception antenna with the first structure.

Figure 28:
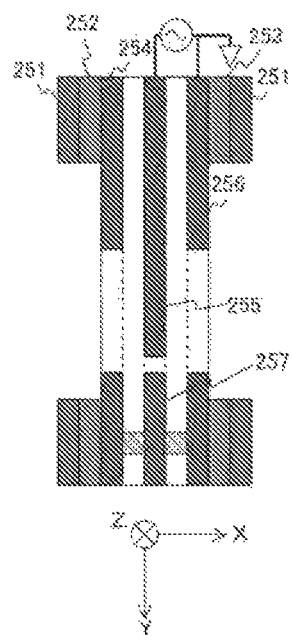
FIG. 28 is another example of a sectional view of the probe with the second structure when seen from the front according to the first embodiment of the present technology.

FIG. 28 is a sectional view representing another example of the second structure when the sensor device 200 is seen from the front similarly to FIG. 4b according to the first embodiment of the present technology. The drawing is an example of a sectional view of the transmission antenna 223 and the vicinity thereof when seen from the Z-axis direction.

Figure 29:
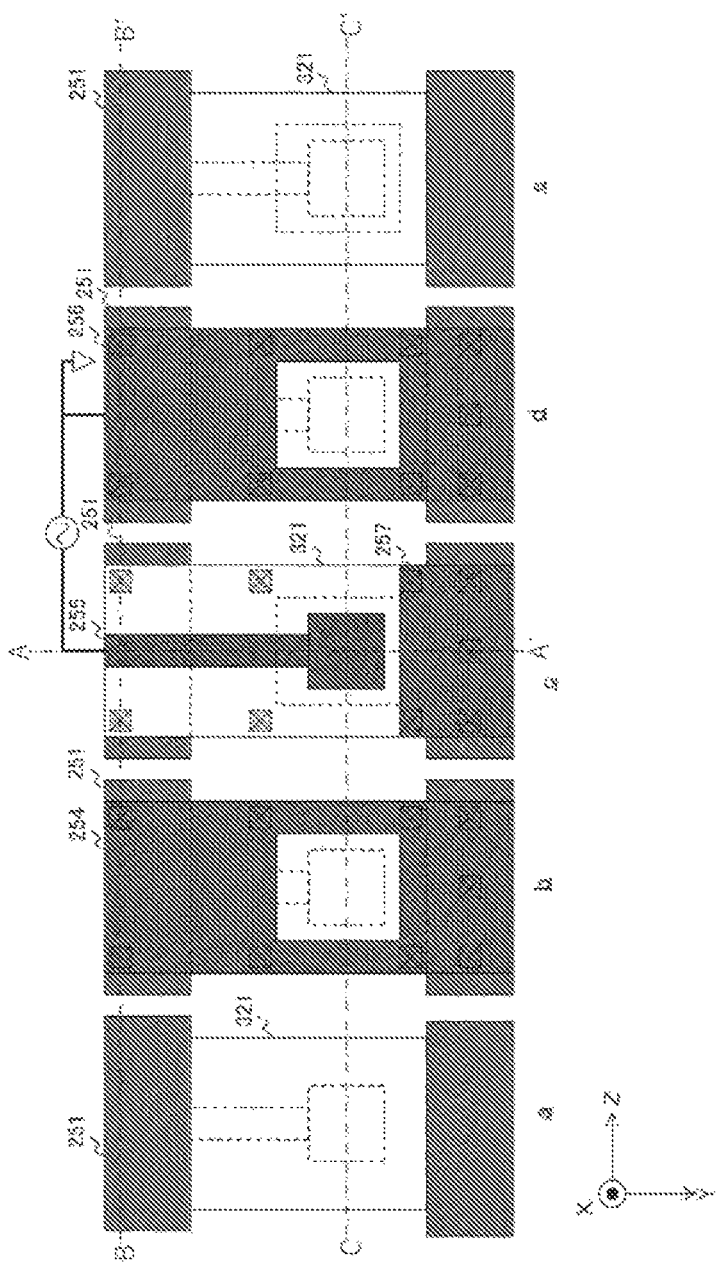
FIG. 29 is another example of a plan view of each layer in the probe casing with the second structure according to the first embodiment of the present technology.

FIG. 29 is a plan view of each layer in another example of the second structure, the section of which is illustrated in FIG. 28.

FIG. 230 is a sectional view of another example of the second configuration, the section of which is illustrated in FIG. 28, when seen from the above.

Figure 30:
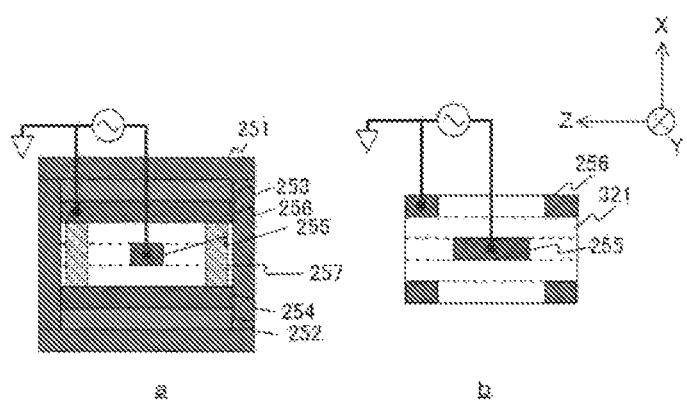
FIG. 30 is another example of a sectional view of the probe with the second structure when seen from the top according to the first embodiment of the present technology.

In another example of the second structure as illustrated as an example in FIGS. 28 to 30, the points that (1) the first wiring layer (shield layer 254) passes through a side of projection of the radiation element to the first wiring layer (the dotted line in FIG. 29b) extends on the further side than the radiation element while avoiding the projection to prevent superimposition on the radiation element, (2) a part of the second wiring layer that is different from the radiation element and the signal line is used to form the conductor 257 to which the ground potential is given in the region on the further side than the radiation element, and (3) the third wiring layer (the shield layer 256) passes through a side of projection of the radiation element to the third wiring layer (the dotted line in FIG. 29d) extends on the further side than the radiation element while avoiding the projection to prevent superimposition on the radiation element are different from those in the second structure. The shape leads to an effect that it is possible to easily arrange the shield layers 254 and 256, at least to which the ground potential is given, in the case where the transmission antenna that is different from the transmission antenna 223 illustrated in FIGS. 28 to 30 is disposed at the tip of the transmission antenna 223. The same applies to the reception antenna. The points that (1) the first wiring layer (shield layer 254) passes through a side of projection of the reception element to the first wiring layer (the dotted line in FIG. 29b) and extends on the further side than the reception element while avoiding the projection to prevent superimposition on the reception element, (2) a part of the second wiring layer that is different from the reception element and the signal line is used to form the conductor 257 to which the ground potential is given on the further side than the reception element, and (3) the third wiring layer (shield layer 256) passes through a side of projection of the reception element to the third wiring layer (the dotted line in FIG. 29d) and extends on the further side than the reception element while avoiding the projection to prevent superimposition on the reception element are different from those in the second structure. The shape leads to an effect that it is possible to easily arrange the shield layers 254 and 256, at least to which the ground potential is given, in a case where the reception antenna that is different from the reception antenna 223 illustrated in FIGS. 28 to 30 is disposed at the tip of the reception antenna 223.

FIG. 31 is an example of a sectional view of the third structure regarding the transmission antenna 223 included in the intra-probe substrate 321 and the vicinity thereof when the sensor device 200 is seen from the front similarly to FIG. 4b according to the first embodiment of the present technology.

Figure 32:
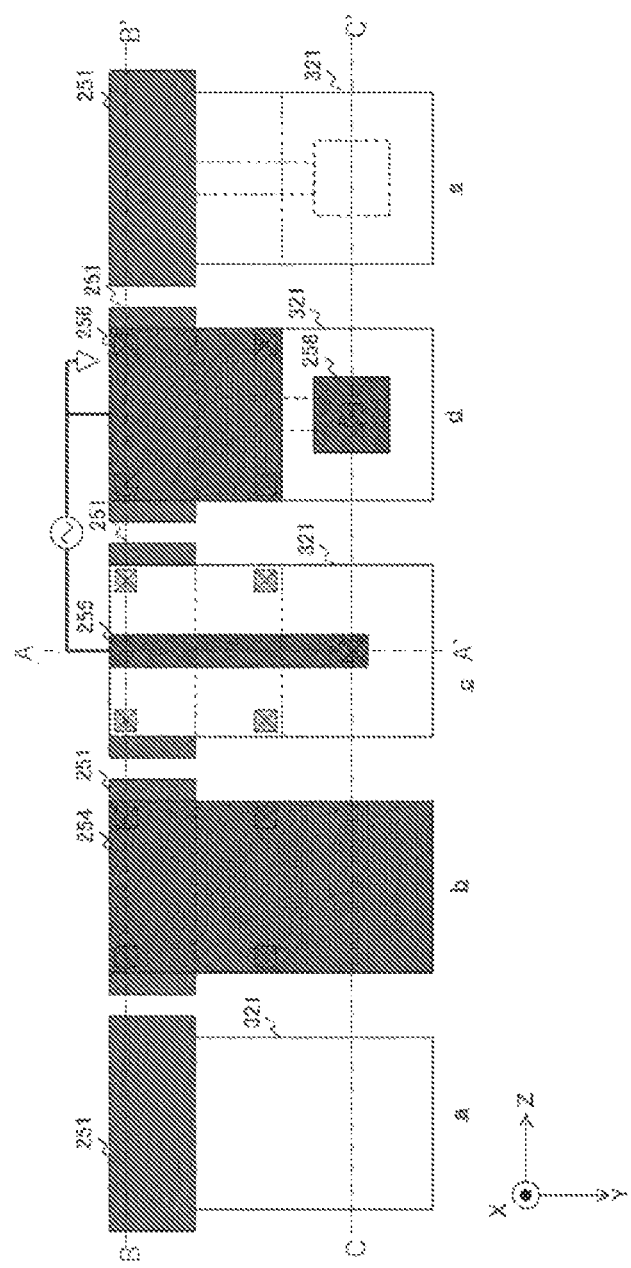
FIG. 32 is an example of a plan view of each layer in a probe casing with the third structure according to the first embodiment of the present technology.

FIG. 32 is an example of a plan view of each layer of the third structure, the section of which is illustrated in FIG. 31.

Figure 33:
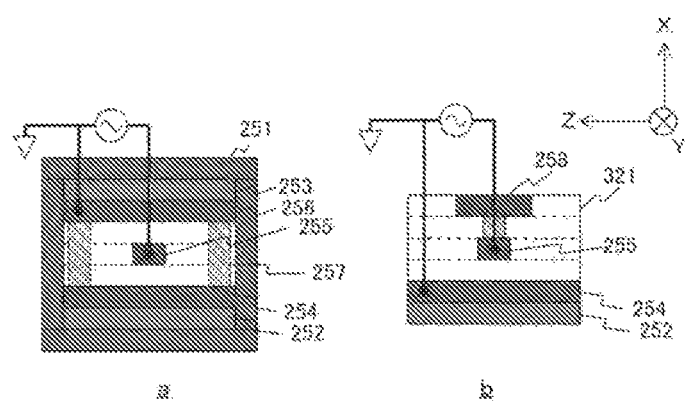
FIG. 33 is an example of a sectional view of the probe with the third structure when seen from the top according to the first embodiment of the present technology.

FIG. 33 is an example of a sectional view of the third structure, the section of which is illustrated in FIG. 31, when seen from the above.

As illustrated in FIGS. 31 and 32, in the third structure, (1) a part of the third wiring layer that is a wiring layer on the frontmost surface side (the rightmost side on the paper plane in FIG. 30, the most positive direction of X axis) is used to form the shield layer 256 in the third wiring layer. (2) Furthermore, a part of the third wiring layer that is different from the shield layer 256 is used to form the radiation element (conductor 258) in the region on the further side than the shield layer 256. Also, the radiation element and the signal line 255 are electrically connected by providing a via for connection between the radiation element formed using the third wiring layer and the signal line 255 formed using the second wiring layer. In FIG. 31, the colored part (the hatched part) between the radiation element and the signal line 255 represents the via. In FIG. 32, the signs connecting the squares and the diagonals thereof with the line segments disposed in the radiation element in FIG. 32d and the same sign as above disposed in the signal line 255 in FIG. 32c represent the position of the via. The point that (3) the first wiring layer (the shield layer 254), which is the wiring layer on the rearmost surface side (the rightmost side on the paper plane in FIG. 31, the most negative direction of the X axis), to which the ground potential s given, extends on the further side than the radiation element is the same as that in the first structure. With this shape, the wiring layer on the frontmost surface (the wiring layer on the surface layer) on one side of the intra-probe substrate 321 forming the transmission antenna is used to form the radiation element, and this serves as a one-side radiation antenna exposed to the space in the third structure. The transmission antenna with this structure leads to an effect that it is possible to more efficiently emit electromagnetic waves (transmission waves) as compared with the transmission antenna with the first structure. In the case of the reception antenna, the wiring layer on the frontmost surface (the wiring layer on the surface layer) on one side of the intra-probe substrate 322 forming the reception antenna is used to form the reception element, and the one-side reception antenna obtained by exposing this to the space corresponds to the third structure. The reception antenna with this structure leads to an effect that it is possible to more efficiently receive the electromagnetic waves (the transmission waves propagated and coming from the transmission antenna through the medium, in other words, the reception waves) as compared with the reception antenna with the first structure.

Figure 34:
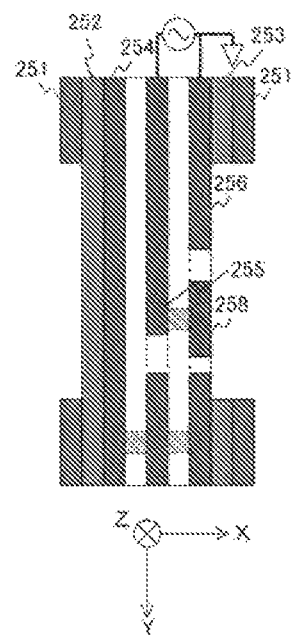
FIG. 34 is another example of a sectional view of the probe with the third structure when seen from the front according to the first embodiment of the present technology.

FIG. 34 is a sectional view representing another example of the third structure when the sensor device 200 is seen from the front similarly to FIG. 4b according to the first embodiment of the present technology. The drawing is an example of a sectional view of the transmission antenna 223 and the vicinity thereof when seen from the Z-axis direction.

Figure 35:
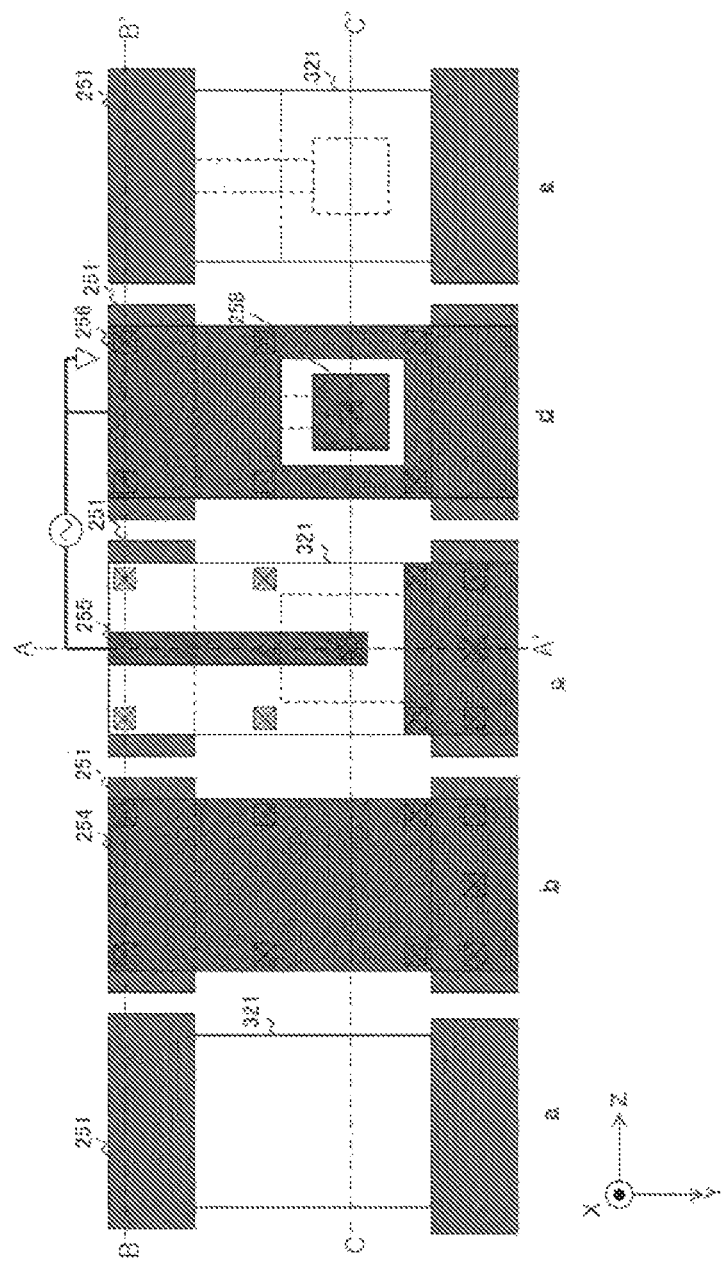
FIG. 35 is another example of a plan view of each layer in the probe casing with the third structure according to the first embodiment of the present technology.

FIG. 35 is an example of a plan view of each layer according to another example of the third structure, the section of which is illustrated in FIG. 34.

Figure 36:
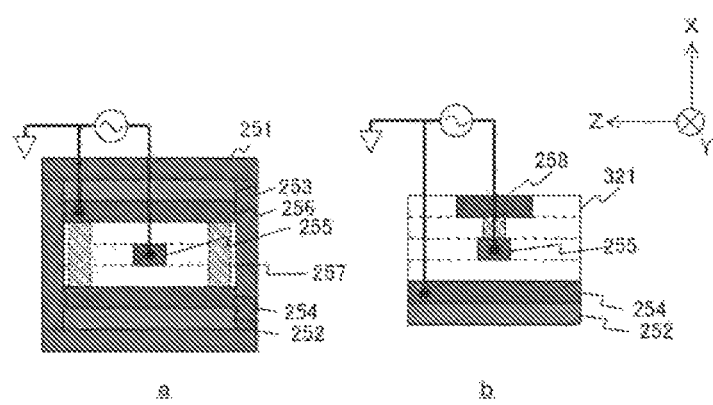
FIG. 36 is another example of a sectional view of the probe with the third structure when seen from the top according to the first embodiment of the present technology.

FIG. 36 is an example of a sectional view of another example of the third structure, the section of which is illustrated in FIG. 34, when seen from the above.

In another example of the third structure illustrated as an example in FIGS. 34 to 36, the point that (1) the first wiring layer (shield layer 254) to which the ground potential is given extends on the further side than the radiation element is the same as that in the third structure, while the points (2) a part of the second wiring layer that is different from the signal line is used to form the conductor 257 to which the ground potential is given in the region on the further side than the signal line, and (3) the shield layer 256 passes through a side of the radiation element and extends on the further side than the radiation element out of the shield layer 256 and the radiation element formed using the third wiring layer are different from those in the third structure. The shape leads to an effect that it is possible to easily arrange the conductor 256, at least to which the ground potential is given, in a case where the transmission antenna that is different from the transmission antenna 223 illustrated in FIGS. 34 to 36 is disposed at the tip of the transmission antenna 223. The same applies to the reception antenna. The point that (1) the first wiring layer (shield layer 254) to which the ground potential is given extends on the further side than the radiation element is the same as that in the third structure, while the points that (2) a part of the second wiring layer that is different from the signal line is used to form the conductor 257 to which the ground potential is given is formed in the region on the further side than the signal line and (3) the shield layer 256 passes through a side of the reception element and extends on the further side than the radiation element out of the shield layer 256 and the reception element (conductor 258) formed using the third wiring layer are different from those in the third structure. The shape leads to an effect that it is possible to easily arrange the shield layer 256, at least to which the ground potential is given, in a case where the reception antenna that is different from the reception antenna 223 illustrated in FIGS. 34 to 36 is disposed at the tip of the reception antenna 223.

FIG. 37 is an example of a sectional view of the fourth structure regarding the transmission antenna 223 included in the intra-probe substrate 321 and the vicinity thereof when the sensor device 200 according to the first embodiment of the present technology is seen from the front similarly to FIG. 4b.

Figure 38:
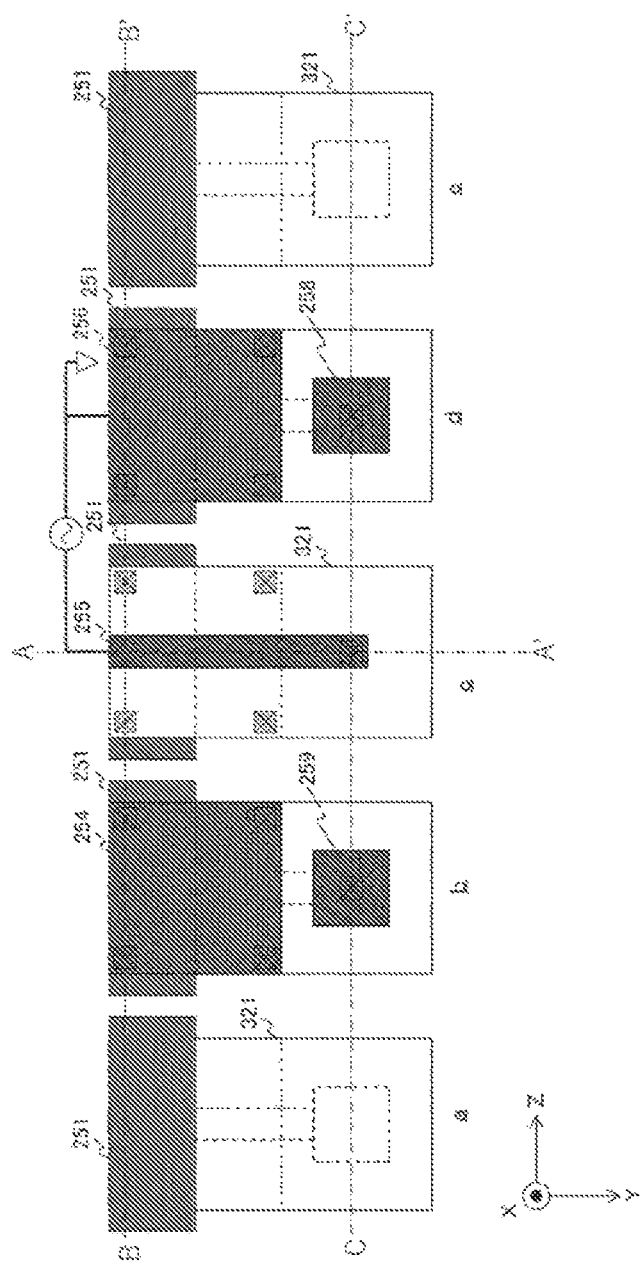
FIG. 38 is an example of a plan view of each layer in a probe casing with the fourth structure according to the first embodiment of the present technology.

FIG. 38 is an example of a plan view of each layer of the fourth structure, the section of which is illustrated in FIG. 37.

Figure 39:
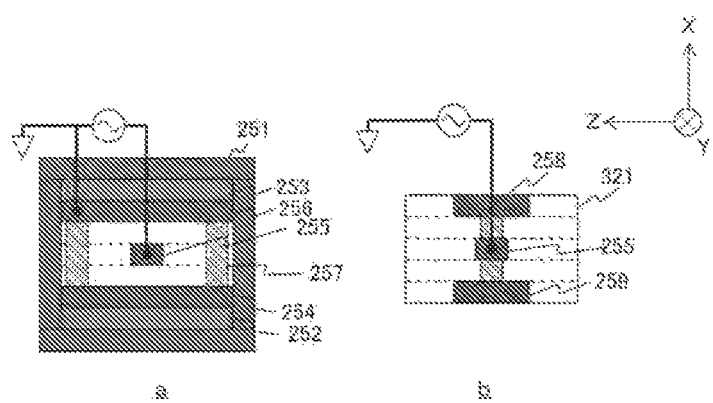
FIG. 39 is an example of a sectional view of the probe with the fourth structure when seen from the top according to the first embodiment of the present technology.

FIG. 39 is an example of a sectional view of the fourth structure, the section of which is illustrated in FIG. 37, when seen from the above.

In the fourth structure, as illustrated in FIGS. 37 and 38, in the fourth structure, (1) a part of the third wiring layer that is used to form the shield layer 256 in the third wiring layer that is the wiring layer on the frontmost surface side (the rightmost side on the paper surface in FIG. 37, the most positive direction of the X axis) similarly to the third structure. (2) Furthermore, a part of the third wiring layer that is different from the shield layer 256 is used to form the radiation element in the region on the further side than the shield layer 256 similarly to the third structure. Also, the radiation element and the signal line 255 are electrically connected by providing a via for connection between the radiation element formed using the third wiring layer and the signal line 255 formed using the second wiring layer. (3) In the same manner as in (1) above, a part of the first wiring layer is used to form the shield layer 254 in the first wiring layer that is a wiring layer on the rearmost side (the leftmost side on the paper surface in FIG. 37, the most negative direction of the X axis). (4) Furthermore, in the same manner as in (2) above, a part of the first wiring layer that is different from the shield layer 254 is used to form the radiation element (conductor 259) in the region on the further side than the shield layer 254. Additionally, the radiation element and the signal line 255 are electrically connected by providing a via for connection between the radiation element formed using the first wiring layer and the signal line 255 formed using the second wiring layer. With this shape, the radiation element is formed using the frontmost wiring layers (the wiring layers on the surface layer) on both sides of the intra-probe substrate 321 forming the transmission antenna, and this serves as the double-side radiation antenna exposed to the space in the fourth structure. The transmission antenna with this structure leads to an effect that it is possible to more efficiently emit electromagnetic waves (transmission waves) as compared with any of the transmission antennas with the first to third structures. In the case of the reception antenna, the double-side reception antenna that has the reception element formed using the wiring layers on the frontmost surfaces (the wiring layers on the surface layer) on both sides of the intra-probe substrate 322 forming the reception antenna and is exposed to the space corresponds to the fourth structure. The reception antenna with this structure leads to an effect that it is possible to more efficiently receive the electromagnetic waves (the transmission waves propagated and coming from the transmission antenna through the medium, in other words, the reception waves) as compared with the reception antenna with the first structure.

Figure 40:
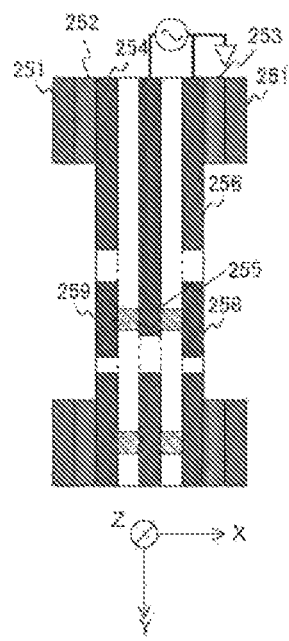
FIG. 40 is another example of a sectional view of the probe with the fourth structure when seen from the front according to the first embodiment of the present technology.

FIG. 40 is a sectional view representing another example of the fourth structure when the sensor device 200 is seen from the front similarly to FIG. 4b according to the first embodiment of the present technology. The drawing is an example of a sectional view of the transmission antenna 223 and the vicinity thereof when seen from the Z-axis direction.

Figure 41:
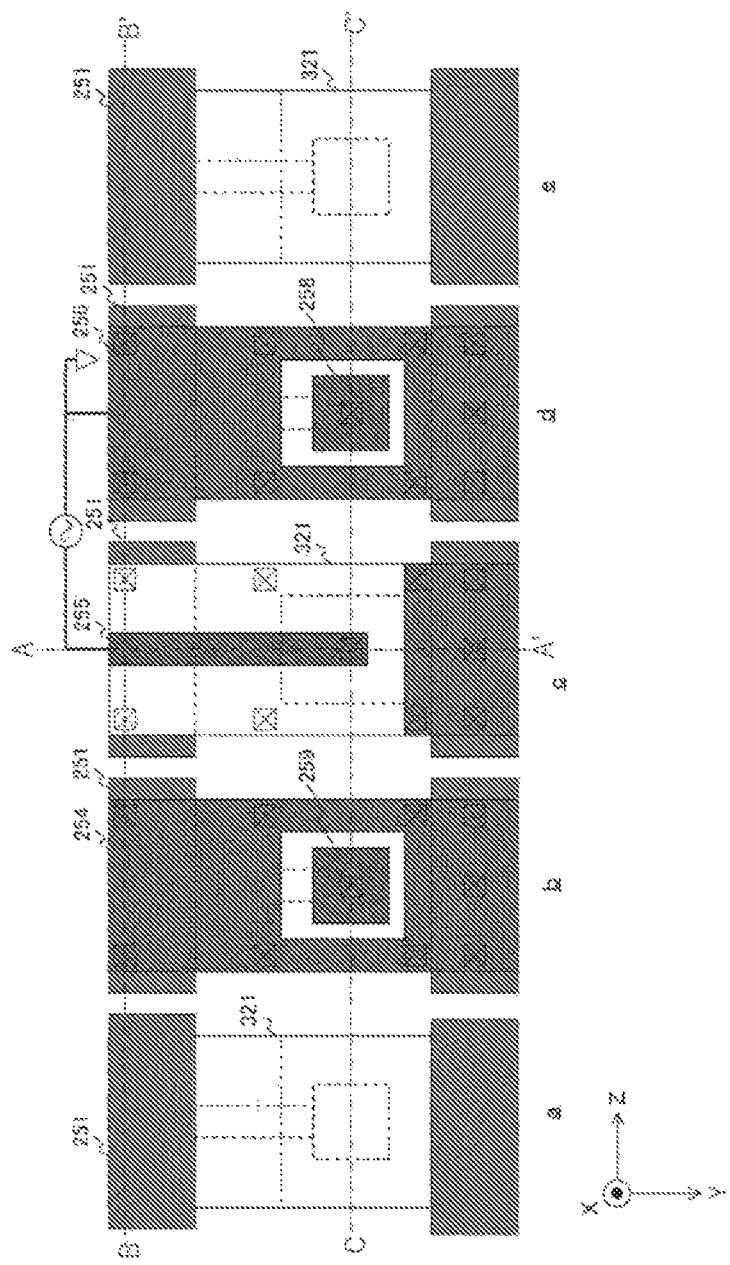
FIG. 41 is another example of a plan view of each layer in the probe casing with the fourth structure according to the first embodiment of the present technology.
Figure 42:
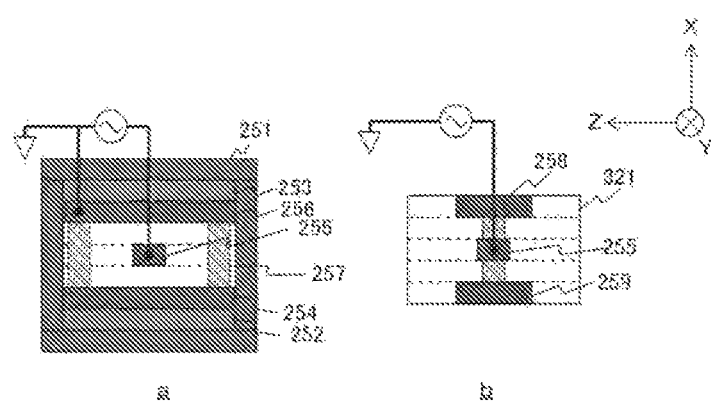
FIG. 42 is another example of a sectional view of the probe with the fourth structure when seen from the top according to the first embodiment of the present technology.

FIG. 41 is an example of a plan view of each layer according to another example of the fourth structure, the section of which is illustrated in FIG. 40. FIG. 42 is an example of a sectional view of another example of the fourth structure, the section of which is illustrated in FIG. 40, when seen from the above.

In another example of the fourth structure illustrated as an example in FIGS. 40 to 42, the points that (1) the shield layer 254 passes through a side of the radiation element and extends on the further side than the radiation element out of the shield layer 254 and the radiation element formed using the first wiring layer, (2) a part of the second wiring layer that is different from the signal line is used to form the conductor 257 to which a ground potential is given in the region on the further side than the signal line, and (3) the shield layer 256 passes through a side of the radiation element and extends on the further side than the radiation element out of the shield layer 256 and the radiation element formed using the third wiring layer are different from those in the fourth structure. The shape leads to an effect that it is possible to easily arrange the shield layers 254 and 256, at least to which the ground potential is given, in a case where the transmission antenna that is different from the transmission antenna 223 illustrated in FIGS. 40 to 42 is disposed at the tip of the transmission antenna 223. The same applies to the reception antenna. The points that (1) the shield layer 254 passes through a side of the reception element and extends on a further side than the reception element out of the shield layer 254 and the reception element formed using the first wiring layer, (2) a part of the second wiring layer that is different from the signal line is used to form the conductor 257, to which the ground potential is given, in the region on the further side than the signal line, and (3) the shield layer 256 passes through a side of the reception element and extends on the further side than the radiation element out of the shield layer 256 and the reception element formed using the third wiring layer are different from those in the fourth structure. The shape leads to an effect that it is possible to easily arrange the shield layers 254 and 256, at least to which the ground potential is given, in a case where the reception antenna that is different from the reception antenna 223 illustrated in FIGS. 40 to 42 is disposed at the tip of the reception antenna 223.

Figure 43:
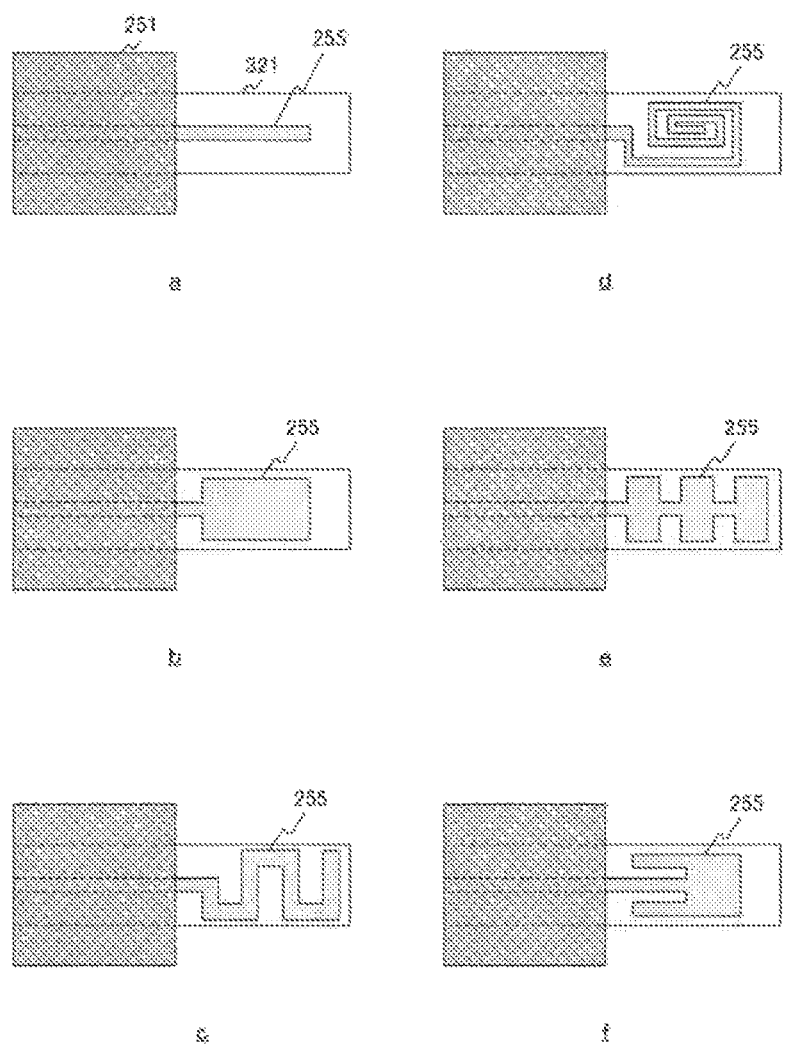
FIG. 43 is an example illustrating an example of the shape of a transmission antenna applied to the first structure according to the first embodiment of the present technology.

FIG. 43 is a diagram illustrating an example of the shape of the transmission antenna 223 applied to the first structure according to the first embodiment of the present technology. In the drawing, the distal end of the electromagnetic wave absorption material 251 and the distal end of the shield layer are at the same positions, and the signal line 255 (the radiation element illustrated by the solid line) giving transmission waves (transmission signals) is exposed on a further tip side than the distal ends thereof. In this manner, it is also possible to adopt the configuration in which the shield layer 256 (shield section) is not exposed from the distal end of the electromagnetic wave absorption material 251 in the transmission antenna 223. At that time, it is possible to cause the signal line 255 (in other words, the radiation element illustrated by the solid line) exposed from the distal end of the electromagnetic wave absorption material 251 to have the same line (signal line 255) width as that of the strip line illustrated by the dotted line on the paper surface lower side of the electromagnetic wave absorption material 251 as illustrated as an example in a in the drawing. The paper surface vertical direction is the main radiation direction (X-axis direction) of the radio waves. Note that the shape of the reception antenna 233 can be the shape illustrated in FIG. 43a. In this case, the radiation element in the transmission antenna 223 corresponds to the reception element in the reception antenna 233. The gain of the antennas is improved by using this antenna to face the transmission antenna and the reception antenna.

As illustrated as an example in b in FIG. 43, it is also possible to increase the width of the radiation element illustrated by the solid line as compared with the line (signal line 255) width of the strip line illustrated by the dotted line. As illustrated as an example in c in the drawing, it is also possible to form the radiation element with the meander structure. As illustrated as an example in d in the drawing, it is also possible to form the radiation element with the spiral shape. As illustrated as an example in e in the drawing, it is also possible to form a plurality of thicker radiation elements than the line (signal line 255) width of the strip line. As illustrated as an example in f in the drawing, it is also possible to form the thicker radiation element than the line width of the strip line and to provide a slit at the portion connected to the strip line.

With the shapes in b to e in the drawing, it is possible to further improve the gain in the main radiation direction as compared with a in the drawing. With the shape in f in the drawing, it is possible to achieve impedance matching as compared with b in the drawing and to efficiently emit the radio waves. Note that the shape of the reception antenna 233 can be the shapes illustrated in FIGS. 43a to 43f. In this case, the radiation element in the transmission antenna 223 corresponds to the reception element in the reception antenna 233.

FIG. 44 is a diagram illustrating another example of the shape of the transmission antenna 223 applied to the first structure according to the first embodiment of the present technology. In FIG. 44, a to f correspond to structures obtained by exposing the shield layer 256 (shield section) from the distal end of the electromagnetic wave absorption material 251 in a to f in FIG. 43.

In a in FIG. 44, a high-frequency current also flows through the shield layer in the main radiation direction and becomes a part of the antennas, and the gain is further improved as compared with a in FIG. 43. With the shapes in b to e in FIG. 44, it is possible to further improve the gain in the main radiation direction as compared with a in the drawing. With the shape in f in the drawing, it is possible to achieve impedance matching as compared with b in the drawing and to efficiently emit radio waves. Note that the shape of the reception antenna 233 can be the shapes as illustrated in FIGS. 44a to 44f. In this case, the radiation element in the transmission antenna 223 corresponds to the reception element in the reception antenna 233.

Also, each shape in FIGS. 43 and 44 can also be applied to the second structure.

Figure 45:
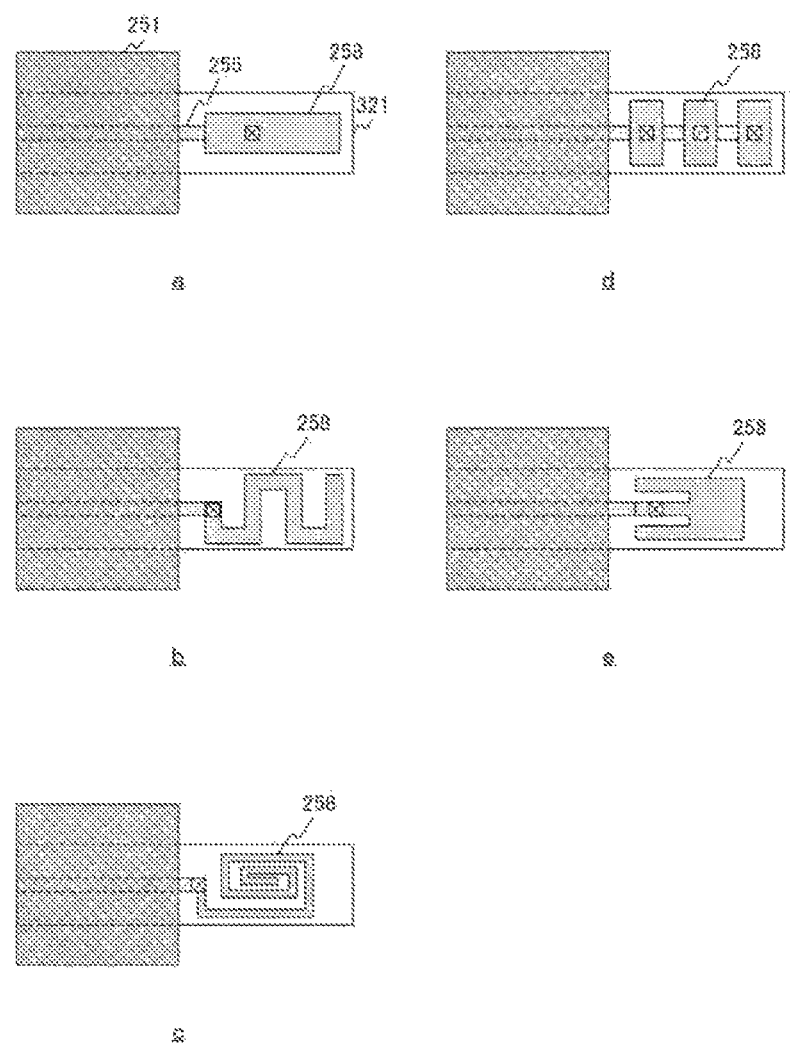
FIG. 45 is a diagram illustrating an example of the shape of a transmission antenna applied to the third structure according to the first embodiment of the present technology.

FIG. 45 is a diagram illustrating an example of the shape of the transmission antenna 223 applied to the third structure according to the first embodiment of the present technology. In the drawing, the distal end of the electromagnetic wave absorption material 251 and the distal end of the shield layer are at the same position, and the signal line 255 (radiation element) giving transmission waves (transmission signals) is exposed on a further tip side than the distal end. In this manner, it is also possible to adopt a configuration in which the shield layer 256 (shield section) is not exposed from the distal end of the electromagnetic wave absorption material 251 in the transmission antenna 223. At that time, it is also possible to increase the width of the radiation element as compared with the width of the line of the strip line illustrated by the dotted line as illustrated as an example in a in the drawing. It is also possible to form a radiation element with a meander structure as illustrated as an example in b in the drawing. It is also possible to form a spiral-shaped radiation element as illustrated as an example in c in the drawing. It is also possible to form a plurality of thicker radiation elements than the line width of the strip line as illustrated as an example in d in the drawing. It is also possible to form a thicker radiation element than the width of the line (signal line 255) of the strip line and to provide a slit at the portion connected to the strip line as illustrated as an example in e in the drawing.

With the shape in a in FIG. 45, it is possible to achieve impedance matching as compared with a in FIG. 43 and to efficiently emit radio waves. With the shapes in b to d in FIG. 45, it is possible to improve the gain in the main radiation direction as compared with a in the drawing. With the shape in e in the drawing, it is possible to achieve impedance matching as compared with a in the drawing and to efficiently emit the radio waves. Note that the shape of the reception antenna 233 can be the shapes illustrated in FIGS. 45a to 45e. In this case, the radiation element in the transmission antenna 223 corresponds to the reception element in the reception antenna 233.

Figure 46:
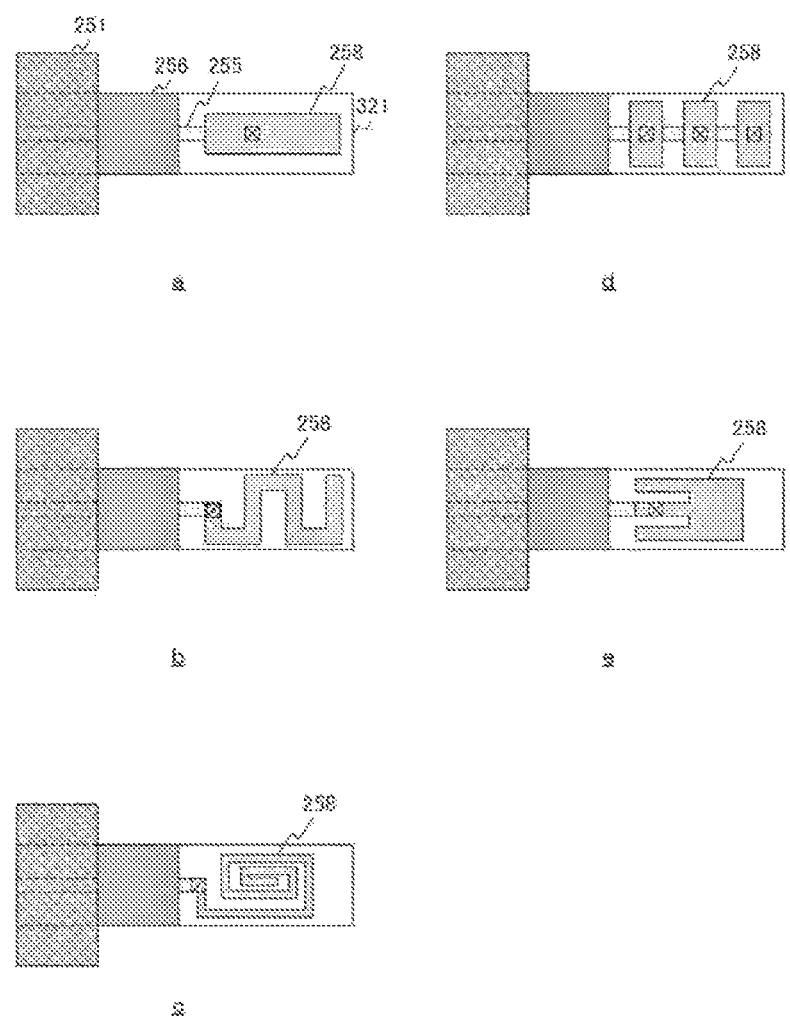
FIG. 46 is a diagram illustrating another example of the shape of the transmission antenna applied to the third structure according to the first embodiment of the present technology.

FIG. 46 is a diagram illustrating another example of the shape of the transmission antenna 223 applied to the third structure according to the first embodiment of the present technology. In FIG. 46, a to e correspond to structures obtained by exposing the shield layer 256 (shield section) from the distal end of the electromagnetic wave absorption material 251 in a to e in FIG. 45.

In a in FIG. 46, a high-frequency current flows through the shield layer in the main radiation direction and becomes a part of the antenna, and the gain is thus improved as compared with a in FIG. 45. It is possible to improve the gain in the main radiation direction by the shapes in b to d in FIG. 46 as compared with a in the drawing. With the shape in e in the drawing, it is possible to achieve impedance matching as compared with a in the drawing and to efficiently emit radio waves. Note that the shape of the reception antenna 233 can be the shape as illustrated in FIGS. 46a to 46e. In this case, the radiation element in the transmission antenna 223 corresponds to the reception element in the reception antenna 233.

Also, each shape in FIGS. 45 and 46 can also be applied to the fourth structure.

Figure 47:
FIG. 47 is a sectional view of the transmission antenna applied to the third structure when seen from the front according to the first embodiment of the present technology.

FIG. 47 is a sectional view of the transmission antenna 233 applied to the third structure when seen from the front similarly to FIG. 4b according to the first embodiment of the present technology. In FIG. 47, a corresponds to a sectional view of a in FIG. 46 when seen from the front (Z-axis direction).

As illustrated as an example in a in FIG. 47, the radiation element (conductor 258) is formed using the surface layer of the intra-probe substrate 321. Note that as illustrated as an example in b in the drawing, the radiation element 258 may be formed using the inner layer of the intra-probe substrate 321 instead of being formed using the surface layer. At the time of the application to the fourth structure, both the conductors 258 and 259 may be formed using the inner layer as illustrated in c in the drawing.

Figure 48:
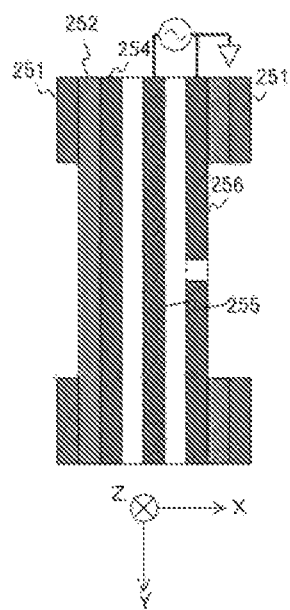
FIG. 48 is an example of a sectional view of a probe with a slot formed therein in a fifth structure including the slot formed therein when seen from the front according to the first embodiment of the present technology.

FIG. 48 is an example of a sectional view of the fifth structure regarding the transmission antenna 223 included in the intra-probe substrate 321 and the vicinity thereof when the sensor device 200 is seen from the front similarly to FIG. 4b (seen from the Z-axis direction) according to the first embodiment of the present technology.

Figure 49:
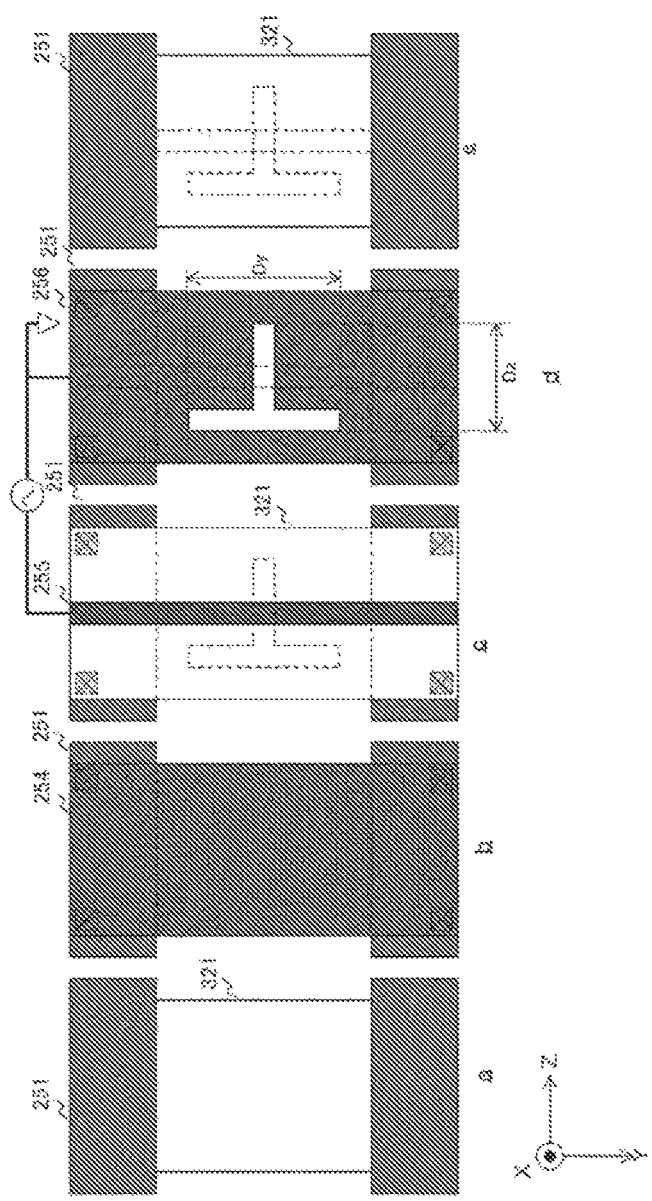
FIG. 49 is an example of a plan view of each layer in a probe casing with the fifth structure including the slot formed therein according to the first embodiment of the present technology.

FIG. 49 is an example of a plan view of each layer of the fifth structure, the section of which is illustrated in FIG. 48.

Figure 50:
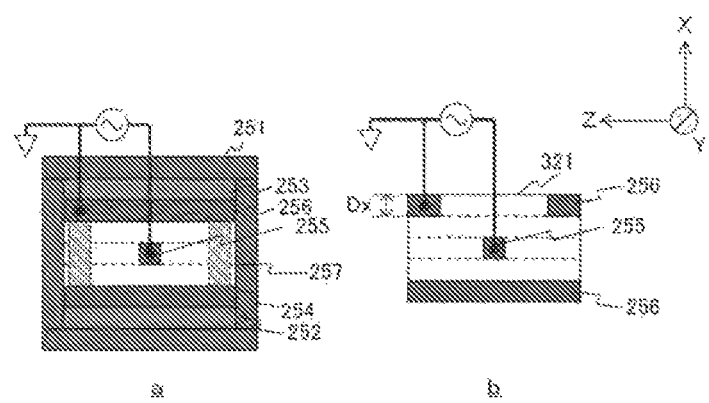
FIG. 50 is an example of a sectional view of the probe with the fifth structure including the slot formed therein when seen from the top according to the first embodiment of the present technology.

FIG. 50 is an example of a sectional view of the fifth structure, the section of which is illustrated in FIG. 48, when seen from the above.

The transmission antenna 223 with the fifth structure illustrated in FIGS. 48 to 50 is obtained by changing the transmission antenna 232 with the first structure illustrated in FIGS. 19 to 21 to a plane-shaped and slot-shaped antenna.

The "plane-shaped and slot-shaped antenna" is the shield layer exposed from the electromagnetic wave absorption material 251 and exposed to the space in the case of the transmission antenna, and the shield layer (the shield layer 256 in the example in FIGS. 48 to 50 including the slot is the radiation element. The "plane-shaped and slot-shaped antenna" includes the radiation element 256, the dielectric element (or an insulator), and a power supply section (the signal line 255 to which signals are given) that is superimposed on the slot with the dielectric element (or the insulator) interposed therebetween and crosses the slot. Similarly, in the case of the reception antenna, the shield layer that is exposed from the electromagnetic wave absorption material 251 and exposed to the space and includes the slot (the shield layer 256 in the example in FIGS. 48 to 50) is the reception element 256. The "plane-shaped and slot-shaped antenna" includes the reception element, a dielectric element (or an insulator), and a power supply section (the signal line 255 to which signals are given) which is superimposed on the slot with the dielectric element (or the insulator) interposed therebetween and crosses the slot.

In FIG. 48, the layer with no color disposed between the signal line 255 and the shield layer 256 (the radiation element 256) corresponds to the above dielectric element (or the insulator).

As illustrated in FIGS. 48 to 50, the plane-shaped and slot-shaped antenna is formed in the electronic substrate (such as the intra-probe substrate 321) including a plurality of wiring layers. Also, both the size Dz of the slot in a second direction (the widthwise direction of the electronic substrate, the Z-axis direction in FIG. 49) orthogonal to the first direction and the size Dy of the slot in a third direction (the lengthwise direction in which the electronic substrate extends, the y-axis direction in FIG. 50) orthogonal to the first direction and the second direction are greater than the size (in other words, the size in the direction of the slot included in the radiation element) Dx in the first direction (the thickness direction of the electronic substrate, the X-axis direction in FIG. 50) of the radiation element (the shield layer 256 including the slot). In the specification, in the case where both Dz and Dy are larger than Dx for the radiation element (the shield layer 256 in the example in FIGS. 48 to 50) included in the transmission antenna including the slot, the transmission antenna is defined as the "plane-shaped and slot-shaped antenna" and the "plane-shaped and slot-shaped transmission antenna". Also, a part of the radiation element extending on the plane defined by the second direction and the third direction is defined as the "plane of the radiation element". Also, the quadrangular region defined by the width Dz of the slot and the length Dy of the slot illustrated in FIG. 49d is defined as a transmission antenna region for convenience. The same applies to the reception antenna. In the specification, in a case where both Dz and Dy are greater than Dx for the reception element (the shield layer 256 in the example in FIGS. 48 to 50) included in the reception antenna including the slot, the reception antenna is defined as the "plane-shaped and slot-shaped antenna" and the "plane-shaped and slot-shaped reception antenna". Also, a part of the reception element, which is a part extending in a plane defined by the second direction and the third direction, is defined as "a plane of the reception element". Also, the quadrangular region defined by the width Dz of the slot and the length Dy of the slot illustrated in FIG. 49d is defined as a reception antenna region for convenience. Note that Dy may be preferably greater than both Dx and Dz in relation to the transmission antenna and the reception antenna.

In the fifth structure illustrated in FIGS. 48 to 50, the slot is not formed in the first wiring layer (the shield layer 254) on the rearmost surface side (the negative direction of the X axis) in the intra-probe substrate forming the "plane-shaped and slot-shaped antenna", and the slot is formed in the third wiring layer on the frontmost surface side (the positive direction of the X axis). With such a shape, the plane-shaped and slot-shaped antenna with the fifth structure serves as a one-side radiation antenna.

Figure 51:
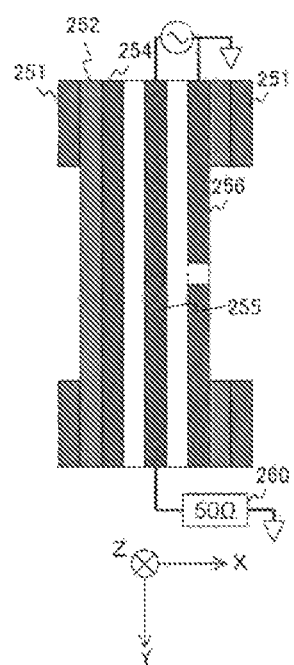
FIG. 51 is another example of a sectional view of the probe with the fifth structure including the slot formed therein when seen from the front according to the first embodiment of the present technology.

FIG. 51 is a sectional view representing another example of the fifth structure when the sensor device 200 is seen from the front (seen from the Z-axis direction) similarly to FIG. 4b according to the first embodiment of the present technology.

Figure 52:
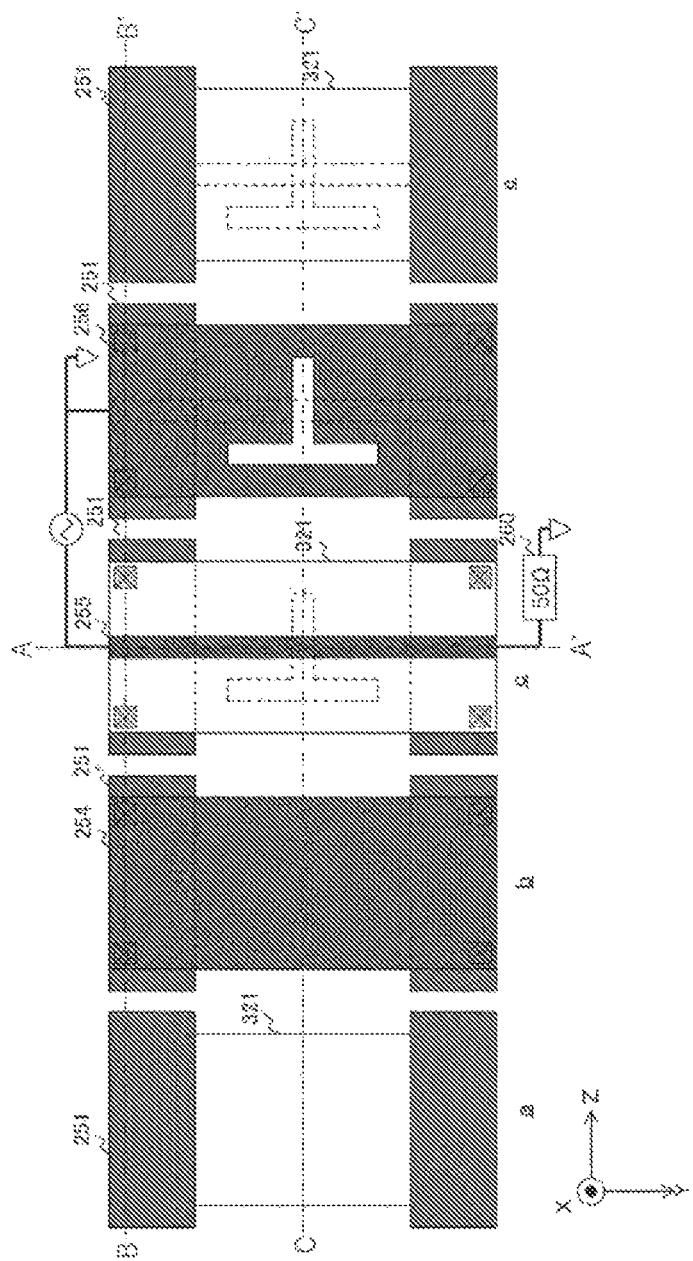
FIG. 52 is another example of a plan view of each layer in the probe casing with the fifth structure including the slot formed therein according to the first embodiment of the present technology.

FIG. 52 is an example of a plan view of each layer in another example of the fifth structure, the section of which is illustrated in FIG. 51.

Figure 53:
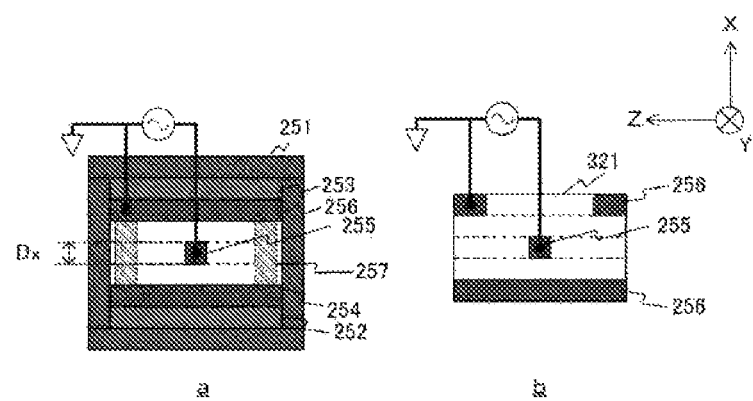
FIG. 53 is another example of a sectional view of the probe with the fifth structure including the slot formed therein when seen from the top according to the first embodiment of the present technology.

FIG. 53 is an example of a sectional view of another example of the fifth structure, the section of which is illustrated in FIG. 51, when seen from the above.

Figure 54:
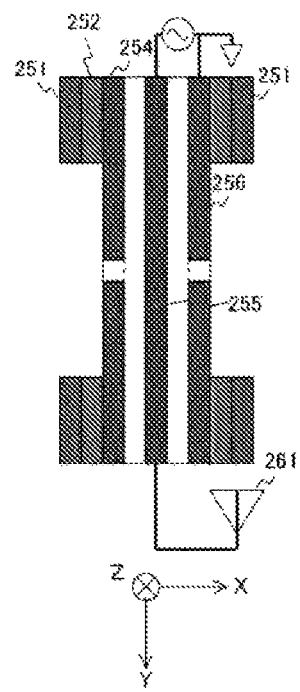
FIG. 54 is another example of a sectional view of the probe with the fifth structure including the slot formed therein when seen from the front according to the first embodiment of the present technology.

FIG. 54 is a sectional view representing yet another example of the fifth structure when the sensor device 200 is seen from the front (seen from the Z-axis direction) similarly to FIG. 4b according to the first embodiment of the present technology.

Figure 55:
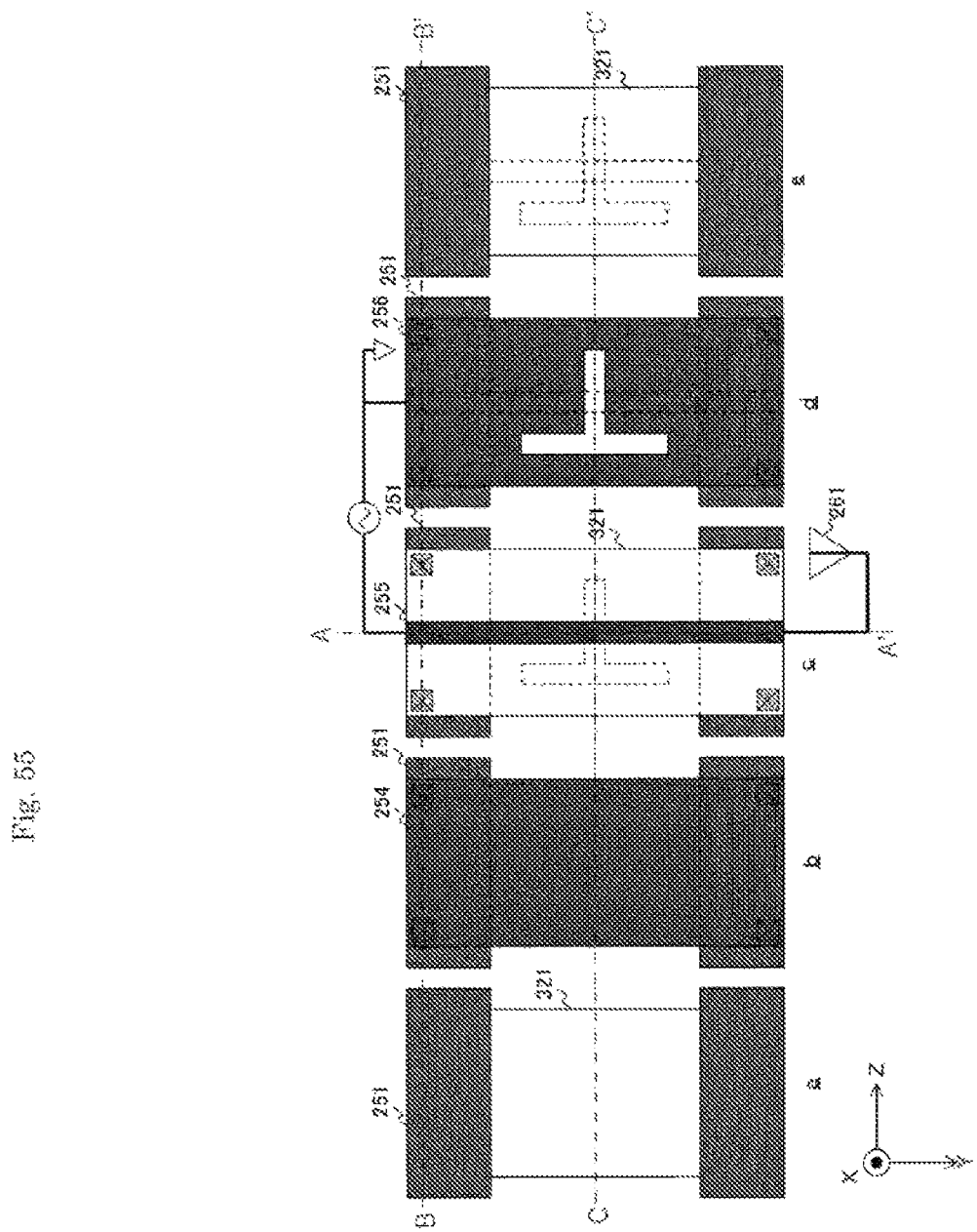
FIG. 55 is another example of a plan view of each layer in the probe casing with the fifth structure including the slot formed therein according to the first embodiment of the present technology.

FIG. 55 is an example of a plan view of each layer in yet another example of the fifth structure, the section of which is illustrated in FIG. 54.

Figure 56:
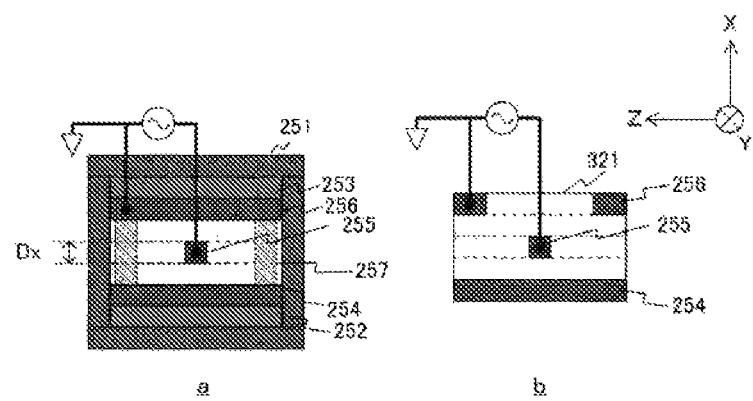
FIG. 56 is another example of a sectional view of the probe with the fifth structure including the slot formed therein when seen from the top according to the first embodiment of the present technology.

FIG. 56 is an example of a sectional view of yet another example of the fifth structure, the section of which is illustrated in FIG. 54, when seen from the above.

As illustrated as an example in FIGS. 51 to 53, it is also possible to terminate the signal line 255 included in the "plane-shaped and slot-shaped antenna" by connecting it to the ground via a resistor 260 of 50 ohms (Ω) or the like in a region on the further side than the slot included in the antenna in another example of the fifth structure. Also, as illustrated as an example in FIGS. 54 to 56, it is also possible to terminate the signal line 255 included in the "plane-shaped and slot-shaped antenna" by connecting it to another antenna 261 in a region on the further side than the slot included in the antenna in yet another example of the fifth structure.

Figure 57:
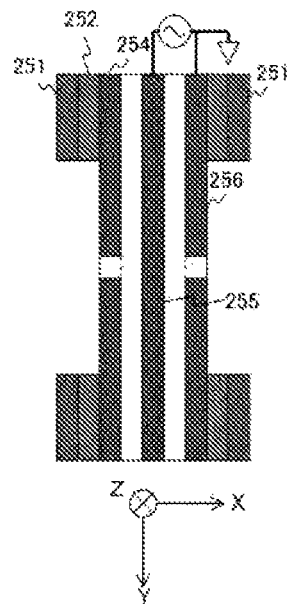
FIG. 57 is an example of a sectional view of a probe with a sixth structure including a slot formed therein when seen from the front according to the first embodiment of the present technology.

FIG. 57 is an example of a sectional view of the sixth structure regarding the transmission antenna 223 included in the intra-probe substrate 321 and the vicinity thereof when the sensor device 200 is seen from the front (seen from the Z-axis direction) similarly to FIG. 4b according to the first embodiment of the present technology.

Figure 58:
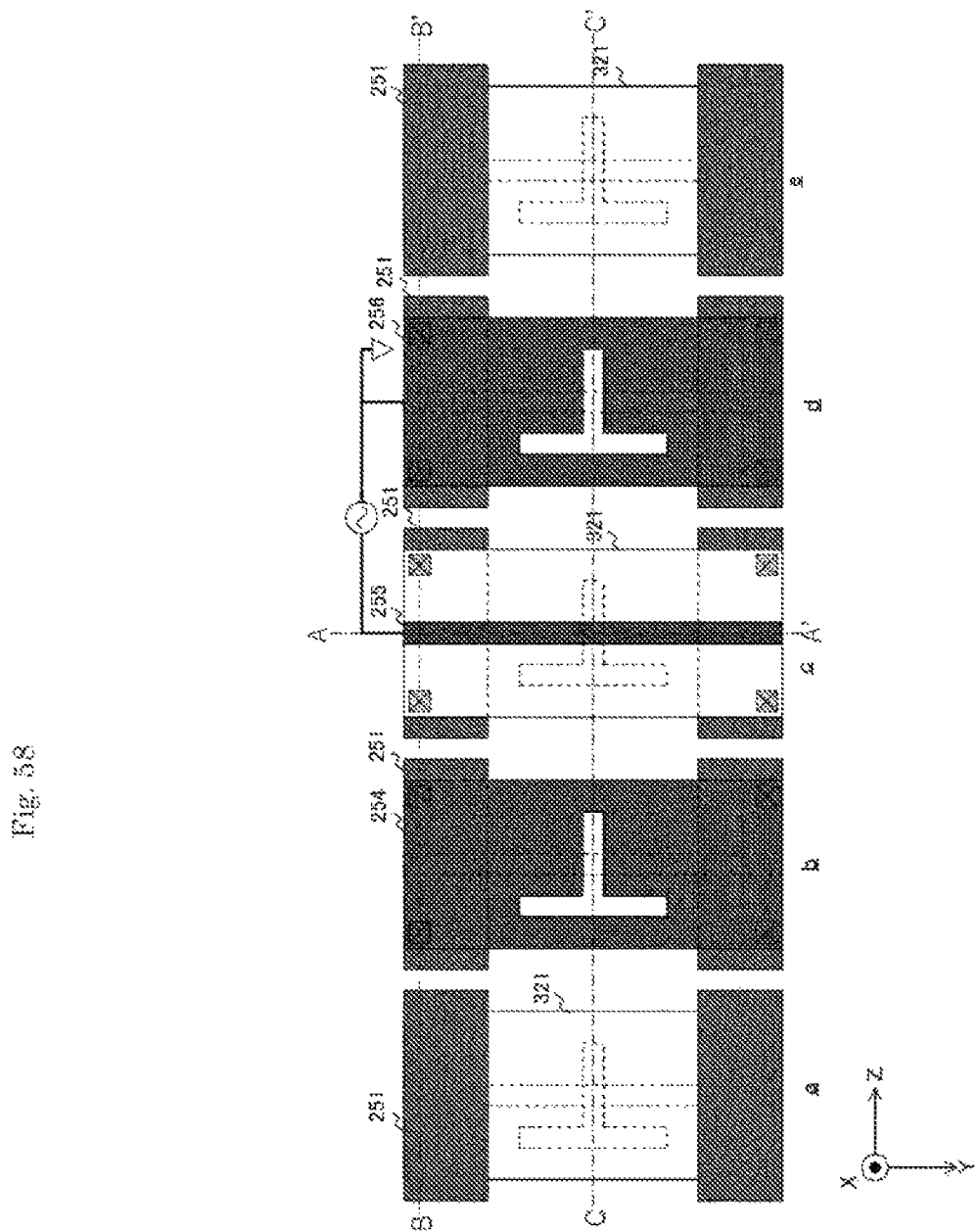
FIG. 58 is an example of a plan view of each layer in a probe casing with the sixth structure including the slot formed therein according to the first embodiment of the present technology.

FIG. 58 is an example of the plan view of each layer of the sixth structure, the section of which is illustrated in FIG. 57.

Figure 59:
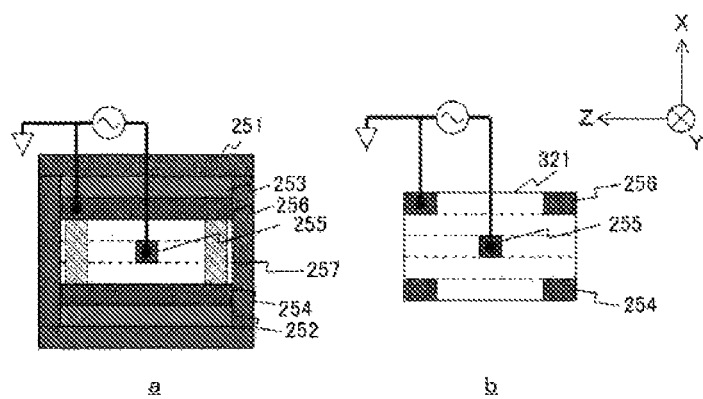
FIG. 59 is an example of a sectional view of the probe with the sixth structure including the slot formed therein when seen from the top according to the first embodiment of the present technology.

FIG. 59 is an example of a sectional view of the sixth structure, the section of which is illustrated in FIG. 57, when seen from the above.

The transmission antenna 223 with the sixth structure illustrated in FIGS. 57 to 59 is obtained by changing the plane-shaped and slot-shaped antenna with the fifth structure illustrated in FIGS. 48 to 50 to a double-side radiation antenna. In a case where the "plane-shaped and slot-shaped antenna" with the sixth structure is the transmission antenna, the shield layers exposed from the electromagnetic wave absorption material 251, exposed to the space, and including the slots (the shield layers 256 and 254) are radiation elements. With such a shape, the plane-shaped and slot-shaped antennas with the sixth structure is the double-side radiation antenna. The same applies to the reception antenna. In a case where the "plane-shaped and slot-shaped antenna" with the sixth structure illustrated in FIGS. 57 to 59 is the reception antenna, the shield layers exposed from the electromagnetic wave absorption material 251, exposed to the space, and including the slots (the shield layers 256 and 254) are reception elements.

Figure 60:
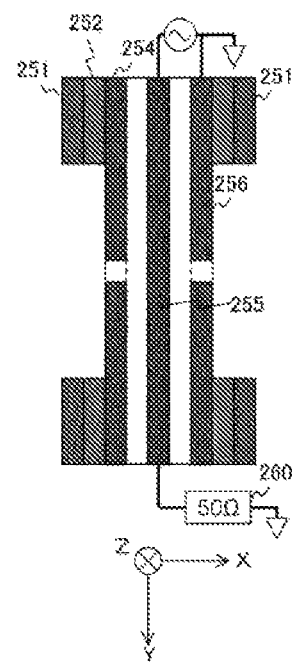
FIG. 60 is another example of a sectional view of the probe with the sixth structure including the slot formed therein when seen from the front according to the first embodiment of the present technology.

FIG. 60 is a sectional view illustrating another example of the sixth structure when the sensor device 200 is seen from the front (seen from the Z-axis direction) similarly to FIG. 4b according to the first embodiment of the present technology.

Figure 61:
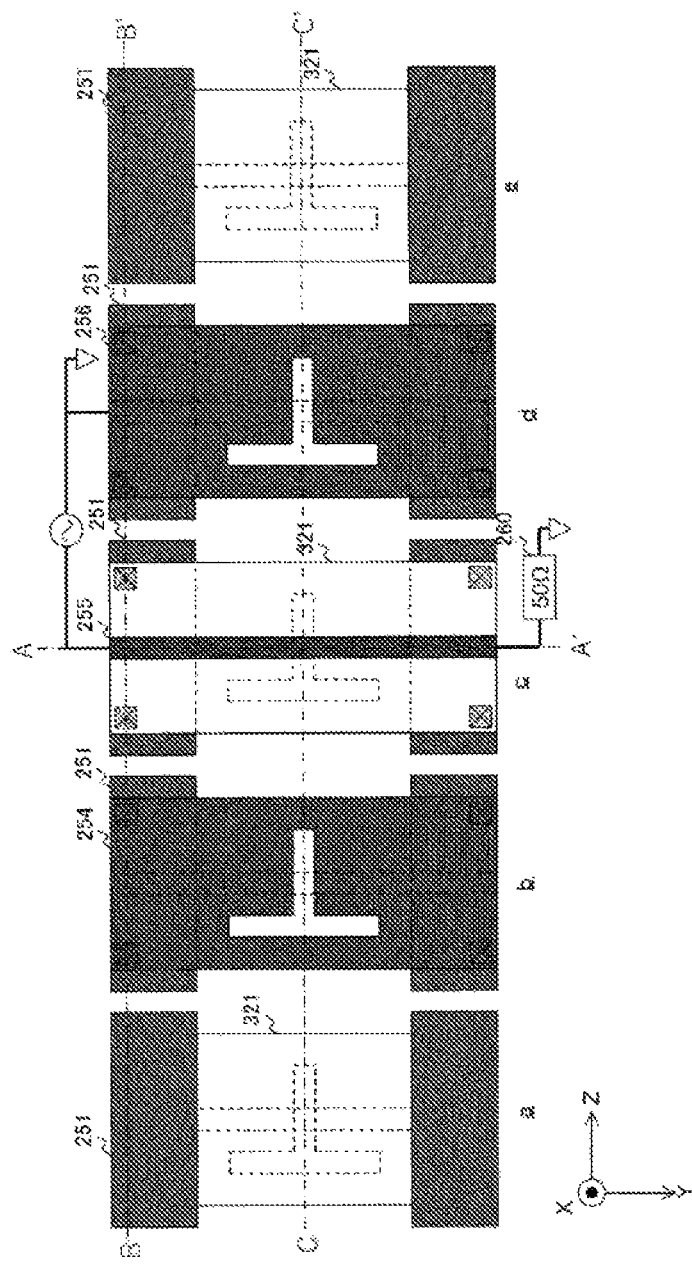
FIG. 61 is another example of a plan view of each layer in the probe casing with the sixth structure including the slot formed therein according to the first embodiment of the present technology.

FIG. 61 is an example of a plan view of each layer in another example of the sixth structure, the section of which is illustrated in FIG. 60.

Figure 62:
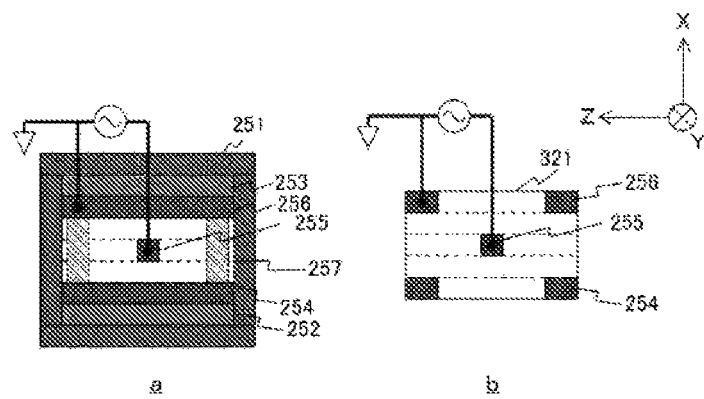
FIG. 62 is another example of a sectional view of the probe with the sixth structure including the slot formed therein when seen from the top according to the first embodiment of the present technology.

FIG. 62 is an example of a sectional view of another example of the sixth structure, the section of which is illustrated in FIG. 60, when seen from the above.

Figure 63:
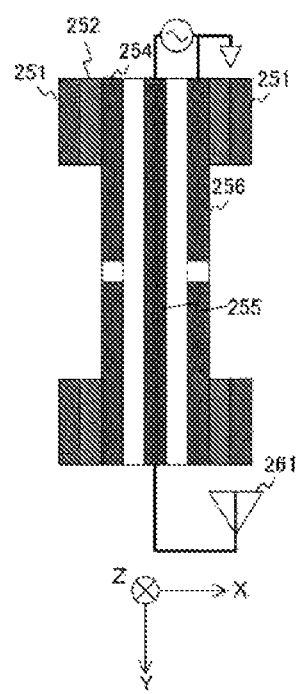
FIG. 63 is another example of a sectional view of the probe with the sixth structure including the slot formed therein when seen from the front according to the first embodiment of the present technology.

FIG. 63 is a sectional view illustrating yet another example of the sixth structure when the sensor device 200 is seen from the front (seen from the Z-axis direction) similarly to FIG. 4b according to the first embodiment of the present technology.

Figure 64:
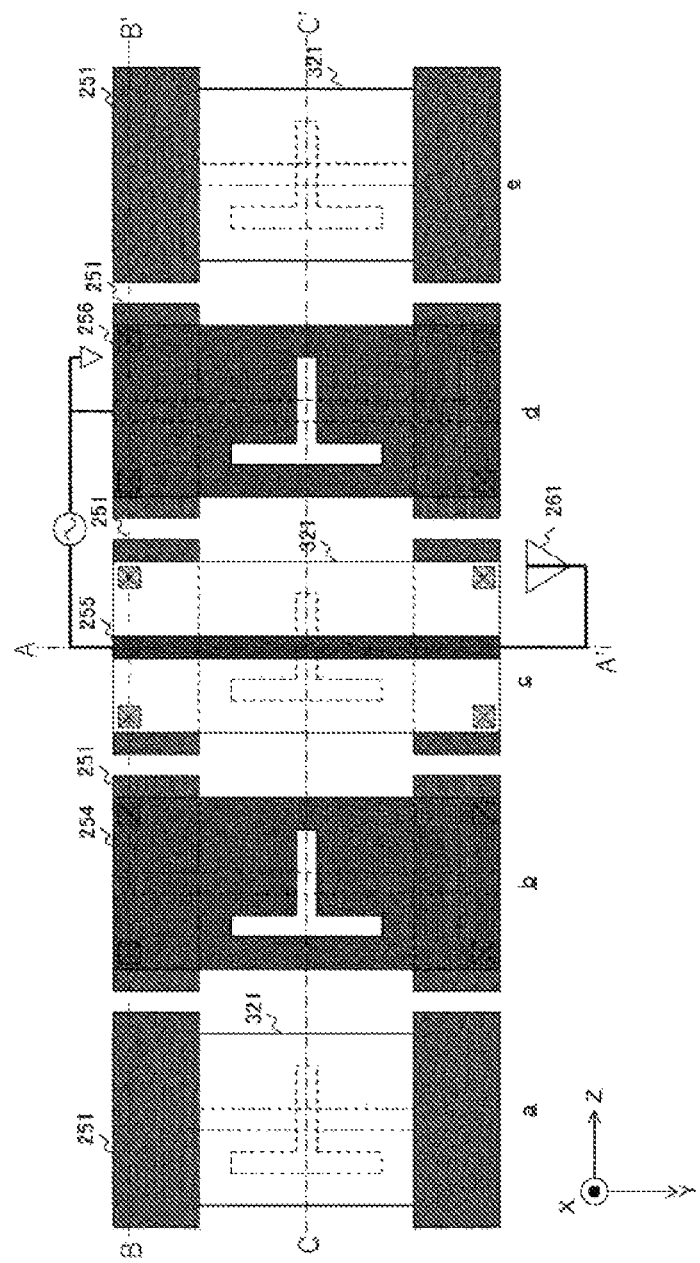
FIG. 64 is another example of a plan view of each layer in the probe casing with the sixth structure including the slot formed therein according to the first embodiment of the present technology.

FIG. 64 is an example of a plan view of each layer in yet another example of the sixth structure, the section of which is illustrated in FIG. 63.

Figure 65:
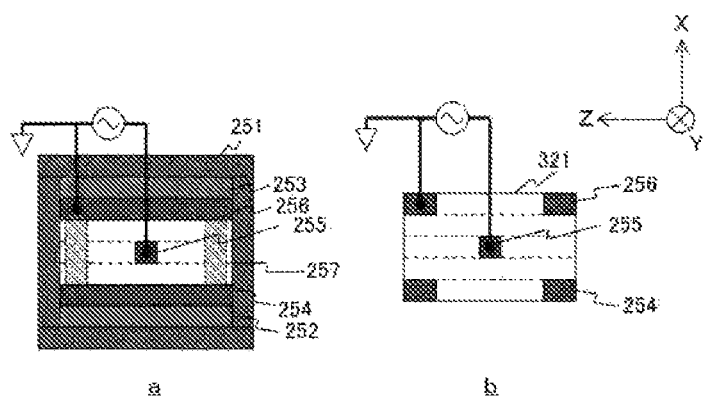
FIG. 65 is another example of a sectional view of the probe with the sixth structure including the slot formed therein when seen from the top according to the first embodiment of the present technology.

FIG. 65 is an example of a sectional view of yet another example of the sixth structure, the section of which is illustrated in FIG. 63, when seen from the above.

As illustrated as examples in FIGS. 60 to 62, it is also possible to terminate the signal line 255 included in the "plane-shaped and slot-shaped antenna" by connecting it to the ground via the resistor 260 of 50 ohms (Ω) or the like in a region on the further side than the slot included in the antenna in another example of the sixth structure. Also, as illustrated as examples in FIGS. 63 to 65, it is also possible to terminate the signal line 255 included in the "plane-shaped and slot-shaped antenna" by connecting it to another antenna 261 in a region on the further side than the slot included in the antenna in yet another example of the sixth structure.

Figure 66:
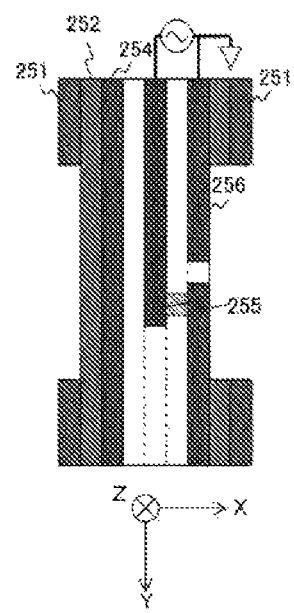
FIG. 66 is an example of a sectional view of a probe with a seventh structure including a slot formed therein when seen from the top according to the first embodiment of the present technology.

FIG. 66 is an example of a sectional view of the seventh structure regarding the plane-shaped and slot-shaped transmission antenna 223 included in the intra-probe substrate 321 and the vicinity thereof when the sensor device 200 is seen from the front (seen from the Z-axis direction) similarly to FIG. 4b according to the first embodiment of the present technology.

Figure 67:
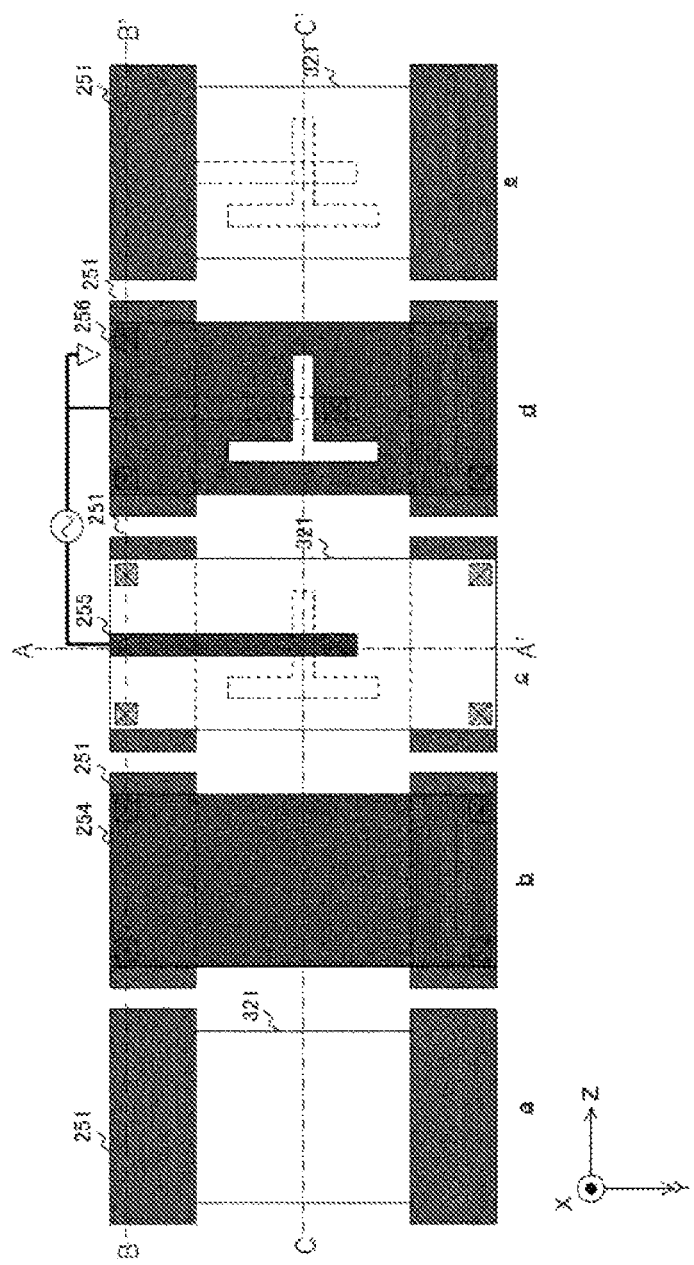
FIG. 67 is an example of a plan view of each layer in a probe casing with the seventh structure including the slot formed therein according to the first embodiment of the present technology.

FIG. 67 is an example of the plan view of each layer of the seventh structure, the section of which is illustrated in FIG. 66.

Figure 68:
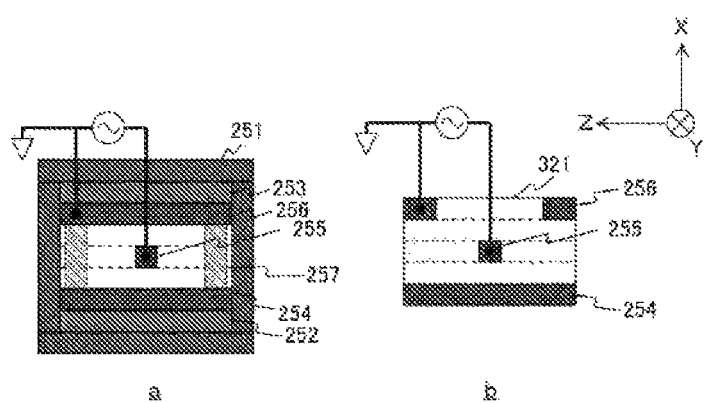
FIG. 68 is another example of a sectional view of the probe with the seventh structure including the slot formed therein when seen from the front according to the first embodiment of the present technology.

FIG. 68 is an example of a sectional view of the seventh structure, the section of which is illustrated in FIG. 66, when seen from the above.

The plane-shaped and slot-shaped transmission antenna 223 with the seventh structure illustrated in FIGS. 66 to 68 is different from the transmission antenna 223 with the fifth structure in the following points. In other words, in the plane-shaped and slot-shaped transmission antenna 223 with the seventh structure, the signal line 255 extending from the transmission source direction is connected to the radiation element (shield layer 256) including the slot via a via illustrated by the hatching in FIG. 66 and is terminated in a region on the further side than the point at which the signal line 255 crosses a part of the slot (in other words, the region on the further side than the point at which the signal line 255 extending from the transmission source direction is superimposed on a part of the slot), which is a region in the vicinity of the slot (more preferably, in a transmission antenna region defined for convenience by the quadrangular region defined by the width Dz of the slot and the length Dy of the slot). According to the plane-shaped and slot-shaped antenna with the seventh structure, the current flowing from the signal line 255 to the radiation element 256 across the slot increases as compared with the antenna with the fifth structure, and it is possible to efficiently emit electromagnetic waves by including the structure. The same applies to the case of the reception antenna. In a case where the "plane-shaped and slot-shaped antenna" with the seventh structure illustrated in FIGS. 66 to 68 is the reception antenna, the shield layer 256 exposed from the electromagnetic wave absorption material 251, exposed to the space, and including the slot is the reception element.

Figure 69:
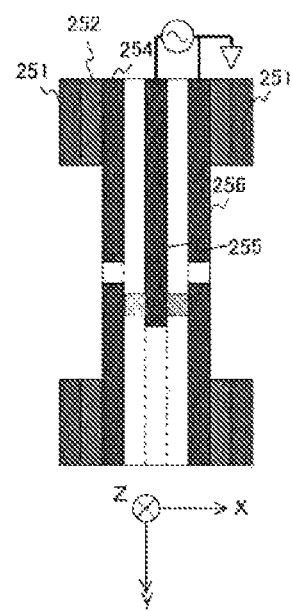
FIG. 69 is an example of a sectional view of a probe with an eighth structure including a slot formed therein when seen from the top according to the first embodiment of the present technology.

FIG. 69 is an example of a sectional view of the eighth structure regarding the transmission antenna 223 included in the intra-probe substrate 321 and the vicinity thereof when the sensor device 200 is seen from the front (seen from the Z-axis direction) similarly to FIG. 4b according to the first embodiment of the present technology.

Figure 70:
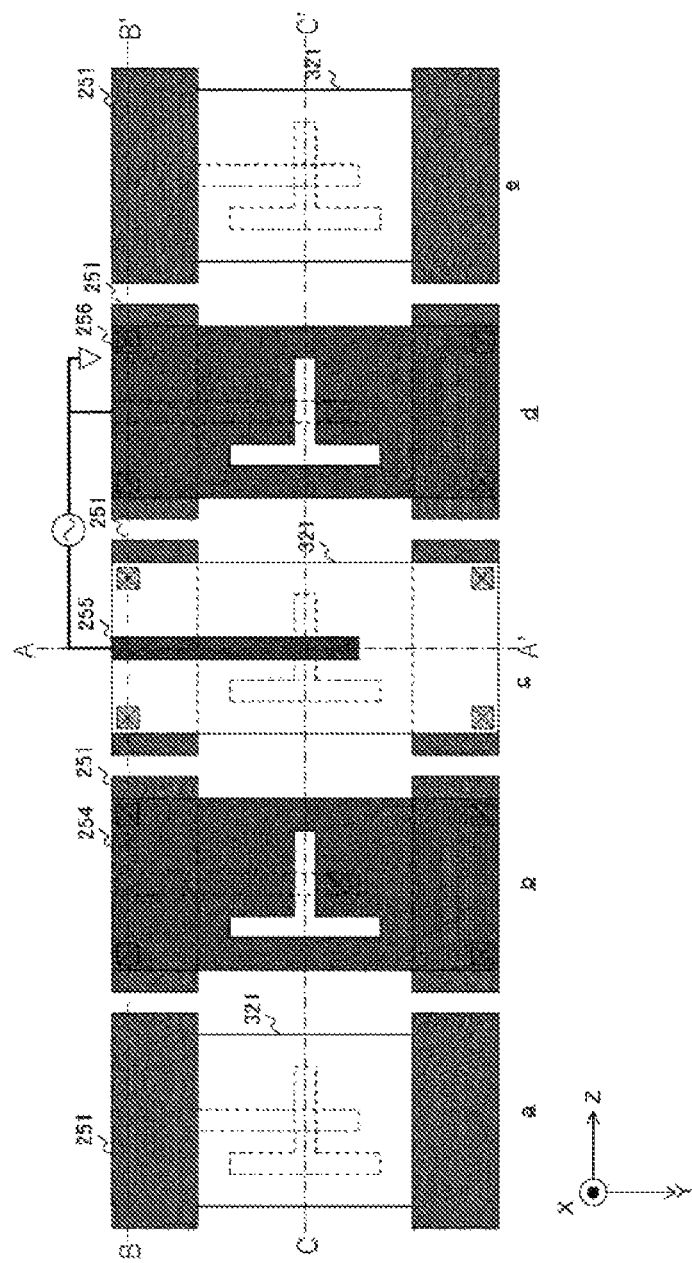
FIG. 70 is an example of a plan view of each layer in a probe casing with the eighth structure including the slot formed therein according to the first embodiment of the present technology.

FIG. 70 is an example of a plan view of each layer of the eighth structure, the section of which is illustrated in FIG. 69.

Figure 71:
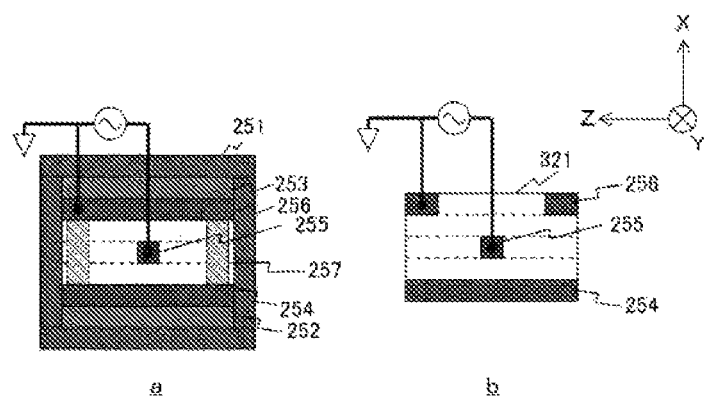
FIG. 71 is another example of a sectional view of the probe with the eighth structure including the slot formed therein when seen from the front according to the first embodiment of the present technology.

FIG. 71 is an example of a sectional view of the eighth structure, the section of which is illustrated in FIG. 69, when seen from the above.

The transmission antenna 223 with the eighth structure illustrated in FIGS. 69 to 71 is obtained by changing the plane-shaped and slot-shaped antenna with the seventh structure illustrated in FIGS. 66 to 68 to a double-side radiation antenna. In a case where the "plane-shaped and slot-shaped antenna" with the eighth structure is the reception antenna, the shield layers exposed from the electromagnetic wave absorption material 251, exposed to the space, and including the slots (the shield layers 256 and 254) are radiation elements. Furthermore, the signal line 255 extending from the transmission source direction is connected to both the radiation elements (the shield layers 256 and 254) including the slots via the vias illustrated by the hatching in FIG. 69 in the region on the further side than the point at which the signal line 255 crosses a part of the slots (in other words, the region on the further side than the point at which the signal line 255 extending from the transmission source direction is superimposed on a part of the slots), which is a region in the vicinity of the slot (more preferably, in the transmission antenna region defined for convenience by the quadrangular region defined by the width Dz of the slot and the length Dy of the slot) and is terminated. With such a shape, the plane-shaped and slot-shaped antenna with the eighth structure serves as a double-side radiation antenna. The same applies to the case of the reception antenna. In a case where the "plane-shaped and slot-shaped antenna" with the eighth structure illustrated in FIGS. 69 to 71 is the reception antenna, the shield layers exposed from the electromagnetic wave absorption material 251, exposed to the space, and including the slots (the shield layers 256 and 254) are reception elements.

Figure 72:
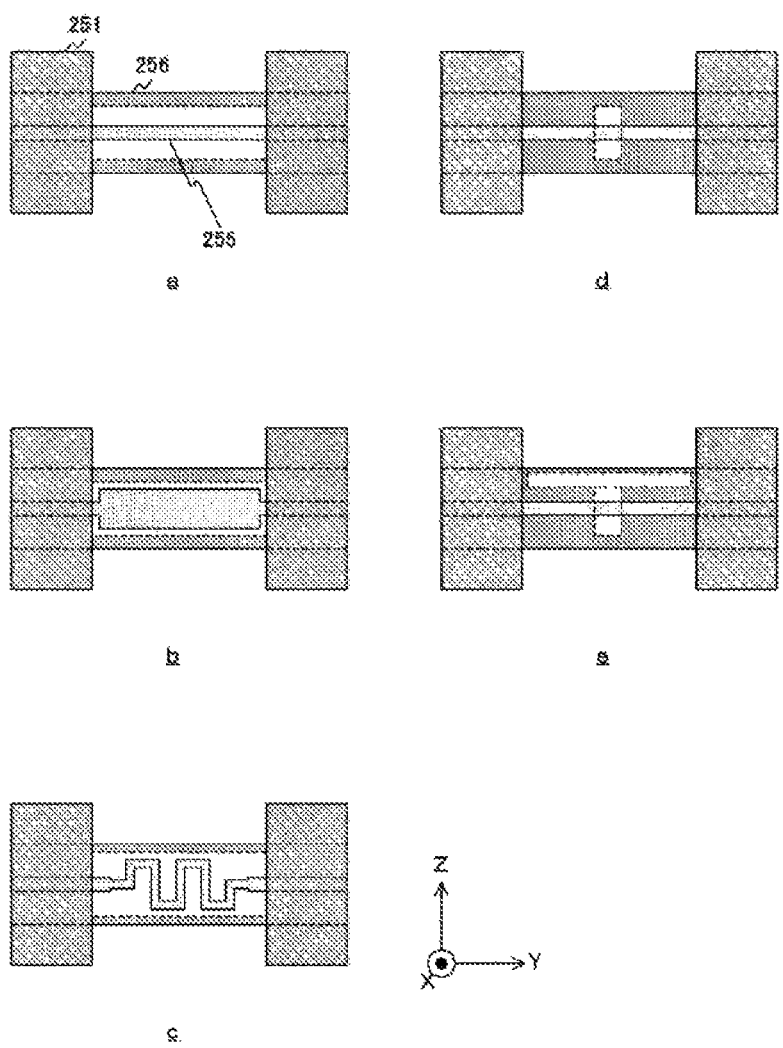
FIG. 72 is a diagram illustrating an example of the shape of a transmission antenna applied to the fifth structure including the slot formed therein according to the first embodiment of the present technology.

FIG. 72 is a diagram illustrating an example of the shape of the transmission antenna applied to the fifth structure of the plane-shaped and slot-shaped antenna according to the first embodiment of the present technology. As illustrated as an example in a in the drawing, it is also possible to form the entire region of the shield layer 256 exposed from the electromagnetic wave absorption material 251 superimposing the signal line 255 as a slot. As illustrated as an example in b in the drawing, it is also possible to set the line width of the signal line 255 exposed from the electromagnetic wave absorption material 251 to be wider than the width of the signal line 255 extending in the region where the electromagnetic wave absorption material 251 is disposed and to form the entire region of the shield layer 256 superimposed on the signal line 255 with the increased width as a slot. As illustrated as an example in c in the drawing, it is also possible to adopt a meander structure for the signal line 255 exposed from the electromagnetic wave absorption material 251 and form the entire region of the shield layer 256 superimposed on the signal line 255 with the meander structure as a slot. As illustrated as an example in d in the drawing, it is also possible to cause the slot provided in the shield layer 256 exposed from the electromagnetic wave absorption material 251 to cross the signal line 255 exposed from the electromagnetic wave absorption material 251. As illustrated as an example in e in the drawing, it is also possible to cause the slot provided in the shield layer 256 exposed from the electromagnetic wave absorption material 251 to cross the signal line 255 exposed from the electromagnetic wave absorption material 251 and to branch the slot in the region on the further side than the slot crossing the signal line 255 (to branch it into a T shape, for example)

With the shapes in a and d in the drawing, the paper plane vertical direction (X-axis direction) is the main radiation direction of the radio waves, and antenna gains are improved. With the shapes in b and c in the drawing, the radiation resistance becomes higher than that in a in the drawing, and it is thus possible to efficiently emit radio waves. With the shape in e in the drawing, the radiation resistance becomes higher than that in d in the drawing, and it is thus possible to efficiently emit radio waves.

Additionally, it is also possible to apply the shape in a in the drawing to the sixth structure of the plane-shape and slot-shaped antenna. In this case, impedance matching is more easily achieved as compared with the case where a in the drawing is applied to the fifth structure, and it is possible to efficiently perform the radiation.

FIG. 73 is a diagram illustrating an example of the shape of the transmission antenna applied to the seventh structure of the plane-shaped and slot-shaped antenna according to the first embodiment of the present technology. In FIG. 73, a to e are terminated by connecting the distal ends of the signal lines 255 in a to e in FIG. 72 to the radiation element (in other words, connecting the slot to the shield layer 256) via the via. The circle indicates the via. The current flowing from the signal line 255 to the radiation element across the slot increases by including the structure as compared with the antenna illustrated in FIG. 72, and it is possible to efficiently emit electromagnetic waves.

FIG. 74 is a diagram illustrating an example of the shape of the transmission antenna applied to the eighth structure of the plane-shaped and slot-shaped antenna according to the first embodiment of the present technology.

Figure 75:
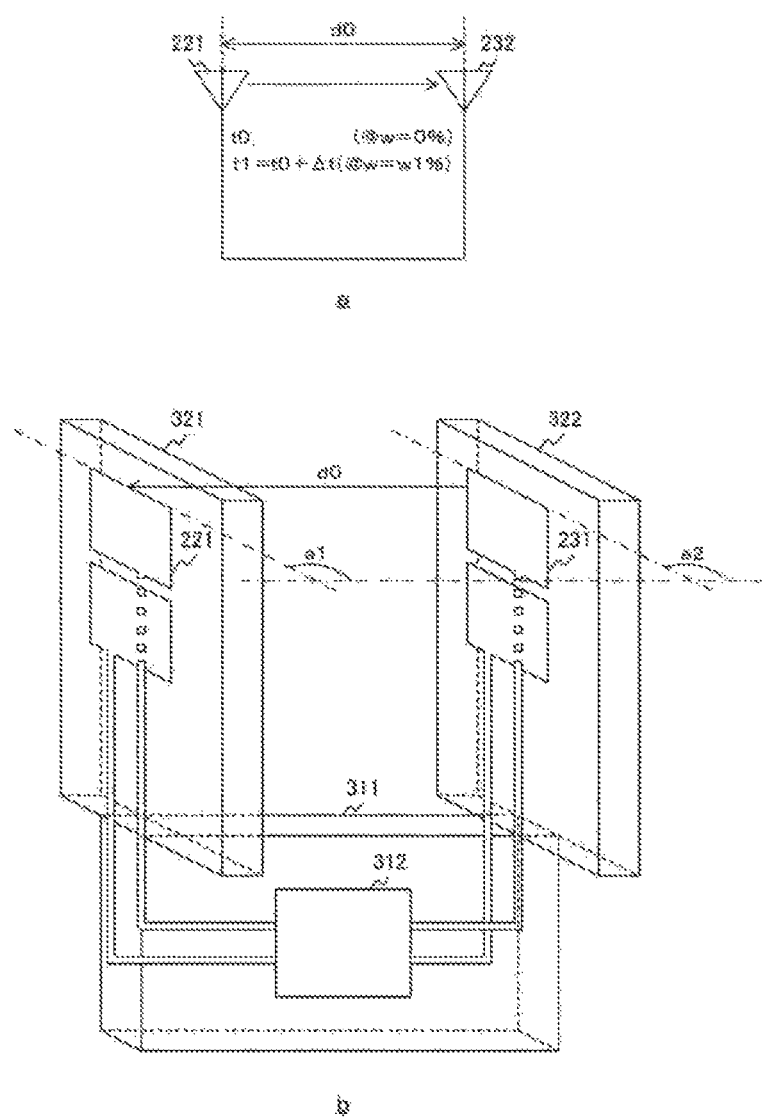
FIG. 75 is a diagram for explaining an operation principle of the sensor device according to the first embodiment of the present technology.

FIG. 75 is a diagram for explaining operation principles of the sensor device 200 and effects that the structure of the sensor device 200 has according to the first embodiment of the present technology. As illustrated as an example in a in the drawing, the distance between the transmission antenna 221 and the reception antenna 231 is fixed to a predetermined distance d0 in the sensor device 200 according to the present technology. The propagation delay time Δt of electromagnetic waves is measured, and the amount of moisture is obtained, by focusing on the fact that the propagation time required for the electromagnetic waves to be propagated by the predetermined distance d0 increases in proportion to the amount of moisture in the medium between the transmission antenna 221 and the reception antenna 231.

In order to accurately measure the moisture, the sensor device 200 includes a plane-shaped or plane-shaped and slit-shaped transmission antenna 221 and reception antenna 231 with high gain as illustrated as an example in b in the drawing. In order to improve working precision and positioning precision of the antennas and to maintain a constant environment in the surroundings of the antennas and the transmission paths (for example, the size of the space in the surroundings of the antennas and the transmission paths, the distances from the antennas and the transmission paths to the casing, and the distances from the antennas and the transmission paths to the soil), the transmission antenna and the transmission path connected to the transmission antenna are formed using the same first electronic substrate (the intra-probe substrate 321), and the reception antenna and the transmission path connected to the reception antenna are formed using the same second electronic substrate (the intra-probe substrate 322).

Also, the sensor device 200 has a novel structure such that the measurement results are always constant even if the measurement of the amount of moisture is repeatedly performed under a condition at which the amount of moisture in the medium between the antenna is a specific value (in other words, the time required for the electromagnetic waves to be propagated from the transmission antenna to the reception antenna and the size of the propagated signal are always constant even if the measurement is repeatedly performed). In other words, the sensor device 200 includes plane-shaped or plane-shaped and slot-shaped transmission antenna and reception antenna as illustrated as an example in b in the drawing and has a structure in which the positions of transmission antenna and the reception antenna are fixed such that the orientations of the antennas are fixed with the planes thereof caused to face each other and the distance between the antennas is always a predetermined distance.

Furthermore, the transmission path for transmission connected to the transmission antenna and the transmission path for reception connected to the reception antenna are connected to the measurement section 312. The measurement section 312 transmits transmission waves to the transmission antenna and receives reception waves from the reception antenna. The measurement section substrate 311 including the measurement section 312 is orthogonal to the first electronic substrate and the second electronic substrate. The transmission paths electrically extend between these orthogonal to substrates via the transmission lines including a plurality of shielded signal lines, which are transmission line cables with higher flexibility than the measurement section substrate 311 and the intra-probe substrates 321 and 322.

PTL 1 does not describe the mode in which the planes of the transmission antenna and the reception antenna are caused to face each other and the orientations thereof are fixed.

On the other hand, there may be a case where plane-shaped or plane-shaped and slot-shaped antennas are used in the field of wireless communication terminal devices. However, a transmitter and a receiver are accommodated in different casings in a typical wireless communication device, the distance between the transmission antenna and the reception antenna is thus not fixed, and the orientations of the transmission antenna and the reception antenna are also not fixed.

PTL 1 does not include any recognition of the problem to accurately measure the moisture by causing the plane-shaped transmission antenna and the reception antenna to face each other to fix the orientations thereof and does not include any motivation to combine the structure of causing the plane-shaped transmission antenna and reception antenna to face each other to fix the orientations.

The function of the present invention of enabling accurate measurement of the propagation delay time of the electromagnetic waves propagated by a predetermined distance and the amount of moisture in the medium through which the electromagnetic waves are propagated is not obtained until the configuration in which the plane-shaped or plane-shaped and slit-shaped transmission antenna and reception antenna are fixed at predetermined orientations, namely, fixed at the facing orientations and the antennas are fixed at the positions with the predefined distance provided therebetween is adopted.

Also, the effect that the moisture is accurately measured with the configuration in which the plane-shaped or plane and slit-shaped transmission antenna and reception antenna are fixed at the predetermined orientations, namely the facing orientations and the antennas are fixed at the positions with the predefined distance provided therebetween can also be obtained not only in the modes illustrated in FIGS. 4 and 74 in which the measurement section substrate extends parallel with one plane defined by the X axis and the Y axis but also in the mode in FIG. 348 in which the measurement section substrate extends parallel with one plane defined by the X axis and the Z axis. As another example of the first embodiment of the present technology, a mode in which the extending direction of the measurement section substrate according to the first embodiment of the present technology illustrated in FIG. 4 is changed to extend parallel with the one plane defined by the X axis and the Z axis as illustrated in FIG. 348 and the measurement section substrate, the transmission probe substrate, and the reception probe substrate are accommodated in one sensor casing similarly to FIG. 4 may also be adopted.

Here, a comparative example in which the antennas are not formed in the electronic substrates (the intra-probe substrate 321 and the like), for example, an example in which the antennas are assembled by using a plurality of components will be assumed. As compared with the comparative example, the antennas are formed in the electronic substrates in the sensor device 200, and it is thus possible to improve working precision of the antennas and to accurately measure the moisture. Moreover, it is possible to reduce the volume of the antennas and the probe casing 320 included in the sensor device 200. In this manner, it is possible to reduce the amount of mud to be pushed aside by the probe casing 320 in the direction of the soil as a target of measurement when the probe casing 320 is inserted into the ground. It is possible to curb a change in state of the soil as the target of measurement when the probe casing is inserted and thereby to accurately measure the moisture in the soil as the target of measurement by reducing the amount of mud pushed aside and leading to an increase in the amount.

Note that the angle formed by the transmission antenna plane with respect to the measurement section substrate and the angle formed by the reception antenna plane with respect to the measurement section substrate can be arbitrary angles between 0° and 90°.

Figure 76:
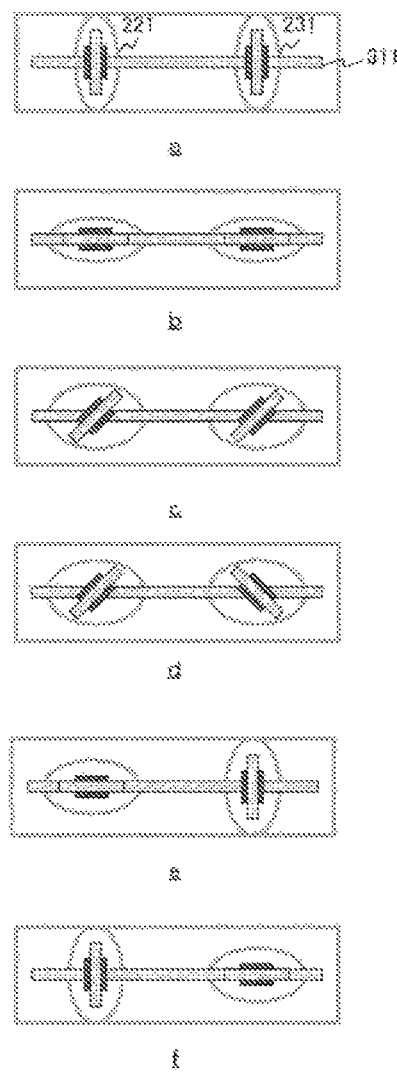
FIG. 76 is a diagram illustrating an example of an angle formed by an antenna plane and a measurement section substrate according to the first embodiment of the present technology.

FIG. 76 is a diagram illustrating an example of an angle formed between the antenna planes and the measurement section substrate according to the first embodiment of the present technology. As illustrated as an example in a in the drawing, it is possible to set the angle formed between the antenna planes on both the transmission side and the reception side and the measurement section substrate to 90 degrees. As illustrated as an example in b in the drawing, it is also possible to set the angle formed between the antenna planes on both the transmission side and the reception side and the measurement section substrate to 0 degrees.

As illustrated as an example in c in the drawing, it is also possible to set the angle formed between the antenna planes on both the transmission side and the reception side and the measurement section substrate to an angle other than 0 degrees and 90 degrees. As illustrated as an example in d in the drawing, it is possible to set the angle formed between the antenna planes on both the transmission side and the reception side and the measurement section substrate to an angle other than 0 degrees and 90 degrees, with one of the angles set to $+\alpha$ while the other angle set to $-\alpha$. Also, as illustrated as an example in e and f in the drawing, it is also possible to set one of the angles on the transmission side and the reception side to 90 degrees and to set the other to 0 degrees.

Figure 77:
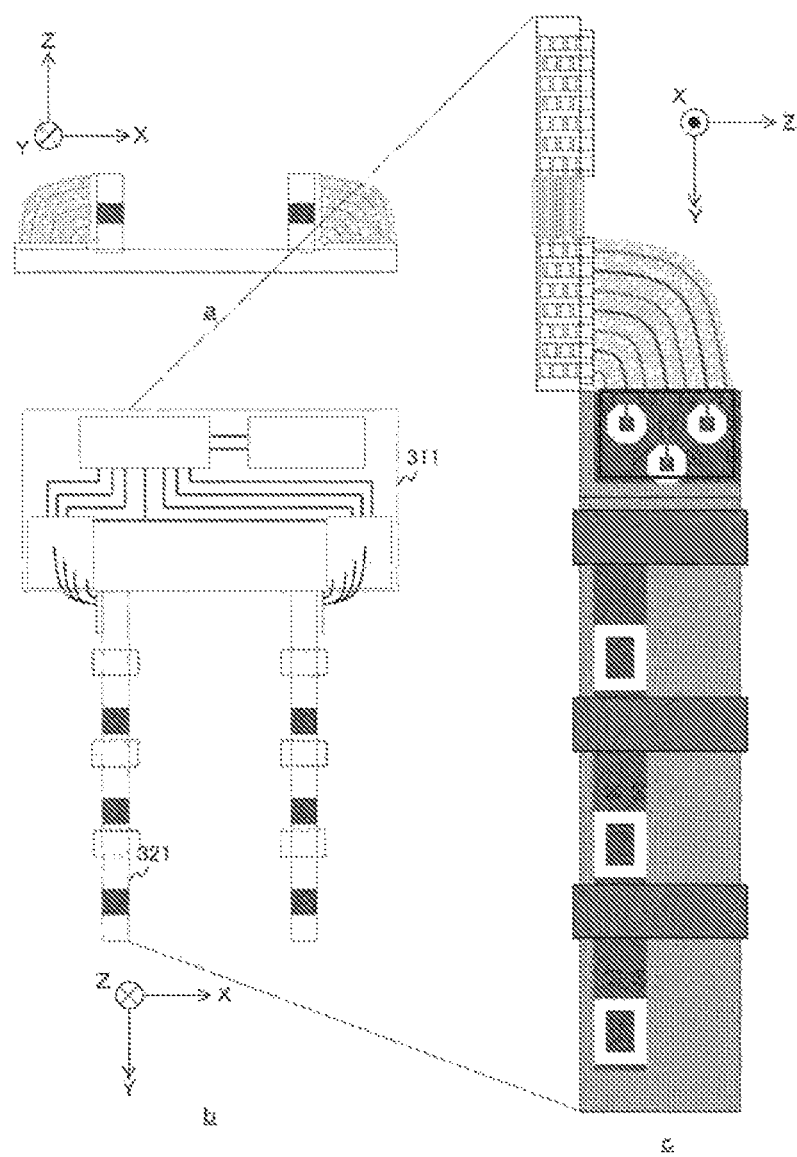
FIG. 77 is a diagram for explaining a method for connecting substrates according to the first embodiment of the present technology.
Figure 78:
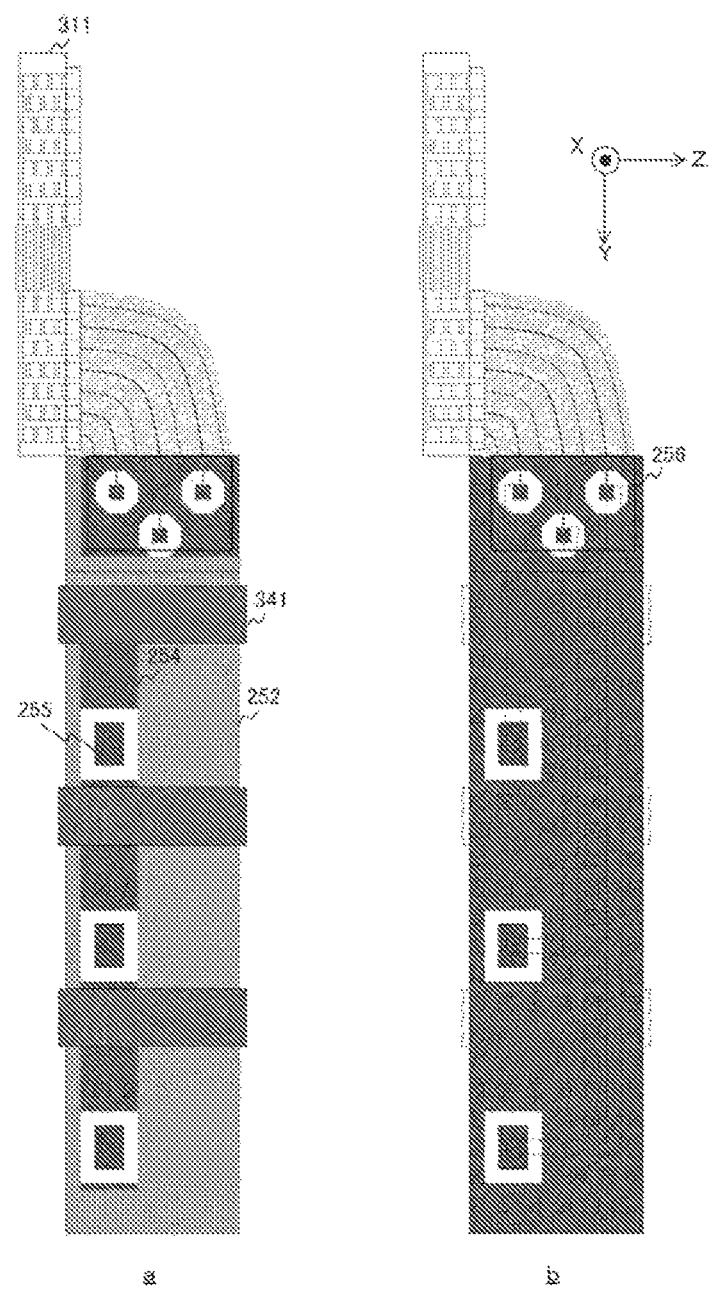

FIG. 77 is a diagram for explaining a method for connecting the measurement section substrate 311 to the intra-probe substrates 321 and 322 included in the sensor device 200 according to the first embodiment of the present technology. In the drawing, a is a view of the connecting location between these substrates when seen from above the sensor device 200. In the drawing, b is a diagram of these substrates when seen from the front of the sensor device 200. In the drawing, c is a detailed view of these substrates when seen from a side surface (X-axis direction) of the sensor device 200. The configuration in the drawing corresponds to the component (7).

The transmission path connecting portion illustrated in FIG. 77c electrically connects the transmission path in the measurement section substrate 311 to the transmission path in the intra-probe substrate 321 or 322. The transmission path connecting portion includes the same number of signal lines as the number of antennas, and each of the signal lines is shielded. In the drawing, a parallel cable is used as the transmission path connecting portion. In the parallel cable, the shield lines are further arranged on both sides of each signal line and are disposed in an aligned manner. On the assumption that the number of signal lines is three, for example, four shield lines are arranged and are disposed in an aligned manner. The shield layer is disposed on each of the upper side and the lower side of the signal lines and the shield lines disposed in the aligned manner. The surroundings of the signal lines are shielded by the shield wirings between the signal lines and the shield layers on the upper side and the lower side of the signal lines. The outer periphery of the integrated structure including the signal lines, the shield lines, and the shield layers is covered with an insulating protective material. Note that it is also possible to use the same number of coaxial cables as the number of antennas as the transmission path connecting portions.

Figure 78:
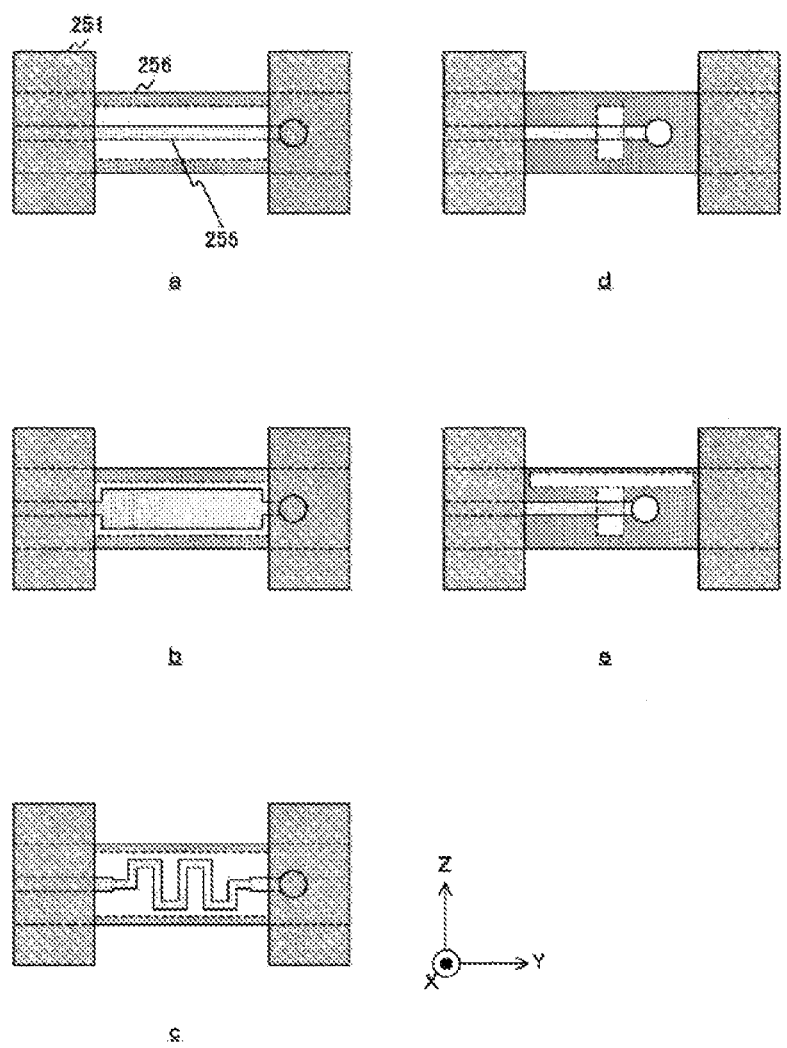
FIG. 78 is an example of a detailed view of the substrate according to the first embodiment of the present technology.

FIG. 78 is an example of a detailed view of the measurement section substrate 311, the intra-probe substrate 321 or 322, or the transmission path connecting portion included in the sensor device 200 according to the first embodiment of the present technology. The intra-probe substrate is illustrated in a in the drawing in a state where it is seen from the outside. In the intra-probe substrate illustrated in b in the drawing, the shape of the wiring layer on the surface layer is illustrated by a colored pattern, and the shapes of the vias connected to the wiring layer on the surface layer and the wiring layer in the inner layer are illustrated by the dotted lines.

Figure 79:
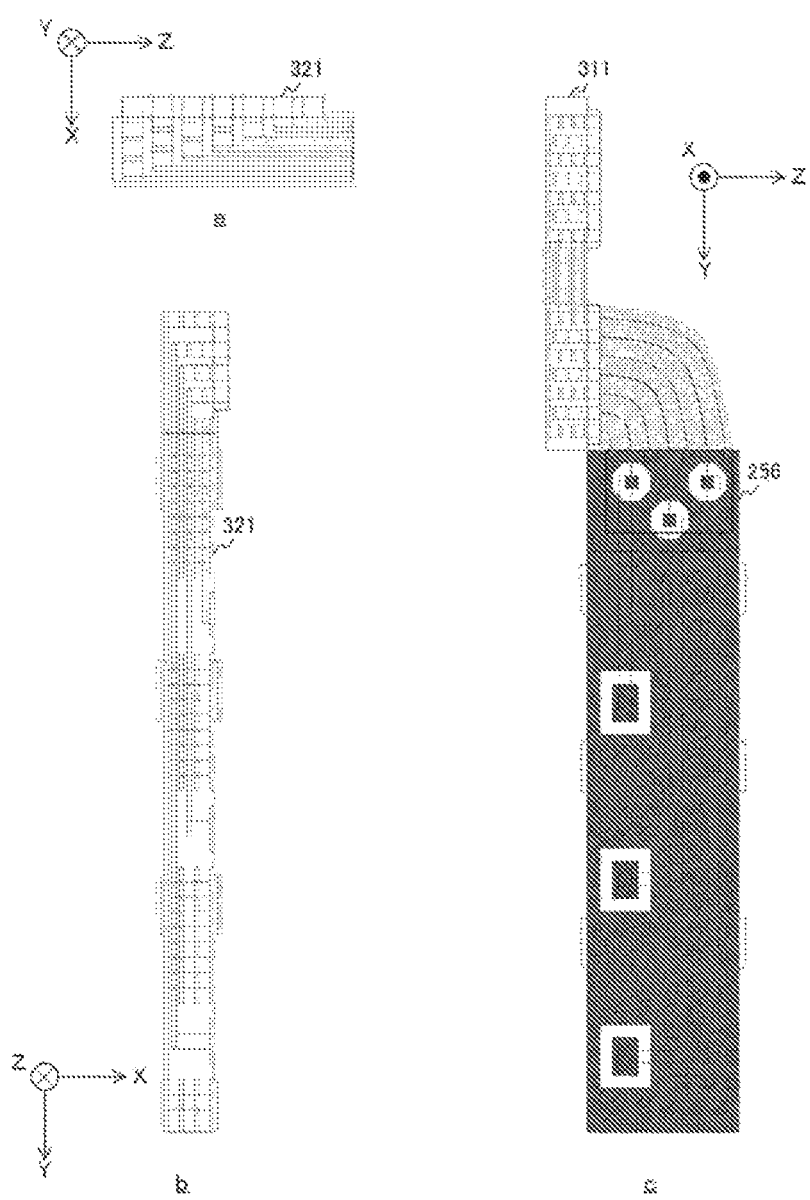
FIG. 79 is an example of a detailed view and a sectional view of the substrate according to the first embodiment of the present technology.

FIG. 79 is an example of a detailed view and a sectional view of the measurement section substrate 311, the intra-probe substrate 321, and the transmission path connecting portion included in the sensor device 200 according to the first embodiment of the present technology. In the drawing, a illustrates a sectional view of the intra-probe substrate 321 when seen from above (Y-axis direction) the sensor device 200. In the drawing, b illustrates a sectional view of the intra-probe substrate 321 when seen from the front (Z-axis direction) of the sensor device 200. In the drawing, c represents the shape of the wiring in the intra-probe substrate 321 when seen from a lateral side (X-axis direction) of the sensor device 200. In the intra-probe substrate illustrated in c in the drawing, the shape of the wiring layer on the surface layer is illustrated by the colored pattern, and the shapes of the vias connected to the wiring layer on the surface layer and the wiring layer in the inner layer are illustrated by the dotted lines. The number of antennas is three.

Figure 80:
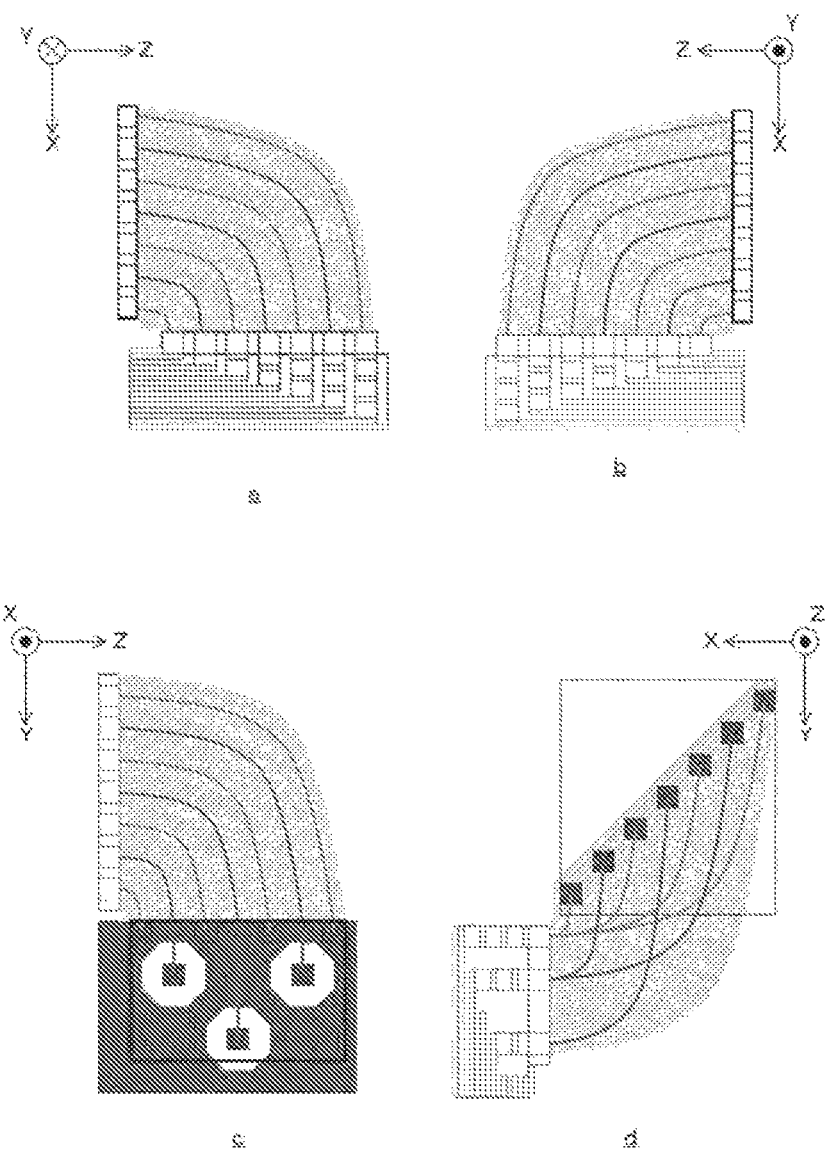
FIG. 80 is an example of a detailed view of a connected part according to the first embodiment of the present technology.

FIG. 80 is an example of a detailed view of the transmission path connecting portion included in the sensor device 200 according to the first embodiment of the present technology. In the drawing, a is a view of the transmission path connecting portion when the sensor device 200 is seen in the positive direction of the Y axis from the above. On the lower side of the drawing, a sectional view when the connector 323 for connecting the transmission path connecting portion to the intra-probe substrate 321 is seen from the above and a sectional view when the intra-probe substrate 321 is seen from the above are illustrated. On the left side of the drawing, a sectional view when the connector 314 for connecting the transmission path connecting portion to the measurement section substrate 311 is seen from the above is illustrated. In the drawing, b is a diagram of the transmission path connecting portion when the sensor device 200 is seen in the negative direction of the Y axis from the lower side. On the lower side of the drawing, a sectional view when the connector 323 for connecting the transmission path connecting portion to the intra-probe substrate 321 is seen from the lower side and a sectional view when the intra-probe substrate 321 is seen from the lower side are illustrated. On the right side of the drawing, a sectional view when the connector 314 for connecting the transmission path connecting portion and the measurement section substrate 311 is seen from the lower side is illustrated. In the drawing, c is a diagram of the transmission path connecting portion when the sensor device 200 is seen in the positive direction of the X axis from a lateral side. On the lower side in the drawing, a plan view when the connector 323 for connecting the transmission path connecting portion and the intra-probe substrate 321 is seen in the positive direction of the X axis from the lateral side is illustrated. On the left side in the drawing, a sectional view when the connector 314 for connecting the transmission path connecting portion and the measurement section substrate 311 is seen from the lateral side is illustrated.

In the drawing, d is a diagram of the transmission path connecting portion and the connector 314 for connecting the transmission path connecting portion and the measurement section substrate 311 when the sensor device 200 is seen in the negative direction of the Z axis from the rear side of the front surface. On the lower side of the drawing, a sectional view when the connector 323 for connecting the transmission path connecting portion and the intra-probe substrate 321 is seen in the negative direction of the Z axis from the rear side of the front surface and a sectional view of the part for connection to the connector 323 when the intra-probe substrate 321 is seen in the negative direction of the Z axis from the rear side of the front surface are illustrated.

As illustrated as an example in a to d in the drawing, the transmission path connecting portion having higher flexibility than the measurement section substrate 311 and the intra-probe substrate 321 and including a plurality of transmission lines connects the transmission paths included in each of the two substrates (the measurement section substrate 311 and the intra-probe substrate 321) disposed to be orthogonal to each other.

Figure 81:
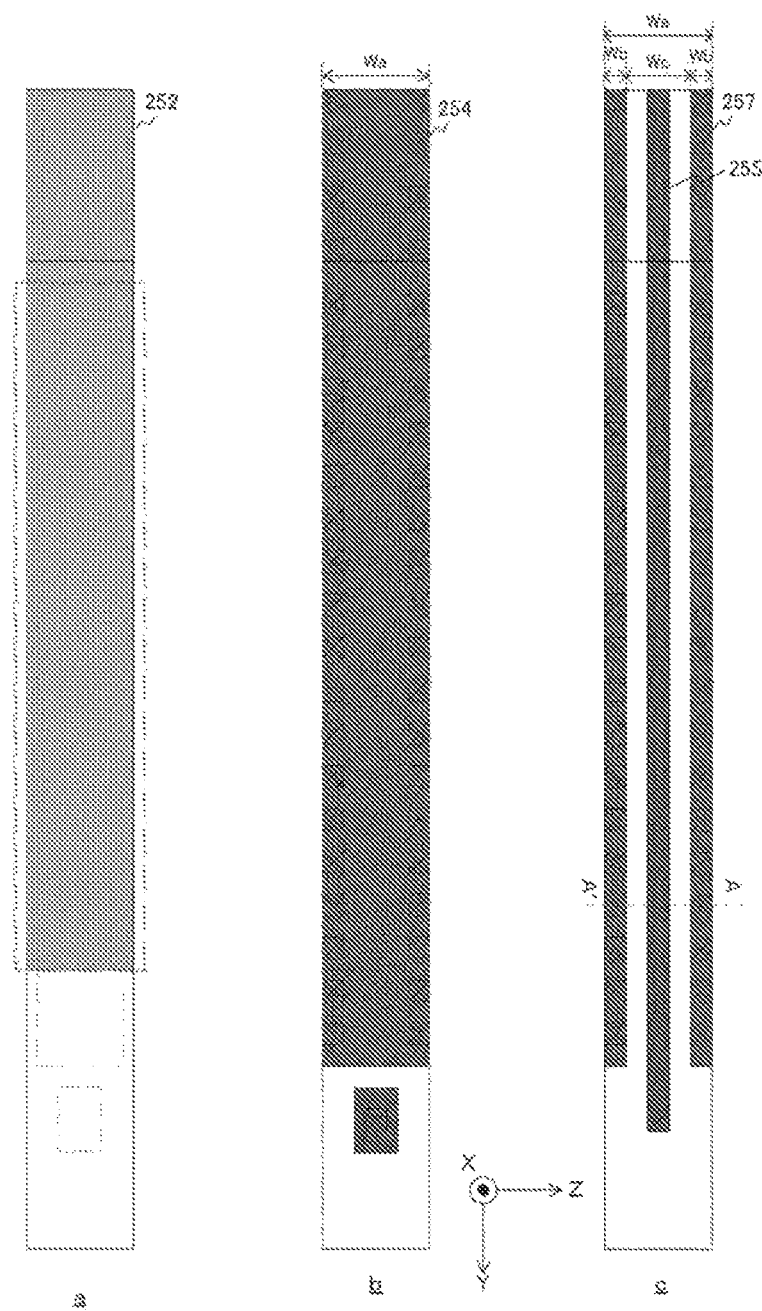
FIG. 81 is an example of a plan view of the first to third layers in an intra-probe substrate according to the first embodiment of the present technology.
Figure 82:
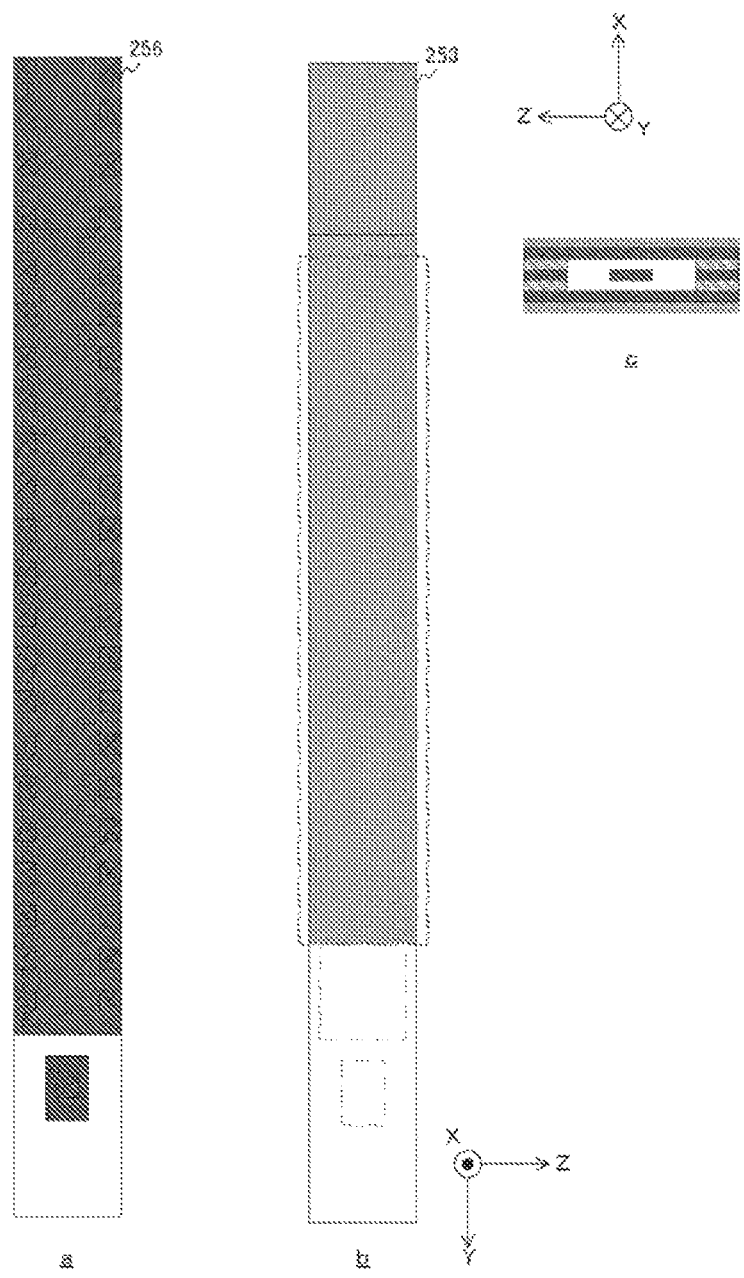
FIG. 82 is an example of a plan view of the fourth and fifth layers in the intra-probe substrate and a sectional view of the substrate according to the first embodiment of the present technology.

FIGS. 81 and 82 illustrate an example of a planar shape of the intra-probe substrate 321 according to the first embodiment of the present technology. The example illustrated in FIGS. 81 and 82 illustrates the planar shape of the intra-probe substrate 321 in which one antenna is included and the transmission path to the antenna includes a total of three wiring layers including one signal line layer and two shield layers with the signal line layer sandwiched therebetween.

Additionally, the example illustrated in FIGS. 81 and 82 illustrates an example in which the shield wirings are disposed on sides of the signal lines 255 by using a part of the wiring layer that is the same as that of the signal lines 255. In FIG. 81, a illustrates planar shapes of the solder resist 252 and the electromagnetic wave absorption material 251 disposed outside the first wiring layer. The solder resist 252 is a colored pattern, and the outer shape of the electromagnetic wave absorption material 251 is illustrated by the dotted line. In FIG. 81, b illustrates a planar shape of the first wiring layer (the shield layer 254 and the radiation element). In FIG. 81, c illustrates the second wiring layer (signal line) and the shield wirings: conductors 257) disposed on both sides of the signal lines 255 by using a part of the second wiring layer. The signs connecting quadrangles to diagonals with line segments disposed at the shield wiring 257 represent vias, and in c in FIG. 81, in particular, a via for connection between the shield layer 254 and the shield wiring (conductor 257) and a via for connection between the shield wiring and the shield layer 256, which will be described later, are illustrated on the pattern of the shield wiring 257. In the drawing, Wa indicates the width of the intra-probe substrate 321. Also, Wb indicates the width of the shield wirings, and Wc indicates the interval between the shield wiring ends.

In FIG. 82, a illustrates a planar shape of the third wiring layer (the shield layer 256 and the radiation element). In FIG. 82, b illustrates planar shapes of the solder resist 253 and the electromagnetic wave absorption material 251 disposed outside the third wiring layer. The solder resist 253 is illustrated by the colored pattern, and the outer shape of the electromagnetic wave absorption material 251 is illustrated by the dotted line. In FIG. 82, c is a sectional view of the intra-probe substrate 321 cut along the line A-A' in c in FIG. 81.

In the sectional view in c in FIG. 82, the solder resist 252 and the first wiring layer (shield layer 254) are disposed in order from the lower side of the paper plane, and the signal line 255 and the shield wirings 257 on both sides thereof are disposed thereon by using the second wiring layer. On these layers, the shield layer 256 and the solder resist 253 are disposed. The electromagnetic wave absorption material 251 (not illustrated) is disposed in the surroundings of the section in the region of the intra-probe substrate 321 where the transmission path is formed.

Figure 83:
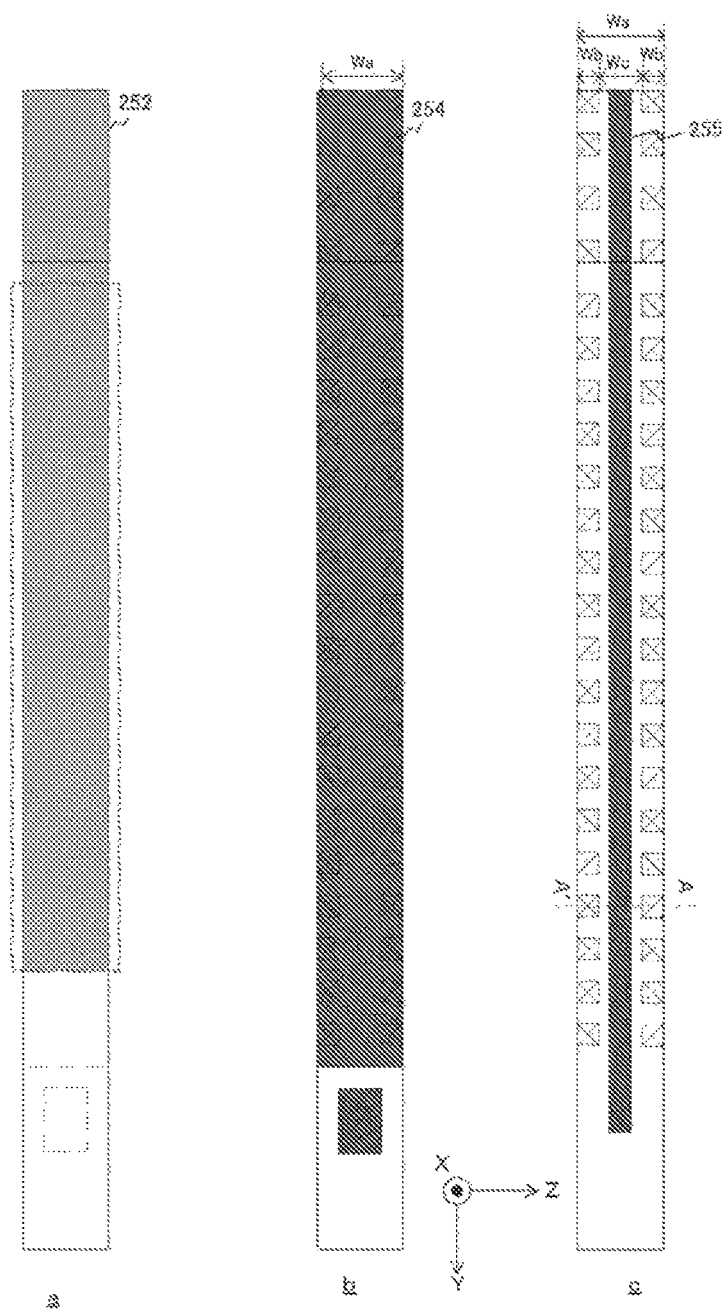
FIG. 83 is an example of a plan view of the first to third layers in the intra-probe substrate with no shield wiring according to the first embodiment of the present technology.
Figure 84:
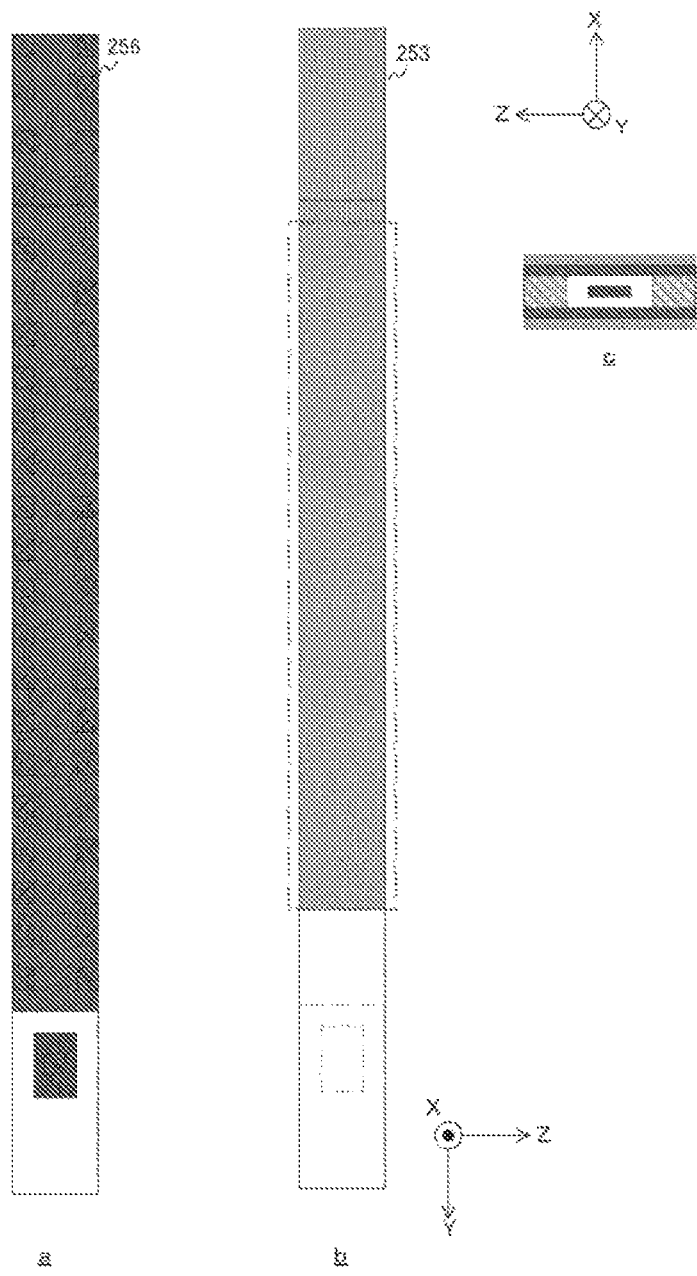
FIG. 84 is an example of a plan view of the fourth and fifth layers in the intra-probe substrate with no shield wiring and a sectional view of the substrate according to the first embodiment of the present technology.

FIGS. 83 and 84 illustrate another example of a planar shape of the intra-probe substrate 321 according to the first embodiment of the present technology. The example illustrated in FIGS. 83 and 84 illustrates the intra-probe substrate 321 including one antenna and a total of three wiring layers including one signal line layer for the transmission path to the antenna and two shield layers with the signal line layer sandwiched therebetween. Additionally, the example illustrated in FIGS. 83 and 84 illustrates an example in which sides of the signal lines 255 are shielded by using vias that pass through the sides of the signal lines 255 from the shield layer 256 disposed above the signal lines 255 and reach the shield layer 254 disposed below the signal lines 255 and arranging the vias in the array shape along the signal lines 255. In FIG. 83, c illustrates the via arrays of the shield. In the drawing, the signs connecting the quadrangles and the diagonals thereof with the line segments disposed on both sides of the signal lines 255 represent the vias. Also, the drawing illustrates that these vias with no colors in the drawing are not formed by the second wiring layer that is the same layer as that of the signal lines 255 but the vias passing through a side of the signal lines 255 from the upper layer than the signal lines 255 and extending to the lower layer than the signal lines 255. Since the planar shapes illustrated in FIGS. 83 and 84 other than c in FIG. 83 are similar to those illustrated in FIGS. 81 and 82, description thereof will be omitted. Note that c in FIG. 84 is a sectional view of the intra-probe substrate 321 cut along the line A-A' in c in FIG. 83. In FIG. 83, Wa indicates the width of the intra-probe substrate 321. Also, Wb indicates the width of the shield via arrays, and We indicates the interval between the via array ends.

Next, effects that the structure illustrated in c in FIG. 83 has will be described. In a case of the structure in which the sides of the signal lines 255 are shielded by using the shield wiring illustrated in c in FIG. 81, the signal lines 255 and the shield wiring are formed using the same wiring layer (the second wiring layer). Therefore, it is not possible to perform working such that the gap between the signal lines 255 and the shield wiring is equal to or less than a minimum working dimension that a pattern forming device has when the pattern of the signal lines 255 and the pattern of the shield wiring 257 are formed by working the second wiring layer. It is necessary to provide at least a distance corresponding to the minimum working dimension that the pattern forming device has between them. On the contrary, the signal lines 255 and the vias for shield passing through the sides of the signal lines 255 from the upper layer than the signal lines 255 and extending to the lower layer than the signal lines 255 are formed using different wiring layers in the case of the structure in which the sides of the signal lines 255 are shielded by using the via arrays for shield illustrated in c in FIG. 83. In other words, the pattern of the signal lines 255 is formed alone by using the pattern forming device. The vias for shield are also formed alone on the upper layer than the signal lines 255 by using the pattern forming device. Therefore, the distance between the signal lines 255 and the vias passing through the sides of the signal lines 255 can be set to an arbitrary value when the pattern layout is designed. In this manner, it is possible to reduce the distance between the signal line 255 and the via arrays for shield (the shield wiring in the case of FIG. 81) in the case of the structure illustrated in c in FIG. 83 as compared with the structure illustrated in c in FIG. 81. As a result, the effect that the width of the intra-probe substrate 321 illustrated in FIGS. 83 and 84 can be smaller than the width of the intra-probe substrate 321 illustrated in FIGS. 81 and 82 is achieved. Also, if it is possible to reduce the width of the intra-probe substrate, then it is possible to reduce the sectional area of the probe casing accommodating the intra-probe substrate, and this leads to a further effect that it is possible to accurately measure moisture. Details of this will be described later.

Figure 85:
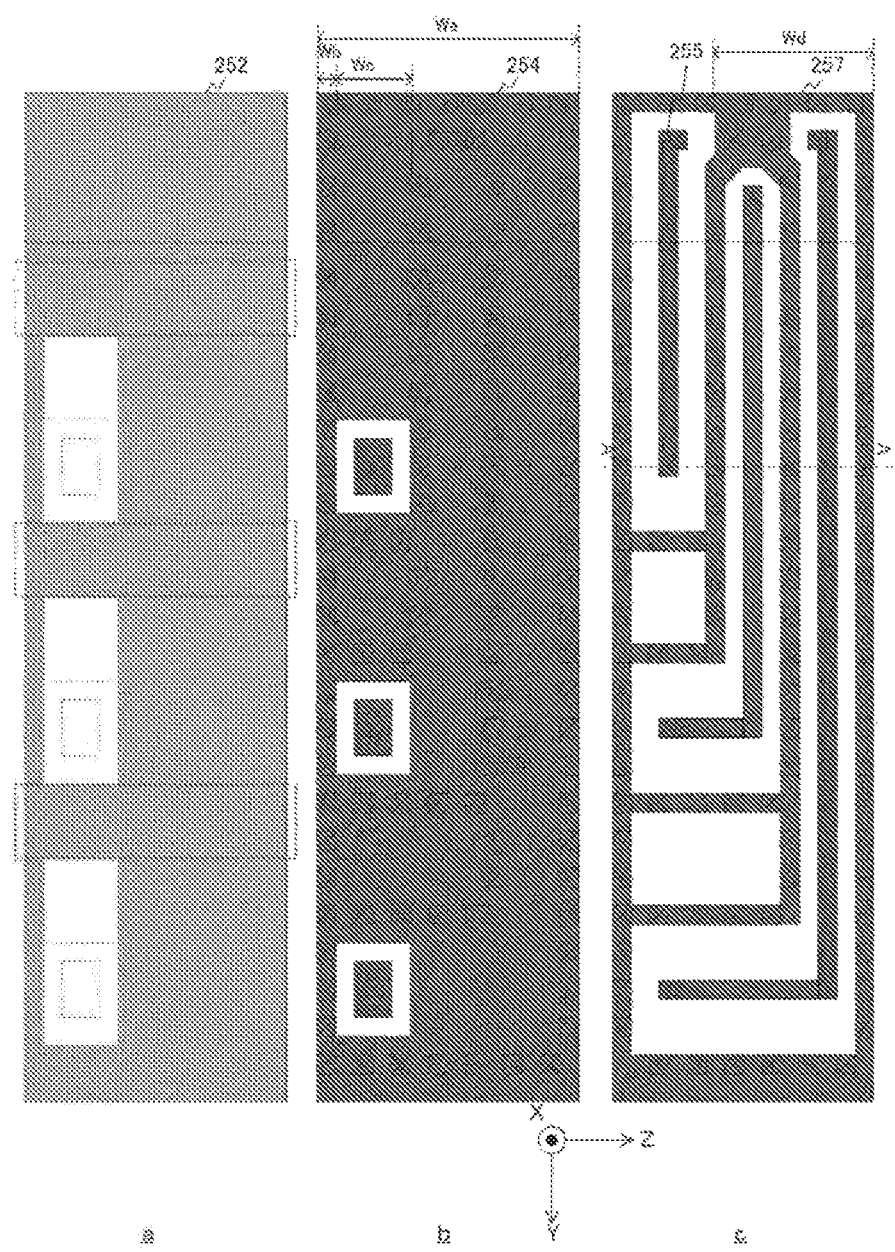
FIG. 85 is an example of a plan view of the first to third layers in the intra-probe substrate in which the number of antennas is three according to the first embodiment of the present technology.
Figure 86:
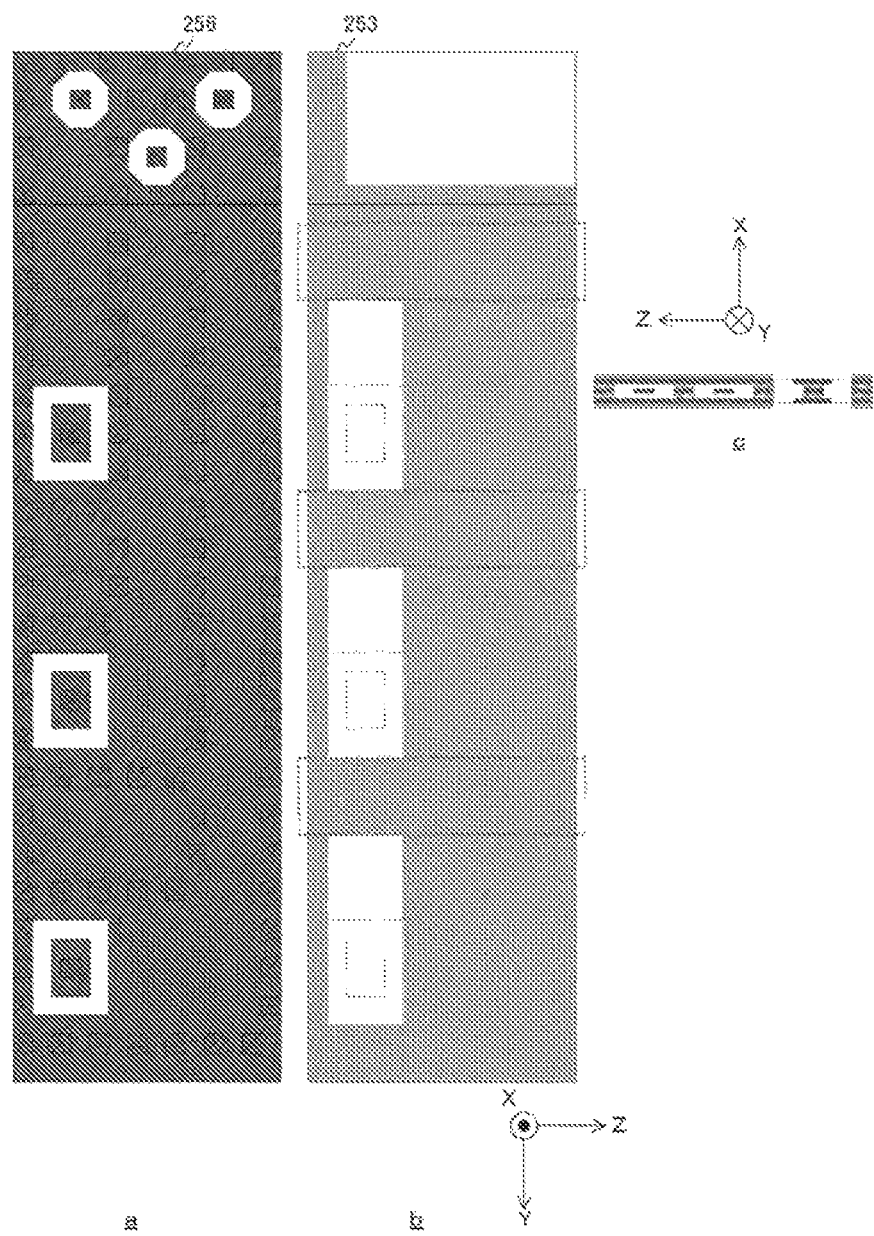
FIG. 86 is an example of a plan view of the fourth and fifth layers in the intra-probe substrate in which the number of antennas is three and a sectional view of the substrate according to the first embodiment of the present technology.

FIGS. 85 and 86 illustrate yet another example of a planar shape of the intra-probe substrate 321 according to the first embodiment of the present technology. The example illustrated in FIGS. 85 and 86 illustrate the intra-probe substrate 321 including n (n=3 in an example) antennas and a total of three wiring layers including one signal line layer for the transmission path to the antenna and the two shield layers with the signal line layer sandwiched therebetween. Additionally, the example illustrated in FIGS. 85 and 86 illustrates an example in which sides of the signal lines 255 are shielded by using a part of the wiring layer that is the same as that of the signal line 255. Since a role of each layer illustrated in each of FIGS. 85 and 86 is the same as that in FIGS. 81 and 82, description thereof will be omitted.

In b in FIG. 85, the shield layers 254 are formed by a part of the first wiring layer, and the three radiation elements included in the three antennas are formed by the other part of the first wiring layer. In FIG. 85, c illustrates an example in which the shield wirings are disposed on sides of the signal lines 255 by using a part of the wiring layer that is the same as that of the signal line 255 similarly to c in FIG. 81. In c in FIG. 85, the three signal lines 255 for connection to the three radiation elements illustrated in b in FIG. 85 are formed using a part of the second wiring layer. Additionally, in order to shield the sides of each of the three signal lines 255, a total of four shield wirings 257 are formed using the second wiring layer that is the same as that of the three signal lines 255 between and outside the three signal lines. Note that c in FIG. 86 is a sectional view of the intra-probe substrate 321 cut along the line A-A' in c in FIG. 85. In FIG. 85, Wa indicates the width of the intra-probe substrate 321. Also, Wb indicates the width of the shield layers, and We illustrates the interval between the shield layer ends. Wd indicates the width of the two transmission paths and the three shield wirings.

Figure 87:
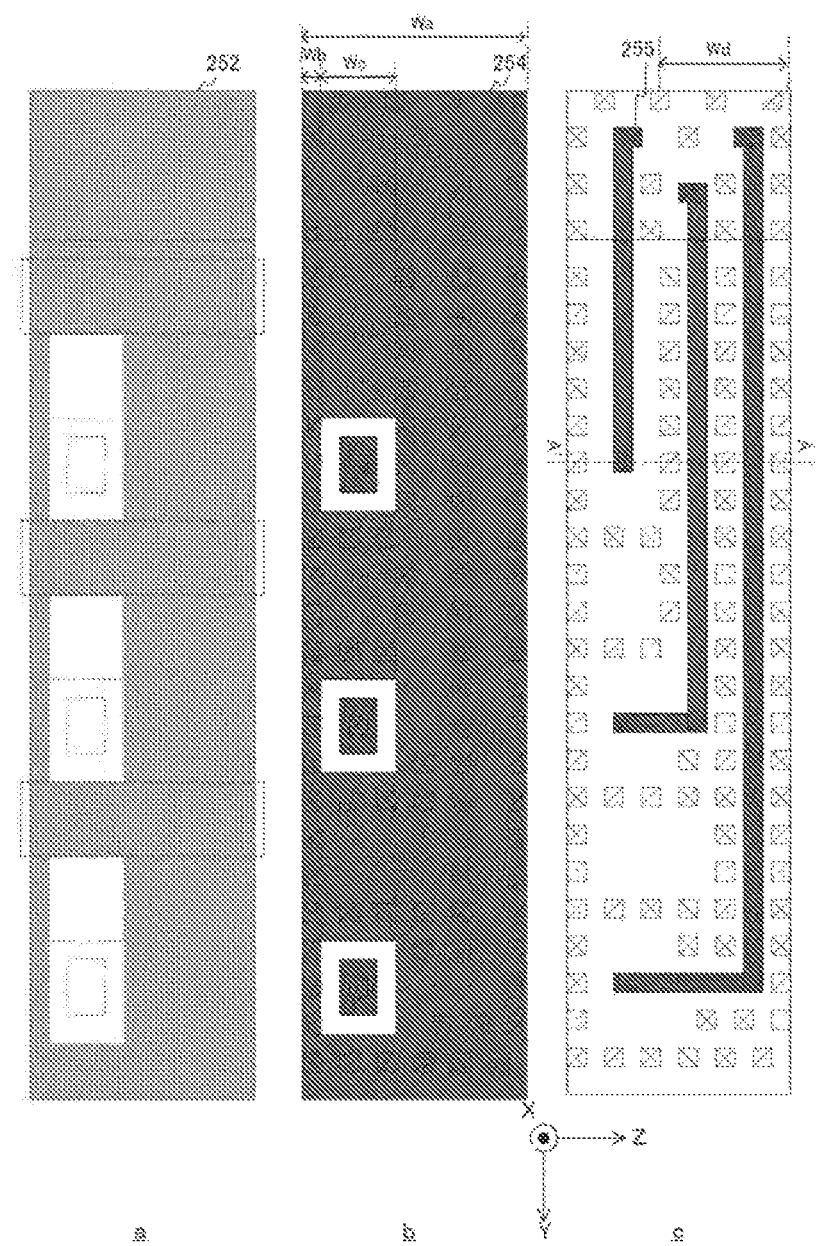
FIG. 87 is an example of a plan view of the first to third layers in the intra-probe substrate in which there is no shield wiring and the number of antennas is three according to the first embodiment of the present technology.
Figure 88:
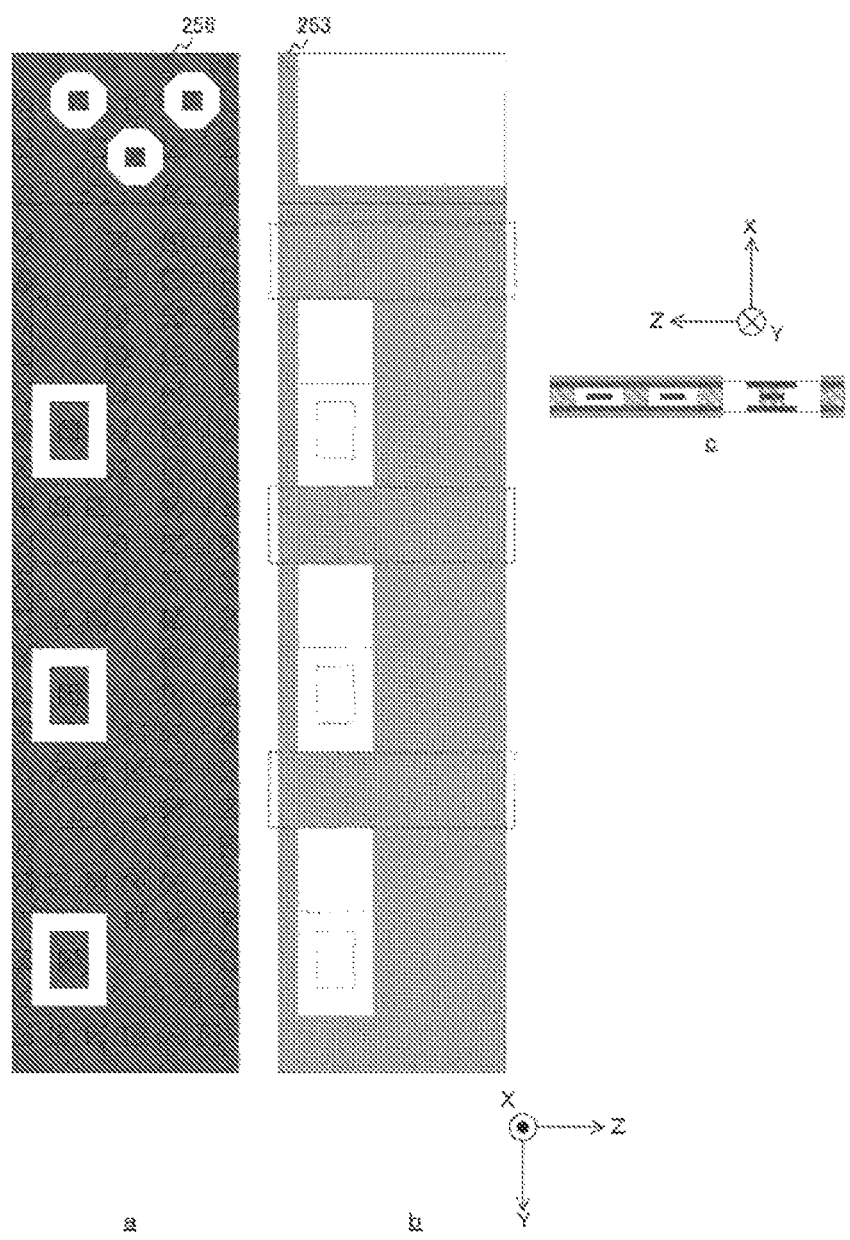
FIG. 88 is an example of a plan view of the fourth and fifth layers in the intra-probe substrate in which there is no shield wiring and the number of antennas is three and a sectional view of the substrate according to the first embodiment of the present technology.

FIGS. 87 and 88 illustrate yet another example of a planar shape of the intra-probe substrate 321 according to the first embodiment of the present technology. The example illustrated in FIGS. 87 and 88 illustrate the intra-probe substrate 321 including n (n=3 in an example) antennas and a total of three wiring layers including one signal line layer for the transmission path to the antenna and the two shield layers with the signal line layer sandwiched therebetween. Additionally, the example illustrated in FIGS. 87 and 88 illustrates an example in which sides of the signal lines 255 are shielded by using vias that pass through the sides of the signal lines 255 from the shield layer 256 disposed above the signal lines 255 and reach the shield layer 254 disposed below the signal lines 255 and arranging the vias in the array shape along the signal lines 255. In b in FIG. 87, the shield layers 254 are formed using a part of the first wiring layer, and the three radiation elements included in the three antennas are formed using the other part of the first wiring layer. In FIG. 87, c illustrates an example in which sides of the signal lines 255 are shielded by using via arrays for shield similarly to c in FIG. 83. In c in FIG. 87, the three signal lines 255 for connection to the three radiation elements illustrated in b in FIG. 87 are formed using a part of the second wiring layer. Additionally, in order to shield the lateral sides of these three signal lines 255, a total of four via arrays for shield are disposed between and outside the three signal lines.

Note that c in FIG. 88 is a sectional view of the intra-probe substrate 321 cut along the line A-A' in c in FIG. 87. In FIG. 87, Wa indicates the width of the intra-probe substrate 321. Also, Wb indicates the width of the shield layers, and Wc illustrates the interval between the shield layer ends. Wd indicates the width of the two transmission paths and the three shield wirings.

Next, effects that the structure illustrated in c in FIG. 87 has will be described.

Similarly to c in FIG. 83, the three signal lines 255 and the four via arrays illustrated in c in FIG. 87 are separately (independently in other words) pattern-formed. As a result, the distance between the three signal line 255 and the four via arrays illustrated in c in FIG. 87 can be shorter than the distance between the three signal lines 255 and the four shield wirings illustrated in c in FIG. 85. As a result, the width of the intra-probe substrate 321 illustrated in FIGS. 87 and 88 can be smaller than the width of the intra-probe substrate 321 illustrated in FIGS. 85 and 86. Also, if it is possible to reduce the width of the intra-probe substrate, then it is possible to reduce the sectional area of the probe casing accommodating the intra-probe substrate, and this leads to a further effect that it is possible to accurately measure moisture. Details of this will be described later.

Figure 89:
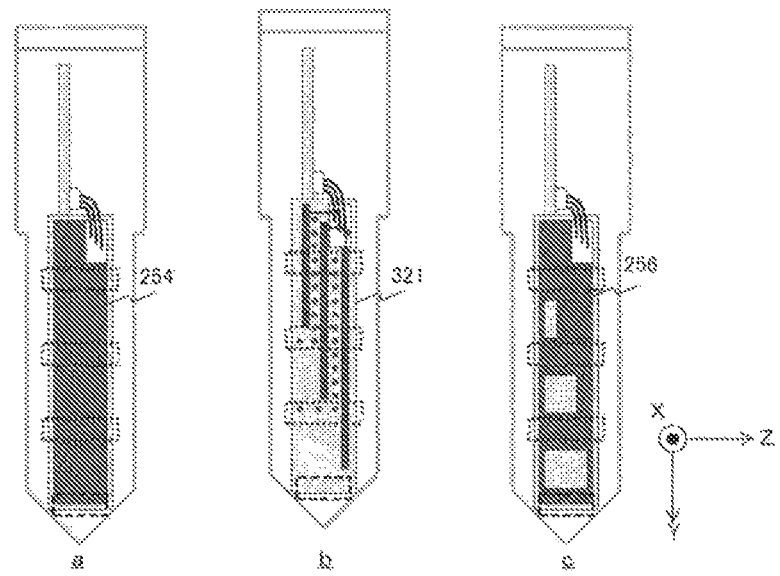
FIG. 89 is a diagram for explaining a shield based on a via array according to the first embodiment of the present technology.

FIG. 89 is a diagram for explaining shield achieved by via arrays according to the first embodiment of the present technology. In the drawing, a illustrates the first wiring layer, and b in the drawing illustrates the second wiring layer. In the drawing, c illustrates the third wiring layer. It is also possible to align the via arrays in the surroundings of the signal lines 255 and shield them without providing the shield wirings in the second wiring layer. Since electrical coupling between the transmission paths is reduced by these vias, it is possible to curb radiation of unintended antenna opening portion (radiation element) and to measure moisture with high accuracy.

Also, it is desirable that the intervals between adjacent vias be equal to or less than 1/10 the wavelength of the center frequency of the electromagnetic waves, and it is further desirable that the intervals be equal to or less than 1/10 the wavelength of the maximum frequency. When the measurement frequency band ranges from 1 to 9 GHz, for example, the center frequency is 5 GHz, it is thus desirable that the intervals between the vias be equal to or less than 6 mm, and is further desirable that the intervals be equal to or less than 3.3 mm since the maximum frequency is 9 GHz.

Figure 90:
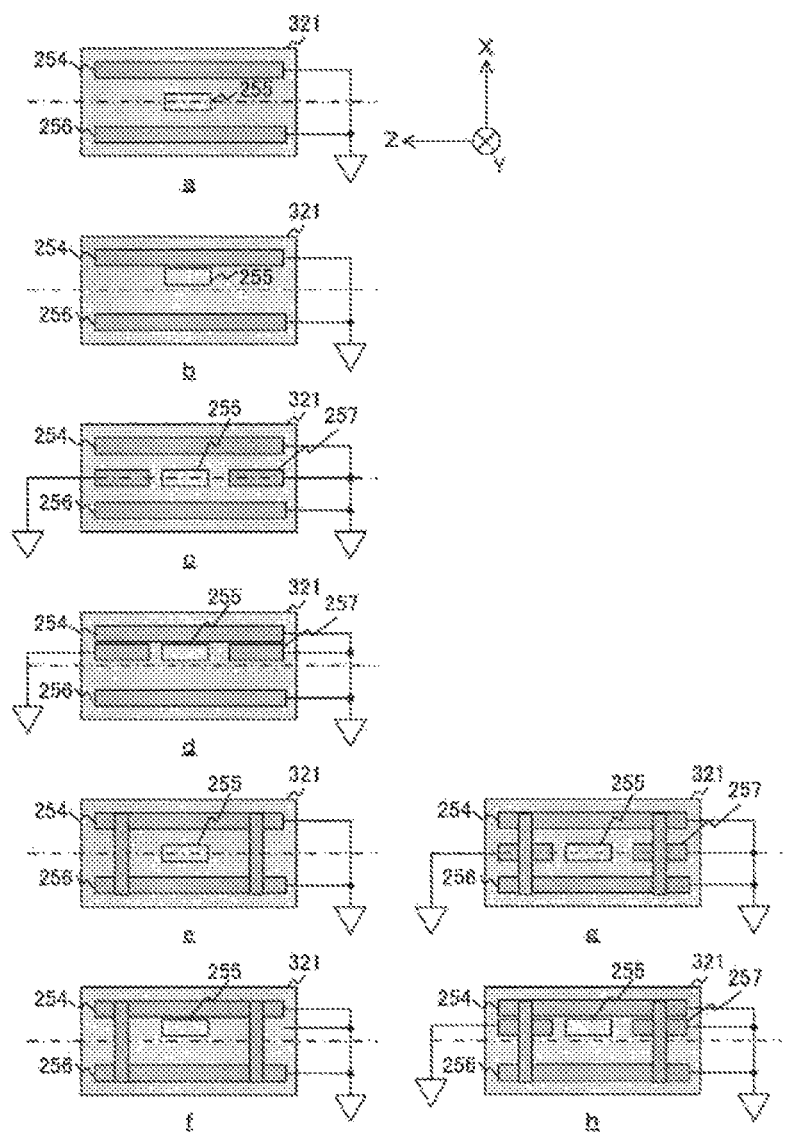
FIG. 90 is a diagram illustrating an example of a strip line according to the first embodiment of the present technology.

FIG. 90 is a diagram illustrating an example of the strip line according to the first embodiment of the present technology. The drawing illustrates a sectional shape of the strip line formed in the intra-probe wiring substrate, for example. As illustrated as an example in a in the drawing, the strip line may be a vertically symmetrical with the shield layers 254 and 256 caused to serve as upper and lower surfaces. As illustrated as an example in b in the drawing, this may be a strip line using wiring layers in which the distance from the layer with the signal lines 255 formed therein to the layer with the shield layers 254 formed therein and the distance from the layer with the signal lines 255 formed therein to the layer with the shield layers 254 formed therein are different distances by using a strip line that is vertically asymmetrical, that is, an electronic substrate including more than three wiring layers. As illustrated as an example in c in the drawing, this may be a strip line that is vertically symmetrical with the shield wirings disposed on lateral sides and both sides of the signal lines 255. As illustrated as an example in d in the drawing, this may be a vertically asymmetrical strip line with the shield wirings disposed on the sides of the signal lines 255.

As illustrated as an example in e in the drawing, this may be a vertically symmetrical strip line with a post wall. Here, the post wall indicates the plurality of via arrays disposed substantially in parallel with the transmission paths. The disposition of the post wall reduces radiation from the substrate end to the outside of the substrate and electrical coupling between adjacent lines. As illustrated as an example in f in the drawing, this may be a vertically asymmetrical strip line with a post wall. As illustrated as an example in g in the drawing, this may be a vertically symmetrical strip line including both the post wall and the shield wirings. As illustrated as an example in h in the drawing, this may be a vertically asymmetrical strip line including both the post wall and the shield wirings.

Also, although the intra-probe substrate 321 is typically a glass epoxy substrate using FR-4 as a base material, the intra-probe substrate 321 may be a substrate using modified-polyphenylene ether (m-PPE), polytetrafluoro ethylene (PTFE), or the like with excellent high-frequency properties. Also, the intra-probe substrate 321 may be a substrate using ceramics with high dielectric constant or may be a build-up substrate as a combination of a plurality of types of above substrates. Moreover, the intra-probe substrate 321 may be a flexible substrate using polyimide, polyester, polyethylene terephthalate, or the like with flexibility or may be a rigid flexible substrate as a combination of a rigid substrate and a flexible substrate.

Figure 91:
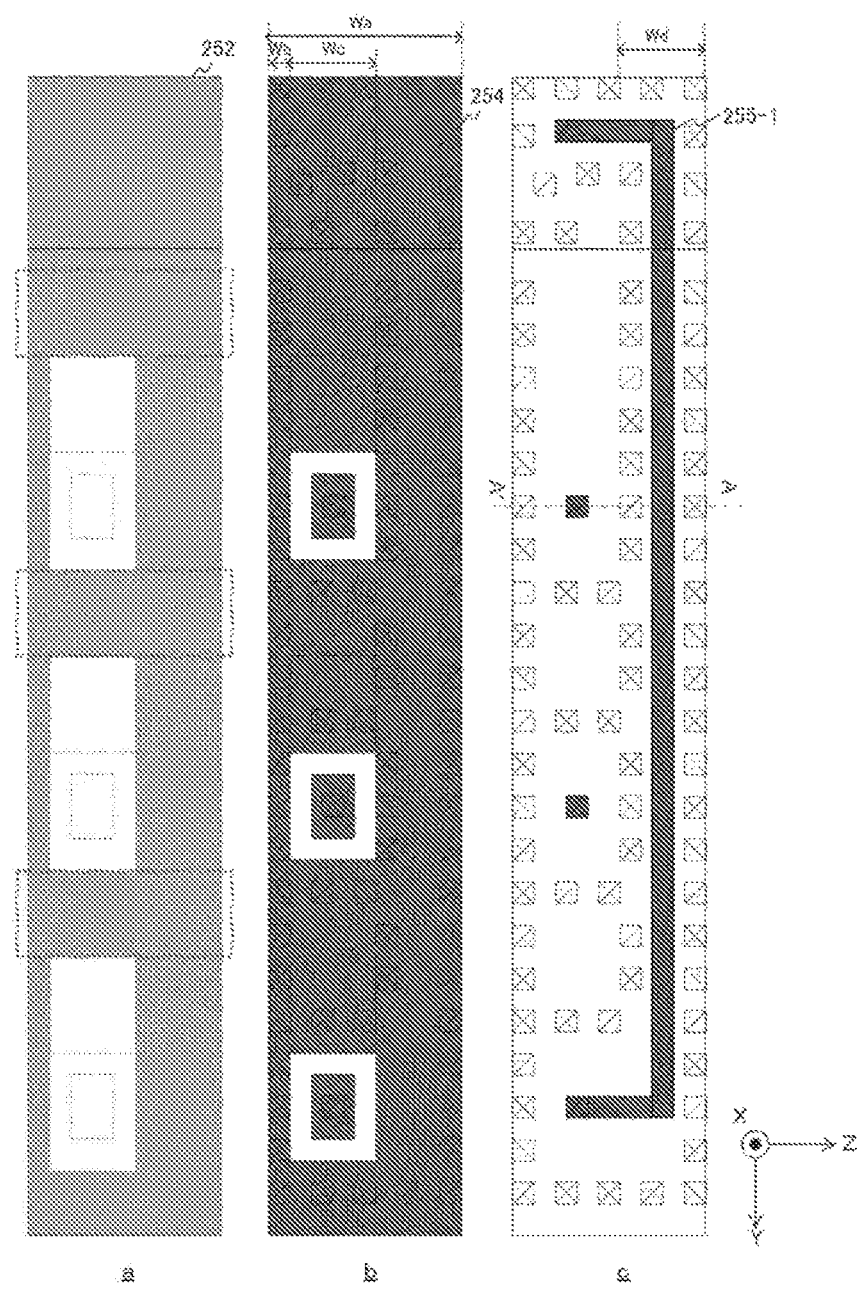
FIG. 91 is an example of a plan view of the first to third layers from among seven layers in the intra-probe substrate according to the first embodiment of the present technology.
Figure 92:
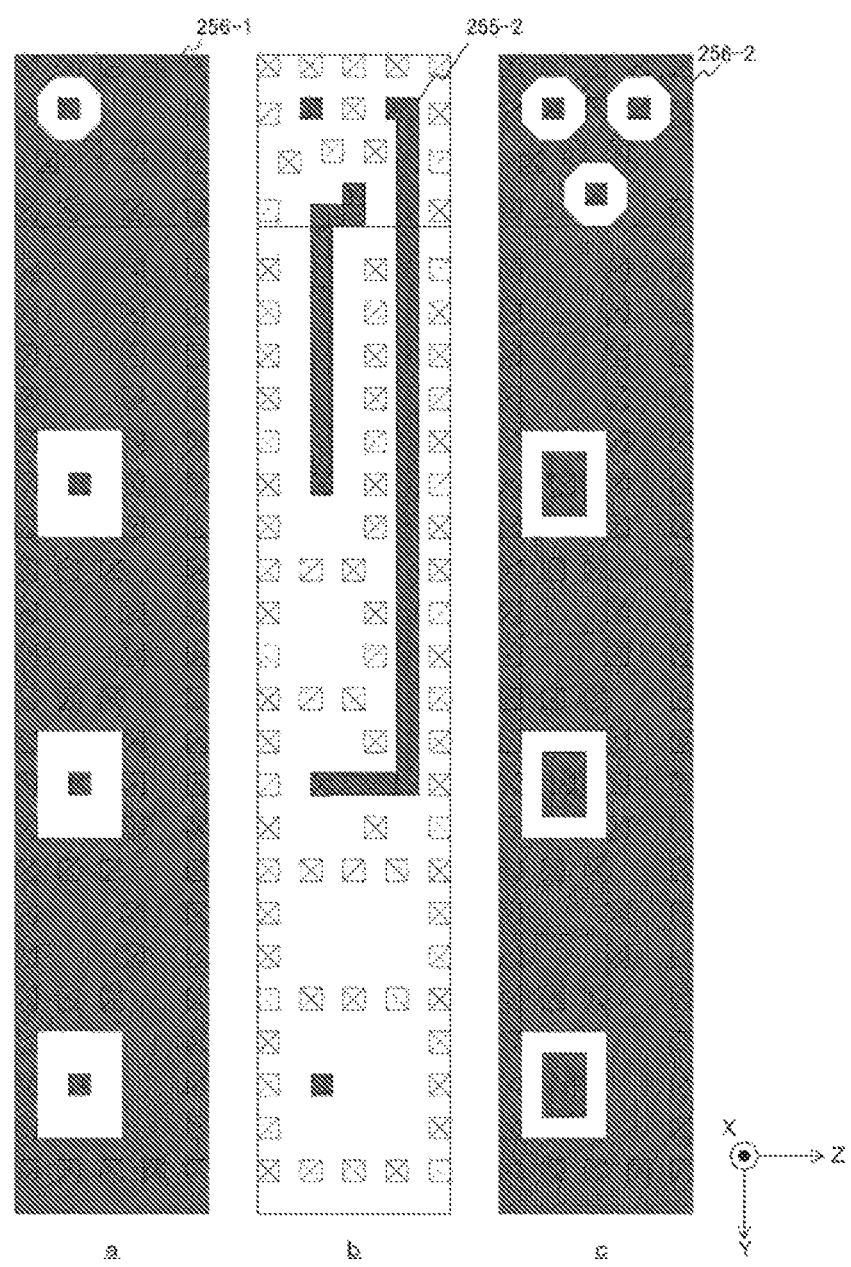
FIG. 92 is an example of a plan view of the fourth to sixth layers from among the seven layers in the intra-probe substrate according to the first embodiment of the present technology.
Figure 93:
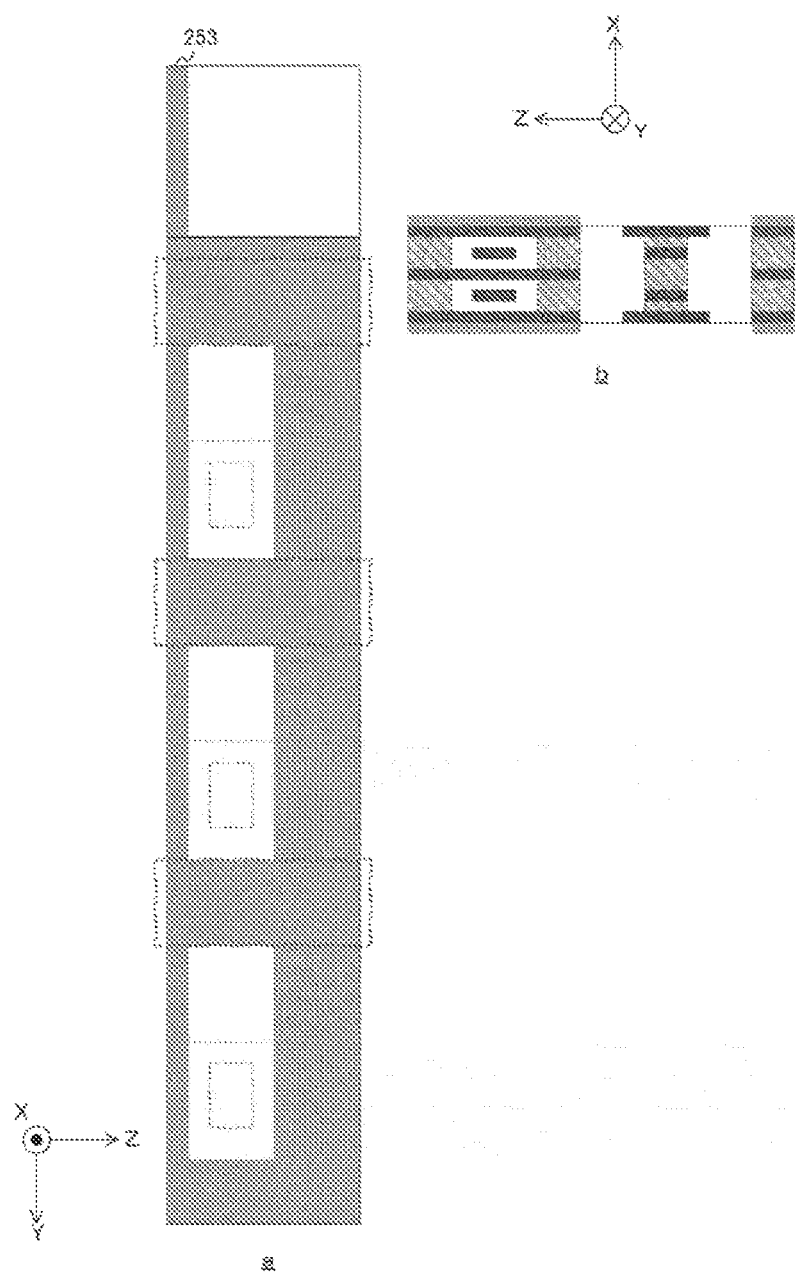
FIG. 93 is an example of a plan view of the seventh layer in the intra-probe substrate and a sectional view of the substrate according to the first embodiment of the present technology.

FIGS. 91 to 93 illustrate yet another example of a planar shape of the intra-probe substrate 321 according to the first embodiment of the present technology. The example illustrated in FIGS. 91 to 93 illustrates an example in which n (n=3 in an example) antennas are included and n transmission paths connected to the n antennas are formed in the intra-probe substrate 321 including a total of 2n−1 wiring layers including n−1 signal line layers and n shield layers with the signal line layers sandwiched therebetween. Additionally, the example illustrated in FIGS. 91 to 93 illustrates an example in which sides of the signal lines 255 are shielded by using vias that pass through the sides of the signal lines 255 from the shield layer disposed above the signal lines 255 and reach the shield layer disposed below the signal lines 255 and arranging the vias in the array shape along the signal lines 255.

In b in FIG. 91, the shield layers 254 are formed using a part of the first wiring layer, and three radiation elements 259 included in the three antennas are formed using the other part of the first wiring layer. In FIG. 91, Wa indicates the width of the intra-probe substrate 321. Also, Wb indicates the width of the shield layers, and Wc illustrates the interval between the shield layer ends. Wd indicates the width of the one transmission path and the two shield wirings.

Also, in the example illustrated in FIGS. 91 to 93, the three signal lines connected to each of the three antennas are formed using the two signal line layers (the second and fourth wiring layers) included in the substrate including the five wiring layers.

In the second wiring layer illustrated in c in FIG. 91,
(1) one signal line 255 for connection to the first radiation element from among the three radiation elements illustrated in b in FIG. 91 is formed.
(2) In order to connect the three radiation elements 259 disposed on one surface layer (first wiring layer) of the intra-probe substrate 321 to the three radiation elements disposed on the other surface layer (fifth wiring layer) with the signal lines 255 for connection to each of the radiation elements 259 sandwiched therebetween, the vias for connection to the second and third radiation elements are formed at positions immediately below these radiation elements, to which the signal lines 255 are not connected in the second wiring layer.
(3) In order to shield sides of the signal lines 255 in (1) above, via arrays for shield are disposed on both sides of the signal lines.
(4) In order to tightly connect the shield layer 254 formed using the wiring layer in the first layer to the shield layer 256 formed using the wiring layers in the third layer and the fifth layer, the via arrays are also disposed in the vicinity of the outer edges of these shield layers.

On the other hand, in the fourth wiring layer illustrated in b in FIG. 92,
(1) Two signal lines 255 for connection to the second and third radiation elements, for which the signal lines 255 are not connected in the second wiring layer, from among the three radiation elements illustrated in b in FIG. 91 are formed.
(2) In order to connect the three radiation elements 259 disposed on one surface layer (first wiring layer) of the intra-probe substrate 321 to the three radiation elements disposed on the other surface layer (fifth wiring layer) with the signal lines 255 for connection to each of the radiation elements 259 sandwiched therebetween, the vias for connection to the first radiation element are formed at positions immediately below the radiation element, to which the signal lines 255 are not connected in the fourth wiring layer.
(3) In order to shield sides of the signal lines 255 in (1) above, via arrays for shield are disposed on both sides of the signal lines.
(4) In order to tightly connect the shield layer 254 formed using the wiring layer in the first layer to the shield layer 256 formed using the wiring layers in the third layer and the fifth layer, the via arrays are also disposed in the vicinity of the outer edges of these shield layers.

Note that b in FIG. 93 is a sectional view of the intra-probe substrate 321 cut along the line A-A' in c in FIG. 91.

Next, effects that the structures illustrated in c in FIG. 91 and b in FIG. 92 have will be described. With this structure illustrated in these drawings, the effect of reducing the width of the intra-probe substrate 321 is achieved by shielding the sides of the signal lines 255 by using the via arrays for shield illustrated in c in FIG. 87. In the structures illustrated in c in FIG. 91 and b in FIG. 92, the number of signal lines to be disposed in one signal line layer is reduced by using more signal line layers as compared with the structure illustrated in c in FIG. 87. With this structure, the effect of reducing the width of the intra-probe substrate 321 as compared with the structure illustrated in c in FIG. 87 is achieved.

Figure 94:
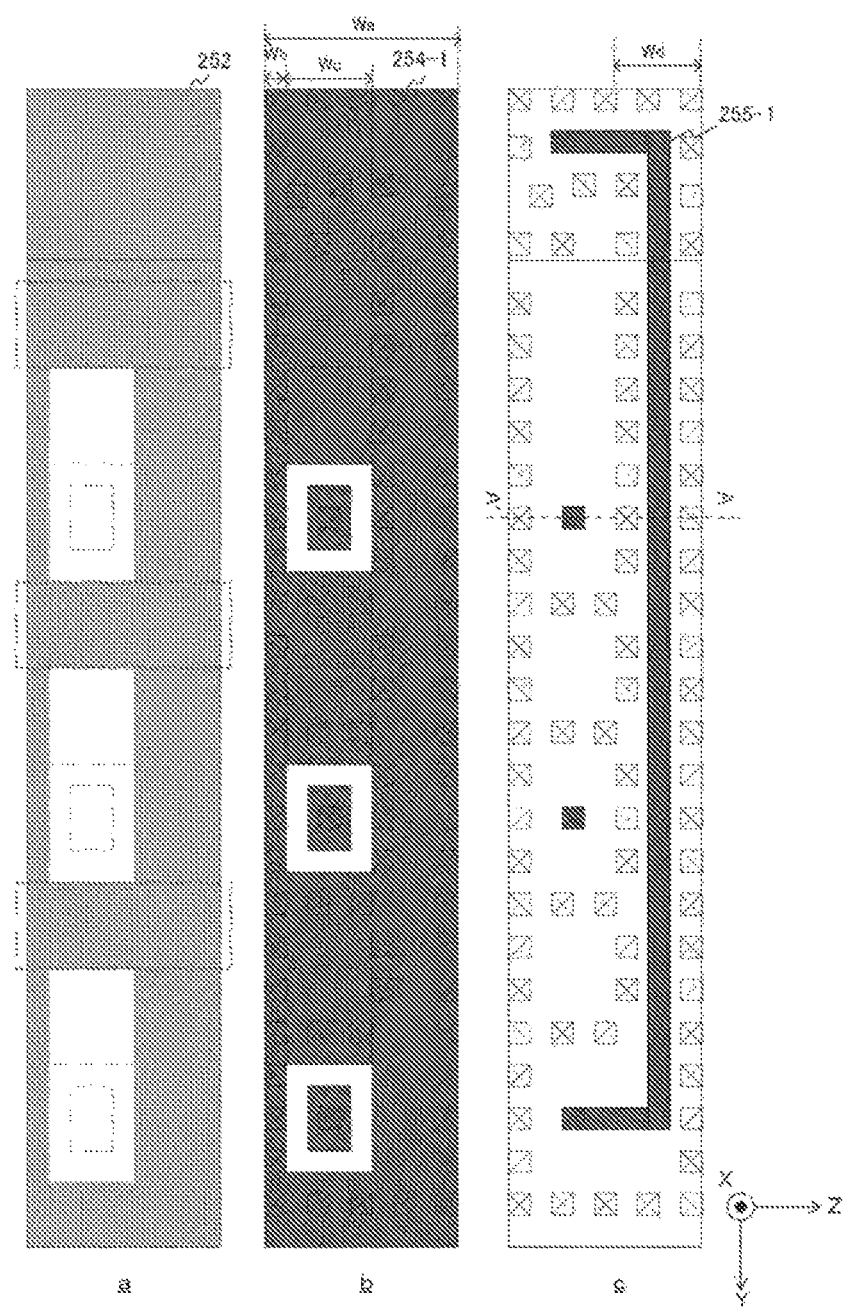
FIG. 94 is an example of a plan view of the first to third layers from among nine layers in the intra-probe substrate according to the first embodiment of the present technology.
Figure 95:
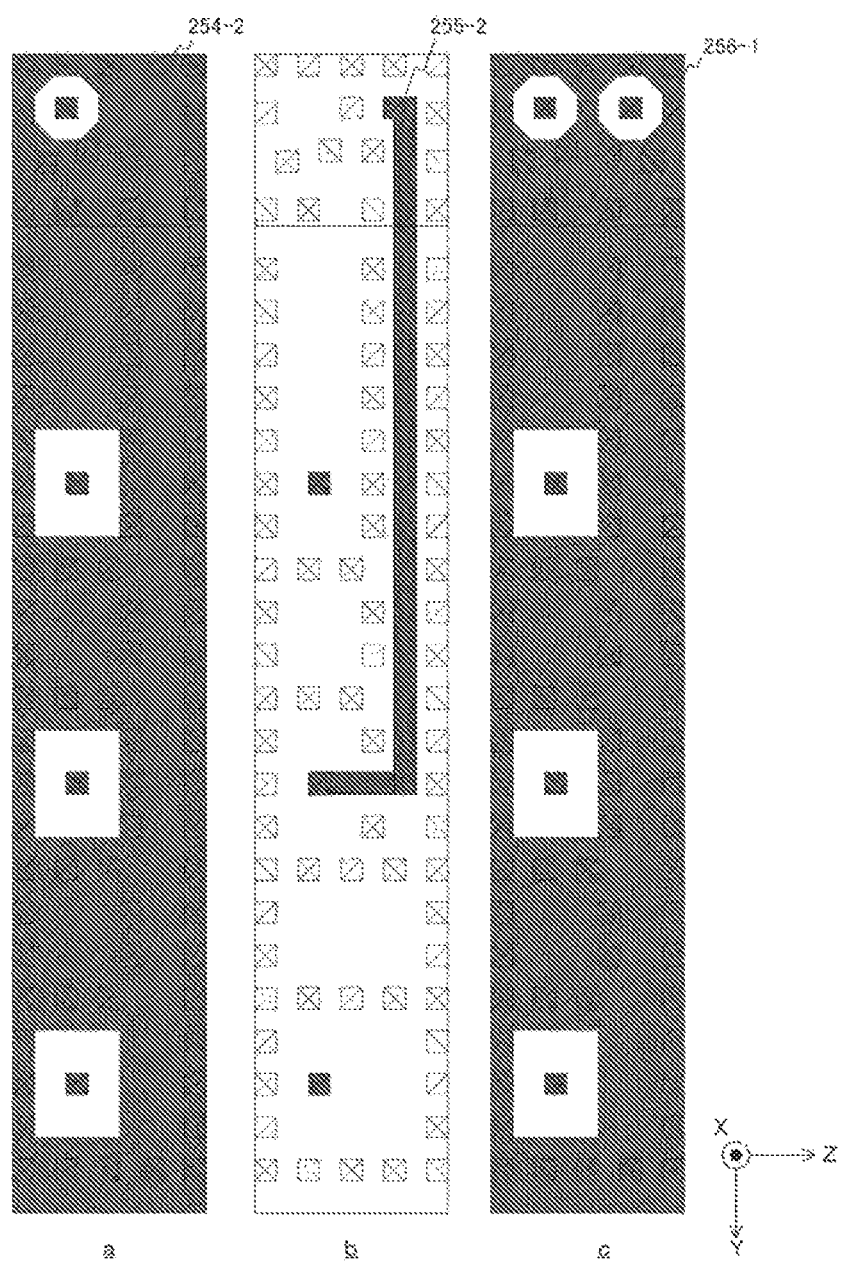
FIG. 95 is an example of a plan view of the fourth to sixth layers from among the nine layers in the intra-probe substrate according to the first embodiment of the present technology.
Figure 96:
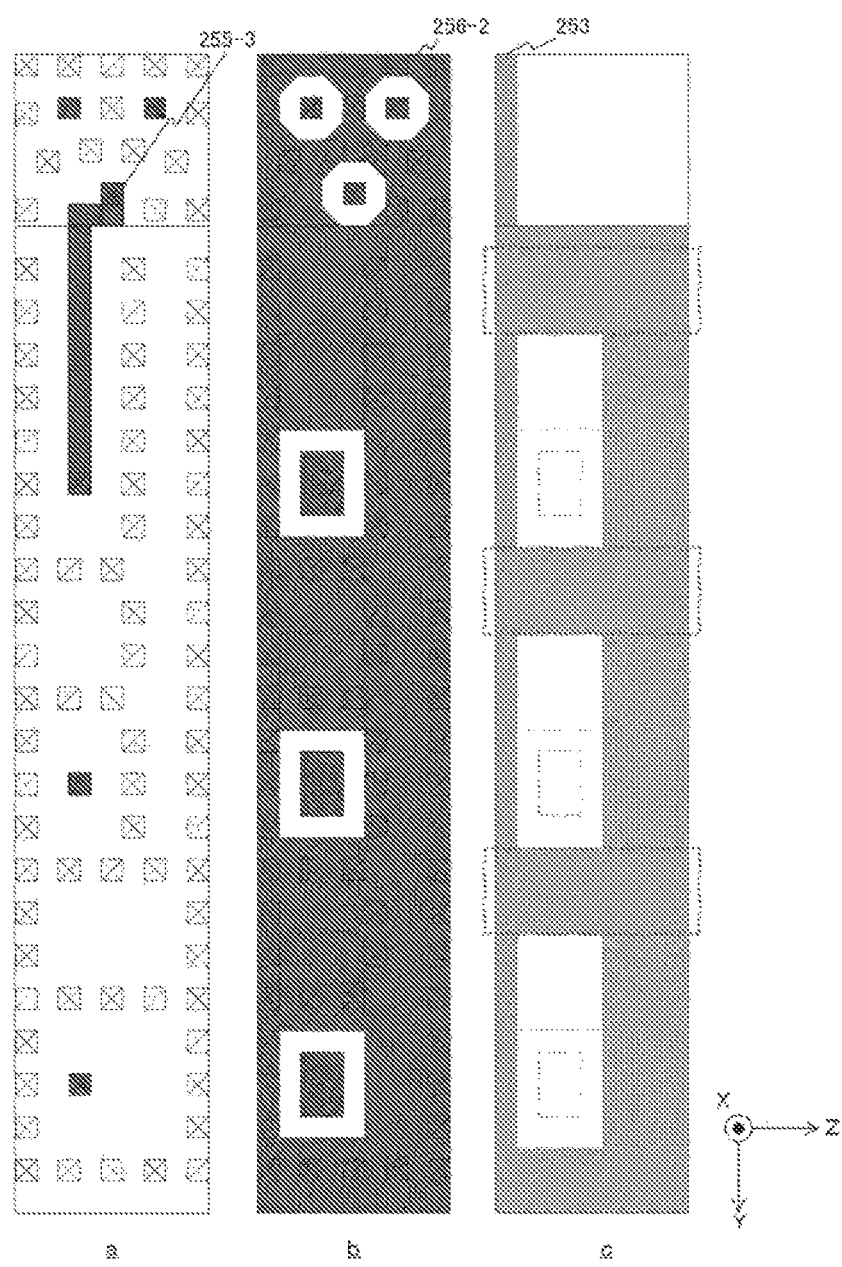
FIG. 96 is an example of a plan view of the seventh to ninth layers from among the nine layers in the intra-probe substrate according to the first embodiment of the present technology.

FIGS. 94 to 96 illustrate yet another example of a planar shape of the intra-probe substrate 321 according to the first embodiment of the present technology. The example illustrated in FIGS. 94 to 96 illustrates an example in which n (n=3 in an example) antennas are included and n transmission paths for connection to the n antennas are formed in the intra-probe substrate 321 including a total of 2n+1 wiring layers including n signal line layers and n+1 shield layers with the signal line layers sandwiched therebetween. Additionally, the example illustrated in FIGS. 94 to 96 illustrates an example in which sides of the signal lines 255 are shielded by using vias that pass through the sides of the signal lines 255 from the shield layer disposed above the signal lines 255 and reach the shield layer disposed below the signal lines 255 and arranging the vias in the array shape along the signal lines 255.

In b in FIG. 94, the shield layers 254 are formed using a part of the first wiring layer, and three radiation elements 259 included in the three antennas are formed using the other part of the first wiring layer.

Also, in the example illustrated in FIGS. 94 to 96, the three signal lines connected to each of the three antennas are formed using the three signal line layers (the second, fourth, and sixth wiring layers) included in the substrate including seven wiring layers. In FIG. 91, Wa indicates the width of the intra-probe substrate 321. Also, Wb indicates the width of the shield layers, and Wc illustrates the interval between the shield layer ends. Wd indicates the width of the one transmission path and the two shield wirings.

In the second wiring layer illustrated in c in FIG. 94,
(1) one signal line 255 for connection to the first radiation element from among the three radiation elements illustrated in b in FIG. 94 is formed.
(2) In order to connect the three radiation elements disposed on one surface layer (first wiring layer) of the intra-probe substrate 321 to the three radiation elements disposed on the other surface layer (fifth wiring layer) with the signal lines 255 for connection to each of the radiation elements sandwiched therebetween, the vias for connection to the second and third radiation elements are formed at positions immediately below these radiation elements, to which the signal lines 255 are not connected in the second wiring layer.
(3) In order to shield sides of the signal lines 255 in (1) above, via arrays for shield are disposed on both sides of the signal lines.
(4) In order to tightly connect the shield layer formed using the wiring layer in the first layer to the shield layers formed using the wiring layers in the third layer, the fifth layer, and the seventh layer, the via arrays are also disposed in the vicinity of the outer edges of these shield layers.

In the fourth wiring layer illustrated in b in FIG. 95,
(1) one signal line 255 for connection to the second radiation element from among the three radiation elements illustrated in b in FIG. 94 is formed.
(2) In order to connect the three radiation elements disposed on one surface layer (first wiring layer) of the intra-probe substrate 321 to the three radiation elements disposed on the other surface layer (fifth wiring layer) with the signal lines 255 for connection to each of the radiation elements sandwiched therebetween, the vias for connection to the first and third radiation elements are formed at positions immediately below these radiation elements, to which the signal lines 255 are not connected in the fourth wiring layer.

(3) In order to shield sides of the signal lines 255 in (1) above, via arrays for shield are disposed on both sides of the signal lines.

(4) In order to tightly connect the shield layer formed using the wiring layer in the first layer to the shield layers formed using the wiring layers in the third layer, the fifth layer, and the seventh layer, the via arrays are also disposed in the vicinity of the outer edges of these shield layers.

In the sixth wiring layer illustrated in a in FIG. 96, (1) one signal line 255 for connection to the third radiation element from among the three radiation elements illustrated in b in FIG. 94 is formed.

(2) In order to connect the three radiation elements disposed on one surface layer (first wiring layer) of the intra-probe substrate 321 to the three radiation elements disposed on the other surface layer (fifth wiring layer) with the signal lines 255 for connection to each of the radiation elements sandwiched therebetween, the vias for connection to the first and second radiation elements are formed at positions immediately below these radiation elements, to which the signal lines 255 are not connected in the sixth wiring layer.

(3) In order to shield sides of the signal lines 255 in (1) above, via arrays for shield are disposed on both sides of the signal lines.

(4) In order to tightly connect the shield layer formed using the wiring layer in the first layer to the shield layers formed using the wiring layers in the third layer, the fifth layer, and the seventh layer, the via arrays are also disposed in the vicinity of the outer edges of these shield layers.

Note that FIG. 97 is a sectional view of the intra-probe substrate 321 cut along the line A-A' in c in FIG. 94.

Next, effects that the structures illustrated in c in FIG. 94, b in FIG. 95, and a in FIG. 96 have will be described. With this structure illustrated in these drawings, the effect of reducing the width of the intra-probe substrate 321 is achieved by shielding the sides of the signal lines 255 by using the via arrays for shield illustrated in c in FIG. 87. In the structures illustrated in c in FIG. 94, b in FIG. 95, and a in FIG. 96, the number of signal lines to be disposed in one signal line layer is reduced by using more signal line layers as compared with the structure illustrated in c in FIG. 87. With this structure, the effect of reducing the width of the intra-probe substrate 321 as compared with the structure illustrated in c in FIG. 87 is achieved.

Note that the width of the intra-probe substrate 321 illustrated in FIGS. 94 to 96 is the same as the width of the intra-probe substrate 321 illustrated in FIGS. 91 to 93.

Figure 98:
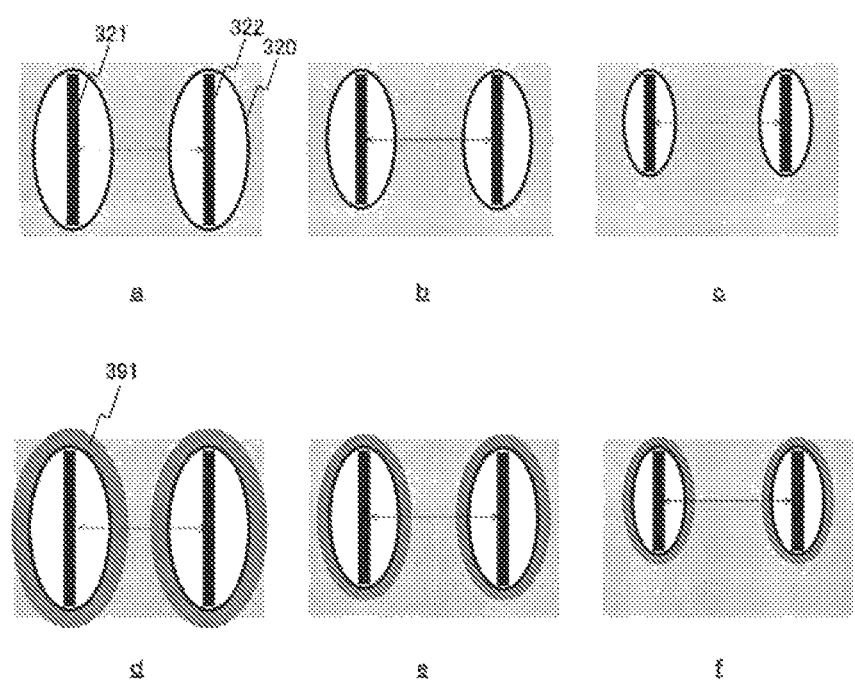
FIG. 98 is a diagram for explaining, from two viewpoints, influences of the width of the intra-probe substrate and the sectional area of the probe casing on measurement of the amount of moisture according to the first embodiment of the present technology.

FIG. 98 is a diagram for explaining, from two viewpoints, influences of the width of the intra-probe substrate and the sectional area of the probe casing on the measurement of the amount of moisture according to the first embodiment of the present technology.

[First Viewpoint]

In the drawing, a, b, and c are sectional views of the transmission probe casing 320a and the reception probe casing 320b when the sensor device 200 is seen in the positive direction of the Y axis from the above according to the first embodiment of the present technology. In each of a, b, and c in the drawing, the oblong on the left side represents the transmission probe substrate 321, and the oval disposed at the outer periphery thereof represents the transmission probe casing 320a. The oblong on the right side represents the reception probe substrate 322, and the oval disposed at the outer periphery thereof represents the reception probe casing 320b. The white part inside the probe casing represents the space inside the probe casing. The colored part outside the probe casing represents soil. In the drawing, a, b, and c are diagrams for explaining (1) in a case where the transmission probe substrates 321 and the reception probe substrate 322 of three types with different widths are accommodated in the oval transmission probe casing 320a and reception probe casing 320b with a length ratio of 2:1 between the long axis and the short axis and (2) the transmission probe substrates 321 and the reception probe substrates 322 of the three types are disposed such that the distances therebetween are the same, (3) how the proportions of the soil regions in the regions between the transmission probe substrates 321 and the reception probe substrates 322 change in accordance with the widths of the probe substrates of the three types. In comparison of a, b, and c in the drawing, the proportion of the soil region in the region between the transmission probe substrate 321 and the reception probe substrate 322 decreases as the width of the intra-probe substrates increases. The moisture measurement system 100 according to the present invention obtains the amount of moisture in the soil by focusing on the fact that the time required for the electromagnetic waves to be propagated from the transmission antenna to the reception antenna has a linear relationship with the amount of moisture in the soil and measuring the propagation delay time of the electromagnetic waves. Therefore, the relationship between the propagation delay time of the electromagnetic waves and the amount of moisture in the soil is separated from the linear relationship as the proportion of the soil region in the region between the transmission probe substrate 321 and the reception probe substrate 322 decreases. An error included in the measurement result thus increases. On the contrary, the proportion of the soil region in the region between the transmission probe substrate 321 and the reception probe substrate 322 increases as the width of the intra-probe substrate decreases. As a result, the relationship between the propagation delay time of the electromagnetic waves and the amount of moisture in the soil approaches the linear relationship, the error included in the measurement result decreases, and it is thus possible to accurately measure the amount of moisture in the soil.

[Second Viewpoint]

In the drawing, d, e, and f are diagrams in which moving destinations of mud pushed aside by the transmission probe casings 320a and the reception probe casings 320b illustrated in a, b, and c in the drawing a being inserted into the soil when these probe casings are inserted are added. In d, e, and f in the drawing, the region (the reference sign 391) with the dark color added at the outer periphery of the probe casings represents the region to which the pushed mud has moved as a result of the insertion of the probe casings, in which the density of mud has thus increased to be higher than the original density of mud as a target of the measurement.

The region, to which the pushed mud has been moved by the insertion of the probe casings, in which the density of mud has thus increased, has a wider width as the width of the intra-probe substrate increases in comparison of d, e, and f in the drawing. As a result, the proportion of the region where the density of mud has increased increases in the region between the transmission probe substrate 321 and the reception probe substrate 322 as the width of the intra-probe substrate increases. How easy the moisture penetrates therethrough and the surface area of the grain boundary of the mud change with the increase in density of mud, and the amount of moisture held in the soil changes. Therefore, the result of measuring the amount of moisture in the soil is more significantly separated from the original amount of moisture in the soil as the target of measurement as the proportion of the region where the density of mud has increased increases.

On the contrary, the width of the region where the density of the mud has increased as described above decreases as the width of the intra-probe substrates decreases. As a result, the proportion of the region where the density of mud has increased in the region between the transmission probe substrate 321 and the reception probe substrate 322 decreases as the width of the intra-probe substrates decreases. Therefore, the result of measuring the amount of moisture in the soil becomes closer to the original amount of moisture in the soil as the target of measurement. In other words, it is possible to accurately measure the amount of moisture in the soil.

From the above first and second viewpoints, the sensor device including the intra-probe substrates in the probe casings can further accurately measure the amount of moisture in the soil as the width of the intra-probe substrates decreases.

The sensor device 200 according to the first embodiment of the present technology
  (1) can reduce the width of the intra-probe substrates by using a via array for shield as a structure for shielding sides of signal lines in the intra-probe substrates. Additionally, it is thus possible to obtain the effect that the amount of moisture in the soil is accurately measured.
  (2) In a case where the sensor device 200 includes a plurality of antennas in the intra-probe substrates and a plurality of signal lines for connection to these plurality of antennas, it is possible to reduce the width of the intra-probe substrates by forming at least one or more signal lines from among the plurality of signal lines in different wiring layers by using the plurality of wiring layers. Additionally, it is thus possible to obtain the effect that the amount of moisture in the soil is accurately measured.

Figure 99:
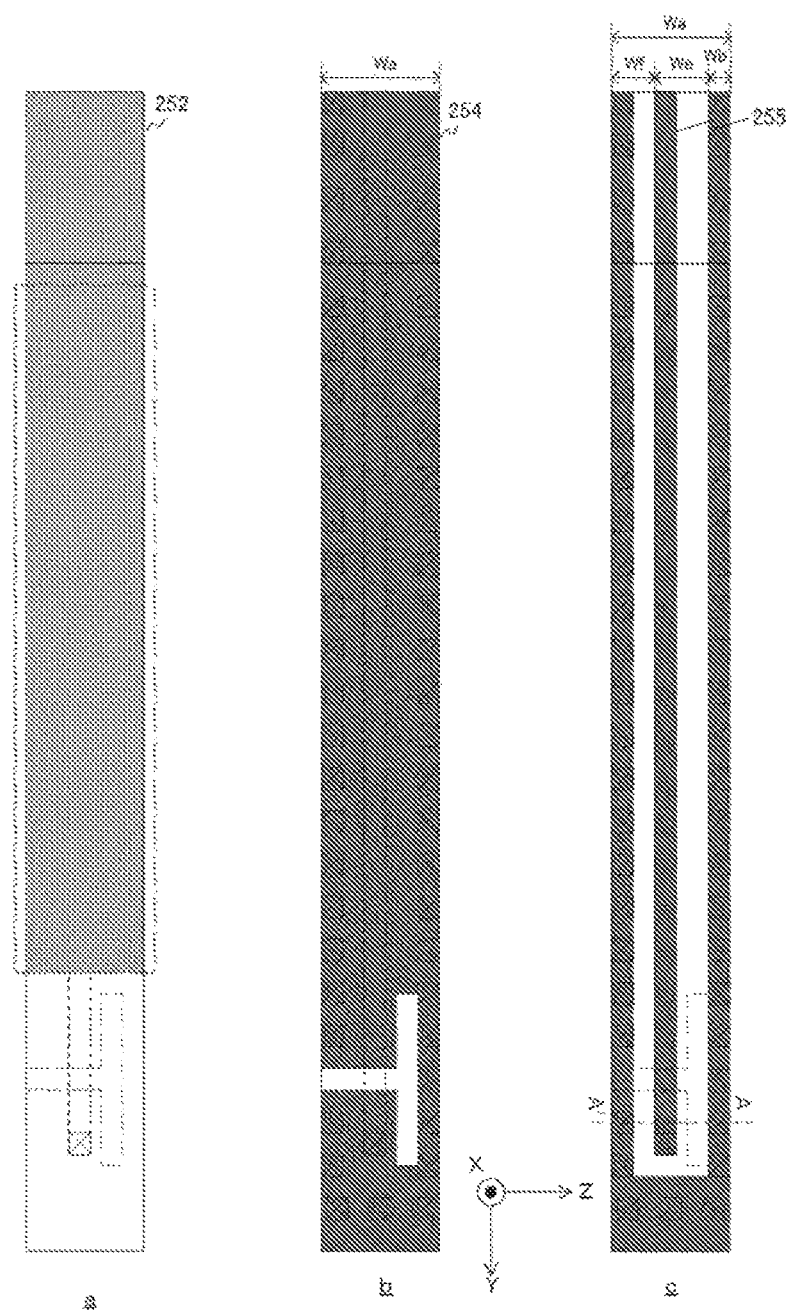
FIG. 99 is an example of a plan view of the first to third layers in the intra-probe substrate including the slot formed therein according to the first embodiment of the present technology.
Figure 100:
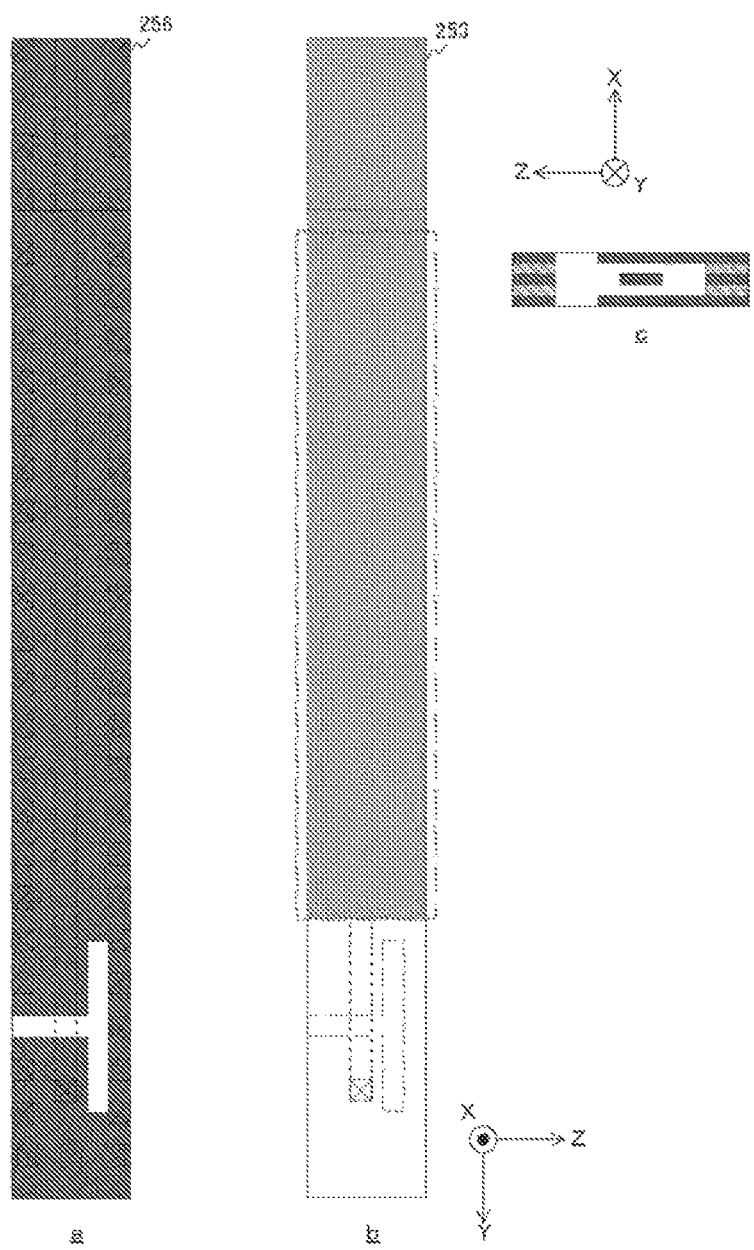
FIG. 100 is an example of a plan view of the fourth and fifth layers in the intra-probe substrate including the slot formed therein and a sectional view of the substrate according to the first embodiment of the present technology.

FIGS. 99 and 100 illustrate another example of a planar shape of the intra-probe substrate 321 according to the first embodiment of the present technology. The example illustrated in FIGS. 99 and 92 illustrates the planar shape of the intra-probe substrate 321 including one plane-shaped and slot-shaped antenna and a total of three wiring layers including one signal line layer for a transmission paths to the antennas and two shield layers with the signal line layer sandwiched therebetween. Additionally, the example illustrated in FIGS. 99 and 100 illustrate an example in which a shield wiring is disposed on a side of the signal line 255 by using a part of the wiring layer that is the same as that of the signal line 255.

In FIG. 99, a illustrates planar shapes of the solder resist 252 and the electromagnetic wave absorption material 251 disposed outside the first wiring layer. The solder resist 252 is illustrated as a colored pattern, and the outer shape of the electromagnetic wave absorption material 251 is illustrated by the dotted line. In FIG. 99, b illustrates a planar shape of the first wiring layer (the shield layer 254 including a slot, that is, the radiation element 254). In FIG. 99, c illustrates the second wiring layer (the signal line 255 and the shield wirings 257 disposed on both sides of the signal line 255 by using a part of the second wiring layer). The signs of connecting quadrangles and diagonals thereof with the line segments disposed at the shield wiring 257 represent vias, and in c in FIG. 99, in particular, a via for connection between the shield layer 254 and the shield wiring and a via for connection between the shield wiring and the shield layer 256, which will be described later, are illustrated on the pattern of the shield wiring. In FIG. 99, Wa indicates the width of the intra-probe substrate 321. Also, Wb indicates the width of the shield wiring. We indicates the length from the slot to the shield wiring, and Wf indicates the length from the signal line end to the shield wiring.

In FIG. 100, a illustrates a planar shape of the third wiring layer (the shield layer 256 including a slot, that is, radiation element 256). In FIG. 100, b illustrates planar shapes of the solder resist 253 and the electromagnetic wave absorption material 251 disposed outside the third wiring layer. The solder resist 253 is illustrated by the colored pattern, and the outer shape of the electromagnetic wave absorption material 251 are illustrated by the dotted line. In FIG. 100, c is a sectional view of the intra-probe substrate 321 cut along the line A-A' in c in FIG. 99.

In the sectional view in c in FIG. 100, the first wiring layer (the shield layer 254) is disposed on the lower most side on the paper plane, and the signal line and the shield wirings on both sides thereof are disposed thereon by using the second wiring layer. The shield layer 256 is disposed thereon. In the region of the intra-probe substrate 321 where the transmission path is formed, solder resists are disposed on sides above and below the section, and the electromagnetic wave absorption material 251 is disposed in the surroundings of the section.

Figure 101:
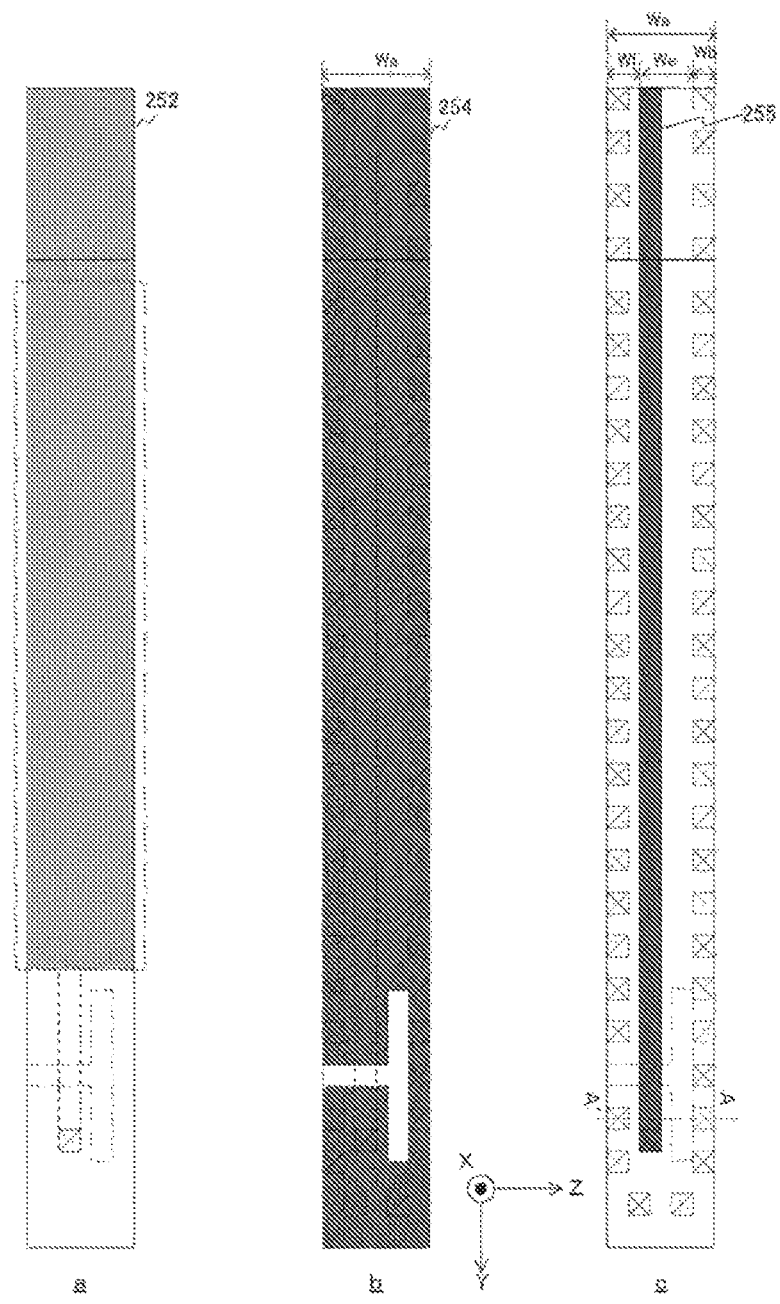
FIG. 101 is an example of a plan view of the first to third layers in the intra-probe substrate with the slot formed therein and with the shield wiring removed therefrom according to the first embodiment of the present technology.
Figure 102:
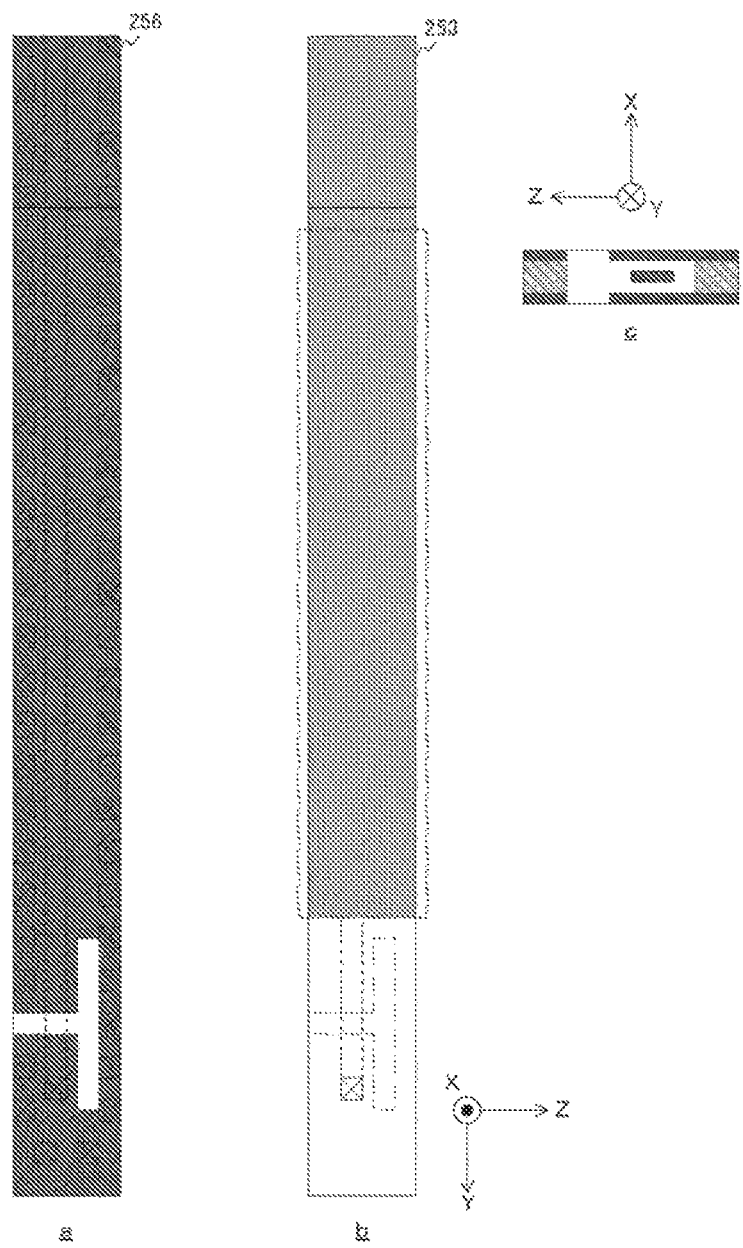
FIG. 102 is an example of a plan view of the fourth and fifth layers in the intra-probe substrate with the slot formed therein and with the shield wiring removed therefrom and a sectional view of the substrate according to the first embodiment of the present technology.

FIGS. 101 and 102 illustrate another example of the planar shape of the intra-probe substrate 321 according to the first embodiment of the present technology. The example illustrated in FIGS. 101 and 102 illustrates the intra-probe substrate 321 including one plane-shaped and slot-shaped antenna and a total of three wiring layers including one signal line layer for the transmission path to the antenna and the two shield layers with the signal line layer sandwiched therebetween. Additionally, the example illustrated in FIGS. 101 to 102 illustrates an example in which sides of the signal lines 255 are shielded by using vias that pass through the sides of the signal lines 255 from the shield layer 256 disposed above the signal lines 255 and reach the shield layer 254 disposed below the signal lines 255 and arranging the vias in the array shape along the signal lines 255. In FIG. 101, c indicates the via arrays for shield. In the drawing, the signs connecting the quadrangles and diagonals with line segments disposed on both sides of the signal lines 255 represent the vias. Also, these vias with no color in the drawing indicates that the vias are not formed by the second wiring layer that is the same layer as that of the signal lines 255 and vias extending to the lower layer than the signal lines 255 through the sides of the signal lines 255 from the upper layer than the signal lines 255. Since the planar shapes illustrated in FIGS. 101 and 102 other than c in FIG. 101 are similar to those illustrated in FIGS. 99 and 100, description thereof will be omitted. Note that c in FIG. 102 is a sectional view of the intra-probe substrate 321 when a part of the slot antenna is cut in the structure illustrated in FIGS. 102 and 103.

Next, effects that the structure illustrated in c in FIG. 101 has will be described. The planar shape illustrated in c in FIG. 101 includes the structure in which the sides of the signal lines 255 are shielded by using the via arrays for shield similarly to c in FIG. 83. In this manner, it is possible to reduce the distance between the signal lines 255 and the via arrays for shield (the shield wirings in the case of FIG. 99) as compared with the structure illustrated in c in FIG. 99.

As a result, the effect that the width of the intra-probe substrate 321 illustrated in FIGS. 101 and 102 can be smaller than the width of the intra-probe substrate 321 illustrated in FIGS. 99 and 100 is achieved. Also, if it is possible to reduce the width of the intra-probe substrate, then it is possible to reduce the sectional area of the probe casing accommodating the intra-probe substrate, and this leads to a further effect that it is possible to accurately measure moisture. Details of this is as described above with reference to FIG. 98. In FIG. 101, Wa indicates the width of the intra-probe substrate 321. Also, Wb indicates the width of the shield via arrays. We indicates the length from the slot to the shield wiring, and Wf indicates the length from the signal line end to the shield wiring.

Figure 103:
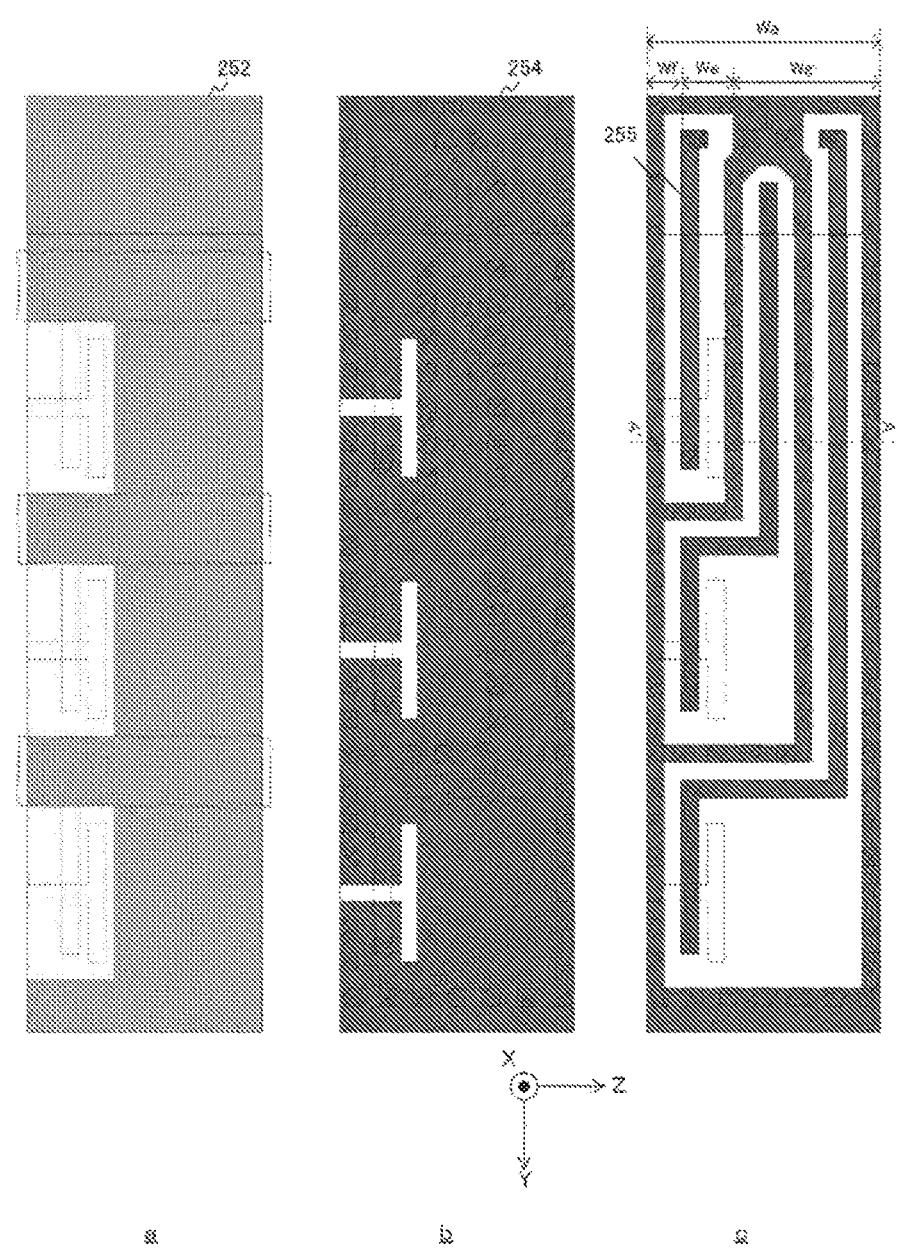
FIG. 103 is an example of a plan view of the first to third layers in the intra-probe substrate including the slot formed therein and provided with three antennas according to the first embodiment of the present technology.
Figure 104:
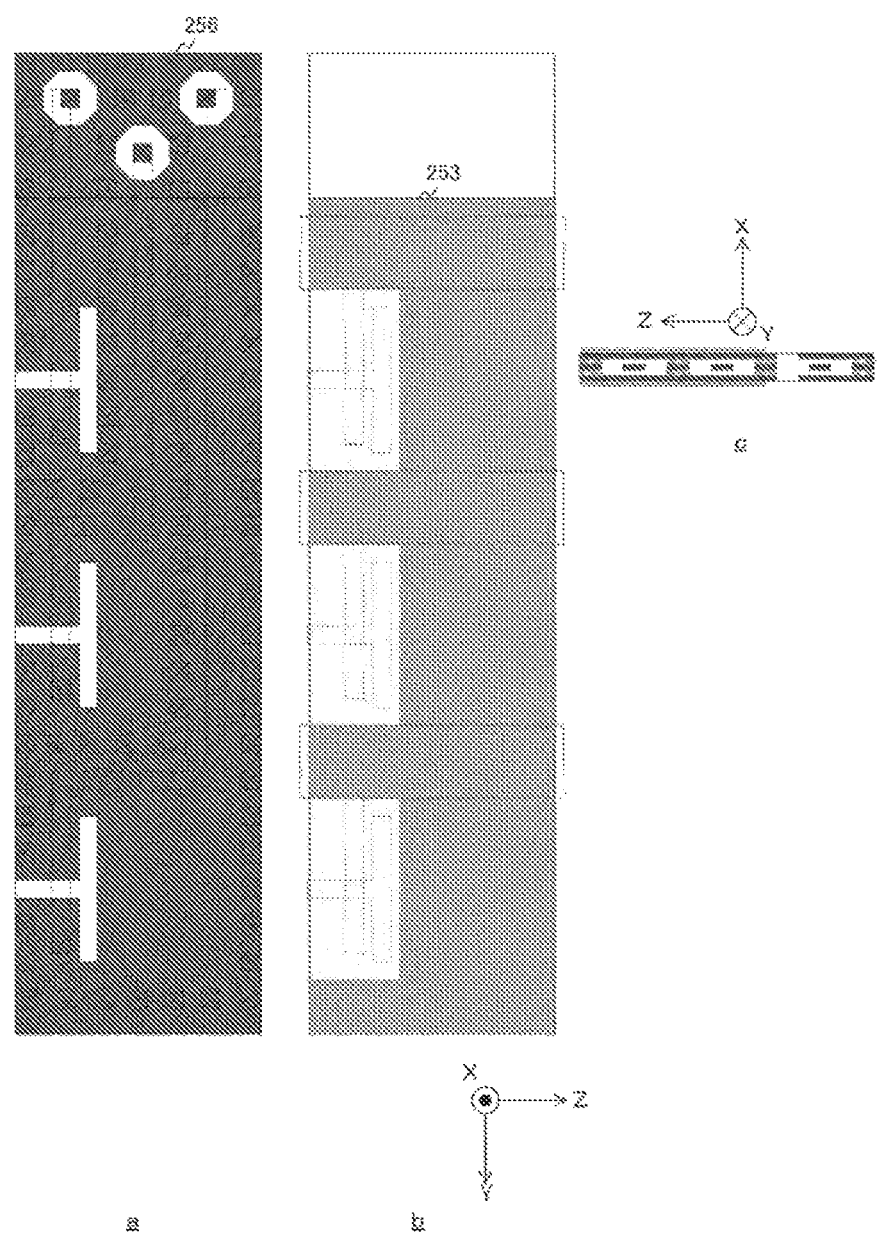
FIG. 104 is an example of a plan view of the fourth and fifth layers in the intra-probe substrate including the slot formed therein and provided with three antennas and a sectional view of the substrate according to the first embodiment of the present technology.

FIGS. 103 and 104 illustrate yet another example of a planar shape of the intra-probe substrate 321 according to the first embodiment of the present technology. The example illustrated in FIGS. 103 and 104 illustrates the intra-probe substrate 321 in which n (n=3 in an example) plane-shaped and slot-shaped antennas are included and the transmission path to the antenna includes a total of three wiring layers including one signal line layer and two shield layers with the signal line layer sandwiched therebetween. Additionally, the example illustrated in FIGS. 103 and 104 illustrates an example in which sides of the signal lines 255 are shield by using a part of the wiring layer that is the same as that of the signal line 255. Since a role of each layer illustrated in each of FIGS. 103 and 104 is the same as that in FIGS. 99 and 100, description thereof will be omitted.

In FIG. 103, b illustrates a planar shape in which slots of three plane-shaped and slot-shaped antennas are disposed by using the first wiring layer (the shield layer 254 including the slots, that is, the radiation element 254).

In FIG. 103, c illustrates an example in which the shield wirings are disposed on sides of the signal lines 255 by using a part of the wiring layer that is the same as that of the signal line 255 similarly to c in FIG. 99. In c in FIG. 103, the three signal lines 255 for intersection with the three slots illustrated in b in FIG. 101 are formed using a part of the second wiring layer. Additionally, in order to shield a side of each of these three signal lines 255, a total of four shield wirings are formed using the second wiring layer that is the same as that of the three signal lines are formed between and outside the three signal lines 255. Note that c in FIG. 104 is a sectional view of the intra-probe substrate 321 cut along the line A-A' in c in FIG. 103. In FIG. 103, Wa indicates the width of the intra-probe substrate 321. Also, We indicates the length from the slot to the signal line, and Wf indicates the length from the signal line end to the shield wiring. Wg indicates the width of the two signal line and the three shield via arrays.

Figure 105:
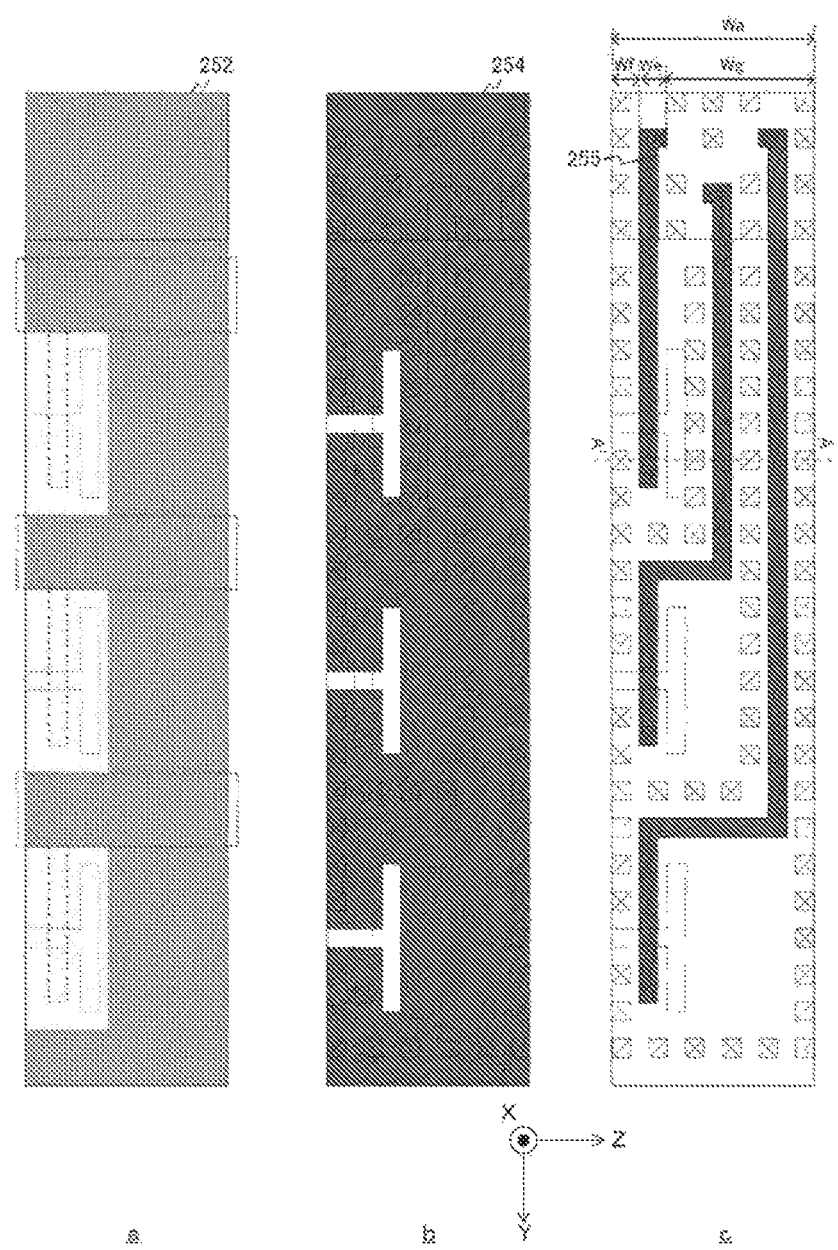
FIG. 105 is an example of a plan view of the first to third layers in the intra-probe substrate including the slot formed therein, including no shield wiring, and provided with three antennas according to the first embodiment of the present technology.
Figure 106:
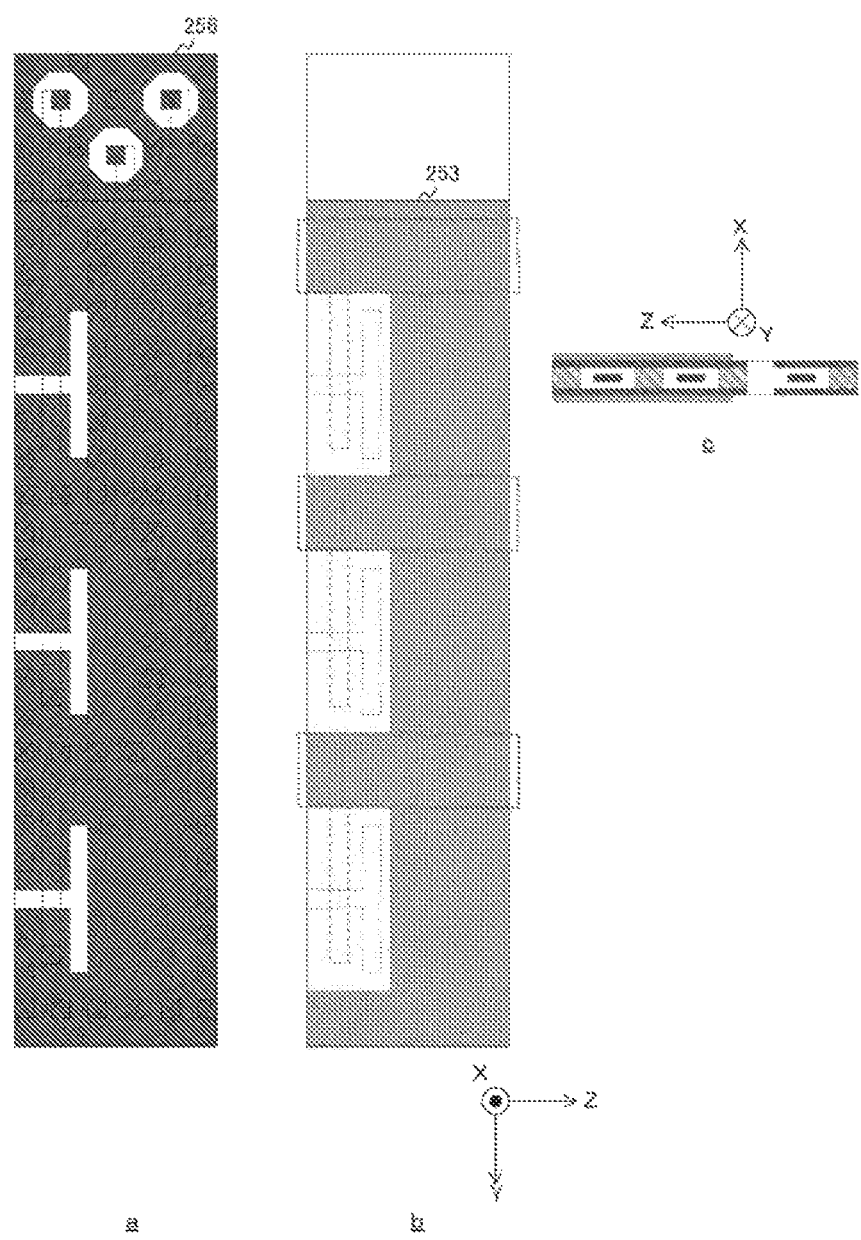
FIG. 106 is an example of a plan view of the fourth and fifth layers in the intra-probe substrate including the slot formed therein, including no shield wiring, and provided with three antennas and a sectional view of the substrate according to the first embodiment of the present technology.

FIGS. 105 and 106 illustrate yet another example of a planar shape of the intra-probe substrate 321 according to the first embodiment of the present technology. The example illustrated in FIGS. 105 and 106 illustrates the intra-probe substrate 321 in which n (n=3 in an example) plane-shaped and slot-shaped antennas are included and the transmission path to the antenna includes a total of three wiring layers including one signal line layer for transmission paths for the antenna and two shield layers with the signal line layer sandwiched therebetween. Additionally, the example illustrated in FIGS. 105 to 106 illustrates an example in which sides of the signal lines 255 are shielded by using vias that pass through the sides of the signal lines 255 from the shield layer 256 disposed above the signal lines 255 and reach the shield layer 254 disposed below the signal lines 255 and arranging the vias in the array shape along the signal lines 255.

In FIG. 105, b illustrates a planar shape in which slots of three plane-shaped and slot-shaped antennas are disposed by using the first wiring layer (the shield layer 254 including the slots, that is, the radiation element). In FIG. 105, Wa indicates the width of the intra-probe substrate 321. Also, We indicates the length from the slot to the shield via array, and Wf indicates the length from the signal line end to the shield wiring. Wg indicates the width of the two signal lines and the three shield via arrays.

In FIG. 105, c illustrates an example in which sides of the signal lines 255 are shield by using the via arrays for shield similarly to c in FIG. 101. In c in FIG. 105, the three signal lines 255 for intersection with the three radiation elements illustrated in b in FIG. 105 are formed using a part of the second wiring layer. Additionally, in order to shield each side of these three signal lines 255, a total of four via arrays for shield are disposed between and outside the three signal lines. Note that c in FIG. 106 is a sectional view of the intra-probe substrate 321 cut along the line A-A' in c in FIG. 105.

Next, effects that the structure illustrated in c in FIG. 105 has will be described. Similarly to c in FIG. 101, the three signal lines 255 and the four via arrays illustrated in c in FIG. 105 are separately (independently in other words) pattern-formed. As a result, the distance between the three signal lines 255 and the four via arrays illustrated in c in FIG. 105 can be smaller than the distance between the three signal lines 255 and the four shield wirings illustrated in c in FIG. 103. As a result, the width of the intra-probe substrate 321 illustrated in FIGS. 105 and 106 can be smaller than the width of the intra-probe substrate 321 illustrated in FIGS. 103 and 104. Also, if it is possible to reduce the width of the intra-probe substrate, then it is possible to reduce the sectional area of the probe casing accommodating the intra-probe substrate, and this leads to a further effect that it is possible to accurately measure moisture. Details of this is as described above with reference to FIG. 98.

Figure 107:
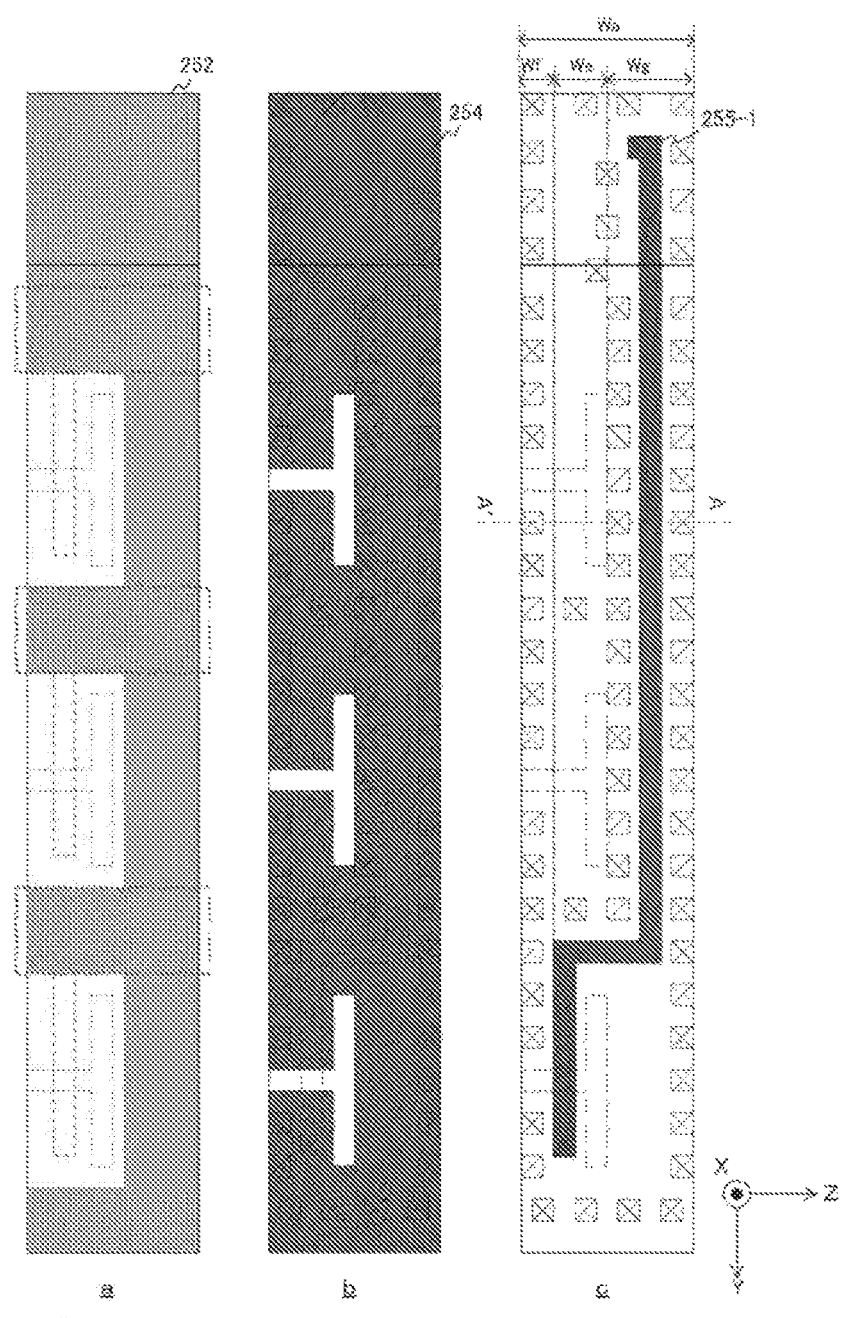
FIG. 107 is an example of a plan view of the first to third layers from among seven layers in the intra-probe substrate including the slot formed therein according to the first embodiment of the present technology.
Figure 108:
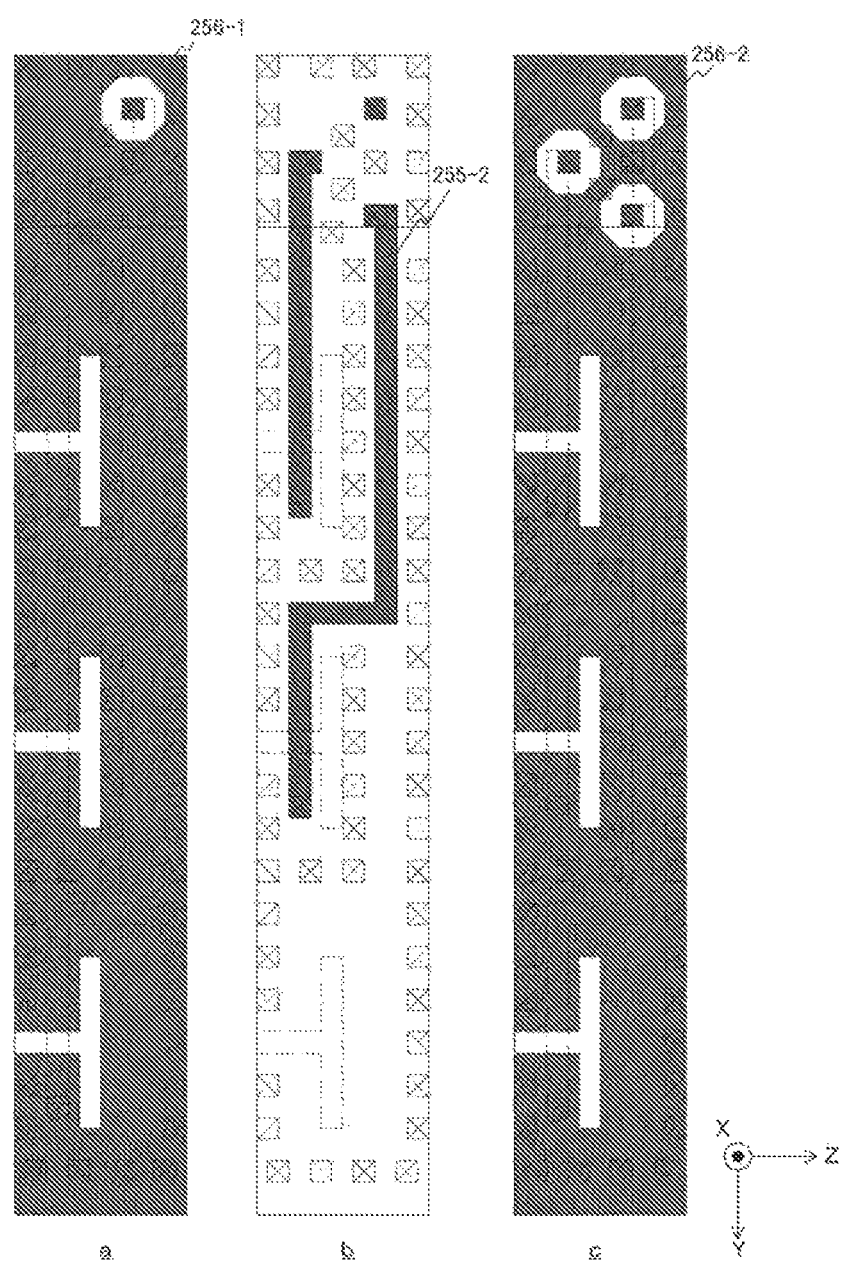
FIG. 108 is an example of a plan view of the fourth to sixth layers from among the seven layers in the intra-probe substrate including the slot formed therein according to the first embodiment of the present technology.
Figure 109:
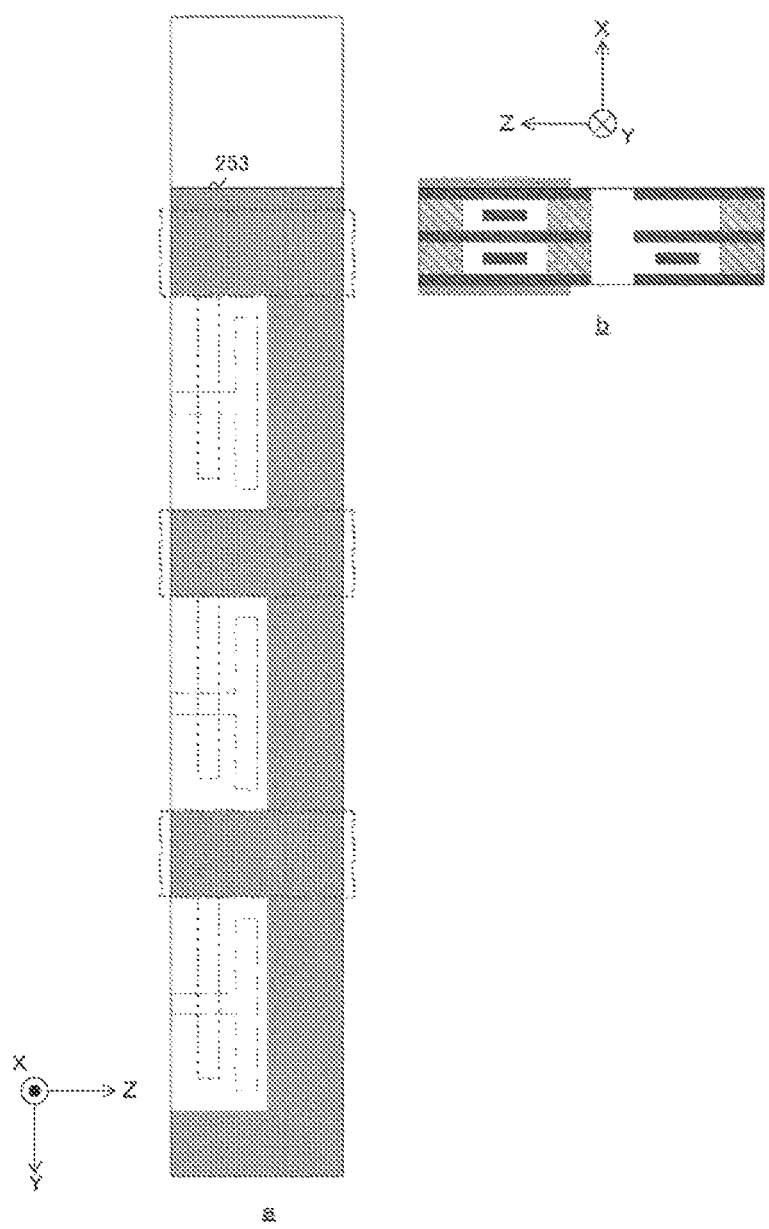
FIG. 109 is an example of a sectional view of the seventh layer in the intra-probe substrate including the slot formed therein and the substrate according to the first embodiment of the present technology.

FIGS. 107 to 109 illustrate yet another example of a planar shape of the intra-probe substrate 321 according to the first embodiment of the present technology. The example illustrated in FIGS. 107 to 109 illustrates an example in which n (n=3 in an example) plane-shaped and slot-shaped antennas are included and n transmission paths to be caused to intersect the slots of the n antennas are formed in the intra-probe substrate 321 including a total of 2n−1 wiring layers including n−1 signal line layers and n shield layers with the signal line layers sandwiched therebetween. Additionally, the example illustrated in FIGS. 107 to 109 illustrates an example in which sides of the signal lines 255 are shielded by using vias that pass through the sides of the signal lines 255 from the shield layer disposed above the signal lines 255 and reach the shield layer disposed below the signal lines 255 and arranging the vias in the array shape along the signal lines 255.

In FIG. 107, b illustrates a planar shape in which slots of three plane-shaped and slot shaped antennas are disposed by using the first wiring layer (the shield layer 254 including the slots, that is, the radiation element). In FIG. 108, a illustrates a planar shape in which slots of three plane-shaped and slot-shaped antennas are disposed by using the third wiring layer (the shield layer 256-1 including the slots, that is, the radiation element 256-1). In FIG. 108, c illustrates a planar shape in which slots of three plane-shaped and slot-shaped antennas are disposed by using the fifth wiring layer (the shield layer 256-2 including the slot, that is, the radiation element 256-2). In FIG. 107, Wa indicates the width of the intra-probe substrate 321. Also, We indicates the length from the slot to the shield via array, and Wf indicates the length from the signal line end to the shield wiring. Wg indicates the width of the one signal line and the two shield via arrays.

Also, in the example illustrated in FIGS. 107 to 109, three signal lines for intersection with each of three antennas are formed using two signal line layers (the second and fourth wiring layers) included in the substrate including five wiring layers.

In the second wiring layer illustrated in c in FIG. 107,
(1) one signal lines 255 to be caused to intersect the first slot from among the three slots illustrated in b in FIG. 107 are formed.
(2) In order to shield sides of the signal lines 255 in (1) above, via arrays for shield are disposed on both sides of the signal lines.
(3) In order to tightly connect the shield layer formed using the wiring layer in the first layer to the shield layers formed using the wiring layers in the third layer and the fifth layer, the via arrays are also disposed in the vicinity of the outer edges of these shield layers.

On the other hand, in the fourth wiring layer illustrated in b in FIG. 108,
(1) two signal lines 255 for intersection with the second and third slots, for which the signal line 255 is not disposed for intersection therewith in the second wiring layer, from among the three slots illustrated in b in FIG. 107 are formed.
(2) In order to shield sides of the signal lines 255 in (1) above, via arrays for shield are disposed on both sides of the signal lines.
(3) In order to tightly connect the shield layer formed using the wiring layer in the first layer to the shield layers formed using the wiring layers in the third layer and the fifth layer, the via arrays are also disposed in the vicinity of the outer edges of these shield layers.

Note that b in FIG. 109 is a sectional view of the intra-probe substrate 321 cut along the line A-A' in c in FIG. 107.

Next, effects of the structures illustrated in c in FIG. 107 and b in FIG. 108 will be described. With the structures illustrated in these drawing, an effect of reducing the width of the intra-probe substrate 321 is achieved by shielding a side of the signal line 255 by using the via array for shield illustrated in c in FIG. 101. In the structures illustrated in c in FIG. 107 and b in FIG. 108, the number of signal lines to be disposed in one signal line layer is reduced by using more signal line layers as compared with the structure illustrated in c in FIG. 105. With this structure, the effect of reducing the width of the intra-probe substrate 321 as compared with the structure illustrated in c in FIG. 105 is achieved.

Figure 110:
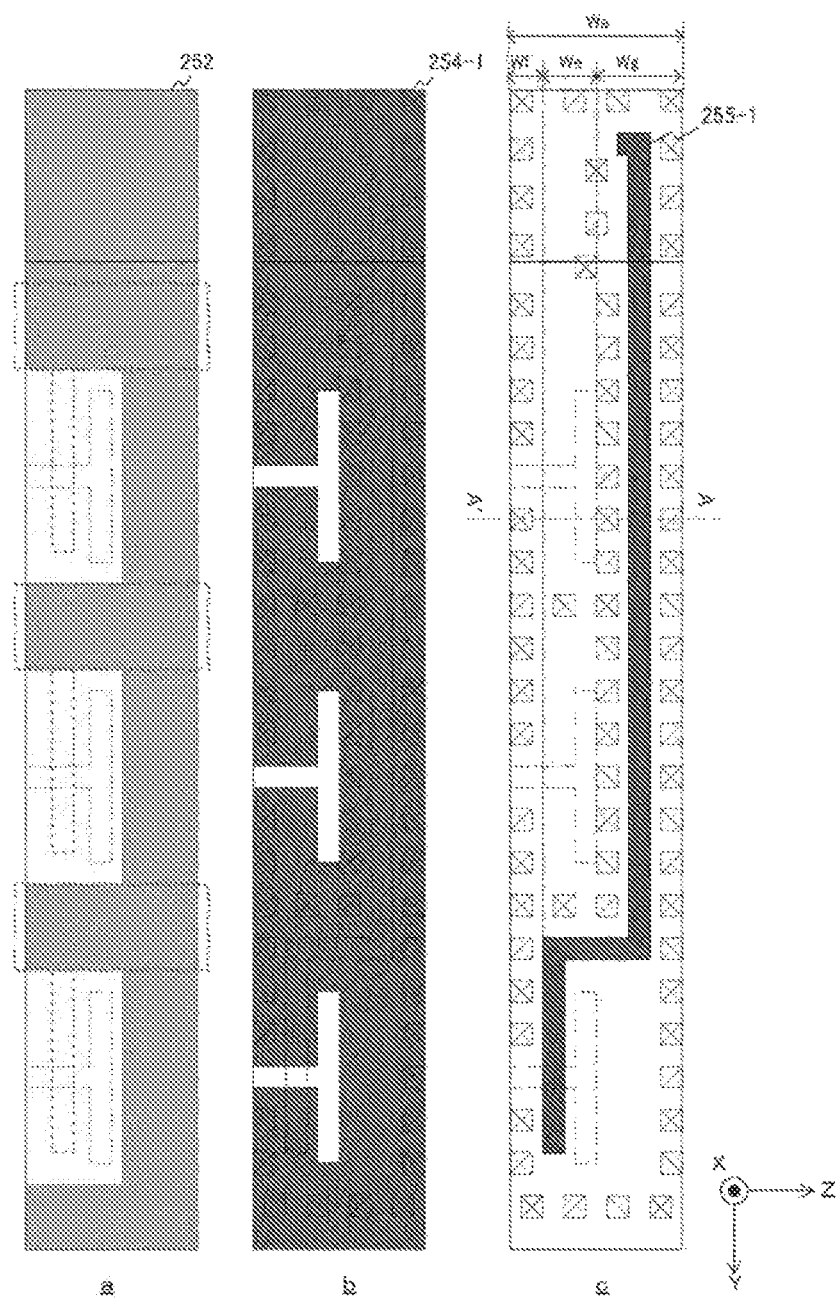
FIG. 110 is an example of a plan view of the first to third layers from among nine layers in the intra-probe substrate including the slot formed therein according to the first embodiment of the present technology.
Figure 111:
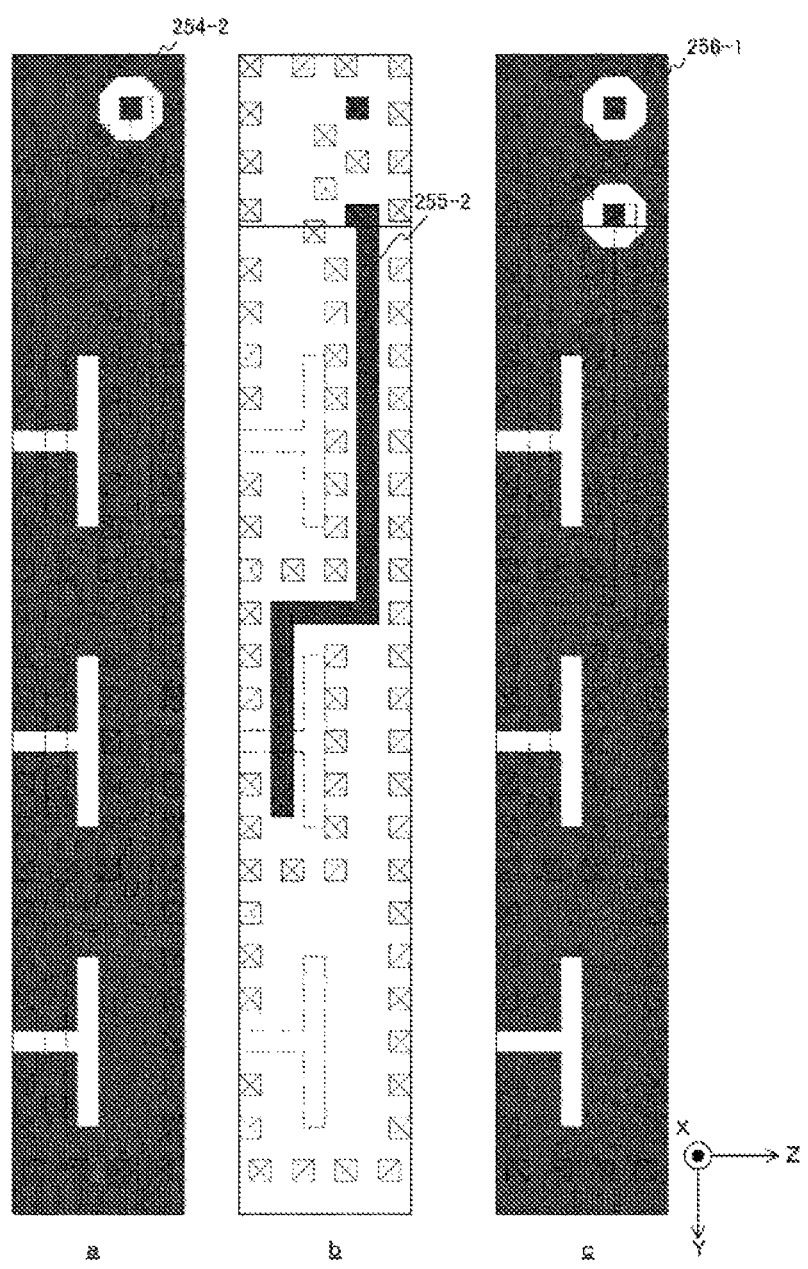
FIG. 111 is an example of a plan view of the fourth to sixth layers from among the nine layers in the intra-probe substrate including the slot formed therein according to the first embodiment of the present technology.
Figure 112:
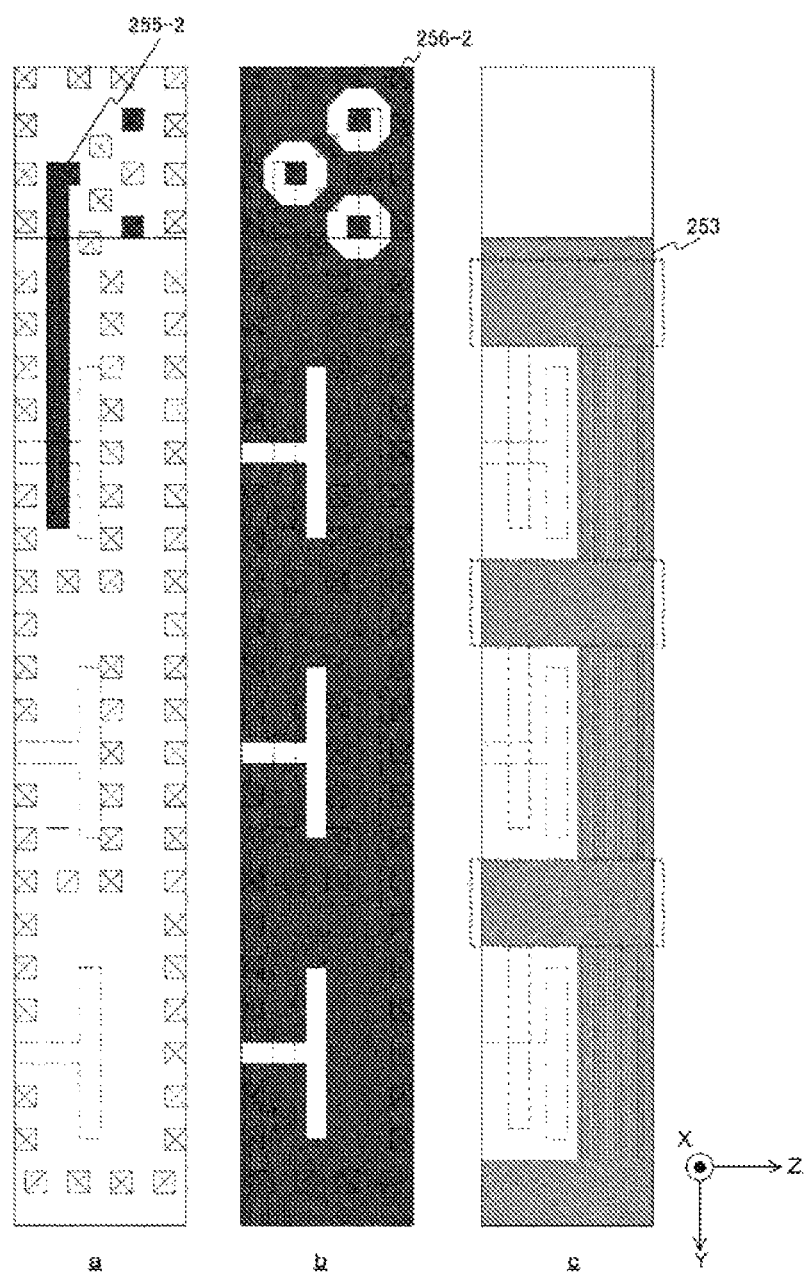
FIG. 112 is an example of a plan view of the seventh to ninth layers from among the nine layers in the intra-probe substrate including the slot formed therein according to the first embodiment of the present technology.

FIGS. 110 to 113 illustrate yet another example of a planar shape of the intra-probe substrate 321 according to the first embodiment of the present technology. The example illustrated in FIGS. 110 to 112 illustrates an example in which n (n=3 in an example) plane-shaped and slot location antennas are included and n transmission paths for intersection with the n antennas are formed in the intra-probe substrate 321 including a total of 2n+1 wiring layers including n signal line layers and n+1 shield layers with the signal line layers sandwiched therebetween. Additionally, the example illustrated in FIGS. 110 to 112 illustrates an example in which sides of the signal lines 255 are shielded by using vias that pass through the sides of the signal lines 255 from the shield layer disposed above the signal lines 255 and reach the shield layer disposed below the signal lines 255 and arranging the vias in the array shape along the signal lines 255.

In FIG. 110, b illustrates a planar shape in which slots of three plane-shaped and slot-shaped antennas are disposed by using the first wiring layer (the shield layer 254-1 including the slots, that is, the radiation element). In FIG. 111, a illustrates a planar shape in which slots of three plane-shaped and slot-shaped antennas are disposed by using the third wiring layer (the shield layer 254-2 including the slots, that is, the radiation element). In FIG. 111, c illustrates a planar shape in which slots of three plane-shaped and slot-shaped antennas are disposed by using the fifth wiring layer (the shield layer 256-1 including the slots, that is, the radiation element). In FIG. 112, b illustrates a planar shape in which slots of three plane-shaped and slot-shaped antennas are disposed by using the seventh wiring layer (the shield layer 256-2 including the slots, that is, the radiation element). In FIG. 110, Wa indicates the width of the intra-probe substrate 321. Also, We indicates the length from the slot to the shield via array, and Wf indicates the length from the signal line end to the shield wiring. Wg indicates the width of the one signal line and the two shield via arrays.

Also, in the example illustrated in FIGS. 110 to 112, the three signal lines to be caused to intersect each of the three antennas are formed using three signal line layers (the second, fourth, and sixth wiring layers) included in the substrate including seven wiring layers.

In the second wiring layer illustrated in c in FIG. 110,
(1) one signal line 255 for intersection with the first slot from among the three slots illustrated in b in FIG. 110 is formed.
(2) In order to shield sides of the signal lines 255 in (1) above, via arrays for shield are disposed on both sides of the signal lines.
(3) In order to tightly connect the shield layer formed using the wiring layer in the first layer to the shield layers formed using the wiring layers in the third layer, the fifth layer, and the seventh layer, the via arrays are also disposed in the vicinity of the outer edges of these shield layers.

On the other hand, in the fourth wiring layer illustrated in b in FIG. 111,
(1) two signal lines 255 to be caused to intersect the second slot out of the second and third slots, for which the signal line 255 is not disposed for intersection therewith in the second wiring layer, from among the three slots illustrated in b in FIG. 111 are formed.
(2) In order to shield sides of the signal lines 255 in (1) above, via arrays for shield are disposed on both sides of the signal lines.
(3) In order to tightly connect the shield layer formed using the wiring layer in the first layer to the shield layers formed using the wiring layers in the third layer, the fifth layer, and the seventh layer, the via arrays are also disposed in the vicinity of the outer edges of these shield layers.

Furthermore, in the sixth wiring layer illustrated in a in FIG. 112,
(1) two signal lines 255 to be caused to intersect the third slot, for which the signal line 255 is not disposed for intersection therewith in the second wiring layer and the fourth wiring layer, from among the three slots illustrated in b in FIG. 111 are formed.
(2) In order to shield sides of the signal lines 255 in (1) above, via arrays for shield are disposed on both sides of the signal lines.

(3) In order to tightly connect the shield layer formed using the wiring layer in the first layer to the shield layers formed using the wiring layers in the third layer, the fifth layer, and the seventh layer, the via arrays are also disposed in the vicinity of the outer edges of these shield layers.

Figure 113:
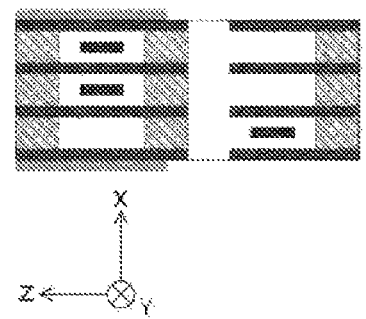
FIG. 113 is an example of a sectional view of the intra-probe substrate with the nine-layer structure including the slot formed therein according to the first embodiment of the present technology.

Note that FIG. 113 is a sectional view of the intra-probe substrate 321 cut along the line A-A' in c in FIG. 110.

Next, effects of the structures illustrated in c in FIG. 110, b in FIG. 111, and a in FIG. 112 will be described. The structures illustrated in these drawings have an effect that the width of the intra-probe substrate 321 is reduced by shielding a side of the signal line 255 using a via array for shield illustrated in c in FIG. 101. In the structures illustrated in c in FIG. 110, b in FIG. 111, and a in FIG. 112, the number of signal lines to be disposed in one signal line layer is reduced by using more signal line layers as compared with the structure illustrated in c in FIG. 105. With this structure, the effect of reducing the width of the intra-probe substrate 321 as compared with the structure illustrated in c in FIG. 105 is achieved.

Note that the width of the intra-probe substrate 321 illustrated in FIGS. 110 to 113 is the same as the width of the intra-probe substrate 321 illustrated in FIGS. 107 to 109.

Figure 114:
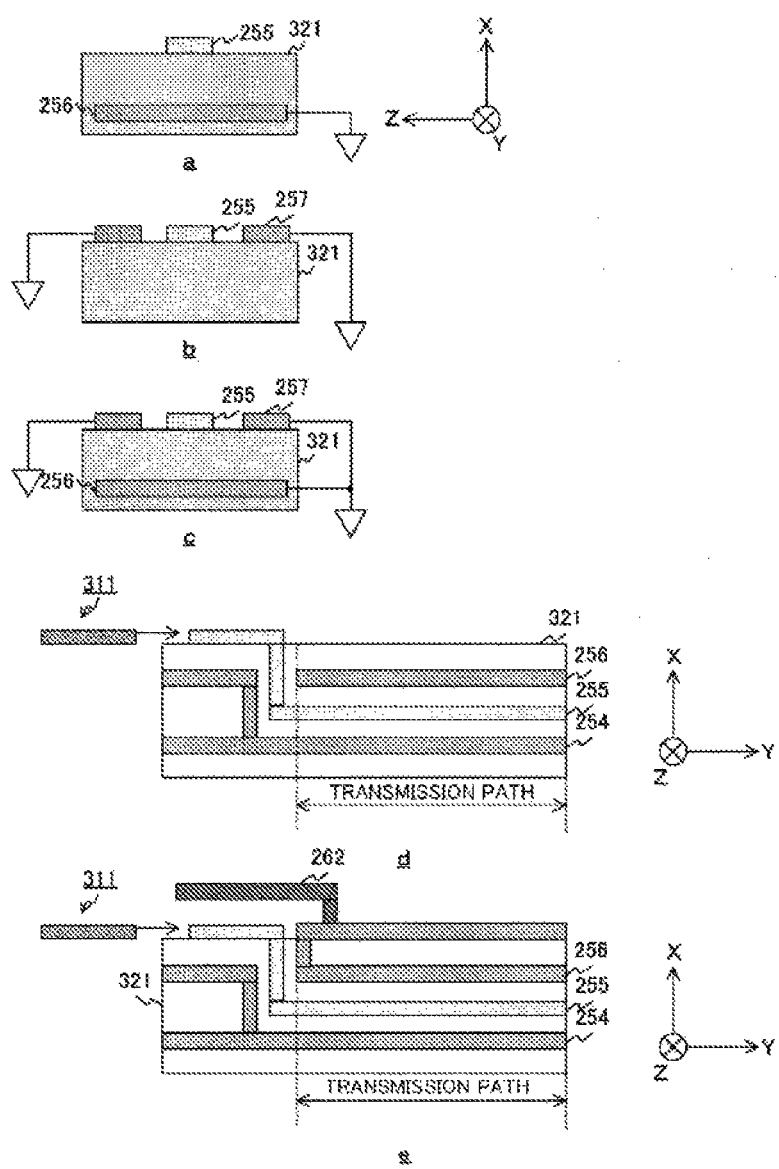
FIG. 114 is a diagram for supplementarily explaining a structure of the strip line according to the first embodiment of the present technology.

FIG. 114 is a diagram for explaining a sectional structure of the substrate in the region where the connector 323 (and 324) used for connection between the intra-probe substrate 321 and the transmission path connecting portion is disposed in the intra-probe substrate 321 (and 322) and the structure of the transmission line used in the region included in the first embodiment of the present technology. In the intra-probe substrate 321, the transmission path for connecting the transmission antenna 223 and the like included in the substrate to the connector 323 is formed using a strip line as described above. On the other hand, it is necessary for pulling out the signal line 255 disposed in the inner layer of the intra-probe substrate 321 to the surface layer of the substrate in order to electrically connect the signal line 255 disposed in the inner layer of the intra-probe substrate 321 using the strip line to the transmission path connecting portion via the connector 323 in the region where the connector 323 is disposed. The signal line 255 pulled out to the surface layer of the intra-probe substrate 321 can use, as a structure of the transmission line, the transmission line with the structure illustrated in a, b, or c in the drawing. More specifically, it is also possible to adopt a micro strip line in which the signal line 255 to transmit signals is disposed in the surface layer and the shield layer 256 is disposed in the inner layer as illustrated as an example in a in the drawing. As illustrated as an example in b in the drawing, it is also possible to adopt a coplanar line in which the signal line 255 and the shield wiring are disposed in the surface layer. As illustrated as an example in c in the drawing, it is also possible to adopt a coplanar line in which the signal line 255 is disposed in the surface layer and the shield wiring 257 and the shield layer 256 are disposed in the surface layer and the inner layer.

Also, d and e in the drawing are diagrams for explaining the sectional structure of the substrate in the region where the connector 323 (and 324) used for connection between the intra-probe substrate 321 and the transmission path connecting portion is disposed. In d in the drawing, the region described as the transmission path represents the strip line extending to the transmission antenna. The structure illustrated on the left side of the strip line represents the structure of pulling out the signal line 255 formed in the inner layer of the substrate to the surface layer of the substrate via the via extending in the paper surface up-down direction. In the surroundings of the via connected to the signal line 255, a via for shielding to connect the shield layers 254 and 256 is disposed. In this manner, the surroundings of the via connected to the signal line 255 is shielded. The reference sign 311 in the drawing represents the transmission path connecting portion that is brought into electrical contact with the signal line 255 disposed in the surface layer. In the drawing, e represents a structure in which the shield layer 254 or a shield wiring is further disposed in the surface layer of the substrate and a can shield (or a shield case) is further disposed to cover the surroundings of the transmission line pulled out to the surface layer. The can shield more preferably has a structure in which it is connected to the shield layer and is given a ground potential. It is possible to reduce emission of electromagnetic waves from the transmission path in the surface layer to the outside or reception of the electromagnetic waves (noise) from the outside to the transmission path in the surface layer by disposing the can shield. In a case where the substrate includes a plurality of transmission lines, parts between the plurality of signal lines 255 pulled out to the surface layer may be parallel-shielded by using the plurality of shield wirings 257 disposed in the surface layer. It is better that the micro strip line in the surface layer has a shorter length.

Example of Time Division Driving of Antennas

Figure 115:
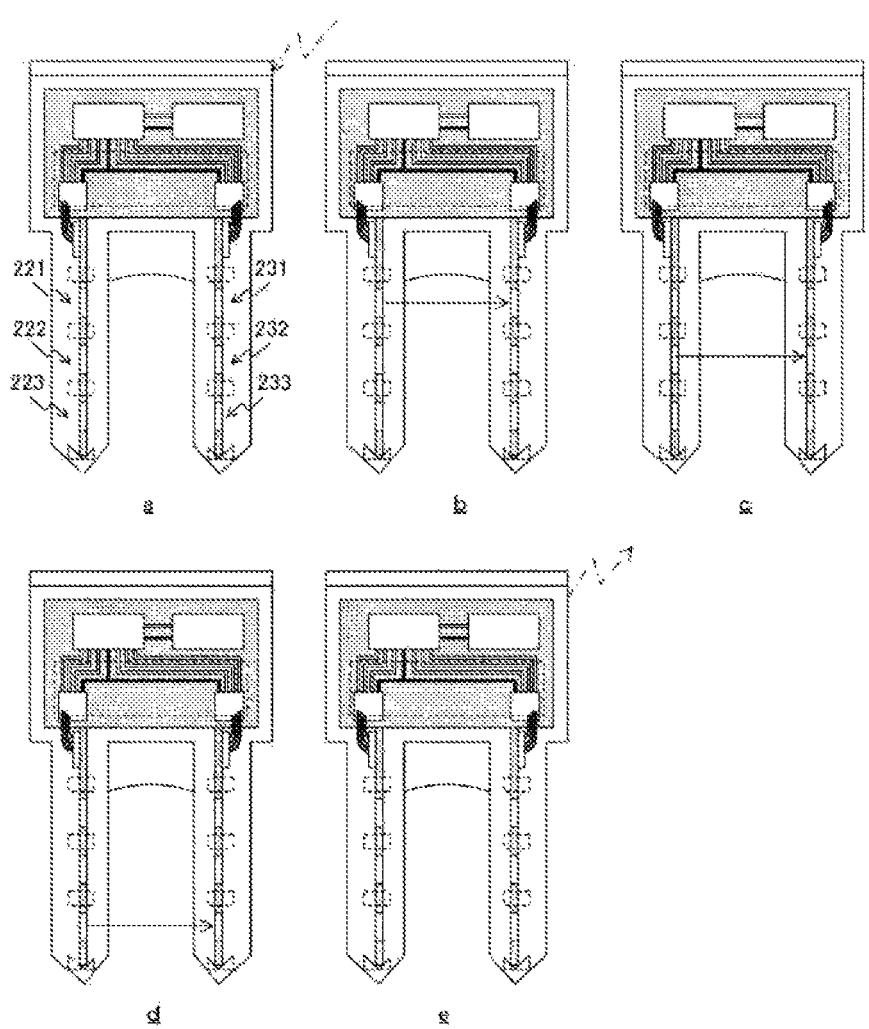
FIG. 115 is a diagram for explaining time-division driving of the antennas according to the first embodiment of the present technology.

FIG. 115 is a diagram for explaining measurement of the amount of moisture in the soil by causing the plurality of antennas included in the sensor device 200 to perform scanning operations in a time division manner according to the first embodiment of the present technology.

The sensor device 200 is illustrated in FIG. 115 as a view seen from the front (seen from the Z-axis direction) similarly to FIG. 4b. The sensor device 200 illustrated in FIG. 115 includes three transmission antennas and three reception antennas as one example. One transmission antenna and one reception antenna disposed to be the closest to the transmission antenna when seen from the transmission antenna out of the three transmission antennas and the three reception antennas are the combination of the transmission antenna and the reception antenna suitable for measurement of the amount of moisture. In the specification, the combination of the transmission antenna and the reception antenna suitable for measurement of the amount of moisture may be referred to as a "transmission and reception antenna pair".

The sensor device 200 illustrated as an example in FIGS. 115a to 115e includes three transmission and reception antenna pairs. More specifically, the sensor device 200 includes (1) a first transmission and reception antenna pair including the transmission antenna 221 and the reception antenna 231, (2) a second transmission and reception antenna pair including the transmission antenna 222 and the reception antenna 232, and (3) a third transmission and reception antenna pair including the transmission antenna 233 and the reception antenna 223.

Here, in regard to the plurality of transmission and reception antenna pairs included in the sensor device 200, a gap between one transmission and reception antenna pair included therein and a transmission and reception antenna pair that is adjacent thereto (in other words, a gap between two adjacent transmission and reception antenna pairs) will be described. The description will be given on the assumption that all the transmission antennas included in all the transmission and reception antenna pairs that the sensor device 200 has concurrently perform the operation of emitting the electromagnetic waves and all the reception antennas included therein concurrently perform the operation of receiving the electromagnetic waves when the amount of moisture in the soil is measured.

Here, in a case where electromagnetic waves are emitted from plane-shaped antennas, it is difficult to emit the electromagnetic waves with high directionality only in the direction vertical to the planes of the antennas in general, and the electromagnetic waves are emitted with some spreading in practice.

[First Problem]

In a case where the gap between two adjacent transmission and reception antenna pairs is small, a part of electromagnetic waves emitted from the transmission antenna of the second transmission and reception antenna pair, for example, may be received by the reception antenna of the first transmission and reception antenna pair. In this case, the reception antenna included in the first transmission and reception antenna pair receives, in a mixed manner, the electromagnetic waves emitted by the transmission antenna (a so-called desired transmission antenna) included in the first transmission and reception antenna pair and the part of the electromagnetic waves emitted by the transmission antenna (the transmission antenna that is not desired) included in the second transmission and reception antenna pair. In other words, a state where jamming has occurred may be achieved. In such a state where jamming has occurred, an occurrence of an error in the measurement result of the amount of moisture in the soil is problematic.

[Second Problem]

The above jamming is further reduced as the gap between two adjacent transmission and reception antenna pairs is increased. Thus, the error included in the measurement result of the amount of moisture in the soil decreases. However, if the gap between the two adjacent transmission and reception antenna pairs is increased, it is not possible to measure only the amount of moisture at only some points in regard to the soil where the sensor device 200 is disposed, which is problematic.

[Conditions of Occurrence of First Problem]

Here, when the first problem occurs will be considered. As schemes for measuring the amount of moisture in the soil, some schemes have been proposed. However, the first problem that electromagnetic waves are received not only from a desired antenna but also undesirable antennas and an error occurs in the reception result if a plurality of antennas are caused to concurrently operate when a plurality of transmission antennas and a plurality of reception antennas are included and the amount of moisture disposed between the transmission antennas and the reception antennas is measured is originally a problem caused by a radiation range (or directionality) of the electromagnetic waves emitted from the transmission antennas. Therefore, the first problem is a problem unique to the sensor device that includes the transmission antennas and the reception antennas and measures the amount of moisture in the medium disposed between the antennas by transmitting and receiving the electromagnetic waves between the antennas.

[Means for Solving First and Second Problems]

In order to concurrently solve these two problems, that is, in order (1) to enhance the density at the point where the amount of moisture is measured (in other words, perform measurement of the amount of moisture at as many points as possible in the soil where the sensor device 200 is disposed) in regard to the soil where the sensor device 200 is disposed and (2) to reduce an error included in the measurement result, the sensor device 200 according to the present invention causes the plurality of antennas included therein to perform scanning operations in a time division manner and measures the amount of moisture in the soil. Thus, the sensor device 200 includes a configuration for causing the plurality of antennas included therein to perform scanning operations in a time division manner, and the measurement section 312 included in the sensor device 200 performs control for causing the plurality of antennas to perform scanning operations in a time division manner to measure the amount of moisture between the antennas. The overview of the operations of causing the sensor device 200 to perform scanning operations in a time division manner and perform measurement (time division scanning measurement operations) will be briefly described. (1) A transmission and reception antenna pair is selected one by one in accordance with a predefined order from among the plurality of transmission and reception antenna pairs included in the sensor device 200, and operations for measuring the moisture in the soil (measurement operations, for example, an operation of transmitting electromagnetic waves from the transmission antenna for measurement, or an operation of receiving the transmitted electromagnetic waves by the reception antenna and detecting the waves by the receiver in the measurement section, or an operation of performing the transmission operation and the wave detecting operation and obtaining the amount of moisture in the soil from the wave detecting result, and the like). Then, (2) the measurement operations are performed by all the transmission and reception antenna pairs defined in advance, and the measurement operations are executed in order by each transmission and reception antenna pair until the results are acquired. The overview of the time division scanning measurement has been described hitherto. Details thereof will be described below.

[Operations of Time Division Scanning Measurement]

Operations for causing the plurality of antennas included in the sensor device 200 to perform scanning operations in a time division manner to measure the amount of moisture in the soil will be described with reference to a to e in FIG. 115.

As illustrated as an example in a in the drawing, once a command for measuring the moisture is received at a certain timing 1, then the sensor device 200 wakes up. As illustrated as an example in b in the drawing, the sensor device 200 executes moisture measurement using a first transmission and reception antenna pair at a timing 2.

Then, the sensor device 200 executes moisture measurement using a second transmission and reception antenna pair at a timing 3 as illustrated as an example in c in the drawing. As illustrated as an example in d in the drawing, the sensor device 200 executes moisture measurement using a third transmission and reception antenna pair at a timing 4.

As illustrated as an example in e in the drawing, the sensor device 200 transmits each of measurement results of all the antennas at a timing 5. Thereafter, the sensor device 200 transitions to a sleep mode. As illustrated as an example in the drawing, the sensor device 200 executes the moisture measurement in order for each of the plurality of sets of antennas while using the set of transmission antenna and the reception antenna one by one and dividing the time zone for the measurement. Finally, it is possible to obtain the measurement result of the moisture over the entire soil region where the plurality of antennas are disposed. The control corresponds to the time division scanning measurement driving of the component (6).

[Hardware Configurations for Time Division Scanning Measurement]

Here, as hardware configurations for performing time division scanning measurement, a configuration including a plurality of transmission paths individually connecting the measurement section substrate 311 in the component (6) to each of a plurality of transmission antennas (FIG. 3) and a first comparative example (FIG. 116) in which the plurality of transmission paths individually connecting the measurement section substrate 311 to each of the plurality of reception antennas are not included will be assumed.

Figure 116:
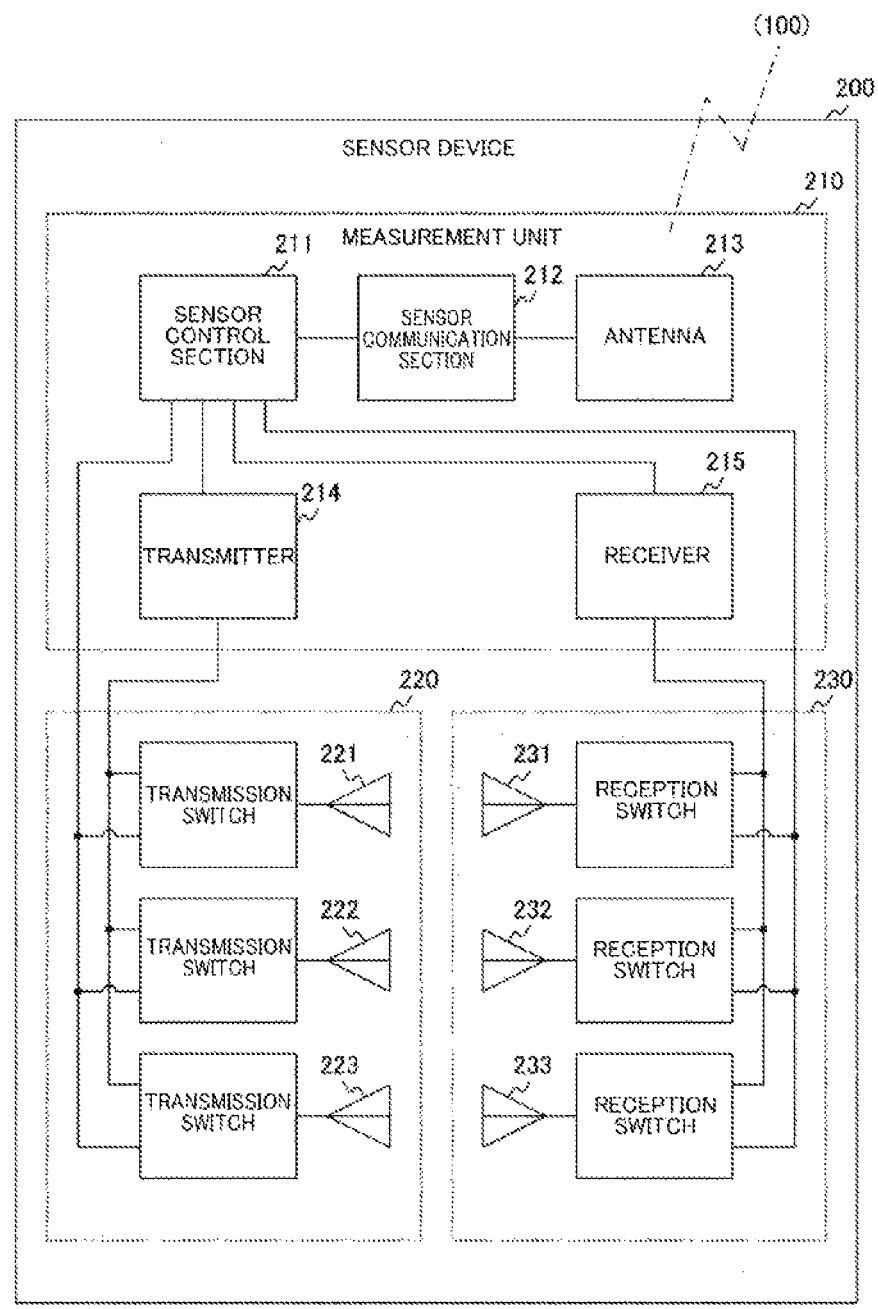
FIG. 116 is a block diagram illustrating a configuration example of a sensor device according to a first comparative example.

FIG. 116 is a block diagram illustrating a configuration example of the sensor device according to the first comparative example. In the first comparative example, it is assumed that one transmission path is branched into a plurality of paths on each of the transmission side and the reception side and is then connected to a plurality of antennas.

In the first comparative example, the transmission path has a plurality of branches, signal reflection may occur at distal ends of the branches at a plurality of locations, this may become noise, and measurement accuracy of the amount of moisture in the soil may thus be degraded. Also, the switch is disposed together with each of the plurality of antennas disposed in the casing, and the volume of the probe casing accommodating the antennas and the switches thus becomes larger than the volume of the probe casing 320 according to the present invention. In this manner, more mud is pushed aside by the probe casing when the probe casing of the moisture sensor device is inserted into the soil, and the pushed mud is added to the soil at the part of the target of the measurement, and the density of the soil at the part of the target of the measurement becomes higher than the original density of the soil. This may also lead to degradation of measurement accuracy of the amount of moisture in the soil.

Next, a second comparative example in which the transmission switch 216 and the reception switch 217 are not provided will be assumed.

Figure 117:
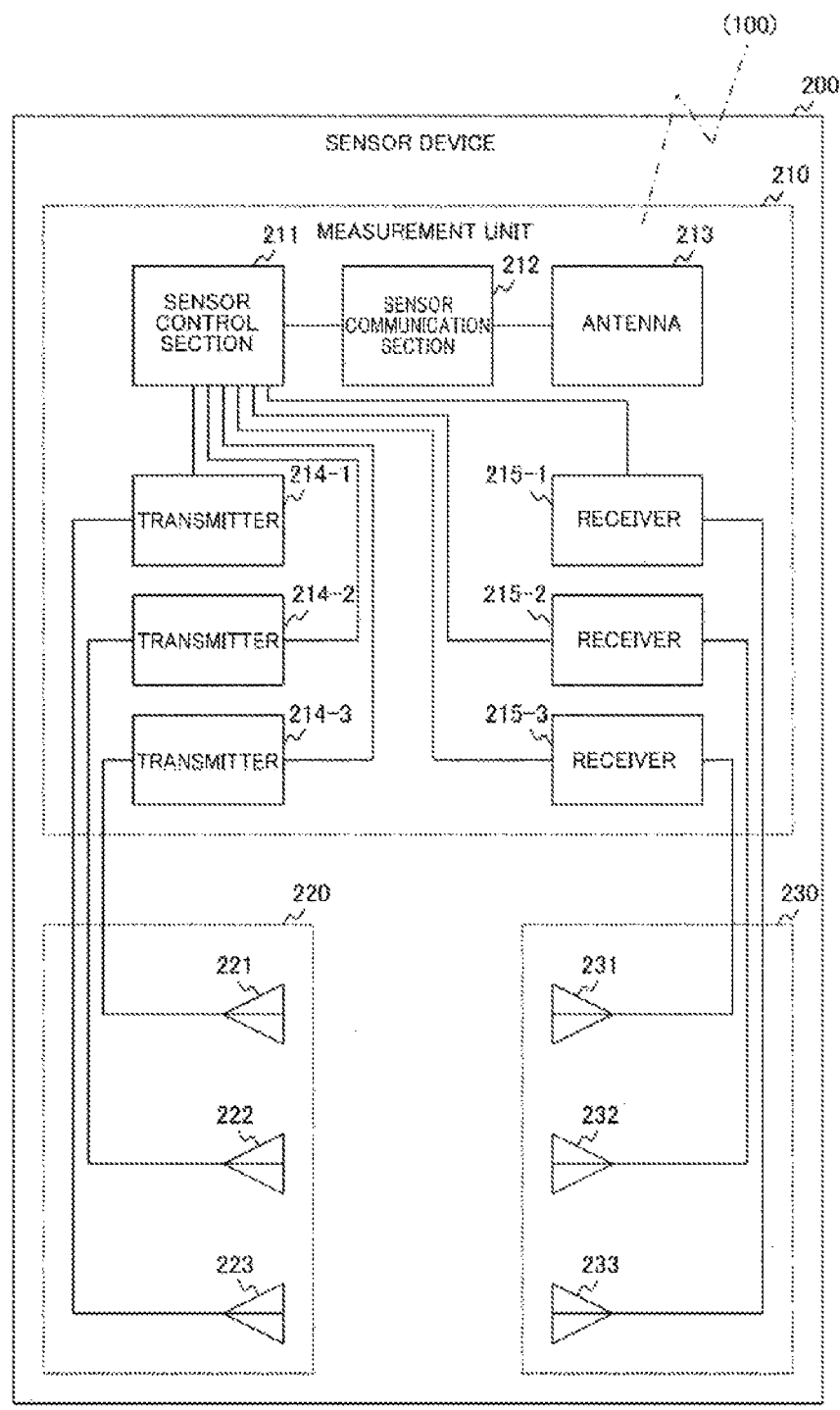
FIG. 117 is a block diagram illustrating a configuration example of a sensor device according to a second comparative example.

FIG. 117 is a block diagram illustrating a configuration example of the sensor device according to the second comparative example. In the second comparative example, the measurement section substrate 311 is provided with a transmitter or a receiver for each antenna on the transmission side and the reception side.

In the second comparative example, it is necessary to provide a plurality of transmitters and a plurality of receivers such that the numbers thereof are the same as the number of antennas included in the sensor device. Therefore, the area of the measurement section substrate 311 increases as compared with a case where only one set of a transmitter and a receiver is provided, and the length of the transmission path connecting them to the antennas on the measurement section substrate 311 has to become longer. As a result, in a case of causing a set of a transmitter and a receiver on the substrate to operate, the power consumption must be larger in the second comparative example in which the transmission path length is longer.

Furthermore, in the second comparative example, the area of the measurement section substrate 311 increases, and the measurement section casing 310 accommodating the measurement section substrate 311 has to become larger. In this case, the likelihood that the sensor casing 305 breaks at the boundary between the measurement section casing 310 receiving lateral wind and the probe casing 320 buried in the soil increases in a case where the lateral wind blows against the sensor device, for example.

Furthermore, in the second comparative example, the area of the measurement section substrate 311 increases, and this leads to a problem that sprinkle water from the lateral direction provided by a sprinkler, for example, is interrupted by the measurement section casing 310 or in a case where a plant is in an initial growth state and has a short height, sunshine for the plant or adjacent plants is disturbed, for example.

The sensor device 200 according to the present invention has the following structure illustrated as an example in FIG. 3 as hardware to perform time division scanning measurement and to prevent the above problems that occur in the first and second comparative examples. In other words, (1) transmission paths 218-1 to 218-3 for transmission that connect each transmission antenna and the measurement circuit 210 are included for each transmission antenna such that it is possible to select only one transmission antenna to be caused to operate from among all the transmission antennas 221 to 223 included in the sensor device 200. Thus, a plurality of transmission paths for transmission are included. (2) As a device for selecting one transmission antenna and transmission path for transmission from among all the transmission antennas 221 to 223 included in the sensor device 200 and the transmission paths 218-1 to 218-3 for transmission connected thereto, a transmission switch 216 is included between the transmitter 214 and the plurality of transmission paths 218-1 to 218-3 for transmission. (3) The transmission paths 219-1 to 219-3 for reception connecting each reception antenna and the measurement circuit 210 are included independently for each reception antenna such that it is possible to select only one reception antenna to be caused to operate from among all the reception antennas 231 to 233 included in the sensor device 200. Thus, a plurality of transmission paths for reception are included. (4) As a device for selecting one reception antenna and transmission path for reception from among all the reception antennas 221 to 223 included in the sensor device 200 and the transmission paths 219-1 to 219-3 for reception connected thereto, a reception switch 217 is included between the receiver 215 and the plurality of transmission paths 219-1 to 219-3 for reception.

Figure 118:
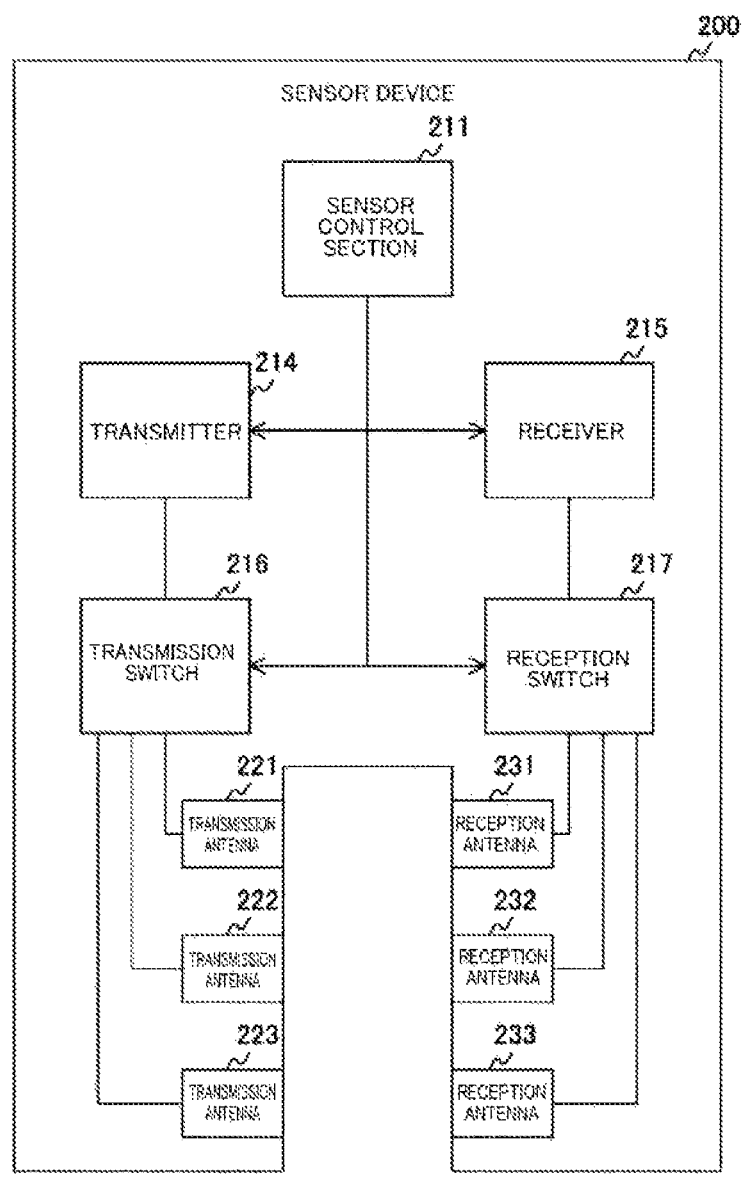
FIG. 118 is a block diagram illustrating a configuration example of the sensor device, in which time-division driving of the antennas is focused, according to the first embodiment of the present technology.

FIG. 118 is a block diagram illustrating a configuration example illustrating, in a simplified manner, the sensor device 200 by focusing on time division driving of the antennas according to the first embodiment of the present technology illustrated as an example in FIG. 3.

The sensor device 200 includes the transmission switch 216 and the reception switch 217, and the sensor control section 211 controls them in a time division manner and selects one transmission path for each of transmission and reception. It is thus possible to select an antenna in a desired depth direction.

Note that as already described above with reference to the measurement circuit 210 in FIG. 3 and the measurement section 312 in FIG. 4, the measurement section 312 in FIG. 4 and the measurement circuit 210 including the sensor control section 211, the transmitter 214, the transmission switch 216, the receiver 215, and the reception switch 217 may be configured of one semiconductor device or may be configured using a plurality of semiconductor devices. In other words, the sensor control section 211, the transmitter 214, the transmission switch 216, the receiver 215, and the reception switch 217 in FIG. 118 illustrated by simplifying FIG. 3 may also be configured of one semiconductor device or may be configured using a plurality of semiconductor devices.

Figure 119:
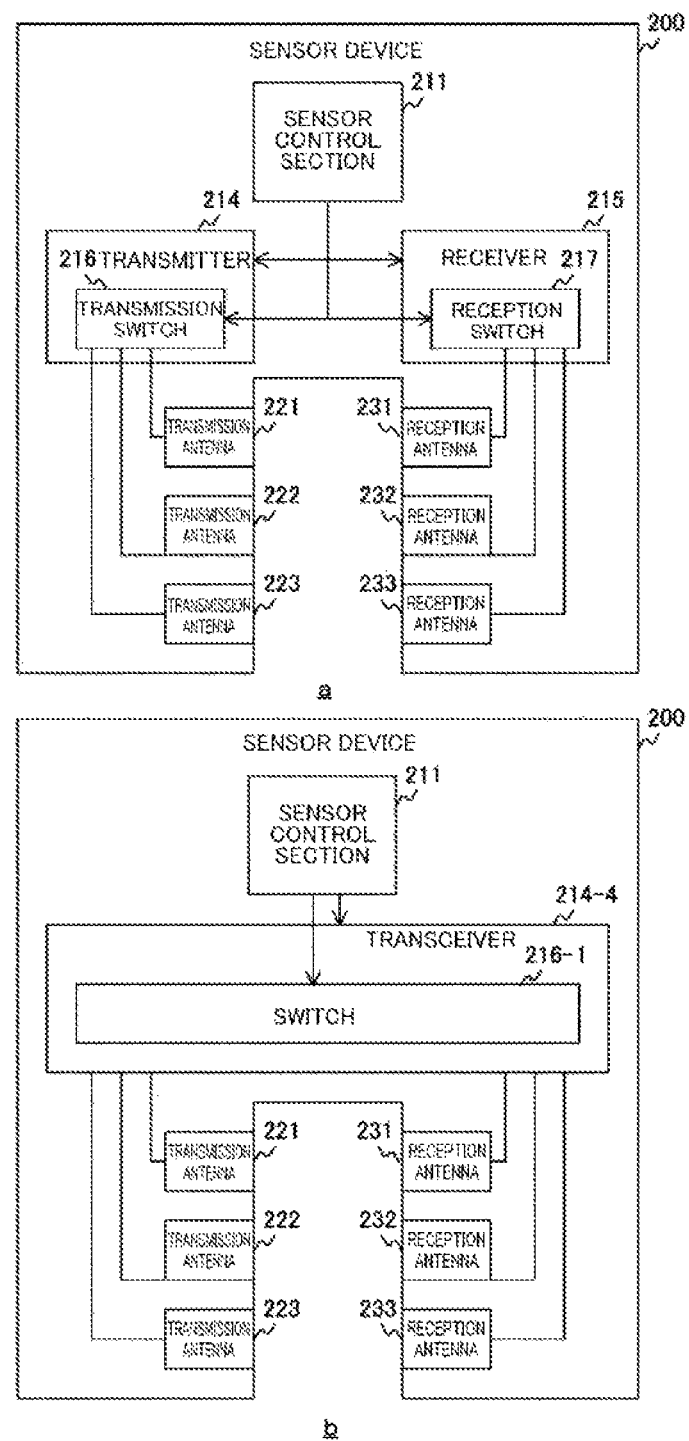
FIG. 119 is a block diagram illustrating a configuration example of the sensor device in which a transmission switch and a reception switch are incorporated in a transmitter and a receiver according to the first embodiment of the present technology.

FIG. 119 is a block diagram illustrating a configuration example in which the transmission switch 216 and the reception switch 217 are incorporated in the transmitter 214 and the receiver 215 as another configuration example of the sensor device 200 according to the first embodiment of the present technology. As illustrated as an example in a in the drawing, it is also possible to provide the transmission switch 216 in the transmitter 214 and to provide the reception switch 217 in the receiver 215. Here, the transmitter 214 and the receiver 215 refer to, for example, a transmitter integrated circuit (IC) and a receiver IC, or a transmitter module and a receiver module. In other words, a in the drawing is one of examples in which the measurement circuit 210 and the measurement section 312 are configured using a plurality of semiconductor devices. Additionally, a is an example in which each of the sensor control section 211, the transmitter 214, and the receiver 215 is configured using a different semiconductor device. In addition, a in the drawing is an example in which each of the sensor control section 211, the transmission switch 216, and the reception switch 217 is configured using a different semiconductor device. As illustrated as an example in b in the drawing, it is also possible to provide, instead of the transmitter 214 and the receiver 215, a transceiver 214-4 having the functions thereof. Also, it is also possible to provide, instead of the transmission switch 216 and the reception switch 217, a switch 216-1 having the functions thereof and to incorporate the switch 216-1 in the transceiver 214-4. In other words, b in the drawing is another example in which the measurement circuit 210 and the measurement section 312 are configured of a plurality of semiconductor devices. Additionally, b is an example in which each of the sensor control section 211 and the transceiver 214-4 is configured using a different semiconductor device. Also, b in the drawing is an example in which each of the sensor control section 211 and the switch 216-1 is configured using a different semiconductor device.

FIG. 120 is a block diagram illustrating a configuration example of the sensor device 200 with a switch provided only on the reception side as yet another configuration example of the sensor device 200 according to the first embodiment of the present technology. As illustrated as an example in a in the drawing, it is also possible to adopt a configuration in which the transmission switch 216 is not provided. In a in the drawing, it is possible to configure the sensor control section 211, the transmitter 214, the receiver 215, and the reception switch 217 by one semiconductor device or to configure them by different semiconductor devices. As illustrated as an example in b in the drawing, it is also possible to provide the reception switch 217 in the receiver 215 without providing the transmission switch 216. In b in the drawing, the sensor control section 211, the transmitter 214, and the receiver 215 may be configured of one semiconductor device or may be configured of different semiconductor devices.

As illustrated as an example in FIGS. 119 and 120, the switches are incorporated, and it is thus possible to save the space as compared with FIG. 118. Since the switch is provided only on the reception side in FIG. 120, the configuration is simpler than in FIG. 119, and the space can be further saved. Note that although according to the sensor device 200 illustrated as an example in FIG. 120, it is not possible to avoid jamming at the time of the measurement as described above, the effect of enabling size reduction of the device can be obtained.

Figure 121:
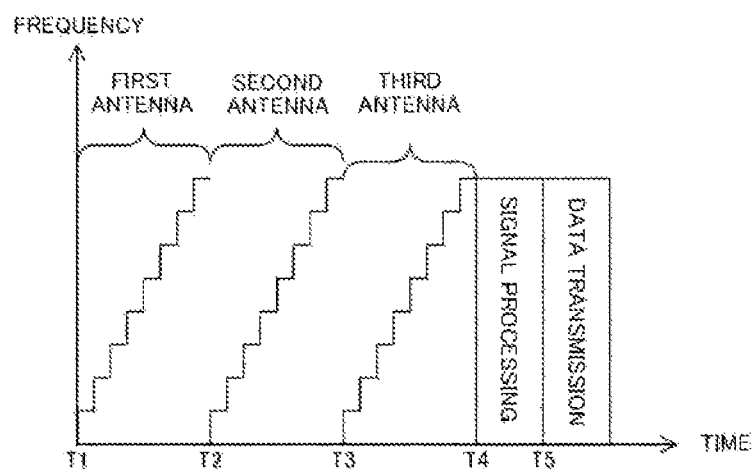

FIG. 121 is an example of a timing chart of time division driving according to the first embodiment of the present technology.

Figure 122:
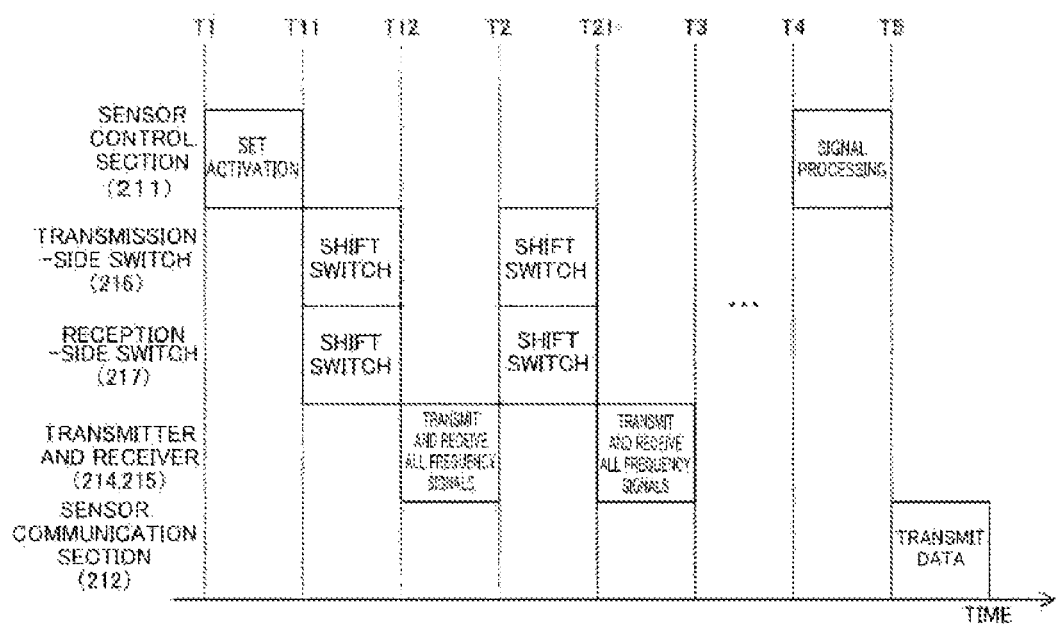

FIG. 122 is an example of a timing chart illustrating operations of each section in the sensor device 200.

As illustrated as an example in FIGS. 121 and 122, the sensor device 200 is caused to sleep during a period scheduled in advance and is then activated. The transmission switch 216 and the reception switch 217 selects one antenna from among the plurality of antennas in a time division manner. The transmitter 214 and the receiver 215 performs transmission and reception wave detecting operations for measurement at each of all the frequencies used for the measurement while changing the frequencies used for the measurement in a stepwise manner with respect to the time by using the one selected antenna. In the transmission and reception wave detecting operations, transmission, reception, and detection of a signal, AD conversion of a complex amplitude as a result of wave detection, and storing of the conversion result in the memory are performed. The memory is provided in the measurement section substrate 311, for example.

Note that it is desirable that the electromagnetic waves to be detected be transmitted from the transmission antenna to the reception antenna over a plurality of cycles to perform the wave detecting operation once. In other words, it is desirable that the electromagnetic waves corresponding to a plurality of cycles be transmitted from the transmission antenna and these be detected by the measurement circuit 210 in transmission and reception wave detecting operation performed once.

Note that although details will be described later, the reason of performing the measurement while changing the frequency will be briefly described here. The moisture measurement system 100 according to the first embodiment of the present technology calculates a reflection coefficient and a transmission coefficient, which will be described later, from the wave detecting result (complex amplitude) after performing the above transmission and reception wave detecting operations (in other words, the transmission, the reception, and the detection of the signal, the AD conversion of the complex amplitude that is a wave detecting result, and the storing of the conversion result in the memory), performs inverse Fourier transformation of these to obtain an impulse response, obtains a delay time on the basis of this, and further obtains the amount of moisture on the basis of this. In order to obtain one impulse response, the moisture measurement system 100 executes the transmission and reception wave detecting operations at a plurality of frequencies. This is why the measurement is performed while the frequency is changed as described above with reference to FIG. 121.

The sensor device 200 finishes the execution of the above series of operations at all the frequencies for the measurement by using one transmission and reception antenna pair and then performs the above operations by using each of the remaining transmission and reception antenna pairs in a time division manner. The selection of the transmission and reception antenna pair is performed in accordance with a predefined order. The order may be selected in accordance with the order of the positions of the disposed antennas, or an arbitrary order that is different from this may be defined in advance.

If the execution of the above operations is finished by all the transmission and reception antenna pairs, the sensor control section 211 performs signal processing for each transmission and reception antenna pair. The signal processing is, for example, processing of calculating the reflection coefficient and the transmission coefficient from the wave detecting result (complex amplitude) at each frequency, performing inverse Fourier transformation on this to obtain an impulse response, and obtaining a delay time on the basis of this.

If the signal processing is ended for each of all the transmission and reception antenna pairs, the sensor communication section 212 collectively transmits the signal processing result data of all the transmission and reception antenna pairs to the central processing unit in a wireless manner.

The central processing unit 150 calculates the amount of moisture in the soil for each transmission and reception antenna pair on the basis of the received result. If the wireless transmission is ended, the sensor device 200 sleeps again during the period scheduled in advance.

Note that instead of the central processing unit 150, the sensor device 200 may calculate the amount of moisture in the soil for each transmission and reception antenna pair and transmit the calculation result to the central processing unit 150. Also, the order of switch shifting on the transmission side and the switch shifting on the reception side may be concurrent, the switch shifting on the transmission side may be performed first, or the switch shifting on the reception side may be performed first. Also, the method of changing the frequency in a stepwise manner may be performed in a direction of moving up the steps or in a direction of moving down the steps, or alternatively, the order of the frequencies may be switched, and the frequency may be changed in a discontinuous manner or in a predefined arbitrary order.

Additionally, the above transmission and reception wave detecting operations for measurement excited at one measurement frequency by one transmission and reception antenna pair may be repeatedly performed a plurality of times (100 times, for example) in order to enhance accuracy of the measurement (in order to enhance reproducibility of the measurement result).

In a case where the operations is repeated 100 times at each measurement frequency by each antenna, the sensor device 200 performs the transmission and reception wave detecting operations 100 times at the first frequency of the first transmission and reception antenna pair and then performs the transmission and reception wave detecting operations 100 times at the second frequency by the first transmission and reception antenna pair. If the repeated operations at each of the remaining frequencies are ended by the first transmission and reception antenna pair, the above repeated operations may be performed by each of the remaining transmission and reception antenna pairs. Note that the order of executing the operations may not be limited to the above order as long as the operation results corresponding to a predetermined number of repetitions can be obtained at each measurement frequency by each transmission and reception antenna pair.

The control example in FIGS. 121 and 122 is defined as a control example a.

Figure 123:
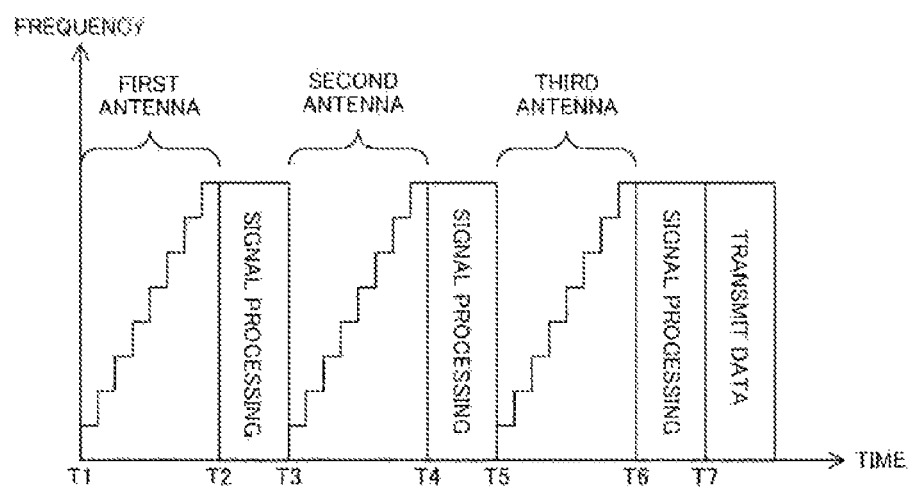

FIG. 123 is an example of a timing chart of time division driving when the timing of the signal processing is changed according to the first embodiment of the present technology.

Figure 124:
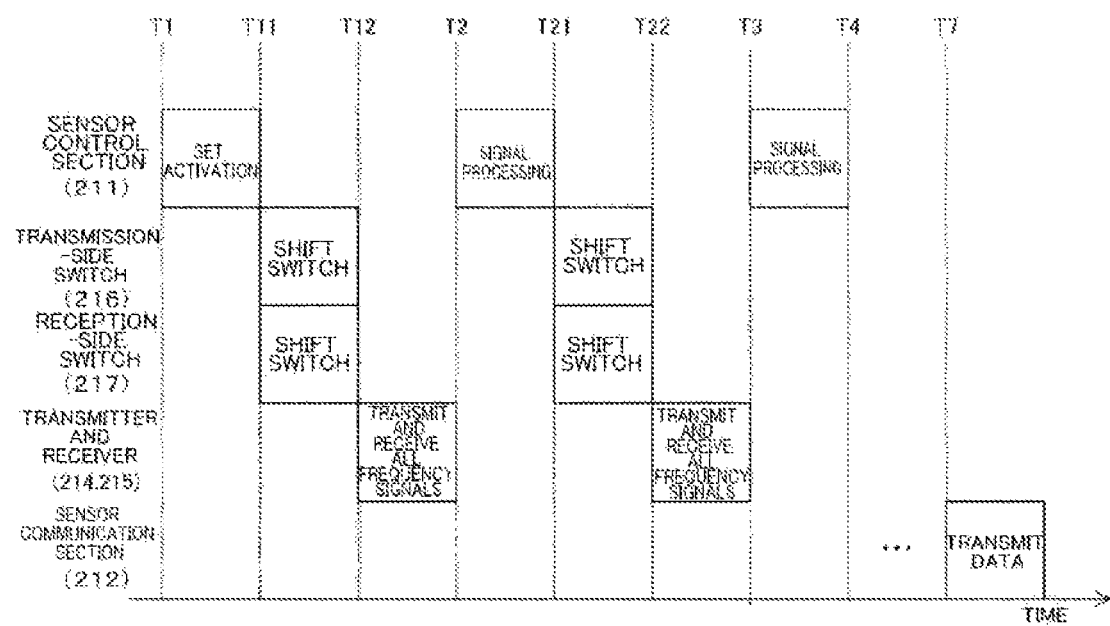

FIG. 124 is an example of a timing chart illustrating operations of each section in the sensor device when the timing of the signal processing is changed according to the first modification example of the present technology.

As illustrated as an example in FIGS. 123 and 124, it is also possible to change the timing of the signal processing. In the control example b, the sensor control section 211 performs signal processing every time it ends the series of transmission and reception wave detecting operations at a plurality of frequencies. In this manner, it is possible to reduce the amount of data of the wave detecting result to be stored to perform the above signal processing as compared with the control example a.

Specifically, in a case where the sensor device includes n transmission and reception antenna pairs, it is possible to reduce the scale of the memory to 1/n. Additionally, the number of times the wireless transmission of data, which will be described later, is performed may be 1/n the number of times in the control example c. In this manner, the number of times the processing before and after transmission of payload data is executed becomes 1/n in the wireless transmission performed each time, and the power consumption required for the processing also becomes 1/n the power consumption in the control example c, which will be described later.

Figure 125:
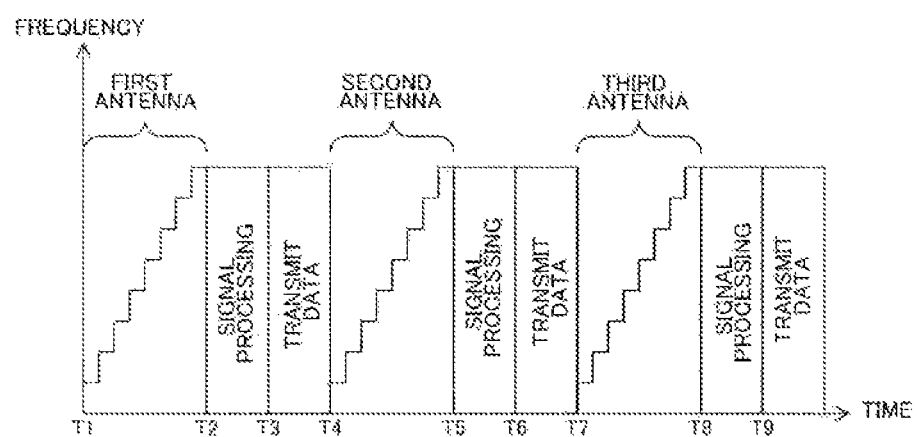

FIG. 125 is an example of a timing chart of time-division driving when timings of signal processing and data transmission are changed according to the first embodiment of the present technology.

Figure 126:
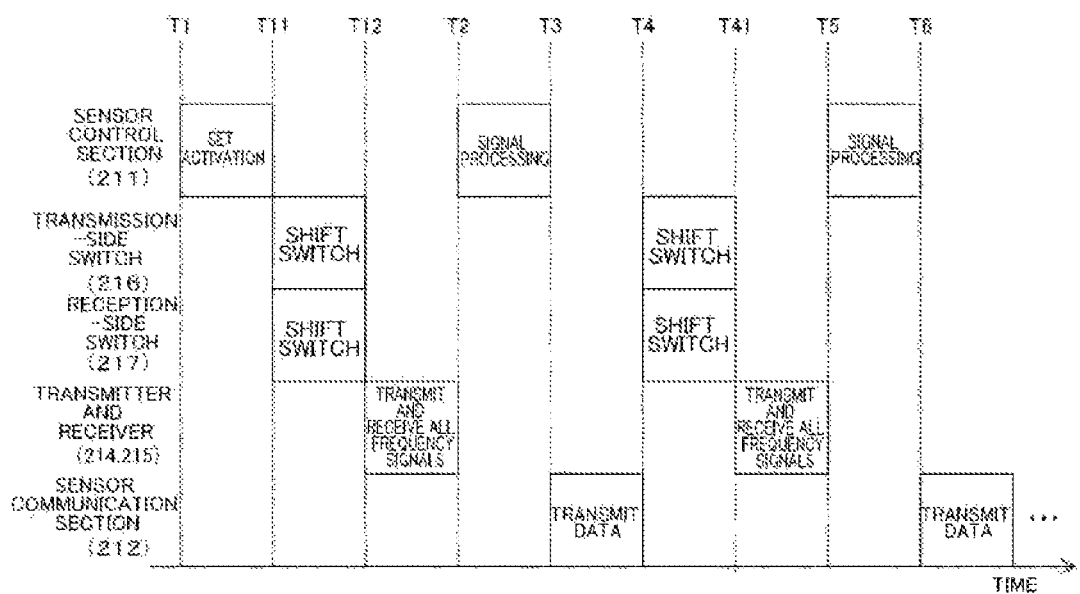

FIG. 126 is an example of a timing chart illustrating operations of each section in the sensor device when the timings of the signal processing and the data transmission are changed according to the first embodiment of the present technology.

As illustrated as examples in FIGS. 125 and 126, it is also possible to change the timings of the signal processing and the data transmission. In the control example c, the sensor communication section 212 transmits obtained data in a wireless manner every time all the transmission and reception wave detecting operations and subsequent signal processing are ended at a series of frequencies for each transmission and reception antenna pair. In this manner, the amount of data of the signal processing result to be held to perform the wireless transmission becomes smaller than that in the control example b. Specifically, in a case where the sensor device includes n transmission and reception antenna pairs, the scale of the memory for holding the data of the signal processing result may be 1/n the scale in the control example b.

Figure 127:
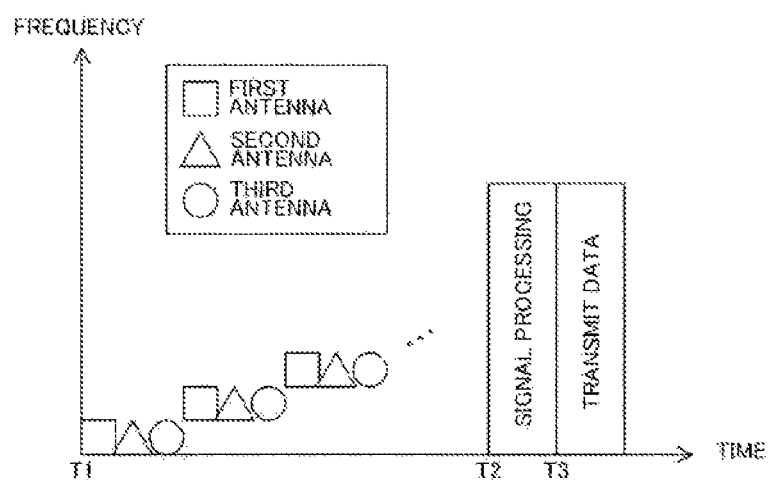

FIG. 127 is an example of a timing chart of time-division driving when the order of the transmission and reception wave detecting operations is changed according to the first embodiment of the present technology.

Figure 128:
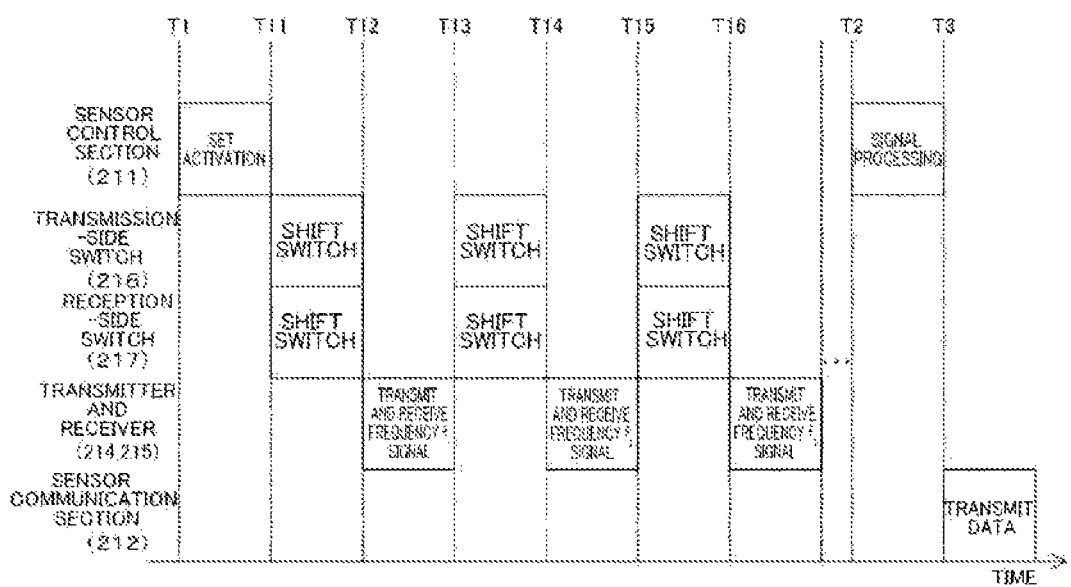

FIG. 128 is an example of a timing chart illustrating operations of each section in the sensor device when the order of the transmission and reception wave detecting operations is changed according to the first embodiment of the present technology.

As illustrated as examples in FIGS. 127 and 128, it is also possible to change the order of the transmission and reception wave detecting operations. In the control example d, the transmitter 214 and the receiver 215 change the frequencies in a stepwise manner, and the transmission switch 216 and the reception switch 217 select all the transmission and reception antenna pairs in order for each frequency. In this manner, the amount of data of the signal processing result to be held to perform the wireless transmission becomes smaller than that in the control example b. Specifically, in a case where the sensor device includes n transmission and reception antenna pairs, the scale of the memory for holding data of the signal processing result may be 1/n the scale in the control example b.

Differences between the operations in the control example d described above with reference to FIGS. 127 and 128, that is, "the operations of the transmitter 214 and the receiver 215 changing the frequencies in a stepwise manner and of the transmission switch 216 and the reception switch 217 selecting all transmission and reception antenna pairs in order for each frequency and performing transmission and reception wave detecting operations" and the operations in the control example a described above will be described in a comparing manner.

The operations in the control example an illustrated in FIGS. 121 and 122 include, as described above, (1) performing "transmission and reception wave detecting operations on electromagnetic waves in order at each of all the frequencies at which the measurement is performed while changing the frequencies of the electromagnetic waves (transmission and reception wave detecting operation)" by using one transmission and reception antenna pair, and (2) performing "a transmission and reception wave detecting operations on electromagnetic waves in order at each of all the frequencies at which the measurement is performed while changing the frequencies of the electromagnetic waves" by each of the remaining transmission and reception antenna pairs used for the measurement from among the plurality of transmission and reception antenna pairs included in the sensor device 200 after finishing the execution of the above operations by the one transmission and reception antenna pair.

On the other hand, the operations in the control example d illustrated in FIGS. 127 and 128 include, as described above, (1) performing "the transmission and reception wave detecting operations on electromagnetic waves in order (transmission and reception wave detecting operations) by each of all the transmission and reception antenna pairs used for the measurement from among the plurality of transmission and reception antenna pairs included in the sensor device 200 while switching the transmission and reception antenna pair to be caused to transmit and receive the electromagnetic waves" at one frequency, and (2) performing "the believing and receiving wave detecting operations on the electromagnetic waves in order by each of all the transmission and reception antenna pairs used for the measurement from among the plurality of transmission and reception antenna pairs included in the sensor device 200 while switching the transmission and reception antenna pairs" at each of remaining frequencies after finishing the execution of the above operation at one frequency.

As an example of the control example d, the example illustrated in FIG. 127 illustrates an example including (i) performing the transmission and reception wave detecting operations on electromagnetic waves in order by each of all the transmission and reception antenna pairs used for the measurement from among the plurality of transmission and reception antenna pairs included in the sensor device 200 while switching the transmission and reception antenna pair to be caused to transmit and receive the electromagnetic waves by using a first frequency, (ii) performing the transmission and reception wave detecting operations on the electromagnetic waves in order by each of all the transmission and reception antenna pairs used for the measurement while switching the transmission and reception antenna pairs to be caused to transmit and receive the electromagnetic waves by using a second frequency after finishing the execution of the above operation by using the first frequency, (iii) performing the transmission and reception wave detecting operations on electromagnetic waves in order by each of all the transmission and reception antenna pairs used for the measurement while switching the transmission and reception antenna pair to be caused to transmit and receive the electromagnetic waves by using a third frequency after finishing the execution of the above operation by using the second frequency, (iv) repeating the operations similar to those described above, that is, the transmission and reception wave detecting operations on electromagnetic waves in order by each of all the transmission and reception antenna pairs used for the measurement from among the plurality of transmission and reception antenna pairs included in the sensor device 200 while switching the transmission and reception antenna pair to be caused to transmit and receive the electromagnetic waves at a remaining frequency used for the measurement after finishing the execution of the above operation by using the third frequency, and (V) performing signal processing on the result obtained by the transmission and reception wave detecting operations and transmitting data of the signal processing result after finishing the execution of the transmission and reception wave detecting operations on the electromagnetic waves by each of all the transmission and reception antenna pairs used for the measurement at all the frequencies used for the measurement.

The operations can be represented as in FIG. 349 as a timing chart illustrating operations of each section in the sensor device. FIG. 349 is a timing chart illustrating operations of each section in the sensor device when the order of the transmission and reception wave detecting operations is changed according to the first embodiment of the present technology and illustrates the operations (i) to (v) above.

Also, in comparison between the number of times the transmitter switches the frequency of the transmission signal from the activation to the sleep of the sensor device 200, the number of times the frequency is switched is the smallest in the control example d from among the control examples a to d. Since it is possible to minimize the total time of switching the frequency of the phase locked loop (PLL) in the transmitter 214 from the activation to the sleep of the sensor device 200 in the control example d as compared with the control examples a, b, and c, it is possible to shorten the measurement time and to reduce power consumption. Typically, the frequency switching time of the PLL is about 100 microseconds (μs), and the switching time of the transmission switch 216 is about 100 nanoseconds (ns). On the assumption that the number of channels is 161 and the number of antennas is three, the time regarding switching in the control examples a, b, and c is obtained by the following expression.

$$161 \times 3 \times 100 \text{ μs} + 50 \text{ ns} \times 3 = 0.048 \text{s} \quad \text{Expression 1}$$

On the other hand, the time regarding switching in the control example d is obtained by the following expression.

$$161 \times 1 \times 100 \text{ μs} + 50 \text{ ns} \times 161 \times 3 = 0.016 \text{s} \quad \text{Expression 2}$$

From Expressions 1 and 2, the time regarding the switching is about ⅓.

Figure 129:
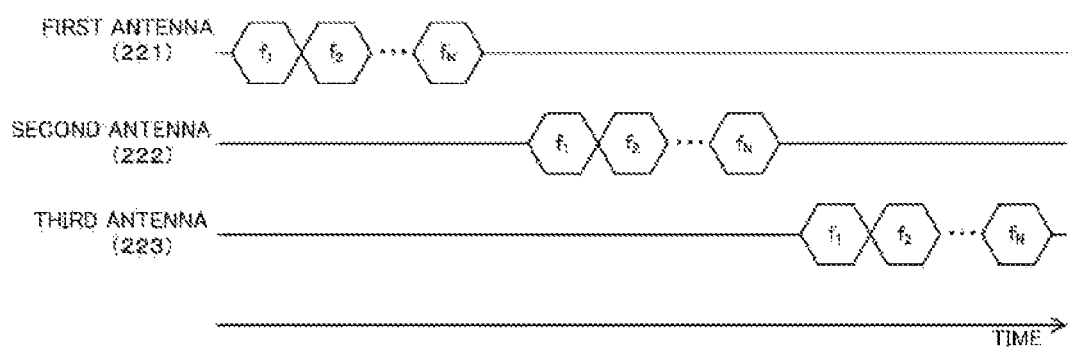

FIG. 129 is a diagram illustrating an example of a transmission signal of each antenna (each transmission and reception antenna pair) in the control examples a, b, and c according to the first embodiment of the present technology. As illustrated as an example in the drawing, the first antenna (transmission antenna 221) outputs the transmission signals at frequencies $f_1$ to $f_N$ in order, and then the second antenna (transmission antenna 222) outputs transmission signals at frequencies $f_1$ to $f_N$ in order. Then, the third antenna (transmission antenna 223) outputs transmission signals at frequencies $f_1$ to $f_N$ in order next.

Figure 130:
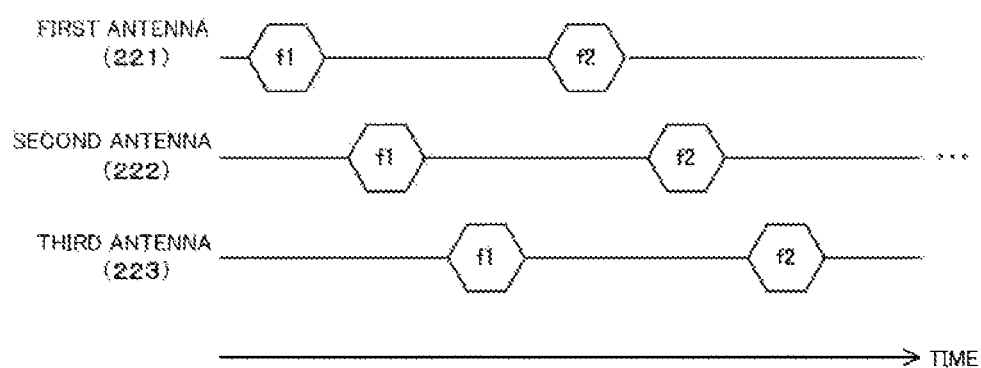

FIG. 130 is a diagram illustrating an example of a transmission signal of each antenna (each transmission and reception antenna pair) in the control example d according to the first embodiment of the present technology. As illustrated as an example in the drawing, the first to third antennas output transmission signals at the frequency f1 in order, and the first to third antennas then output transmission signals at the frequency f2 in order. Hereinafter, similar control is executed until the frequency $f_N$.

Configuration Example of Casing

Figure 131:
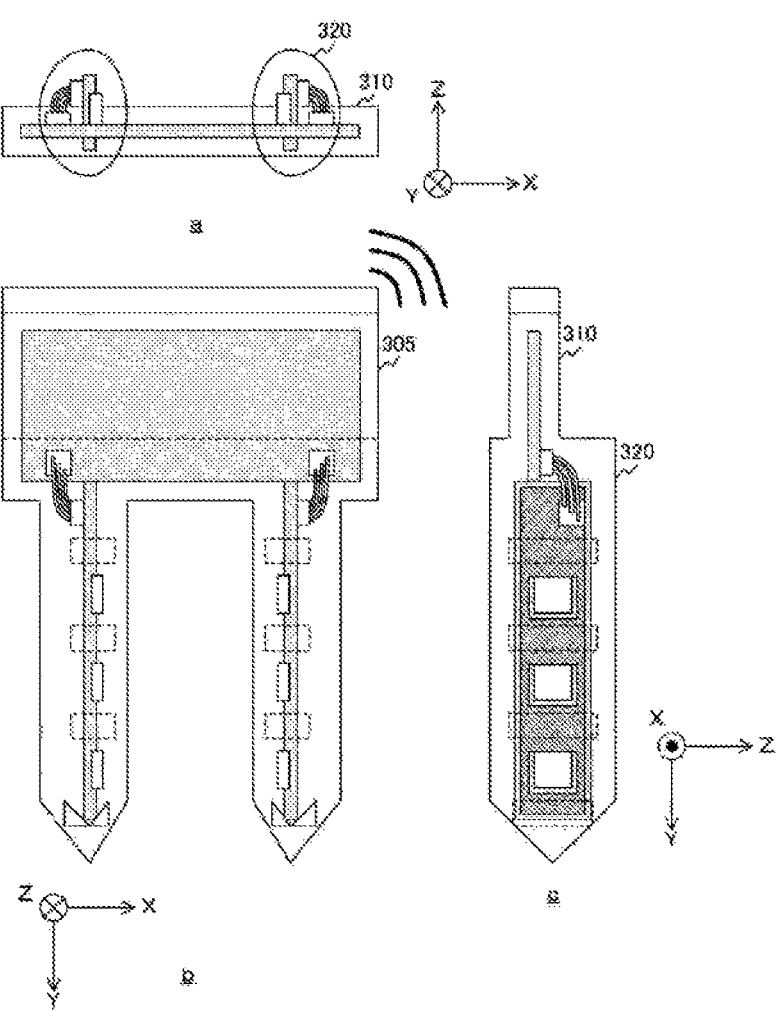

FIG. 131 is a diagram illustrating another example of the sensor device 200 according to the first embodiment of the present technology. In comparison between the sensor device 200 illustrated in FIG. 4 and the sensor device 200 illustrated in FIG. 131, the former (FIG. 4) includes the battery inside the measurement section casing 310 while the latter (FIG. 131) does not include any battery inside the measurement section casing 310 and adopts a mode on the assumption that power is supplied from the outside of the sensor device 200 or power is produced by the sensor device 200 itself using a solar battery or the like.

In the sensor device 200 illustrated in FIG. 131, the measurement section substrate 311 is disposed such that the sizes thereof in the X-axis direction and the Y-axis direction are larger than the size thereof in the Z-axis direction. In other words, the measurement section substrate 311 is disposed in a state where the largest surface included therein is caused to extend in the direction vertical to the ground surface. In regard to the relationship with the two probe casings 320 included in the sensor device 200, the measurement section substrate 311 is disposed such that one plane including two line segments, namely a center line of the transmission probe casing 320a indicating the extending direction of the transmission probe casing 320a and a center line of the reception probe casing 320b indicating the extending direction of the reception probe casing 320b and the largest surface included in the measurement section substrate 311 are parallel with each other.

Also, in the sensor device 200 illustrated in FIG. 131, the measurement section casing 310 to accommodate the measurement section substrate 311 therein is similarly disposed such that the sizes thereof in the X-axis direction and the Y-axis direction are larger than the size thereof in the Z-axis direction. In other words, the measurement section casing 310 is disposed in a state where the largest surface included therein is caused to extend in the direction vertical to the ground surface. In regard to the relationship with the two probe casings 320 included in the sensor device 200, the measurement section casing 310 is disposed such that one plane including two line segments, namely a center line of the transmission probe casing 320a indicating the extending direction of the transmission probe casing 320a and a center line of the reception probe casing 320b indicating the extending direction of the reception probe casing 320b and the largest surface included in the measurement section casing 310 are parallel with each other.

The sensor device 200 illustrated in FIG. 131 has an effect that rainfall and sprinkle water from above the sensor device 200 are likely to enter the soil as a target of the measurement of the amount of moisture (in other words, it is likely to become soil where the sensor device is not disposed) located between the two probe casings 320 by including the disposition structure as compared with the mode in which the disposition structure is not included.

FIG. 132 is a diagram illustrating, in a simplified manner, an example of the sensor device 200 illustrated in FIG. 4 according to the first embodiment of the present technology. The sensor device 200 illustrated in FIG. 132 is illustrated in a mode in which a battery is included inside the measurement section casing 310 similarly to the sensor device 200 illustrated in FIG. 4. Therefore, the sensor device 200 illustrated in FIG. 132 has the measurement section casing 310 with a larger size in the Z-axis direction than the sensor device 200 illustrated in FIG. 131.

Also, the measurement section substrate 311 is disposed such that the sizes thereof in the X-axis direction and the Y-axis direction are larger than the size thereof in the Z-axis direction in the sensor device 200 illustrated in FIG. 132 as well. In other words, the measurement section substrate 311 is disposed in a state in which the largest surface included therein is caused to extend in the direction vertical to the ground surface. In regard to a relationship with the two probe casings 320 included in the sensor device 200, the measurement section substrate 311 is disposed such that one pane including two line segments, namely a center line of the transmission probe casing 320a indicating the extending direction of the transmission probe casing 320a and a center line of the reception probe casing 320b indicating the extending direction of the reception probe casing 320b and the largest surface included in the measurement section substrate 311 are parallel with each other.

Also, in the sensor device 200 illustrated in FIG. 132, the measurement section casing 310 is disposed such that the sizes thereof in the X-axis direction and the Y-axis direction are larger than the size thereof in the Z-axis direction. In other words, the measurement section casing 310 is disposed in a state where the largest surface included therein is caused to extend in the direction vertical to the ground surface. In regard to the relationship with the two probe casings 320 included in the sensor device 200, the measurement section casing 310 is disposed such that one plane including two line segments, namely a center line of the transmission probe casing 320a indicating the extending direction of the transmission probe casing 320a and a center line of the reception probe casing 320b indicating the extending direction of the reception probe casing 320b and the largest surface included in the measurement section casing 310 are parallel with each other.

The sensor device 200 illustrated in FIG. 132 has an effect that rainfall and sprinkle water from above the sensor device 200 are likely to enter the soil as a target of the measurement of the amount of moisture (in other words, it is likely to become soil where the sensor device is not disposed) located between the two probe casings 320 by including the disposition structure as compared with the mode in which the disposition structure is not included.

FIGS. 133 and 134 are diagrams illustrating an example of the sensor device 200 obtained by adding gutters on the basis of the sensor device 200 illustrated in FIGS. 131 and 132. As illustrated as an example in FIGS. 133 and 134, it is also possible to add gutters 362 to 364 for discharging rainfall or sprinkle water to the outside. The gutter 362 is provided at a lower portion of the measurement section casing 310, and the gutters 363 and 364 are provided at an upper portion of the probe casing 320. In this manner, it is possible to reduce the situations in which the measurement section casing 310 collects rainfall or sprinkle water that has flown from the lateral direction and causes it to flow into the interface between the probes and the soil.

FIG. 135 is a diagram for explaining the strength of the probe casing 320 included in the sensor device 200 according to the first embodiment of the present technology.

In the drawing, a illustrates a state before deformation when one end of the probe casing 320 is fixed and a specific load is applied to the other end. In the drawing, b illustrates a state of the probe casing 320 after deformation. In the drawing, c illustrates a state before deformation in a case where one end of the intra-probe substrate 321 is fixed and a specific load is applied to the other end. In the drawing, d illustrates a state of the intra-probe substrate 321 after deformation. The strength of the intra-probe substrate 322 is similar to that of the intra-probe substrate 321.

The strength of the probe casing 320 is assumed to be higher than those of the intra-probe substrates 321 and 322. Here, "the strength is higher" means that the amount of deformation of the casing when one end of the probe casing 320 is fixed and the specific load is applied to the other end as illustrated as an example in the drawing is smaller than the amount of deformation of the intra-probe substrate 321 when one end thereof is fixed and the specific load is applied to the other end.

In this manner, the sensor device 200 according to the present invention is
  (1) a sensor device that includes the transmission probe casing 320a accommodating the transmission antenna (223, for example) for transmitting electromagnetic waves and the reception probe casing 320b accommodating the reception antenna (233, for example) for receiving the electromagnetic waves to measure propagation properties of the electromagnetic waves transmitted from the transmission antenna and received by the reception antenna and thereby to measure the amount of moisture in the medium, in which
  (2) both the transmission probe casing 320a and the reception probe casing 320b are formed of a material (electromagnetic wave transmissive material) that transmits the electromagnetic waves transmitted from the transmission antenna and received by the reception antenna therethrough, and
  (3) the structure in which the strength of the transmission probe casing 320a and the reception probe casing 320b formed of the electromagnetic wave transmissive material is higher than the strength of the electronic substrates (wiring substrates) accommodated in these casings is included.

Also, the sensor device 200 according to the present invention prevents the situation in which "the probe casings are deformed, and as a result, the electronic substrates accommodated inside the casings are deformed, and further, the distance between the transmission antenna and the reception antenna formed in the electronic substrates changes from a predetermined value, and an error thus occurs in the measurement result of the amount of moisture when the probe casing is inserted into the soil" by including the structure and thus obtains the effect that it is possible to accurately measure the moisture.

[Method for Measuring Amount of Moisture]

FIG. 136 is a block diagram illustrating a configuration example of the measurement circuit 210 according to the first embodiment of the present technology. The measurement circuit 210 includes a directional coupler 410, a transmitter 420, an incident wave receiver 430, a reflected wave receiver 440, a transmitted wave receiver 450, a sensor control section 470, a sensor communication section 212, and an antenna 213. A vector network analyzer, for example, is used as the measurement circuit 210.

The transmitter 420 in FIG. 136 corresponds to the transmitter 214 in FIG. 3. Also, the incident wave receiver 430, the reflected wave receiver 440, and the transmitted wave receiver 450 correspond to the receiver 215 in FIG. 3. The sensor control section 470 corresponds to the sensor control section 211 in FIG. 3. In FIG. 3, the directional coupler 410 is omitted.

The directional coupler 410 is adapted to separate the electrical signal transmitted through the transmission paths 229-1 to 229-3 for transmission into incident waves and reflected waves. The incident waves are waves of the electrical signal transmitted by the transmitter 420 while the reflected waves are the incident waves reflected by the termination end of the transmission probe. The directional coupler 410 supplies the incident waves to the incident wave receiver 430 and supplies the reflected waves to the reflected wave receiver 440.

The transmitter 420 is adapted to transmit the electrical signal at a predetermined frequency as a transmission signal to the transmission probe via the directional coupler 410 and the transmission paths 229-1 to 229-3 for transmission. As the incident waves in the transmission signal, continuous waves (CW) are used, for example. The transmitter 420 switches the frequency in order in a step of 50 megahertz (MHz) within the frequency band of 1 to 9 gigahertz (GHz) and transmits the transmission signal.

The incident wave receiver 430 is adapted to receive the incident waves from the directional coupler 410. The reflected wave receiver 440 is adapted to receive the reflected waves from the directional coupler 410. The transmitted wave receiver 450 is adapted to receive a transmitted waves from the reception probe. Here, the transmitted waves are obtained by the reception probe converting the electromagnetic waves transmitted through the medium between the transmission probe and the reception probe into an electrical signal.

The incident wave receiver 430, the reflected wave receiver 440, and the transmitted wave receiver 450 perform quadrature detection and analog-to-digital (AD) conversion on the received incident wave, reflected wave, and transmitted wave and supply the resultant waves to the sensor control section 470 as reception data.

The sensor control section 470 performs control of the transmitter 420 to cause the transmission signal including the incident waves to be transmitted and processing of obtaining a reflection coefficient and a transmission efficient. Here, the reflection coefficient is a ratio between complex amplitudes of the incident wave and the reflected wave, as described above. The transmission coefficient is a ratio between complex amplitudes of the incident wave and the transmitted wave. The sensor control section 470 supplies the obtained reflection coefficient and transmission coefficient to the sensor communication section 212.

The sensor communication section 212 is adapted to transmit data indicating the reflection coefficient and the transmission coefficient as measurement data to the central processing unit 150 via the communication path 110.

Note that in order to measure an accurate reflection coefficient and transmission coefficient, calibration of frequency characteristics of the directional coupler 410, the transmitter 420, and the receiver (incident wave receiver 430 and the like) is executed before measurement.

FIG. 137 is a diagram illustrating a configuration example of the directional coupler 410 according to the first embodiment of the present technology. The directional coupler 410 includes transmission lines 411, 412, and 413 and terminating resistors 414 and 415. The directional coupler 410 can be implemented as, for example, a bridge coupler suitable for miniaturization.

One end of the transmission line 411 is connected to the transmitter 420, and the other end thereof is connected to the transmission probe via the transmission switch 216. The transmission line 412 is shorter than the transmission line 411 and is a line coupled to the transmission line 411 through electromagnetic field coupling. One end of the transmission line 412 is connected to the terminating resistor 414 and the other end is connected to the reflected wave receiver 440. The transmission line 413 is shorter than the transmission line 411 and is a line coupled to the transmission line 411 through electromagnetic field coupling. One end of the transmission line 413 is connected to the terminating resistor 415 and the other end is connected to the incident wave receiver 430.

According to the aforementioned configuration, the directional coupler 410 separates an electrical signal into an incident wave and a reflected wave and supplies the incident wave and the reflected wave to the incident wave receiver 430 and the reflected wave receiver 440.

FIG. 138 is a circuit diagram illustrating a configuration example of the transmitter 420 and the receivers in the first embodiment of the present technology. In the drawing, a is a circuit diagram illustrating a configuration example of the transmitter 420 and b in the drawing is a circuit diagram illustrating a configuration example of the incident wave receiver 430. In the drawing, c is a circuit diagram illustrating a configuration example of the reflected wave receiver 440, and d in the drawing is a circuit diagram illustrating a configuration example of the transmitted wave receiver 450.

As illustrated as an example in a in the drawing, the transmitter 420 includes a transmission signal oscillator 422 and a driver 421.

The transmission signal oscillator 422 is adapted to generate an electrical signal as a transmission signal in accordance with control performed by the sensor control section 470. The driver 421 is adapted to output the transmission signal to the directional coupler 410. The transmission signal S(t) is represented by the following expression, for example.

$S(t)=|A|\cos(2\pi ft+\theta)$

In the above expression, t represents a clock time, and the unit is nanoseconds (ns), for example. |A| indicates the amplitude of the transmission signal. cos( ) indicates a cosine function. f indicates a frequency, and the unit is, for example, hertz (Hz). θ represents a phase, and the unit is, for example, radian (rad).

As illustrated as an example in b in the drawing, the incident wave receiver 430 includes a mixer 431, a band pass filter 432, and an ADC 433.

The mixer 431 performs quadrature detection by mixing two local signals having a phase difference of 90 degrees therebetween and the transmission signal. A complex amplitude composed of an in-phase component $I_I$ and a quadrature component $Q_I$ is obtained according to the quadrature detection. These in-phase component $I_I$ and quadrature component $Q_I$ are represented by the following expression, for example. The mixer 431 supplies the complex amplitude to the ADC 433 via the band pass filter 432.

$I_I=|A|\cos(\theta)$ $Q_I=|A|\sin(\theta)$

In the above expression, sin( ) represents a sine function.

The band pass filter 432 is adapted to allow a component of a predetermined frequency band to pass therethrough. The ADC 433 is adapted to perform AD conversion. The ADC 433 generates data indicating the complex amplitude through the AD conversion and supplies the data as reception data to the sensor control section 470.

As illustrated as an example in c in the drawing, the reflected wave receiver 440 includes a mixer 441, a band pass filter 442, and an ADC 443. The configurations of the mixer 441, the band pass filter 442, and the ADC 443 are similar to those of the mixer 431, the band pass filter 432, and the ADC 433. The reflected wave receiver 440 performs quadrature detection on reflected waves to acquire a complex amplitude composed of an in-phase component $I_R$ and a quadrature component $Q_R$ and supplies reception data representing the complex amplitude to the sensor control section 470.

As illustrated as an example in d in the drawing, the transmitted wave receiver 450 includes a receiver 451, a local signal oscillator 452, a mixer 453, a band pass filter 454, and an ADC 455. The configurations of the mixer 453, the band pass filter 454, and the ADC 455 are similar to those of the mixer 431, the band pass filter 432, and the ADC 433.

The receiver 451 receives an electrical signal including transmitted waves through the reception switch 217 and outputs the electrical signal to the mixer 453. The local signal oscillator 452 generates two local signals having a phase difference of 90 degrees therebetween.

The transmitted wave receiver 450 performs quadrature detection on the transmitted waves to acquire a complex amplitude composed of an in-phase component $I_T$ and a quadrature component $Q_T$ and supplies data representing the complex amplitude to the sensor control section 470 as reception data.

Note that the circuits of the transmitter 420 and the receivers (incident wave receiver 430 and the like) are not limited to the circuits illustrated as examples in the drawing as long as they can transmit and receive incident waves and the like.

FIG. 139 is a block diagram illustrating a configuration example of the sensor control section 470 according to the first embodiment of the present technology. The sensor control section 470 includes a transmission control section 471, a reflection coefficient calculation section 472, and a transmission coefficient calculation section 473.

The transmission control section 471 is adapted to control the transmitter 420 such that the transmitter 420 transmits a transmission signal.

The reflection coefficient calculation section 472 calculates a reflection coefficient Γ for each frequency. The reflection coefficient calculation section 472 receives complex amplitudes of an incident wave and a reflected wave from the incident wave receiver 430 and the reflected wave receiver 440 and calculates a ratio between the complex amplitudes as a reflection coefficient Γ according to the following expression.

$\Gamma=(I_R+jQ_R)/(I_I+j Q_I)$      Expression 3

In the above expression, j is an imaginary unit. IR and $Q_R$ are an in-phase component and a quadrature component generated by the reflected wave receiver 440.

The reflection coefficient calculation section 472 calculates reflection coefficients for N (N is an integer) frequencies $f_1$ to $f_N$ according to Expression 3. These N reflection coefficients are denoted by $\Gamma_1$ to $\Gamma_N$. The reflection coefficient calculation section 472 supplies the reflection coefficients to the sensor communication section 212.

The transmission coefficient calculation section 473 calculates a transmission coefficient T for each frequency. The transmission coefficient calculation section 473 receives complex amplitudes of incident waves and transmitted waves from the incident wave receiver 430 and the transmitted wave receiver 450 and calculates a ratio between the complex amplitudes as a transmission coefficient T according to the following Expression.

$$T=(I_T+jQ_T)/(I_I+jQ_I)$$ Expression 4

$I_T$ and $Q_T$ are an in-phase component and a quadrature component generated by the transmitted wave receiver 450.

The transmission coefficient calculation section 473 calculates transmission coefficients for the N frequencies $f_1$ to $f_N$ according to Expression 4. These N reflection coefficients are denoted by $T_1$ to $T_N$. The transmission coefficient calculation section 473 supplies the transmission coefficients to the central processing unit 150 via the sensor communication section 212.

FIG. 140 is a block diagram illustrating a configuration example of the signal processing section 154 in the central processing unit 150 according to the first embodiment of the present technology. The central processing unit 150 includes a reciprocation delay time calculation section 162, a propagation transmission time calculation section 163, a moisture amount measurement section 164, and a coefficient storing section 165 in the signal processing section 154. In the drawing, the antenna 152, the central control section 151, the storage section 155, and the output section 156 in FIG. 2 are omitted.

The central communication section 153 supplies reflection coefficients $\Gamma_1$ to $\Gamma_N$ in measurement data to the reciprocation delay time calculation section 162 and supplies the transmission coefficients $T_1$ to $T_N$ in measurement data to the propagation transmission time calculation section 163.

The reciprocation delay time calculation section 162 is adapted to calculate, as the reciprocation delay time, the time during which the electrical signal reciprocates through the transmission paths 229-1 to 229-3 for transmission on the basis of the reflection coefficients. The reciprocation delay time calculation section 162 obtains an impulse response $h\Gamma(t)$ by performing inverse Fourier transformation on the reflection coefficients $\Gamma_1$ to $\Gamma_N$. Then, the reciprocation delay time calculation section 162 obtains, as the reciprocation delay time iii, a time difference between the timing of the peak value of the impulse response $h\Gamma(t)$ and the transmission timing of the CW waves and supplies the reciprocation delay time $\tau_{11}$ to the moisture amount measurement section 164.

The propagation transmission time calculation section 163 is adapted to calculate, as the propagation transmission time, the time during which the electromagnetic waves and the electrical signal are propagated and transmitted through the medium, the transmission paths 229-1 to 229-3 for transmission, and the transmission paths 239-1 to 239-3 for reception on the basis of the transmission coefficients. The propagation transmission time calculation section 163 obtains the impulse response $hT(t)$ by performing inverse Fourier transformation on the transmission coefficients $T_1$ to $T_N$. Then, the propagation transmission time calculation section 163 obtains, as the propagation transmission time $\tau_{21}$, a time difference between the timing of the peak value of the impulse response $hT(t)$ and the transmission timing of the CW waves and supplies the propagation transmission time $\tau_{21}$ to the moisture amount measurement section 164.

The moisture amount measurement section 164 is adapted to measure the amount of moisture on the basis of the reciprocation delay time $\tau_{11}$ and the propagation transmission time $\tau_{21}$. The moisture amount measurement section 164 calculates the propagation delay time $\tau_d$ from the reciprocation delay time $\tau_{11}$ and the propagation transmission time $\tau_{21}$ first. Here, the propagation delay time is a time during which electromagnetic waves propagate through the medium between the transmission probe and the reception probe. The propagation delay time Td is calculated by the following Expression.

$$\tau_d = \tau_{21} - \tau_{11}$$ Expression 5

In the above expression, the unit of each of the reciprocation delay time $\tau_{11}$, the propagation transmission time $\tau_{21}$, and the propagation delay time $\tau_d$ is, for example, nanoseconds (ns).

Then, the moisture amount measurement section 164 reads the coefficients a and b indicating the relationship between the amount of moisture and the propagation delay time $\tau_d$ from the coefficient storing section 165, substitutes the propagation delay time $\tau_d$ calculated by Expression 5 into the following expression, and measures the amount of moisture x. In addition, the moisture amount measurement section 164 outputs the measured amount of moisture to an external device or apparatus as necessary.

$$\tau_d = a \cdot x + b$$ Expression 6

In the above expression, the unit of the amount of moisture x is, for example, percent by volume (%).

The coefficient storing section 165 stores the coefficients a and b. A nonvolatile memory is used as the coefficient storing section 165.

FIG. 141 is a diagram for explaining a propagation path and a transmission path of electromagnetic waves and an electrical signal according to the first embodiment of the present technology. As described above, the transmitter 420 transmits an electrical signal including the incident waves as a transmission signal to the transmission probe via transmission paths 229-1 to 229-3 for transmission with distal ends thereof embedded in the transmission probe. In the drawing, only one of the transmission paths 239-1 to 239-3 for reception is illustrated. Also, only one of the transmission paths 229-1 to 229-3 for transmission is illustrated.

The incident waves are reflected by the termination end of the transmission probe, and the reflected waves thereof are received by the reflected wave receiver 440. Therefore, the electrical signal including the incident waves and the reflected waves reciprocates in the transmission paths 229-1 to 229-3 for transmission. The arrow of the thick solid line in the drawing illustrates a path along which the electrical signal has reciprocated in the transmission paths 229-1 to 229-3 for transmission. The time during which the electrical signal reciprocates in the paths corresponds to a reciprocation delay time $\tau_{11}$.

Also, the electrical signal including the incident waves is converted into electromagnetic waves EW by the transmission probe and permeates (in other words, propagated through) the medium between the transmission probe and the reception probe. The reception probe converts the electromagnetic waves EW into an electrical signal. The transmitted wave receiver 450 receives the transmitted waves in the electrical signal via the transmission paths 239-1 to 239-3 for reception. In other words, the electrical signal including the incident waves is transmitted through the transmission paths 229-1 to 229-3 for transmission, is converted into the electromagnetic waves EW, is propagated through the medium, is then converted into the electrical signal including the transmitted waves, and is transmitted through the transmission paths 239-1 to 239-3 for reception. The arrow of the thick dotted line in the drawing illustrates the path through which the electromagnetic waves and the electrical signal (the incident waves and the transmitted waves) are propagated and transmitted through the medium, the transmission paths 229-1 to 229-3 for transmission, and the transmission paths 239-1 to 239-3 for reception. The time during which the electromagnetic waves and the electrical signals propagated and transmitted through the paths corresponds to the propagation transmission time $\tau_{21}$.

The sensor control section 470 obtains a reflection coefficient $\Gamma$ and a transmission coefficient T by Expressions 3 and 4. Then, the central processing unit 150 obtains the reciprocation delay time $\tau_{11}$ and the propagation transmission time $\tau_{21}$ from the reflection coefficient $\Gamma$ and the transmission coefficient T.

Here, the path from the transmission of the incident waves and the reception of the transmitted waves includes the medium, the transmission paths 229-1 to 229-3 for transmission, and the transmission paths 239-1 to 239-3 for reception. Therefore, the propagation delay time $\tau_d$ during which the electromagnetic waves are propagated through the medium is obtained by a difference between the propagation transmission time $\tau_{21}$ and the delay time of the transmission of the electrical signal through the transmission paths 229-1 to 229-3 for transmission and the transmission paths 239-1 to 239-3 for reception. On the assumption that the lengths of the transmission paths 229-1 to 229-3 for transmission and the transmission paths 239-1 to 239-3 for reception are the same, the delay time of the transmission through the transmission paths 229-1 to 229-3 for transmission and the delay time of transmission through the transmission paths 239-1 to 239-3 for reception are the same. In this case, a total of the delay times of the transmission of the electrical signal through the transmission paths 229-1 to 229-3 for transmission and the transmission paths 239-1 to 239-3 for reception is equal to the reciprocation delay time $\tau_{11}$ of reciprocation through the transmission paths 229-1 to 229-3 for transmission. Therefore, Expression 5 is established, and the central processing unit 150 can calculate the propagation delay time is by Expression 5.

Then, the central processing unit 150 performs processing of calculating the propagation delay time from the obtained reciprocation delay time $\tau_{11}$ and the propagation transmission time $\tau_{21}$ and measuring the amount of moisture contained in the medium from the propagation delay time and the coefficients a and b.

FIG. 142 is a graph illustrating an example of a relationship between a reciprocation delay time and a propagation transmission time and an amount of moisture according to the first embodiment of the present technology. In the drawing, a vertical axis represents a reciprocating delay time or a propagation transmission time and a horizontal axis represents an amount of moisture.

The dotted line in the drawing illustrates a relationship between the reciprocation delay time and the amount of moisture. The solid line illustrates a relationship between the propagation transmission time and the amount of moisture. As illustrated as an example in the drawing, the reciprocation delay time is constant regardless of the amount of moisture. On the other hand, the propagation transmission delay time increases as the amount of moisture increases.

FIG. 143 is a graph illustrating an example of a relationship between a propagation delay time and an amount of moisture according to the first embodiment of the present technology. In the drawing, a vertical axis represents a propagation delay time and a horizontal axis represents an amount of moisture. In the drawing, a straight line is acquired by obtaining a difference between the propagation transmission time and the reciprocation delay time for each amount of moisture in FIG. 142.

As illustrated as an example in FIG. 143, the propagation delay time increases as the amount of moisture increases, and thus both are in a proportional relationship. Accordingly, Expression 6 is established. The coefficient a in Expression 6 is an inclination of the straight line in the drawing and the coefficient b is the intercept.

FIG. 144 is a block diagram illustrating another configuration example of the measurement circuit 210 according to the first embodiment of the present technology. The measurement circuit 210 in FIG. 136 includes two receivers for receiving reflected waves and transmitted waves, namely the reflected wave receiver 440 and the transmitted wave receiver 450. On the other hand, the measurement circuit 210 in FIG. 144 is configured to share one second receiver 455 as a receiver for receiving the reflected waves and transmitted waves. More specifically, the reflected waves and the transmitted waves are switched by the switch 445 controlled by the sensor control section 470 and are received by one second receiver 455 in a time division manner in the measurement circuit 210. The reception result of the second receiver 455 is output to the sensor control section 470. With this configuration, the size of the measurement circuit 210 is reduced as compared with that in the case of FIG. 136, and as a result, the size and the manufacturing cost of the moisture measurement system 100 are also reduced.

FIG. 145 is a block diagram illustrating another configuration example of the sensor device 200 according to the first embodiment of the present technology. The measurement circuit 210 in the drawing is different from the circuit in FIG. 136 in that the measurement circuit 210 includes a sensor signal processing section 460 instead of the sensor communication section 212. The configuration of the sensor signal processing section 460 is similar to that of the signal processing section 154 in the central processing unit 150 according to the first embodiment. Also, the functions of the sensor control section 470 are realized by a digital signal processing (DSP) circuit, for example.

Also, the measurement circuit 210 may be mounted on a single semiconductor chip. It is thus possible to realize the functions of the measurement circuit 210 and the signal processing section 154 by the single semiconductor chip.

In comparison between FIG. 145 and FIG. 136, the functions required for the central processing unit 150 are reduced. As a result, functions and performance required for electronic equipment for implementing the central processing unit 150 are reduced, and it becomes easier to use a commercially available terminal device such as a smartphone or a tablet terminal, for example, as the electronic equipment for implementing the central processing unit 150 than in FIG. 136.

FIG. 146 is a flowchart illustrating an example of operations of the moisture measurement system 100 according to the first embodiment of the present technology. The operations in the drawing are started when a predetermined application for measuring the amount of moisture is executed, for example.

A pair of the transmission probe and the reception probe transmits and receives electromagnetic waves (Step S901). The measurement circuit 210 calculates a reflection coefficient from incident waves and reflected waves (Step S902)

and calculates a transmission coefficient from incident waves and transmitted waves (Step S903).

Then, the central processing unit 150 calculates a reciprocation delay time from the reflection coefficient (Step S904) and calculates a propagation transmission time from the transmission coefficient (Step S905). The central processing unit 150 calculates a propagation delay time from the reciprocation delay time and the propagation transmission time (Step S906) and calculates the amount of moisture from the propagation delay time and the coefficients a and b (Step S907). After Step S907, the moisture measurement system 100 ends the operations for the measurement.

Configuration Example of Radio Wave Absorption Section

Next, the radio wave absorption section will be described. Unlike the time domain reflectometry (TDR) and time domain transmissometry (TDT) schemes, it is necessary for the moisture sensor according to the invention of the present application of the transmissive type to transmit radio waves in a wide band, and it is necessary for the transmitted radio waves to be received by the receiver. However, the radio waves may be reflected and becomes noise, and there may be a case where the position of the peak of an impulse response deviates at the time of calculation of the peak and a delay time deviates. Therefore, a measure for preventing a noise source from being generated in the wide band and noise removal in a case where it occurs are required. In a case where a plurality of antennas are included in one probe, in particular, unnecessary radiation significantly increases, and it is difficult to restrict radio waves.

Thus, the radio wave absorption section 341 and the like are placed in the surroundings of the probes except for the antennas in the sensor device 200.

As methods for placing the radio wave absorber sections, three methods are conceivable. The first one is a method of placing the radio wave absorber on substrates or coaxial cables. For example, a method of fitting them to the substrates, a method of placing them on the substrates, a method of attaching them to the substrates, or a method of winding them around the substrates is used. In a case where the substrates are placed only on upper and lower sides or only on left and right sides, it is only necessary to cause them to have a larger width than the substrate width. The second one is a method of placing the radio wave absorbing sections on an external casing in advance or concurrently placing them at the time of placing the substrate layers. For example, a method of burying them in a resin at the time of molding the casing or a method of mixing the radio wave absorber in a resin and molding them is used. In a case where the radio wave absorber has moisture absorbency, it is only necessary to separately cover the outside with another resin or coat it by paint or the like. In addition, a method of fitting the radio wave absorber after molding the casing, a method of attaching it, or a method of pouring and fixing the substrates and a solution with the radio wave absorber mixed therein at the time of molding of the casing is used. At that time, it is desirable that the radio wave transmitting and receiving parts be covered with another resin, an O ring, or the like such that the radio wave absorber does not adhere thereto. A method of applying a radio wave absorbing material to the inside of the casing is also conceivable.

The third one is a method of combining the radio wave absorption section with ferrite, a sheet, a radio wave absorber film, or a coating material. In this case, coating may be applied to a clearance of ferrite or the like.

In regard to the placement position and the placement method of the radio wave absorber with respect to the substrate, the radio wave absorber is placed on upper and lower surfaces with a width that is equal to or greater than the substrate width. However, the wider width than the substrate width can lead to a higher radio wave absorption section placement effect, and further, it is desirable that the entire surface be covered therewith.

Also, it is desirable that the lower ends of the radio wave absorption sections correspond to the upper ends of the antennas. It is desirable that the distance from the lower ends of the antennas to the lower ends of the radio wave absorption sections be equal to or less than a half the wavelength of the center frequency including the length of the antennas themselves or fall within a wavelength bandwidth. In a case where 1 to 9 gigahertz (GHz) is used, for example, the center frequency is 5 gigahertz (GHz), and the wavelength is 60 millimeters (mm). In this case, it is desirable that the distance from the lower ends of the antennas to the lower ends of the radio wave absorption sections fall within 30 millimeters. Since the bandwidth is 8 gigahertz, resolution is 37.5 millimeters (mm), and the distance to the lower ends of the radio wave absorption sections can be less than the resolution.

Also, the radio wave absorber may be placed at the probe or may be placed at the exterior case. In a case of the placement at the exterior, it may be applied and placed when the exterior is molded, cut, or kneaded or after the exterior is completed.

As components of the material for the radio wave absorption sections,
 (1) a magnetic material
 (2) a conductive polymer
 (3) dielectric polymer
 (4) meta material
can be used.

Also, examples of states of the materials include
 (a) a member that is formed only by the radio wave absorption material and has rigidity (a plate of a ferrite sintered body, a molded article of a conductive polymer, or the like)
 (b) a sheet that is formed only by the radio wave absorption material and has flexibility (a sheet of a conductive polymer or the like)
 (c) a member that is formed by dispersing the radio wave absorption material in a dispersion medium and has rigidity (an organic resin rigid element with ferrite dispersed therein or the like)
 (d) a sheet that is formed by dispersing the radio wave absorption material in a dispersion medium and has flexibility (a sheet with ferrite dispersed therein or the like)
 (e) a fluid (a material solidified after application or the like)

In regard to combinations of the material states and components, any of the components (1), (2), (3), and (4) may be adopted in the state (a). The same applies to the states (b), (c), and (d). In the state (e), the components (1), (2), and (3) are used.

In regard to how to produce the radio wave absorption section, it is possible to use an adhering method, a fitting method using a fixing material such as an O ring, a burying method, an inserting method, a winding method, and an applying method.

FIG. 147 is a diagram illustrating an example of covering locations of the radio wave absorption sections 341 and 344 according to the first embodiment of the present technology.

The number of antennas on each of the transmission side and the reception side is set to one. The transmission antenna 221 including the radiation element 330 is disposed on the transmission side, and the reception antenna 231 including the radiation element 333 is disposed on the reception side. The radio wave absorption sections 341 and 344 are formed at locations other than these antennas.

As illustrated as an example in a in the drawing, it is the most desirable that the radio wave absorption sections cover the entire probes other than the antennas. In a case where a part of the probes other than the antennas is covered, it is desirable that the lower ends of the radio wave absorption sections correspond to the upper ends of the antennas as illustrated as an example in b in the drawing. As illustrated as an example in c in the drawing, it is also possible to separate the lower ends of the radio wave absorption sections from the upper ends of the antennas. However, it is desirable that the distance from the lower ends of the antennas to the lower ends of the radio wave absorption sections be equal to or less than a half wavelength of the wavelength of the center frequency including the length of the antennas themselves or fall within the wavelength bandwidth.

FIG. 148 is a diagram illustrating a comparative example in which covering with the radio wave absorption sections is not performed. It is possible to absorb radio waves of unnecessary radiation which may cause noise by providing the radio wave absorption sections at parts other than the antennas as compared with the comparative example.

FIG. 149 is a diagram illustrating an example in which surfaces on one side of the intra-probe substrates 321 and 322 are covered according to the first embodiment of the present technology. As illustrated as an example in a in the drawing, it is possible to further cover the surface on which the transmission antenna 221 is not formed out of the both surfaces of the intra-probe substrate 321 with the radio wave absorption section 347. The surface on which the reception antenna 231 is not formed out of the both surfaces of the intra-probe substrate 322 is also covered with the radio wave absorption section 348.

When surfaces on one side of the intra-probe substrates 321 and 322 are covered, it is also possible to cover a part of the probes other than the antennas. In this case, it is desirable that the lower ends of the radio wave absorption sections correspond to the upper ends of the antennas as illustrated as an example in b in the drawing. As illustrated as an example in c in the drawing, it is also possible to separate the lower ends of the radio wave absorption sections from the upper ends of the antennas.

FIG. 150 is a diagram illustrating an example in which the distal ends of the probes are further covered according to the first embodiment of the present technology. As illustrated as an example in a in the drawing, it is also possible to further cover the distal ends of the probes provided with the positioning sections 351 and 352 with the radio wave absorption sections 349 and 350.

When the distal ends of the probes are covered, it is also possible to cover a part of the probes other than the antennas. In this case, it is desirable that the lower ends of the radio wave absorption sections correspond to the upper ends of the antennas as illustrated as an example in b in the drawing. As illustrated as an example in c in the drawing, it is also possible to separate the lower ends of the radio wave absorption sections from the upper ends of the antennas.

FIG. 151 is a diagram illustrating an example in which only the distal ends are covered according to the first embodiment of the present technology. As illustrated as an example in the drawing, it is also possible to cover only the distal ends with the radio wave absorption sections 349 and 350.

FIG. 152 is a diagram illustrating an example in which surfaces on one side and distal ends of the intra-probe substrates 321 and 322 are covered according to the first embodiment of the present technology. As illustrated as an example in a in the drawing, both surfaces on one side of the intra-probe substrates 321 and 322 and the distal ends of the probes can be further covered.

When the surfaces on one side and the distal ends are further covered, it is also possible to cover a part of the probes other than the antennas. In this case, it is desirable that the lower ends of the radio wave absorption sections correspond to the upper end of the antennas as illustrated as an example in b in the drawing. As illustrated as an example in c in the drawing, it is also possible to separate the lower ends of the radio wave absorption sections from the upper ends of the antennas.

FIG. 153 is a diagram illustrating an example of the shape of the radio wave absorption section 341 according to the first embodiment of the present technology. The radio wave absorption section 341 is configured of one or more components. The outer and inner shapes of the radio wave absorption section 341 may be circular shapes or polygonal shapes.

In the drawing, a illustrates a top view (the upper part in FIG. 153a) and a side view (the lower part in FIG. 153a) of the radio wave absorption section 341 with circular or oval outer and inner shapes. In the drawing, b illustrates a top view and a side view of the radio wave absorption section 341 with a circular or oval outer shape and a rectangular inner shape. In the drawing, c illustrates a top view and a side view of the radio wave absorption section 341 with a rectangular outer shape and a circular or oval inner shape. In the drawing, d illustrates a top view and a side view of the radio wave absorption section 341 with rectangular outer and inner shapes. In the drawing, e illustrates a side view of the radio wave absorption section 341 with a spiral groove formed therein. A structure for facilitating installation of the casing into which the substrates and semi-rigid cables are inserted in advance may be adopted at the time of forming the spiral groove. In a case where a ferrite material is used, the thickness of the radio wave absorption section 341 is set to be equal to or greater than 5 mm. In a case of a film or a coating film, the thickness is set to be equal to or greater than 100 μm. The structures of the radio wave absorption sections other than the radio wave absorption section 341 (in other words, the structures of the radio wave absorption sections described in the specification other than the radio wave absorption section 341) are similar to that of the radio wave absorption section 341.

The intra-probe substrates 321 and 322 are disposed inside the radio wave absorption section 341 illustrated in FIG. 153 and the other radio wave absorption sections (in other words, the radio wave absorptions sections 341 to 346) described in the specification. More precisely, parts of the intra-probe substrates 321 and 322 are disposed inside the radio wave absorption section 341 illustrated in FIG. 153 and the other radio wave absorption sections (in other words, the radio wave absorption sections 341 to 346) described in the specification.

FIGS. 350a to 350d are top views of the sensor device 200 in a case where the radio wave absorption sections 341 illustrated in FIGS. 153a to 153d are applied to each of the radio wave absorption sections 341 and 344 included in the sensor device 200 illustrated in FIG. 147a as examples of applications to the sensor device 200. Here, FIG. 350 is a transparent view (the view in which characteristics of each section are overwritten) similarly to the various three-view-drawings in the specification. Therefore, the measurement section substrate 311, the transmission antenna 221, the reception antenna 231, and the radio wave absorption sections 341 and 344 are overwritten in one drawing. In regard to the measurement section substrate 311, the transmission antenna 221, the reception antenna 231, and the radio wave absorption sections 341 and 344, the positional relationship thereof in the Y direction is illustrated in the front view and the side view in FIG. 147*a*. Note that the front view and the side view of the sensor device 200 in a case where the radio wave absorption sections 341 illustrated in FIGS. 153*a* to 153*d* are applied to each of the radio wave absorption sections 341 and 344 included in the sensor device 200 illustrated in FIG. 147*a* are the same as the front view and the side view of the sensor device 200 illustrated in FIG. 147*a*.

In FIG. 350, a illustrates a top view of the sensor device 200 including the radio wave absorption section 341 with an oval outer or inside shape. In the drawing, b illustrates a top view of the sensor device 200 including the radio wave absorption section 341 with an oval outer shape and a rectangular inner shape. In the drawing, c illustrates a top view of the sensor device 200 including the radio wave absorption section 341 with a rectangular outer shape and an oval inner shape. In the drawing, d illustrates a top view of the sensor device 200 including the radio wave absorption section 341 with rectangular outer and inner shapes.

As the positional relationship of the transmission intra-probe substrate 321, the transmission antenna 221, the reception intra-probe substrate 322, the reception antenna 231, and the radio wave absorption sections 341 and 344 in the top view (the top view which is a transparent view), FIGS. 350*a* to 350*d* illustrate that the positions where the transmission intra-probe substrate 321, the transmission antenna 221, the reception intra-probe substrate 322, and the reception antenna 231 are disposed are the inside of the positions where the radio wave absorption sections 341 and 344 are disposed.

Also, as the positional relationship of the transmission intra-probe substrate 321, the transmission antenna 221, the reception intra-probe substrate 322, the reception antenna 231, and the radio wave absorption sections 341 and 344 in the top view (the top view which is a transparent view), FIGS. 350*a* to 350*d* illustrate that the positions where the radio wave absorption sections 341 and 344 are disposed are outside and over the entire periphery of the positions where the transmission intra-probe substrate 321, the transmission antenna 221, the reception intra-probe substrate 322, and the reception antenna 231 are disposed.

It is possible to ascertain from the top view (transparent view) illustrated in FIG. 350 that the radio wave absorption section 341 is disposed over the entire periphery of the outside of the transmission intra-probe substrate 321 and the radio wave absorption section 344 is disposed over the entire periphery of the outside of the reception intra-probe substrate 322, and also, it is possible to ascertain from the front view and the side view in FIG. 147 that the region where the radio wave absorption sections 341 and 344 over the entire periphery of the outside of the transmission intra-probe substrate 321 and the reception intra-probe substrate 322 are disposed is a region where the transmission antenna (221 in the example in FIG. 147) and the reception antenna (231 in the example in FIG. 147) are not disposed in the Y-axis direction of the sensor device 200.

Note that the modes of the radio wave absorption sections illustrated in FIGS. 153 and 350 can be applied not only to the sensor device 200 illustrated in FIG. 147*a* but also to the various sensor devices 200 illustrated in the specification.

The radio wave absorption sections 341 and the like illustrated in FIGS. 153 and 350 may be configured of one structure (component) formed using the aforementioned radio wave absorbable material or may be configured of a plurality of structures (components) formed using the radio wave absorbable material.

FIG. 236 is a diagram illustrating an example in which the electromagnetic wave absorption section 341 illustrated in FIG. 153 is configured of one structure (component) and an example in which the electromagnetic wave absorption section 341 is configured of a plurality of structures (components). Here, a to e in FIG. 236 illustrate top views of the radio wave absorption section 341, and f to j in the drawing illustrate side views of the radio wave absorption section 341. The radio wave absorption section 341 may be configured of one structure in a case where it is seen from the top as illustrated in a and c in FIG. 236. Also, the radio wave absorption section 341 may be configured of two structures in a case where it is seen from the top as illustrated in b and d in FIG. 236. Additionally, the radio wave absorption section 341 may be configured of a plurality of structures, the number of which is equal to or greater than two, in a case where it is seen from the top as illustrated in e in FIG. 236.

Also, the radio wave absorption section 341 may be configured of one structure in a case where it is seen from a side as illustrated in f in FIG. 236. Additionally, the radio wave absorption section 341 may be configured of a plurality of structures in the extending direction of the radio wave absorption section 341 (in other words, the Y direction in the side view of the sensor device 200 illustrated in FIG. 147*a*) in a case where it is seen from a side as illustrated in g and h in FIG. 236. Also, the radio wave absorption section 341 may be configured of two structures in the direction orthogonal to the extending direction of the radio wave absorption section 341 (in other words, the direction orthogonal to the Y direction, that is, the X direction or the Z direction in the side view of the sensor device 200 illustrated in FIG. 147*a*) in a case where it is seen from a side as illustrated in i in FIG. 236. Additionally, the radio wave absorption section 341 may be configured of a plurality of structures, the number of which is equal to or greater than two, in the direction orthogonal to the extending direction of the radio wave absorption section 341 (in other words, the direction orthogonal to the Y direction, that is, the X direction or the Z direction in the side view of the sensor device 200 illustrated in FIG. 147*a*) in a case where it is seen from a side as illustrated in j in FIG. 236.

FIG. 235 is a top view illustrating another example of the shape of the radio wave absorption section 341 according to the first embodiment of the present technology. As illustrated as examples in a, b, c, d, and e in the drawing, projections may be formed at the radio wave absorption section 341, and a groove may be formed on the side of the sensor casing 305, such that the projections are fitted thereto. As illustrated as examples in f, g, h, i, and j in the drawing, a groove may be formed in the radio wave absorption section 341, and projections may be formed on the side of the sensor casing 305, such that the projections are fitted thereto. Note that the radio wave absorption sections illustrated in FIGS. 236 and 235 can be applied not only to the sensor device 200 illustrated in FIG. 147*a* but also to various sensor devices 200 described in the specification.

FIGS. 351 and 352 are diagrams illustrating yet another example of the shape of the radio wave absorption section 341 according to the first embodiment of the present technology. The upper part in FIG. 351 is a top view of the radio wave absorption section 341, and the lower part is a side view of the radio wave absorption section 341. FIGS. 352a to 352d are top views (transparent views) of the sensor device 200 in a case where the radio wave absorption section 341 illustrated in FIGS. 351a to 351d is applied to each of the radio wave absorption section 341 and 344 included in the sensor device 200 illustrated in FIG. 147a as examples of applications thereof to the sensor device 200. Here, FIG. 352 is a transparent view (the diagram in which features of each section are overwritten) similarly to FIG. 350. Therefore, the measurement section substrate 311, the transmission antenna 221, and the reception antenna 231, and the radio wave absorption sections 341 and 344 are overwritten in one diagram. In regard to the measurement section substrate 311, the transmission antenna 221, the reception antenna 231, and the radio wave absorption sections 341 and 344, the positional relationship thereof in the Y direction is illustrated in the front view and the side view in FIG. 147a. The radio wave absorption sections illustrated in FIGS. 153 and 350 are disposed at positions outside and over the entire periphery of the transmission intra-probe substrate 321 and the reception intra-probe substrate 322 in the top views illustrated in the drawings. On the contrary, the radio wave absorption sections illustrated in FIGS. 351 and 352 are disposed at positions outside the transmission intra-probe substrate 321 and the reception intra-probe substrate 322 and at parts of the peripheries thereof in the top views illustrated in the drawings. More specifically, the radio wave absorption sections illustrated in FIGS. 351 and 352 are disposed outside the transmission intra-probe substrate 321 and the reception intra-probe substrate 322 as parts of the peripheries thereof in the top views illustrated in the drawings and in a region including positions at which they overlap a part of a line segment connecting a part of the transmission intra-probe substrate 321 and the reception intra-probe substrate 322 or positions intersecting the line segment. Additionally, it is possible to ascertain from the front view and the side view in FIG. 147 that the region where the radio wave absorption sections 341 and 344 are disposed at parts of the outside of the transmission intra-probe substrate 321 and the reception intra-probe substrate 322 is a region where the transmission antenna (221 in the example in FIG. 147) and the reception antenna (231 in the example in FIG. 147) are not disposed in the Y-axis direction of the sensor device 200. The manufacturing is simpler and manufacturing cost can be lowered while the radio wave absorption power is degraded in the modes illustrated in FIGS. 351 and 352 than in the modes illustrated in FIGS. 153 and 350.

Note that the radio wave absorption section illustrated in FIGS. 351 and 352 can be applied not only to the sensor device 200 illustrated in FIG. 147a but also various sensor devices 200 described in the specification.

In this manner, according to the first embodiment of the present technology, the plane-shaped transmission antenna 221 is fixed and disposed to face the reception antenna 231 such that the distance between the antennas is the predetermined distance, and it is thus possible to reduce a transmission loss and to accurately measure moisture in the soil.

First Modification Example

Although the intra-probe substrates 321 and 322 are connected in the direction orthogonal to the measurement section substrate 311 and the antennas are caused to face each other in the aforementioned first embodiment, the configuration requires a connector and a cable for connection in addition to the three substrates, and the structure becomes complicated. The sensor device 200 according to the first modification example of the first embodiment is different from that in the first embodiment in that the antennas are caused to face each other by twisting a part of a flexible substrate.

FIG. 154 is a diagram illustrating an example of the sensor device 200 using a flexible substrate 271 according to the first modification example of the first embodiment of the present technology. One flexible substrate 271 is provided instead of the three substrates, namely the measurement section substrate 311, the intra-probe substrate 321, and the intra-probe substrate 322 in the sensor device 200 according to the first modification example of the first embodiment of the present technology.

In the drawing, a illustrates the flexible substrate 271 before the distal end is twisted, and b in the drawing illustrates the flexible substrate 271 after the distal end is twisted. The sensor casing 305 is omitted. The flexible substrate 271 includes a pair of projecting portions, and the transmission antenna 221 and the reception antenna 231 are disposed at the distal ends thereof. Also, the measurement circuit 210 is disposed on the flexible substrate 271.

As illustrated as an example in b in the drawing, it is possible to achieve a state in which the transmission antenna 221 and the reception antenna 231 are caused to face each other by twisting the distal end of the flexible substrate 271. With this configuration, it is possible to reduce the number of components and to simplify the structure as compared with the first embodiment in which the three substrates are connected.

FIG. 155 is a diagram illustrating an example of the sensor device 200 using flexible substrates and rigid substrates according to the first modification example of the first embodiment of the present technology. In the drawing, a is an example in which one rigid substrate is used, and b in the drawing is an example in which three rigid substrates are used.

As illustrated as an example in a in the drawing, it is also possible to connect the rigid substrate 275 and the thin and long flexible substrates 271 and 272 and to dispose them in the sensor device 200. The measurement circuit 210 is disposed on the rigid substrate 275. The transmission antenna 221 is disposed on the flexible substrate 271, and the reception antenna 231 is disposed on the flexible substrate 272.

For example, there may be a case where the rigid substrates are needed because multiple layers are needed for convenience of arrangement around the measurement circuit 210 or a substrate with high heat conductivity is needed in relation to heat discharge. It is also possible to realize the disposition in which the antennas are caused to face each other while satisfying the requirement by using the rigid substrates for this purpose as well.

As illustrated as an example in b in the drawing, it is also possible to connect the rigid substrates 275, 276, and 277 to the thin and long flexible substrates 271 and 272 and to dispose them in the sensor device 200. The rigid substrate 276 is connected to the distal end of the flexible substrate 271, and the rigid substrate 276 is provided with the transmission antenna 221. The rigid substrate 277 is connected to the distal end of the flexible substrate 272, and the rigid substrate 277 is provided with the reception antenna 231.

FIG. 156 is a diagram illustrating an example of the sensor device 200 when the number of antennas is increased according to the first modification example of the first embodiment of the present technology. In the drawing, a illustrates the flexible substrate 271 before the distal end is twisted, and b in the drawing illustrates the flexible substrate 271 after the distal end is twisted.

As illustrated as an example in the drawing, it is also possible to dispose a plurality of pairs of antennas. It is possible to measure the moisture at a plurality of points in the depth direction by providing the plurality of pairs of antennas.

FIG. 157 is a diagram illustrating an example of the sensor device 200 using flexible substrates and rigid substrates when the number of antennas is increased according to the first modification example of the first embodiment of the present technology. In the drawing, a is an example in which a plurality of pairs of antennas are provided and one rigid substrate is used, and b in the drawing is an example in which a plurality of pairs of antennas are provided and five rigid substrates are used.

In b in the drawing, the rigid substrate 276 is connected to the distal end of the flexible substrate 271, and the rigid substrate 276 is provided with the transmission antenna 221. The rigid substrate 277 is connected to the distal end of the flexible substrate 272, and the rigid substrate 277 is provided with the reception antenna 231. Also, the flexible substrate 273 is provided between the rigid substrate 276 and the rigid substrate 278, and the rigid substrate 278 is provided with the transmission antenna 222. The flexible substrate 274 is provided between the rigid substrate 277 and the rigid substrate 279, and the rigid substrate 278 is provided with the reception antenna 232.

FIG. 158 is a diagram illustrating an example of the sensor device 200 in which the transmission path is arranged for each antenna according to the first modification example of the first embodiment of the present technology. In the drawing, a illustrates the flexible substrate 271 before the distal end is twisted, and b in the drawing illustrates the flexible substrate 271 after the distal end is twisted.

In a case where a plurality of pairs of antennas are disposed, it is possible to arrange the transmission path for each antenna as illustrated as an example in the drawing.

FIG. 159 is a diagram illustrating an example of the sensor device 200 in which the transmission path is arranged for each antenna and the flexible substrates and rigid substrates are used according to the first modification example of the first embodiment of the present technology. In the drawing, a is an example in which a plurality of pairs of antennas are provided and one rigid substrate is used, and b in the drawing is an example in which a plurality of pairs of antennas are provided and five rigid substrates are used.

FIG. 160 is a diagram illustrating an example of the sensor device 200 in which the substrates are disposed in the hard shell sensor casing 305 according to the first modification example of the first embodiment of the present technology. In the drawing, a is an example in which one rigid substrate 275 and flexible substrates 271 and 272 are connected to each other and disposed, and b in the drawing is an example in which the flexible substrates 271 and 272 are covered with the radio wave absorption sections 341 and 344.

Since the flexible substrate 271 and the like are soft and are likely to be deformed, they may be placed in the hard shell sensor casing 305 as illustrated as an example in a in the drawing for the purpose of maintaining the shape. As illustrated as an example in b in the drawing, it is also possible to cover it with the radio wave absorption sections 341 and 344. It is possible to maintain the shape by using the hard shell. Since the distance between the antennas affects properties, in particular, the fact that the distance between the antennas can be maintained is significantly advantageous. Also, the utilization of the radio wave absorption section 341 and the like for the purpose as well enables absorption of unnecessary reflected waves and leads to an improvement in properties.

FIG. 161 is a diagram illustrating an example of the sensor device in which the number of antennas is increased and substrates are disposed in the hard shell sensor casing 305 according to the first modification example of the first embodiment of the present technology. In the drawing, a is an example in which a plurality of pairs of antennas are provided and one rigid substrate is used, and b in the drawing is an example in which a plurality of pairs of antennas are provided and five rigid substrates are used.

In this manner, according to the first modification example of the first embodiment of the present technology, the antennas are caused to face each other by twisting a part of the flexible substrate, and it is thus possible to further simplify the configuration of the sensor device 200 as compared with the first embodiment.

Second Modification Example

Although the intra-probe substrates 321 and 322 are connected in the direction orthogonal to the measurement section substrate 311 and the antennas are caused to face each other in the aforementioned first embodiment, the configuration requires a connector and a cable for connection in addition to the three substrates, and the structure becomes complicated. The sensor device 200 according to the second modification example of the first embodiment is different from that in the first embodiment in that a part of a flexible rigid substrate is bent and the antennas are caused to face each other.

FIG. 162 is a diagram illustrating an example of the sensor device 200 according to the second modification example of the first embodiment of the present technology and a comparative example. In the drawing, a illustrates an example of the sensor device 200 according to the second modification example of the first embodiment, and b in the drawing illustrates an example of the sensor device 200 in the comparative example in which three substrates are connected.

In the sensor device 200 according to the second modification example of the first embodiment, a flexible rigid substrate obtained by bonding the flexible substrates 271 and 272 and the rigid substrates 275 and 276 is disposed.

The measurement circuit 210 is disposed on the rigid substrate 275. The transmission antenna 221 (not illustrated) is disposed on the rigid substrate 276, and the reception antenna 231 (not illustrated) is disposed on the rigid substrate 277.

The rigid substrate 275 and the rigid substrate 276 are connected by the flexible substrate 271, and the rigid substrate 275 and the rigid substrate 277 are connected by the flexible substrate 272. The flexible substrates 271 and 272 are folded such that the antenna on the rigid substrate 276 and the antenna on the rigid substrate 277 are in a facing state.

As illustrated as an example in b in the drawing, a comparative example in which the rigid substrate 275 and the rigid substrates 276 and 277 are connected by connectors 314 and 315 is also conceivable. As compared with the comparative example, no connectors are used in the configuration in which a part of the flexible rigid substrate is bent as in a in the drawing, and it is thus possible to reduce the cost of the connectors and expense for the assembly. Also, it is possible to integrate the three rigid substrates and thereby to reduce the cost of the substrates. Moreover, it is possible to use the directionality of the antennas in the related art as it is and to reduce a transmission loss.

In this manner, according to the second modification example of the first embodiment of the present technology, a part of the flexible rigid substrate is bent to cause the antennas to face each other, and it is thus possible to reduce the cost of the connectors and expense for the assembly.

Third Modification Example

Although the plane-shaped antennas or the plane-shaped and slit-shaped antennas are connected to the measurement section substrate 311 with transmission paths (such as strip lines) in the intra-probe substrates in the aforementioned first embodiment, it is also possible to connect them with coaxial cables. The sensor device 200 according to the third modification example of the first embodiment is different from that in the first embodiment in that the plane-shaped antennas or plane-shaped and slit-shaped antennas and the measurement section substrate 311 are connected with the coaxial cables.

FIG. 163 is a diagram illustrating an example of the sensor device 200 according to the third modification example of the first embodiment of the present technology. The sensor device 200 according to the third modification example of the first embodiment is different from that in the first embodiment in that the three pairs of antennas and the measurement section substrate 311 are connected with the coaxial cables 281 to 286.

The transmission antennas 221 to 223 and the measurement section substrate 311 are connected with the coaxial cables 281 to 283, and the reception antennas 231 to 233 and the measurement section substrate 311 are connected with the coaxial cables 284 to 286.

In order to use the coaxial cables that are flexible materials (materials with flexibility) to dispose the antennas at desired positions, it is only necessary to use the frames 291 to 294 formed to have a constant thermal expansion coefficient, for example. It is only necessary to sandwich the transmission antennas and the corresponding coaxial cables with the frames 291 and 292, to sandwich the reception antennas and the corresponding coaxial cables with the frames 293 and 294, and to insert them into the sensor casing 305. Here, if the frames 291 and 292 for sandwiching the transmission antennas and the corresponding coaxial cables are formed of materials with different thermal expansion coefficients, for example, these two frames may be curved due to a change in temperature of the environment where the sensor device 200 is disposed. Therefore, all the components configuring the frames are preferably formed of the materials with the same thermal expansion coefficient in the third modification example. Also, these components are preferably formed of an electromagnetic wave transmissive material in order not to prevent emission and reception of the electromagnetic waves.

FIG. 164 is a diagram illustrating an example of a top view and a sectional view of the sensor device 200 according to the third modification example of the first embodiment of the present technology. In the drawing, a illustrates an example of a top view of the measurement section casing 310. In the drawing, b illustrates a sectional view of the probe casing 320 at the part with no antennas, and c in the drawing illustrates a sectional view of the probe casing 320 at the part with the antennas.

As illustrated as an example in a in the drawing, the measurement section casing 310 is provided with the positioning sections 353 and 354 for defining the position of the measurement section substrate 311. Also, as illustrated as an example in b and c in the drawing, the coaxial cable 281 and the like are connected to the transmission antenna 221 and the like.

FIG. 165 is a diagram for explaining the method for accommodating the substrates according to the third modification example of the first embodiment of the present technology. First, the antenna on the transmission side connected to the coaxial cable is sandwiched between the frames 291 and 292, and the antenna on the reception side is sandwiched between the frames 293 and 294 as illustrated as an example in a in the drawing. Also, as illustrated as an example in b in the drawing, the positioning sections 353 and 354 are attached to the lower portion of the measurement section substrate 311, and the positioning sections 351 and 352 are attached to the distal ends of the intra-probe substrates 321 and 322. Then, the structure with the positioning sections attached thereto is inserted into the sensor casing 305 as illustrated as an example in c in the drawing.

FIG. 166 is a diagram for explaining another example of the method for accommodating the substrates according to the third modification example of the first embodiment of the present technology. As illustrated as an example in a in the drawing, it is also possible to attach the positioning sections 351 to 354 and the frames 291 to 294 beforehand in the sensor casing 305. In this case, the measurement section substrate 311 and the like are inserted into the sensor casing 305 as illustrated as an example in b and c in the drawing, and the sensor casing 305 is tightly closed as illustrated as an example in d in the drawing.

FIG. 167 is a diagram for explaining another example of the method for accommodating the substrates according to the third modification example of the first embodiment of the present technology. As illustrated as an example in the drawing, it is also possible to use the sensor casing 305 that can be split into the front casing 305-1 and the rear casing 305-2. For example, it is only necessary to place the rear casing 305-2 as illustrated as an example in a in the drawing, to insert the measurement section substrate 311 and the like as illustrated as an example in b and c in the drawing, and to attach the front casing 305-1 as illustrated as an example in d and e in the drawing.

In this manner, according to the third modification example of the first embodiment of the present technology, the antennas are connected to the measurement section substrate 311 with the coaxial cables, and it is thus possible to realize the predetermined distance between the antennas by disposing the transmission antenna and the reception antenna at the predetermined positions even in a case where the transmission path is long. It is thus possible to accurately measure the moisture.

Fourth Modification Example

In the aforementioned first embodiment, the positioning sections 351 and 352 are provided in the probe casing 320 as structures for fixing the orientations and the positions of the transmission antenna and the reception antenna to be accommodated in the probe casing.

The structure for fixing the orientations and the positions of the transmission antenna and the reception antenna to be accommodated in the probe casing is not limited to the structure illustrated in FIG. 4 according to the first embodiment, and various modification examples are conceivable.

These modification examples of the structure for fixing the orientations and the positions of the transmission antenna and the reception antenna will be collectively referred to as a fourth modification example.

Note that in these various fourth modification examples, the structure (for example, a positioning section or a groove for positioning) for fixing the orientations and the positions of the transmission antenna and the reception antenna may adopt a mode in which a structure formed separately from the casing is attached to the casing after the casing is formed or may adopt a mode in which the structure for fixing the positions of the antennas is included in the casing from the time of the formation thereof unless particularly stated otherwise.

FIG. 168 is a diagram illustrating an example of the sensor device 200 according to the fourth modification example 1 of the first embodiment of the present technology. The sensor device 200 according to the fourth modification example 1 of the first embodiment is different from that in the first embodiment in that positioning sections 353 and 354 are further disposed in the measurement section casing 310.

The positioning sections 351 and 352 are disposed at the distal end of the probe casing 320. The positioning sections 351 and 352 are components used to fix the orientations of the intra-probe substrates 321 and 322 to predetermined orientations and fixing the positions thereof at predetermined positions (positions at a predetermined distance from the two substrates). These positioning sections may be integrated with the sensor casing 305.

The positioning sections 353 and 354 are components used to fix the position of the measurement section substrate 311 at a predetermined position. These positioning sections may further include a shape for facilitating disposition of the transmission antenna and the reception antenna at the predetermined positions in a predetermined direction (such as a Y-axis direction) defined in advance while moving the antennas in the probe casing 320. For example, the positioning sections may include inclined surfaces toward the predetermined direction defined in advance. The positioning sections may include the inclined surfaces toward the predetermined positions defined in advance to guide the antennas to the positions. As a material for each positioning section, an electromagnetic transmissive material, for example, is used.

FIG. 169 is a diagram illustrating an example of a top view and a sectional view of the sensor device 200 according to the fourth modification example 1 of the first embodiment of the present technology. In the drawing, a illustrates an example of a top view of the measurement section casing 310. In the drawing, b illustrates a sectional view of the probe casing at the positions where the positioning sections 351 and 352 are disposed. Each of the measurement section casing 310 and the probe casing 320 is provided with a groove for attachment of the positioning section 351 and the like.

FIG. 170 is a diagram for explaining a method for accommodating the substrates according to the fourth modification example 1 of the first embodiment of the present technology. As illustrated as an example in a in the drawing, the positioning sections 351 to 354 are attached to the inside of the sensor casing 305. Also, the measurement section substrate 311 and the like are inserted into the sensor casing 305 as illustrated as an example in b and c in the drawing, and the sensor casing 305 is tightly closed as illustrated as an example in d in the drawing.

FIG. 171 is a diagram for explaining another example of the method for accommodating the substrates according to the fourth modification example 1 of the first embodiment of the present technology. As illustrated as an example in the drawing, it is also possible to use the sensor casing 305 that can be split into the front casing 305-1 and the rear casing 305-2.

FIG. 172 is a diagram illustrating an example of the sensor device 200 with the position of the positioning section changed according to the fourth modification example 2 of the first embodiment of the present technology. As illustrated as an example in the drawing, it is also possible to dispose the positioning sections 351 and 352 near the upper end of the probe casing 320. Note that the positioning sections 351 and 352 may be disposed at the center portion of the probe casing 320.

FIG. 173 is a diagram illustrating an example of a top view and a sectional view of the sensor device 200 with the position of the positioning section changed according to the fourth modification example 2 of the first embodiment of the present technology.

FIG. 174 is a diagram illustrating an example of the sensor device 200 with the positioning section added thereto according to the fourth modification example 3 of the first embodiment of the present technology. As illustrated as an example in the drawing, it is also possible to add the positioning sections 355 and 356 near the upper end of the probe casing 320. Note that the positioning sections 355 and 356 may be disposed at the center portion of the probe casing 320. The positioning sections are not limited to the example illustrated in FIG. 174 and can be disposed at a plurality of locations in the probe casing 320.

FIG. 175 is a diagram illustrating an example of a top view and a sectional view of the sensor device 200 with the positioning section added thereto according to the fourth modification example 3 of the first embodiment of the present technology.

FIG. 176 is a diagram illustrating an example of the sensor device 200 including the positioning section with a different shape according to the fourth modification example 4 of the first embodiment of the present technology.

FIG. 177 is a diagram illustrating an example of a top view and a sectional view of the sensor device including the positioning section with a different shape according to the fourth modification example 4 of the first embodiment of the present technology. As illustrated as an example in FIGS. 176 and 177, the positioning sections 351, 352, 355, and 356 may adopt a mode in which sectional end portions of the intra-probe substrates 321 and 322 are pressed therewith in the probe section. Also, the intra-probe substrate 321 is sandwiched between the frames 291 and 292, and the intra-probe substrate 322 is sandwiched between the frames 293 and 294.

Also, the positioning sections 355 and 356 may extend in the lengthwise direction (Y-axis direction) of the substrate in the probe casing such that the positions of the substrates inserted into the probe casing 320 are constant. The length thereof may be equal to or greater than the length (that is, the width) of the intra-probe substrate 321 and the like in the Z-axis direction or may be equal to or greater than ½ the length of the intra-probe substrate 321 and the like in the Y-axis direction.

FIG. 178 is a diagram for explaining a method for accommodating the substrates in a case where the shape of the positioning section is different according to the fourth modification example 4 of the first embodiment of the present technology. As illustrated as an example in a in the drawing, the positioning sections 351 to 354 and the frames 291 to 294 are attached to the inside of the sensor casing 305. Also, the measurement section substrate 311 and the like are inserted into the sensor casing 305 as illustrated as an example in b and c in the drawing, and the sensor casing 305 is tightly closed as illustrated as an example in d in the drawing. Note that various shapes can be selected as the shape of the frames 291 to 294 as long as it is possible to facilitate the insertion of the substrates and to maintain the substrate at the constant positions. In one example, the shape may be a groove-type or may be a rail shape.

FIG. 179 is a diagram for explaining another example of the method for accommodating the substrates in a case where the shape of the positioning section is different according to the fourth modification example 4 of the first embodiment of the present technology. As illustrated as an example in a in the drawing, it is also possible to sandwich the intra-probe substrate 321 with the frames 291 and 292 and to sandwich the intra-probe substrate 322 with the frames 293 and 294 before the insertion into the sensor casing 305. In this case, as illustrated as an example in b in the drawing, the positioning sections 351 to 354 are attached. Then, as illustrated as an example in c in the drawing, the structure with the positioning sections attached thereto is inserted into the sensor casing 305.

FIG. 180 is a diagram illustrating an example of the sensor device 200 with the frames extended according to the fourth modification example 5 of the first embodiment of the present technology. As illustrated as an example in the drawing, it is also possible to extend the frames 291 to 294 up to the upper end of the sensor casing 305.

FIG. 181 is a diagram illustrating an example of a top view and a sectional view of the sensor device with the frames extended according to the fourth modification example 5 of the first embodiment of the present technology. In the drawing, a illustrates an example of a top view of the measurement section casing 310. In the drawing, b illustrates a sectional view of the probe casing 320 at a part with no antennas, and c in the drawing illustrates a sectional view of the probe casing 320 at a part with antennas.

FIG. 182 is a diagram illustrating an example of the sensor device 200 further including a structure for fixing the position of the measurement section substrate according to the fourth modification example 6 of the first embodiment of the present technology. As illustrated as an example in the drawing, a structure in which the measurement section substrate and the intra-probe substrate are fitted to each other may be included. More specifically, a structure in which a notch is provided in any of the measurement section substrate and the intra-probe substrate and this is used to fit the two substrates may be included.

FIG. 183 is a diagram illustrating an example of a sectional view of the sensor device 200 further including another structure for fixing the position of the measurement section substrate according to the fourth modification example 6 of the first embodiment of the present technology. In the drawing, a illustrates a sectional view of the probe casing at the positions at which the positioning sections 351-1 and 352-1 are disposed.

FIG. 184 is a diagram illustrating an example of the sensor device 200 with jigs added thereto according to the fourth modification example 7 of the first embodiment of the present technology. As illustrated as an example in the drawing, it is also possible to add jigs 359-1 and 359-2 for fixing the measurement section substrate 311 to the intra-probe substrates 321 and 322. These jigs include both the part for fitting or fixing the measurement section substrate 311 and the part for fitting or fixing the intra-probe substrate 321 and the like. It is possible to fix the positions of the substrates by fixing any part of the measurement section substrate 311, the intra-probe substrate 321, and the like integrated through the above fitting or fixing to the sensor casing 305.

FIG. 185 is a diagram illustrating an example of a top view and a sectional view of the sensor device 200 with jigs added thereto according to the fourth modification example 7 of the first embodiment of the present technology. In the drawing, a illustrates an example of a top view of the measurement section casing 310. In the drawing, b illustrates a sectional view of the probe casing at the positions where the positioning sections 351-1 and 352-1 are disposed.

FIG. 186 is a diagram illustrating an example of the sensor device 200 including a structure in which the intra-probe substrates 321 and 322 are caused to abut the sensor casing 305 according to the fourth modification example 8 of the first embodiment of the present technology. It is possible to fix the positions of the intra-probe substrates 321 and 322 by causing the distal ends thereof (the parts surrounded by the dotted lines) to abut the sensor casing 305 (in other words, bringing the distal ends into contact with the sensor casing 305) without providing the positioning sections.

FIG. 187 is an example of a sectional view of the sensor casing and the intra-probe substrates of the sensor device 200 including the structure in which the intra-probe substrates 321 and 322 are caused to abut the sensor casing 305 according to the fourth modification example 8 of the first embodiment of the present technology. In the drawing, a illustrates a sectional view of the sensor casing 305 cut along the line A-A' in FIG. 186. In FIG. 187, b illustrates a sectional view of the sensor casing 305 cut along the line B-B' in FIG. 181. In FIG. 187, c illustrates a sectional view of the sensor casing 305 cut along the line C-C' in FIG. 186. In the structure in which the intra-probe substrates 321 and 322 are cause to abut the probe casing 300 as illustrated as an example in FIGS. 186 and 187, the positions of the intra-probe substrates 321 and 322 in the casing are fixed by the intra-probe substrates coming into contact with the probe casing 300 casing at least two points out of a total of four points including the two points in the widthwise direction (Z-axis direction) of the substrates x the two points in the thickness direction (Z-axis direction) of the substrates.

FIG. 188 is a diagram for explaining the fourth modification example (a modification example of a structure in which orientations and positions of the transmission antenna and the reception antenna are foxed) 9 according to the first embodiment of the present technology. The sensor device 200 illustrated in FIG. 188 as the fourth modification example 9 does not include the sensor casing 305 included in the first embodiment (FIG. 4) of the present technology. The sensor device 200 illustrated in FIG. 188 does not include the sensor casing 305 and includes at least (1) a transmission probe formed by a structure in which the periphery of the transmission substrate (the same as the transmission probe substrate 321 in the sensor device 200 illustrated in FIG. 4) including a transmission antenna and a transmission path for transmission connected thereto is hardened with a resin, and (2) a reception probe formed by a structure in which the periphery of the reception substrate (the same as the reception probe substrate 322 in the sensor device 200 illustrated in FIG. 4) including a reception antenna and a transmission path for reception connected thereto is hardened with a resin, the transmission probe in (1) above and the reception probe in (2) above being fixed to each other in the structure.

Also, the sensor device 200 included in the fourth modification example 9 may include a structure including the transmission probe in (1) above, and the reception probe in (2) above, in which the sensor device 200 further includes (3) the third structure part that is different from (1) and (2) above, and the transmission probe in (1) above and the reception probe in (2) are thereby fixed to each other. Here, an example of the third structure part in (3) above is a reinforcing member such as the reinforcing section 260 in FIG. 4.

The sensor device 200 illustrated in FIG. 188 includes the transmission probe in (1) above, the reception probe in (2) above, and the structure part obtained by hardening the periphery of the measurement section substrate 311 with a resin as the third structure part in (3) above, the structures in (1) to (3) above being integrated and fixed in the structure.

Here, in regard to the transmission probe in (1) above and the reception probe in (2) above, It is desirable that the strength of the resin part included in (1) the transmission probe formed by the structure obtained by hardening the periphery of the transmission substrate with a resin be higher than the strength of the transmission substrate alone included in the probe in order to prevent the situation in which "the probes are deformed, the electronic substrates disposed in the probes are deformed, and as a result, the distance between the transmission antenna and the reception antenna formed in the electronic substrates thus changes from the predetermined value, and an error thus occurs in the measurement result of the amount of moisture when these probes are inserted into the soil". In other words, it is desirable that the strength of the transmission probe obtained by hardening the periphery of the transmission substrate with a resin be equal to or greater than a double the strength of the transmission substrate alone included in the probe. In yet other words, in a case where the amount of deformation of the transmission probe obtained by hardening the periphery of the transmission substrate with a resin and the amount of deformation of the transmission substrate alone included in the probe are compared with each other by using the method illustrated in FIG. 135, it is desirable that the amount of deformation of the amount of deformation of the transmission probe obtained by hardening the periphery of the transmission substrate with a resin be equal to or less than ½ the amount of deformation of the transmission substrate alone included in the probe.

Similarly, it is desirable that in (2) the reception probe formed by the structure obtained by hardening the periphery of the reception substrate with a resin, the strength of the resin part included in the probe be higher than the strength of the reception substrate alone included in the probe. In other words, it is desirable that the strength of the reception probe obtained by hardening the periphery of the reception substrate with a resin be equal to or greater than a double the strength of the reception substrate alone included in the probe. In yet other words, in a case where the amount of deformation of the reception probe obtained by hardening the periphery of the reception substrate with a resin and the amount of deformation of the reception substrate alone included in the probe are compared with each other by using the method illustrated in FIG. 135, it is desirable that the amount of deformation of the amount of deformation of the reception probe obtained by hardening the periphery of the reception substrate with a resin be equal to or less than ½ the amount of deformation of the reception substrate alone included in the probe.

In this manner, according to the fourth modification example of the first embodiment of the present technology, various structures for fixing the orientations and the positions of the transmission antenna and the reception antenna to be accommodated in the probe casings are included, and it is thus possible to fix the transmission antenna and the reception ante in predetermined orientations and at predetermined positions.

Fifth Modification Example

The aforementioned first embodiment has a structure in which the strength of the probe casing 320 is enhanced as compared with the intra-probe substrates 321 and 322 accommodated inside the probe casing 320 in order to prevent deformation of the probe casing 320 when the probe casing 320 included in the sensor device 200 is inserted into the soil as described above with reference to FIG. 135. Also, the thickness (component thickness) of the probe casing 320 is a predetermined thickness such that the strength of the casing is above the strength of the above substrate. However, in a case where hardness of the soil for which the sensor device 200 according to the first embodiment is used is significantly high, the probe casing 320 may be required to have yet higher strength in order to prevent deformation when the probe casing 320 is inserted into the soil. In order to enhance the strength of the probe casing 320, it is necessary to increase the component thickness of the casing. However, if the component thickness of the probe casing 320 is unnecessarily increased (if the component thickness of the casing near the antennas is significantly increased, for example), degradation of measurement accuracy of the amount of moisture is conceivable in some cases. Thus, as the fifth modification example of the first embodiment, a structure for further enhancing the strength of the probe casing 320 included in the sensor device 200 than in the first embodiment without any concern of degradation of measurement accuracy of the amount of moisture will be described with reference to FIGS. 191 to 199.

Before the sectional shape of the probe casing 320 included in the sensor device 200 according to the fifth modification example of the first embodiment of the present technology is described, the sectional shape of the probe casing 320 included in the sensor device 200 according to the first embodiment of the present technology will be described with reference to FIGS. 189 and 190.

Referring to FIG. 4, the first embodiment of the present technology has described, as the component (9), that in the section in the direction orthogonal to the extending direction (Y-axis direction) of the probe casings 320a and 320b, (1) the distance from the center of the intra-probe substrate 321 to the casing end of the probe casing 320a in the direction that is vertical to the intra-probe substrate 321 and approaches the reception antenna is shorter than (2) the distance from the center of the intra-probe substrate 321 to the casing end of the probe casing 320*a* in the direction parallel with the intra-probe substrate 321.

Similarly, it has described that (1') the distance from the center of the intra-probe substrate 322 to the casing end of the probe casing 320*b* in the direction that is vertical to the intra-probe substrate 322 and approaches the transmission antenna is shorter than (2') the distance from the center of the intra-probe substrate 322 to the casing end of the probe casing 320*b* in the direction parallel with the intra-probe substrate 322.

FIG. 189 is a diagram for more specifically explaining the structure of the above component (9) and the structure in the comparative example.

FIG. 189*a* is a diagram in which characteristic structures included in the sensor device 200 are overwritten when the sensor device 200 is seen from the positive direction of the Y axis from the above according to the first embodiment of the present technology. The drawing illustrates the measurement section casing 310, the measurement section substrate 311, the probe casing 320, and the intra-probe substrates 321 and 322. In the drawing, (1) the distance from the center of the intra-probe substrate 321 to the casing end of the probe casing 320*a* in the direction of the reception antenna which is vertical to the intra-probe substrate 321 is illustrated with a reference sign dx. On the other hand, (2) the distance from the center of the intra-probe substrate 321 to the casing end of the probe casing 320*a* in the direction parallel with the intra-probe substrate 321 is illustrated with a reference sign dz. Also, in the drawing, the sensor device 200 according to the first embodiment of the present technology has a structure in which the probe casing 320 included in the sensor device 200 has shorter dx described than dz in the section orthogonal to the extending direction thereof as the component (9).

On the contrary, b in FIG. 189 illustrates a comparative example in which the structure of the above component (9) is not included, that is, a structure in which the distance from the center of the intra-probe substrate 321 to the casing end of the probe casing 320*a* in the direction of the reception antenna which is vertical to the intra-probe substrate 321 is equal to the distance from the center of the intra-probe substrate 321 to the casing end of the probe casing 320*a* in the direction parallel with the intra-probe substrate 321.

Here, various examples of the component (9) of the sensor device 200 according to the first embodiment of the present technology will be described with reference to FIG. 190. The drawing represents the sectional shape of the probe casing 320 in a direction orthogonal to the extending direction of the probe casing 320. In the drawing, the sectional shape of the probe casing 320 may be a shape in which (1) a distance dx from the center of the intra-probe substrate 321 to the casing end of the probe casing 320*a* in the direction of the reception antenna that is a direction vertical to the intra-probe substrate 321 is smaller than (2) a distance dy from the center of the intra-probe substrate 321 to the casing end of the probe casing 320*a* in the direction parallel with the intra-probe substrate 321, and also, it may be an oval having a short axis in the direction orthogonal to the intra-probe substrate or the shape that is substantially the same as this as illustrated in a in the drawing, or may be a shape, in which the width of the probe casing in the direction orthogonal to the intra-probe substrate is shorter than the width of the probe casing in the direction parallel with the intra-probe substrate, which is asymmetrical in the paper surface left-right direction, which projects on the rear surface side (the side opposite to the direction in which the facing antennas are present) of the intra-probe substrate, as illustrated in b in the drawing, or may be a shape, in which the width of the probe casing in the direction orthogonal to the intra-probe substrate is shorter than the width of the probe casing in the direction parallel with the intra-probe substrate, which is asymmetrical in the paper surface left-right direction, which projects on the front surface side (the side on which the facing antennas are present) of the intra-probe substrate, as illustrated in c in the drawing, or may be an oblong having a short side in the direction orthogonal to the intra-probe substrate or the shape that is substantially the same as this as illustrated in d in the drawing.

The shape of the probe casing including the reception antenna is the shape that is line-symmetrical with the shape of the probe casing including the transmission antenna, and the description thereof will thus be omitted.

Note that a rectangular figure is illustrated in the direction closer to the center of the sensor device 200 than the intra-probe substrate in b, c, and d in the drawing. This represents the positions of the radiation element and the reception element of the antennas in an emphasized manner. These elements are formed in the surface layer or the inner layer of the intra-probe substrate.

Returning to FIG. 189, an effect of the component (9) of the sensor device 200 according to the first embodiment of the present technology will be described.

In comparison between a (the component (9) of the present technology) and b (comparative example) in the drawing, the distance between the transmission intra-probe substrate 321 and the reception intra-probe substrate 322 is equal in the two drawings, and therefore, the distance between the transmission antenna included in the transmission intra-probe substrate 321 and the reception antenna included in the reception intra-probe substrate 322 is also equal. In comparison between a and b in the drawing, only the sectional shapes of the probe casing 320 are different.

Next, in comparison between the proportions of the region outside the casing (that is, the soil region) in the region between the transmission probe substrate 321 and the reception probe substrate 322 in a and b in the drawing, the proportion of the region outside the casing (that is, the soil region) is smaller in b in the drawing than in a in the drawing.

As already described above with reference to FIG. 98, the moisture measurement system 100 according to the present invention obtains the amount of moisture in the soil by focusing on the fact that the time required for the electromagnetic waves to be propagated from the transmission antenna to the reception antenna has a linear relationship with the amount of moisture in the soil. Therefore, the above relationship between the propagation delay time and the amount of moisture in the soil is further separated from the linear relationship, and an error included in the measurement result increases, as the proportion of the soil region in the region between the transmission probe substrate 321 and the reception probe substrate 322 decreases. On the contrary, the relationship between the propagation delay time and the amount of moisture in the soil further approaches the linear relationship as the proportion of the soil region in the region between the two substrates increases, and it becomes possible to accurately measure the amount of moisture in the soil.

The sensor device 200 according to the first embodiment of the present technology illustrated in a in FIG. 189 has a higher proportion of the soil region in the region between the transmission probe substrate 321 and the reception probe substrate 322 than in the comparative example illustrated in b in the drawing by including the structure of the component (9), and the effect of accurately measuring the amount of moisture in the soil is thus obtained.

Next, the fifth modification example of the first embodiment of the present technology will be described with reference to FIGS. 191 to 199.

FIGS. 191 to 199 are diagrams representing the fifth modification example of the first embodiment of the present technology, that is, a structure for enhancing the strength of the probe casing 320 without any concern of degradation of measurement accuracy of the amount of moisture. The probe casing 320 illustrated in these drawings has a component thickness of a part of the casing increased in order to enhance the strength thereof as compared with the probe casing 320 illustrated in a in FIG. 190. However, the component thickness of the casing is not increased in the region where the transmitted and received electromagnetic waves are transmitted in order to prevent measurement accuracy of the amount of moisture from being degraded when the thickness of the casing is increased. Note that the shape of the casing in a in FIG. 190 will be referred to as a comparative example in which the thick casing is not included when the sectional shape of the casing illustrated in FIGS. 191 to 199 will be described.

FIG. 191 is a diagram for explaining the fifth modification example 1 of the first embodiment of the present technology, which includes a sectional shape of the probe casing 320 illustrated in a in FIG. 190 and the shape in which plane-shaped double-side radiation antennas are disposed to face each other. The probe casing 320 illustrated in FIG. 191 has a component thickness increased at two locations in the paper surface upper direction and the lower direction while avoiding the paper surface inward direction in which the electromagnetic waves are mainly transmitted through the casing since the double-side radiation antennas are disposed to face each other.

In FIG. 191, the component thickness of the casing may be increased in the shape in which neither discontinuous points nor inflection points are present at both the outer periphery and the inner periphery of the casing as illustrated in a in FIG. 191 as the shape for increasing the component thickness of the casing. As illustrated in b in FIG. 191, the component thickness of the casing may be increased in the inward direction. In this case, the discontinuous points or inflection points increase at the inner periphery of the casing as compared with the comparative example. As illustrated in c in FIG. 191, the component thickness of the casing may be increased in the outward direction. In this case, the discontinuous points or inflection points increase at the outer periphery of the casing as compared with the comparative example. As illustrated in d in FIG. 191, the component thickness of the casing may be increased in both the inward direction and the outward direction. In this case, the discontinuous points or inflection points increase at both the inner periphery and the outer periphery of the casing as compared with the comparative example.

FIG. 192 is a diagram for explaining the fifth modification example 2 of the first embodiment of the present technology, which includes a sectional shape of the probe casing 320 illustrated in a in FIG. 190 and a shape in which plane-shaped double-side radiation antennas are disposed to face each other. The probe casing 320 illustrated in FIG. 192 has a component thickness increased at one location in the paper surface outward direction while avoiding the paper surface inward direction in which electromagnetic waves are mainly transmitted through the casing since double-side radiation antennas are disposed to face each other.

In FIG. 192, the component thickness of the casing may be increased with a shape in which neither discontinuous points nor inflection points are present at both the outer periphery and the inner periphery of the casing as illustrated in a in FIG. 192 as the shape for increasing the component thickness of the casing. As illustrated in b in FIG. 192, the component thickness of the casing may be increased in the inward direction. In this case, the discontinuous points or inflection points increase at the inner periphery of the casing as compared with the comparative example. As illustrated in c in FIG. 192, the component thickness of the casing may be increased in the inward direction. In this case, the discontinuous points or inflection points increase at the outer periphery of the casing as compared with the comparative example. As illustrated in d in FIG. 192, the component thickness of the casing may be increased in both the inward direction and the outward direction. In this case, the discontinuous points or inflection points increase at both the inner periphery and the outer periphery of the casing as compared with the comparative example.

FIG. 193 is a diagram for explaining an exceptional case according to the fifth modification example of the first embodiment of the present technology, which includes a sectional shape of the probe casing 320 illustrated in a in FIG. 190 and the shape in which plane-shaped double-side radiation antennas are disposed to face each other. Although the double-side radiation antennas are disposed to face each other in the probe casing 320 illustrated in FIG. 193, the component thickness thereof is exceptionally increased at two locations in the paper surface left-right direction including the paper surface inward direction in which the electromagnetic waves are mainly transmitted through the casing. Although there is a concern of degradation of measurement accuracy of the amount of moisture in this case, the effect of enhancing the strength of the probe casing 320 is obtained.

In FIG. 193, the component thickness of the casing may be increased with a shape in which neither discontinuous points nor inflection points are present at both the outer periphery and the inner periphery of the casing as illustrated in a in FIG. 193 as the shape for increasing the component thickness of the casing. As illustrated in b in FIG. 193, the component thickness of the casing may be increased in the inward direction. In this case, the discontinuous points or inflection points increase at the inner periphery of the casing as compared with the comparative example. As illustrated in c in FIG. 193, the component thickness of the casing may be increased in the inward direction. In this case, the discontinuous points or inflection points increase at the outer periphery of the casing as compared with the comparative example. As illustrated in d in FIG. 193, the component thickness of the casing may be increased in both the inward direction and the outward direction. In this case, the discontinuous points or inflection points increase at both the inner periphery and the outer periphery of the casing as compared with the comparative example.

FIG. 194 is a diagram for explaining the fifth modification example 3 according to the first embodiment of the present technology, which includes a sectional shape of the probe casing 320 illustrated in a in FIG. 190 and the shape in which the plane-shaped double-side radiation antennas are disposed to face each other. The probe casing 320 illustrated in FIG. 194 has a component thickness increased at three locations except for the paper surface inward direction while avoiding the paper surface inward direction in which the electromagnetic waves are mainly transmitted through the casing since the one-side radiation antennas are disposed to face each other.

In FIG. 194, the component thickness of the casing may be increased with a shape in which neither discontinuous points nor inflection points are present at both the outer periphery and the inner periphery of the casing as illustrated in a in FIG. 194 as the shape for increasing the component thickness of the casing. As illustrated in b in FIG. 194, the component thickness of the casing may be increased in the inward direction. In this case, discontinuous points or inflection points increase at the inner periphery of the casing as compared with the comparative example. As illustrated in c in FIG. 194, the component thickness of the casing may be increased in the outward direction. In this case, the discontinuous points or inflection points increase at the outer periphery of the casing as compared with the comparative example. As illustrated in d in FIG. 194, the component thickness of the casing may be increased in both the inward direction and the outward direction. In this case, the discontinuous points or inflection points increase at both the inner periphery and the outer periphery of the casing as compared with the comparative example.

FIG. 195 is a diagram for explaining the fifth modification example 4 of the first embodiment of the present technology.

The structure illustrated in the FIG. 195 includes the casing with the same shape which is obtained merely by changing the antenna with the structure illustrated in FIG. 191 to one-side radiation.

FIG. 196 is a diagram for explaining the fifth modification example 5 of the first embodiment of the present technology.

The structure illustrated in FIG. 196 includes the casing with the same shape which is obtained merely by changing the antenna with the structure illustrated in FIG. 192 to one-side radiation.

FIG. 197 is a diagram for explaining an exceptional case of the fifth modification example of the first embodiment of the present technology. The structure illustrated in the FIG. 197 includes the casing with the same shape which is obtained merely by changing the antenna with the structure illustrated in FIG. 193 to one-side radiation.

FIG. 198 is a diagram for explaining the fifth modification example 6 of the first embodiment of the present technology.

The structure illustrated in the FIG. 198 includes the casing with the same shape which is obtained merely by changing the antenna with the structure illustrated in FIG. 194 to one-side radiation.

Each configuration in FIGS. 191 to 198 can be applied to each configuration in FIG. 190.

FIG. 199 is a diagram for explaining a setting example of the component thickness of the sensor casing 305 according to the fifth modification example of the first embodiment of the present technology. As illustrated as an example in a in the drawing, the component thickness of the probe casing 320 on the inner side is defined as $d1$, and the component thickness on the outer side is defined as $d2$. The component thickness of the probe casing 320 in the direction (Z-axis direction) that is parallel with the intra-probe substrate 321 or the like is defined as $d3$. The thickness of the reinforcing section 360 in the Z-axis direction is defined as $d6$.

As illustrated as an example in b in the drawing, the component thickness of the measurement section casing 310 in the surface of the measurement section casing 310 connected to the probe casing 320 among the surfaces of the measurement section casing 310 (in other words, the bottom surface) is defined as $d4$. The component thickness of the measurement section casing 310 in the surfaces other than the bottom surface is defined as $d5$. As illustrated as an example in b in the drawing, the thickness of the measurement section casing 310 in the Z-axis direction is defined as $d8$.

It is desirable that the sensor casing 305 according to the fifth modification example of the first embodiment of the present technology satisfy a condition 1 which is $d2>d1$ or $d3>d1$. In this manner, it is possible to enhance mechanical strength of the casing as compared with the mode which does not include the structure (in other words, the mode which does not include the thick casing), and as a result, it is possible to reduce deformation of the casing and a change in distance between the transmission and reception antennas and to accurately measure moisture.

Furthermore, according to the mode in which the above condition 1 is satisfied, it is possible to enhance the strength of the casing without reducing the proportion of the soil region in the region between the transmission antenna and the reception antenna as compared with the mode in which the thickness of the casing at the entire periphery thereof is increased or the mode in which the thickness of the casing at the portion corresponding to $d1$ is increased in order to enhance the mechanical strength of the casing. In this manner, it is possible to reduce deformation of the casing and a change in distance between the transmission and reception antennas while maintaining the relationship between the electromagnetic wave propagation delay time and the amount of moisture in the soil in a linear relationship and thereby to accurately measure the moisture.

Also, it is desirable that a condition 2 which is $d6>d1$ or $d4>d1$ be satisfied. In this manner, it is possible to enhance the strength of the casing without reducing the proportion of the soil region in the region between the transmission antenna and the reception antenna. In this manner, it is possible to reduce deformation of the casing and a change in distance between the transmission and reception antennas while maintaining the relationship between the electromagnetic wave propagation delay time and the amount of moisture in the soil in a linear relationship and thereby to accurately measure the moisture. Also, an increase in thickness of $d6$ leads to an effect that an increase or decrease in the distance between the transmission probe and the reception probe with respect to a predetermined distance is curbed even if a stress is applied to the probes when a stress is applied to these probes at the time of insertion of the transmission probe and the reception probe into the soil, that is, an effect of maintaining the distance between the transmission and reception antennas at a predetermined distance, and it is also possible to accurately measure the moisture by the effect.

Also, the increase in thickness of $d4$ leads to an effect that an application of a stress to the bottom surface of the measurement section casing 310 at the time of insertion of the transmission probe and the reception probe into the soil, deformation of the bottom surface due to the stress, and thus a change in angle of attachment of the probes to the bottom surface are curbed. This leads to an effect that the increase or decrease in distance between the probes as compared with the predetermined distance is prevented, that is, the effect that the distance between the transmission and reception antennas is maintained at a predetermined distance, and it is also possible to accurately measure moisture by the effect.

In the case where the condition 2 is satisfied, it is preferable to satisfy $d6>d5$ or $d4>d5$ at the same time. In this case, it is possible to prevent the thickness of a part of the casing that has less contribution to accurate measurement of moisture from being unnecessarily increased as compared with the mode in which d1<d6<d5 or d1<d4<d5. As a result, the effects that manufacturing of the casing is facilitated, the weights of the casing and the sensor device are reduced, and the manufacturing cost of the casing is reduced are achieved.

In the case where the condition 2 is satisfied, d6>d4 may be concurrently satisfied. The increase in thickness of d4 leads to an effect that deformation of the bottom surface of the measurement section casing 310 is prevented and the distance between the antennas is maintained at the predetermined distance. On the other hand, an increase in thickness of d6 can lead to an effect that the distance between the antennas is more effectively maintained at the predetermine distance at the position closer to the antennas than the bottom surface. As a result, it is possible to accurately measure the moisture.

Also, it is desirable that a condition 3 which is d6<d8 be satisfied. Even if the reinforcing section 360 is formed of the electromagnetic wave transmissive material, the electromagnetic wave transmissive materials that are currently commercially available do not have an electromagnetic wave reflectance of zero. Therefore, reflection of electromagnetic waves by the reinforcing section 360 may occur. It is possible to reduce noise due to reflection of electromagnetic waves emitted from the antenna by the reinforcing section 360 and reception thereof by the reception antenna by satisfying the above condition 3 as compared with a case where the condition 3 is not satisfied. As a result, it is possible to accurately measure the moisture.

Also, it is desirable that a condition 4 which is d7>d6 be satisfied. It is possible to curb an increase or decrease of the distance between the transmission probe and the reception probe as compared with the predetermined distance even if a stress is applied to these probes when the probes are inserted into the soil by the disposition of the reinforcing section 360. Also, it is possible to achieve the effect that the distance between the antennas is more effectively maintained at the predetermined distance at a position closer to the antennas by satisfying d7>d6 as compared with a case where the condition is not satisfied. As a result, it is possible to accurately measure the moisture.

In this manner, according to the fifth modification example of the first embodiment of the present technology, the component thickness of the probe casing 320 is adjusted, and the sensor device 200 can thus more accurately measure moisture. Note that although the structure illustrated in FIG. 194a is used as the structure of the casing illustrated in the drawing in the above description with reference to FIG. 199, the above description is also applied to any of the structures in FIGS. 191 to 198.

Sixth Modification Example

Although a plurality of pairs of antennas transmit and receive electromagnetic waves one by one in order in the aforementioned first embodiment, it is difficult to shorten the measurement time with this configuration. The sensor device 200 according to the sixth modification example of the first embodiment is different from that in the first embodiment in that it is possible for the plurality of pairs of antennas to concurrently transmit and receive electromagnetic waves by frequency division.

FIG. 200 is a diagram illustrating a configuration example of the sensor device 200 in which a transceiver is provided for each antenna according to the sixth modification example of the first embodiment of the present technology.

The sensor device 200 according to the sixth modification example of the first embodiment is different from that in the first embodiment in that a transceiver is included for each antenna set. In a case where three antenna sets are included, transmitters 214-1, 214-2, and 214-3 and receivers 215-1, 215-2, and 215-3 are provided. Note that the number of antenna sets is not limited to three as long as it is two or more.

The transmitters 214-1 to 214-3 are connected to the transmission antennas 221 to 223, and the receivers 215-1 to 215-3 are connected to the reception antennas 231 and 232. The transmission switch 216 and the reception switch 217 are not needed. It is thus possible to lower the price.

The transmitters 214-1, 214-2, and 214-3 transmit transmission signals at mutually different frequencies. Also, the receivers 215-1, 215-2, and 215-3 receive reception signals at frequencies of the corresponding transmitters. It is possible to separate the signals from the transmission antennas 221 to 223 on the reception side through such control based on frequency division.

FIG. 201 is a diagram illustrating a configuration example of the sensor device 200 in which one transmitter and one receiver are included according to the sixth modification example of the first embodiment of the present technology. As illustrated as an example in the drawing, the transmitter 214 may be connected to the transmission antennas 221 to 223, and the receiver 215 may be connected to the reception antennas 231 and 232. The transmitter 214 has a function that is equivalent to those of the transmitters 214-1 to 214-3, and the receiver 215 has a function that is equivalent to those of the receivers 215-1 to 215-3.

FIG. 202 is a diagram illustrating a configuration example of the sensor device 200 including one receiver according to the sixth modification example of the first embodiment of the present technology. As illustrated as an example in the drawing, the transmitters 214-1 to 214-3 may be connected to the transmission antennas 221 to 223, and the receiver 215 may be connected to the reception antennas 231 and 232. The receiver 215 has a function that is equivalent to those of the receivers 215-1 to 215-3.

FIG. 203 is a diagram illustrating a configuration example of the sensor device 200 including one transmitter according to the sixth modification example of the first embodiment of the present technology. As illustrated as an example in the drawing, the transmitter 214 may be connected to the transmission antennas 221 to 223, and the receivers 215-1 to 215-3 may be connected to the reception antennas 231 and 232. The transmitter 214 has a function that is equivalent to those of the transmitters 214-1 to 214-3.

FIG. 204 is a diagram illustrating another example of the sensor device 200 including a plurality of receivers according to the sixth modification example of the first embodiment of the present technology. As illustrated as an example in the drawing, the transmitter 214-1 may be connected to the transmission antennas 221 and 223, the transmitter 214-2 may be connected to the transmission antenna 222, and the receiver 215 may be connected to the reception antennas 231 and 232. The receiver 215 has a function that is equivalent to those of the receivers 215-1 to 215-3. Also, the transmitter 214-1 supplies transmission signals at the same frequency to the transmission antennas 221 and 223. Therefore, it is desirable that the transmission antenna 221 and the transmission antenna 223 be separated from each other by such a distance that no jamming occurs.

FIG. 205 is a block diagram illustrating a configuration example of the receivers 215-1 to 215-3 according to the sixth modification example of the first embodiment of the present technology. In the drawing, a is a block diagram of the receiver 215-1. In the drawing, b is a block diagram of the receiver 215-2. In the drawing, c is a block diagram of the receiver 215-3.

The receiver 215-1 includes a mixer 241-1, a local oscillator 242-1, a low pass filter 243-1, and an analog-to-digital converter (ADC) 244-1. The local oscillator 242-1 generates a local signal at a frequency $f_{LO1}$. The mixer 241-1 receives the reception signal at the frequency f1 from the reception antenna 231, mixes it with the local signal, and supplies the signal at the middle frequency $f_{IF}$ to the ADC 244-1 via the low pass filter 243-1. The ADC 244-1 converts the signal at the middle frequency $f_{IF}$ into a digital signal and supplies the digital signal to the sensor control section 211.

The receiver 215-2 includes a mixer 241-2, a local oscillator 242-2, a low pass filter 243-2, and an ADC 244-2. The receiver 215-3 includes a mixer 241-3, a local oscillator 242-3, a low pass filter 243-3, and an ADC 244-3. Configurations of these circuits are similar to those with the same names in the receiver 215-1.

FIG. 206 is a diagram illustrating an example of a frequency property of the reception signal according to the sixth modification example of the first embodiment of the present technology. Although the number of reception systems is three in FIG. 205, FIG. 206 will be considered on the assumption of two systems for simplification of explanation.

The middle frequency is one wave $f_{IF}$ that is common for all receivers. It is assumed that a cutoff frequency $f_{cutoff}$ of the low pass filter of each of the two systems is the same. The reception frequency of the first antenna is defined as f1, and the reception frequency of the second antenna is defined as f2 (f1<f2). At this time, the relationship of the local frequencies $f_{lo1}$ and $f_{lo2}$ corresponding to the respective systems is $f_{lo1}<f_{lo2}$. Also, the middle frequency $f_{IF}$ is represented by the following expression.

$$f_{IF} = f1 - f_{lo1} = f2 - f_{lo2} \quad \text{Expression 7}$$

In a case where the signal of the reception frequency f2 leaks into the reception system of the first antenna, the disturbing wave feria is represented by the following expression.

$$f_{IF21} = f2 - f_{lo1} \quad \text{Expression 8}$$

In a case where the signal of the reception frequency f1 leaks into the reception system of the second antenna, the disturbing wave $f_{IF21}$ is represented by the following expression.

$$f_{IF21} = f1 - f_{lo2} \quad \text{Expression 9}$$

At this time, the condition that the disturbing wave s not within the reception band is represented by the following expressions.

$$f_{IF21} < -f_{cutoff} \quad \text{Expression 10}$$

$$f_{cutoff} < f_{IF12} \quad \text{Expression 11}$$

If Expressions 8 and 9 are substituted into Expressions 10 and 11, the following expressions are obtained.

$$f1 - f_{lo2} < -f_{cutoff} \quad \text{Expression 12}$$

$$f_{cutoff} < f2 - f_{lo1} \quad \text{Expression 13}$$

If Expressions 12 and 13 are modified, the following expressions are obtained.

$$f_{cutoff} < f_{lo2} - f1 \quad \text{Expression 14}$$

$$f_{cutoff} < f2 - f_{lo1} \quad \text{Expression 15}$$

If Expression 7 is substituted into Expressions 14 and 15, the following expressions are obtained.

$$f_{cutoff} < f2 - f_{IF} - f1 = f2 - f1 - f_{IF} \quad \text{Expression 16}$$

$$f_{cutoff} < f2 + f_{IF} - f1 = f2 - f1 + f_{IF} \quad \text{Expression 17}$$

Therefore, it is only necessary for $f_1$, f2, and $f_{IF}$ to satisfy Expressions 16 and 17. In practice, $f_{cutoff} > f_{IF}$ is satisfied, and only Expression 16 is a restriction condition.

If Expression 16 is modified, the following expression is obtained.

$$f_{cutoff} + f_{IF} < f2 - f1 \quad \text{Expression 18}$$

In other words, the condition that the difference between adjacent frequencies f2 and f1 is always greater than the sum of $f_{cutoff}$ and $f_{IF}$ is the condition for performing measurement on the basis of frequency division.

On the assumption that there is no restriction regarding how large or small f1 and f2 are, it is possible to eliminate the condition f1>f2, and it is only necessary for the adjacent frequencies f1 and f2 to satisfy the condition based on the following expression from Expression 18.

$$f_{cutoff} + f_{IF} < |f2 - f1| \quad \text{Expression 19}$$

FIG. 207 is an example of a timing chart of frequency division driving according to the sixth modification example of the first embodiment of the present technology. In the drawing, a illustrates sweep of a frequency of a first antenna (the transmission antenna 221 and the reception antenna 231 or the like). In the drawing, b illustrates sweep of a frequency of a second antenna (the transmission antenna 222 and the reception antenna 232 or the like). In the drawing, c illustrates sweep of a frequency of a third antenna (the transmission antenna 223 and the reception antenna 233 or the like).

FIG. 208 is an example of a timing chart illustrating operations of each section in the sensor device according to the sixth modification example of the first embodiment of the present technology.

In FIGS. 207 and 208, the first antenna sweeps the frequencies a1 to a2, and during that time, the second antenna sweeps the frequencies a3 to a4, and the third antenna sweeps the frequencies a5 to a6.

Then, the first antenna sweeps the frequencies a3 to a4, and during that time, the second antenna sweeps the frequencies a5 to a6, and the third antenna sweeps the frequencies a1 to a2. Next, the first antenna sweeps the frequencies a5 to a6, and during that time, the second antenna sweeps the frequencies a1 to a2, and the third antenna sweeps the frequencies a3 to a4. Any frequency sweeping method may be used as long as the frequencies for each antenna are independent and may not be up chirp as in FIG. 207. All the transmission frequency bands are swept for all the antennas. According to the control, it is possible to use all the frequency bands, and the resolution of the moisture sensor is improved.

FIG. 209 is an example of a timing chart of frequency division driving when the sweep period is shortened according to the sixth modification example of the first embodiment of the present technology.

FIG. 210 is an example of a timing chart of operations of each section in the sensor device when the sweep period is shortened according to the sixth modification example of the first embodiment of the present technology.

In FIGS. 209 and 210, the first antenna sweeps the frequencies a1 to a2, and during that time, the second antenna sweeps the frequencies a3 to a4, and the third antenna sweeps the frequencies a5 to a6. It is possible to shorten the sweep period by narrowing the frequency bands to be swept. It is possible to apply the control in FIGS. 207 to 210 to the sensor device 200 in each of FIGS. 200 to 203.

FIG. 211 is an example of a timing chart of frequency division driving in which the frequencies of two antennas are the same according to the sixth modification example of the first embodiment of the present technology. In the drawing, a illustrates sweep of frequencies of first and third antennas. In the drawing, b illustrates sweep of the frequency of the second antenna.

FIG. 212 is an example of a timing chart illustrating operations of each section in the sensor device in which frequencies of two antennas are the same according to the sixth modification example of the first embodiment of the present technology.

In FIGS. 211 and 212, the first and third antennas sweep the frequencies a1 to a2, and during that time, the second antenna sweeps the frequencies a4 to a6. Also, the first and third antennas sweep the frequencies a4 to a6, and during that time, the second antenna sweeps the frequencies a1 to a2. It is possible to shorten the sweep period by narrowing the frequency bands to be swept. The control is applied to the sensor device 201 in FIG. 204.

In this manner, according to the sixth modification example of the first embodiment of the present technology, the transmitters supply transmission signals at mutually different frequencies to the plurality of transmission antennas, and the transmission switch 216 and the reception switch 217 are thus not needed.

Seventh Modification Example

In the aforementioned first embodiment, independent transmission paths are connected to the plurality of antennas, and an increase in size of the probes in accordance with the number of antennas is not inevitable. The sensor device 200 according to the seventh modification example of the first embodiment is different from that in the first embodiment in that a plurality of antennas are connected to one transmission path including a delay line.

FIG. 213 is a diagram illustrating an example of a sectional view of the intra-probe substrate 321 according to the seventh modification example of the first embodiment of the present technology. In the drawing, a illustrates a sectional view of the intra-probe substrate 321 when seen in the Z-axis direction. In the drawing, b illustrates a sectional view of the intra-probe substrate 321 when seen in the Y-axis direction.

As illustrated as an example in the drawing, a plurality of transmission antennas such as transmission antennas 221, 222, and 223 are formed in the intra-probe substrate 321. These transmission antennas are connected by transmission paths such as strip lines. The transmission path for each transmission antenna is not independent and corresponds to a state in which the plurality of transmission antennas are commonly electrically connected to one transmission path on an equivalent circuit. The configuration of the intra-probe substrate 322 on the reception side is horizontally symmetrical with the transmission side.

FIG. 214 is a diagram illustrating a transmission path of a signal of each antenna according to the seventh modification example of the first embodiment of the present technology. The transmission source is defined as TX, and the points of the transmission antennas 221, 222, and 223 are defined as A, B, and C. The reception destination is defined as RX, and the points of the reception antennas 231, 232, and 233 are defined as P, Q, and R. The arrow indicates the signal transmission direction. The solid line indicates the signal as a target of transmission and reception. The dotted line indicates an interference signal and a disturbing signal.

In a case where it is desirable to measure moisture at three points by concurrently transmitting electromagnetic waves from the three transmission antennas, it is necessary to mainly measure the propagation delay time of each of the routes TX-A-P-RX, TX-B-Q-RX, and TX-C-R-RX as illustrated as an example in the drawing.

However, a plurality of antennas are electrically connected to one common transmission path on the transmission side and the reception side in the sensor device 200 as described above. Therefore, the reception signal is measured as a signal on which all the signals having passed through each of the reception antennas P, Q, and R are superimposed for the transmission antennas A, B, and C. In other words, signals of routes passing TX-A-Q-RX, TX-A-R-RX, TX-B-P-RX, TX-B-R-RX, TX-C-P-RX, and TX-C-Q-RX in addition to the above three routes are also included.

Furthermore, in a case where the transmission antenna matching has not sufficiently been achieved, reflection in the transmission probe occurs. Therefore, the route emitted from the transmission antenna after being reflected in the transmission probe is also superimposed on the reception signal. In other words, signals in the routes passing TX-C-B-Q-RX, TX-B-A-P-RX, and the like in addition to the aforementioned nine routes are also included. Note that it is needless to say that the event in which reflection occurs because matching of the antennas connected to the transmission path (in other words, matching) has not been established is an event in which electromagnetic waves are reflected by an interface between the transmission path and the antennas because matching of the impedance of the transmission path and the antenna has not been established. Similarly, in a case where matching of the reception antenna has not sufficiently been established, reflection in the reception probe occurs. Therefore, the route in which the signal received from the transmission antenna is reflected in the reception probe is also superimposed on the reception signal. In other words, signals in the routes passing TX-B-Q-R-RX, TX-A-P-Q-RX, and the like in addition to the aforementioned routes are also included.

FIG. 215 is a diagram illustrating signal transmission paths of two systems according to the seventh modification example of the first embodiment of the present technology. As illustrated as an example in the drawing, two transmission paths TX-C-B-Q-RX and TX-C-R-RX will be focused.

In a case where the main transmission paths of the antennas of the transmission probe and the reception probe have the same structure, for example, the two routes in the drawing are substantially the same, and it is thus not possible to divide the both, and it is not possible to accurately obtain the propagation delay between C and R.

FIG. 216 is a diagram illustrating an example of the sensor device 200 provided with a delay line according to the seventh modification example of the first embodiment of the present technology. The delay line is inserted into a main transmission path of any one of the antennas of the transmission probe and the reception probe.

For example, delay lines 265 and 266 are inserted between P and Q and between Q and R of the reception probe as in the drawing. A route difference occurs between the two routes TX-C-B-Q-RX and TX-C-R-RX, which cannot be separated from each other in FIG. 215, due to the delay lines. It is thus possible to separate the reception signals of the routes.

As described above, it is possible to prevent the signals in the routes TX-A-P-RX, TX-B-Q-RX, and TX-C-R-RX as targets of measurement from overlapping those in other routes by appropriately providing the delay lines in the intra-probe substrates 321 and 322. Therefore, it is possible to measure the amount of moisture with high accuracy.

FIG. 217 is a diagram illustrating an example of the shape of the delay line 265 according to the seventh modification example of the first embodiment of the present technology. The shape of the delay line 265 may be a meander shape as illustrated as an example in a in the drawing, or the shape of the delay line 265 may be a zigzag shape as illustrated as an example in b in the drawing. As illustrated as an example in c in the drawing, the shape of the delay line 265 may be a spiral shape. The shape of the delay line 265 is not limited to the shape in the drawing as long as it is possible to arrange a longer transmission path than that in a case where the delay line is not provided.

As illustrated as examples in d, e, and f in the drawing, vias may be provided along the delay line 265. In this manner, it is possible to prevent leap of radio waves due to electromagnetic coupling between adjacent lines and thereby to increase the effect of delay as compared with a case where no vias are provided.

FIG. 218 is a diagram illustrating another example of the shape of the delay line 265 according to the seventh modification example of the first embodiment of the present technology. As illustrated as examples in a and b in the drawing, it is possible to set the amplitude direction of the delay line to the wiring direction of the transmission path at the time of formation into a meander shape or a zigzag shape. At this time, it is also possible to provide a via as illustrated as examples in c and d in the drawing.

FIG. 219 is a diagram for explaining a method for setting the amount of delay of the delay line according to the seventh modification example of the first embodiment of the present technology. The structure for separating two routes has been described hitherto. How large the propagation delay difference to occur has to be in practice will be discussed. If the two routes have a propagation delay difference that is equal to or greater than a resolution at the time of transformation into an impulse response through inverse Fourier transformation of a frequency response, it is possible to separate the both and thereby to accurately measure the amount of moisture. Specifically, it is desirable that the propagation delay difference be equal to or greater than 1/df when the frequency band is defined as df.

A case where there are two routes, namely a route A and a route B from TX to RX and as in a in the drawing and the numbers of passing points thereof are equal to each other will be considered. The transmission delay TA from TX to RX in the route A is obtained by accumulating the propagation delays between the points and is represented by the following expression.

[Math. 1]

$$T_A = \sum_{n=1}^{N} T_{an}$$

Expression 20

Similarly, the propagation delay TB from TX to RX in the route B is represented by the following expression.

[Math. 2]

$$T_B = \sum_{n=1}^{N} T_{Bn}$$

Expression 21

Therefore, it is desirable that the positions of the antennas and the amount of delay of the delay line be determined such that the propagation delay difference dT satisfies the following expression.

$$dT = |TB - TA| \geq 1/df$$

Expression 22

Also, a case where there are two routes, namely a route A and a route B from TX to RX as in b in the drawing and the numbers of passing points thereof are different will be considered. Here, the number of passing points in the route A is defined as N, and the number of passing points in the route B is defined as M. The transmission propagation delay TB from TX to RX in the route A and the route B is represented by the following expression similarly to the case in a in the drawing. The propagation delay TA is similar to that in Expression 20.

[Math. 3]

$$T_B = \sum_{m=1}^{M} T_{Bm}$$

Expression 23

Therefore, it is desirable that the positions of the antennas and the delay amount of the delay line be determined such that the propagation delay difference dT satisfies Expression 22. In a case where a frequency range of the measurement is 1 GHz to 9 GHz, for example, it is desirable that the propagation delay difference of the two routes be equal to or greater than 125 ps.

In this manner, according to the seventh modification example of the first embodiment of the present technology, the delay line 265 and the like are inserted into the transmission path, and it is thus possible to separate the signals of different routes.

2. Second Embodiment

Although the intra-probe substrates 321 and 322 are connected such that they are orthogonal to the measurement section substrate 311 in the aforementioned first embodiment, it is necessary to arrange connectors, cables, and the like between the substrates with the configuration, which leads to a complicated structure. The second embodiment is different from the first embodiment in that the number of the substrates is reduced and the numbers of connectors and cables connecting the substrates are reduced. In this manner, the second embodiment achieves the effect that it is possible to reduce the numbers of components such as the substrates, the connectors, and the cables included in the sensor device 200 as compared with the first embodiment.

FIG. 220 is a diagram illustrating an example of a sensor device 200 according to the second embodiment of the present technology. Inside the sensor device 200 according to the second embodiment, only an electronic substrate 311-1 is disposed in the sensor casing 305 instead of the measurement section substrate 311, the intra-probe substrate 321, and the intra-probe substrate 322. A part of the electronic substrate 311-1 is a rectangle, a pair of substrate projecting portions (a transmission substrate projecting portion and a reception substrate projecting portion) are connected to the substrate rectangular part, and they are integrated. Therefore, the directions in which the substrate rectangular part, the transmission substrate projecting portion, and the reception substrate projecting portion extend (in other words, the plane direction of these substrates) are parallel with each other, and further, these substrates are formed in the same plane. Also, the circuit on the measurement section substrate 311 is disposed at the substrate rectangular part. The circuits on the intra-probe substrates 321 and 322 such as transmission antennas 221 to 223 are formed at the substrate projecting portion. With this configuration, the components (4) and (7) are not needed.

Note that FIG. 220 represents that the sensor device 200 according to the second embodiment of the present technology can include plane-shaped antennas illustrated in FIGS. 19 to 47 as all antennas (the transmission antennas 221 to 223 and the reception antennas 231 to 233) included in the sensor device 200 in one example. Similarly, the sensor device 200 according to the second embodiment of the present technology can also use the plane-shaped and slot-shaped antennas illustrated in FIGS. 48 to 74 as all antennas (the transmission antennas 221 to 223 and the reception antennas 231 to 233) included in the sensor device 200 in one example.

Also, similarly to the sensor device 200 (FIG. 4) according to the first embodiment of the present technology in which the measurement section substrate 311 is accommodated in the measurement section casing 310, the transmission intra-probe substrate 321 is accommodated in the transmission probe casing 320a, and the reception intra-probe substrate 322 is accommodated in the reception probe casing 320b, the substrate rectangular portion of the electronic substrate 311-1 is accommodated in the measurement section casing 310, the transmission substrate projecting portion of the electronic substrate 311-1 is accommodated in the transmission probe casing 320a, and the reception substrate projecting portion of the electronic substrate 311-1 is accommodated in the reception probe casing 320b in the sensor device 200 (FIG. 220) according to the second embodiment of the present technology.

However, in comparison between the sensor device 200 according to the first embodiment of the present technology and the sensor device 200 according to the second embodiment of the present technology, the sectional shapes of the transmission probe casing 320a and the reception probe casing 320b have different points. This will be described with reference to FIGS. 189 and 221, and effects of the sectional shapes of the transmission probe casing 320a and the reception probe casing 320b according to the second embodiment of the present technology will be described with reference to FIG. 221.

FIG. 221 is an example of a sectional view in which characteristics of the structure of the sensor device 200 are overwritten when seen from the upper side in the second embodiment and a comparative example of the present technology. In the drawing, a is an example of a sectional view of the sensor device 200 when seen from the above according to the second embodiment of the present technology. In the drawing, b is an example of a sectional view of the sensor device 200 in the comparative example. The two ovals in a in the drawing represent the transmission probe casing and the reception probe casing. Similarly, the two true circles in b in the drawing also represent the transmission probe casing and the reception probe casing.

In a and b in the drawing, the colored region outside the transmission probe casing and the reception probe casing represents the soil. Also, the soil located between the transmission probe casing and the reception probe casing is the soil as a target of measurement of the amount of moisture. Note that the rectangle illustrated with the broken lines in a and b in the drawing represents the outer shape of the measurement section casing 310.

As illustrated in a in FIG. 221, the sensor device 200 according to the second embodiment of the present technology includes the following configuration instead of the component (9). The length (width) of the substrate projecting portion of the electronic substrate 311-1 in the X-axis direction is greater than the thickness (the size in the Z-axis direction) thereof. Also, as illustrated as an example in a in the drawing, a distance dz from the center of the substrate projecting portion to the casing end of the probe casing 320 in a direction vertical to the electronic substrate 311-1 (Z-axis direction) is shorter than a distance dx from the center of the substrate projecting portion to the casing end of the probe casing 320 in a direction that is parallel with the electronic substrate 311-1 (X-axis direction). The configuration will be referred to as a component (9'). As illustrated as an example in b in the drawing, dz is assumed to be the same as dx in the comparative example. In comparison between the probe casing of the sensor device 200 according to the second embodiment of the present technology illustrated in a in FIG. 221 and the probe casing of the sensor device 200 according to the first embodiment of the present technology illustrated in a in FIG. 189, the structures (the configuration (9) and the configuration (9')) in which the distance from the center of the substrate to the probe casing end in the direction vertical to the substrate is shorter than the distance from the center of the substrate to the probe casing end in the direction that is parallel with the substrate are the same. However, the orientations of the substrates to be accommodated in the probe casings are different (rotated by 90°) in a in FIG. 221 and a in FIG. 189. Therefore, the orientations of the probe casing sections are also different (rotated by 90°) in these drawings.

In a and b in FIG. 221, rainfall from above the sensor device 200 with the two probe casings (the transmission probe casing and the reception probe casings) illustrated in each drawing pours to the region outside the measurement section casing 310 illustrated by the broken line in the drawing. The rain pouring to the region outside the measurement section casing 310 penetrates through (in other words, spreads to) the soil as the target of the measurement of the amount of moisture located between the two probe casings.

Here, in comparison between the thicknesses of the probe casings in the component (9') and the comparative example (in other words, the sizes of the probe casings in the spreading direction in which the rainfall spreads from the measurement section casing 310 to the measurement target region), the size of the probe casing in the component (9') is smaller than that in the comparative example.

In a case of a comparative example, moisture only linearly spreads from the soil limited to the paper surface upper direction and the lower direction in the measurement target region outside the measurement section casing 310 to the soil in the measurement target region. In this case, the concentration of moisture in the soil decreases as the moisture spreads from the outside of the measurement section casing 310 to the measurement target region, and there is no replenishment with moisture from the outside of the spreading route in the middle of the spreading route.

On the other hand, in the case of the component (9'), moisture planarly spreads from the soil in the paper surface upper direction and the lower direction to the probe casing in a wide region from one probe casing outside the measurement section casing 310 to the other probe casing. Additionally, a part of the moisture that has spread to the probe casing on the plane spreads while replenishment with water from the soil in the paper surface upper and lower directions of the probe casing is performed when the part of moisture spreads to the moisture measurement target region between the probe casings.

Therefore, the concentration of moisture in the soil in the moisture measurement target region in the component (9') illustrated in a in FIG. 221 is closer to the original amount of moisture in the soil (the amount of moisture in the soil in the region where the sensor device 200 is not disposed) than the concentration of moisture in the soil in the moisture measurement target region in the comparative example illustrated in b in FIG. 221. It is thus possible to more accurately perform the measurement of the moisture in the soil by the sensor device 200 according to the second embodiment of the present technology than that in the comparative example.

FIG. 222 is a diagram illustrating an example of covered parts of the radio wave absorption sections at the time of double-side radiation in an example in which one transmission antenna and one reception antenna are included according to the second embodiment of the present technology. In the drawing, the radio wave absorption sections 341 and 344 are illustrated as rectangles of the dotted lines similarly to FIG. 4 and the like. As illustrated as an example in a in the drawing, it is desirable that the radio wave absorption section cover the entire probe other than the antenna. In a case where a part of the probe other than the antenna is covered, it is desirable that the lower ends of the radio wave absorption sections be the upper ends of the antennas as illustrated as an example in b in the drawing. As illustrated as an example in c in the drawing, it is also possible to separate the lower ends of the radio wave absorption sections from the upper ends of the antennas.

FIGS. 353a to 353d are top views (transparent views) of the sensor device 200 in a case where the radio wave absorption section 341 illustrated in FIGS. 153a to 153d is applied to each of the radio wave absorption sections 341 and 344 included in the sensor device 200 illustrated in FIG. 222a as one example of an application to the sensor device 200. Note that in regard to the electronic substrate 311-1, the transmission antenna 221, the reception antenna 231, and the radio wave absorption sections 341 and 344, the positional relationships thereof in the Y direction are illustrated in the front view and the side view in FIG. 222a. The front view and the side view of the sensor device 200 in a case where the radio wave absorption section 341 illustrated in FIGS. 153a to 153d is applied to each of the radio wave absorption sections 341 and 344 included in the sensor device 200 illustrated in FIG. 222a are the same as the front view and the side view of the sensor device 200 illustrated in FIG. 222a.

In FIG. 353, a illustrates a top view of the sensor device 200 including the radio wave absorption section 341 with oval outer and inner shapes. In the drawing, b illustrates a top view of the sensor device 200 including the radio wave absorption section 341 with an oval outer shape and a rectangular inner shape. In the drawing, c illustrates a top view of the sensor device 200 including the radio wave absorption section 341 with a rectangular outer shape and an oval inner shape. In the drawing, d illustrates a top view of the sensor device 200 including the radio wave absorption section 341 with rectangular outer and inner shapes.

As the positional relationships of the transmission substrate projecting portion of the electronic substrate 311-1, the transmission antenna 221, the reception substrate projecting portion of the electronic substrate 311-1, the reception antenna 231, and the radio wave absorption sections 341 and 344 in the top view (the top view which is a transparent view), FIGS. 353a to 353d illustrate that the positions at which the radio wave absorption sections 341 and 344 are disposed are the outside and the entire periphery of the position where the transmission substrate projecting portion of the electronic substrate 311-1, the transmission antenna 221, the reception substrate projecting portion of the electronic substrate 311-1, and the reception antenna 231 are disposed.

It is possible to ascertain from the top view (transparent view) illustrated in FIG. 353 that the radio wave absorption section 341 is disposed over the entire periphery outside the transmission substrate projecting portion of the electronic substrate 311-1 and the radio wave absorption section 344 is disposed over the entire periphery outside the reception substrate projecting portion of the electronic substrate 311-1, and it is possible to ascertain from the front view and the side view in FIG. 222 that such a region where the radio wave absorption section 341, the radio wave absorption sections 341 and 344 are disposed over the entire peripheries outside the transmission substrate projecting portion and the reception substrate projecting portion of the electronic substrate 311-1 is a region where the transmission antenna (221 in the example in FIG. 222) and the reception antenna (231 in the example in FIG. 222) are not disposed in the Y-axis direction of the sensor device 200.

Note that the mode of the radio wave absorption section illustrated in FIGS. 153 and 353 can be applied not only to the sensor device 200 illustrated in FIG. 222a but also to the various sensor devices 200 illustrated in the specification.

FIG. 223 is a diagram illustrating an example in which covering with the radio wave absorption section is not performed at the time of double-side radiation in an example in which one transmission antenna and one reception antenna are included according to the second embodiment of the present technology. As illustrated as an example in the drawing, covering with the radio wave absorption section may not be performed.

FIG. 224 is a diagram illustrating an example of covered parts of the radio wave absorption sections at the time of one-side radiation according to the second embodiment of the present technology, The drawing is similar to FIG. 222 other than that the antenna is adapted for one-side radiation.

FIG. 225 is a diagram illustrating an example in which covering with the radio wave absorption section is not performed at the time of one-side radiation according to the second embodiment of the present technology. The drawing is similar to FIG. 223 other than that the antenna is adapted for one-side radiation.

FIG. 226 is a diagram illustrating an example in which one surface is covered at the time of one-side radiation according to the second embodiment of the present technology. As illustrated as an example in the drawing, it is also possible to further cover the surface of the electronic substrate 311-1 on the side on which no antenna is formed with the radio wave absorption section.

FIG. 227 is a diagram illustrating an example in which the transmission path and the distal end are covered at the time of double-side radiation according to the second embodiment of the present technology. As illustrated as an example in the drawing, it is possible to further cover the distal end of the probe with the radio wave absorption sections 349 and 350.

FIG. 228 is a diagram illustrating an example in which only the distal end is covered at the time of double-side radiation according to the second embodiment of the present technology. As illustrated as an example in the drawing, it is possible to further cover only the distal end of the probe with the radio wave absorption sections 349 and 350.

FIG. 229 is a diagram illustrating an example in which the transmission path and the distal end are covered at the time of one-side radiation according to the second embodiment of the present technology. The drawing is similar to FIG. 227 other than that the antenna is adapted for one-side radiation.

FIG. 230 is a diagram illustrating an example in which only a distal end is covered at the time of one-side radiation according to the second embodiment of the present technology. The drawing is similar to FIG. 228 other than that the antenna is adapted for one-side radiation.

FIG. 231 is a diagram illustrating an example in which the transmission path, one side, and the distal end are covered at the time of one-side radiation according to the second embodiment of the present technology. As illustrated as an example in the drawing, it is also possible to cover the surface of the electronic substrate 311-1 where no antennas are formed in addition to the transmission path and the distal end with the radio wave absorption section at the time of one-side radiation.

FIG. 232 is a diagram illustrating an example of covered parts of the radio wave absorption sections when a plurality of antenna pairs of double-side radiation are provided according to the second embodiment of the present technology. As illustrated as an example in the drawing, the radio wave absorption sections 341, 342, 344, 345, and the like are disposed between the antennas when the two or more antenna pairs are formed.

FIG. 233 is a diagram illustrating another example of the covered parts of the radio wave absorption sections when a plurality of antenna pairs of double-side radiation are provided according to the second embodiment of the present technology. As illustrated as an example in the drawing, it is also possible to cover a part of the probe other than the antennas.

FIG. 234 is a diagram illustrating an example in which the radio wave absorption sections are formed in the sensor casing according to the second embodiment of the present technology. In the drawing, a illustrates a comparative example in which the radio wave absorption sections are not formed in the sensor casing 305. In the drawing, b and c illustrate an example in which the radio wave absorption section is formed in the sensor casing 305. The black parts in the drawings illustrate radio wave absorption materials.

As illustrated as an example in b in the drawing, it is also possible to embed the radio wave absorption material such as ferrite in the sensor casing 305 at the time of formation of an exterior. The black parts in the drawing illustrate the radio wave absorption material. The radio wave absorption material functions as the radio wave absorption sections. Also, as illustrated as an example in c in the drawing, it is also possible to provide a layer of the radio wave absorption material inside an exterior case after forming the exterior case.

In this manner, according to the second embodiment of the present technology, antennas are formed in one electronic substrate 311-1, and it is thus possible to reduce the number of substrates as compared with the first embodiment in which the measurement section substrate 311 and the intra-probe substrates 321 and 322 are connected.

First Modification Example

FIG. 237 is a diagram illustrating an example of the sensor device 200 provided with a plane-shaped and slot-shaped antenna, which is a lateral radiation-type antenna as will be described later, according to the first modification example of the second embodiment of the present technology. In the drawing, the sensor device 200 according to the second embodiment of the present technology is characterized by using plane-shaped, slot-shaped, and lateral radiation-type antennas illustrated in FIGS. 238 to 240, which will be described later, are used as all the antennas (transmission antennas 221 to 223 and reception antennas 231 to 233) included in the sensor device 200 in one example.

FIGS. 238 to 240 are diagrams for explaining a structure of the plane-shaped, slot-shaped, and lateral radiation-type antenna. The lateral radiation-type antenna illustrated in FIGS. 238 to 240 is obtained by changing the shape of the slot included in the plane-shaped and slot-shaped antenna illustrated in FIGS. 69 to 71.

Note that the plane-shaped and slot-shaped antenna illustrated in FIGS. 69 to 71 is suitable for utilization in the sensor devices 200 according to the first embodiment and the modification examples thereof of the present technology, and the plane-shaped, slot-shaped, and lateral radiation-type antenna illustrated in FIGS. 238 to 240 is suitable for utilization in the sensor device 200 according to the first modification example of the second embodiment of the present technology.

Here, the transmission probe substrate 321 including the transmission antenna and the reception probe substrate 322 including the reception antenna in the sensor device 200 (FIG. 4, for example) according to the first embodiment of the present technology and the transmission substrate projecting portion including the transmission antenna and the reception substrate projecting portion including the reception antenna in the sensor device 200 (FIG. 237) according to the first modification example of the second embodiment of the present technology have different orientations of the substrate planes where the antennas are formed (rotated by 90°). Therefore, the antennas illustrated in FIGS. 69 to 71 and the antennas illustrated in FIGS. 238 to 240 have coordinate axes with different orientations in the drawings. Specifically, in FIG. 239, for example, the thickness direction of the substrate is the Z-axis direction, the direction in which the signal line 255 extends (in other words, the direction in which the probe casing and the substrate projecting portion extend) is the Y-axis direction, and the direction in which the slot intersecting the signal line 255 extends is the X-axis direction.

The plane-shaped, slot-shaped, and lateral radiation-type antenna illustrated in FIGS. 238 to 240 has a structure in which the slot at the part which the signal line 255 intersects extends to the outer edges of the shield layers 254 and 256 (in other words, the outer edges of the substrate projecting portions where the antennas are formed) in the slot extending direction (X-axis direction) from among the slots included in the shield layers (the shield layers 256 and 254) exposed from the electromagnetic wave absorption material 251 to the space.

According to the plane-shaped, slot-shaped, and lateral radiation-type antenna illustrated in FIGS. 238 to 240, the electromagnetic waves are emitted from the slot opening portion provided at the shield layer outer edges (the outer edges of the substrate projecting portions) to the outside of the substrate by a structure in which the slots included in the shield layers 254 and 256 extend to the outer edges of the shield layers (in other words, the outer edges of the substrate projecting portions where the antennas are formed) that serve as radiation elements in the transmission antenna (the reception element in the reception antenna). Also, the electromagnetic waves are mainly emitted to the side ahead in the direction in which the slot extends up to the opening portion. In other words, the direction in which the slot intersecting the signal line 255 extends toward the opening portion (X-axis direction) is the direction of the main radiation of the electromagnetic waves of the antennas. In FIG. 239, since the electromagnetic waves are mainly emitted in the X-axis direction, that is, the direction which is parallel with the substrate plane where the antennas are formed and in the direction orthogonal to the extending direction of the signal line 255 (in other words, the probe extending direction), the antennas illustrated in FIGS. 238 to 240 will be referred to as plane-shaped, slot-shaped, and lateral radiation-type antennas, or simply as lateral radiation antennas in the specification for convenience.

According to the plane-shaped, slot-shaped, and lateral radiation-type antennas illustrated in FIGS. 238 to 240, the electromagnetic waves are mainly emitted in the direction that is parallel with the substrate plane where the antennas are formed and the direction that is orthogonal to the probe extending direction, and the antennas are thus suitable for utilization in the sensor device 200 according to the second embodiment of the present technology in which the transmission substrate projecting portion forming the transmission antenna and the reception substrate projecting portion forming the reception antenna are formed in the same plane.

Note that according to the plane-shaped, slot-shaped, and lateral radiation-type antennas illustrated in FIGS. 237 and 238 to 240, some of the electromagnetic waves are emitted in the direction orthogonal to the shield layers 254 and 256 where the slots are disposed.

Also, according to the plane-shaped, slot-shaped, and lateral radiation-type antennas illustrated in FIGS. 237 and 238 to 240, the proportion between the electromagnetic waves emitted in the main radiation direction (the direction that is parallel with the substrates where the antennas are formed) and the electromagnetic waves emitted in the direction orthogonal to the main radiation (the direction that is orthogonal to the substrates where the antennas are formed) changes depending on
  (1) the width of the substrates where the antennas are formed (more specifically, the size of the substrates, which is the size of the substrates in the direction orthogonal to the extending direction of the signal line 255 that intersects the slot), and
  (2) the frequency of the electromagnetic waves emitted from the antennas.

In order to set a sufficiently large proportion of the electromagnetic waves emitted in the main radiation direction out of the electromagnetic waves emitted from the antennas, it is desirable that (1) the width of the substrates where the antennas are formed be set to be equal to or less than about one fifth (2) the wavelength of the electromagnetic waves at the center frequency of the electromagnetic waves emitted from the antennas.

In one example, in a case where the frequency band of the electromagnetic waves emitted from the antennas ranges from 1 gigahertz (GHz) to 9 gigahertz (GHz), it is desirable that (1) the width W of the substrates where the antennas are formed be equal to or less than 12 millimeters (mm).

FIG. 241 is a diagram illustrating a configuration example of the electronic substrate 311-1 according to the first modification example of the second embodiment of the present technology. Three sets of antennas are provided, and the plane-shaped, slot-shaped, and lateral radiation-type antennas illustrated in FIGS. 238 to 240 are adopted. In the drawing, a is a top view of the electronic substrate 311-1 when seen from the above, and b in the drawing is a front view of the electronic substrate 311-1 when seen from the Z-axis direction. In the drawing, c is a side view of the electronic substrate 311-1 when seen from the X-axis direction.

FIGS. 242 to 250 illustrate a planar shape and a sectional shape of the transmission substrate projecting portion in the electronic substrate 311-1 according to the first modification example of the second embodiment of the present technology.

In FIGS. 242 to 250, the planar shape of the intra-probe substrate 321 according to the first embodiment of the present technology illustrated in FIGS. 105 to 113 is changed to be adapted to the transmission substrate projecting portion according to the second embodiment of the present technology. The changed part is the part for connection to the measurement section illustrated on the paper surface upper side (the negative direction of the Y axis) (as for the intra-probe substrate 321 according to the first embodiment of the present technology, the location for connection to the transmission path connecting portion, and as for the transmission substrate projecting portion according to the second embodiment of the present technology, the location for connection to the substrate rectangular part). The other shapes are the same, and detailed description thereof will thus be omitted.

FIGS. 242 and 243 represent a planar shape and a sectional shape in a case where the electronic substrate 311-1 according to the first modification example of the second embodiment of the present technology is formed of an electronic substrate including three wiring layers. FIGS. 242 and 243 correspond to FIGS. 105 and 106.

FIGS. 244 and 246 represent a planar shape and a sectional shape in a case where the electronic substrate 311-1 according to the first modification example of the second embodiment of the present technology is formed of an electronic substrate including five wiring layers. FIGS. 244 to 246 correspond to FIGS. 107 to 109.

FIGS. 247 to 250 represent a planar shape and a sectional shape in a case where the electronic substrate 311-1 is formed of an electronic substrate including seven wiring layers according to the first modification example of the second embodiment of the present technology. FIGS. 247 to 250 correspond to FIGS. 110 to 113.

The transmission intra-probe substrate according to the first modification example of the present technology illustrated in FIGS. 105 and 106 uses the via array for shielding as a structure for shielding a side of the signal line included in the substrate and thereby obtains the effect that the width of the substrate is reduced as compared with the transmission intra-probe substrate illustrated in FIGS. 103 and 104 which does not include the structure.

The substrate projecting portion according to the second embodiment of the present technology illustrated in FIGS. 242 and 243 also uses the via array for shielding as the structure for shielding a side of the signal line included in the substrate and thereby obtains an effect that the width of the substrate is reduced as compared with the substrate that does not include the structure.

On the other hand, the transmission intra-probe substrate according to the first embodiment of the present technology illustrated in FIGS. 107 to 109 and FIGS. 110 to 113 uses more signal line layers than those of the transmission intra-probe substrate illustrated in FIGS. 105 and 106 and thereby obtains an effect that the number of signal lines disposed in one signal line layer is reduced and the width of the substrate is thus reduced.

The substrate projecting portion according to the second embodiment of the present technology illustrated in FIGS. 244 to 246 and FIGS. 247 to 250 also uses more signal line layers than those of the transmission intra-probe substrate illustrated in FIGS. 242 and 243 and thereby obtains an effect that the number of signal lines disposed in one signal line layer is reduced and the width of the substrate is thus reduced.

FIG. 251 is a diagram for explaining influences of the width of the substrate projecting portion and the sectional area of the probe casing accommodating the substrate projecting portion on measurement of the amount of moisture in the sensor device 200 according to the first modification example of the second embodiment of the present technology illustrated in FIG. 237.

In FIG. 251, a, b, and c are sectional views of the transmission probe casing 320a and the reception probe casing 320b when the sensor device 200 is seen from the positive direction of the Y axis from the above according to the first modification example of the second embodiment of the present technology. In each of a, b, and c in the drawing, the oblong on the left side represents the transmission substrate projecting portion, and the thin oval line arranged in the outer circumference represents the transmission probe casing 320a. The oblong on the right side represents the reception substrate projecting portion, and the thin oval line arranged in the outer circumference represents the reception probe casing 320b. The white part inside the probe casing represents the space inside the probe casing. The part colored with a light color outside the probe casing represents soil that is similar to that before the insertion of the probe casing. On the other hand, the part colored with a dark color in the vicinity of the outside of the probe casing represents a region, to which pushed mud has moved as a result of the insertion of the probe casing, in which the density of the mud has thus become higher than the density of the mud before the insertion of the probe.

Also, a, b, and c in the drawing illustrates that (1) the three types of transmission substrate projecting portions and reception substrate projecting portions with different widths are accommodated in the transmission probe casing 320a and the reception probe casing 320b with oval shapes with a ratio of 2:1 between the lengths of the long axes and the short axes and (2) these three types are disposed such that the distances between the transmission substrate projecting portions and the reception substrate projecting portions are the same. Here, the sensor device 200 illustrated in FIGS. 237 and 251 include the plane-shaped, slot-shaped, and lateral radiation-type antennas described above with reference to FIGS. 238 to 240. Therefore, a, b, and c in the drawing illustrate that the transmission antennas and the reception antennas are disposed such that the distances between the radiation end portions and the reception end portions are the same, in yet other words, the transmission antennas and the reception antennas are disposed such that the distances therebetween are the same.

In comparison of the regions, to which the mud pushed by the insertion of the probe casing into the soil has moved, in which the density of the mud has thus increased, among a, b, and c in the drawing, the width of the region is larger as the width of the substrate projecting portion accommodated in the probe casing is larger. As a result, the proportion of the region where the density of mud has increased is larger in the region between the transmission antenna and the reception antenna as the width of the substrate projecting portion is larger. If the density of mud increases, easiness of penetration of moisture and the surface area of the grain boundaries of the mud change, and the amount of moisture held in the soil changes. Therefore, as the proportion of the region where the density of mud has increased is higher, the measurement result of the amount of moisture in the soil is more significantly separated from the original amount of moisture in the soil as a target of the measurement.

On the contrary, as the width of the substrate projecting portion accommodated in the probe casing decreases, the width of the aforementioned region where the density of the mud has increased is smaller. As a result, as the width of the substrate projecting portion is smaller, the proportion of the region where the density of mud has increased is smaller in the region between the transmission antenna and the reception antenna. In this manner, the measurement result of the amount of moisture in the soil becomes closer to the original amount of moisture in the soil as a target of the measurement. In other words, it is possible to accurately measure the amount of moisture in the soil.

From the above viewpoints, the sensor device including the substrate projecting portion in the probe casing can more accurately measure the amount of moisture in the soil as the width of the substrate projecting portion is reduced.

The sensor device 200 according to the second embodiment of the present technology can
  (1) reduce the width of the substrate projecting portion by using the via array for shielding as the structure for shielding a side of the signal line in the substrate projecting portion accommodated in the probe casing. Also, it is thus possible to obtain the effect that the amount of moisture in the soil is accurately measured.
  (2) In a case where the substrate projecting portion accommodated in the probe casing includes a plurality of antennas, and a plurality of signal lines for connection to the plurality of antennas are included, it is possible to reduce the width of the substrate projecting portion by forming at least one or more signal lines from among the plurality of signal lines in a different wiring layer using the plurality of wiring layers. Also, it is thus possible to obtain the effect that the amount of moisture in the soil is accurately measured.

Second Modification Example

The sensor devices 200 according to the second embodiment (FIG. 220) and the first modification example thereof (FIG. 237) of the present technology include the positioning section similarly to the first embodiment (FIG. 4) of the present technology as a structure for fixing the orientation and the position of the substrate projecting portion (and the electronic substrate 311-1) forming an antenna.

On the other hand, the second modification example of the second embodiment of the present technology includes, as another example of the structure for fixing the orientation and the position of the substrate projecting portion (electronic substrate 311-1), a structure in which the substrate is caused to abut the sensor casing (more specifically, the probe casing 320).

FIG. 252 is a diagram illustrating an example of the sensor device 200 according to the second modification example of the second embodiment of the present technology.

FIG. 253 is an example of a sectional view of the sensor casing 305 and the electronic substrate 311-1 according to the second modification example of the second embodiment of the present technology illustrated in FIG. 252. In FIG. 253, a illustrates a sectional view of the sensor casing 305 cut along the line A-A' in FIG. 252. In FIG. 253, b illustrates a sectional view of the sensor casing 305 cut along the line B-B' in FIG. 252.

In the structure in which the electronic substrate 311-1 is caused to abut the probe casing 320, the substrate projecting portion included in the electronic substrate 311-1 fixes the positions of the substrate projecting portion in the probe casing 320 and the antenna included in the substrate projecting portion by coming into contact with the probe casing 320 at least at two points out of a total of four points which is a product of two points in the width direction (X-axis direction) of the substrate illustrated in a in FIG. 252 and two points in the thickness direction (Z-axis direction) of the substrate illustrated in b in FIG. 253.

Third Modification Example

FIG. 254 is a diagram for explaining another example of a structure for fixing the orientations and the positions of the transmission antenna and the reception antenna according to a yet another example of the second embodiment of the present technology. The sensor device 200 illustrated in FIG. 254 does not include the sensor casing 305 included in the second embodiment (FIG. 220) of the present technology. The sensor device 200 illustrated in FIG. 254 does not include the sensor casing 305 and instead, the sensor device 200 includes at least (1) a transmission probe formed by a structure in which the periphery of a transmission substrate projecting portion (the same as the transmission probe substrate 321 in the sensor device 200 illustrated in FIG. 4) including a transmission antenna and a transmission path for transmission connected thereto is hardened with a resin, and (2) a reception probe formed by a structure in which the periphery of a reception substrate projecting portion (the same as the reception probe substrate 322 in the sensor device 200 illustrated in FIG. 4) including a reception antenna and a transmission path for reception connected thereto is hardened with a resin, the transmission probe in (1) above and the reception probe in (2) being fixed in the structure.

Also, the sensor device 200 illustrated in FIG. 254 may include a structure in which the transmission probe in (1) above and the reception probe in (2) above are fixed by including the transmission probe in (1) above and the reception probe in (2) above and (3) further including a third structure part that is different from (1) and (2) above. The sensor device 200 illustrated in FIG. 254 includes the transmission probe in (1) above, the reception probe in (2) above, and (3) as the third structure part, a structure part in which the periphery of the substrate rectangular part included in the electronic substrate 311-1 is hardened with the resin, and has a structure in which the structures in (1) to (3) above are integrated.

Here, in regard to the transmission probe (1) above and the reception probe in (2) above, it is desirable that the strength of the resin part included in the transmission probe formed by the structure in which the periphery of the transmission substrate projecting portion is hardened with a resin in (1) above be higher than the strength of the transmission substrate projecting portion alone included in the probe in order to prevent the situation in which "these probes are deformed, the electronic substrates disposed in the probes are deformed, and as a result, the distance between the transmission antenna and the reception antenna formed in the electronic substrates changes from a predetermine value, and an error thus occurs in the measurement result of the amount of moisture when these probes are inserted into the soil". In other words, it is desirable that the strength of the transmission probe obtained by hardening the periphery of the transmission substrate projecting portion with a resin be equal to or greater than double the strength of the transmission substrate projecting portion alone included in the probe. In yet other words, in a case where the amount of deformation of the transmission probe obtained by hardening the periphery of the transmission substrate projecting portion with a resin and the amount of deformation of the transmission substrate projecting portion alone included in the probe are compared by using the method illustrated in FIG. 135, it is desirable that the amount of deformation of the transmission probe obtained by hardening the periphery of the transmission substrate projecting portion with a resin be equal to or less than ½ the amount of deformation of the transmission substrate projecting portion alone included in the probe.

Similarly, in regard to the reception probe formed by the structure in which the periphery of the reception substrate projecting portion is hardened with a resin in (1) above, it is desirable that the strength of the resin part included in the probe be higher than the strength of the reception substrate projecting portion alone included in the probe. In other words, it is desirable that the strength of the reception probe obtained by hardening the periphery of the reception substrate projecting portion with a resin be equal to or greater than double the strength of the reception substrate projecting portion alone included in the probe. In yet other words, in a case where the amount of deformation of the reception probe obtained by hardening the periphery of the reception substrate projecting portion with a resin and the amount of deformation of the reception substrate projecting portion alone included in the probe are compared with each other by the method illustrated in FIG. 135, it is desirable that the amount of deformation of the reception probe obtained by hardening the periphery of the reception substrate projecting portion with a resin be equal to or less than ½ the amount of deformation of the reception substrate projecting portion alone included in the probe.

Fourth Modification Example

As described above with reference to FIGS. 191 to 199, the fifth modification example of the first embodiment of the present technology includes a structure for enhancing the strength of 320 of the probe casing without any concern of degrading measurement accuracy of the amount of moisture as a structure for preventing deformation when the probe casing 320 is inserted into the soil even in a case where the hardness of the soil for which the sensor device 200 is used is significantly high.

The fourth modification example of the second embodiment of the present technology illustrated in FIGS. 255 to 264 is an example in which the structure for enhancing the strength of the probe casing 320 without the above concern of degrading measurement accuracy of the amount of moisture is adapted to the second embodiment of the present technology. The probe casing 320 illustrated in FIGS. 255 to 264 is adapted such that the component thickness of the probe casing 320 is increased in a region other than the region where the electromagnetic waves transmitted and received are transmitted while avoiding the region in order not to degrade measurement accuracy of the amount of moisture similarly to the probe casing 320 illustrated in FIGS. 191 to 199.

Note that the shape of the casing in a in FIG. 221 will be referred to as a comparative example in which no thick casing is included when the sectional shape of the casing illustrated in FIGS. 255 to 264 is described.

FIG. 255 is a diagram for explaining the fourth modification example 1 of the second embodiment of the present technology.

The probe casing 320 illustrated in the drawing has a component thickness increased in the paper surface outward direction while avoiding the paper surface inward direction in which the electromagnetic waves are mainly transmitted through the casing.

In FIG. 255, the component thickness of the casing may be increased in a shape in which neither discontinuous points nor inflection points are present both at the outer periphery and at the inner periphery of the casing as illustrated in a in FIG. 255 as the shape for increasing the component thickness of the casing. As illustrated in b in FIG. 255, the component thickness of the casing may be increased in the inward direction. In this case, the discontinuous points or inflection points increase at the inner periphery of the casing as compared with the comparative example. As illustrated in c in FIG. 255, the component thickness of the casing may be increased in the outward direction. In this case, the discontinuous points or inflection points increase at the outer periphery of the casing as compared with the comparative example. As illustrated in d in FIG. 255, the component thickness of the casing may be increased both in the inward direction and in the outward direction. In this case, the discontinuous points or inflection points increase at both the inner periphery and the outer periphery of the casing as compared with the comparative example.

FIG. 256 is a diagram for explaining the fourth modification example 2 of the second embodiment of the present technology.

The probe casing 320 illustrated in the drawing has a component thickness increased at one location out of the paper surface upper direction and the lower direction while avoiding the paper surface inward direction in which the electromagnetic waves are mainly transmitted through the casing.

In FIG. 256, the component thickness of the casing may be increased in a shape in which neither discontinuous points nor inflection points are present both at the outer periphery and at the inner periphery of the casing as illustrated in a in FIG. 256 as the shape for increasing the component thickness of the casing. As illustrated in b in FIG. 256, the component thickness of the casing may be increased in the inward direction. In this case, the discontinuous points or inflection points increase at the inner periphery of the casing as compared with the comparative example. As illustrated in c in FIG. 256, the component thickness of the casing may be increased in the outward direction. In this case, the discontinuous points or inflection points increase at the outer periphery of the casing as compared with the comparative example. As illustrated in d in FIG. 256, the component thickness of the casing may be increased both in the inward direction and in the outward direction. In this case, the discontinuous points or inflection points increase at both the inner periphery and the outer periphery of the casing as compared with the comparative example.

FIG. 257 is a diagram for explaining the fourth modification example 3 of the second embodiment of the present technology.

The probe casing 320 illustrated in the drawing has a component thickness increased at two locations in the paper surface upper direction and the lower direction while avoiding the paper surface inward direction in which the electromagnetic waves are mainly transmitted through the casing.

In FIG. 257, the component thickness of the casing may be increased in a shape in which neither discontinuous points nor inflection points are present both at the outer periphery and at the inner periphery of the casing as illustrated in a in FIG. 257 as the shape for increasing the component thickness of the casing. As illustrated in b in FIG. 257, the component thickness of the casing may be increased in the inward direction. In this case, the discontinuous points or inflection points increase at the inner periphery of the casing as compared with the comparative example. As illustrated in c in FIG. 257, the component thickness of the casing may be increased in the outward direction. In this case, the discontinuous points or inflection points increase at the outer periphery of the casing as compared with the comparative example. As illustrated in d in FIG. 257, the component thickness of the casing may be increased both in the inward direction and in the outward direction. In this case, the discontinuous points or inflection points increase at both the inner periphery and the outer periphery of the casing as compared with the comparative example.

FIG. 258 is a diagram for explaining an exceptional case according to the fourth modification example of the second embodiment of the present technology. The probe casing 320 illustrated in the drawing exceptionally has a component thickness increased at two locations in the paper surface left-right direction including the paper surface inward direction in which the electromagnetic waves are mainly transmitted through the casing. In this case, although there is a concern that the measurement accuracy of the amount of moisture may be degraded, the effect of enhancing the strength of the probe casing 320 is obtained.

In FIG. 258, the component thickness of the casing may be increased in a shape in which neither discontinuous points nor inflection points are present both at the outer periphery and at the inner periphery of the casing as illustrated in a in FIG. 258 as the shape for increasing the component thickness of the casing. As illustrated in b in FIG. 258, the component thickness of the casing may be increased in the inward direction. In this case, the discontinuous points or inflection points increase at the inner periphery of the casing as compared with the comparative example.

As illustrated in c in FIG. 258, the component thickness of the casing may be increased in the outward direction. In this case, the discontinuous points or inflection points increase at the outer periphery of the casing as compared with the comparative example. As illustrated in d in FIG. 258, the component thickness of the casing may be increased both in the inward direction and in the outward direction. In this case, the discontinuous points or inflection points increase at both the inner periphery and the outer periphery of the casing as compared with the comparative example.

FIG. 259 is a diagram for explaining the fourth modification example 4 of the second embodiment of the present technology.

The probe casing 320 illustrated in the drawing has a component thickness increased at three locations except for the paper surface inward direction while avoiding the paper surface inward direction in which the electromagnetic waves are mainly transmitted through the casing.

In FIG. 259, the component thickness of the casing may be increased in a shape in which neither discontinuous points nor inflection points are present both at the outer periphery and at the inner periphery of the casing as illustrated in a in FIG. 259 as the shape for increasing the component thickness of the casing. As illustrated in b in FIG. 259, the component thickness of the casing may be increased in the inward direction. In this case, the discontinuous points or inflection points increase at the inner periphery of the casing as compared with the comparative example. As illustrated in c in FIG. 259, the component thickness of the casing may be increased in the outward direction. In this case, the discontinuous points or inflection points increase at the outer periphery of the casing as compared with the comparative example. As illustrated in d in FIG. 259, the component thickness of the casing may be increased both in the inward direction and in the outward direction. In this case, the discontinuous points or inflection points increase at both the inner periphery and the outer periphery of the casing as compared with the comparative example.

FIG. 260 is a diagram for explaining the fourth modification example 5 of the second embodiment of the present technology. The structure illustrated in the drawing includes the casing with the same shape which is obtained merely by changing the antenna with the structure illustrated in FIG. 255 to one-side radiation.

FIG. 261 is a diagram for explaining the fourth modification example 6 of the second embodiment of the present technology. The structure illustrated in the drawing includes the casing with the same shape which is obtained merely by changing the antenna with the structure illustrated in FIG. 256 to one-side radiation.

FIG. 262 is a diagram for explaining the fourth modification example 7 of the second embodiment of the present technology.

The structure illustrated in the drawing includes the casing with the same shape which is obtained merely by changing the antenna with the structure illustrated in FIG. 257 to one-side radiation.

FIG. 263 is a diagram for explaining an exceptional case according to the fourth modification example of the second embodiment of the present technology. The structure illustrated in the drawing includes the casing with the same shape which is obtained merely by changing the antenna with the structure illustrated in FIG. 258 to one-side radiation.

FIG. 264 is a diagram for explaining the fourth modification example 8 of the second embodiment of the present technology.

The structure illustrated in the drawing includes the casing with the same shape which is obtained merely by changing the antenna with the structure illustrated in FIG. 259 to one-side radiation.

The fourth modification example of the second embodiment of the present technology illustrated in FIGS. 255 to 264 is obtained by applying the structure in which a part of the probe casing described in the fifth modification example of the first embodiment of the present technology illustrated in FIGS. 191 to 199 is caused to have an increased thickness to the probe casing according to the second embodiment of the present technology illustrated as an example in a in FIG. 221.

Here, although the probe casing illustrated as an example in a in FIG. 221 represents a component (9') according to the second embodiment of the present technology, the probe casing illustrated in the drawing is obtained by rotating, by 90°, the probe casing that is a component (9) in the first embodiment of the present technology illustrated as an example in a in FIG. 190.

Also, examples of the component (9) in the first embodiment of the present technology includes b to d in FIG. 190 in addition to a in FIG. 190. Similarly to the fact that the structure obtained by rotating the casing in a in FIG. 190 by 90° becomes the component (9') in the second embodiment, it is also possible to use, in the second embodiment, the structure obtained by rotating the casing in b to d in FIG. 190 by 90° as the component (9') in the second embodiment. Also, it is also possible to apply the structure illustrated in FIGS. 255 to 264 to each structure obtained by rotating the above casing in b to d in FIG. 190 by 90° in the fourth modification example of the second embodiment of the present technology.

In this manner, according to the fourth modification example of the second embodiment of the present technology, the component thickness of the probe casing 320 in the region other than the region where the transmitted and received electromagnetic waves are mainly transmitted is increased while avoiding the region in order not to degrade the measurement accuracy of the amount of moisture, it is thus possible to reduce deformation of the probe casing 320 and the substrate therein when the probe is inserted into the soil even when the hardness of the soil is significantly high, and as a result, it is possible to more accurately measure the moisture.

Fifth Modification Example

Although the sensor device 200 measures moistures at a predetermined one point in an X-Z plane that is parallel with the ground in the aforementioned second embodiment, this configuration requires a plurality of sensor devices 200 to perform measurement at a plurality of points. A sensor device 200 according to the fifth modification example of the second embodiment is different from that in the first embodiment in that measurement is performed at a plurality of points in the X-Z plane.

FIG. 265 is a diagram illustrating a configuration example of the sensor device 200 according to the fifth modification example of the second embodiment of the present technology. The sensor device 200 according to the second embodiment is different from that in the second embodiment in that an electronic substrate 311-1 with two or more (for example, three pairs of) projecting portions formed thereon is included. An antenna is formed at each projecting portion, and the projecting portion functions as a probe. In the drawing, a illustrates an example in which a measurement circuit is disposed for each probe pair, and b in the drawing illustrates an example in which one measurement circuit is shared.

As illustrated as an example in a in the drawing, a transmission antenna 221-1 and a reception antenna 231-1 are formed at the first pair of probes (projecting portions). These antennas are connected to a measurement circuit 210-1. A transmission antenna 221-2 and a reception antenna 231-2 are formed at the second pair of probes. These antennas are connected to a measurement circuit 210-2. A transmission antenna 221-3 and a reception antenna 231-3 are formed at the third pair of probes. These antennas are connected to a measurement circuit 210-3. The electronic substrate 311-1 may be stored in a casing and is then inserted into the soil, or the electronic substrate 311-1 may be inserted into the soil as it is without being stored in the casing.

Since the electronic substrate 311-1 includes two or more probes, it is possible to measure the amounts of moisture at a plurality of locations by the one sensor device 200.

Also, as illustrated as an example in b in the drawing, three pairs of probes can share one measurement circuit 210.

FIG. 266 is a diagram illustrating an example of the sensor device 200 before and after connection of the electronic substrate according to the fifth embodiment of the second embodiment of the present technology. In the drawing, a illustrates the electronic substrate before the connection, and b in the drawing illustrates the electronic substrate after the connection.

It is possible to prepare electronic substrates 311-1, 311-2, and 311-3 as illustrated as an example in a in the drawing and to connect them to coupling sections 370 and 371 as illustrated as an example in b in the drawing.

FIG. 267 is a diagram illustrating a configuration example of the sensor device 200 with a plurality of pairs of antennas provided for each probe according to the fifth modification example of the second embodiment of the present technology. In the drawing, a illustrates an example in which a measurement circuit is disposed for each probe pair, and b in the drawing illustrates an example in which one measurement circuit is shared. It is also possible to provide a plurality of pairs of antennas for each probe pair as illustrated as an example in the drawing.

FIG. 268 is a diagram illustrating a configuration example of the sensor device 200 in which each probe pair has a different length according to the fifth modification example of the second embodiment of the present technology. In the drawing, a illustrates an example in which the number of antennas is different for each probe pair. In the drawing, b illustrates an example in which the number of antennas for each probe pair is the same.

As illustrated as an example in a in the drawing, the length may be changed for each probe pair, the first pair of probes may be provided with three pairs of antennas, the second pair of probes may be provided with two pairs of antennas, and the third pair of probes may be provided with one pair of antennas. As illustrated as an example in b in the drawing, the length may be changed for each probe pair, and each probe pair may be provided with a pair of antennas. The sensor device 200 can measure the amounts of moisture at different depths at each point with the configuration in the drawing.

FIG. 269 is a diagram illustrating a configuration example of the sensor device 200 in which a transmission antenna is shared by a plurality of reception antenna according to the fifth modification example of the second embodiment of the present technology. In the drawing, a illustrates an example in which two reception antennas share one transmission antenna. In the drawing, b illustrates an example in which four reception antennas share one transmission antenna.

It is also possible to set the number of probes to three as illustrated as an example in a in the drawing, to form the transmission antenna 221-1 at the probe in the middle, to form the reception antenna 231-1 at one of the two remaining probes, and to form the reception antenna 231-2 at the other probe. Additionally, it is also possible to set the number of probes to three as illustrated as an example in b in the drawing, to form the transmission antenna 221-1 at the probe in the middle, to form the reception antennas 231-1 and 232-1 at one of the two remaining probes, and to form the reception antennas 231-2 and 232-2 at the other probe. It is possible to reduce the number of probes by sharing the transmission antennas.

FIG. 270 is a diagram illustrating a configuration example of the sensor device 200 in which substrate surfaces of the electronic substrates face each other according to the fifth modification example of the second embodiment of the present technology. In the drawing, a illustrates a perspective view when end portions of the electronic substrates are coupled. In the drawing, b illustrates a top view when the end portions of the electronic substrates are coupled. In the drawing, c illustrates a perspective view when parts other than the end portions of the electronic substrates are coupled. In the drawing, d illustrates a top view when the parts other than the end portions of the electronic substrates are coupled.

As illustrated as an example in a and b in the drawing, it is also possible to connect and fix the end portions of the electronic substrates 311-1, 311-2, and 311-3 with the coupling section 370 such that the substrate planes thereof are parallel with each other. As illustrated as an example in c and d in the drawing, it is also possible to connect and fix the parts other than the end portions (such as center portions) of the electronic substrates 311-1, 311-2, and 311-3 with the coupling sections 370 and 371 such that the substrate planes thereof are parallel with each other.

FIG. 271 is a diagram illustrating a configuration example of the sensor device 200 which performs measurement at a plurality of points aligned in a two-dimensional grid shape according to the fifth embodiment of the second embodiment of the present technology. As illustrated as an example in the drawing, it is also possible to connect the electronic substrates 311-1, 311-2, and 311-3, each of which includes three pairs of probes aligned in the X-axis direction, with the coupling sections 370 to 375 such that the substrate planes thereof face each other. In this manner, the sensor device 200 can measure the amounts of moisture at 3×3 points aligned in the two-dimensional grid shape in the X-Z plane that is parallel with the ground.

FIG. 272 is a diagram illustrating a configuration example of the sensor device 200 with a level added thereto according to the fifth modification example of the second embodiment of the present technology. As illustrated as an example in a in the drawing, it is also possible to provide a level 376 in the electronic substrate 311-1 provided with three pairs of probes. Additionally, as illustrated as an example in b in the drawing, it is also possible to provide levels 376 and 377. The level 376 is adapted to detect an inclination in a direction in which the probes are aligned (X-axis direction). The level 377 is adapted to detect an inclination in a direction that is vertical to the direction in which the probes are aligned (Z-axis direction).

As illustrated as an example in c in the drawing, it is also possible to provide the levels 376 and 377 in the sensor device 200 that performs measurement at a plurality of points aligned in the two-dimensional grid shape.

FIG. 273 is a diagram illustrating a configuration example of the sensor device 200 in which transmission and reception directions of electromagnetic waves intersect each other according to the fifth modification example of the second embodiment of the present technology. As illustrated as an example in a in the drawing, it is also possible to connect the electronic substrates 311-1 and 311-2 with the coupling section 370 and to receive the transmission signal of the transmission antenna 221-1 by the reception antenna 232-1 at a different position from that of the antenna in the Y axis direction. In addition, it is also possible to receive the transmission signal of the transmission antenna 222-1 by the reception antenna 231-1 at a different position from that of the antenna in the Y-axis direction. In this manner, the sensor device 200 can measure the amount of moisture at an intermediate depth of the transmission antennas 221-1 and 222-1.

Additionally, as illustrated as an example in b in the drawing, it is possible to provide three probes and to perform transmission and reception such that transmission and reception directions of electromagnetic waves intersect each other.

In this manner, according to the fifth modification example of the second embodiment of the present technology, the electronic substrates are provided with three or more probes, and the sensor device 200 can thus measure the amount of moisture at a plurality of points.

Sixth Modification Example

Although the positions of the antennas in the transmission probe and the reception probe are symmetrical in the aforementioned second embodiment, it is difficult to further reduce the size of the sensor device 200 with this configuration. The sixth modification example of the second embodiment is different from the second embodiment in that the positions of the antennas in the transmission probe and the reception probe are asymmetrical.

FIG. 274 is a diagram for explaining an effect achieved when the positions of the antennas are asymmetrical in the sixth modification example of the second embodiment of the present technology. An electronic substrate 311-1 in the sensor device 200 is assumed to include a quadrangular portion with a quadrangular shape (such as a rectangle) and a pair of projecting portions. The transmission antenna 221 is formed at one of the pair of projecting portions, and the reception antenna 231 is formed at the other one. These projecting portions function as a transmission probe and a reception probe.

As illustrated as an example in a in the drawing, a configuration in which the positions of the antennas in the depth (Y-axis direction) are the same in the transmission probe and the reception probe is assumed as a comparative example. On the other hand, the antennas are disposed at different positions in the Y-axis direction in the transmission probe and the reception probe as illustrated as an example in b and c in the drawing in the sixth modification example of the second embodiment.

The distance d between the antennas in each of a, b, and c in the drawing is assumed to be the same. The distance (in other words, the width) between the probes is defined as w. An angle formed by the direction from the transmission antenna to the reception antenna and the X axis is defined as θ. θ is 45 degrees in b in the drawing, and θ is 60 degrees in x in the drawing. In this case, the following expression is established between the width w and the distance d.

$$w = d \times \cos(\theta) \quad \text{Expression 24}$$

In the above expression, cos( ) is a cosine function.

Since θ is θ degrees in a in the drawing, the width w is equal to the distance d on the basis of Expression 24. Since θ is 45 degrees in b in the drawing, the width w is $d/2^{1/2}$ on the basis of Expression 24. Since θ is 60 degrees in b in the drawing, the width w is $d/2$ on the basis of Expression 24. In this manner, it is possible to reduce the width w without changing the distance between the antennas by setting the positions of the antennas to be asymmetrical on the transmission side and the reception side. Since the distance between the antennas is the same, it is possible to maintain measurement accuracy. Therefore, it is possible to reduce the size of the sensor device 200 while maintaining the measurement accuracy.

FIG. 275 is a diagram illustrating a configuration example of the sensor device according to the sixth modification example of the second embodiment of the present technology. As illustrated as an example in a in the drawing, the lengths of the probes may be changed on the reception side and the transmission side, and the antennas may be formed at the distal ends thereof. As illustrated as an example in b and c in the drawing, the lengths of the probes may be set to be the same on the reception side and the transmission side, and the positions of the transmission antenna and the reception antenna in the depth direction (Y-axis direction) may be changed.

FIG. 276 is a diagram illustrating a configuration example of the sensor device 200 in which the quadrangular portion is formed into a parallelogram according to the sixth modification example of the second embodiment of the present technology. It is also possible to form the quadrangular portion into a parallelogram in order to set the transmission path length from the transmission antenna 221 to the measurement circuit 210 and the transmission path length from the reception antenna 231 to the measurement circuit 210 to be the same. In the drawing, a is an example in which the depth on the transmission side is set to be deeper than that on the reception side, and b in the drawing is an example in which the depth on the reception side is set to be deeper than that on the transmission side. In the drawing, c and d are examples in which the lengths of the probes are set to be the same on the transmission side and the reception side.

It is possible to apply a correction value on one of the transmission side and the reception side to the other by setting the same transmission path length on the reception side and the transmission side.

FIG. 277 is a diagram illustrating a configuration example of the sensor device 200 in which the quadrangular portion is formed into a rectangle and the transmission path lengths are caused to coincide with each other on the transmission side and the reception side according to the sixth modification example of the second embodiment of the present technology. It is also possible to form the quadrangular portion into a rectangle and to cause the transmission path lengths to coincide with each other on the transmission side and the reception side. In the drawing, a is an example in which the depth on the transmission side is set to be deeper than that on the reception side, and b in the drawing is an example in which the depth on the reception side is set to be deeper than that on the transmission side. In the drawing, c and d are examples in which the lengths of the probes are set to be the same on the transmission side and the reception side.

FIG. 278 is a diagram illustrating a configuration example of the sensor device 200 that performs measurement at a plurality of points according to the sixth modification example of the second embodiment of the present technology. It is also possible to form a plurality of antennas for each probe and to perform measurement at a plurality of points in the Y-axis direction.

In the drawing, a is an example in which the depth on the transmission side is set to be deeper than that on the reception side, and b in the drawing is an example in which the depth on the reception side is set to be deeper than that on the transmission side. In the drawing, c and d are examples in which the lengths of the probes are set to be the same on the transmission side and the reception side. In the drawing, e and f are examples in which the quadrangular portion is formed into a parallelogram. In the drawing, g and h are examples in which the quadrangular portion is formed into a parallelogram and the lengths of the probes are set to be the same on the transmission side and the reception side.

FIG. 279 is a diagram illustrating a configuration example of the sensor device 200 that shares an antenna to perform measurement at two points according to the sixth modification example of the second embodiment of the present technology. As illustrated as an example in a in the drawing, it is also possible to share the reception antenna 231 by the transmission antennas 221 and 222. As illustrated as an example in b in the drawing, it is also possible to share the transmission antenna 221 by the reception antennas 231 and 232.

In the drawing, c and d are examples in which the lengths of the probes are set to be the same on the transmission side and the reception side. In the drawing, e and f are examples in which the quadrangular portion is formed into a parallelogram. In the drawing, g and h are examples in which the quadrangular portion is formed into a parallelogram and the lengths of the probes are set to be the same on the transmission side and the reception side.

FIG. 280 is a diagram illustrating a configuration example of the sensor device 200 that shares an antenna to perform measurement at three or more points according to the sixth modification example of the second embodiment of the present technology. It is also possible to provide two pairs of antennas and to share the antennas to perform measurement at three or more points.

For example, as illustrated as an example in a in the drawing, it is also possible to form the transmission antennas 221 and 222 and the reception antennas 231 and 232 and to share the reception antennas 232 by the transmission antennas 221 and 222. As illustrated as an example in b in the drawing, it is also possible to form the transmission antennas 221 and 222 and the reception antennas 231 and 232 and to share one transmission antenna by the plurality of reception antennas.

In the drawing, c and d are examples in which the lengths of the probes are set to be the same on the transmission side and the reception side. In the drawing, e and f are examples in which the quadrangular portion is formed into a parallelogram. In the drawing, g and h are examples in which the quadrangular portion is formed into a parallelogram and the lengths of the probes are set to be the same on the transmission side and the reception side.

FIG. 281 is a diagram illustrating another example of the sensor device 200 that shares an antenna to perform measurement at two points according to the sixth modification example of the second embodiment of the present technology. As illustrated as an example in a in the drawing, it is also possible to set the positions of the transmission antenna 221 and the reception antenna 231 in the Y-axis direction to be the same when the reception antenna 231 is shared by the transmission antennas 221 and 222. As illustrated as an example in b in the drawing, it is also possible to set the positions of one of the reception antennas and the transmission antenna in the Y-axis direction to be the same when the transmission antenna is shared by the two reception antennas.

In the drawing, c and d are examples in which the lengths of the probes are set to be the same on the transmission side and the reception side. In the drawing, e and f are examples in which the quadrangular portion is formed into a parallelogram. In the drawing, g and h are examples in which the quadrangular portion is formed into a parallelogram and the lengths of the probes are set to be the same on the transmission side and the reception side.

FIG. 282 is a diagram illustrating another example of the sensor device 200 that performs measurement at three or more points by sharing an antenna according to the sixth modification example of the second embodiment of the present technology. As illustrated as an example in a in the drawing, it is also possible to form two pairs of antennas and to set the positions of the transmission antenna 221 and the reception antenna 232 in the Y-axis direction to be the same when the reception antenna 232 is shared by the transmission antennas 221 and 222. As illustrated as an example in b in the drawing, it is also possible to form two pairs of antennas and to set the positions of one of the reception antennas and one of the transmission antennas in the Y-axis direction to be the same when the transmission antennas are shared by the two reception antennas.

In the drawing, c and d are examples in which the lengths of the probes are set to be the same on the transmission side and the reception side. In the drawing, e and f are examples in which the quadrangular portion is formed into a parallelogram. In the drawing, g and h are examples in which the quadrangular portion is formed into a parallelogram and the lengths of the probes are set to be the same on the transmission side and the reception side.

FIG. 283 is a diagram illustrating a configuration example of the sensor device in which the number of probes is increased according to the sixth modification example of the second embodiment of the present technology. As illustrated as an example in a in the drawing, it is possible to set the number of probes to three and to share the transmission antenna 221 in the middle by the reception antennas 231-1 and 231-2 on both sides. As illustrated as an example in b in the drawing, it is also possible to set the number of probes to three and to share the reception antenna 231 in the middle by the transmission antennas 221-1 and 222-2 on both sides. In the drawing, c and d are examples in which the lengths of the three probes are set to be the same.

FIG. 284 is a diagram illustrating a configuration example of the sensor device in which the number of probes and the number of antennas are increased according to the sixth modification example of the second embodiment of the present technology. As illustrated as an example in a in the drawing, it is also possible to set the number of probes to three and to share the transmission antenna 221 in the middle by the reception antennas 231-1, 232-1, 231-2, and 232-2 on both sides. As illustrated as an example in b in the drawing, it is also possible to set the number of probes to three and to share the reception antenna 231 in the middle by the transmission antennas 221-1, 222-1, 221-2, and 222-2 on both sides. In the drawing, c and d are examples in which the lengths of the three probes are set to be the same.

In this manner, according to the sixth modification example of the second embodiment of the present technology, the positions of the antennas on the transmission side and the reception side are asymmetrical, and it is thus possible to further reduce the size of the sensor device 200.

3. Third Embodiment

Although the plane-shaped antennas are formed in the intra-probe substrates 321 and 322 in the aforementioned first embodiment, the shape of the antennas is not limited to the plane shape. A sensor device 200 according to the third embodiment is different from that in the first embodiment in that the sensor device 200 according to the third embodiment includes columnar antennas.

FIG. 285 is a diagram illustrating an example of the sensor device 200 according to the third embodiment of the present technology. The sensor device 200 according to the third embodiment is different from that in the first embodiment in that the sensor device 200 does not include the intra-probe substrates 321 and 322 and includes coaxial cables 281 to 286. Transmission antennas 221 to 223 are formed at ends of the coaxial cables 281 to 283 on one side, and reception antennas 231 to 233 are formed at ends of the coaxial cables 284 to 286 on one side. The other ends of the coaxial cables 281 to 286 are connected to the measurement section substrate 311.

FIG. 286 is an example of a sectional view and a side view of the antenna according to the third embodiment of the present technology. In the drawing, a is a sectional view of the antenna seen from the above. In the drawing, b is a side view of the antenna seen from the front (Z-axis direction) of the sensor device 200, and c in the drawing is a side view of the antenna seen from the side surface (X-axis) direction of the sensor device 200.

The coaxial cable 281 and the like are configured of a linear signal line 281-3, a shield layer 281-2 covering the signal line 281-3, and a covering layer 281-1 covering the shield layer 281-2. A part of the shield layer 281-2 is exposed at one end of the coaxial cable 281 and the like, and a part of the signal line 281-3 is exposed at the end of the exposed shield layer 281-2. The exposed signal line 281-3 and the exposed shield layer 281-2 configure the antennas (the transmission antenna and the reception antenna). Also, the exposed signal line 281-3 of the antennas functions as a transmission element of the transmission antenna and a reception element of the reception antenna. In this manner, the transmission path (coaxial cable 281) between the measurement section substrate 311 and the antennas and the antennas are formed using the same continuous material.

FIG. 287 is a diagram illustrating an example of a sectional view of the coaxial cable according to the third embodiment of the present technology. As illustrated as an example in a in the drawing, it is also possible to form a hollow in the probe casing 320 for each coaxial cable and to dispose the coaxial cable in the hollow.

As illustrated as an example in b in the drawing, it is also possible to fix a plurality of coaxial cables with a fixing tool 380 and to dispose the plurality of coaxial cables in the hollow in the probe casing 320. A cable tie, an adhesive, or the like is used as the fixing tool 380. The strength in the cable extending direction is enhanced as compared with that of one coaxial cable by fixing the plurality of coaxial cables with the fixing tool 380.

As illustrated as an example in c in the drawing, it is also possible to fix the plurality of coaxial cables with a fixing tool 381 and to dispose the plurality of coaxial cables in the hollow in the probe casing 320. A guide structure, a case, or the like is used as the fixing tool 381. As illustrated as an example in d in the drawing, it is also possible to the minimum component thickness of the casing mainly on the side on which the electromagnetic waves pass in one section of the probe casing in regard to the structure in c in the drawing.

FIG. 288 is a diagram illustrating an example of the sensor device in which the number of antennas is reduced according to the third embodiment of the present technology. As illustrated as an example in the drawing, it is also possible to set the number of antenna pairs to one.

FIG. 289 is an example of a sectional view and a side view of the antenna when the number of antennas is reduced according to the third embodiment of the present technology.

FIG. 290 is a diagram illustrating an example of a sectional view of the coaxial cable when the number of antennas is reduced according to the third embodiment of the present technology. As illustrated as an example in a in the drawing, it is also possible to dispose the coaxial cable in the hollow in the probe casing 320. As illustrated as an example in b in the drawing, it is also possible to fix the coaxial cable with the fixing tool 381 and to dispose the coaxial cable in the hollow in the probe casing 320. As illustrated as an example in c in the drawing, it is also possible to have the minimum component thickness of the casing mainly on the side on which the electromagnetic waves are transmitted in one section of the probe casing in regard to the structure in b in the drawing.

In this manner, according to the third embodiment of the present technology, the columnar antenna is formed at the distal end of the coaxial cable, and the intra-probe substrate is thus not needed.

4. Fourth Embodiment

Although the watering nozzle is disposed separately from the sensor device 200 when the watering nozzle is added to the moisture measurement system 100 in the aforementioned first embodiment, it is difficult to dispose them at appropriate positions with this configuration. A moisture measurement system 100 according to the fourth embodiment is different from that in the first embodiment in that the watering nozzle is fixed at an appropriate position. Note that it is possible to use various sensor devices described in the specification (for example, the sensor devices according to the first to third embodiments and the modification examples thereof) as the sensor device included in the moisture measurement system 100 according to the fourth embodiment.

FIG. 291 is a diagram illustrating an example of moisture measurement systems 100 according to the fourth embodiment of the present technology and a comparative example. In the drawing, a is a diagram illustrating an example of the moisture measurement system in the comparative example in which the sensor device 200 is not coupled to the watering nozzle 530. In the drawing, b is a diagram illustrating an example of the moisture measurement system 100 according to the fourth embodiment.

As illustrated as an example in a in the drawing, it is necessary for the user to install the sensor device 200 and the watering nozzle 530 by relying on his/her intuition when they are disposed separately. However, in this case, there is a concern that variation may occur in a time delay until a change in amount of moisture is detected if the distance between the sensor device 200 and the watering nozzle 530 is not constant when watering control is performed using the sensor device 200. As a result, there is a problem that the watering control does not function appropriately and an excessive water stress may be applied to plants.

Thus, in the fourth embodiment, the sensor device 200 and the watering nozzle holder 520 are coupled with a coupling section 370 as illustrated as an example in b in the drawing. The watering nozzle 530 is held in the watering nozzle holder 520. The watering nozzle 530 is attached to an end of a watering tube 510. With the configuration in b in the drawing, it is possible to keep the constant distance between the sensor device 200 and the watering nozzle holder 520 without causing variations.

However, in the configuration in which the watering nozzle holder 520 is coupled to the one sensor device 200, the position of the sensor device 200 is likely to deviate due to the weight of the watering tube 510, and there may be a case where a clearance is generated between the soil and the moisture sensor and it is not possible to measure the amount of moisture with high accuracy. Therefore, the watering nozzle holders 520 may be provided among a plurality of sensor devices 200 to obtain a stronger support structure.

FIG. 292 is a diagram illustrating an example of the moisture measurement system 100 in which a plurality of sensor devices are coupled according to the fourth embodiment of the present technology. As illustrated as an example in a in the drawing, it is also possible to couple a sensor device 200, a sensor device 201, and the watering nozzle holders 520 with the coupling section 370. Note that the number of sensor devices to be coupled is not limited to two.

As illustrated as an example in b in the drawing, the lengths of the sensor device 200 and the sensor device 201 in the depth direction (Y-axis direction) of the probe casing 320 may be different from each other.

FIG. 293 is an example of a top view of the moisture measurement system 100 in which the plurality of sensor devices are coupled according to the fourth embodiment of the present technology. The drawing illustrates a top view when seen from the upper direction (Y-axis direction).

The shape of the coupling section 370 when seen from the upper side may be a linear shape as illustrated as an example in a in the drawing, or the shape may be a shape obtained by folding a line segment at a predetermined angle as illustrated as an example in b in the drawing. As illustrated as an example in c in the drawing, the shape of the coupling section 370 may be an arc shape.

FIG. 294 is a diagram illustrating an example of the moisture measurement system 100 provided with a support member according to the fourth embodiment of the present technology. A support member 540 couples the sensor device 200, the sensor device 201, and the watering nozzle holder 520 similarly to the coupling section 370.

In the drawing, the upper half of a is the top view of the moisture measurement system 100, and the lower half thereof is a side view. The moisture measurement system 100 illustrated in FIG. 294a has a side surface with a shape including the two sensor devices 200 and 201 with different lengths in the depth direction (Y-axis direction) of the probe casing 320 similarly to that in FIG. 292b. The above system illustrated in FIG. 294a has an upper surface with a shape including an arc-shaped support member 540 similarly to that in FIG. 293c. The top view illustrated in the upper half in FIG. 294a illustrates a state in which the moisture sensor system 100 including the above arc-shaped support member 540 is disposed to surround a plant as a target of watering.

In the drawing, the upper half of b is a top view of the moisture measurement system 100, and the lower half thereof is a side view as well. The moisture measurement system 100 illustrated in FIG. 294b has a side surface with a shape including the two sensor devices 200 and 201 with different lengths in the depth direction (Y-axis direction) of the probe casing 320 similarly to that in FIG. 292b. The above system illustrated in FIG. 294b has an upper surface with a shape in which a linear support member 540 is folded similarly to that in FIG. 293b. The top view illustrated in the upper half of FIG. 294b illustrates a state in which the moisture sensor system 100 including the above folded support member 540 is disposed to surround a plant as a target of watering.

According to the moisture measurement system 100 illustrated in FIG. 294, it is possible to dispose the plurality of sensor devices in different forms at positions at an equal distance from the plant as the target of watering and at an equal distance from the watering nozzle as well and at positions surrounding the plant. In this manner, it is possible to measure a plurality of pieces of information using the sensor devices in the different forms in the vicinity of the plant as the target of watering and at locations where the distance conditions from both the plant and the watering nozzle are the same.

FIG. 295 is a diagram illustrating an example of the moisture measurement system 100 in which the plurality of sensor devices and a plurality of watering nozzle holders are coupled according to the fourth embodiment of the present technology. As illustrated as an example in the drawing, it is also possible to couple the sensor devices 200 and 201 to the watering nozzle holders 520 to 522 with the coupling section 370. The number of each of the watering nozzle holders and the sensor devices is not limited to three or two in the drawing.

FIG. 296 is a diagram illustrating an example of the moisture measurement system 100 in which a watering tube holder is coupled according to the fourth embodiment of the present technology. As illustrated as an example in a in the drawing, it is also possible to use a watering tube holder 550 instead of the watering nozzle holder 520. The watering tube holder 550 is attached to a predetermined position of the sensor device 200. In this case, the coupling section 370 and the watering nozzle 530 are not needed, and it is thus possible to reduce the cost. In the drawing, b illustrates a top view of the moisture measurement system 100 in a in the drawing.

Additionally, as illustrated as an example in c in the drawing, it is also possible to attach the watering tube holder 550 to a predetermined position of the coupling section 370 that couples the plurality of sensor devices. In the drawing, d illustrates a top view of the moisture measurement system 100 in c in the drawing.

In addition, as illustrated as an example in e in the drawing, it is also possible to couple the sensor devices 200 and 201 with the coupling section 370 and to attach watering tube holders 550 and 551 of the sensor devices 200 and 201, respectively. In the drawing, f illustrates a top view of the moisture measurement system 100 in e in the drawing.

FIG. 297 is a diagram illustrating an example of the moisture measurement system 100 that performs watering via the watering nozzle according to the fourth embodiment of the present technology. As illustrated as an example in a in the drawing, a configuration in which the watering tube 510 causes water to flow into the watering nozzle 530 may be adopted. In this configuration, water is delivered along the watering nozzle 530 and flows to the soil. In this case, it is also possible to couple the plurality of sensor devices with the coupling section 370 as illustrated as an example in b in the drawing. Also, as illustrated as an example in c in the drawing, the lengths of the sensor device 200 and the sensor device 201 in the depth direction (Y-axis direction) of the probe casing 320 may be different from each other.

FIG. 298 is a diagram illustrating an example of the moisture measurement system 100 in which the probe alignment direction and a line segment that is parallel with the coupling section are orthogonal to each other according to the fourth embodiment of the present technology. The drawing illustrates a top view of the moisture measurement system 100. As illustrated as an example in the drawing, it is also possible to couple the sensor devices such that the probe alignment direction of each of the sensor devices 200 and 201 and the line segment that is parallel with the linear coupling section 370 are orthogonal to each other. In this case, an H-shape seen from the above is obtained.

As illustrated as an example in a in the drawing, the watering tube holder 550 may be attached to the coupling section 370. As illustrated as an example in b in the drawing, the watering nozzle holder 520 may be attached to the coupling section 370.

In this manner, according to the fourth embodiment of the present technology, the sensor device 200 and the watering nozzle 530 are fixed at appropriate positions, and it is thus possible to keep a constant distance therebetween.

5. Fifth Embodiment

In the aforementioned first embodiment, the transmission antenna and the reception antenna and the transmission path connected thereto are accommodated in strong casing probes in order to avoid a situation in which the orientations of the antennas and the distances between the antennas deviate from the predetermined orientation and distance due to an application of a stress to the transmission antenna and the reception antenna included in the sensor device 200 when these antennas are installed in the soil.

However, in a case where hardness of the soil as a target of measurement such as a well-plowed field, for example, is low, the sensor device 200 may be able to be used even with a structure in which no strong casings are included. Thus, a sensor device 200 according to the fifth embodiment of the present technology does not include a sensor casing 305 and includes a structure that realizes high durability without including the sensor casing. In this manner, the sensor device 200 according to the fifth embodiment of the present technology has an effect that the number of components is reduced, the outer shape size is reduced, the weight is reduced, the manufacturing method is simplified, and the manufacturing cost is reduced as compared with the sensor device 200 according to the present technology including the sensor casing 305.

FIGS. 299 and 300 are diagrams illustrating an example of a front view and a side view of the sensor device 200 according to the fifth embodiment of the present technology. The sensor device 200 according to the fifth embodiment of the present technology illustrated in FIGS. 299 and 300 is obtained by changing the second embodiment and the modification examples thereof of the present technology into a form in which the probe casing 305 is not included. In FIG. 299, a illustrates a front view of the sensor device 200, and b in the drawing illustrates a side view of the sensor device 200. In FIG. 300, a is an example of a back view of the sensor device 200. In the drawing, b is an example of a sectional view of the sensor device 200 cut along the line C-C' in a in the drawing. In the drawing, c is an example of a sectional view of the sensor device 200 cut along the line D-D' in a in the drawing. In the drawing, d is an example of a sectional view of the sensor device 200 cut along the line E-E' in a in the drawing. As illustrated as examples in FIGS. 299 and 300, the sensor device 200 according to the fifth embodiment of the present technology includes one electronic substrate 311-1. The configuration of the electronic substrate 311-1 is similar to that in the second embodiment. A battery 313 and the like are provided on the rear surface of the electronic substrate 311-1.

As illustrated in FIGS. 299 and 300, the electronic substrate 311-1 is covered with a covering resin in the sensor device 200 according to the fifth embodiment of the present technology. The covering resin is illustrated by the black thick line outside the electronic substrate 311-1 in FIGS. 299 and 300. It is desirable that the covering resin have electromagnetic wave permeability and water resistance, and it is further desirable that the covering resin have chemical resistance and higher flexibility than that of the electronic substrate 311-1. It is necessary for the sensor device 200 according to the present technology to have predetermined mechanical strength such that the antennas and the transmission path are not deformed when the antennas included in the sensor device 200 and the transmission path connected to the antennas are inserted into predetermined soil. In the sensor device 200 according to the fifth embodiment of the present technology, the electronic substrate 311-1 plays a role in securing the predetermined mechanical strength. On the other hand, the covering resin plays a role in protecting the electronic substrate 311-1 from water and pesticide. Here, there is a concern that if a hollow is generated between the covering resin and the electronic substrate 311-1 (in other words, if the covering resin flows from the surface of the electronic substrate 311-1), a stress may be applied to the floating covering resin, and the covering resin may break when the sensor device 200 is inserted into the soil. Thus, in the sensor device 200 according to the fifth embodiment of the present technology, a flexible resin is used as the covering resin in order to cover the electronic substrate 311-1 without generating any hollow at the part between itself and the electronic substrate 311-1. Moreover, the sensor device 200 according to the fifth embodiment of the present technology measures the amount of moisture in the medium between the two antennas by transmitting an electromagnetic wave from the transmission antenna covered with the covering resin and receiving the electromagnetic wave by the reception antenna covered with the covering resin. Thus, a resin with electromagnetic wave permeability is used as the covering resin in the sensor device 200 according to the fifth embodiment of the present technology.

FIGS. 301 and 302 are diagrams illustrating an example of a front view and a side view of the sensor device 200 according to another example 1 of the fifth embodiment of the present technology.

In FIG. 301, a illustrates a front view of the sensor device 200, and b in the drawing illustrates a side view of the sensor device 200. In FIG. 302, a is an example of a back view of the sensor device 200. In the drawing, b is an example of a sectional view of the sensor device 200 cut along the line C-C' in a in the drawing. In the drawing, c is an example of a sectional view of the sensor device 200 cut along the line D-D' in a in the drawing. In the drawing, d is an example of a sectional view of the sensor device 200 cut along the line E-E' in a in the drawing. Note that in FIGS. 299 and 300, the black thick line outside the measurement section substrate 311 and the intra-probe substrates 321 and 322 represents the covering resin.

A user of the sensor device 200 according to the fifth embodiment of the present technology holds the part including the measurement section in the sensor device 200 and inserts the antenna parts of the sensor device 200 into the soil. Therefore, it is desirable that the intra-probe substrates 321 and 322 be fixed to the measurement section substrate 311 without intervention of the probe casing 305 such that the orientations and the positions of the intra-probe substrates 321 and 322 do not change when they are inserted into the soil in order to realize the sensor device 200 that does not include the probe casing 305 as in the fifth embodiment of the present technology on the basis of the sensor device 200 in the form in which the measurement section substrate 311 and the intra-probe substrates 321 and 322 are different substrates as in the first embodiment of the present technology.

Thus, a sensor device 200 according to another example 1 of the fifth embodiment of the present technology illustrated in FIGS. 301 and 302 includes frames 291 to 294 similarly to the sensor device 200 illustrated as an example in FIGS. 180 and 181. These frames integrate and fix the measurement section substrate 311 and the intra-probe substrates 321 and 322 in a orthogonal to state, and the fixed structure thus has the predetermined mechanical strength.

Also, in the sensor device 200 according to another example 1 of the fifth embodiment of the present technology illustrated in FIGS. 301 and 302, the outside of the fixed structure is covered with a covering resin having higher flexibility than that of the measurement section substrate 311 and the intra-probe substrates 321 and 322 and having electromagnetic wave permeability and water resistance, and preferably chemical resistance.

FIGS. 303 and 304 are diagrams illustrating an example of a front view and a side view of the sensor device 200 according to another example 2 of the fifth embodiment of the present technology.

In FIG. 303, a illustrates a front view of the sensor device 200, and b in the drawing illustrates a side view of the sensor device 200. In FIG. 304, a is an example of a back view of the sensor device 200. In the drawing, b is an example of a sectional view of the sensor device 200 cut along the line C-C' in a in the drawing. In the drawing, c is an example of a sectional view of the sensor device 200 cut along the line D-D' in a in the drawing. In the drawing, d is an example of a sectional view of the sensor device 200 cut along the line E-E' in a in the drawing. Note that in FIGS. 303 and 304, the black thick line outside the measurement section substrate 311 and the intra-probe substrates 321 and 322 represents the covering resin.

A sensor device 200 according to another example 2 of the fifth embodiment of the present technology illustrated in FIGS. 303 and 304 has a structure in which any of the measurement section substrate and the intra-probe substrates has a notch and two substrates are fitted using the notch similarly to the sensor device 200 illustrated as an example in FIGS. 182 and 183. The measurement section substrate 311 and the intra-probe substrates 321 and 322 are integrated and fixed in a orthogonal to state through the fitting, and the fixed structure thus has the predetermined mechanical strength.

Also, in the sensor device 200 according to another example 2 of the fifth embodiment of the present technology illustrated in FIGS. 303 and 304, the outside of the fixed structure is covered with a covering resin having higher flexibility than that of the measurement section substrate 311 and the intra-probe substrates 321 and 322 and having electromagnetic wave permeability and water resistance, and preferably chemical resistance.

FIGS. 305 and 306 are diagrams illustrating an example of a front view and a side view of the sensor device 200 according to another example 3 of the fifth embodiment of the present technology.

In FIG. 305, a illustrates a front view of the sensor device 200, and b in the drawing illustrates a side view of the sensor device 200. In FIG. 306, a is an example of a back view of the sensor device 200. In the drawing, b is an example of a sectional view of the sensor device 200 cut along the line C-C' in a in the drawing. In the drawing, c is an example of a sectional view of the sensor device 200 cut along the line D-D' in a in the drawing. In the drawing, d is an example of a sectional view of the sensor device 200 cut along the line E-E' in a in the drawing. Note that in FIGS. 303 and 304, the black thick line outside the measurement section substrate 311 and the intra-probe substrates 321 and 322 represents the covering resin.

A sensor device 200 according to another example 3 of the fifth embodiment of the present technology illustrated in FIGS. 305 and 306 can include a jig for fixing the measurement section substrate to the intra-probe substrates similarly to the sensor device 200 illustrated as an example in FIGS. 184 and 185. The measurement section substrate 311 and the intra-probe substrates 321 and 322 are integrated and fixed in a orthogonal to state with the jig, and the fixed structure thus has the predetermined strength.

Also, in the sensor device 200 according to another example 3 of the fifth embodiment of the present technology illustrated in FIGS. 305 and 306, the outside of the fixed structure is covered with a covering resin having higher flexibility than that of the measurement section substrate 311 and the intra-probe substrates 321 and 322 and having electromagnetic wave permeability and water resistance, and preferably chemical resistance.

In this manner, according to the fifth embodiment of the present technology, the substrates included in the sensor device 200 are covered with a resin, and the sensor device 200 without using the sensor casing 305 is thereby realized. As a result, the sensor device 200 according to the fifth embodiment of the present technology has effects that the number of components is reduced, the outer shape size is reduced, the weight is reduced, the manufacturing method is simplified, and the manufacturing cost is reduced as compared with the sensor device 200 according to the present technology including the sensor casing 305.

6. Sixth Embodiment

In the aforementioned first embodiment, the substrate is stored in the sensor casing 305 provided with the pair of projecting portions (probes). A sensor device 200 according to the sixth embodiment is different from that in the first embodiment in that a stem is connected to the probes. In other words, the sensor device according to the sixth embodiment has a structure obtained by adding a stem to the various sensor devices (for example, the sensor devices in the first to third embodiments and the modification examples thereof) described in the specification.

FIG. 307 is a diagram illustrating an example of the sensor device 200 according to the sixth embodiment of the present technology. In the drawing, a is a diagram illustrating an example of an internal structure of the sensor device 200. In the drawing, b is an example of an appearance view of the sensor device 200.

The sensor casing 305 according to the fifth embodiment includes a rectangular main body section 305-3, a pipe-shaped stem 305-4, and a projecting portion 305-5, a part of which is split into two branches and projects. A measurement section substrate 311 is stored in the main body section 305-3, and a level 376 is attached to an upper portion thereof. A transmission antenna 221 and a reception antenna 231 are stored in the projecting portion 305-5. The projecting portion 305-5 functions as a probe. The stem 305-4 connects the main body section 305-3 to the projecting portion 305-5 (probe), and coaxial cables 281 and 282 are arranged therein. The transmission antenna 221, the reception antenna 231, and the measurement section substrate 311 are connected with these cables. Note that the level 376 is provided as needed.

Also, as illustrated as an example in b in the drawing, a scale indicating a depth is written on the surface of the sensor casing 305, and a temperature sensor 390 is attached as needed. Note that it is also possible to further attach a pH sensor, an electro conductivity (EC) sensor, or the like. However, it is necessary to dispose the various sensors at positions at which the electromagnetic waves emitted from the probe are not reflected by the sensors. Therefore, it is preferable that the temperature sensor 390 and the like be disposed on ferrite (radio wave absorption section) of the probe or further from it.

It is possible to easily insert the probe to a deep position in the mud by connecting the main body section 305-3 to the probe with the stem 305-4. It is possible to accurately know the depth of the measurement point of the sensor device 200 by the scale on the surface of the step 305-4. It is possible to insert the step 305-4 vertically to the ground by the level 376. It is possible to measure the soil states from various perspectives by the various sensors.

FIG. 308 is a diagram illustrating an example of a sensor device in which the position of the main body section has been changed according to the sixth embodiment of the present technology. In the drawing, a is a diagram illustrating an example of an internal structure of the sensor device 200. In the drawing, b is an example of an appearance view of the sensor device 200.

As illustrated as an example in the drawing, it is also possible to add a rectangular antenna section 305-6 and to connect the antenna section 305-6 to the main body section 305-3 with the stem 305-4. The antenna 213 is stored in the antenna section 305-6. The projecting portion 305-5 (probe) is connected to a lower portion of the main body section 305-3.

In this manner, according to the sixth embodiment of the present technology, the stem 305-4 is connected to the probe, and it is thus possible to easily insert the probe to a deep position in the mud.

7. Seventh Embodiment

Although the pair of probes for insertion into the mud are provided at the sensor device 200 in the aforementioned first embodiment, the distance between the probes may change due to degradation of the probes and deformation of the members due to stones or hard soils with this configuration. Although it is possible to prevent the deformation by increasing the thickness of the probes to enhance the strength, there is a concern that the size and the weight of the sensor device 200 increase and it becomes difficult to insert them into the soil. A sensor device 200 according to the seventh embodiment is different from that in the first embodiment in that the strength of the sensor device 200 is enhanced by adding pillars.

FIG. 309 is a diagram illustrating an example of sensor devices 200 according to the seventh embodiment of the present technology and comparative examples. In the drawing, a illustrates a first comparative example. In the drawing, b, c, and d illustrate sectional views cut along the line A-A', the line B-B', and the line C-C' in a in the drawing.

As illustrated as an example in a in the drawing, the first comparative example in which a spacer 600 is disposed between columnar probe casings 320-3 and 320-4 is assumed. Transmission antennas 221 to 223 are formed at the probe casing 320-3, and the probe casing 320-3 functions as a transmission probe. Reception antennas 231 to 233 are formed at the probe casing 320-4, and the probe casing 320-4 functions as a reception probe.

If the spacer 600 is provided between the antennas as in the first comparative example, soil does not enter the part between the antennas, and it is not possible to measure the amount of moisture.

In the drawing, e illustrates a second comparative example. In the drawing, f, g, and h illustrate sectional views cut along the line A-A', the line B-B', and the line C-C' in e in the drawing. In the second comparative example, a spacer is separated into a plurality of spacers 600 to 603 or the like, and spaces are formed between the antennas. Although mud enters the parts between the antennas, there is a concern that the spacer 600 or the like may interrupt the soil sufficiently entering the parts between the antennas in the second comparative example.

In the drawing, i is a perspective view of the sensor device 200 according to the seventh embodiment. A third pillar 610 is added to the sensor device 200 according to the seventh embodiment. No spacer is disposed between the probe casings 320-3 and 320-4. The pillar 610 and the probe casings 320-3 and 320-4 are connected with reinforcing sections 620 and 621. With this shape, no space is disposed between the antennas, and mud thus enters the parts between the antennas without any interruption of the spacer.

Also, water is sufficiently delivered to the soil, and the amount of water delivered along the probe decreases. Furthermore, since the gap between the probes is large, the gap reduces the concern of interrupting growth of plant roots, FIG. 310 is a diagram illustrating an example of a cut surface of the sensor device 200 according to the seventh embodiment of the present technology. In the drawing, the pillar 610 behind the sensor device 200 is omitted. Sectional views cut along the line B-B' in the drawing (the region where the transmission antenna 221 and the transmission intra-probe substrate 321 and the reception antenna 231 and the reception intra-probe substrate 322 are disposed) and the line C-C' (the region where the transmission antenna 221 and the reception antenna 231 are not disposed and the transmission intra-probe substrate 321 and the reception intra-probe substrate 322 are disposed) are illustrated in FIG. 311 and the following diagrams.

FIGS. 354 and 355 are diagrams illustrating examples of a sectional view of the sensor device 200 according to the seventh embodiment of the present technology similarly to FIG. 310. FIGS. 354 and 355 illustrates the pillar 610 included behind the sensor device 200, which is omitted in the illustration in FIG. 310, and the reinforcing sections 620 and 621. FIG. 354 illustrates a form in which the sensor device 200 includes a columnar pillar 610, and FIG. 355 illustrates a form in which the sensor device 200 includes a quadrangular prism-shaped pillar 610. In the region in which the antennas (the transmission antennas 221 to 223 and the reception antennas 231 to 233) included in the sensor device 200 are not disposed in the Y-axis direction of the sensor device 200, the pillar 610 included behind the sensor device 200 is connected to the transmission probe casing 320-3 via the reinforcing section 620 and is connected to the reception probe casing 320-4 via the reinforcing section 621.

FIG. 311 is a diagram illustrating an example of a sectional view of the sensor device 200 according to the seventh embodiment of the present technology. In the drawing, each of a and b is an example of a sectional view cut along the line B-B'. In the drawing, c is an example of a sectional view cut along the line C-C'. It is possible to apply any of a and b in the drawing to c in the drawing. In other words, it is possible to configure the sensor device 200 by combining any of the structures illustrated as a structure of the section along the line B-B' in a and b in the drawing with the structure illustrated as a structure of the section along the line C-C' in c in the drawing.

A structure of the sensor device 200 in a case where a and c in FIG. 311 are combined is illustrated in FIG. 356. The sensor device 200 illustrated in FIG. 356 is adapted in the form in which (1) the reinforcing sections 620 and 610 extend from the region where the transmission antennas 221 to 223 and the reception antennas 231 to 233 are disposed to the region where these antennas are not disposed in the Y-axis direction and (2) the probe casing 320-3 and the probe casing 320-4 are connected with the reinforcing sections 620 and 621 while avoiding a linear region connecting the probe casing 320-3 and the probe casing 320-4 in both the region where the transmission antennas 221 to 223 and the reception antennas 231 to 233 are disposed in the Y-axis direction and the region where these antennas are not disposed in the Y-axis direction.

A structure of the sensor device 200 in a case where b and c in FIG. 311 are combined is illustrated in FIG. 357. The sensor device 200 illustrated in FIG. 357 is adapted in the form in which (1) the probe casing 320-3 and the probe casing 320-4 are connected with the reinforcing sections 620 and 621 while avoiding the linear region connecting the probe casing 320-3 and the probe casing 320-4 in the region where the transmission antennas 221 to 223 and the reception antennas 231 to 233 are not disposed in the Y axis direction, (2) the pillars 610 are disposed on sides of the probe casing 320-3 and the probe casing 320-4 in the region where the transmission antennas 221 to 223 and the reception antennas 231 to 233 are disposed, and (3) the reinforcing sections 620 and 621 in (1) above and the pillars 610 in (2) above are connected at the boundary portion between the region in (1) above and the region in (2) above.

Note that unlike the examples illustrated in FIGS. 310d, 310e, and 310f, which will be described later, neither antennas nor sensors are provided in the pillars 610 in the examples illustrated in FIGS. 310a, 310b, and 310c.

In FIG. 311, each of d and e is an example of a sectional view cut along the line B-B'. In the drawing, f is an example of a sectional view cut along the line C-C'. It is possible to apply any of d and e in the drawing to f in the drawing. In other words, it is possible to configure the sensor device 200 by combining any of the structures illustrated in d and e in the drawing as structures of the section along the line B-B' with the structure illustrated in f in the drawing as a structure of the section along the line C-C'.

A structure of the sensor device 200 in a case where d and f in FIG. 311 are combined is illustrated in FIG. 358. The sensor device 200 illustrated in FIG. 358 is adapted in the form in which (1) the pillar 610 extends from the region where the transmission antennas 221 to 223 and the reception antennas 231 to 233 are disposed to the region where these antennas are not disposed in the Y-axis direction, and (2) the probe casing 320-3 and the probe casing 320-4 are connected with the reinforcing sections 620 and 621 and the pillar 610 while avoiding the linear region connecting the probe casing 320-3 and the probe casing 320-4 in both the region where the transmission antennas 221 to 223 and the reception antennas 231 to 233 are disposed in the Y-axis direction and the region where these antennas are not disposed in the Y-axis direction.

A structure of the sensor device 200 in a case where e and f in FIG. 311 are combined is illustrated in FIG. 359. The sensor device 200 illustrated in FIG. 359 is adapted in the form in which (1) the pillar 610 extends from the region where the transmission antennas 221 to 223 and the reception antennas 231 to 233 are disposed to the region where these antennas are not disposed in the Y-axis direction, and (2) the probe casing 320-3 and the probe casing 320-4 are connected with the reinforcing sections 620 and 621 and the pillar 610 while avoiding the linear region connecting the probe casing 320-3 and the probe casing 320-4 in the region where the transmission antennas 221 to 223 and the reception antennas 231 to 233 are not disposed in the Y-axis direction, and (3) the pillar 610 is disposed on sides of the probe casing 320-3 and the probe casing 320-4 in the region where the transmission antennas 221 to 223 and the reception antennas 231 to 233 are disposed in the Y-axis direction.

As illustrated as examples in d, e, and f in FIGS. 311, it is possible to provide, in the pillar 610, an antenna or a sensor such as a temperature sensor, a PH sensor (hydrogen ion concentration sensor), an electro conductivity sensor (EC sensor) in any, or some, or all of these regions and to use it as the third probe.

In FIG. 311, g is an example of a sectional view cut along the line B-B'. In the drawing, h is an example of a sectional view cut along the line C-C'. A structure of the sensor device 200 in a case where g and h in FIG. 311 are combined is illustrated in FIG. 360. As illustrated as examples in g and h in FIG. 311, it is also possible to achieve reinforcement with the reinforcing sections 620 and 621 without providing the pillar 610.

In the drawing, i is an example of a sectional view cut along the line B-B'. In the drawing, j is an example of a sectional view cut along the line C-C'. A structure of the sensor device 200 in a case where i and j in FIG. 311 are combined is illustrated in FIG. 361. As illustrated as examples in i and j in FIG. 311, it is also possible to form a circular or oval section in a case where the pillar 610 is not provided. In other words, it is also possible to adopt a form in which the probe casing 320-3 and the probe casing 320-4 are connected at a plurality of locations with the reinforcing sections 620 and 621 while avoiding the linear region connecting the probe casing 320-3 and the probe casing 320-4 in these sections. Additionally, the probe casing 320-3, the probe casing 320-4, the reinforcing section 620, and the reinforcing section 621 connected to each other can configure a closed curved line such as a circle or an oval in these sections.

FIG. 312 is a diagram illustrating an example of a sectional view of a rectangle of the sensor device 200 according to the seventh embodiment of the present technology. In other words, FIG. 312 is a diagram illustrating an example in which the probe casing 320-3 and the probe casing 320-4 and the reinforcing section 620 and the reinforcing section 621 connected thereto are disposed in a rectangular shape.

In the drawing, a and b are examples of a sectional view cut along the line B-B'. In the drawing, c is an example of a sectional view cut along the line C-C'. It is possible to apply any of a and b in the drawing to c in the drawing. In other words, it is possible to configure the sensor device 200 by combining any of the structures illustrated in a and b in the drawing with the structure illustrated in c in the drawing. In the drawing, d is an example of a sectional view cut along the line B-B'. In the drawing, i is an example of a sectional view cut along the line C-C'. It is possible to apply d in the drawing to f in the drawing. In other words, it is possible to apply configuring of the sensor device 200 by combining the structure illustrated in d in the drawing with the structure illustrated in f in the drawing. As illustrated as examples in a to c in the drawing, it is possible to form a rectangular sectional shape and to provide two pillars 610.

In the drawing, g and e are examples of a sectional view cut along the lines B-B'. In the drawing, i is an example of a sectional view cut along the line C-C'. It is possible to apply any of g and e in the drawing to i in the drawing. In other words, it is possible to configure the sensor device 200 by combining any of the structures illustrated in g and e in the drawing with the structure illustrated in i in the drawing. As illustrated as an example in e in the drawing, it is also possible to form a rectangular sectional shape and to provide two pillars 610.

In the drawing, j and h are examples of a sectional view cut along the line B-B'. In the drawing, k is an example of a sectional view cut along the line C-C'. It is possible to configure the sensor device 200 by combining any of the structures illustrated in j and h in the drawing with the structure illustrated in k in the drawing. It is possible to form a rectangular sectional shape and to provide four pillars 610 as illustrated by the combination of h and k in the drawing. Additionally, it is also possible to achieve reinforcement with the reinforcing sections without providing the inside of the pillars 610 as illustrated in j and k in the drawing.

FIG. 313 is a diagram illustrating an example of a sectional view of the sensor device 200 including three probes according to the seventh embodiment of the present technology.

In the drawing, a and b are examples of a sectional view cut along the line B-B'. In the drawing, c is an example of a sectional view cut along the line C-C'. It is possible to apply any of a and b in the drawing to c in the drawing. In other words, it is possible to configure the sensor device 200 by combining any of the structures illustrated in a and b in the drawing with the structure illustrated in c in the drawing.

In the drawing, d and e are examples of a sectional view cut along the line B-B'. In the drawing, f is an example of a sectional view cut along the line C-C'. It is possible to apply any of d and e in the drawing to fin the drawing. In other words, it is possible to configure the sensor device 200 by combining any of the structures illustrated in d and e in the drawing with the structure illustrated in fin the drawing.

In the drawing, g and h are examples of a sectional view cut along the line B-B'. In the drawing, i is an example of a sectional view cut along the line C-C'. It is possible to apply any of g and h in the drawing to i in the drawing. In other words, it is possible to configure the sensor device 200 by combining any of the structures illustrated in g and h in the drawing with the structure illustrated in i in the drawing.

FIG. 314 is a diagram illustrating another example of a sectional view of the sensor device 200 including three probes according to the seventh embodiment of the present technology. In the drawing, a, c, and e are examples of a sectional view cut along the line B-B'. In the drawing, b, d, and f are examples of a sectional view cut along the line C-C'. It is possible to configure the sensor device 200 by combining any of the structures illustrated in a and e in the drawing with the structure illustrated in b in the drawing. Also, it is possible to configure the sensor device 200 by combining the structure illustrated in c in the drawing with the structure illustrated in d in the drawing.

As illustrated as examples in FIGS. 313 and 314, it is also possible to provide an antenna or a sensor in the pillar 610 and to use it as a third probe.

FIG. 315 is a diagram illustrating an example of a sectional view of the sensor device 200 including four probes according to the seventh embodiment of the present technology. In the drawing, a, c, and e are examples of a sectional view cut along the line B-B'. In the drawing, b, d, and f are examples of a sectional view cut along the line C-C'. As illustrated as an example in the drawing, it is also possible to store antenna or a sensor of each of the pillars 610 and 611 and to use it as a third or fourth probe.

FIG. 316 is another example of a perspective view of the sensor device 200 according to the seventh embodiment of the present technology. The drawing is a view of the sensor device 200 seen from the Y+ direction (the distal end side of the probe casings 320-3 and 320-4) to the Y-direction (the side of the measurement section casing 310). The measurement section casing 310 at the root is disposed between the probe casings 320-3 and 320-4. The measurement section casing 310 functions as a reinforcing section. It is desirable that the reinforcing section have a larger size than that of the reinforcing section 360 at the distal end or the like.

FIG. 317 is an example of a sensor device 200 with a groove provided in a spacer according to the seventh embodiment of the present technology. As illustrated as an example in the drawing, it is also possible to form a wave-shaped groove in the spacer 601 or the like. The groove escaping water prevents the water from being delivered along the sensor device 200 and creating a gap. Also, it is possible to curb a clearance created by the sensor device 200 when the sensor device 200 is inserted.

FIG. 318 is a diagram illustrating an example of the groove in the spacer according to the seventh embodiment of the present technology. As illustrated as examples in a, b, and c in the drawing, it is possible to form holes in a net shape in the spacer. The formation of the holes can facilitate delivery of moisture in the soil in the surroundings and prevent inhibition of root growth.

Note that it is possible to use the configurations described in the first to third embodiments and the modification examples thereof as configurations inside the sensor casing 305 (for example, the configurations of the substrate, the antennas, the transmission path, the radio wave absorption material, and the like) in the seventh embodiment described above with reference to FIGS. 309 to 318 and FIGS. 354 to 361.

In this manner, according to the seventh embodiment of the present technology, the probes are reinforced with the pillars and the reinforcing sections, and it is thus possible to enhance the strength of the sensor device 200.

8. Eighth Embodiment

Although the measurement section casing 310 and the probe casing 320 are integrated in the aforementioned first embodiment, there is a concern that the casings may be deformed and the distance between the antennas may change when the probe casing 320 is inserted into the soil with this configuration. Variations in distance between the antennas may cause an error of the measurement value of the amount of moisture. A sensor device 200 according to the eighth embodiment is different from that in the first embodiment in that the probe casing is separated.

FIG. 319 is a diagram illustrating an example of the sensor devices 200 according to a comparative example and the eighth embodiment of the present technology. In the drawing, a is a diagram illustrating an example of the sensor device 200 in a comparative example in which the measurement section casing 310 and the probe casings 320-3 and 320-4 are integrated. In the drawing, b illustrates a state in which the probe casings 320-3 and 320-4 are inserted into the soil in the comparative example. In the drawing, c is a diagram illustrating an example of the sensor device 200 according to the eighth embodiment of the present technology in which the measurement section casing 310 and the probe casings 320-3 and 320-4 are separated. In the drawing, d illustrates a state in which the probe casings 320-3 and 320-4 are inserted into the soil according to the eighth embodiment of the present technology.

As illustrated as an example in a in the drawing, the comparative example in which the measurement section casing 310 and the probe casings 320-3 and 320-4 are integrated is assumed. The probe casings 320-3 and 320-4 include a transmission antenna 221 and a reception antenna 231, and these function as a pair of probes. There may be a case where the connecting location between the measurement section casing 310 and the probes is deformed as illustrated as an example in b in the drawing when the probes are inserted into the soil. Although it is possible to prevent the deformation by sufficiently enhancing the rigidity of the casings, it may be difficult for some reasons, such as cost and usability.

Thus, and in the eighth embodiment of the present technology, the measurement section casing 310 and the probe casings 320-3 and 320-4 (probes) are separated as illustrated as an example in c in the drawing. The measurement section casing 310 and the probe casings 320-3 and 320-4 are electrically connected with coaxial cables 281 and 284 and the like.

Also, transmission antennas 221 to 223, for example, are formed at the probe casing 320-3, and reception antennas 231 to 233, for example, are formed at the probe casing 320-4.

It is possible to prevent the connecting location between the measurement section casing 310 and the probes from being deformed when the probes are inserted into the soil as illustrated as an example in d in the drawing by separating the measurement section casing 310 and the pair of probes.

FIG. 320 is a diagram illustrating an example of the sensor device 200 provided with scales and stoppers according to the eighth embodiment of the present technology. As illustrated as an example in a in the drawing, it is also possible to provide a scale indicating the distance (that is, the depth) from the distal end at each of the probe casings 320-3 and 320-4. In this manner, the user can visually recognize the insertion depth.

Also, as illustrated as an example in b in the drawing, it is also possible to attach stoppers 630 and 631 to the upper portions of the probe casings 320-3 and 320-4 to prevent insertion to a depth exceeding a predetermined distance. It is also possible to provide both the scales and the stoppers.

FIG. 321 is a diagram illustrating an example of the numbers of antennas on the transmission side and the reception side according to the eighth embodiment of the present technology. When the user inserts the pair of probes into arbitrary positions in a separated manner, the distance between the antennas is a different value depending on the insertion positions. Therefore, it is necessary for the moisture measurement system 100 to measure the distance between the antennas. For the measurement of the distance between the antennas, the number of antennas on at least one of the transmission side and the reception side has to be three or more. The reason and the measurement method thereof will be described later.

For example, it is also possible to set the number of antennas on the transmission side to one and to set the number of antennas on the reception side to three as illustrated as an example in a in the drawing. Additionally, it is also possible to set the number of antennas on the transmission side to three and to set the number of antennas on the reception side to one as illustrated as an example in b in the drawing. It is also possible to set the numbers of antennas on both the transmission side and the reception side to three as illustrated as an example in c in the drawing.

FIG. 322 is a block diagram illustrating a configuration example of the signal processing section 154 in the central processing unit according to the eighth embodiment of the present technology. The signal processing section 154 further includes a memory 166 and a distance calculation section 167.

The reciprocation delay time calculation section 162 supplies the calculated reciprocation delay time to the moisture amount measurement section 164 and the memory 166. Also, the propagation transmission time calculation section 163 supplies the calculated propagation transmission time to the moisture amount measurement section 164 and the memory 166. The memory 166 holds these parameter values.

The distance calculation section 167 reads the values held in the memory 166 and calculates the distance between the antennas using the values. The calculation method will be described later. The distance calculation section 167 supplies the calculated distance between the antennas to the moisture amount measurement section 164.

The moisture amount measurement section 164 measures the amount of moisture on the basis of the reciprocation delay time and the propagation transmission time and the distance between the antennas calculated by the distance calculation section 167. If the distance between the antennas varies, the coefficient a and the coefficient b in Expression 6 vary. Therefore, the moisture amount measurement section 164 corrects the coefficient a and the coefficient b in accordance with the measured distance between the antennas and calculates the amount of moisture by Expression 6.

FIG. 323 is a diagram illustrating an example including a plate-shaped member according to the eighth embodiment of the present technology, which is an example of the sensor device 200 provided with a scale and a stopper. In the drawing, a is a diagram illustrating an example of the plate-shaped member 632. A pair of holes from which the pair of probes are inserted are open in the plate-shaped member 632. When the user uses the sensor device 200 according to the present embodiment, (1) the user disposes the plate-shaped member 632 on the surface of the soil as a target of the measurement first, (2) then, the user inserts the two probes into the soil through the pair of holes included in the plate-shaped member 632, and (3) the sensor device 200 measures the moisture in the soil using the two probes inserted into the soil. More specifically, the propagation transmission time between the antennas included in the two probes and the reciprocation delay time related to each of the antennas are measured, the coefficients a and b in Expression 6 are corrected in accordance with the distance between the antennas included in the two probes inserted into the soil, and the amount of moisture is calculated and output using the coefficients after the correction.

In the drawing, b is a diagram illustrating an example of the sensor device 200 with the probes inserted into the holes in the plate-shaped member 632. It is assumed that the probes are provided with scales. Note that as illustrated as an example in c in the drawing, it is also possible to insert the probes provided with stoppers 630 and 631 into the holes in the plate-shaped member 632.

As illustrated as an example in b and c in the drawing, it is possible to keep a constant distance between the probes by using the plate-shaped member 632. Also, the amount of moisture is corrected and output in accordance with the distance between the antennas included in the inserted probes even if the probes are obliquely inserted relative to the ground as a result of inserting the probes into the ground through the holes included in the plate-shaped member 632. Note that in a case where it is possible to insert the probes vertically to the ground, the distance between the antennas is a designed value, and it is thus not necessary to measure the distance between the antennas.

FIG. 324 is a diagram illustrating an example including a rectangular parallelepiped member according to the eighth embodiment of the present technology, which is an example of a sensor device provided with a scale and a stopper. In the drawing, a is a diagram illustrating a rectangular parallelepiped member 633. A pair of holes into which the pair of probes are inserted are open in the rectangular parallelepiped member 633. A method for measuring moisture using the rectangular parallelepiped member 633 is similar to a method for measuring moisture using the plate-shaped member 632.

In the drawing, b is a diagram illustrating an example of the sensor device 200 with the probes inserted into the holes in the rectangular parallelepiped member 633. It is assumed that the probes are provided with scales. Note that as illustrated as an example in c in the drawing, it is also possible to insert the probes provided with stoppers 630 and 631 into the holes in the rectangular parallelepiped member 633.

Also, as illustrated as an example in d in the drawing, it is also possible to attach levels 376 and 377 to the rectangular parallelepiped member 633 and to insert the probes to the holes in the member.

FIG. 325 is a diagram illustrating an example of the sensor device from which the probe casings are not separated according to the eighth embodiment of the present technology. In the drawing, a is a diagram illustrating an example of the sensor device 200 in which the measurement section casing 310 and the probe casings 320-3 and 320-4 are not separated and are integrated. In the drawing, b illustrates an example of a state in which the sensor device 200 in a in the drawing is inserted into the soil.

As illustrated as an example in b in the drawing, there may be a case where a connecting location between the measurement section casing 310 and the probes is deformed and the distance between the antennas changes even in a case where the probes are not separated. Alternatively, deformation may occur due to aging. Therefore, it is also possible to apply the signal processing section 154 in FIG. 320 to the moisture measurement system 100 including the sensor device 200 in which the measurement section casing 310 and the probe casings 320-3 and 320-4 are integrated. It is thus possible to accurately calculate the varying distance between the antennas and to improve accuracy of measurement of the amount of moisture on the basis of the calculated value.

FIG. 326 is a diagram for explaining a method for measuring the distance between the antennas according to the eighth embodiment of the present technology. As illustrated as an example in a in the drawing, it is assumed that the sensor device 200 has transmitted an electromagnetic wave from the transmission antenna 221 and has received the electromagnetic wave by each of the reception antennas 231 to 233.

The aforementioned distance calculation section 167 calculates, as $\tau_{d1}$, a propagation delay time between the transmission antenna 221 and the reception antenna 231 by Expression 5. Similarly, the distance calculation section 167 calculates, as $\tau_{d2}$, a propagation delay time between the transmission antenna 221 and the reception antenna 232 and calculates, as $\tau_{d3}$, a propagation delay time between the transmission antenna 221 and the reception antenna 233.

Here, the following relationship expression is established between the propagation delay time $\tau_d$ and the distance d between the antennas.

$$\tau_d = \{(\varepsilon_b)^{1/2}/C\}d \qquad \text{Expression 25}$$

In the above expression, $\varepsilon_b$ denotes a dielectric constant of the medium, and C denotes a light speed.

On the assumption that the dielectric constant is uniform over the entire medium, the distance d between the antennas is proportional to the propagation delay time $\tau_d$, and $\tau_{d1}$, $\tau_{d2}$, and $\tau_{d3}$ can be replaced with d1, d2, and d3 by Expression 25. d1 denotes the distance between the transmission antenna 221 and the reception antenna 231, and d2 denotes the distance between the transmission antenna 221 and the reception antenna 232. d3 denotes the distance between the transmission antenna 221 and the reception antenna 233.

In the drawing, b illustrates a circle with a constant distance ratio from arbitrary two points. Such a circle is called an Apollonius' circle.

It is assumed that the transmission antenna 221 and the reception antennas 231 to 233 are located on a predetermined x-y plane. The direction in which the reception probe extends is defined as an x-axis direction, and the positions of the reception antennas 231 to 233 on the x axis are defined as x1, x2, and x3. The distance calculation section 167 obtains a circle (Apollonius' circle) with a distance ratio of d1:d2 from x1 and x2 in the x-y plane. The circle corresponds to the circle of the one-dotted chain line in a in the drawing. Also, the distance calculation section 167 obtains a circle with a distance ratio of d2:d3 from x2 and x3. The circle corresponds to the circle of the dashed line in a in the drawing.

The distance calculation section 167 calculates the coordinates of the intersection of the obtained two circles. The coordinates correspond to the position of the transmission antenna 221. The distance calculation section 167 calculates the distance between the calculated coordinates of the transmission antenna 221 and any of x1 to x3 (such as x2) and supplies the distance to the moisture amount measurement section 164.

Note that although consideration has been made on the assumption of the two-dimensional coordinate system in the drawing, it is also possible to perform the arithmetic operation in a three-dimensional coordinate system. In this case, the distance calculation section 167 can obtain the distance by replacing the circles with spheres and performing the calculation.

The distance calculation section 167 uses not only the propagation delay time $\tau_{d2}$ between the transmission antenna 221 and the reception antenna 232 but also the propagation delay time $\tau_{d1}$ between the transmission antenna 221 and the reception antenna 231 and the like when the amount of moisture between the transmission antenna 221 and the reception antenna 232 is measured. In this manner, it is possible to more accurately measure the amount of moisture.

Note that it is possible to use the configurations described in the first to third embodiments and the modification examples thereof in the eighth embodiment described with reference to FIGS. 319 to 326 other than that the probe casings are separated.

In this manner, according to the eighth embodiment of the present technology, the pair of probe casings are separated from the measurement section casing 310, and it is thus possible to prevent deformation of the casings and thus a change in distance between the antennas when the probe casings are inserted into the soil. It is thus possible to more accurately measure the amount of moisture.

9. Ninth Embodiment

Although the pair of probes of the sensor device 200 are inserted into the soil in the aforementioned first embodiment, there is a concern that the probes may be deformed with this configuration when the soil is hard. A moisture measurement system 100 according to the ninth embodiment is different from that in the first embodiment in that deformation of the probes is prevented by inserting a guide into the soil before the insertion of the probes.

FIG. 327 is a diagram illustrating an example of a method for inserting the sensor device 200 according to the ninth embodiment of the present technology. The moisture measurement system according to the ninth embodiment is different from that in the first embodiment in that the moisture measurement system in the ninth embodiment further includes a guide 640. Also, the outer shape of the sensor device 200 according to the ninth embodiment is similar to that in the sixth embodiment including a stem, for example. Note that it is also possible to use the sensor device 200 with an outer shape different from that in the sixth embodiment.

The guide 640 is made of metal, and a pair of projecting portions are formed at the distal end thereof. The shape of these projecting portions is substantially the same as that of the probes. It is desirable that the outer shape of the guide 640 be smaller than the outer shape of the sensor device 200. Particularly, the outer shape of the projecting portions of the guide 640 is preferably smaller than that of the outer shape of the probes of the sensor device 200. It is possible to address various sensor devices 200 with shapes not including any stem by setting the outer shape of the guide 640 to be slightly smaller than that of the sensor device 200.

The user inserts the guide 640 into the soil as illustrated as an example in a in the drawing. The one-dotted chain line in the drawing illustrates the position of the ground surface. Also, the user pulls out the guide 640 as illustrated as an example in b in the drawing. As a result, a hole with the same shape as that of the guide 640 is opened in the ground.

Then, the user inserts the sensor device 200 into the hole as illustrated as an example in c in the drawing and starts measurement of the amount of moisture as illustrated as an example in d in the drawing.

FIG. 328 is a diagram illustrating another example of a method for inserting the sensor device 200 according to the ninth embodiment of the present technology. It is also possible to insert the sensor device 200 into the guide 640 and then to pull out the guide 640. In this case, a hollow member with a hole opened at the distal end such that the inserted sensor device 200 can be pulled out of the hole is used as the guide 640.

The user inserts the guide 640 into the soil as illustrated as an example in a in the drawing. Then, the user inserts the sensor device 200 into the guide 640 as illustrated as an example in b and c in the drawing. Next, the user pulls out the guide 640 as illustrated as an example in d in the drawing. Then, the sensor device 200 starts the measurement of the amount of moisture.

In this manner, according to the ninth embodiment of the present technology, the guide 640 is inserted before the insertion of the sensor device 200, and it is thus possible to prevent deformation of the probes when the sensor device 200 is inserted. It is thus possible to improve accuracy of measurement of the amount of moisture.

10. Tenth Embodiment

Although the pair of probes of the sensor device 200 are inserted into the soil in the aforementioned first embodiment, there may be a case where it is difficult to achieve the insertion with this configuration when the soil is hard. A sensor device 200 according to the tenth embodiment is different from that in the first embodiment in that a spiral-shaped member or a shovel-shaped casing facilitates the insertion.

FIG. 329 is a diagram illustrating an example of the sensor device 200 according to the tenth embodiment of the present technology. In the drawing, a illustrates an example of the sensor device 200 with antennas formed at the spiral-shaped member, and b in the drawing illustrates an example of the sensor device 200 with antennas formed at a sensor casing 305.

As illustrated as examples in a and b in the drawing, the sensor device 200 according to the tenth embodiment includes a spiral-shaped member 650. The spiral-shaped member 650 is a tubular casing formed of a resin or ceramics and extending in a helix shape.

As illustrated as an example in a in the drawing, it is possible to form antennas such as a transmission antenna 221 and a reception antenna 231 at the spiral-shaped member 650. The spiral-shaped member 650 is connected to a rectangular measurement section casing 310. The spiral-shaped member 650 with the antennas formed thereat functions as a probe.

Also, as illustrated as an example in b in the drawing, it is also possible to provide a sensor casing 305 with a pair of projecting portions provided thereon and to connect the spiral-shaped member 650 to the casing. In this case, the antennas are formed at the projecting portions of the sensor casing 305, and the projecting portions function as probes. A rotation movable section 661 is attached to the spiral-shaped member 650, and the spiral-shaped member 650 is connected to the sensor casing 305 via the rotation movable section 661. This. The rotation movable section 661 is a member that is rotatable about the Y axis along the direction in which the probes project.

The spiral-shaped member 650 enables insertion using a torque, and it thus becomes easier to achieve the insertion as compared with the first embodiment including only a two-pronged configuration. Also, more soil is present between the antennas and in the surroundings of the antennas according to the sensor devices 200 illustrated in FIGS. 329a and 329b as compared with a form in which both the transmission antenna and the reception antenna are disposed on the surface of a casing with one screw or pile-shaped casing (related art document: WO 2018/0224382, FIG. 3), and it is thus possible to measure the amount of moisture with high accuracy.

Also, the distal end of the spiral-shaped member 650 may have a shape that is sharpened into a needle shape. This further facilitates the insertion into the soil. Also, the distal end portion of the spiral-shaped member 650 may be formed of metal. Since this further enhances strength of the distal end portion, it becomes yet easier to perform the insertion into the soil.

When the distal end portion of the spiral-shaped member 650 is metal, the transmission antenna 221 and the reception antenna 231 are disposed to be separated from the distal end portion by a predetermined distance or more. It is thus possible to facilitate the insertion into the soil without leading to degradation of accuracy of measurement of moisture.

FIG. 330 is a diagram illustrating an example of the spiral-shaped member and the sensor casing according to the tenth embodiment of the present technology. In the drawing, a illustrates an example of the spiral-shaped member 650, and b in the drawing illustrates an example of the sensor casing 305.

In a case where the rotation movable section 661 is provided, the rotation movable section 661 is fixed to the spiral-shaped member 650 as illustrated as an example in a in the drawing. The lower end of the rotation movable section 661 projects, and the fitting section 662 for fitting to the lower end of the rotation movable section 661 is attached to the upper portion of the sensor casing 305 as illustrated as an example in b in the drawing.

Also, as illustrated as an example in b in the drawing, the distal end of the projecting portion (probe) of the sensor casing 305 is sharp. This facilitates the insertion into the soil. The distal end portion of the probe and the rotation movable section 661 may be formed of metal. This enhances the strength of the distal end portion and the rotation movable section 661 and thus further facilitates the insertion into the soil.

Also, the fitting section 662 enables the rotation movable section 661 and the sensor casing 305 to be detached. Also, in this case, the spiral-shaped member 650 may be formed of metal. In this manner, it is possible to remove the spiral-shaped member 650 from the soil after the probe is inserted into the soil by using the spiral-shaped member 650. Therefore, it is possible to achieve both facilitating of the insertion and measurement of moisture with high accuracy.

FIG. 331 is a diagram illustrating another example of the spiral-shaped member and the sensor casing according to the tenth embodiment of the present technology. In the drawing, a illustrates an example of the spiral-shaped member 650, and b in the drawing illustrates an example of the sensor casing 305. As illustrated as an example in the drawing, it is also possible to fix the rotation movable section 661 to the sensor casing 305 and to provide the fitting section 662 at the spiral-shaped member 650.

FIG. 332 is a diagram illustrating an example of the sensor device provided with double-spiral probes according to the tenth embodiment of the present technology. As illustrated as an example in the drawing, it is possible to cause the spiral-shaped member 650 to have a double-spiral shape and to form antennas such as the transmission antenna 221 at the spiral-shaped member 650. In comparison between the form in FIG. 329a and the form in FIG. 332, both the transmission antenna and the reception antenna cannot be disposed at the same position in the Y direction in the former form while it is possible to dispose both the transmission antenna and the reception antenna at the same position in the Y direction in the latter form.

FIG. 333 is a diagram illustrating an example of the sensor device provided with a spiral-shaped member of double spirals according to the tenth embodiment of the present technology. As illustrated as an example in the drawing, it is also possible to provide the sensor casing 305 with a pair of projecting portions formed thereon and to connect the spiral-shaped member 650 with a double-spiral shape to the casing.

FIG. 334 is a diagram illustrating an example of the spiral shaped-member and the sensor casing of the double spirals according to the tenth embodiment of the present technology. It is also possible to fix the rotation movable section 661 to the spiral-shaped member 650 as illustrated as an example in a in the drawing and to attach the fitting section 662 to an upper portion of the sensor casing 305 as illustrated as an example in b in the drawing. It is also possible to provide the fitting section 662 at the spiral-shaped member 650 as illustrated as an example in c in the drawing and to fix the rotation movable section 661 to the sensor casing 305 as illustrated as an example in d in the drawing.

FIG. 335 is a diagram illustrating an example of a positional relationship of the spiral-shaped member and the antennas according to the tenth embodiment of the present technology. The drawing illustrates the positional relationship when seen from the upper direction. In a case where no antennas are formed at the spiral-shaped member 650 (in a case as in FIG. 329b, for example), the transmission antenna 221 and the reception antenna 231 are disposed inside the spiral-shaped member 650 when seen from the upper side as illustrated as an example in a in FIG. 335. Alternatively, as illustrated as an example in b in the drawing, it is also possible to dispose three antennas inside the spiral-shaped member 650. In this case, the three probes are included in the sensor casing 305, and each of the three antennas is formed at each probe as in FIG. 311d and FIG. 358, for example.

Also, as illustrated as an example in c in FIG. 335, it is also possible to form two antennas at the spiral-shaped member 650 (as in the case of FIG. 329a, for example). Alternatively, as illustrated as an example in d in FIG. 335, it is also possible to form three antennas at the spiral-shaped member 650.

As illustrated as examples in the drawing, the numbers of the transmission antennas and the reception antennas may not be the same. In other words, measurement may be performed not only by a measurement method in which the transmission antenna and the reception antenna have a one-to-one correspondence but also by a route of one-to-multiple antennas or multiple-to-one antennas.

FIG. 336 is an example of a sectional view of the spiral-shaped member according to the tenth embodiment of the present technology. As illustrated as an example in a in the drawing, a coaxial cable 653 is stored inside the tubular casing 651, and a part between the coaxial cable 653 and the tubular casing 651 is filled with a radio wave absorption material 652, in the spiral-shaped member 650. As illustrated as an example in b in the drawing, it is also possible to arrange two or more coaxial cables 653 in a circular space and to fill the part between the space and the tubular casing 651 with the radio wave absorption material 652.

Also, as illustrated as an example in c in the drawing, it is also possible to fill the part between the two or more coaxial cables 653 and the tubular casing 651 with the radio wave absorption material 652. As illustrated as an example in d in the drawing, it is also possible to cover each of the coaxial cables 653 with the radio wave absorption material 652 and to store them in the tubular casing 651. As illustrated as an example in e in the drawing, it is also possible to cover the flexible substrate 654 with the radio wave absorption material 652 and to store them in the tubular casing 651.

FIG. 337 is a diagram illustrating an example of the sensor device including the shovel-shaped casing according to the tenth embodiment of the present technology. It is also possible to incorporate the sensor casing 305 in the shovel-shaped casing 670 without using the spiral-shaped member 650.

The shovel-shaped casing 670 includes a grip 671 and a flat plate section 672. A blade 673 is formed at a distal end of the flat plate section 672. Also, a space is formed inside the flat plate section 672, and projecting portions (probes) of the sensor casing 305 project into the space. The grip 671 and the blade 673 facilitate insertion into the soil, the space formed in the surroundings of the probes enables the soil to be present in the surroundings of the probes, and it is thus possible to prevent accuracy of measuring moisture from being degraded.

The flat plate section 672 is formed of a resin or ceramics. It is desirable that the grip 671 and the blade 673 be formed of a resin, ceramics, or metal. Here, the flat plate section 662 reflects electromagnetic waves emitted from the probes and is thus a portion which is likely to adversely affect measurement of moisture in the soil. Therefore, it is desirable that the flat plate section 662 be formed of a resin or ceramics that well transmits the electromagnetic waves rather than metal that strongly reflects the electromagnetic waves. On the other hand, metal may be used for the grip 671 and the blade 673 located far from the probes in order to enhance the strength.

In the drawing, b is an example of a sectional view cut along the line A-A' in a in the drawing. As illustrated as an example in b in the drawing, it is desirable that each of the pair of probes be located on the center line of the flat plate section 662. Also, as illustrated as an example in c in the drawing, the size (thickness) of the flat plate section 662 in the Z-axis direction may be smaller than the diameter of the probes.

Also, as illustrated as an example in d in the drawing, the grip 671, the blade 673, and the flat plate section 672 may be separate members. As illustrated as an example in e in the drawing, the flat plate section 672 and the grip 671 may be separate members. Also, in the form illustrated as an example in a in the drawing, the flat plate section 672 is adapted such that the material configuring the flat plate section 672 is disposed only at the outer edge part of the flat plate section 672 and the inside of the outer edge portion is hollow. On the other hand, a form in which the material configuring the flat plate section 672 is disposed both at the outer edge of the flat plate section 672 and at the partitioning section located inside the outer edge portion and the hollow region disposed inside the outer edge portion is disposed such that it is split into a plurality of parts by the partitioning section as illustrated as an example in e in the drawing may be adopted. Also, a structure in which the probes are incorporated in the partitioning section may be adopted. As illustrated as an example in f in the drawing, a structure in which the blade 673 and the flat plate section 672 are separate members and two or more hollow regions are included inside the outer edge portion included in the flat plate section 672 may be adopted. As illustrated as an example in g in the drawing, a structure in which the probes are incorporated in the outer edge portion of the flat plate section 672 and one hollow region is disposed inside the outer edge portion may be adopted.

FIG. 338 is a diagram illustrating an example of a shovel-shaped casing according to the tenth embodiment of the present technology. The drawing illustrates only the part corresponding to the shovel-shaped casing 670 in FIG. 337.

FIG. 339 is a diagram illustrating an example of the shape of a grip according to the tenth embodiment of the present technology. As illustrated as an example in a in the drawing, the columnar grip 671 is vertically attached to the center position of the flat plate section 672. As illustrated as an example in b in the drawing, it is also possible to attach the grip 671 to a side further outward than the center of the flat plate section 672.

As illustrated as an example in c in the drawing, the grip 671 may have a shape including a bent portion. As illustrated as examples in d and e in the drawing, there may be a plurality of bent portions. In e in the drawing, a hollow rectangle is formed.

As illustrated as an example in f in the drawing, it is also possible to connect the grip 671 to the flat plate section 672 with a handle 675. At that time, the grip 671 may have a hollow rectangular shape as illustrated as an example in g in the drawing or may have a hollow triangular shape as illustrated as an example in h in the drawing.

These structures are determined in consideration of the type of soil into which the probes are inserted, the depth of insertion, conditions at the time of installation, and an environment after the installation.

FIG. 340 is a diagram illustrating an example of the shape of the blade according to the tenth embodiment of the present technology. The blade 673 may be a one-sided blade as illustrated as an example in a in the drawing or may be a double-sided blade as illustrated as an example in b in the drawing. The one-sided blade is suitable for relatively soft soil since it is more easily inserted thereinto but has lower strength, and the double-sided blade is suitable for hard soil since it has excellent strength. In the drawing, a and b illustrate sectional shapes of the blades, and c and the following drawings illustrate shapes of the blades seen from the front.

In the case of the double-sided blade, the shape may be an isosceles triangle as illustrated as an example in c in the drawing or may be a right triangle as illustrated as an example in d in the drawing. As illustrated as an example in e in the drawing, the shape may be another triangle. Also, as illustrated as examples in f, g, and h in the drawing, sides thereof may be curved. These structures are determined in consideration of the type of soil into which the probes are inserted, depth of insertion, conditions at the time of installation, and an environment after the installation.

FIG. 341 is a diagram illustrating an example of the sensor device 200 with a scaffold member added thereto according to the tenth embodiment of the present technology. In the drawing, a is an example of a front view of the sensor device 200 with a scaffold member 675 added thereto. In the drawing, b is an example of a top view of the sensor device 200 in a in the drawing.

The scaffold member 675 is a member with a wider area than the flat plate member 672 when seen from the above (in the depth direction). The user can place his/her feet on corresponding locations by attaching the scaffold member 675 to an end surface of the flat plate member 672. It becomes easier to insert the probes into the soil by the user applying his/her weight to the scaffold member 675.

In this manner, according to the tenth embodiment of the present technology, the spiral-shaped member and the shovel-shaped casing are provided, and it thus becomes easier to insert the probes into the soil.

11. Eleventh Embodiment

In the aforementioned first embodiment, the sensor device 200 performs measurement using differences in dielectric constants of air, mud, and water in the soil. However, there may be a case where radio waves are absorbed by the medium, the signal-noise (SN) ratio of an impulse response decreases, and an error occurs in calculation of a propagation delay time which is a peak of the impulse response.

FIG. 342 is a block diagram illustrating an example of a sensor device 200 according to the eleventh embodiment of the present technology. Configurations other than a sensor control section 211, a transmitter 214, a receiver 215, a transmission antenna 221, and a reception antenna 231 in the sensor device 200 are omitted in the drawing.

As illustrated as an example in a in the drawing, the sensor device 200 according to the eleventh embodiment is different from that in the first embodiment in that the sensor device 200 according to the eleventh embodiment includes a variable attenuator 720 in addition to a signal source 710 in the transmitter 214. The signal source 710 generates a transmission signal of predetermined power and supplies the transmission signal to the variable attenuator 720. The variable attenuator 720 attenuates the transmission signal (transmission wave) and supplies the transmission signal to the transmission antenna 221 in accordance with a control signal from the sensor control section 211. In other words, the variable attenuator 720 reduces the amplitude of the transmission signal (transmission wave) and supplies the transmission signal to the transmission antenna 221.

The sensor control section 211 adjusts the amount of attenuation of the variable attenuator 720 to compensate for the amount of attenuation of the electromagnetic wave in the soil on the basis of the power of the reception signal (reception wave) received by the receiver 215, that is, the amount by which the electromagnetic wave has been attenuated until the electromagnetic wave transmitted from the transmission antenna 221 is received by the reception antenna 231. For example, (1) the variable attenuator 720 attenuates the power of the transmission signal generated by the signal source 710 (or the amplitude of the generated transmission signal) at the first attenuation rate and causes the transmission antenna 221 to transmit this as a first electromagnetic wave in a stage in which the transmission of the electromagnetic wave from the transmission antenna 221 is started or a stage before outputting "the result of measuring the propagation delay amount of the electromagnetic wave in the soil used to calculate the amount of moisture in the soil". (2) The amount by which the electromagnetic wave is attenuated while it is propagated in the soil from the transmission antenna 221 to the reception antenna 231 is obtained by the reception antenna 231 receiving the first electromagnetic wave. Then, the variable attenuator 720 adjusts the amount by which the variable attenuator 720 is caused to attenuate the electromagnetic wave to compensate for the amount by which the electromagnetic wave is attenuated in the soil. In other words, the variable attenuator 720 attenuates the power of the transmission signal generated by the signal source 710 (or the amplitude of the generated transmission signal) at the second attenuation rate that is lower than the first attenuation rate (in other words, increases the power or the amplitude of the transmission signal as compared with the above case in (1)) to compensate for the amount by which the electromagnetic wave is attenuated in the soil in advance) and causes the transmission antenna to transmit this as a second electromagnetic wave. (2') The power (or the amplitude) of the electromagnetic wave (reception signal) received by the reception antenna 231 is obtained by the reception antenna 231 receiving the first electromagnetic wave. Then, the variable attenuator 720 adjusts the amount by which the variable attenuator 720 is caused to attenuate the electromagnetic wave such that the power (or the amplitude) of the electromagnetic wave (reception signal) received by the reception antenna 231 becomes a predefined value (target value). In other words, the variable attenuator 720 attenuates the power of the transmission signal generated by the signal source 710 (or the amplitude of the generated transmission signal) at the second attenuation rate that is lower than the first attenuation rate (in other words, increases the power or the amplitude of the transmission signal as compared with the above case in (1) such that the power or the amplitude of the reception signal becomes the predefined value (target value) and causes the transmission antenna to transmit this as the second electromagnetic wave.

Also, as illustrated as an example in b in the drawing, it is also possible to provide the variable amplifier 721 instead of the variable attenuator 720 in the transmitter 214 and to adjust the amount of amplification of the transmission signal (transmission wave) by the sensor control section 211.

In the form in which the variable amplifier 721 illustrated as an example in b in the drawing is included, the sensor control section 211 adjusts the amount of amplification of the variable amplifier 721 to compensate for the amount of attenuation of the electromagnetic wave in the soil, that is, the amount by which the electromagnetic wave transmitted from the transmission antenna 221 has been attenuated in the soil until it is received by the reception antenna 231 on the basis of the power of the reception signal (reception wave) received by the receiver 215. For example, (1) the variable amplifier 721 amplifies the power of the transmission signal generated by the signal source 710 (or the amplitude of the generated transmission signal) at the first amplification rate and causes the transmission antenna 221 to transmit this as the first electromagnetic wave in the stage in which the transmission of the electromagnetic wave from the transmission antenna 221 is started or the stage before outputting "the result of measuring the propagation delay amount of the electromagnetic wave in the soil used to calculate the amount of moisture in the soil". (2) The amount by which the electromagnetic wave is attenuated while it is propagated in the soil from the transmission antenna 221 to the reception antenna 231 is obtained by the reception antenna 231 receiving the first electromagnetic wave. Then, the variable amplifier 721 adjusts the amount by which the electromagnetic wave is amplified by the variable amplifier 721 to compensate for the amount by which the electromagnetic wave is attenuated in the soil. In other words, the variable amplifier 721 amplifies the power of the transmission signal generated by the signal source 710 (or the amplitude of the generated transmission signal) at the second amplification rate that is greater than the first amplification rate (that is, increases the power or the amplitude of the transmission signal as compared with the above case in (1)) to compensate for the amount by which the electromagnetic wave is attenuated in the soil in advance, and causes the transmission antenna to transmit this as the second electromagnetic wave. Alternatively, (2') the power (or the amplitude) of the electromagnetic wave (reception signal) received by the reception antenna 231 is obtained by the reception antenna 231 receiving the first electromagnetic wave. Then, the variable amplifier 721 adjusts the amount by which the variable amplifier 721 amplifies the electromagnetic wave is adjusted such that the power (or the amplitude) of the electromagnetic wave (reception signal) received by the reception antenna 231 becomes a predefined value (target value). In other words, the variable amplifier 721 amplifies the power of the transmission signal generated by the signal source 710 (or the amplitude of the generated transmission signal) at the second amplification rate that is greater than the first amplification rate (in other words, increases the power or the amplitude of the transmission signal as compared with the above case in (1)) such that the power or the amplitude of the reception signal becomes the predefined value (target value), and causes the transmission antenna to transmit this as the second electromagnetic wave.

In this manner, the sensor device 200 according to the eleventh embodiment of the present technology includes the variable attenuator 720 or the variable amplifier 721 between the signal source 710 and the transmission antenna 221 of the transmission signal. Additionally, the amount by which the electromagnetic wave is attenuated while it is propagated in the soil from the transmission antenna to the reception antenna is obtained when the transmission signal (electromagnetic wave) transmitted from the transmission antenna 221 is received as a reception signal (electromagnetic wave) by the reception antenna 231 and the amount of moisture contained in the soil is measured, and adjustment to increase the power or the amplitude of the transmission signal transmitted from the transmission antenna 221 to compensate for the amount of attenuation is performed. Then, the transmission signal after the adjustment transmitted from the transmission antenna 221 is received by the reception antenna 231, and the amount of moisture contained in the soil between the transmission antenna 221 and the reception antenna 231 is measured. In this manner, the SN ratios of the transmission signal transmitted from the transmission antenna 221 and the reception signal received by the reception antenna 231 are improved, and accuracy of measuring the amount of moisture is thus improved.

FIG. 343 is an example of a timing chart illustrating operations of each section in the sensor device 200 according to the eleventh embodiment of the present technology, which is an example of a timing chart in a case where the configuration illustrated in FIG. 342a is used.

(1) At the beginning of the timing chart illustrated in FIG. 343, the sensor control section 211 activates the sensor device 200 first ("set activation" in FIG. 343).

(2) Next, the sensor control section 211 sets the aforementioned first attenuation rate for the variable attenuator 720 as the attenuation rate thereof. In this manner, attenuation of the power of the transmission signal generated by the signal source 710 (or the amplitude of the generated transmission signal) at the aforementioned first attenuation rate by the variable attenuator 720 is set ("set amount of attenuation" in FIG. 343).

(3) Next, the transmission signal attenuated at the first attenuation rate is transmitted from the transmission antenna 221, and this is received as a reception signal by the reception antenna 231 ("perform transmission" and "perform reception" in FIG. 343).

(4) Next, the amount by which the electromagnetic wave (transmission signal) transmitted from the transmission antenna 221 is attenuated in the soil until it is received by the reception antenna 231 is obtained ("calculate difference" in FIG. 343).

(5) The sensor control section 211 sets the aforementioned second attenuation rate for the variable attenuator 720 as the attenuation rate thereof to compensate for the amount of attenuation in the soil obtained in (4) above. In this manner, attenuation of the power of the transmission signal generated by the signal source 710 (or the amplitude of the generated transmission signal) at the aforementioned second attenuation rate by the variable attenuator 720 to compensate for the amount of attenuation in the soil is set ("set amount of attenuation" in FIG. 343).

(6) The formal measurement of the amount of moisture in the soil is started by the variable attenuator 720 attenuating the transmission signal generated by the signal source 710 at the second attenuation rate and by the transmission antenna transmitting the transmission signal ("start measurement" in FIG. 343).

(7) As described above in the section of the time-division scanning measurement, the sensor device 200 according to the present technology repeats the operations of transmitting, receiving, and examining the electromagnetic wave (wave transmission, reception, and examination operations) at one measurement frequency of one transmission and reception antenna pair a plurality of times to enhance reproducibility of the measurement result. Once the operations of transmitting, receiving, and examining the electromagnetic wave are repeatedly executed a plurality of times and are then ended, one-time measurement is completed ("complete measurement" in FIG. 343).

Here, as illustrated in FIG. 343, the period from (1) to (5) above is the period during which the power or the amplitude of the transmission signal is adjusted ("output adjustment period" in FIG. 343). Then, the period from (6) to (7) above is the measurement period during which the amount of moisture in the soil is formally measured ("measurement period" in FIG. 343). Note that although FIG. 343 is an example of the timing chart in the case where the configuration illustrated in FIG. 342a is used, the timing chart in a case where the configuration illustrated in FIG. 342b is used is the same as that in FIG. 343 other than that "set amount of attenuation" in FIG. 343, that is, the setting of the amount of attenuation by the variable attenuator 720 is the setting of the amount of amplification by the variable amplifier 721.

FIG. 344 is a diagram illustrating an example of a transmission waveform according to the eleventh embodiment of the present technology. As illustrated as an example in the drawing, the sensor device 200 starts transmission of a first electromagnetic wave, the amplitude of which is a first amplitude, at the timing T0. Then, the first electromagnetic wave, the amplitude of which is the first amplitude, is transmitted during the output adjustment period described with reference to FIG. 343. In the output adjustment period, a second amplitude as an amplitude of the transmission signal at the time of formal measurement of the amount of moisture in the soil is determined. The second electromagnetic wave, the amplitude of which is the second amplitude, is transmitted from the timing T1, which is the formal measurement period of the amount of moisture in the soil. After the second electromagnetic wave, the amplitude of which is the second amplitude, is transmitted for a specific measurement period, the transmission of the electromagnetic wave is ended, and the sensor device 200 outputs a measurement result at the timing T2. Once the measurement result is output at the timing T2, the sensor device 200 may transition to a sleep state.

FIG. 345 is a diagram illustrating an example of a transmission waveform when transmission power is adjusted in accordance with the amount of moisture according to the eleventh embodiment of the present technology. More specifically, the drawing represents a waveform of a transmission signal transmitted by the sensor device 200 in first and second states in a case where (1) the sensor device 200 performs first moisture measurement in the first state in which the amount of moisture in the soil is the first amount of moisture first, and (2) then, the sensor device 200 performs second moisture measurement in the second state in which the amount of moisture in the soil has changed to the second amount of moisture that is greater than the first amount of moisture.

(1) First, in the first state in which the amount of moisture in the soil is the first amount of moisture, the sensor device 200

(1-1) is activated at the timing T0, (1-2) transmits the first electromagnetic wave (transmission signal) with the first amplitude generated by the variable attenuator 720 performing attenuation at a first attenuation rate or by the variable amplifier 721 performing amplification at a first amplification rate and thereby performs output adjustment in the first measurement from the timing T0 to T1, (1-3) transmits the second electromagnetic wave (transmission signal) with the second amplitude generated by the variable attenuator 720 performing attenuation at a second attenuation rate or by the variable amplifier 721 performing amplification at a second amplification rate and thereby performs formal measurement of the amount of moisture in the first measurement from the timing T1 to T2, (1-4) outputs a measurement result and transitions to the sleep state at the timing T2, and (2) then, in the second state in which the amount of moisture in the soil has changed to the second amount of moisture that is greater than the first amount of moisture, the sensor device 200

(2-1) is activated at the timing T3, (2-2) transmits the first electromagnetic wave (transmission signal) with the first amplitude generated by the variable attenuator 720 performing attenuation at the first attenuation rate or by the variable amplifier 721 performing amplification at the first amplification rate and thereby performs output adjustment in second measurement from the timing T3 to T4, (2-3) transmits a third electromagnetic wave (transmission signal) with a third amplitude that is greater than the second amplitude generated by the variable attenuator 720 performing attenuation at a third attenuation rate that is lower than the second attenuation rate or by the variable amplifier 721 performing amplification at a third amplification rate that is higher than the second amplification rate and thereby performs formal measurement of the amount of moisture in the second measurement from the timing T4 to T5, and (2-4) outputs a measurement result and then transitions to the sleep state at the timing T2. As described above with reference to FIG. 140, the moisture measurement system 100 and the central processing unit 150 included therein according to the present technology obtain the amount of moisture contained in the soil using the fact that the propagation delay time τd of the electromagnetic wave propagated in the soil has a linear relationship (Expression 6) with the amount x of moisture in the soil. However, the propagation delay time τd changes depending on the specific dielectric constant ε of the medium as well. Therefore, there may be a case where it is not possible to accurately measure the amount of moisture contained in the medium (air in this case) in a case where the sensor device 200 (more specifically, the transmission antenna 221 and the reception antenna 231 included in the sensor device 200) is disposed in a second medium (for example, air) with a significantly different dielectric constant ε from that of a first medium (for example, soil) assumed as a target of measurement of the amount of moisture and the sensor device 200 is caused to perform a measurement operation. For example, if the amount x of moisture is calculated from the propagation delay time τd of the electromagnetic wave using the above linear relationship (Expression 6) in a state in which the sensor device 200 is exposed to the air and is caused to operate, the calculation value of the amount of moisture may be a negative value.

In such a case, the sensor device 200 may not perform the aforementioned operation of increasing the power of the transmission signal (or the amplitude of the transmission signal) using the variable attenuator 720 or the variable amplifier 721. Then, a message representing that the measurement has not been accurately performed may be output from the output section 156. For example, an error message, a message representing that the amount of moisture as a measurement target is outside the measurable range of the amount of moisture, or a negative value as the amount of moisture may be displayed on the output section 156.

FIG. 346 is a diagram illustrating another example of the transmission waveform when transmission power is adjusted in accordance with the amount of moisture according to the eleventh embodiment of the present technology, and illustrates an example of the transmission waveform transmitted by the sensor device 200 including a case where the sensor device 200 is disposed in a medium in which the amount of moisture cannot accurately be measured as described above. More specifically, it illustrates an example of the waveform of the transmission signal transmitted by the sensor device 200 in first to third states in a case where (1) first, similarly to FIG. 345, the sensor device 200 performs first moisture measurement in the first state in which the amount of moisture contained in the medium is the first amount of moisture by disposing the sensor device 200 (more specifically, the transmission antenna 221 and the reception antenna 231 included in the sensor device 200) in the first medium (that is, soil), the dielectric constant of which is within a range defined in advance as a measurement target from the timing T0 to T2, (2) then, similarly to FIG. 345, the sensor device 200 performs second moisture measurement in the second state in which the amount of moisture contained in the first medium has changed to a second amount of moisture that is greater than the first amount of moisture by disposing the sensor device 200 (more specifically, the transmission antenna 221 and the reception antenna 231 included in the sensor device 200) in the first medium (that is, soil), the dielectric constant of which is within the range defined in advance as the measurement target from the timing T3 to T5, and (3) then, the sensor device 200 performs third moisture measurement in the third state which is a state in which the sensor device 200 (more specifically, the transmission antenna 221 and the reception antenna 231 included in the sensor device 200) is disposed in the second medium (for example, air), the dielectric constant of which is outside the range defined in advance as the measurement target.

Here, since the waveform of the transmission signal transmitted by the sensor device 200 during (1) above (in other words, from the timing T0 to T2) and during (2) above (in other words, from the timing T3 to T5) is the same as the waveform illustrated in FIG. 345, description thereof will be omitted here.

Also, in the third state in which the sensor device 200 is disposed in the second medium, the dielectric constant of which is outside the range of the dielectric constant of the first medium defined in advance as the measurement target in (3) above, the sensor device 200

(3-1) is activated at the timing T6, and (3-2) transmits a first electromagnetic wave (transmission signal) with the first amplitude generated by the variable attenuator 720 performing attenuation at the first attenuation rate or by the variable amplifier 721 performing amplification at the first amplification rate and receives and examines the first electromagnetic wave from the timing T6 to T7. Then, as a result, the dielectric constant of the medium through which the electromagnetic wave is propagated between the transmission antenna 221 and the reception antenna 231 is determined to be outside the range defined in advance as the target of measurement of the amount of moisture.

(3-3) At the timing T7, a message representing that it is not possible to accurately measure the amount of moisture in the medium, an error message, or a negative value as the amount of moisture is output to the output section 156. Then, the sensor device 200 transitions to the sleep state.

FIG. 347 is a diagram illustrating an example of waveforms of transmission and reception signals according to the eleventh embodiment of the present technology. In the drawing, the solid line illustrates the waveform of the transmission signal transmitted from the transmission antenna 221, the dashed line illustrates the waveform of the reception signal received by the reception antenna 231, and the two-dotted chain line illustrates the magnitude of the amplitude as a target value of reception power. Also, in the drawing, the first wave of the transmission waveform and the reception waveform corresponds to the electromagnetic wave in the output adjustment period illustrated in FIG. 344, and the second wave of the transmission waveform and the reception waveform corresponds to the electromagnetic wave in the measurement period illustrated in FIG. 344. In the drawing, a represents a case where the amplitude of the first electromagnetic wave received by the reception antenna 231 during the output adjustment period has become the same magnitude as that of the amplitude as a target value of reception power. It represents that in this case, the second electromagnetic wave during the measurement period is transmitted at the same amplitude as that of the first electromagnetic wave from the transmission antenna and is received at the same amplitude as that of the first electromagnetic wave by the reception antenna. In the drawing, b represents a case where the amplitude of the first electromagnetic wave received by the reception antenna 231 during the output adjustment period has become smaller than the amplitude as the target value of reception power. It represents that in this case, the amplitude of the second electromagnetic wave during the measurement period is set to be greater than that of the first electromagnetic wave, and the second electromagnetic wave is then transmitted from the transmission antenna, such that the amplitude of the reception waveform received by the reception antenna has the same magnitude as that of the amplitude as the target value of reception power.

As illustrated as an example in b in the drawing, the sensor device 200 increases transmission power in accordance with the reception power.

In this manner, according to the eleventh embodiment of the present technology, the sensor device 200 can improve an SN ratio by adjusting the magnitude of the transmission power in accordance with the magnitude of the reception power.

Note that in a case where the magnitude of the transmission power of the electromagnetic wave is limited by laws or rules in the country where the sensor device 200 is used, the sensor device 200 may adjust the transmission power to follow the magnitude of the transmission power limited by the laws or the rules.

12. Twelfth Embodiment

Although the measurement section substrate 311 is disposed at a position at which the probe extending direction (Y-axis direction) and the substrate plane are parallel with each other in the aforementioned first embodiment, it is also possible to dispose the measurement section substrate 311 at a position at which the Y-axis direction and the substrate plane are parallel with each other. A sensor device 200 according to the twelfth embodiment is different from that in the first embodiment in that the measurement section substrate 311 is disposed at the position at which the Y-axis direction and the substrate plane are vertical to each other.

FIG. 348 is a diagram for explaining the twelfth embodiment of the present technology. The effect that moisture is accurately measured by disposing the plane-shaped transmission antenna and reception antenna to face each other at positions with the predetermined distance provided therebetween and fixing the orientations and positions of the transmission antenna and the reception antenna can be obtained not only in the mode illustrated in FIGS. 4 and 75, and the like in which the measurement section substrate extends parallel with the one surface defined by the X axis and the Y axis but also in the mode in FIG. 348 in which the measurement section substrate extends parallel with the one surface defined by the X axis and the Z axis.

The sensor device 200 included in the twelfth embodiment of the present technology adopts the mode in which the measurement section substrate extends parallel with the one surface defined by the X axis and the Z axis.

Note that in the above twelfth embodiment of the present technology, it is possible to apply the configurations included in the first embodiment and the modification examples thereof of the present technology as the configurations other than the above extending direction of the measurement section substrate. In one example, a mode in which the measurement section substrate extending parallel with the XZ plane, the transmission probe substrate, and the reception probe substrate are accommodated in one sensor casing 305 can also be adopted.

It should be noted that the above-described embodiments show examples for embodying the present technology, and matters in the embodiments and matters specifying the invention in the claims have a corresponding relationship with each other. Similarly, the matters specifying the invention in the claims and the matters in the embodiments of the present technology having the same name have a corresponding relationship with each other. However, the present technology is not limited to the embodiments and can be embodied by applying various modifications to the embodiments without departing from the gist thereof.

The effects described in the present specification are merely examples and are not intended as limiting, and other effects may be obtained.

Note that the configuration included in the sensor device 200 according to the first embodiment of the present technology can also be represented as follows, for example.

A sensor device including: a transmission antenna (for example, the transmission antenna 221) that sends a signal (an electrical signal, an AC signal, a transmission signal) as an electromagnetic wave; a reception antenna (for example, the reception antenna 231) that receives the electromagnetic wave sent from the transmission antenna and transmitted through a medium (M); a measurement section (for example, the measurement circuit 210, a part of the measurement circuit 210 such as a circuit excluding the antenna 213 from the measurement circuit 210, for example) that measures the electromagnetic wave propagated to the reception antenna; and a sensor casing (sensor casing 305), the sensor device further including: a transmission substrate (the transmission intra-probe substrate 321) that is an electronic substrate including a plurality of wiring layers (for example, the first wiring layer in which the conductor: shield layer 254 is arranged and the second wiring layer in which the conductor: signal line 255 is arranged); and a reception substrate (reception intra-probe substrate 322) that is an electronic substrate including a plurality of wiring layers (for example, the first wiring layer in which the conductor 254 is arranged and the second wiring layer in which the conductor: signal line 255 is arranged), or further including: a first covering layer that partially covers an outer periphery of the transmission substrate and is formed of an electromagnetic wave absorption material (for example, the electromagnetic wave absorption material 251 or the radio wave absorption section 341); and a second covering layer that partially covers an outer periphery of the reception substrate and is formed of an electromagnetic wave absorption material (for example, the electromagnetic wave absorption material 251 or the radio wave absorption section 344), in which the sensor casing includes a transmission probe casing that is a part of the sensor casing and accommodates the transmission substrate and a reception probe casing that is another part of the sensor casing and accommodates the reception substrate, the transmission substrate includes a transmission path for transmission (for example, the signal line 255 and the shield layers 254 and 256 in FIGS. 87 and 88) and a transmission exposure section (for example, the radiation element 330 in FIG. 4, the radiation element: signal line 255 in FIG. 19, or the conductors 258 and 259 in FIG. 37) configuring a part of the transmission antenna, the transmission path for transmission is a conductor that is formed using the wiring layers included in the transmission substrate, includes a first shield layer and a first signal line in a superimposed manner, and is electrically connected to the measurement section, the transmission exposure section is a conductor that is formed using the wiring layers included in the transmission substrate, is electrically connected to the first signal line, and is exposed from the first shield layer or the first covering layer, the reception substrate includes a transmission path for reception (for example, the same as the signal line 255 and the shield layers 254 and 256 included in the transmission substrate illustrated as an example in FIGS. 86 and 87) and a reception exposure section (for example, the same as the radiation element 330 in FIG. 4, the radiation element 255 in FIG. 19, or the conductors 258 and 259 in FIG. 37) that configures a part of the reception antenna, the transmission path for reception is formed using the wiring layers included in the reception substrate, includes a second shield layer and a second signal line in a superimposed manner, and is electrically connected to the measurement section, the reception exposure section is a conductor that is formed using the wiring layers included in the reception substrate, is electrically connected to the second signal line, and is exposed from the second shield layer or the second covering layer, each of the transmission exposure section and the reception exposure section has a larger size both in a second direction (the lengthwise direction of the substrate such as the Y-axis direction in FIGS. 4, 35, and 88, for example) that is a direction orthogonal to a first direction (the thickness direction of the substrate such as the X-axis direction in FIGS. 4, 37, and 88, for example) and is parallel with the extending direction of the transmission path and in a third direction (the widthwise direction of the substrate such as the Z-axis direction in FIGS. 4, 37, and 88, for example) that is orthogonal to the first and second directions than in the first direction that is the direction of the superimposition, and extends parallel with the plane defined by the second direction and the third direction, and the transmission path for transmission and the transmission exposure section formed using the wiring layers included in the transmission substrate and the transmission path for reception and the reception exposure section formed using the wiring layers included in the reception substrate are disposed to face each other such that the extending direction of the plane of the transmission exposure section and the extending direction of the plane of the reception exposure section are parallel with each other, and are disposed at positions separated from each other by a predetermined distance, with the extending directions and the positions fixed in the sensor casing.

Also, the configuration included in the sensor device 200 according to the first modification example of the second embodiment of the present technology can also be represented as follows, for example.

A sensor device including: a transmission antenna (the transmission antenna 221 in FIG. 237, for example) that sends a signal (an electrical signal, an AC signal, a transmission signal) as an electromagnetic wave; a reception antenna (the reception antenna 231 in FIG. 237, for example) that receives the electromagnetic wave sent from the transmission antenna and transmitted through a medium (M); a measurement section (for example, the measurement circuit 210, a part of the measurement circuit 210 such as a circuit excluding the antenna 213 from the measurement circuit 210, for example) that measures the electromagnetic wave propagated to the reception antenna; and a sensor casing (the sensor casing 305), the sensor device further including: a transmission substrate (transmission substrate projecting portion) that is an electronic substrate including a plurality of wiring layers (for example, the first wiring layer with the conductor: shield layer 254 arranged therein and the second wiring layer with the conductor: signal line 255 arranged therein in FIGS. 242 and 243); and a reception substrate (reception substrate projecting portion) that is an electronic substrate including a plurality of wiring layers (for example, the same as the first wiring layer with the conductor: shield layer 254 arranged therein and the second wiring layer with the conductor: signal line 255 arranged therein in FIGS. 242 and 243); and a measurement section substrate (the substrate rectangular part of the electronic substrate 311-1) that is an electronic substrate including a plurality of wiring layers and includes the measurement section, or further including: a first covering layer that partially covers an outer periphery of the transmission substrate and is formed of an electromagnetic wave absorption material (for example, the electromagnetic wave absorption material 251 or the radio wave absorption section 341); and a second covering layer that partially covers an outer periphery of the reception substrate and is formed of an electromagnetic wave absorption material (for example, the electromagnetic wave absorption material 251 or the radio wave absorption section 344), in which the sensor casing includes a transmission probe casing that is a part of the sensor casing and accommodates the transmission substrate and a reception probe casing that is another part of the sensor casing and accommodates the reception substrate, the transmission substrate includes a transmission path for transmission (for example, the part, which is located outside the rectangles illustrated with the reference signs Dy and Dz, in which the signal line 255 and the shield layers 254 and 256 are superimposed, in FIGS. 49b to 49d or the part, which is located outside the rectangular region circumscribing the slot, in which the signal line 255 and the shield layers 254 and 256 are superimposed, in FIGS. 242 and 243) and a transmission slot antenna (the region located inside the rectangles illustrated with the reference signs Dy and Dz in FIGS. 48 to 50 or FIGS. 238 to 240, particularly, in FIGS. 49b to 49d), the transmission path for transmission is a conductor that is formed using the wiring layers included in the transmission substrate, includes a first shield layer and a first signal line in a superimposed manner, and is electrically connected to the measurement section, the transmission slot antenna includes a radiation element (for example, a part of the conductor: shield layer 254, which corresponds to the inside of the rectangles illustrated with the reference signs Dy and Dz in FIG. 49d) including a slot and a transmission slot signal line section (for example, the signal line 255 intersecting the slot in FIG. 49d) that is electrically connected to the first signal line and intersects the slot, and the radiation element is a conductor that is electrically connected to the first shield layer (a part of the conductor: shield layer 254, which corresponds to the outside of the rectangles illustrated with the reference signs Dy and Dz in FIG. 49d), the transmission slot antenna is connected to the transmission path for transmission, the reception substrate includes a transmission path for reception (same as the part, which is located outside the rectangles illustrated with the reference signs Dy and Dz, in which the signal lines 255 and the shield layers 254 and 256 are superimposed, in FIGS. 49b to 49d, or the part, which is located outside the rectangular region circumscribing the slot, in which the signal line 255 and the shield layers 254 and 256 are superimposed, in FIGS. 242 and 243) and a reception slot antenna (the same as the region located inside the rectangles illustrated with the reference signs Dy and Dz in FIGS. 48 to 50 or FIGS. 238 to 240, particularly, FIGS. 49b to 49d).

the transmission path for reception is formed using the wiring layers included in the reception substrate, includes a second shield layer and a second signal line in a superimposed manner, and is electrically connected to the measurement section, the reception slot antenna includes a reception element (for example, a part of the conductor 254, which is the same as the inside of the rectangles illustrated with the reference signs Dy and Dz in FIG. 48d) including slots and a reception slot signal line section (for example, the same as the signal line 255 intersecting the slot in FIG. 49d) that is electrically connected to the second signal line and intersects the slot, and the reception element is a conductor that is electrically connected to the second shield layer (a part of the conductor: shield layer 254, which is the same as the outside of the rectangles illustrated with the reference signs Dy and Dz in FIG. 49d), the reception slot antenna is connected to the transmission path for reception, Each of the radiation element including the transmission slot and the reception element including the reception slot has a larger size both in a second direction (the substrate lengthwise direction, for example, the Y-axis direction in FIGS. 237, 238 to 240, and 242 to 246) and in a third direction (the substrate widthwise direction, for example, the X-axis direction in FIGS. 237, 238 to 240, and 242 to 246) than in a first direction (the substrate thickness direction, for example, the Z-axis direction in FIGS. 237, 238 to 240, and 244 to 246) and extends parallel with the plane defined by the second direction and the third direction, the first direction being the direction of the superimposition, the second direction being a direction orthogonal to the first direction and parallel with the extending direction of the transmission path, the third direction orthogonal to the first and second directions, and the transmission path for transmission and the radiation element formed using the wiring layers included in the transmission substrate and the transmission path for reception and the reception element formed using the wiring layers included in the reception substrate are disposed such that the plane of the radiation element and the plane of the reception element are in the same plane and are disposed at positions separated from each other by a predetermined distance with the extending directions and the positions fixed in the sensor casing.

13. Thirteenth Embodiment

Although the plane-shaped or plane-shaped and slot-shaped antennas (in other words, slot antennas) are used as the transmission antennas 221 to 223 in the above first embodiment, it is desirable to further improve performance such as reflectance, transmittance, and radioactivity. A sensor device 200 according to the thirteenth embodiment is different from that in the first embodiment in that the performance of the antennas is improved by increasing the thickness of a part of the signal lines in the split line.

FIG. 362 is an example of a sectional view and a plan view illustrating a configuration example of a transmission antenna 221 according to the thirteenth embodiment. In the drawing, a is an example of a sectional view of a transmission antenna 221 seen from the Z-axis direction and a transmission probe substrate 321 forming the transmission antenna 221, similarly to FIG. 19, for example. In the drawing, b to d are views (views in the substrate plane direction) of the transmission antenna 221 and the transmission probe substrate 321 forming the transmission antenna 221 seen from the X-axis direction, similarly to FIG. 20, for example. In the drawing, b is an example of a plan view of an L1 layer. In the drawing, c is an example of a plan view of an L2 layer. In the drawing, d is an example of a plan view of an L3 layer. In FIG. 362, the direction in which the transmission signal is transmitted is the Y-axis direction. The arrow illustrated near the center of a in the drawing and extending in the Y-axis direction represents the direction in which the transmission signal is transmitted.

Here, the L1 to L3 layers are layers (wiring layers) formed by conductors in the transmission intra-probe substrate 321 (the intra-probe substrate forming the transmission antenna 221). The L1 layer is a layer in which a shield layer 254 on a side closer to a reception antenna 231 from among shield layers 254 and 256 is formed. Also, the L2 layer is a layer in which at least a part of the signal line 255 is arranged. The L3 layer is a layer in which the shield layer 256 on the side far from the reception antenna 231 is formed. The line segment L1A-L1B in a in the drawing is a line segment of the L1, and the line segment L2A-L2B is a line segment of the L2 layer. The line segment L3A-L3B is a line segment of the L3 layer.

Note that although the layers formed in the transmission intra-probe substrate 321 are assumed to be three layers in the drawing for convenience of illustration, it is also possible to form four or more layers. Also, the structures of the transmission antennas 222 and 223 and the reception antennas 231 to 233 are similar to that of the transmission antenna 221. Moreover, in a case where the antenna illustrated in the drawing is used as the transmission antennas 221 to 223 and the reception antennas 231 to 233, the orientation in which the antennas are disposed in the sensor device 200 is similar to the orientation when the antennas illustrated in FIGS. 19 and 20 and the antennas illustrated in FIGS. 31 and 32 are disposed in the sensor device 200 according to the first embodiment illustrated in FIG. 4, for example. Note that the direction in which the transmission signal is transmitted is the Y+ direction (the direction of the arrow illustrated near the center of a in the drawing) in a case where the antenna illustrated in FIG. 362 is used as the transmission antennas 221 to 223, and the direction in which the reception signal is transmitted is the Y- direction (the direction opposite to the arrow illustrated near the center of a in the drawing) in a case where the antenna illustrated in FIG. 362 is used as the reception antennas 231 to 233.

As illustrated as an example in a in the drawing, the signal line 255 is arranged in the Y-axis direction inside the intra-probe substrate 321. However, a part of the signal line 255 is exposed to the surface of the intra-probe substrate 321 in a region corresponding to the transmission antennas 221 to 223. In other words, at least a part of the signal line 255 is exposed from the shield layer 254 and a radio wave absorption material 251, which will be described later, in the region from the coordinates Y1 to Y2 corresponding to the transmission antennas 221 to 223, and the part corresponding to a part of the signal line 255 and exposed from the shield layer 254 and the radio wave absorption material 251 is disposed on a side closer to the above substrate surface (more specifically, the side closer to the reception antenna 231) using the conductor disposed in the intra-probe substrate 321 on the side closer to the substrate surface than the part which is a part of the signal line 255 and is covered with the shield layer 254 and the radio wave absorption material 251 (or the part in which the shield layer 254 and the radio wave absorption material 251 are superimposed). The part of the signal line 255 which is not exposed from the shield layer 254 and the radio wave absorption material 251 (the part in which the shield layer 254 and the radio wave absorption material 251 establish covering or are superimposed) is defined as a signal line section 255-5, and the part that is exposed from the shield layer 254 and the radio wave absorption material 251 is defined as an exposure pattern section 255-6.

In a case where the antenna illustrated as an example in a in the drawing is used as the transmission antennas 221 to 223, electromagnetic waves are emitted from the exposure pattern section 255-6 similarly to the radiation element (conductor 258) of the antenna illustrated in FIGS. 19 and 31, for example.

On the other hand, in a case where the antenna illustrated as an example in FIG. 362 is used as the reception antennas 231 to 233, electromagnetic waves (transmission waves emitted from the transmission antennas 221 to 223) are received by the exposure pattern section 255-6 similarly to the reception element described in the paragraphs for explaining FIGS. 19 to 31.

The shield layer 254 is formed on one of both surfaces of the intra-probe substrate 321, and the shield layer 256 is formed on the other surface. The shield layers 254 and 256 are connected to the ground. Also, a region other than the predetermined region corresponding to the transmission antennas 221 to 223 in the intra-probe substrate 321 where the shield layers 254 and 256 are formed is covered with a radio wave absorption material 251 (such as ferrite). More specifically, the entire surroundings of the intra-probe substrate 321 may be covered with the radio wave absorption material 251 except for the predetermined region corresponding to the transmission antennas 221 to 223 as illustrated in FIGS. 4 and 350. Additionally, the region from the coordinates Y1 to Y2, for example, in the drawing functions as the transmission antenna 221, and the L1 layer and the L3 layer in the region are exposed and disposed from the shield layer 254 and the radio wave absorption material 251.

As illustrated as an example in a to c in the drawing, the exposure pattern section 255-6 is formed in the L1 layer and is connected to the signal line section 255-5 in the L2 layer via a via. The black part in the drawing illustrates a via. Also, the width (the width in the direction orthogonal to the transmission direction of the transmission signal; the width in the Z direction in the drawing) of the exposure pattern section 255-6 is greater (thicker in other word) than the width of the signal line section 255-5 in the direction. Also, the exposure pattern section 255-6 and the shield layer 254 are separated from each other and are not connected to the ground.

As illustrated as an example in d in the drawing, the pattern in the predetermined region (such as from the coordinates Y1 to Y2) corresponding to the transmission antennas 221 to 223 in the shield layer 256 has a different shape from that in the part that is not exposed from the electromagnetic wave absorption material 251, and the part is defined as a shield-side pattern section 256-5. In other words, a part of the shield layer 256 exposed from the electromagnetic wave absorption material 251 and including the transmission antennas 221 to 223 formed therein (in other words, the region from the coordinates Y1 to Y2 or the region where the exposure pattern section 255-6 is disposed) will be referred to as a shield-side pattern section 256-5, in particular. The width (the width in the direction orthogonal to the transmission direction of the transmission signal; the width in the Z direction in the drawing) of the shield-side pattern section 256-5 is smaller than the width of the exposure pattern section 255-6 in the direction. Also, the width (the width in the direction orthogonal to the transmission direction of the transmission signal; the width in the Z direction in the drawing) of the shield-side pattern section 256-5 is smaller than the width in the direction of the shield layer 256 in the region where a part of the shield layer 256 is covered with the electromagnetic wave absorption material 251 (or the region where the electromagnetic wave absorption material 251 is superimposed).

As illustrated as an example in a to d in the drawing, a structure in which the shield layer 254 is disposed on the side closer to one surface of the substrate than a part of the signal line 255 (the signal line section 255-5) in the region (the region except for the part form the coordinates Y1 to Y2) except for the transmission antennas 221 to 223, the shield layer 256 is disposed on the side closer to the other surface of the substrate than the part of the signal line 255, and a part (the signal line section 255-5) of the signal line 255 is disposed between the shield layer 254 and the shield layer 256 forms the strip line. Also, the strip line is disposed on each of (1) a closer side (a side serving as a signal transmission source) than a predetermined region (such as from the coordinates Y1 to Y2) corresponding to the transmission antennas 221 to 223 and (2) a further side (a side serving as a signal transmission destination) than the predetermined region (such as from the coordinates Y1 to Y2) corresponding to the transmission antennas 221 to 223 in the Y-axis direction (the direction in which the signals are transmitted) in the drawing In these regions where the strip lines are disposed, the radio wave absorption material 251 is disposed to cover the outside of the strip lines or superimpose on the strip line.

Note that although the exposure pattern section 255-6 is formed by the same wiring layer as that in the shield layer 254 using the substrate including the three wiring layers (conductor layers) in L1 to L3 in the example illustrated in a to d in the drawing, the structure that can be adopted in the present embodiment is not limited thereto. The exposure pattern section 255-6 may be disposed on the side closer to the substrate surface than the shield layer 254 using the wiring layers disposed on the side closer to the substrate surface than the shield layer 254. In one example, the L1 layer may form the exposure pattern section 255-6, the L2 layer may form the shield layer 254, the L3 layer may form the part of the signal line 255 (signal line section 255-5) configuring the strip line, and the L4 layer may form the shield layer 256 using the substrate including the four wiring layers L1 to L4. Alternatively, the exposure pattern section 255-6 may be disposed on the side further inward in the substrate than the shield layer 254 using the wiring layers disposed on the side further inward in the substrate than the shield layer 254. In one example, the L1 layer may form the shield layer 254, the L2 layer may form the exposure pattern section 255-6, the L3 layer may form the part of the signal line 255 (the signal line section 255-5) configuring the strip line, and the L4 layer may form the shield layer 256, by using the substrate including the four wiring layers L1 to L4.

(13-1)

In short, the sensor device 200 includes:

the signal line 255 that is at least partially arranged in a predetermined substrate (intra-probe substrate 321) and has a width in a predetermined region (such as from the coordinates Y1 to the coordinates Y2) that is greater than the width other than the predetermined region; the first shield layer (254) that is formed on one of both surfaces of the substrate;

the second shield layer (256) that is formed on the other one of both surfaces of the substrates; and the radio wave absorption material 251 that covers a part of the substrate in which the first and second shield layers are formed other than the predetermined region.

It is thus possible to achieve all of low reflectance, high transmittance, and high radioactivity.

(13-2)

Also, in (13-1) above, the signal line 255 includes the first exposure pattern section (255-6) that is exposed in the predetermined region in the one of the surfaces, the first shield layer (254) is formed in a region other than the predetermined region on the one of the surfaces, the second shield layer (256) includes the second shield-side pattern section (256-5) formed in the predetermined region, and the width of the second shield-side pattern section is smaller than the first exposure pattern section.

A principle of an improvement in performance such as reflectance, transmittance, and radioactivity will be described with reference to FIG. 363. Typically, a slot antenna provided with a slit in an external conductor or a ground is adopted as an antenna exhibiting satisfactory transmittance while keeping consistency with transmission lines. However, if it is attempted to form the slot antenna with a small structure, there is a trend that a most part allows for transmission and leads to significant degradation of radiation efficiency, or there is a trend that consistency is degraded regardless of satisfactory radiation efficiency.

In the drawing, the inductance per unit length of the signal line is defined as Ls, and the inductance per unit length of the return line is defined as Lr. These inductances increases as the width of the line decreases. A degree of balancing h of the transmission line including the signal line and the return line is represented by the following expression.

$$h=Lr/(Ls+Lr)$$  Expression 26

As illustrated as an example in a in the drawing, $0<h<<0.5$ is obtained by Expression 26 in a case where the width of the signal line is set to be smaller than that of the return line. On the other hand, as illustrated as an example in b in the drawing, $0.5<<h<1$ is obtained by Expression 20 in a case where the width of the signal line is set to be greater than that of the return line.

Typically, a current flowing through the signal line and a current flowing through the return line have the same size and opposite directions. When transmission lines with different degrees of balancing are connected, common mode signal propagation occurs even if impedances of the plurality of connected transmission lines are the same. The common mode is a propagation mode in which directions of the currents flowing through the signal line and the return line are the same.

As illustrated as an example in c in the drawing, when transmission lines with different degrees of balancing are simply connected, inconsistency of the degrees of balancing occurs, and the electromagnetic field propagation mode is not smoothly converted and is converted into a common mode in which a part of power deviates in the same phase in the signal line and the return line. The proportion of the conversion into the common mode increases as the difference of the degrees of balancing increases, radiation easily occurs at structure discontinuous points in the common mode, and this can thus be used as an antenna.

In a case where this is used as an antenna, it is possible to split this to a signal transmission section for the purpose of transmitting a signal regard to two types of transmission lines with different degrees of balancing and an antenna section for the purpose of radiation. In order to transmit the signal to an antenna or the like in a later stage, a signal transmission section is included in a stage later than the antenna section as well. In other words, it is desirable that the antenna section have a structure in which it is sandwiched by two signal transmission sections.

According to the principle as described above, the common mode occurs in the signal transmission section as well. Thus, it is desirable that the outer surface of the signal transmission section be covered with the radio wave absorption material 251 such as ferrite to remove the common mode occurring in the signal transmission section as illustrated in FIG. 362. Moreover, it is desirable that the signal transmission section have a structure including an inner layer line such as a strip line in order not to attenuate a transmitted signal due to the radio wave absorption material as illustrated in the drawing.

It is thus possible to achieve all of low reflectance, high transmittance, and high radioactivity in a wide band. The antenna section in the drawing corresponds to an antenna such as the transmission antenna 221. The signal line corresponds to the signal line 255, and the return line corresponds to the shield layers 254 and 256.

FIG. 364 is an example of a sectional view and a plan view illustrating a configuration example of the transmission antenna 221 of another type according to the thirteenth embodiment of the present technology. In the drawing, a is an example of a sectional view of the transmission antenna 221 seen from the Z-axis direction. In the drawing, b is an example of a plan view of the L1 layer. In the drawing, c is an example of a plan view of the L2 layer. In the drawing, d is an example of a plan view of the L3 layer.

As illustrated as an example in a to c in the drawing, a pattern of a predetermined region (such as from the coordinates Y1 to Y2) corresponding to the transmission antennas 221 to 223 in the signal line 255 has a different shape from that of a part that is not exposed from the electromagnetic wave absorption material 251. A part of the signal line 255 corresponding to the transmission antenna 221 is defined as an inner layer pattern section 255-7, and a remaining part is defined as a signal line section 255-5. As illustrated as an example in c in the drawing, the width of the inner layer pattern section 255-7 is greater than that of the signal line section 255-5. The inner layer pattern section 255-7 has functions similar to those of the exposure pattern section 255-6 illustrated in FIG. 362, in the transmission antenna 221.

Also, as illustrated as an example in d in FIG. 364, the shield-side pattern section 256-5 is formed in the L3 layer, and the width thereof is smaller than that of the inner layer pattern section 255-7.

(13-3)

In short, in (13-1) above, the signal line 255 includes the inner layer pattern section (255-7) formed in the substrate,
the first shield layer (254) is formed in a region other than the predetermined region on the one of the surfaces,
the second shield layer (256) includes the second shield-side pattern section (256-5) formed in the predetermined region, and the width of the second shield-side pattern section is smaller than that of the inner layer pattern section.

FIG. 365 is an example of a sectional view and a plan view illustrating a configuration example of the transmission antenna 221 of another type according to the thirteenth embodiment of the present technology. In the drawing, a is an example of a sectional view of the transmission antenna 221 seen from the Z-axis direction. In the drawing, b is an example of a plan view of the L1 layer. In the drawing, c is an example of a plan view of the L2 layer. In the drawing, d is an example of a plan view of the L3 layer.

As illustrated as an example in b in the drawing, a pattern in a predetermined region (such as from the coordinates Y1 to Y2) corresponding to the transmission antennas 221 to 223 in the shield layer 254 has a shape that is different from that of the shield layer 254 in a region where the shield layer 254 is covered with the radio wave absorption material 251 or the radio wave absorption material 251 is superimposed on the shield layer 254. The part is defined as a shield-side pattern section 254-5. The width of the shield-side pattern section 254-5 is smaller than that of the inner layer pattern section 255-7.

As illustrated as an example in c in the drawing, the width of the inner layer pattern section 255-7 is greater than that of the signal line section 255-5. As illustrated as an example in d in the drawing, the shield-side pattern section 256-5 is formed in the L3 layer, and the width thereof is smaller than that of the inner layer pattern section 255-7.

(13-4)

In short, in (13-1) above, the signal line 255 includes the inner layer pattern section 255-7 formed in the substrate,
the first shield layer (254) includes the first shield-side pattern (254-5) section formed in the predetermined region,
the second shield layer (256) includes the second shield-side pattern section (256-5) formed in the predetermined region, and
the widths of the first and second shield-side patterns are smaller than that of the inner layer pattern section 255-7.

FIG. 366 is an example of a sectional view and a plan view illustrating a configuration example of the transmission antenna 221 of another type according to the thirteenth embodiment of the present technology. In the drawing, a is an example of a sectional view of the transmission antenna 221 seen from the Z-axis direction. In the drawing, b is an example of a plan view of the L1 layer. In the drawing, c is an example of a plan view of the L2 layer. In the drawing, d is an example of a plan view of the L3 layer.

As illustrated as an example in c in the drawing, the inner layer pattern section 255-7 is formed at a part corresponding to the transmission antenna 221 and the signal line section 255-5 is formed at a part corresponding to the signal transmission section in the L2 layer, and the width of the inner layer pattern section 255-7 is greater than that of the signal line section 255-5. As illustrated as an example in d in the drawing, the shield-side pattern section 256-5 is formed in the L3 layer, and the width thereof is smaller than that of the inner layer pattern section 255-7. Furthermore, as illustrated as an example in d in the drawing, the exposure pattern sections 255-8a and 255-8b connected to the inner layer pattern section 255-7 via vias are formed in the L3 layer.

(13-5)

In short, in (13-1) above, the signal line 255 includes the inner layer pattern section (255-7) formed in the substrate and second exposure pattern sections (255-8a and 255-8b) exposed from the other surface,
the first shield layer (254) is formed in a region other than the predetermined region on the one of the surfaces,
the second shield layer (256) includes the second shield-side pattern section (256-5) formed in the predetermined region, and
the width of the second shield-side pattern section is smaller than that of the inner layer pattern section.

FIG. 367 is an example of a sectional view and a plan view illustrating a configuration example of the transmission antenna 221 of another type according to the thirteenth embodiment of the present technology. In the drawing, a is an example of a sectional view of the transmission antenna 221 seen from the Z-axis direction. In the drawing, b is an example of a plan view of the L1 layer. In the drawing, c is an example of a plan view of the L2 layer. In the drawing, d is an example of a plan view of the L3 layer.

As illustrated as an example in b in the drawing, the exposure pattern section 255-6 connected to the signal line section 255-5 via a via is formed in the L1 layer. As illustrated as an example in c in the drawing, the signal line section 255-5 is formed in the L2 layer. As illustrated as an example in d in the drawing, the shield-side pattern section 256-5 is formed in the L3 layer, and the width thereof is smaller than that of the exposure pattern section 255-6.

Furthermore, as illustrated as an example in d in the drawing, the exposure pattern sections 255-8a and 255-8b connected to the exposure pattern section 255-6 via vias are formed in the L3 layer.

(13-6)

In short, in (13-1) above, the signal line 255 includes the first exposure pattern section (255-5) exposed from the one surface and the second exposure pattern sections (255-8a and 255-8b) exposed from the other surface,
  the first shield layer (254) is formed in a region other than the predetermined region on the one of the surfaces,
  the second shield layer (256) includes the second shield-side pattern section (256-5) formed in the predetermined region, and
  the width of the second shield-side pattern section is smaller than that of the first exposure pattern section.

FIG. 368 is an example of a sectional view and a plan view illustrating a configuration example of the transmission antenna 221 of another type according to the thirteenth embodiment of the present technology. In the drawing, a is an example of a sectional view of the transmission antenna 221 seen from the Z-axis direction. In the drawing, b is an example of a plan view of the L1 layer. In the drawing, c is an example of a plan view of the L2 layer. In the drawing, d is an example of a plan view of the L3 layer.

As illustrated as an example in b in the drawing, the exposure pattern section 255-6 connected to the signal line section 255-5 via a via and the shield layer 254 are formed in the L1 layer. As illustrated as an example in c in the drawing, the inner layer line 255-9 and the signal line section 255-5 are formed in the L2 layer. The inner layer line 255-9 is connected to the shield layer 254 and the shield layer 256 via vias and is thereby connected to the ground. The width of the inner layer line 255-9 is equivalent to that of the signal line section 255-5.

Furthermore, as illustrated as d in the drawing, the exposure pattern section 255-6 connected to the ground is not formed, and the exposure pattern section 255-8c connected to the signal line section 255-5 via a via is formed in the L3 layer. The widths of the exposure pattern sections 255-6 and 255-8c are greater than that of the signal line section 255-5.

(13-7)

In short, in (13-1) above, the inner layer line 255-9 connected to the ground is further formed in the substrate,
  the signal line 255 includes the first exposure pattern section (255-6) exposed from the one surface and the second exposure pattern section (255-8c) exposed from the other surface,
  the first shield layer (254) is formed in a region other than the predetermined region on the one of the surfaces, and
  the second shield layer (256) is formed in a region other than the predetermined region on the other surface.

(13-8)

Note that it is also possible to connect a predetermined terminating resistor (such as a resistor 260) to one end of the signal line 255 as illustrated as an example in FIG. 51 in each of the transmission antennas 221 in FIGS. 362 and 364 to 368.

(13-9)

Additionally, it is also possible to connect another antenna 261 to one end of the signal line 255 as illustrated as an example in FIG. 54 in each of the transmission antennas 221 in FIGS. 362 and 364 to 368.

In this manner, a part of the signal line 255 is configured to be thick in the thirteenth embodiment of the present technology, and it is thus possible to improve performance of the slot antenna.

The present technology can also have the following configurations.

(1) A sensor device including: a transmission antenna that sends a signal as an electromagnetic wave; a reception antenna that receives the electromagnetic wave sent from the transmission antenna and transmitted through a medium; a measurement section that measures the electromagnetic wave propagated to the reception antenna; and a sensor casing, the sensor device further including
  a transmission substrate that is an electronic substrate including a plurality of wiring layers and a reception substrate that is an electronic substrate including a plurality of wiring layers, or
  a first covering layer that partially covers an outer periphery of the transmission substrate and is formed of an electromagnetic wave absorption material and a second covering layer that partially covers an outer periphery of the reception substrate and is formed of an electromagnetic wave absorption material,
  in which the sensor casing includes a transmission probe casing that is a part of the sensor casing and accommodates the transmission substrate and a reception probe casing that is another part of the sensor casing and accommodates the reception substrate,
  the transmission substrate includes a transmission path for transmission and a transmission exposure section that configures a part of the transmission antenna,
  the transmission path for transmission is formed using the wiring layers included in the transmission substrate, includes a first shield layer and a first signal line in a superimposed manner, and is electrically connected to the measurement section,
  the transmission exposure section is a conductor that is formed using the wiring layers included in the transmission substrate, is electrically connected to the first signal line, and is exposed from the first shield layer or the first covering layer,
  the reception substrate includes a transmission path for reception and a reception exposure section that configures a part of the reception antenna,
  the transmission path for reception is formed using the wiring layers included in the reception substrate, includes a second shield layer and a second signal line in a superimposed manner, and is electrically connected to the measurement section,
  the reception exposure section is a conductor that is formed using the wiring layers included in the reception substrate, is electrically connected to the second signal line, and is exposed from the second shield layer or the second covering layer,
  each of the transmission exposure section and the reception exposure section has a larger size both in a second direction and in a third direction than in a first direction and extends parallel with a plane defined by the second direction and the third direction, the first direction being a direction of the superimposition, the second direction being a direction that is orthogonal to the first direction and is parallel with an extending direction of the transmission path, the third direction orthogonal to the first and second directions, and the transmission path for transmission and the transmission exposure section formed using the wiring layers included in the transmission substrate and the transmission path for reception and the reception exposure section formed using the wiring layers included in the reception substrate are disposed to face each other such that an extending direction of the plane of the transmission exposure section and an extending direction of the plane of the reception exposure section are parallel with each other, and are disposed at positions separated from each other by a predetermined distance, with the extending directions and the positions fixed in the sensor casing.

(2) The sensor device according to (1) above, in which the transmission exposure section is a transmission element included in the transmission antenna, and the reception exposure section is a reception element included in the reception antenna.

(3) The sensor device according to (1) or (2) above, in which in the transmission probe casing, a distance from a center of the transmission substrate to a casing end of the transmission probe casing in a direction vertical to the plane of the transmission substrate is shorter than a distance from the center of the transmission substrate to a casing end of the transmission probe casing in a direction parallel to the plane of the transmission substrate, and in the reception probe casing, a distance from a center of the reception substrate to a casing end of the reception probe casing in a direction vertical to the plane of the reception substrate is shorter than a distance from the center of the reception substrate to a casing end of the reception probe casing in a direction parallel to the plane of the reception substrate.

(4) The sensor device according to any one of (1) to (3) above, further including:

a positioning section that fixes the extending directions and the positions of the transmission substrate and the reception substrate.

(5) The sensor device according to (4) above, in which the positioning section is fixed to the sensor casing and is integrated with the sensor casing.

(6) The sensor device according to (4) above, in which the sensor casing itself has a structure including the positioning section.

(7) The sensor device according to any one of (1) to (3) above, in which the extending directions and the positions of the transmission substrate and the reception substrate are fixed by each of the transmission substrate and the reception substrate being caused to abut the casing at least at two or more points.

(8) The sensor device according to any one of (1) to (3) above, in which the sensor device includes a structure obtained by curing a resin in the surroundings of each of the transmission substrate and the reception substrate, the strength of the structure obtained by curing the resin in the surroundings of the transmission substrate is equal to or greater than double the strength of the transmission substrate, and the strength of the structure obtained by curing the resin in the surroundings of the reception substrate is equal to or greater than double the strength of the reception substrate.

(9) The sensor device according to any one of (1) to (8) above, in which the transmission probe casing is formed using an electromagnetic wave transmissive material such that the strength of the casing is higher than the strength of the transmission base plate, and the reception probe casing is formed using an electromagnetic wave transmissive material such that the strength of the casing is higher than the strength of the reception substrate.

(10) The sensor device according to any one of (1) to (9) above, in which the component thickness of a part of the transmission probe casing is thicker than the component thickness of the other parts in a section that is orthogonal to the extending direction of the casing, and the component thickness of a part of the reception probe casing is thicker than the component thickness of the other parts in a section that is orthogonal to the extending direction of the casing.

(11) The sensor device according to (10) above, in which the component thickness of the transmission probe casing end portion located in a direction parallel to the transmission substrate from the center of the substrate is thicker than the component thickness of the transmission probe casing located in a direction orthogonal to the transmission substrate from the center of the substrate in a section that is orthogonal to the extending direction of the transmission probe casing, and the component thickness of the reception probe casing end portion located in a direction parallel to the reception substrate from the center of the substrate is thicker than the component thickness of the reception probe casing located in a direction orthogonal to the reception substrate from the center of the substrate in a section that is orthogonal to the extending direction of the reception probe casing.

(12) The sensor device according to (10) above, in which in regard to the component thicknesses at end portions of the transmission probe casing located in a direction orthogonal to the transmission substrate from the center of the substrate, the component thickness at the end portion located on a side further from the reception substrate is thicker than the component thickness at the end portion located on a side closer to the reception substrate in a section that is orthogonal to the extending direction of the transmission probe casing, and in regard to the component thicknesses at end portions of the reception probe casing located in a direction orthogonal to the reception substrate from the center of the substrate, the component thickness at the end portion located on a side further from the transmission substrate is thicker than the component thickness at the end portion located on a side closer to the transmission substrate in a section that is orthogonal to the extending direction of the reception probe casing.

(13) The sensor device according to any one of (1) to (12) above, in which the transmission substrate includes a plurality of vias that are connected to the first shield layer and a shield structure that is configured of an array of the plurality of vias on a side of the first signal line, and the reception substrate includes a plurality of vias that are connected to the second shield layer and a shield structure that is configured of an array of the plurality of vias on a side of the second signal line.

(14) The sensor device according to according to any one of (1) to (13) above,
in which the transmission substrate includes a plurality of the transmission antennas, and
the reception substrate includes a plurality of the reception antennas.

(15) The sensor device according to any one of (1) to (14), in which the transmission path for transmission connected to the plurality of transmission antennas is provided independently for each of the plurality of antennas in the transmission substrate, and
the transmission path for reception connected to the plurality of reception antennas is provided independently for each of the plurality of antennas in the reception substrate.

(16) The sensor device according to (15) above, in which the measurement circuit performs control of selecting the transmission antennas one by one in accordance with a predefined order from among the plurality of transmission antennas and causing the selected transmission antenna to transmit the electromagnetic wave.

REFERENCE SIGNS LIST

100 Moisture measurement system
110 Communication path
150 Central processing unit
151 Central control section
152 Antenna
153 Central communication section
154 Signal processing section
155 Storage section
156 Output section
162 Reciprocation delay time calculation section
163 Propagation transmission time calculation section
164 Moisture amount measurement section
165 Coefficient storing section
166 Memory
167 Distance calculation section
200, 201 Sensor device
210, 210-1 to 210-3 Measurement circuit
211 Sensor control section
212 Sensor communication section
213 Antenna
214, 214-1, 214-2, 214-3, 420 Transmitter
214-4 Transceiver
215, 215-1, 216-2, 215-3 Receiver
216 Transmission switch
216-1, 445 Switch
217 Reception switch
218-1 to 218-3, 219-1 to 219-3 Transmission path
220 Transmission probe unit
221 to 223, 221-1 to 221-3, 222-1 to 222-3, 223-1 Transmission antenna
230 Reception probe unit
231 to 233, 231-1 to 231-3, 232-1 to 232-3, 233-1 Reception antenna
241-1, 241-2, 241-3, 431, 441, 453 Mixer
242-1, 242-2, 242-3 Local oscillator
243-1, 243-2, 243-3 Low pass filter
244-1, 244-2, 244-3, 433, 443, 455 ADC
254-5, 256-5 Shield-side pattern section
251, 652 Radio wave absorption material
252, 253 Solder resist
254, 256 Shield layer
255 Signal line
255-5 Signal line section
255-6, 255-8a, 255-8b, 255-8c Exposure pattern section
255-7 Inner layer pattern section
255-9 Inner layer line
257 to 259, 254-1, 254-2, 255-1, 255-2, 255-3, 256-1, 256-2 Conductor
260 Resistor
261 Antenna
262 Can shield
265, 266 Delay line
271 to 274, 654 Flexible substrate
275 to 279 Rigid substrate
281 to 286, 653 Coaxial cable
281-1 Covering layer
281-2 Shield layer
281-3 Signal line
291 to 294 Frame
305 Sensor casing
305-1 Front casing
305-2 Rear casing
305-3 Main body section
305-4 Stem
305-5 Projecting portion
305-6 Antenna section
310 Measurement section casing
311 Measurement section substrate
311-1 to 311-3 Electronic substrate
312 Measurement section semiconductor device
313, 340 Battery
314, 315, 323, 324 Connector
320, 320-1 to 320-4 Probe casing
321, 322 Intra-probe substrate
325 Shield layer
330 to 332 Radiation element
333 to 335 Reception element
341 to 350 Radio wave absorption section
351 to 358 Positioning section
359-1, 359-2 Jig
360, 361, 620, 621 Reinforcing section
362 to 364 Gutter
370 to 375 Coupling section
376, 377 Level
380, 381 Fixing tool
390 Temperature sensor
410 Directional coupler
411 to 413 Transmission line
414, 415 Terminating resistor
421 Driver
422 Transmission signal generator
430 Incident wave receiver
432, 442, 454 Band pass filter
440 Reflected wave receiver
450 Transmitted wave receiver
455 Second receiver
451 Receiver
452 Local signal generator
460 Sensor signal processing section
470 Sensor control section
471 Transmission control section
472 Reflection coefficient calculation section
473 Transmission coefficient calculation section
510 Watering tube
520 to 522 Watering nozzle holder
530 Watering nozzle
540 Support member
550, 551 Watering tube holder
600 to 603 Spacer
610, 611 Pillar 620, 621 Reinforcing section
630, 631 Stopper
632 Plate-shaped member
633 Rectangular parallelepiped member
640 Guide
650 Spiral-shaped member
651 Tubular casing
661 Movable movable section
662 Fitting section
670 Shovel-shaped casing
671 Grip
672 Flat plate section
673 Blade
674 Handle
675 Scaffold member
710 Signal source
720 Variable attenuator
721 Variable amplitude

What is claimed is:

1. A sensor device comprising: a transmission antenna that sends a signal as an electromagnetic wave; a reception antenna that receives the electromagnetic wave sent from the transmission antenna and transmitted through a medium; a measurement section that measures the electromagnetic wave propagated to the reception antenna; and a sensor casing, the sensor device further comprising
a transmission substrate that is an electronic substrate including a plurality of wiring layers and a reception substrate that is an electronic substrate including a plurality of wiring layers, or
a first covering layer that partially covers an outer periphery of the transmission substrate and is formed of an electromagnetic wave absorption material and a second covering layer that partially covers an outer periphery of the reception substrate and is formed of an electromagnetic wave absorption material,
wherein the sensor casing includes a transmission probe casing that is a part of the sensor casing and accommodates the transmission substrate and a reception probe casing that is another part of the sensor casing and accommodates the reception substrate,
the transmission substrate includes a transmission path for transmission and a transmission exposure section that configures a part of the transmission antenna,
the transmission path for transmission is formed using the wiring layers included in the transmission substrate, includes a first shield layer and a first signal line in a superimposed manner, and is electrically connected to the measurement section,
the transmission exposure section is a conductor that is formed using the wiring layers included in the transmission substrate, is electrically connected to the first signal line, and is exposed from the first shield layer or the first covering layer,
the reception substrate includes a transmission path for reception and a reception exposure section that configures a part of the reception antenna,
the transmission path for reception is formed using the wiring layers included in the reception substrate, includes a second shield layer and a second signal line in a superimposed manner, and is electrically connected to the measurement section,
the reception exposure section is a conductor that is formed using the wiring layers included in the reception substrate, is electrically connected to the second signal line, and is exposed from the second shield layer or the second covering layer,
each of the transmission exposure section and the reception exposure section has a larger size both in a second direction and in a third direction than in a first direction and extends parallel with a plane defined by the second direction and the third direction, the first direction being a direction of the superimposition, the second direction being a direction that is orthogonal to the first direction and is parallel with an extending direction of the transmission path, the third direction orthogonal to the first and second directions, and
the transmission path for transmission and the transmission exposure section formed using the wiring layers included in the transmission substrate and the transmission path for reception and the reception exposure section formed using the wiring layers included in the reception substrate are disposed to face each other such that an extending direction of the plane of the transmission exposure section and an extending direction of the plane of the reception exposure section are parallel with each other, and are disposed at positions separated from each other by a predetermined distance, with the extending directions and the positions fixed in the sensor casing.

2. The sensor device according to claim 1, wherein the transmission exposure section is a transmission element included in the transmission antenna, and the reception exposure section is a reception element included in the reception antenna.

3. The sensor device according to claim 1,
wherein in the transmission probe casing,
a distance from a center of the transmission substrate to a casing end of the transmission probe casing in a direction vertical to the plane of the transmission substrate is
shorter than a distance from the center of the transmission substrate to a casing end of the transmission probe casing in a direction parallel to the plane of the transmission substrate, and
in the reception probe casing,
a distance from a center of the reception substrate to a casing end of the reception probe casing in a direction vertical to the plane of the reception substrate is
shorter than a distance from the center of the reception substrate to a casing end of the reception probe casing in a direction parallel to the plane of the reception substrate.

4. The sensor device according to claim 1, further comprising:
a positioning section that fixes the extending directions and the positions of the transmission substrate and the reception substrate.

5. The sensor device according to claim 4, wherein the positioning section is fixed to the sensor casing and is integrated with the sensor casing.

6. The sensor device according to claim 4, wherein the sensor casing itself has a structure including the positioning section.

7. The sensor device according to claim 1, wherein the extending directions and the positions of the transmission substrate and the reception substrate are fixed by each of the transmission substrate and the reception substrate being caused to abut the casing at least at two or more points.

8. The sensor device according to claim 1,
wherein the sensor device includes a structure obtained by curing a resin in surroundings of each of the transmission substrate and the reception substrate,
a strength of the structure obtained by curing the resin in the surroundings of the transmission substrate is equal to or greater than double a strength of the transmission substrate, and a strength of the structure obtained by curing the resin in the surroundings of the reception substrate is equal to or greater than double a strength of the reception substrate.

9. The sensor device according to claim 1,
wherein the transmission probe casing is formed using an electromagnetic wave transmissive material such that a strength of the casing is higher than a strength of a transmission base plate, and
the reception probe casing is formed using an electromagnetic wave transmissive material such that the strength of the casing is higher than the strength of the reception substrate.

10. The sensor device according to claim 1,
wherein a component thickness of a part of the transmission probe casing is thicker than a component thickness of the other parts in a section that is orthogonal to the extending direction of the casing, and
a component thickness of a part of the reception probe casing is thicker than a component thickness of the other parts in a section that is orthogonal to the extending direction of the casing.

11. The sensor device according to claim 10, wherein a component thickness of an end portion of the transmission probe casing located in a direction parallel to the transmission substrate from a center of the substrate is thicker than a component thickness of the transmission probe casing located in a direction orthogonal to the transmission substrate from the center of the substrate in a section that is orthogonal to the extending direction of the transmission probe casing, and the component thickness of an end portion of the reception probe casing located in a direction parallel to the reception substrate from the center of the substrate is thicker than the component thickness of the reception probe casing located in a direction orthogonal to the reception substrate from the center of the substrate in a section that is orthogonal to an extending direction of the reception probe casing.

12. The sensor device according to claim 10,
wherein in regard to the component thicknesses at end portions of the transmission probe casing located in a direction orthogonal to the transmission substrate from a center of the substrate, the component thickness at the end portion located on a side further from the reception substrate is thicker than the component thickness at the end portion located on a side closer to the reception substrate in a section that is orthogonal to the extending direction of the transmission probe casing, and
in regard to the component thicknesses at end portions of the reception probe casing located in a direction orthogonal to the reception substrate from the center of the substrate, the component thickness at the end portion located on a side further from the transmission substrate is thicker than the component thickness at the end portion located on a side closer to the transmission substrate in a section that is orthogonal to the extending direction of the reception probe casing.

13. The sensor device according to claim 1,
wherein the transmission substrate includes
a plurality of vias that are connected to the first shield layer and
a shield structure that is configured of an array of the plurality of vias on a side of the first signal line, and
the reception substrate includes
a plurality of vias that are connected to the second shield layer and
a shield structure that is configured of an array of the plurality of vias on a side of the second signal line.

14. The sensor device according to claim 1,
wherein the transmission substrate includes a plurality of the transmission antennas, and
the reception substrate includes a plurality of the reception antennas.

15. The sensor device according to claim 1,
wherein the transmission path for transmission connected to the plurality of transmission antennas is provided independently for each of the plurality of antennas in the transmission substrate, and
the transmission path for reception connected to the plurality of reception antennas is provided independently for each of the plurality of antennas in the reception substrate.

16. The sensor device according to claim 15, wherein a measurement circuit performs control of selecting the transmission antennas one by one in accordance with a predefined order from among the plurality of transmission antennas and causing the selected transmission antenna to transmit the electromagnetic wave.

* * * * *